US011674154B2

(12) United States Patent
Shim et al.

(10) Patent No.: US 11,674,154 B2
(45) Date of Patent: Jun. 13, 2023

(54) GENE THERAPEUTICS FOR FIBRODYSPLASIA OSSIFICANS PROGRESSIVA

(71) Applicant: University of Massachusetts, Boston, MA (US)

(72) Inventors: Jae-Hyuck Shim, Westborough, MA (US); Guangping Gao, Westborough, MA (US); Jun Xie, Shrewsbury, MA (US); Yeon-Suk Yang, Westborough, MA (US); Jung min Kim, Worcester, MA (US); Sachin Chaugule, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 17/541,141

(22) Filed: Dec. 2, 2021

(65) Prior Publication Data

US 2022/0177915 A1 Jun. 9, 2022

Related U.S. Application Data

(60) Provisional application No. 63/251,822, filed on Oct. 4, 2021, provisional application No. 63/121,221, filed on Dec. 3, 2020.

(51) Int. Cl.

| | |
|---|---|
| ***C12N 15/86*** | (2006.01) |
| ***A61P 19/08*** | (2006.01) |
| ***A61K 38/45*** | (2006.01) |
| ***A61K 48/00*** | (2006.01) |
| ***C12N 9/22*** | (2006.01) |
| ***C12N 15/11*** | (2006.01) |

(52) U.S. Cl.

CPC .............. *C12N 15/86* (2013.01); *A61K 38/45* (2013.01); *A61K 48/0066* (2013.01); *A61P 19/08* (2018.01); *C12N 9/22* (2013.01); *C12N 15/111* (2013.01); *C12Y 207/1103* (2013.01); *C12N 2310/141* (2013.01); *C12N 2310/20* (2017.05); *C12N 2320/34* (2013.01); *C12N 2750/14143* (2013.01); *C12N 2830/008* (2013.01)

(58) Field of Classification Search

CPC ................ A61K 48/0066; A61K 38/45; C12Y 207/1103; C12N 2750/14143

See application file for complete search history.

(56) References Cited

U.S. PATENT DOCUMENTS

| | | | |
|---|---|---|---|
| 5,399,363 A | 3/1995 | Liversidge et al. | |
| 5,478,745 A | 12/1995 | Samulski et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,641,515 A | 6/1997 | Ramtoola | |
| 5,656,016 A | 8/1997 | Ogden | |
| 5,697,899 A | 12/1997 | Hillman et al. | |
| 5,738,868 A | 4/1998 | Shinkarenko | |
| 5,741,516 A | 4/1998 | Webb et al. | |
| 5,770,219 A | 6/1998 | Chiang et al. | |
| 5,779,708 A | 7/1998 | Wu | |
| 5,783,208 A | 7/1998 | Venkateshwaran et al. | |
| 5,795,587 A | 8/1998 | Gao et al. | |
| 5,797,898 A | 8/1998 | Santini, Jr. et al. | |
| 6,001,650 A | 12/1999 | Colosi | |
| 6,156,303 A | 12/2000 | Russell et al. | |
| 8,859,752 B2 * | 10/2014 | Kaplan | A61P 19/00 536/24.5 |
| 2016/0187357 A1 | 6/2016 | Brunkow et al. | |
| 2016/0298099 A1 | 10/2016 | Kormann et al. | |
| 2018/0015124 A1 | 1/2018 | Prockop et al. | |
| 2018/0298380 A1 | 10/2018 | Gao et al. | |
| 2020/0231953 A1 | 7/2020 | Gao et al. | |

FOREIGN PATENT DOCUMENTS

| | | | |
|---|---|---|---|
| WO | WO-2007127428 A2 * | 11/2007 | C12N 15/86 |
| WO | WO 2020/118011 A1 | 6/2020 | |
| WO | WO 2020/118239 A1 | 6/2020 | |

OTHER PUBLICATIONS

"Optimal." Merriam-Webster.com Dictionary, Merriam-Webster, https://www.merriam-webster.com/dictionary/optimal. Accessed May 18, 2022. (Year: 2022).*

Wu et al. Self-complementary recombinant adeno-associated viral vectors: Packaging capacity and the role of Rep proteins in vector purity. Human Gene Therapy, vol. 18, pp. 171-182, Feb. 2007. (Year: 2007).*

Koefoed et al. Biological effects of rAAV-caAlk2 coating on structural allograft healing. Molecular Therapy, vol. 12, No. 2, pp. 212-218, Apr. 20, 2005. (Year: 2005).*

Invitation to Pay Additional Fees for Application No. PCT/US2021/061653 dated Feb. 10, 2022.

International Search Report and Written Opinion for Application No. PCT/US2021/061653 dated Apr. 1, 2022.

Asokan et al., The AAV vector toolkit: poised at the clinical crossroads. Mol Ther. Apr. 2012;20(4):699-708. doi: 10.1038/mt.2011.287. Epub Jan. 24, 2012.

Aykul et al., Transforming Growth Factor-beta Family Ligands Can Function as Antagonists by Competing for Type II Receptor Binding. J Biol Chem. May 13, 2016;291(20):10792-804. doi: 10.1074/jbc.M115.713487. Epub Mar. 9, 2016.

(Continued)

*Primary Examiner* — Jennifer Dunston

(74) *Attorney, Agent, or Firm* — Wolf, Greenfield & Sacks, P.C.

(57) ABSTRACT

In some aspects, the disclosure relates to compositions and methods for treating fibrodysplasia ossificans progressiva (FOP) in a subject. In some aspects, the disclosure provides isolated nucleic acids, and vectors such as rAAV vectors, configured to express transgenes that inhibit (e.g., decrease) expression of mutated AVCR1 gene in muscle cells or connective tissues.

12 Claims, 79 Drawing Sheets

Specification includes a Sequence Listing.

(56) References Cited

OTHER PUBLICATIONS

Baujat et al., Prevalence of fibrodysplasia ossificans progressiva (FOP) in France: an estimate based on a record linkage of two national databases. Orphanet J Rare Dis. Jun. 30, 2017;12(1):123. doi: 10.1186/s13023-017-0674-5.
Blankinship et al., Efficient transduction of skeletal muscle using vectors based on adeno-associated virus serotype 6. Mol Ther. Oct. 2004;10(4):671-8. doi: 10.1016/j.ymthe.2004.07.016.
Boshart et al., A very strong enhancer is located upstream of an immediate early gene of human cytomegalovirus. Cell. Jun. 1985;41(2):521-30. doi: 10.1016/s0092-8674(85)80025-8.
Bourlais et al., Ophthalmic drug delivery systems—recent advances. Prog Retin Eye Res. Jan. 1998;17(1):33-58. doi: 10.1016/s1350-9462(97)00002-5.
Chang et al., miR-122, a mammalian liver-specific microRNA, is processed from her mRNA and may downregulate the high affinity cationic amino acid transporter CAT-1. RNA Biol. Jul. 2004;1(2):106-13. doi: 10.4161/rna.1.2.1066. Epub Jul. 1, 2004.
Chu et al., SV40 DNA transfection of cells in suspension: analysis of efficiency of transcription and translation of T-antigen. Gene. Mar. 1981;13(2):197-202. doi: 10.1016/0378-1119(81)90008-1.
Convente et al., Depletion of Mast Cells and Macrophages Impairs Heterotopic Ossification in an Acvrl(R206H) Mouse Model of Fibrodysplasia Ossificans Progressiva. J Bone Miner Res. Feb. 2018;33(2):269-282. doi: 10.1002/jbmr.3304. Epub Jan. 3, 2018.
De Felipe et al., Tricistronic and tetracistronic retroviral vectors for gene transfer. Hum Gene Ther. Sep. 1, 2000;11(13):1921-31. doi: 10.1089/10430340050129530.
De Felipe et al., Use of the 2A sequence from foot-and-mouth disease virus in the generation of retroviral vectors for gene therapy. Gene Ther. Feb. 1999;6(2):198-208. doi: 10.1038/sj.gt.3300811.
Fisher et al., Transduction with recombinant adeno-associated virus for gene therapy is limited by leading-strand synthesis. J Virol. Jan. 1996;70(1):520-32. doi: 10.1128/JVI.70.1.520-532.1996.
Furler et al., Recombinant AAV vectors containing the foot and mouth disease virus 2A sequence confer efficient bicistronic gene expression in cultured cells and rat substantia nigra neurons. Gene Ther. Jun. 2001;8(11):864-73. doi: 10.1038/sj.gt.3301469.
Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.
Gossen et al., Transcriptional activation by tetracyclines in mammalian cells. Science. Jun. 23, 1995;268(5218):1766-9. doi: 10.1126/science.7792603.
Graham et al., A new technique for the assay of infectivity of human adenovirus 5 DNA. Virology. Apr. 1973;52(2):456-67. doi: 10.1016/0042-6822(73)90341-3.
Gregorevic et al., Systemic delivery of genes to striated muscles using adeno-associated viral vectors. Nat Med. Aug. 2004;10(8):828-34. doi: 10.1038/nm1085. Epub Jul. 25, 2004.
Halpin et al., Self-processing 2A-polyproteins—a system for co-ordinate expression of multiple proteins in transgenic plants. Plant J. Feb. 1999;17(4):453-9. doi: 10.1046/j.1365-313x.1999.00394.x.
Harvey et al., Inducible control of gene expression: prospects for gene therapy. Curr Opin Chem Biol. Aug. 1998;2(4):512-8. doi: 10.1016/s1367-5931(98)80128-2.
Hatsell et al., ACVR1R206H receptor mutation causes fibrodysplasia ossificans progressiva by imparting responsiveness to activin A. Sci Transl Med. Sep. 2, 2015;7(303):303ra137. doi: 10.1126/scitranslmed.aac4358.
Hildebrand et al., The Fibrodysplasia Ossificans Progressiva (FOP) mutation p.R206H in ACVR1 confers an altered ligand response. Cell Signal. Jan. 2017;29:23-30. doi: 10.1016/j.cellsig.2016.10.001. Epub Oct. 4, 2016.
Hino et al., Neofunction of ACVR1 in fibrodysplasia ossificans progressiva. Proc Natl Acad Sci U S A. Dec. 15, 2015;112(50):15438-43. doi: 10.1073/pnas.1510540112. Epub Nov. 30, 2015.
Hsieh et al., Evaluation of Salivary Cytokines for Diagnosis of both Trauma-Induced and Genetic Heterotopic Ossification. Front Endocrinol (Lausanne). Apr. 24, 2017;8:74. doi: 10.3389/fendo.2017.00074. eCollection 2017.
Joe et al., Muscle injury activates resident fibro/adipogenic progenitors that facilitate myogenesis. Nat Cell Biol. Feb. 2010; 12(2):153-63. doi: 10.1038/ncb2015. Epub Jan. 17, 2010.
Kaplan et al., Fibrodysplasia ossificans progressiva. Best Pract Res Clin Rheumatol. Mar. 2008;22(1):191-205. doi: 10.1016/i.berh.2007.11.007.
Klump et al., Retroviral vector-mediated expression of HoxB4 in hematopoietic cells using a novel coexpression strategy. Gene Ther. May 2001;8(10):811-7. doi: 10.1038/sj.gt.3301447.
Lagos-Quintana et al., Identification of tissue-specific microRNAs from mouse. Curr Biol. Apr. 30, 2002;12(9):735-9. doi: 10.1016/s0960-9822(02)00809-6.
Levy et al., Cytosine and adenine base editing of the brain, liver, retina, heart and skeletal muscle of mice via adeno-associated viruses. Nat Biomed Eng. Jan. 2020;4(1):97-110. doi: 10.1038/s41551-019-0501-5. Epub Jan. 14, 2020.
Limberis et al., Transduction efficiencies of novel AAV vectors in mouse airway epithelium in vivo and human ciliated airway epithelium in vitro. Mol Ther. Feb. 2009;17(2):294-301. doi: 10.1038/mt.2008.261. Epub Dec. 9, 2008.
Magari et al., Pharmacologic control of a humanized gene therapy system implanted into nude mice. J Clin Invest. Dec. 1, 1997;100(11):2865-72. doi: 10.1172/JCI119835.
Matsumoto et al., Induced pluripotent stem cells from patients with human fibrodysplasia ossificans progressiva show increased mineralization and cartilage formation. Orphanet J Rare Dis. Dec. 9, 2013;8:190. doi: 10.1186/1750-1172-8-190.
Mattion et al., Foot-and-mouth disease virus 2A protease mediates cleavage in attenuated Sabin 3 poliovirus vectors engineered for delivery of foreign antigens. J Virol. Nov. 1996;70(11):8124-7. doi: 10.1128/JVI.70.11.8124-8127.1996.
McCarthy, Self-complementary AAV vectors; advances and applications. Mol Ther. Oct. 2008;16(10):1648-56. doi: 10.1038/mt.2008.171. Epub Aug. 5, 2008.
Medici et al., Conversion of vascular endothelial cells into multipotent stem-like cells. Nat Med. Dec. 2010;16(12):1400-6. doi: 10.1038/nm.2252. Epub Nov. 21, 2010.
Min et al., Diverse repertoire of human adipocyte subtypes develops from transcriptionally distinct mesenchymal progenitor cells. Proc Natl Acad Sci U S A. Sep. 3, 2019;116(36):17970-17979. doi: 10.1073/pnas.1906512116. Epub Aug. 16, 2019.
No et al., Ecdysone-inducible gene expression in mammalian cells and transgenic mice. Proc Natl Acad Sci U S A. Apr. 16, 1996;93(8):3346-51. doi: 10.1073/pnas.93.8.3346.
Olsen et al., Activin A inhibits BMP-signaling by binding ACVR2A and ACVR2B. Cell Commun Signal. Jun. 6, 2015;13:27. doi: 10.1186/s12964-015-0104-z.
Pacifici et al., Common mutations in ALK2/ACVR1, a multi-faceted receptor, have roles in distinct pediatric musculoskeletal and neural orphan disorders. Cytokine Growth Factor Rev. Feb. 2016;27:93-104. doi: 10.1016/j.cytogfr.2015.12.007. Epub Dec. 28, 2015.
Ran et al., In vivo genome editing using *Staphylococcus aureus* Cas9. Nature. Apr. 9, 2015;520(7546):186-91. doi: 10.1038/nature14299. Epub Apr. 1, 2015.
Remington's Pharmaceutical Sciences. 15th Edition. 1975. pp. 1035-1038 and 1570-1580.
Ryan et al., Foot-and-mouth disease virus 2A oligopeptide mediated cleavage of an artificial polyprotein. EMBO J. Feb. 15, 1994;13(4):928-33. doi: 10.1002/j.1460-2075.1994.tb06337.x.
Shore et al., A recurrent mutation in the BMP type I receptor ACVR1 causes inherited and sporadic fibrodysplasia ossificans progressiva. Nat Genet. May 2006;38(5):525-7. doi: 10.1038/ng1783. Epub Apr. 23, 2006.
Shore et al., Insights from a rare genetic disorder of extra-skeletal bone formation, fibrodysplasia ossificans progressiva (FOP). Bone. Sep. 2008;43(3):427-33. doi: 10.1016/j.bone.2008.05.013. Epub May 28, 2008.

(56) References Cited

OTHER PUBLICATIONS

Wang et al., Ligand-inducible and liver-specific target gene expression in transgenic mice. Nat Biotechnol. Mar. 1997;15(3):239-43. doi: 10.1038/nbt0397-239.
Wang et al., Positive and negative regulation of gene expression in eukaryotic cells with an inducible transcriptional regulator. Gene Ther. May 1997;4(5):432-41. doi: 10.1038/sj.gt.3300402.
Wolken et al.,The obligatory role of Activin A in the formation of heterotopic bone in Fibrodysplasia Ossificans Progressiva. Bone. Apr. 2018;109:210-217. doi: 10.1016/j.bone.2017.06.011. Epub Jun. 16, 2017.
Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.
Xie et al., Effective and Accurate Gene Silencing by a Recombinant AAV-Compatible MicroRNA Scaffold. Mol Ther. Feb. 5, 2020;28(2):422-430. doi: 10.1016/j.ymthe.2019.11.018. Epub Nov. 27, 2019.
Yang et al., Bone-Targeting AAV-Mediated Gene Silencing in Osteoclasts for Osteoporosis Therapy. Mol Ther Methods Clin Dev. Apr. 18, 2020; 17:922-935. doi: 10.1016/j.omtm.2020.04.010. eCollection Jun. 12, 2020.
Yang et al., Bone-targeting AAV-mediated silencing of Schnurri-3 prevents bone loss in osteoporosis. Nat Commun. Jul. 4, 2019;10(1):2958. doi: 10.1038/s41467-019-10809-6.

* cited by examiner

*PDGFRa-GFP mice;* rAAV9.mCherry|DAPI rAAV9.LacZ

*PDGFRa-GFP mice*;DAPI

SEQUENCE LISTING

<160> NUMBER OF SEQ ID NOS: 65

<210> SEQ ID NO 1
<211> LENGTH: 1530
<212> TYPE: DNA
<213> ORGANISM: Artificial Sequence
<220> FEATURE:
<223> OTHER INFORMATION: Synthetic

<400> SEQUENCE: 1
atggtcgatg gagtgatgat cctgcctgtc ctgattatga ttgccctgcc cagccccagc 60
atggaagatg aaaaacctaa agtcaaccct aagctgtata tgtgcgtgtg cgagggcctg 120
agctgcggaa acgaggatca ctgcgagggc cagcagtgtt tcagctccct gtccatcaat 180
gacggcttcc acgtgtacca gaagggctgc tttcaggtgt atgagcaggg caagatgacc 240
tgtaagacac caccttcccc aggacaggca gtggagtgct gtcagggcga ttggtgtaac 300
cggaatatca ccgcccagct gccaacaaag ggcaagtctt tccccggcac acagaacttt 360
cacctggaag tgggcctgat catcctgagc gtggtgttcg ccgtgtgcct gctggcatgt 420
ctgctgggag tggccctgag aaagtttaag cggagaaacc aggagcggct gaatccaaga 480
gatgtggagt acggcaccat cgagggcctg atcaccacaa atgtgggcga ctctacactg 540
gccgacctgc tggatcacag ctgcaccagc ggctccggat ctggcctgcc ctttctggtg 600
cagaggaccg tggcccggca gatcaccctg ctggagtgcg tgggcaaggg ccggtacgga 660
gaagtgtgga gaggatcctg gcagggagag aacgtggcag tgaagatctt ctctagccgg 720
gatgagaagt cttggtttag agagacagag ctgtataaca cagtgatgct gaggcacgag 780
aatatcctgg gcttcatcgc ctccgacatg acctctcgcc actcctctac acagctgtgg 840
ctgatcaccc actaccacga gatgggctcc ctgtacgatt acctccagct gaccacactg 900
gacacagtgt cttgcctgcg gatcgtgctg tctatcgcca gcggcctggc acacctgcac 960
atcgagatct ttggaaccca gggcaagcca gcaatcgcac acagagatct gaagtctaag 1020
aacatcctgg tgaagaagaa tggccagtgc tgtatcgccg atctgggcct ggccgtgatg 1080
cacagccagt ccaccaacca gctggacgtg ggcaacaatc ctcgggtggg cacaaagaga 1140
tacatggccc cagaggtgct ggatgagaca atccaggtgg actgcttcga tagctataag 1200
agggtggaca tctgggcctt tggcctggtg ctgtgggagg tggcaaggag gatggtgagc 1260
aacggcatcg tggaggacta caagccaccc ttctatgacg tggtgcctaa tgatccatcc 1320
tttgaggaca tgcgcaaggt ggtgtgcgtg gatcagcaga ggcccaacat ccctaatcgc 1380

-continued

```
tggttcagcg accccaccct gacatccctg gccaagctga tgaaggagtg ttggtatcag   1440

aatcctagcg ccaggctgac cgccctgcgc atcaagaaaa ctctgactaa aatcgacaat   1500

agcctggata aactgaaaac cgactgctga                                    1530
```

<210> SEQ ID NO 2
<211> LENGTH: 6586
<212> TYPE: DNA
<213> ORGANISM: Artificial Sequence
<220> FEATURE:
<223> OTHER INFORMATION: Synthetic

<400> SEQUENCE: 2

```
gctgcgcgct cgctcgctca ctgaggccgc ccgggcaaag cccgggcgtc gggcgacctt     60

tggtcgcccg gcctcagtga gcgagcgagc gcgcagagag ggagtggcca actccatcac    120

taggggttcc ttgtagttaa tgattaaccc gccatgctac ttatctacca gggtaatggg    180

gatcctctag aactatagct agtcgacatt gattattgac tagttattaa tagtaatcaa    240

ttacggggtc attagttcat agcccatata tggagttccg cgttacataa cttacggtaa    300

atggcccgcc tggctgaccg cccaacgacc cccgcccatt gacgtcaata atgacgtatg    360

ttcccatagt aacgccaata gggactttcc attgacgtca atgggtggag tatttacggt    420

aaactgccca cttggcagta catcaagtgt atcatatgcc aagtacgccc cctattgacg    480

tcaatgacgg taaatggccc gcctggcatt atgcccagta catgacctta tgggactttc    540

ctacttggca gtacatctac gtattagtca tcgctattac catggtcgag gtgagcccca    600

cgttctgctt cactctcccc atctcccccc cctccccacc cccaattttg tatttattta    660

tttttaatt attttgtgca gcgatggggg cggggggggg ggggggcgc gcgccaggcg      720

gggcggggcg gggcgagggg cggggcgggg cgaggcggag aggtgcggcg gcagccaatc    780

agagcggcgc gctccgaaag tttcctttta tggcgaggcg gcggcggcgg cggccctata    840

aaaagcgaag cgcgcggcgg gcggggagtc gctgcgacgc tgccttcgcc ccgtgccccg    900

ctccgccgcc gcctcgcgcc gcccgccccg gctctgactg accgcgttac tcccacaggt    960

gagcgggcgg gacggccctt ctcctccggg ctgtaattag cgcttggttt aatgacggct   1020

tgtttctttt ctgtggctgc gtgaaagcct tgaggggctc cgggagggcc ctttgtgcgg   1080

ggggagcggc tcgggggggtg cgtgcgtgtg tgtgtgcgtg gggagcgccg cgtgcggctc   1140

cgcgctgccc ggcggctgtg agcgctgcgg gcgcggcgcg gggctttgtg cgctccgcag   1200

tgtgcgcgag gggagcgcgg ccgggggcgg tgccccgcgg tgcggggggg gctgcgaggg   1260

gaacaaaggc tgcgtgcggg gtgtgtgcgt gggggggtga gcagggggtg tgggcgcgtc   1320

ggtcgggctg caacccccc tgcacccccc tccccgagtt gctgagcacg gcccggcttc    1380

gggtgcgggg ctccgtacgg ggcgtggcgc ggggctcgcc gtgccgggcg gggggtggcg   1440

gcaggtgggg gtgccgggcg gggcggggcc gcctcgggcc ggggagggct cgggggaggg   1500

gcgcggcggc ccccggagcg ccggcggctg tcgaggcgcg gcgagccgca gccattgcct   1560

tttatggtaa tcgtgcgaga gggcgcaggg acttcctttg tcccaaatct gtgcggagcc   1620

gaaatctggg aggcgccgcc gcaccccctc tagcgggcgc ggggcgaagc ggtgcggcgc   1680

cggcaggaag gaaatgggcg gggagggcct tcgtgcgtcg ccgcgccgcc gtccccttct   1740

ccctctccag cctcggggct gtccgcgggg ggacggctgc cttcgggggg gacggggcag   1800

ggcggggttc ggcttctggc gtgtgaccgg cggctctaga gcctctgcta accatgttca   1860

tgccttcttc tttttcctac agctcctggg caacgtgctg gttattgtgc tgtctcatca   1920
```

-continued

```
ttttggcaaa gaattccgcc accatggtcg atggagtgat gatcctgcct gtcctgatta   1980
tgattgccct gcccagcccc agcatggaag atgaaaaacc taaagtcaac cctaagctgt   2040
atatgtgcgt gtgcgagggc ctgagctgcg gaaacgagga tcactgcgag ggccagcagt   2100
gtttcagctc cctgtccatc aatgacggct tccacgtgta ccagaagggc tgctttcagg   2160
tgtatgagca gggcaagatg acctgtaaga caccaccttc cccaggacag gcagtggagt   2220
gctgtcaggg cgattggtgt aaccggaata tcaccgccca gctgccaaca aagggcaagt   2280
ctttccccgg cacacagaac tttcacctgg aagtgggcct gatcatcctg agcgtggtgt   2340
tcgccgtgtg cctgctggca tgtctgctgg gagtggccct gagaaagttt aagcggagaa   2400
accaggagcg gctgaatcca agagatgtgg agtacggcac catcgagggc ctgatcacca   2460
caaatgtggg cgactctaca ctggccgacc tgctggatca cagctgcacc agcggctccg   2520
gatctggcct gccctttctg gtgcagagga ccgtggcccg gcagatcacc ctgctggagt   2580
gcgtgggcaa gggccggtac ggagaagtgt ggagaggatc ctggcaggga gagaacgtgg   2640
cagtgaagat cttctctagc cgggatgaga agtcttggtt tagagagaca gagctgtata   2700
acacagtgat gctgaggcac gagaatatcc tgggcttcat cgcctccgac atgacctctc   2760
gccactcctc tacacagctg tggctgatca cccactacca cgagatgggc tccctgtacg   2820
attacctcca gctgaccaca ctggacacag tgtcttgcct gcggatcgtg ctgtctatcg   2880
ccagcggcct ggcacacctg cacatcgaga tctttggaac ccagggcaag ccagcaatcg   2940
cacacagaga tctgaagtct aagaacatcc tggtgaagaa gaatggccag tgctgtatcg   3000
ccgatctggg cctggccgtg atgcacagcc agtccaccaa ccagctggac gtgggcaaca   3060
atcctcgggt gggcacaaag agatacatgg ccccagaggt gctggatgag acaatccagg   3120
tggactgctt cgatagctat aagagggtgg acatctgggc ctttggcctg gtgctgtggg   3180
aggtggcaag gaggatggtg agcaacggca tcgtggagga ctacaagcca cccttctatg   3240
acgtggtgcc taatgatcca tcctttgagg acatgcgcaa ggtggtgtgc gtggatcagc   3300
agaggcccaa catccctaat cgctggttca gcgaccccac cctgacatcc ctggccaagc   3360
tgatgaagga gtgttggtat cagaatccta gcgccaggct gaccgccctg cgcatcaaga   3420
aaactctgac taaaatcgac aatagcctgg ataaactgaa aaccgactgc tgacctgagg   3480
atccgatctt tttccctctg ccaaaaatta tggggacatc atgaagcccc ttgagcatct   3540
gacttctggc taataaagga aatttatttt cattgcaata gtgtgttgga atttttttgtg   3600
tctctcactc ggaagcaatt cgttgatctg aatttcgacc acccataata cccattaccc   3660
tggtagataa gtagcatggc gggttaatca ttaactacaa ggaaccccta gtgatggagt   3720
tggccactcc ctctctgcgc gctcgctcgc tcactgaggc cgggcgacca aaggtcgccc   3780
gacgcccggg ctttgcccgg gcggcctcag tgagcgagcg agcgcgcagc cttaattaac   3840
ctaattcact ggccgtcgtt ttacaacgtc gtgactggga aaaccctggc gttacccaac   3900
ttaatcgcct tgcagcacat ccccctttcg ccagctggcg taatagcgaa gaggcccgca   3960
ccgatcgccc ttcccaacag ttgcgcagcc tgaatggcga atgggacgcg ccctgtagcg   4020
gcgcattaag cgcggcgggt gtggtggtta cgcgcagcgt gaccgctaca cttgccagcg   4080
ccctagcgcc cgctcctttc gctttcttcc cttcctttct cgccacgttc gccggctttc   4140
cccgtcaagc tctaaatcgg gggctccctt tagggttccg atttagtgct ttacggcacc   4200
tcgaccccaa aaaacttgat tagggtgatg gttcacgtag tgggccatcg ccctgataga   4260
```

-continued

```
cggtttttcg ccctttgacg ttggagtcca cgttctttaa tagtggactc ttgttccaaa   4320
ctggaacaac actcaaccct atctcggtct attcttttga tttataaggg attttgccga   4380
tttcggccta ttggttaaaa aatgagctga tttaacaaaa atttaacgcg aattttaaca   4440
aaatattaac gcttacaatt taggtggcac ttttcgggga aatgtgcgcg gaacccctat   4500
ttgtttattt ttctaaatac attcaaatat gtatccgctc atgagacaat aaccctgata   4560
aatgcttcaa taatattgaa aaaggaagag tatgattgaa caagatggat tgcacgcagg   4620
ttctccggcc gcttgggtgg agaggctatt cggctatgac tgggcacaac agacaatcgg   4680
ctgctctgat gccgccgtgt tccggctgtc agcgcagggg cgcccggttc tttttgtcaa   4740
gaccgacctg tccggtgccc tgaatgaact gcaagacgag gcagcgcggc tatcgtggct   4800
ggccacgacg ggcgttcctt gcgcagctgt gctcgacgtt gtcactgaag cgggaaggga   4860
ctggctgcta ttgggcgaag tgccggggca ggatctcctg tcatctcacc ttgctcctgc   4920
cgagaaagta tccatcatgg ctgatgcaat gcggcggctg catacgcttg atccggctac   4980
ctgcccattc gaccaccaag cgaaacatcg catcgagcga gcacgtactc ggatggaagc   5040
cggtcttgtc gatcaggatg atctggacga agagcatcag gggctcgcgc cagccgaact   5100
gttcgccagg ctcaaggcga gcatgcccga cggcgaggat ctcgtcgtga cccatggcga   5160
tgcctgcttg ccgaatatca tggtggaaaa tggccgcttt tctggattca tcgactgtgg   5220
ccggctgggt gtggcggacc gctatcagga catagcgttg gctacccgtg atattgctga   5280
agagcttggc ggcgaatggg ctgaccgctt cctcgtgctt tacggtatcg ccgctcccga   5340
ttcgcagcgc atcgccttct atcgccttct tgacgagttc ttctgataac tgtcagacca   5400
agtttactca tatatacttt agattgattt aaaacttcat ttttaattta aaaggatcta   5460
ggtgaagatc ctttttgata atctcatgac caaaatccct taacgtgagt tttcgttcca   5520
ctgagcgtca gaccccgtag aaaagatcaa aggatcttct tgagatcctt tttttctgcg   5580
cgtaatctgc tgcttgcaaa caaaaaaacc accgctacca gcggtggttt gtttgccgga   5640
tcaagagcta ccaactcttt ttccgaaggt aactggcttc agcagagcgc agataccaaa   5700
tactgttctt ctagtgtagc cgtagttagg ccaccacttc aagaactctg tagcaccgcc   5760
tacatacctc gctctgctaa tcctgttacc agtggctgct gccagtggcg ataagtcgtg   5820
tcttaccggg ttggactcaa gacgatagtt accggataag gcgcagcggt cgggctgaac   5880
ggggggttcg tgcacacagc ccagcttgga gcgaacgacc tacaccgaac tgagatacct   5940
acagcgtgag ctatgagaaa gcgccacgct tcccgaaggg agaaaggcgg acaggtatcc   6000
ggtaagcggc agggtcggaa caggagagcg cacgagggag cttccagggg gaaacgcctg   6060
gtatctttat agtcctgtcg ggtttcgcca cctctgactt gagcgtcgat ttttgtgatg   6120
ctcgtcaggg gggcggagcc tatggaaaaa cgccagcaac gcggcctttt tacggttcct   6180
ggccttttgc tggccttttg ctcacatgtt ctttcctgcg ttatcccctg attctgtgga   6240
taaccgtatt accgcctttg agtgagctga taccgctcgc cgcagccgaa cgaccgagcg   6300
cagcgagtca gtgagcgagg aagcggaaga gcgcccaata cgcaaaccgc ctctccccgc   6360
gcgttggccg attcattaat gcagctggca cgacaggttt cccgactgga aagcgggcag   6420
tgagcgcaac gcaattaatg tgagttagct cactcattag gcaccccagg ctttacactt   6480
tatgcttccg gctcgtatgt tgtgtggaat tgtgagcgga taacaatttc acacaggaaa   6540
cagctatgac catgattacg ccagatttaa ttaaggcctt aattag                  6586
```

-continued

<210> SEQ ID NO 3
<211> LENGTH: 5973
<212> TYPE: DNA
<213> ORGANISM: Artificial Sequence
<220> FEATURE:
<223> OTHER INFORMATION: Synthetic

<400> SEQUENCE: 3
cttaattagg ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctaccag 180
ggtaatgggg atcctctaga actatagcta gtcgacattg attattgact agttattaat 240
agtaatcaat tacggggtca ttagttcata gcccatatat ggagttccgc gttacataac 300
ttacggtaaa tggcccgcct ggctgaccgc ccaacgaccc ccgcccattg acgtcaataa 360
tgacgtatgt tcccatagta acgccaatag ggactttcca ttgacgtcaa tgggtggagt 420
atttacggta aactgcccac ttggcagtac atcaagtgta tcatatgcca agtacgcccc 480
ctattgacgt caatgacggt aaatggcccg cctggcatta tgcccagtac atgaccttat 540
gggactttcc tacttggcag tacatctacg tattagtcat cgctattacc atgtcgaggc 600
cacgttctgc ttcactctcc ccatctcccc cccctcccca cccccaattt tgtatttatt 660 tatttttttaa ttattttgtg cagcgatggg ggcggggggg gggggcgcgc gccaggcggg 720
gcggggcggg gcgaggggcg gggcggggcg aggcggagag gtgcggcggc agccaatcag 780
agcggcgcgc tccgaaagtt tccttttatg gcgaggcggc ggcggcggcg gccctataaa 840
aagcgaagcg cgcggcgggc gggagcaagc tttcagatcg cctggagacg ccatccacgc 900
tgttttgacc tccatagaag acaccgggac cgatccagcc tccgcggccg ggaacggtgc 960
attggaacgc ggattccccg tgccaagagt gacgtaagta ccgcctatag agtctatagg 1020 cccacccccct tggcttctta tgcatgctat actgtttttg gcttggggtc tatacacccc 1080
cgcttcctca tgtttgctgc ccgtgaccag cacgtcaacg attttgtggg cacgggcgac 1140
accgcagtgt agtctgagca gtactcgttg ctgccgcgcg cgccaccaga cataatagct 1200
gacagactaa cagactgttc ctttccatgg gtcttttctg cagtcaccgt cgccgccacc 1260
ggtgaattcc gccaccatgg tcgatggagt gatgatcctg cctgtcctga ttatgattgc 1320
cctgcccagc cccagcatgg aagatgaaaa acctaaagtc aaccctaagc tgtatatgtg 1380
cgtgtgcgag ggcctgagct gcggaaacga ggatcactgc gagggccagc agtgtttcag 1440
ctccctgtcc atcaatgacg gcttccacgt gtaccagaag ggctgctttc aggtgtatga 1500
gcagggcaag atgacctgta agacaccacc ttccccagga caggcagtgg agtgctgtca 1560
gggcgattgg tgtaaccgga atatcaccgc ccagctgcca acaaagggca agtctttccc 1620
cggcacacag aactttcacc tggaagtggg cctgatcatc ctgagcgtgg tgttcgccgt 1680
gtgcctgctg gcatgtctgc tgggagtggc cctgagaaag tttaagcgga gaaaccagga 1740
gcggctgaat ccaagagatg tggagtacgg caccatcgag ggcctgatca ccacaaatgt 1800
gggcgactct acactggccg acctgctgga tcacagctgc accagcggct ccggatctgg 1860
cctgcccttt ctggtgcaga ggaccgtggc ccggcagatc accctgctgg agtgcgtggg 1920
caagggccgg tacggagaag tgtggagagg atcctggcag ggagagaacg tggcagtgaa 1980
gatcttctct agccgggatg agaagtcttg gtttagagag acagagctgt ataacacagt 2040
gatgctgagg cacgagaata tcctgggctt catcgcctcc gacatgacct ctcgccactc 2100

-continued

```
ctctacacag ctgtggctga tcacccacta ccacgagatg ggctccctgt acgattacct   2160

ccagctgacc acactggaca cagtgtcttg cctgcggatc gtgctgtcta tcgccagcgg   2220

cctggcacac ctgcacatcg agatctttgg aacccagggc aagccagcaa tcgcacacag   2280

agatctgaag tctaagaaca tcctggtgaa gaagaatggc cagtgctgta tcgccgatct   2340

gggcctggcc gtgatgcaca gccagtccac caaccagctg gacgtgggca acaatcctcg   2400

ggtgggcaca aagagataca tggccccaga ggtgctggat gagacaatcc aggtggactg   2460

cttcgatagc tataagaggg tggacatctg ggcctttggc ctggtgctgt gggaggtggc   2520

aaggaggatg gtgagcaacg gcatcgtgga ggactacaag ccacccttct atgacgtggt   2580

gcctaatgat ccatcctttg aggacatgcg caaggtggtg tgcgtggatc agcagaggcc   2640

caacatccct aatcgctggt tcagcgaccc caccctgaca tccctggcca agctgatgaa   2700

ggagtgttgg tatcagaatc ctagcgccag gctgaccgcc ctgcgcatca agaaaactct   2760

gactaaaatc gacaatagcc tggataaact gaaaaccgac tgctgacctg aggatccgat   2820

ctttttccct ctgccaaaaa ttatggggac atcatgaagc cccttgagca tctgacttct   2880

ggctaataaa ggaaatttat tttcattgca atagtgtgtt ggaatttttt gtgtctctca   2940

ctcggaagca attcgttgat ctgaatttcg accacccata atacccatta ccctggtaga   3000

taagtagcat ggcgggttaa tcattaacta caaggaaccc ctagtgatgg agttggccac   3060

tccctctctg cgcgctcgct cgctcactga ggccgggcga ccaaaggtcg cccgacgccc   3120

gggctttgcc cgggcggcct cagtgagcga gcgagcgcgc agccttaatt aacctaattc   3180

actggccgtc gttttacaac gtcgtgactg ggaaaaccct ggcgttaccc aacttaatcg   3240

ccttgcagca catccccctt tcgccagctg gcgtaatagc gaagaggccc gcaccgatcg   3300

cccttcccaa cagttgcgca gcctgaatgg cgaatgggac gcgccctgta gcggcgcatt   3360

aagcgcggcg ggtgtggtgg ttacgcgcag cgtgaccgct acacttgcca gcgccctagc   3420

gcccgctcct ttcgctttct tcccttcctt tctcgccacg ttcgccggct ttccccgtca   3480

agctctaaat cgggggctcc ctttagggtt ccgatttagt gctttacggc acctcgaccc   3540

caaaaaactt gattagggtg atggttcacg tagtgggcca tcgccctgat agacggtttt   3600

tcgccctttg acgttggagt ccacgttctt taatagtgga ctcttgttcc aaactggaac   3660

aacactcaac cctatctcgg tctattcttt tgatttataa gggattttgc cgatttcggc   3720

ctattggtta aaaaatgagc tgatttaaca aaaatttaac gcgaatttta acaaaatatt   3780

aacgcttaca atttaggtgg cacttttcgg ggaaatgtgc gcggaacccc tatttgttta   3840

tttttctaaa tacattcaaa tatgtatccg ctcatgagac aataaccctg ataaatgctt   3900

caataatatt gaaaaaggaa gagtatgagt attcaacatt tccgtgtcgc ccttattccc   3960

ttttttgcgg cattttgcct tcctgttttt gctcacccag aaacgctggt gaaagtaaaa   4020

gatgctgaag atcagttggg tgcacgagtg ggttacatcg aactggatct caacagcggt   4080

aagatccttg agagttttcg ccccgaagaa cgttttccaa tgatgagcac ttttaaagtt   4140

ctgctatgtg gcgcggtatt atcccgtatt gacgccgggc aagagcaact cggtcgccgc   4200

atacactatt ctcagaatga cttggttgag tactcaccag tcacagaaaa gcatcttacg   4260

gatggcatga cagtaagaga attatgcagt gctgccataa ccatgagtga taacactgcg   4320

gccaacttac ttctgacaac gatcggagga ccgaaggagc taaccgcttt tttgcacaac   4380

atgggggatc atgtaactcg ccttgatcgt tgggaaccgg agctgaatga agccatacca   4440

aacgacgagc gtgacaccac gatgcctgta gcaatggcaa caacgttgcg caaactatta   4500
```

actggcgaac tacttactct agcttcccgg caacaattaa tagactggat ggaggcggat 4560
aaagttgcag gaccacttct gcgctcggcc cttccggctg gctggtttat tgctgataaa 4620
tctggagccg gtgagcgtgg gtctcgcggt atcattgcag cactggggcc agatggtaag 4680
ccctcccgta tcgtagttat ctacacgacg gggagtcagg caactatgga tgaacgaaat 4740
agacagatcg ctgagatagg tgcctcactg attaagcatt ggtaactgtc agaccaagtt 4800
tactcatata tactttagat tgatttaaaa cttcattttt aatttaaaag gatctaggtg 4860
aagatccttt ttgataatct catgaccaaa atcccttaac gtgagttttc gttccactga 4920
gcgtcagacc ccgtagaaaa gatcaaagga tcttcttgag atcctttttt tctgcgcgta 4980
atctgctgct tgcaaacaaa aaaaccaccg ctaccagcgg tggtttgttt gccggatcaa 5040
gagctaccaa ctctttttcc gaaggtaact ggcttcagca gagcgcagat accaaatact 5100
gttcttctag tgtagccgta gttaggccac cacttcaaga actctgtagc accgcctaca 5160
tacctcgctc tgctaatcct gttaccagtg gctgctgcca gtggcgataa gtcgtgtctt 5220
accgggttgg actcaagacg atagttaccg gataaggcgc agcggtcggg ctgaacgggg 5280
ggttcgtgca cacagcccag cttggagcga acgacctaca ccgaactgag atacctacag 5340
cgtgagctat gagaaagcgc cacgcttccc gaagggagaa aggcggacag gtatccggta 5400
agcggcaggg tcggaacagg agagcgcacg agggagcttc cagggggaaa cgcctggtat 5460
ctttatagtc ctgtcgggtt tcgccacctc tgacttgagc gtcgattttt gtgatgctcg 5520
tcaggggggc ggagcctatg gaaaaacgcc agcaacgcgg cctttttacg gttcctggcc 5580
ttttgctggc cttttgctca catgttcttt cctgcgttat cccctgattc tgtggataac 5640
cgtattaccg cctttgagtg agctgatacc gctcgccgca gccgaacgac cgagcgcagc 5700
gagtcagtga gcgaggaagc ggaagagcgc ccaatacgca aaccgcctct ccccgcgcgt 5760
tggccgattc attaatgcag ctggcacgac aggtttcccg actggaaagc gggcagtgag 5820
cgcaacgcaa ttaatgtgag ttagctcact cattaggcac cccaggcttt acactttatg 5880
cttccggctc gtatgttgtg tggaattgtg agcggataac aatttcacac aggaaacagc 5940
tatgaccatg attacgccag atttaattaa ggc 5973

<210> SEQ ID NO 4
<211> LENGTH: 5814
<212> TYPE: DNA
<213> ORGANISM: Artificial Sequence
<220> FEATURE:
<223> OTHER INFORMATION: Synthetic

<400> SEQUENCE: 4
cttaattagg ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctaccag 180
ggtaatgggg atcctctaga actatagcta gtcgacattg attattgact agttattaat 240
agtaatcaat tacggggtca ttagttcata gcccatatat ggagttccgc gttacataac 300
ttacggtaaa tggcccgcct ggctgaccgc ccaacgaccc ccgcccattg acgtcaataa 360
tgacgtatgt tcccatagta acgccaatag ggactttcca ttgacgtcaa tgggtggagt 420
atttacggta aactgcccac ttggcagtac atcaagtgta tcatatgcca agtacgcccc 480
ctattgacgt caatgacggt aaatggcccg cctggcatta tgcccagtac atgaccttat 540

-continued

```
gggactttcc tacttggcag tacatctacg tattagtcat cgctattacc atgtcgaggc    600
cacgttctgc ttcactctcc ccatctcccc cccctcccca cccccaattt tgtatttatt    660
tatttttttaa ttattttgtg cagcgatggg ggcggggggg gggggcgcgc gccaggcggg    720
gcggggcggg gcgaggggcg gggcggggcg aggcggagag gtgcggcggc agccaatcag    780
agcggcgcgc tccgaaagtt tccttttatg gcgaggcggc ggcggcggcg gccctataaa    840
aagcgaagcg cgcggcgggc gggagcacca ccgcggtggc ggccctagag tcgatcgagg    900
aactgaaaaa ccagaaagtt aactggtaag tttagtcttt ttgtctttta tttcaggtcc    960
cggatccggt ggtggtgcaa atcaaagaac tgctcctcag tggatgttgc ctttacttct   1020
aggcctgtac ggaagtgtta cttctgctct aaaagctgcg gaattgtacc cgcggccgat   1080
ccaccggtga attccgccac catggtcgat ggagtgatga tcctgcctgt cctgattatg   1140
attgccctgc ccagccccag catggaagat gaaaaaccta aagtcaaccc taagctgtat   1200
atgtgcgtgt gcgagggcct gagctgcgga aacgaggatc actgcgaggg ccagcagtgt   1260
ttcagctccc tgtccatcaa tgacggcttc cacgtgtacc agaagggctg ctttcaggtg   1320
tatgagcagg gcaagatgac ctgtaagaca ccaccttccc caggacaggc agtggagtgc   1380
tgtcagggcg attggtgtaa ccggaatatc accgcccagc tgccaacaaa gggcaagtct   1440
ttccccggca cacagaactt tcacctggaa gtgggcctga tcatcctgag cgtggtgttc   1500
gccgtgtgcc tgctggcatg tctgctggga gtggccctga gaaagtttaa gcggagaaac   1560
caggagcggc tgaatccaag agatgtggag tacggcacca tcgagggcct gatcaccaca   1620
aatgtgggcg actctacact ggccgacctg ctggatcaca gctgcaccag cggctccgga   1680
tctggcctgc cctttctggt gcagaggacc gtggcccggc agatcaccct gctggagtgc   1740
gtgggcaagg gccggtacgg agaagtgtgg agaggatcct ggcagggaga gaacgtggca   1800
gtgaagatct tctctagccg ggatgagaag tcttggttta gagagacaga gctgtataac   1860
acagtgatgc tgaggcacga gaatatcctg ggcttcatcg cctccgacat gacctctcgc   1920
cactcctcta cacagctgtg gctgatcacc cactaccacg agatgggctc cctgtacgat   1980
tacctccagc tgaccacact ggacacagtg tcttgcctgc ggatcgtgct gtctatcgcc   2040
agcggcctgg cacacctgca catcgagatc tttggaaccc agggcaagcc agcaatcgca   2100
cacagagatc tgaagtctaa gaacatcctg gtgaagaaga atggccagtg ctgtatcgcc   2160
gatctgggcc tggccgtgat gcacagccag tccaccaacc agctggacgt gggcaacaat   2220
cctcgggtgg gcacaaagag atacatggcc ccagaggtgc tggatgagac aatccaggtg   2280
gactgcttcg atagctataa gagggtggac atctgggcct ttggcctggt gctgtgggag   2340
gtggcaagga ggatggtgag caacggcatc gtggaggact acaagccacc cttctatgac   2400
gtggtgccta atgatccatc ctttgaggac atgcgcaagg tggtgtgcgt ggatcagcag   2460
aggcccaaca tccctaatcg ctggttcagc gaccccaccc tgacatccct ggccaagctg   2520
atgaaggagt gttggtatca gaatcctagc gccaggctga ccgccctgcg catcaagaaa   2580
actctgacta aaatcgacaa tagcctggat aaactgaaaa ccgactgctg acctgagggc   2640
ggccgcgtcg acggatccga tctttttccc tctgccaaaa attatgggga catcatgaag   2700
ccccttgagc atctgacttc tggctaataa aggaaattta ttttcattgc aatagtgtgt   2760
tggaattttt tgtgtctctc actcggaagc aattcgttga tctgaatttc gaccacccat   2820
aatacccatt accctggtag ataagtagca tggcgggtta atcattaact acaaggaacc   2880
cctagtgatg gagttggcca ctccctctct gcgcgctcgc tcgctcactg aggccgggcg   2940
```

accaaaggtc gcccgacgcc cgggctttgc ccgggcggcc tcagtgagcg agcgagcgcg 3000
cagccttaat taacctaatt cactggccgt cgttttacaa cgtcgtgact gggaaaaccc 3060
tggcgttacc caacttaatc gccttgcagc acatccccct ttcgccagct ggcgtaatag 3120
cgaagaggcc cgcaccgatc gcccttccca acagttgcgc agcctgaatg gcgaatggga 3180
cgcgccctgt agcggcgcat taagcgcggc gggtgtggtg gttacgcgca gcgtgaccgc 3240
tacacttgcc agcgccctag cgcccgctcc tttcgctttc ttcccttcct ttctcgccac 3300
gttcgccggc tttccccgtc aagctctaaa tcgggggctc cctttagggt tccgatttag 3360
tgctttacgg cacctcgacc ccaaaaaact tgattagggt gatggttcac gtagtgggcc 3420
atcgccctga tagacggttt ttcgcccttt gacgttggag tccacgttct ttaatagtgg 3480
actcttgttc caaactggaa caacactcaa ccctatctcg gtctattctt ttgatttata 3540
agggattttg ccgatttcgg cctattggtt aaaaaatgag ctgatttaac aaaaatttaa 3600
cgcgaatttt aacaaaatat taacgcttac aatttaggtg gcacttttcg gggaaatgtg 3660
cgcggaaccc ctatttgttt atttttctaa atacattcaa atatgtatcc gctcatgaga 3720
caataaccct gataaatgct tcaataatat tgaaaaagga agagtatgag tattcaacat 3780
ttccgtgtcg cccttattcc cttttttgcg gcattttgcc ttcctgtttt tgctcaccca 3840
gaaacgctgg tgaaagtaaa agatgctgaa gatcagttgg gtgcacgagt gggttacatc 3900
gaactggatc tcaacagcgg taagatcctt gagagttttc gccccgaaga acgttttcca 3960
atgatgagca cttttaaagt tctgctatgt ggcgcggtat tatcccgtat tgacgccggg 4020
caagagcaac tcggtcgccg catacactat tctcagaatg acttggttga gtactcacca 4080
gtcacagaaa agcatcttac ggatggcatg acagtaagag aattatgcag tgctgccata 4140
accatgagtg ataacactgc ggccaactta cttctgacaa cgatcggagg accgaaggag 4200
ctaaccgctt ttttgcacaa catgggggat catgtaactc gccttgatcg ttgggaaccg 4260
gagctgaatg aagccatacc aaacgacgag cgtgacacca cgatgcctgt agcaatggca 4320
acaacgttgc gcaaactatt aactggcgaa ctacttactc tagcttcccg gcaacaatta 4380
atagactgga tggaggcgga taaagttgca ggaccacttc tgcgctcggc ccttccggct 4440
ggctggttta ttgctgataa atctggagcc ggtgagcgtg ggtctcgcgg tatcattgca 4500
gcactggggc cagatggtaa gccctcccgt atcgtagtta tctacacgac ggggagtcag 4560
gcaactatgg atgaacgaaa tagacagatc gctgagatag gtgcctcact gattaagcat 4620
tggtaactgt cagaccaagt ttactcatat atactttaga ttgatttaaa acttcatttt 4680
taatttaaaa ggatctaggt gaagatcctt tttgataatc tcatgaccaa aatcccttaa 4740
cgtgagtttt cgttccactg agcgtcagac cccgtagaaa agatcaaagg atcttcttga 4800
gatccttttt ttctgcgcgt aatctgctgc ttgcaaacaa aaaaaccacc gctaccagcg 4860
gtggtttgtt tgccggatca agagctacca actctttttc cgaaggtaac tggcttcagc 4920
agagcgcaga taccaaatac tgttcttcta gtgtagccgt agttaggcca ccacttcaag 4980
aactctgtag caccgcctac atacctcgct ctgctaatcc tgttaccagt ggctgctgcc 5040
agtggcgata agtcgtgtct taccgggttg gactcaagac gatagttacc ggataaggcg 5100
cagcggtcgg gctgaacggg gggttcgtgc acacagccca gcttggagcg aacgacctac 5160
accgaactga gatacctaca gcgtgagcta tgagaaagcg ccacgcttcc cgaagggaga 5220
aaggcggaca ggtatccggt aagcggcagg gtcggaacag gagagcgcac gagggagctt 5280
ccagggggaa acgcctggta tctttatagt cctgtcgggt ttcgccacct ctgacttgag 5340
cgtcgatttt tgtgatgctc gtcagggggg cggagcctat ggaaaaacgc cagcaacgcg 5400
gcctttttac ggttcctggc cttttgctgg ccttttgctc acatgttctt tcctgcgtta 5460
tcccctgatt ctgtggataa ccgtattacc gcctttgagt gagctgatac cgctcgccgc 5520
agccgaacga ccgagcgcag cgagtcagtg agcgaggaag cggaagagcg cccaatacgc 5580
aaaccgcctc tccccgcgcg ttggccgatt cattaatgca gctggcacga caggtttccc 5640
gactggaaag cgggcagtga gcgcaacgca attaatgtga gttagctcac tcattaggca 5700
ccccaggctt tacactttat gcttccggct cgtatgttgt gtggaattgt gagcggataa 5760
caatttcaca caggaaacag ctatgaccat gattacgcca gatttaatta aggc 5814

<210> SEQ ID NO 5
<211> LENGTH: 318
<212> TYPE: DNA
<213> ORGANISM: Artificial Sequence
<220> FEATURE:
<223> OTHER INFORMATION: Synthetic

<400> SEQUENCE: 5
gtcttttatt tcaggtccca gatctagggc tctgcgtttg ctccaggtag tccgctgctc 60
ccttgggcct gggcccactg acagccctgg tgcctctggc cggctgcaca cctcctggcg 120
ggcagctgtg agtgtaatct ggtgagccac ttgttctggc aatacctgag tggctctgcg 180
gattacactc acggaggcct gccctgactg cccacggtgc cgtggccaaa gaggatctaa 240
gggcaccgct gagggcctac ctaaccatcg tggggaataa ggacagtgtc acccctgcag 300
gggatccggt ggtggtgc 318

<210> SEQ ID NO 6
<211> LENGTH: 269
<212> TYPE: DNA
<213> ORGANISM: Artificial Sequence
<220> FEATURE:
<223> OTHER INFORMATION: Synthetic

<400> SEQUENCE: 6
agggctctgc gtttgctcca ggtagtccgc tgctcccttg ggcctgggcc cactgacagc 60
cctggtgcct ctggccggct gcacacctcc tggcgggcag ctgtgagtgt aagctggtga 120
gccacttgtt ctggcaatac ctgagtggct ctgcggctta cactcacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 7
<211> LENGTH: 48
<212> TYPE: DNA
<213> ORGANISM: Homo sapiens

<400> SEQUENCE: 7
tcgagggtac aaagaacagt ggctcgccag attacactgt tggagtgc 48

<210> SEQ ID NO 8
<211> LENGTH: 48
<212> TYPE: DNA
<213> ORGANISM: Artificial Sequence
<220> FEATURE:
<223> OTHER INFORMATION: Synthetic

<400> SEQUENCE: 8
tcgagggtac aaagaacagt ggctcaccag attacactgt tggagtgc 48

<210> SEQ ID NO 9
<211> LENGTH: 48
<212> TYPE: DNA
<213> ORGANISM: Artificial Sequence
<220> FEATURE:
<223> OTHER INFORMATION: Synthetic

<400> SEQUENCE: 9
tcgagggtgc agaggaccgt ggcccggcag atcaccctgc tggagtgc 48

<210> SEQ ID NO 10
<211> LENGTH: 5203
<212> TYPE: DNA
<213> ORGANISM: Artificial Sequence
<220> FEATURE:
<223> OTHER INFORMATION: Synthetic

<400> SEQUENCE: 10
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt cggtacaatt cacgcgtcga cattgattat tgactagctc tggtcgttac 180
ataacttacg gtaaatggcc cgcctggctg accgcccaac gacccccgcc cattgacgtc 240
aataatgacg tatgttccca tagtaacgcc aatagggact ttccattgac gtcaatgggt 300
ggagtattta cggtaaactg cccacttggc agtacatcaa gtgtatcata tgccaagtac 360
gccccctatt gacgtcaatg acggtaaatg gcccgcctgg cattatgccc agtacatgac 420
cttatgggac tttcctactt ggcagtacat ctactcgagg ccacgttctg cttcactctc 480
cccatctccc ccccctcccc acccccaatt ttgtatttat ttatttttta attattttgt 540
gcagcgatgg gggcgggggg gggggggggg cgcgcgccag gcggggcggg gcggggcgag 600
gggcggggcg gggcgaggcg gagaggtgcg gcggcagcca atcagagcgg cgcgctccga 660
aagtttcctt ttatggcgag gcggcggcgg cggcggccct ataaaaagcg aagcgcgcgg 720
cgggcgggag cgggatcagc caccgcggtg gcggcctaga gtcgacgagg aactgaaaaa 780
ccagaaagtt aactggtaag tttagtcttt ttgtctttta tttcaggtcc cagatctagg 840
gctctgcgtt tgctccaggt agtccgctgc tcccttgggc ctgggcccac tgacagccct 900
ggtgcctctg gccggctgca cacctcctgg cgggcagctg tgagtgtaat ctggtgagcc 960
acttgttctg gcaatacctg agtggctctg cggattacac tcacggaggc ctgccctgac 1020
tgcccacggt gccgtggcca aagaggatct aagggcaccg ctgagggcct acctaaccat 1080
cgtggggaat aaggacagtg tcacccctgc aggggatccg gtggtggtgc aaatcaaaga 1140
actgctcctc agtggatgtt gcctttactt ctaggcctgt acggaagtgt tacttctgct 1200
ctaaaagctg cggaattgta cccgcggccg atccaccggt cgccaccatg gtgagcaagg 1260
gcgaggagct gttcaccggg gtggtgccca tcctggtcga gctggacggc gacgtaaacg 1320
gccacaagtt cagcgtgtcc ggcgagggcg agggcgatgc cacctacggc aagctgaccc 1380
tgaagttcat ctgcaccacc ggcaagctgc ccgtgccctg gcccaccctc gtgaccaccc 1440
tgacctacgg cgtgcagtgc ttcagccgct accccgacca catgaagcag cacgacttct 1500
tcaagtccgc catgcccgaa ggctacgtcc aggagcgcac catcttcttc aaggacgacg 1560
gcaactacaa gacccgcgcc gaggtgaagt tcgagggcga caccctggtg aaccgcatcg 1620

-continued

```
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
aagatccttg agagttttcg ccccgaagaa cgttttccaa tgatgagcac ttttaaagtt   3360
ctgctatgtg gcgcggtatt atcccgtatt gacgccgggc aagagcaact cggtcgccgc   3420
atacactatt ctcagaatga cttggttgag tactcaccag tcacagaaaa gcatcttacg   3480
gatggcatga cagtaagaga attatgcagt gctgccataa ccatgagtga taacactgcg   3540
gccaacttac ttctgacaac gatcggagga ccgaaggagc taaccgcttt tttgcacaac   3600
atgggggatc atgtaactcg ccttgatcgt tgggaaccgg agctgaatga agccatacca   3660
aacgacgagc gtgacaccac gatgcctgta gcaatggcaa caacgttgcg caaactatta   3720
actggcgaac tacttactct agcttcccgg caacaattaa tagactggat ggaggcggat   3780
aaagttgcag gaccacttct gcgctcggcc cttccggctg gctggtttat tgctgataaa   3840
tctggagccg gtgagcgtgg gtctcgcggt atcattgcag cactggggcc agatggtaag   3900
ccctcccgta tcgtagttat ctacacgacg gggagtcagg caactatgga tgaacgaaat   3960
agacagatcg ctgagatagg tgcctcactg attaagcatt ggtaactgtc agaccaagtt   4020
```

tactcatata tactttagat tgatttaaaa cttcattttt aatttaaaag gatctaggtg 4080
aagatccttt ttgataatct catgaccaaa atcccttaac gtgagttttc gttccactga 4140
gcgtcagacc ccgtagaaaa gatcaaagga tcttcttgag atcctttttt tctgcgcgta 4200
atctgctgct tgcaaacaaa aaaaccaccg ctaccagcgg tggtttgttt gccggatcaa 4260
gagctaccaa ctctttttcc gaaggtaact ggcttcagca gagcgcagat accaaatact 4320
gttcttctag tgtagccgta gttaggccac cacttcaaga actctgtagc accgcctaca 4380
tacctcgctc tgctaatcct gttaccagtg gctgctgcca gtggcgataa gtcgtgtctt 4440
accgggttgg actcaagacg atagttaccg gataaggcgc agcggtcggg ctgaacgggg 4500
ggttcgtgca cacagcccag cttggagcga acgacctaca ccgaactgag atacctacag 4560
cgtgagctat gagaaagcgc cacgcttccc gaagggagaa aggcggacag gtatccggta 4620
agcggcaggg tcggaacagg agagcgcacg agggagcttc cagggggaaa cgcctggtat 4680
ctttatagtc ctgtcgggtt tcgccacctc tgacttgagc gtcgattttt gtgatgctcg 4740
tcaggggggc ggagcctatg gaaaaacgcc agcaacgcgg cctttttacg gttcctggcc 4800
ttttgctggc cttttgctca catgttcttt cctgcgttat cccctgattc tgtggataac 4860
cgtattaccg cctttgagtg agctgatacc gctcgccgca gccgaacgac cgagcgcagc 4920
gagtcagtga gcgaggaagc ggaagagcgc ccaatacgca aaccgcctct ccccgcgcgt 4980
tggccgattc attaatgcag ctggcacgac aggtttcccg actggaaagc gggcagtgag 5040
cgcaacgcaa ttaatgtgag ttagctcact cattaggcac cccaggcttt acactttatg 5100
cttccggctc gtatgttgtg tggaattgtg agcggataac aatttcacac aggaaacagc 5160
tatgaccatg attacgccag atttaattaa ggccttaatt agg 5203

<210> SEQ ID NO 11
<211> LENGTH: 5203
<212> TYPE: DNA
<213> ORGANISM: Artificial Sequence
<220> FEATURE:
<223> OTHER INFORMATION: Synthetic

<400> SEQUENCE: 11
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt cggtacaatt cacgcgtcga cattgattat tgactagctc tggtcgttac 180
ataacttacg gtaaatggcc cgcctggctg accgcccaac gacccccgcc cattgacgtc 240
aataatgacg tatgttccca tagtaacgcc aatagggact ttccattgac gtcaatgggt 300
ggagtattta cggtaaactg cccacttggc agtacatcaa gtgtatcata tgccaagtac 360
gccccctatt gacgtcaatg acggtaaatg gcccgcctgg cattatgccc agtacatgac 420
cttatgggac tttcctactt ggcagtacat ctactcgagg ccacgttctg cttcactctc 480
cccatctccc ccccctcccc acccccaatt ttgtatttat ttatttttta attattttgt 540
gcagcgatgg gggcgggggg gggggggggg cgcgcgccag gcggggcggg gcggggcgag 600
gggcggggcg gggcgaggcg gagaggtgcg gcggcagcca atcagagcgg cgcgctccga 660
aagtttcctt ttatggcgag gcggcggcgg cggcggccct ataaaaagcg aagcgcgcgg 720
cgggcgggag cgggatcagc caccgcggtg gcggcctaga gtcgacgagg aactgaaaaa 780
ccagaaagtt aactggtaag tttagtcttt ttgtctttta tttcaggtcc cagatctagg 840

-continued gctctgcgtt tgctccaggt agtccgctgc tcccttgggc ctgggcccac tgacagccct 900
ggtgcctctg gccggctgca cacctcctgg cgggcagctg tgagtgtaag ctggtgagcc 960
acttgttctg gcaatacctg agtggctctg cggcttacac tcacggaggc ctgccctgac 1020
tgcccacggt gccgtggcca aagaggatct aagggcaccg ctgagggcct acctaaccat 1080
cgtggggaat aaggacagtg tcacccctgc aggggatccg gtggtggtgc aaatcaaaga 1140
actgctcctc agtggatgtt gcctttactt ctaggcctgt acggaagtgt tacttctgct 1200
ctaaaagctg cggaattgta cccgcggccg atccaccggt cgccaccatg gtgagcaagg 1260
gcgaggagct gttcaccggg gtggtgccca tcctggtcga gctggacggc gacgtaaacg 1320
gccacaagtt cagcgtgtcc ggcgagggcg agggcgatgc cacctacggc aagctgaccc 1380
tgaagttcat ctgcaccacc ggcaagctgc ccgtgccctg gcccaccctc gtgaccaccc 1440
tgacctacgg cgtgcagtgc ttcagccgct accccgacca catgaagcag cacgacttct 1500
tcaagtccgc catgcccgaa ggctacgtcc aggagcgcac catcttcttc aaggacgacg 1560
gcaactacaa gacccgcgcc gaggtgaagt tcgagggcga caccctggtg aaccgcatcg 1620
agctgaaggg catcgacttc aaggaggacg gcaacatcct ggggcacaag ctggagtaca 1680
actacaacag ccacaacgtc tatatcatgg ccgacaagca gaagaacggc atcaaggtga 1740
acttcaagat ccgccacaac atcgaggacg gcagcgtgca gctcgccgac cactaccagc 1800
agaacacccc catcggcgac ggccccgtgc tgctgcccga caaccactac ctgagcaccc 1860
agtccgccct gagcaaagac cccaacgaga agcgcgatca catggtcctg ctggagttcg 1920
tgaccgccgc cgggatcact ctcggcatgg acgagctgta caagtaaagc ggccatcaag 1980
cttatcgata ccgtcgacta gagctcgctg atcagcctcg actgtgcctt ctagttgcca 2040
gccatctgtt gtttgcccct cccccgtgcc ttccttgacc ctggaaggtg ccactcccac 2100
tgtcctttcc taataaaatg aggaaattgc atcgcattgt ctgagtaggt gtcattctat 2160
tctggggggt ggggtggggc aggacagcaa gggggaggat tgggaagaca attaggtaga 2220
taagtagcat ggcgggttaa tcattaacta caaggaaccc ctagtgatgg agttggccac 2280
tccctctctg cgcgctcgct cgctcactga ggccgggcga ccaaaggtcg cccgacgccc 2340
gggctttgcc cgggcggcct cagtgagcga gcgagcgcgc agccttaatt aacctaattc 2400
actggccgtc gttttacaac gtcgtgactg ggaaaaccct ggcgttaccc aacttaatcg 2460
ccttgcagca catccccctt tcgccagctg gcgtaatagc gaagaggccc gcaccgatcg 2520
cccttcccaa cagttgcgca gcctgaatgg cgaatgggac gcgccctgta gcggcgcatt 2580
aagcgcggcg ggtgtggtgg ttacgcgcag cgtgaccgct acacttgcca gcgccctagc 2640
gcccgctcct ttcgctttct tcccttcctt tctcgccacg ttcgccggct ttccccgtca 2700
agctctaaat cgggggctcc ctttagggtt ccgatttagt gctttacggc acctcgaccc 2760
caaaaaactt gattagggtg atggttcacg tagtgggcca tcgccctgat agacggtttt 2820
tcgccctttg acgttggagt ccacgttctt taatagtgga ctcttgttcc aaactggaac 2880
aacactcaac cctatctcgg tctattcttt tgatttataa gggattttgc cgatttcggc 2940
ctattggtta aaaaatgagc tgatttaaca aaaatttaac gcgaatttta acaaaatatt 3000
aacgcttaca atttaggtgg cacttttcgg ggaaatgtgc gcggaacccc tatttgttta 3060
tttttctaaa tacattcaaa tatgtatccg ctcatgagac aataaccctg ataaatgctt 3120
caataatatt gaaaaaggaa gagtatgagt attcaacatt tccgtgtcgc ccttattccc 3180
ttttttgcgg cattttgcct tcctgttttt gctcacccag aaacgctggt gaaagtaaaa 3240

-continued gatgctgaag atcagttggg tgcacgagtg ggttacatcg aactggatct caacagcggt 3300
aagatccttg agagttttcg ccccgaagaa cgttttccaa tgatgagcac ttttaaagtt 3360
ctgctatgtg gcgcggtatt atcccgtatt gacgccgggc aagagcaact cggtcgccgc 3420
atacactatt ctcagaatga cttggttgag tactcaccag tcacagaaaa gcatcttacg 3480
gatggcatga cagtaagaga attatgcagt gctgccataa ccatgagtga taacactgcg 3540
gccaacttac ttctgacaac gatcggagga ccgaaggagc taaccgcttt tttgcacaac 3600
atgggggatc atgtaactcg ccttgatcgt tgggaaccgg agctgaatga agccatacca 3660
aacgacgagc gtgacaccac gatgcctgta gcaatggcaa caacgttgcg caaactatta 3720
actggcgaac tacttactct agcttcccgg caacaattaa tagactggat ggaggcggat 3780
aaagttgcag gaccacttct gcgctcggcc cttccggctg gctggtttat tgctgataaa 3840
tctggagccg gtgagcgtgg gtctcgcggt atcattgcag cactggggcc agatggtaag 3900
ccctcccgta tcgtagttat ctacacgacg gggagtcagg caactatgga tgaacgaaat 3960
agacagatcg ctgagatagg tgcctcactg attaagcatt ggtaactgtc agaccaagtt 4020
tactcatata tactttagat tgatttaaaa cttcattttt aatttaaaag gatctaggtg 4080
aagatccttt ttgataatct catgaccaaa atcccttaac gtgagttttc gttccactga 4140
gcgtcagacc ccgtagaaaa gatcaaagga tcttcttgag atcctttttt tctgcgcgta 4200
atctgctgct tgcaaacaaa aaaaccaccg ctaccagcgg tggtttgttt gccggatcaa 4260
gagctaccaa ctctttttcc gaaggtaact ggcttcagca gagcgcagat accaaatact 4320
gttcttctag tgtagccgta gttaggccac cacttcaaga actctgtagc accgcctaca 4380
tacctcgctc tgctaatcct gttaccagtg gctgctgcca gtggcgataa gtcgtgtctt 4440
accgggttgg actcaagacg atagttaccg gataaggcgc agcggtcggg ctgaacgggg 4500
ggttcgtgca cacagcccag cttggagcga acgacctaca ccgaactgag atacctacag 4560
cgtgagctat gagaaagcgc cacgcttccc gaagggagaa aggcggacag gtatccggta 4620
agcggcaggg tcggaacagg agagcgcacg agggagcttc caggggggaaa cgcctggtat 4680 ctttatagtc ctgtcgggtt tcgccacctc tgacttgagc gtcgattttt gtgatgctcg 4740
tcaggggggc ggagcctatg gaaaaacgcc agcaacgcgg cctttttacg gttcctggcc 4800
ttttgctggc cttttgctca catgttcttt cctgcgttat cccctgattc tgtggataac 4860
cgtattaccg cctttgagtg agctgatacc gctcgccgca gccgaacgac cgagcgcagc 4920
gagtcagtga gcgaggaagc ggaagagcgc ccaatacgca aaccgcctct ccccgcgcgt 4980
tggccgattc attaatgcag ctggcacgac aggtttcccg actggaaagc gggcagtgag 5040
cgcaacgcaa ttaatgtgag ttagctcact cattaggcac cccaggcttt acactttatg 5100
cttccggctc gtatgttgtg tggaattgtg agcggataac aatttcacac aggaaacagc 5160
tatgaccatg attacgccag atttaattaa ggccttaatt agg 5203

<210> SEQ ID NO 12
<211> LENGTH: 5203
<212> TYPE: DNA
<213> ORGANISM: Artificial Sequence
<220> FEATURE:
<223> OTHER INFORMATION: Synthetic

<400> SEQUENCE: 12
ctgcgcgctc gctcgctcac tgaggccgcc cgggcaaagc ccgggcgtcg ggcgaccttt 60

-continued

```
ggtcgcccgg cctcagtgag cgagcgagcg cgcagagagg gagtgtagcc atgctctagg    120
aagatcaatt cggtacaatt cacgcgtcga cattgattat tgactagctc tggtcgttac    180
ataacttacg gtaaatggcc cgcctggctg accgcccaac gacccccgcc cattgacgtc    240
aataatgacg tatgttccca tagtaacgcc aatagggact ttccattgac gtcaatgggt    300
ggagtattta cggtaaactg cccacttggc agtacatcaa gtgtatcata tgccaagtac    360
gccccctatt gacgtcaatg acggtaaatg gcccgcctgg cattatgccc agtacatgac    420
cttatgggac tttcctactt ggcagtacat ctactcgagg ccacgttctg cttcactctc    480
cccatctccc ccccctcccc acccccaatt ttgtatttat ttatttttta attattttgt    540
gcagcgatgg gggcgggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggcctaga gtcgacgagg aactgaaaaa    780
ccagaaagtt aactggtaag tttagtcttt ttgtctttta tttcaggtcc cagatctagg    840
gctctgcgtt tgctccaggt agtccgctgc tcccttgggc ctgggcccac tgacagccct    900
ggtgcctctg gccggctgca cacctcctgg cgggcagctg tggtgtaatc tggtgagcca    960
ctgtgttctg gcaatacctg cagtggctgt ctagattaca ccacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
```

-continued ccttgcagca catcccccctt tcgccagctg gcgtaatagc gaagaggccc gcaccgatcg 2520
cccttcccaa cagttgcgca gcctgaatgg cgaatgggac gcgccctgta gcggcgcatt 2580
aagcgcggcg ggtgtggtgg ttacgcgcag cgtgaccgct acacttgcca gcgccctagc 2640
gcccgctcct ttcgctttct tcccttcctt tctcgccacg ttcgccggct ttccccgtca 2700
agctctaaat cgggggctcc ctttagggtt ccgatttagt gctttacggc acctcgaccc 2760
caaaaaactt gattagggtg atggttcacg tagtgggcca tcgccctgat agacggtttt 2820
tcgccctttg acgttggagt ccacgttctt taatagtgga ctcttgttcc aaactggaac 2880
aacactcaac cctatctcgg tctattcttt tgatttataa gggattttgc cgatttcggc 2940
ctattggtta aaaaatgagc tgatttaaca aaaatttaac gcgaatttta acaaaatatt 3000
aacgcttaca atttaggtgg cacttttcgg ggaaatgtgc gcggaacccc tatttgttta 3060
tttttctaaa tacattcaaa tatgtatccg ctcatgagac aataaccctg ataaatgctt 3120
caataatatt gaaaaaggaa gagtatgagt attcaacatt tccgtgtcgc ccttattccc 3180
ttttttgcgg cattttgcct tcctgttttt gctcacccag aaacgctggt gaaagtaaaa 3240
gatgctgaag atcagttggg tgcacgagtg ggttacatcg aactggatct caacagcggt 3300
aagatccttg agagttttcg ccccgaagaa cgttttccaa tgatgagcac ttttaaagtt 3360
ctgctatgtg gcgcggtatt atcccgtatt gacgccgggc aagagcaact cggtcgccgc 3420
atacactatt ctcagaatga cttggttgag tactcaccag tcacagaaaa gcatcttacg 3480
gatggcatga cagtaagaga attatgcagt gctgccataa ccatgagtga taacactgcg 3540
gccaacttac ttctgacaac gatcggagga ccgaaggagc taaccgcttt tttgcacaac 3600
atgggggatc atgtaactcg ccttgatcgt tgggaaccgg agctgaatga agccatacca 3660
aacgacgagc gtgacaccac gatgcctgta gcaatggcaa caacgttgcg caaactatta 3720
actggcgaac tacttactct agcttcccgg caacaattaa tagactggat ggaggcggat 3780
aaagttgcag gaccacttct gcgctcggcc cttccggctg gctggtttat tgctgataaa 3840
tctggagccg gtgagcgtgg gtctcgcggt atcattgcag cactggggcc agatggtaag 3900
ccctcccgta tcgtagttat ctacacgacg gggagtcagg caactatgga tgaacgaaat 3960
agacagatcg ctgagatagg tgcctcactg attaagcatt ggtaactgtc agaccaagtt 4020
tactcatata tactttagat tgatttaaaa cttcattttt aatttaaaag gatctaggtg 4080
aagatccttt ttgataatct catgaccaaa atcccttaac gtgagttttc gttccactga 4140
gcgtcagacc ccgtagaaaa gatcaaagga tcttcttgag atcctttttt tctgcgcgta 4200
atctgctgct tgcaaacaaa aaaaccaccg ctaccagcgg tggtttgttt gccggatcaa 4260
gagctaccaa ctctttttcc gaaggtaact ggcttcagca gagcgcagat accaaatact 4320
gttcttctag tgtagccgta gttaggccac cacttcaaga actctgtagc accgcctaca 4380
tacctcgctc tgctaatcct gttaccagtg gctgctgcca gtggcgataa gtcgtgtctt 4440
accgggttgg actcaagacg atagttaccg gataaggcgc agcggtcggg ctgaacgggg 4500
ggttcgtgca cacagcccag cttggagcga acgacctaca ccgaactgag atacctacag 4560
cgtgagctat gagaaagcgc cacgcttccc gaagggagaa aggcggacag gtatccggta 4620
agcggcaggg tcggaacagg agagcgcacg agggagcttc cagggggaaa cgcctggtat 4680
ctttatagtc ctgtcgggtt tcgccacctc tgacttgagc gtcgattttt gtgatgctcg 4740
tcaggggggc ggagcctatg gaaaaacgcc agcaacgcgg cctttttacg gttcctggcc 4800

-continued

```
ttttgctggc cttttgctca catgttcttt cctgcgttat cccctgattc tgtggataac   4860

cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                     5203
```

```
<210> SEQ ID NO 13
<211> LENGTH: 5203
<212> TYPE: DNA
<213> ORGANISM: Artificial Sequence
<220> FEATURE:
<223> OTHER INFORMATION: Synthetic

<400> SEQUENCE: 13
```

```
ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120

aagatcaatt cggtacaatt cacgcgtcga cattgattat tgactagctc tggtcgttac    180

ataacttacg gtaaatggcc cgcctggctg accgcccaac gacccccgcc cattgacgtc    240

aataatgacg tatgttccca tagtaacgcc aatagggact ttccattgac gtcaatgggt    300

ggagtattta cggtaaactg cccacttggc agtacatcaa gtgtatcata tgccaagtac    360

gccccctatt gacgtcaatg acggtaaatg gcccgcctgg cattatgccc agtacatgac    420

cttatgggac tttcctactt ggcagtacat ctactcgagg ccacgttctg cttcactctc    480

cccatctccc ccccctcccc acccccaatt ttgtatttat ttatttttta attattttgt    540

gcagcgatgg gggcgggggg gggggggggg cgcgcgccag gcggggcggg gcggggcgag    600

gggcggggcg gggcgaggcg gagaggtgcg gcggcagcca atcagagcgg cgcgctccga    660

aagtttcctt ttatggcgag gcggcggcgg cggcggccct ataaaaagcg aagcgcgcgg    720

cgggcgggag cgggatcagc caccgcggtg gcggcctaga gtcgacgagg aactgaaaaa    780

ccagaaagtt aactggtaag tttagtcttt ttgtctttta tttcaggtcc cagatctagg    840

gctctgcgtt tgctccaggt agtccgctgc tcccttgggc ctgggcccac tgacagccct    900

ggtgcctctg gccggctgca cacctcctgg cgggcagctg tggtgtaagc tggtgagcca    960

ctgtgttctg gcaatacctg cagtggctgt ctagcttaca ccacggaggc ctgccctgac   1020

tgcccacggt gccgtggcca aagaggatct aagggcaccg ctgagggcct acctaaccat   1080

cgtggggaat aaggacagtg tcacccctgc aggggatccg gtggtggtgc aaatcaaaga   1140

actgctcctc agtggatgtt gcctttactt ctaggcctgt acggaagtgt tacttctgct   1200

ctaaaagctg cggaattgta cccgcggccg atccaccggt cgccaccatg gtgagcaagg   1260

gcgaggagct gttcaccggg gtggtgccca tcctggtcga gctggacggc gacgtaaacg   1320

gccacaagtt cagcgtgtcc ggcgagggcg agggcgatgc cacctacggc aagctgaccc   1380

tgaagttcat ctgcaccacc ggcaagctgc ccgtgccctg gcccaccctc gtgaccaccc   1440

tgacctacgg cgtgcagtgc ttcagccgct accccgacca catgaagcag cacgacttct   1500

tcaagtccgc catgcccgaa ggctacgtcc aggagcgcac catcttcttc aaggacgacg   1560

gcaactacaa gacccgcgcc gaggtgaagt tcgagggcga caccctggtg aaccgcatcg   1620

agctgaaggg catcgacttc aaggaggacg gcaacatcct ggggcacaag ctggagtaca   1680
```

actacaacag ccacaacgtc tatatcatgg ccgacaagca gaagaacggc atcaaggtga 1740
acttcaagat ccgccacaac atcgaggacg gcagcgtgca gctcgccgac cactaccagc 1800
agaacacccc catcggcgac ggccccgtgc tgctgcccga caaccactac ctgagcaccc 1860
agtccgccct gagcaaagac cccaacgaga agcgcgatca catggtcctg ctggagttcg 1920
tgaccgccgc cgggatcact ctcggcatgg acgagctgta caagtaaagc ggccatcaag 1980
cttatcgata ccgtcgacta gagctcgctg atcagcctcg actgtgcctt ctagttgcca 2040
gccatctgtt gtttgcccct cccccgtgcc ttccttgacc ctggaaggtg ccactcccac 2100
tgtcctttcc taataaaatg aggaaattgc atcgcattgt ctgagtaggt gtcattctat 2160
tctggggggt ggggtggggc aggacagcaa gggggaggat tgggaagaca attaggtaga 2220
taagtagcat ggcgggttaa tcattaacta caaggaaccc ctagtgatgg agttggccac 2280
tccctctctg cgcgctcgct cgctcactga ggccgggcga ccaaaggtcg cccgacgccc 2340
gggctttgcc cgggcggcct cagtgagcga gcgagcgcgc agccttaatt aacctaattc 2400
actggccgtc gttttacaac gtcgtgactg ggaaaaccct ggcgttaccc aacttaatcg 2460
ccttgcagca catccccctt tcgccagctg gcgtaatagc gaagaggccc gcaccgatcg 2520
cccttcccaa cagttgcgca gcctgaatgg cgaatgggac gcgccctgta gcggcgcatt 2580
aagcgcggcg ggtgtggtgg ttacgcgcag cgtgaccgct acacttgcca gcgccctagc 2640
gcccgctcct ttcgctttct tcccttcctt tctcgccacg ttcgccggct ttccccgtca 2700
agctctaaat cgggggctcc ctttagggtt ccgatttagt gctttacggc acctcgaccc 2760
caaaaaactt gattagggtg atggttcacg tagtgggcca tcgccctgat agacggtttt 2820
tcgccctttg acgttggagt ccacgttctt taatagtgga ctcttgttcc aaactggaac 2880
aacactcaac cctatctcgg tctattcttt tgatttataa gggattttgc cgatttcggc 2940
ctattggtta aaaaatgagc tgatttaaca aaaatttaac gcgaatttta acaaaatatt 3000
aacgcttaca atttaggtgg cacttttcgg ggaaatgtgc gcggaacccc tatttgttta 3060
tttttctaaa tacattcaaa tatgtatccg ctcatgagac aataaccctg ataaatgctt 3120
caataatatt gaaaaaggaa gagtatgagt attcaacatt tccgtgtcgc ccttattccc 3180
ttttttgcgg cattttgcct tcctgttttt gctcacccag aaacgctggt gaaagtaaaa 3240
gatgctgaag atcagttggg tgcacgagtg ggttacatcg aactggatct caacagcggt 3300
aagatccttg agagttttcg ccccgaagaa cgttttccaa tgatgagcac ttttaaagtt 3360
ctgctatgtg gcgcggtatt atcccgtatt gacgccgggc aagagcaact cggtcgccgc 3420
atacactatt ctcagaatga cttggttgag tactcaccag tcacagaaaa gcatcttacg 3480
gatggcatga cagtaagaga attatgcagt gctgccataa ccatgagtga taacactgcg 3540
gccaacttac ttctgacaac gatcggagga ccgaaggagc taaccgcttt tttgcacaac 3600
atgggggatc atgtaactcg ccttgatcgt tgggaaccgg agctgaatga agccatacca 3660
aacgacgagc gtgacaccac gatgcctgta gcaatggcaa caacgttgcg caaactatta 3720
actggcgaac tacttactct agcttcccgg caacaattaa tagactggat ggaggcggat 3780
aaagttgcag gaccacttct gcgctcggcc cttccggctg gctggtttat tgctgataaa 3840
tctggagccg gtgagcgtgg gtctcgcggt atcattgcag cactggggcc agatggtaag 3900
ccctcccgta tcgtagttat ctacacgacg gggagtcagg caactatgga tgaacgaaat 3960
agacagatcg ctgagatagg tgcctcactg attaagcatt ggtaactgtc agaccaagtt 4020

-continued tactcatata tactttagat tgatttaaaa cttcattttt aatttaaaag gatctaggtg 4080
aagatccttt ttgataatct catgaccaaa atcccttaac gtgagttttc gttccactga 4140
gcgtcagacc ccgtagaaaa gatcaaagga tcttcttgag atcctttttt tctgcgcgta 4200
atctgctgct tgcaaacaaa aaaaccaccg ctaccagcgg tggtttgttt gccggatcaa 4260
gagctaccaa ctctttttcc gaaggtaact ggcttcagca gagcgcagat accaaatact 4320
gttcttctag tgtagccgta gttaggccac cacttcaaga actctgtagc accgcctaca 4380
tacctcgctc tgctaatcct gttaccagtg gctgctgcca gtggcgataa gtcgtgtctt 4440
accgggttgg actcaagacg atagttaccg gataaggcgc agcggtcggg ctgaacgggg 4500
ggttcgtgca cacagcccag cttggagcga acgacctaca ccgaactgag atacctacag 4560
cgtgagctat gagaaagcgc cacgcttccc gaagggagaa aggcggacag gtatccggta 4620
agcggcaggg tcggaacagg agagcgcacg agggagcttc cagggggaaa cgcctggtat 4680
ctttatagtc ctgtcgggtt tcgccacctc tgacttgagc gtcgattttt gtgatgctcg 4740
tcaggggggc ggagcctatg gaaaaacgcc agcaacgcgg cctttttacg gttcctggcc 4800
ttttgctggc cttttgctca catgttcttt cctgcgttat cccctgattc tgtggataac 4860
cgtattaccg cctttgagtg agctgatacc gctcgccgca gccgaacgac cgagcgcagc 4920
gagtcagtga gcgaggaagc ggaagagcgc ccaatacgca aaccgcctct ccccgcgcgt 4980
tggccgattc attaatgcag ctggcacgac aggtttcccg actggaaagc gggcagtgag 5040
cgcaacgcaa ttaatgtgag ttagctcact cattaggcac cccaggcttt acactttatg 5100
cttccggctc gtatgttgtg tggaattgtg agcggataac aatttcacac aggaaacagc 5160
tatgaccatg attacgccag atttaattaa ggccttaatt agg 5203

<210> SEQ ID NO 14
<211> LENGTH: 5203
<212> TYPE: DNA
<213> ORGANISM: Artificial Sequence
<220> FEATURE:
<223> OTHER INFORMATION: Synthetic

<400> SEQUENCE: 14
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120
aagatcaatt cggtacaatt cacgcgtcga cattgattat tgactagctc tggtcgttac 180
ataacttacg gtaaatggcc cgcctggctg accgcccaac gacccccgcc cattgacgtc 240
aataatgacg tatgttccca tagtaacgcc aatagggact ttccattgac gtcaatgggt 300
ggagtattta cggtaaactg cccacttggc agtacatcaa gtgtatcata tgccaagtac 360
gccccctatt gacgtcaatg acggtaaatg gcccgcctgg cattatgccc agtacatgac 420
cttatgggac tttcctactt ggcagtacat ctactcgagg ccacgttctg cttcactctc 480
cccatctccc ccccctcccc acccccaatt ttgtatttat ttatttttta attattttgt 540
gcagcgatgg gggcgggggg gggggggggg cgcgcgccag gcggggcggg gcggggcgag 600
gggcggggcg gggcgaggcg gagaggtgcg gcggcagcca atcagagcgg cgcgctccga 660
aagtttcctt ttatggcgag gcggcggcgg cggcggccct ataaaaagcg aagcgcgcgg 720
cgggcgggag cgggatcagc caccgcggtg gcggcctaga gtcgacgagg aactgaaaaa 780
ccagaaagtt aactggtaag tttagtcttt ttgtctttta tttcaggtcc cagatctagg 840
gctctgcgtt tgctccaggt agtccgctgc tcccttgggc ctgggcccac tgacagccct 900

-continued

```
ggtgcctctg gccggctgca cacctcctgg cgggcagctg tgtgtaatct ggtgagccac    960
tgttgttctg gcaatacctg acagtggcag atcagattac acacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
```

```
gatgctgaag atcagttggg tgcacgagtg ggttacatcg aactggatct caacagcggt   3300

aagatccttg agagttttcg ccccgaagaa cgttttccaa tgatgagcac ttttaaagtt   3360

ctgctatgtg gcgcggtatt atcccgtatt gacgccgggc aagagcaact cggtcgccgc   3420

atacactatt ctcagaatga cttggttgag tactcaccag tcacagaaaa gcatcttacg   3480

gatggcatga cagtaagaga attatgcagt gctgccataa ccatgagtga taacactgcg   3540

gccaacttac ttctgacaac gatcggagga ccgaaggagc taaccgcttt tttgcacaac   3600

atgggggatc atgtaactcg ccttgatcgt tgggaaccgg agctgaatga agccatacca   3660

aacgacgagc gtgacaccac gatgcctgta gcaatggcaa caacgttgcg caaactatta   3720

actggcgaac tacttactct agcttcccgg caacaattaa tagactggat ggaggcggat   3780

aaagttgcag gaccacttct gcgctcggcc cttccggctg gctggtttat tgctgataaa   3840

tctggagccg gtgagcgtgg gtctcgcggt atcattgcag cactggggcc agatggtaag   3900

ccctcccgta tcgtagttat ctacacgacg gggagtcagg caactatgga tgaacgaaat   3960

agacagatcg ctgagatagg tgcctcactg attaagcatt ggtaactgtc agaccaagtt   4020

tactcatata tactttagat tgatttaaaa cttcattttt aatttaaaag gatctaggtg   4080

aagatccttt ttgataatct catgaccaaa atcccttaac gtgagttttc gttccactga   4140

gcgtcagacc ccgtagaaaa gatcaaagga tcttcttgag atcctttttt tctgcgcgta   4200

atctgctgct tgcaaacaaa aaaaccaccg ctaccagcgg tggtttgttt gccggatcaa   4260

gagctaccaa ctctttttcc gaaggtaact ggcttcagca gagcgcagat accaaatact   4320

gttcttctag tgtagccgta gttaggccac cacttcaaga actctgtagc accgcctaca   4380

tacctcgctc tgctaatcct gttaccagtg gctgctgcca gtggcgataa gtcgtgtctt   4440

accgggttgg actcaagacg atagttaccg gataaggcgc agcggtcggg ctgaacgggg   4500

ggttcgtgca cacagcccag cttggagcga acgacctaca ccgaactgag atacctacag   4560

cgtgagctat gagaaagcgc cacgcttccc gaagggagaa aggcggacag gtatccggta   4620

agcggcaggg tcggaacagg agagcgcacg agggagcttc caggggggaaa cgcctggtat   4680

ctttatagtc ctgtcgggtt tcgccacctc tgacttgagc gtcgattttt gtgatgctcg   4740

tcaggggggc ggagcctatg gaaaaacgcc agcaacgcgg cctttttacg gttcctggcc   4800

ttttgctggc cttttgctca catgttcttt cctgcgttat cccctgattc tgtggataac   4860

cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                     5203


<210> SEQ ID NO 15
<211> LENGTH: 5203
<212> TYPE: DNA
<213> ORGANISM: Artificial Sequence
<220> FEATURE:
<223> OTHER INFORMATION: Synthetic

<400> SEQUENCE: 15

ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120
```

-continued

```
aagatcaatt cggtacaatt cacgcgtcga cattgattat tgactagctc tggtcgttac   180
ataacttacg gtaaatggcc cgcctggctg accgcccaac gacccccgcc cattgacgtc   240
aataatgacg tatgttccca tagtaacgcc aatagggact ttccattgac gtcaatgggt   300
ggagtattta cggtaaactg cccacttggc agtacatcaa gtgtatcata tgccaagtac   360
gccccctatt gacgtcaatg acggtaaatg gcccgcctgg cattatgccc agtacatgac   420
cttatgggac tttcctactt ggcagtacat ctactcgagg ccacgttctg cttcactctc   480
cccatctccc ccccctcccc acccccaatt ttgtatttat ttatttttta attattttgt   540
gcagcgatgg gggcgggggg gggggggggg cgcgcgccag gcggggcggg gcggggcgag   600
gggcggggcg gggcgaggcg gagaggtgcg gcggcagcca atcagagcgg cgcgctccga   660
aagtttcctt ttatggcgag gcggcggcgg cggcggccct ataaaaagcg aagcgcgcgg   720
cgggcgggag cgggatcagc caccgcggtg gcggcctaga gtcgacgagg aactgaaaaa   780
ccagaaagtt aactggtaag tttagtcttt ttgtctttta tttcaggtcc cagatctagg   840
gctctgcgtt tgctccaggt agtccgctgc tcccttgggc ctgggcccac tgacagccct   900
ggtgcctctg gccggctgca cacctcctgg cgggcagctg tgtgtaagct ggtgagccac   960
tgttgttctg gcaatacctg acagtggcag atcagcttac acacggaggc ctgccctgac  1020
tgcccacggt gccgtggcca aagaggatct aagggcaccg ctgagggcct acctaaccat  1080
cgtggggaat aaggacagtg tcacccctgc aggggatccg gtggtggtgc aaatcaaaga  1140
actgctcctc agtggatgtt gcctttactt ctaggcctgt acggaagtgt tacttctgct  1200
ctaaaagctg cggaattgta cccgcggccg atccaccggt cgccaccatg gtgagcaagg  1260
gcgaggagct gttcaccggg gtggtgccca tcctggtcga gctggacggc gacgtaaacg  1320
gccacaagtt cagcgtgtcc ggcgagggcg agggcgatgc cacctacggc aagctgaccc  1380
tgaagttcat ctgcaccacc ggcaagctgc ccgtgccctg gcccaccctc gtgaccaccc  1440
tgacctacgg cgtgcagtgc ttcagccgct accccgacca catgaagcag cacgacttct  1500
tcaagtccgc catgcccgaa ggctacgtcc aggagcgcac catcttcttc aaggacgacg  1560
gcaactacaa gacccgcgcc gaggtgaagt tcgagggcga caccctggtg aaccgcatcg  1620
agctgaaggg catcgacttc aaggaggacg gcaacatcct ggggcacaag ctggagtaca  1680
actacaacag ccacaacgtc tatatcatgg ccgacaagca gaagaacggc atcaaggtga  1740
acttcaagat ccgccacaac atcgaggacg gcagcgtgca gctcgccgac cactaccagc  1800
agaacacccc catcggcgac ggccccgtgc tgctgcccga caaccactac ctgagcaccc  1860
agtccgccct gagcaaagac cccaacgaga agcgcgatca catggtcctg ctggagttcg  1920
tgaccgccgc cgggatcact ctcggcatgg acgagctgta caagtaaagc ggccatcaag  1980
cttatcgata ccgtcgacta gagctcgctg atcagcctcg actgtgcctt ctagttgcca  2040
gccatctgtt gtttgcccct cccccgtgcc ttccttgacc ctggaaggtg ccactcccac  2100
tgtcctttcc taataaaatg aggaaattgc atcgcattgt ctgagtaggt gtcattctat  2160
tctggggggt ggggtggggc aggacagcaa gggggaggat tgggaagaca attaggtaga  2220
taagtagcat ggcgggttaa tcattaacta caaggaaccc ctagtgatgg agttggccac  2280
tccctctctg cgcgctcgct cgctcactga ggccgggcga ccaaaggtcg cccgacgccc  2340
gggctttgcc cgggcggcct cagtgagcga gcgagcgcgc agccttaatt aacctaattc  2400
actggccgtc gttttacaac gtcgtgactg ggaaaaccct ggcgttaccc aacttaatcg  2460
```

-continued

```
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
aagatccttg agagttttcg ccccgaagaa cgttttccaa tgatgagcac ttttaaagtt   3360
ctgctatgtg gcgcggtatt atcccgtatt gacgccgggc aagagcaact cggtcgccgc   3420
atacactatt ctcagaatga cttggttgag tactcaccag tcacagaaaa gcatcttacg   3480
gatggcatga cagtaagaga attatgcagt gctgccataa ccatgagtga taacactgcg   3540
gccaacttac ttctgacaac gatcggagga ccgaaggagc taaccgcttt tttgcacaac   3600
atgggggatc atgtaactcg ccttgatcgt tgggaaccgg agctgaatga agccatacca   3660
aacgacgagc gtgacaccac gatgcctgta gcaatggcaa caacgttgcg caaactatta   3720
actggcgaac tacttactct agcttcccgg caacaattaa tagactggat ggaggcggat   3780
aaagttgcag gaccacttct gcgctcggcc cttccggctg gctggtttat tgctgataaa   3840
tctggagccg gtgagcgtgg gtctcgcggt atcattgcag cactggggcc agatggtaag   3900
ccctcccgta tcgtagttat ctacacgacg gggagtcagg caactatgga tgaacgaaat   3960
agacagatcg ctgagatagg tgcctcactg attaagcatt ggtaactgtc agaccaagtt   4020
tactcatata tactttagat tgatttaaaa cttcattttt aatttaaaag gatctaggtg   4080
aagatccttt ttgataatct catgaccaaa atcccttaac gtgagttttc gttccactga   4140
gcgtcagacc ccgtagaaaa gatcaaagga tcttcttgag atcctttttt tctgcgcgta   4200
atctgctgct tgcaaacaaa aaaaccaccg ctaccagcgg tggtttgttt gccggatcaa   4260
gagctaccaa ctctttttcc gaaggtaact ggcttcagca gagcgcagat accaaatact   4320
gttcttctag tgtagccgta gttaggccac cacttcaaga actctgtagc accgcctaca   4380
tacctcgctc tgctaatcct gttaccagtg gctgctgcca gtggcgataa gtcgtgtctt   4440
accgggttgg actcaagacg atagttaccg gataaggcgc agcggtcggg ctgaacgggg   4500
ggttcgtgca cacagcccag cttggagcga acgacctaca ccgaactgag atacctacag   4560
cgtgagctat gagaaagcgc cacgcttccc gaagggagaa aggcggacag gtatccggta   4620
agcggcaggg tcggaacagg agagcgcacg agggagcttc cagggggaaa cgcctggtat   4680
ctttatagtc ctgtcgggtt tcgccacctc tgacttgagc gtcgattttt gtgatgctcg   4740
tcaggggggc ggagcctatg gaaaaacgcc agcaacgcgg cctttttacg gttcctggcc   4800
ttttgctggc cttttgctca catgttcttt cctgcgttat cccctgattc tgtggataac   4860
```

-continued

```
cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                      5203
```

<210> SEQ ID NO 16
<211> LENGTH: 5203
<212> TYPE: DNA
<213> ORGANISM: Artificial Sequence
<220> FEATURE:
<223> OTHER INFORMATION: Synthetic

<400> SEQUENCE: 16

```
ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120

aagatcaatt cggtacaatt cacgcgtcga cattgattat tgactagctc tggtcgttac    180

ataacttacg gtaaatggcc cgcctggctg accgcccaac gacccccgcc cattgacgtc    240

aataatgacg tatgttccca tagtaacgcc aatagggact ttccattgac gtcaatgggt    300

ggagtattta cggtaaactg cccacttggc agtacatcaa gtgtatcata tgccaagtac    360

gccccctatt gacgtcaatg acggtaaatg gcccgcctgg cattatgccc agtacatgac    420

cttatgggac tttcctactt ggcagtacat ctactcgagg ccacgttctg cttcactctc    480

cccatctccc ccccctcccc acccccaatt ttgtatttat ttatttttta attattttgt    540

gcagcgatgg gggcgggggg gggggggggg cgcgcgccag gcggggcggg gcggggcgag    600

gggcggggcg gggcgaggcg gagaggtgcg gcggcagcca atcagagcgg cgcgctccga    660

aagtttcctt ttatggcgag gcggcggcgg cggcggccct ataaaaagcg aagcgcgcgg    720

cgggcgggag cgggatcagc caccgcggtg gcggcctaga gtcgacgagg aactgaaaaa    780

ccagaaagtt aactggtaag tttagtcttt ttgtctttta tttcaggtcc cagatctagg    840

gctctgcgtt tgctccaggt agtccgctgc tcccttgggc ctgggcccac tgacagccct    900

ggtgcctctg gccggctgca cacctcctgg cgggcagctg tggtaatctg gtgagccact    960

gtttgttctg gcaatacctg aacagtggga cgccagatta ccacggaggc ctgccctgac   1020

tgcccacggt gccgtggcca aagaggatct aagggcaccg ctgagggcct acctaaccat   1080

cgtggggaat aaggacagtg tcacccctgc aggggatccg gtggtggtgc aaatcaaaga   1140

actgctcctc agtggatgtt gcctttactt ctaggcctgt acggaagtgt tacttctgct   1200

ctaaaagctg cggaattgta cccgcggccg atccaccggt cgccaccatg gtgagcaagg   1260

gcgaggagct gttcaccggg gtggtgccca tcctggtcga gctggacggc gacgtaaacg   1320

gccacaagtt cagcgtgtcc ggcgagggcg agggcgatgc cacctacggc aagctgaccc   1380

tgaagttcat ctgcaccacc ggcaagctgc ccgtgccctg gcccaccctc gtgaccaccc   1440

tgacctacgg cgtgcagtgc ttcagccgct accccgacca catgaagcag cacgacttct   1500

tcaagtccgc catgcccgaa ggctacgtcc aggagcgcac catcttcttc aaggacgacg   1560

gcaactacaa gacccgcgcc gaggtgaagt tcgagggcga caccctggtg aaccgcatcg   1620

agctgaaggg catcgacttc aaggaggacg gcaacatcct ggggcacaag ctggagtaca   1680
```

-continued actacaacag ccacaacgtc tatatcatgg ccgacaagca gaagaacggc atcaaggtga 1740
acttcaagat ccgccacaac atcgaggacg gcagcgtgca gctcgccgac cactaccagc 1800
agaacacccc catcggcgac ggccccgtgc tgctgcccga caaccactac ctgagcaccc 1860
agtccgccct gagcaaagac cccaacgaga agcgcgatca catggtcctg ctggagttcg 1920
tgaccgccgc cgggatcact ctcggcatgg acgagctgta caagtaaagc ggccatcaag 1980
cttatcgata ccgtcgacta gagctcgctg atcagcctcg actgtgcctt ctagttgcca 2040
gccatctgtt gtttgcccct cccccgtgcc ttccttgacc ctggaaggtg ccactcccac 2100
tgtcctttcc taataaaatg aggaaattgc atcgcattgt ctgagtaggt gtcattctat 2160
tctggggggt ggggtggggc aggacagcaa gggggaggat tgggaagaca attaggtaga 2220
taagtagcat ggcgggttaa tcattaacta caaggaaccc ctagtgatgg agttggccac 2280
tccctctctg cgcgctcgct cgctcactga ggccgggcga ccaaaggtcg cccgacgccc 2340
gggctttgcc cgggcggcct cagtgagcga gcgagcgcgc agccttaatt aacctaattc 2400
actggccgtc gttttacaac gtcgtgactg ggaaaaccct ggcgttaccc aacttaatcg 2460
ccttgcagca catccccctt tcgccagctg gcgtaatagc gaagaggccc gcaccgatcg 2520
cccttcccaa cagttgcgca gcctgaatgg cgaatgggac gcgccctgta gcggcgcatt 2580
aagcgcggcg ggtgtggtgg ttacgcgcag cgtgaccgct acacttgcca gcgccctagc 2640
gcccgctcct ttcgctttct tcccttcctt tctcgccacg ttcgccggct ttccccgtca 2700
agctctaaat cgggggctcc ctttagggtt ccgatttagt gctttacggc acctcgaccc 2760
caaaaaactt gattagggtg atggttcacg tagtgggcca tcgccctgat agacggtttt 2820
tcgccctttg acgttggagt ccacgttctt taatagtgga ctcttgttcc aaactggaac 2880
aacactcaac cctatctcgg tctattcttt tgatttataa gggattttgc cgatttcggc 2940
ctattggtta aaaaatgagc tgatttaaca aaaatttaac gcgaatttta acaaaatatt 3000
aacgcttaca atttaggtgg cacttttcgg ggaaatgtgc gcggaacccc tatttgttta 3060
tttttctaaa tacattcaaa tatgtatccg ctcatgagac aataaccctg ataaatgctt 3120
caataatatt gaaaaaggaa gagtatgagt attcaacatt tccgtgtcgc ccttattccc 3180
ttttttgcgg cattttgcct tcctgttttt gctcacccag aaacgctggt gaaagtaaaa 3240
gatgctgaag atcagttggg tgcacgagtg ggttacatcg aactggatct caacagcggt 3300
aagatccttg agagttttcg ccccgaagaa cgttttccaa tgatgagcac ttttaaagtt 3360
ctgctatgtg gcgcggtatt atcccgtatt gacgccgggc aagagcaact cggtcgccgc 3420
atacactatt ctcagaatga cttggttgag tactcaccag tcacagaaaa gcatcttacg 3480
gatggcatga cagtaagaga attatgcagt gctgccataa ccatgagtga taacactgcg 3540
gccaacttac ttctgacaac gatcggagga ccgaaggagc taaccgcttt tttgcacaac 3600
atgggggatc atgtaactcg ccttgatcgt tgggaaccgg agctgaatga agccatacca 3660
aacgacgagc gtgacaccac gatgcctgta gcaatggcaa caacgttgcg caaactatta 3720
actggcgaac tacttactct agcttcccgg caacaattaa tagactggat ggaggcggat 3780
aaagttgcag gaccacttct gcgctcggcc cttccggctg gctggtttat tgctgataaa 3840
tctggagccg gtgagcgtgg gtctcgcggt atcattgcag cactggggcc agatggtaag 3900
ccctcccgta tcgtagttat ctacacgacg gggagtcagg caactatgga tgaacgaaat 3960
agacagatcg ctgagatagg tgcctcactg attaagcatt ggtaactgtc agaccaagtt 4020
tactcatata tactttagat tgatttaaaa cttcattttt aatttaaaag gatctaggtg 4080

```
aagatccttt ttgataatct catgaccaaa atcccttaac gtgagttttc gttccactga   4140
gcgtcagacc ccgtagaaaa gatcaaagga tcttcttgag atcctttttt tctgcgcgta   4200
atctgctgct tgcaaacaaa aaaaccaccg ctaccagcgg tggtttgttt gccggatcaa   4260
gagctaccaa ctctttttcc gaaggtaact ggcttcagca gagcgcagat accaaatact   4320
gttcttctag tgtagccgta gttaggccac cacttcaaga actctgtagc accgcctaca   4380
tacctcgctc tgctaatcct gttaccagtg gctgctgcca gtggcgataa gtcgtgtctt   4440
accgggttgg actcaagacg atagttaccg gataaggcgc agcggtcggg ctgaacgggg   4500
ggttcgtgca cacagcccag cttggagcga acgacctaca ccgaactgag atacctacag   4560
cgtgagctat gagaaagcgc cacgcttccc gaagggagaa aggcggacag gtatccggta   4620
agcggcaggg tcggaacagg agagcgcacg agggagcttc caggggggaaa cgcctggtat   4680
ctttatagtc ctgtcgggtt tcgccacctc tgacttgagc gtcgattttt gtgatgctcg   4740
tcaggggggc ggagcctatg gaaaaacgcc agcaacgcgg cctttttacg gttcctggcc   4800
ttttgctggc cttttgctca catgttcttt cctgcgttat cccctgattc tgtggataac   4860
cgtattaccg cctttgagtg agctgatacc gctcgccgca gccgaacgac cgagcgcagc   4920
gagtcagtga gcgaggaagc ggaagagcgc ccaatacgca aaccgcctct ccccgcgcgt   4980
tggccgattc attaatgcag ctggcacgac aggtttcccg actggaaagc gggcagtgag   5040
cgcaacgcaa ttaatgtgag ttagctcact cattaggcac cccaggcttt acactttatg   5100
cttccggctc gtatgttgtg tggaattgtg agcggataac aatttcacac aggaaacagc   5160
tatgaccatg attacgccag atttaattaa ggccttaatt agg                     5203
```

<210> SEQ ID NO 17
<211> LENGTH: 5203
<212> TYPE: DNA
<213> ORGANISM: Artificial Sequence
<220> FEATURE:
<223> OTHER INFORMATION: Synthetic

<400> SEQUENCE: 17

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt cggtacaatt cacgcgtcga cattgattat tgactagctc tggtcgttac    180
ataacttacg gtaaatggcc cgcctggctg accgcccaac gacccccgcc cattgacgtc    240
aataatgacg tatgttccca tagtaacgcc aatagggact ttccattgac gtcaatgggt    300
ggagtattta cggtaaactg cccacttggc agtacatcaa gtgtatcata tgccaagtac    360
gccccctatt gacgtcaatg acggtaaatg gcccgcctgg cattatgccc agtacatgac    420
cttatgggac tttcctactt ggcagtacat ctactcgagg ccacgttctg cttcactctc    480
cccatctccc ccccctcccc acccccaatt ttgtatttat ttatttttta attattttgt    540
gcagcgatgg gggcgggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggcctaga gtcgacgagg aactgaaaaa    780
ccagaaagtt aactggtaag tttagtcttt ttgtctttta tttcaggtcc cagatctagg    840
gctctgcgtt tgctccaggt agtccgctgc tcccttgggc ctgggcccac tgacagccct    900
```

-continued

```
ggtgcctctg gccggctgca cacctcctgg cgggcagctg tggtaagctg gtgagccact    960
gtttgttctg gcaatacctg aacagtggga cgccagctta ccacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
```

-continued aagatccttg agagttttcg ccccgaagaa cgttttccaa tgatgagcac ttttaaagtt 3360
ctgctatgtg gcgcggtatt atcccgtatt gacgccgggc aagagcaact cggtcgccgc 3420
atacactatt ctcagaatga cttggttgag tactcaccag tcacagaaaa gcatcttacg 3480
gatggcatga cagtaagaga attatgcagt gctgccataa ccatgagtga taacactgcg 3540
gccaacttac ttctgacaac gatcggagga ccgaaggagc taaccgcttt tttgcacaac 3600
atgggggatc atgtaactcg ccttgatcgt tgggaaccgg agctgaatga agccatacca 3660
aacgacgagc gtgacaccac gatgcctgta gcaatggcaa caacgttgcg caaactatta 3720
actggcgaac tacttactct agcttcccgg caacaattaa tagactggat ggaggcggat 3780
aaagttgcag gaccacttct gcgctcggcc cttccggctg gctggtttat tgctgataaa 3840
tctggagccg gtgagcgtgg gtctcgcggt atcattgcag cactggggcc agatggtaag 3900
ccctcccgta tcgtagttat ctacacgacg gggagtcagg caactatgga tgaacgaaat 3960
agacagatcg ctgagatagg tgcctcactg attaagcatt ggtaactgtc agaccaagtt 4020
tactcatata tactttagat tgatttaaaa cttcattttt aatttaaaag gatctaggtg 4080
aagatccttt ttgataatct catgaccaaa atcccttaac gtgagttttc gttccactga 4140
gcgtcagacc ccgtagaaaa gatcaaagga tcttcttgag atcctttttt tctgcgcgta 4200
atctgctgct tgcaaacaaa aaaaccaccg ctaccagcgg tggtttgttt gccggatcaa 4260
gagctaccaa ctctttttcc gaaggtaact ggcttcagca gagcgcagat accaaatact 4320
gttcttctag tgtagccgta gttaggccac cacttcaaga actctgtagc accgcctaca 4380
tacctcgctc tgctaatcct gttaccagtg gctgctgcca gtggcgataa gtcgtgtctt 4440
accgggttgg actcaagacg atagttaccg gataaggcgc agcggtcggg ctgaacgggg 4500
ggttcgtgca cacagcccag cttggagcga acgacctaca ccgaactgag atacctacag 4560
cgtgagctat gagaaagcgc cacgcttccc gaagggagaa aggcggacag gtatccggta 4620
agcggcaggg tcggaacagg agagcgcacg agggagcttc cagggggaaa cgcctggtat 4680
ctttatagtc ctgtcgggtt tcgccacctc tgacttgagc gtcgattttt gtgatgctcg 4740
tcaggggggc ggagcctatg gaaaaacgcc agcaacgcgg cctttttacg gttcctggcc 4800
ttttgctggc cttttgctca catgttcttt cctgcgttat cccctgattc tgtggataac 4860
cgtattaccg cctttgagtg agctgatacc gctcgccgca gccgaacgac cgagcgcagc 4920
gagtcagtga gcgaggaagc ggaagagcgc ccaatacgca aaccgcctct ccccgcgcgt 4980
tggccgattc attaatgcag ctggcacgac aggtttcccg actggaaagc gggcagtgag 5040
cgcaacgcaa ttaatgtgag ttagctcact cattaggcac cccaggcttt acactttatg 5100
cttccggctc gtatgttgtg tggaattgtg agcggataac aatttcacac aggaaacagc 5160
tatgaccatg attacgccag atttaattaa ggccttaatt agg 5203

<210> SEQ ID NO 18
<211> LENGTH: 5203
<212> TYPE: DNA
<213> ORGANISM: Artificial Sequence
<220> FEATURE:
<223> OTHER INFORMATION: Synthetic

<400> SEQUENCE: 18
ctgcgcgctc gctcgctcac tgaggccgcc cgggcaaagc ccgggcgtcg ggcgaccttt 60
ggtcgcccgg cctcagtgag cgagcgagcg cgcagagagg gagtgtagcc atgctctagg 120

-continued

```
aagatcaatt cggtacaatt cacgcgtcga cattgattat tgactagctc tggtcgttac    180
ataacttacg gtaaatggcc cgcctggctg accgcccaac gacccccgcc cattgacgtc    240
aataatgacg tatgttccca tagtaacgcc aatagggact ttccattgac gtcaatgggt    300
ggagtattta cggtaaactg cccacttggc agtacatcaa gtgtatcata tgccaagtac    360
gccccctatt gacgtcaatg acggtaaatg gcccgcctgg cattatgccc agtacatgac    420
cttatgggac tttcctactt ggcagtacat ctactcgagg ccacgttctg cttcactctc    480
cccatctccc ccccctcccc acccccaatt ttgtatttat ttatttttta attattttgt    540
gcagcgatgg gggcgggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggcctaga gtcgacgagg aactgaaaaa    780
ccagaaagtt aactggtaag tttagtcttt ttgtctttta tttcaggtcc cagatctagg    840
gctctgcgtt tgctccaggt agtccgctgc tcccttgggc ctgggcccac tgacagccct    900
ggtgcctctg gccggctgca cacctcctgg cgggcagctg tgtaatctgg tgagccactg    960
ttctgttctg gcaatacctg gaacagtgcg ttaccagatt acacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
```

-continued

```
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
aagatccttg agagttttcg ccccgaagaa cgttttccaa tgatgagcac ttttaaagtt   3360
ctgctatgtg gcgcggtatt atcccgtatt gacgccgggc aagagcaact cggtcgccgc   3420
atacactatt ctcagaatga cttggttgag tactcaccag tcacagaaaa gcatcttacg   3480
gatggcatga cagtaagaga attatgcagt gctgccataa ccatgagtga taacactgcg   3540
gccaacttac ttctgacaac gatcggagga ccgaaggagc taaccgcttt tttgcacaac   3600
atgggggatc atgtaactcg ccttgatcgt tgggaaccgg agctgaatga agccatacca   3660
aacgacgagc gtgacaccac gatgcctgta gcaatggcaa caacgttgcg caaactatta   3720
actggcgaac tacttactct agcttcccgg caacaattaa tagactggat ggaggcggat   3780
aaagttgcag gaccacttct gcgctcggcc cttccggctg gctggtttat tgctgataaa   3840
tctggagccg gtgagcgtgg gtctcgcggt atcattgcag cactggggcc agatggtaag   3900
ccctcccgta tcgtagttat ctacacgacg gggagtcagg caactatgga tgaacgaaat   3960
agacagatcg ctgagatagg tgcctcactg attaagcatt ggtaactgtc agaccaagtt   4020
tactcatata tactttagat tgatttaaaa cttcattttt aatttaaaag gatctaggtg   4080
aagatccttt ttgataatct catgaccaaa atcccttaac gtgagttttc gttccactga   4140
gcgtcagacc ccgtagaaaa gatcaaagga tcttcttgag atcctttttt tctgcgcgta   4200
atctgctgct tgcaaacaaa aaaaccaccg ctaccagcgg tggtttgttt gccggatcaa   4260
gagctaccaa ctctttttcc gaaggtaact ggcttcagca gagcgcagat accaaatact   4320
gttcttctag tgtagccgta gttaggccac cacttcaaga actctgtagc accgcctaca   4380
tacctcgctc tgctaatcct gttaccagtg gctgctgcca gtggcgataa gtcgtgtctt   4440
accgggttgg actcaagacg atagttaccg gataaggcgc agcggtcggg ctgaacgggg   4500
ggttcgtgca cacagcccag cttggagcga acgacctaca ccgaactgag atacctacag   4560
cgtgagctat gagaaagcgc cacgcttccc gaagggagaa aggcggacag gtatccggta   4620
agcggcaggg tcggaacagg agagcgcacg agggagcttc cagggggaaa cgcctggtat   4680
ctttatagtc ctgtcgggtt tcgccacctc tgacttgagc gtcgattttt gtgatgctcg   4740
tcaggggggc ggagcctatg gaaaaacgcc agcaacgcgg cctttttacg gttcctggcc   4800
ttttgctggc cttttgctca catgttcttt cctgcgttat cccctgattc tgtggataac   4860
```

-continued

```
cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                      5203


<210> SEQ ID NO 19
<211> LENGTH: 5203
<212> TYPE: DNA
<213> ORGANISM: Artificial Sequence
<220> FEATURE:
<223> OTHER INFORMATION: Synthetic

<400> SEQUENCE: 19

ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120

aagatcaatt cggtacaatt cacgcgtcga cattgattat tgactagctc tggtcgttac    180

ataacttacg gtaaatggcc cgcctggctg accgcccaac gacccccgcc cattgacgtc    240

aataatgacg tatgttccca tagtaacgcc aatagggact ttccattgac gtcaatgggt    300

ggagtattta cggtaaactg cccacttggc agtacatcaa gtgtatcata tgccaagtac    360

gccccctatt gacgtcaatg acggtaaatg gcccgcctgg cattatgccc agtacatgac    420

cttatgggac tttcctactt ggcagtacat ctactcgagg ccacgttctg cttcactctc    480

cccatctccc ccccctcccc acccccaatt ttgtatttat ttatttttta attattttgt    540

gcagcgatgg gggcgggggg gggggggggg cgcgcgccag gcggggcggg gcggggcgag    600

gggcggggcg gggcgaggcg gagaggtgcg gcggcagcca atcagagcgg cgcgctccga    660

aagtttcctt ttatggcgag gcggcggcgg cggcggccct ataaaaagcg aagcgcgcgg    720

cgggcgggag cgggatcagc caccgcggtg gcggcctaga gtcgacgagg aactgaaaaa    780

ccagaaagtt aactggtaag tttagtcttt ttgtctttta tttcaggtcc cagatctagg    840

gctctgcgtt tgctccaggt agtccgctgc tcccttgggc ctgggcccac tgacagccct    900

ggtgcctctg gccggctgca cacctcctgg cgggcagctg tgtaagctgg tgagccactg    960

ttctgttctg gcaatacctg gaacagtgcg ttaccagctt acacggaggc ctgccctgac   1020

tgcccacggt gccgtggcca aagaggatct aagggcaccg ctgagggcct acctaaccat   1080

cgtggggaat aaggacagtg tcacccctgc aggggatccg gtggtggtgc aaatcaaaga   1140

actgctcctc agtggatgtt gcctttactt ctaggcctgt acggaagtgt tacttctgct   1200

ctaaaagctg cggaattgta cccgcggccg atccaccggt cgccaccatg gtgagcaagg   1260

gcgaggagct gttcaccggg gtggtgccca tcctggtcga gctggacggc gacgtaaacg   1320

gccacaagtt cagcgtgtcc ggcgagggcg agggcgatgc cacctacggc aagctgaccc   1380

tgaagttcat ctgcaccacc ggcaagctgc ccgtgccctg gcccaccctc gtgaccaccc   1440

tgacctacgg cgtgcagtgc ttcagccgct accccgacca catgaagcag cacgacttct   1500

tcaagtccgc catgcccgaa ggctacgtcc aggagcgcac catcttcttc aaggacgacg   1560

gcaactacaa gacccgcgcc gaggtgaagt tcgagggcga caccctggtg aaccgcatcg   1620

agctgaaggg catcgacttc aaggaggacg gcaacatcct ggggcacaag ctggagtaca   1680

actacaacag ccacaacgtc tatatcatgg ccgacaagca gaagaacggc atcaaggtga   1740
```

```
actttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
aagatccttg agagttttcg ccccgaagaa cgttttccaa tgatgagcac ttttaaagtt   3360
ctgctatgtg gcgcggtatt atcccgtatt gacgccgggc aagagcaact cggtcgccgc   3420
atacactatt ctcagaatga cttggttgag tactcaccag tcacagaaaa gcatcttacg   3480
gatggcatga cagtaagaga attatgcagt gctgccataa ccatgagtga taacactgcg   3540
gccaacttac ttctgacaac gatcggagga ccgaaggagc taaccgcttt tttgcacaac   3600
atgggggatc atgtaactcg ccttgatcgt tgggaaccgg agctgaatga agccatacca   3660
aacgacgagc gtgacaccac gatgcctgta gcaatggcaa caacgttgcg caaactatta   3720
actggcgaac tacttactct agcttcccgg caacaattaa tagactggat ggaggcggat   3780
aaagttgcag gaccacttct gcgctcggcc cttccggctg gctggtttat tgctgataaa   3840
tctggagccg gtgagcgtgg gtctcgcggt atcattgcag cactggggcc agatggtaag   3900
ccctcccgta tcgtagttat ctacacgacg gggagtcagg caactatgga tgaacgaaat   3960
agacagatcg ctgagatagg tgcctcactg attaagcatt ggtaactgtc agaccaagtt   4020
tactcatata tactttagat tgatttaaaa cttcattttt aatttaaaag gatctaggtg   4080
```

```
aagatccttt ttgataatct catgaccaaa atcccttaac gtgagttttc gttccactga   4140

gcgtcagacc ccgtagaaaa gatcaaagga tcttcttgag atcctttttt tctgcgcgta   4200

atctgctgct tgcaaacaaa aaaaccaccg ctaccagcgg tggtttgttt gccggatcaa   4260

gagctaccaa ctctttttcc gaaggtaact ggcttcagca gagcgcagat accaaatact   4320

gttcttctag tgtagccgta gttaggccac cacttcaaga actctgtagc accgcctaca   4380

tacctcgctc tgctaatcct gttaccagtg gctgctgcca gtggcgataa gtcgtgtctt   4440

accgggttgg actcaagacg atagttaccg gataaggcgc agcggtcggg ctgaacgggg   4500

ggttcgtgca cacagcccag cttggagcga acgacctaca ccgaactgag atacctacag   4560

cgtgagctat gagaaagcgc cacgcttccc gaagggagaa aggcggacag gtatccggta   4620

agcggcaggg tcggaacagg agagcgcacg agggagcttc cagggggaaa cgcctggtat   4680

ctttatagtc ctgtcgggtt tcgccacctc tgacttgagc gtcgattttt gtgatgctcg   4740

tcaggggggc ggagcctatg gaaaaacgcc agcaacgcgg cctttttacg gttcctggcc   4800

ttttgctggc cttttgctca catgttcttt cctgcgttat cccctgattc tgtggataac   4860

cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                       5203
```

<210> SEQ ID NO 20
<211> LENGTH: 5203
<212> TYPE: DNA
<213> ORGANISM: Artificial Sequence
<220> FEATURE:
<223> OTHER INFORMATION: Synthetic

<400> SEQUENCE: 20

```
ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120

aagatcaatt cggtacaatt cacgcgtcga cattgattat tgactagctc tggtcgttac    180

ataacttacg gtaaatggcc cgcctggctg accgcccaac gacccccgcc cattgacgtc    240

aataatgacg tatgttccca tagtaacgcc aatagggact ttccattgac gtcaatgggt    300

ggagtattta cggtaaactg cccacttggc agtacatcaa gtgtatcata tgccaagtac    360

gcccccctatt gacgtcaatg acggtaaatg gcccgcctgg cattatgccc agtacatgac    420

cttatgggac tttcctactt ggcagtacat ctactcgagg ccacgttctg cttcactctc    480

cccatctccc ccccctcccc acccccaatt ttgtatttat ttatttttta attattttgt    540

gcagcgatgg gggcgggggg gggggggggg cgcgcgccag gcggggcggg gcggggcgag    600

gggcggggcg gggcgaggcg gagaggtgcg gcggcagcca atcagagcgg cgcgctccga    660

aagtttcctt ttatggcgag gcggcggcgg cggcggccct ataaaaagcg aagcgcgcgg    720

cgggcgggag cgggatcagc caccgcggtg gcggcctaga gtcgacgagg aactgaaaaa    780

ccagaaagtt aactggtaag tttagtcttt ttgtctttta tttcaggtcc cagatctagg    840

gctctgcgtt tgctccaggt agtccgctgc tcccttgggc ctgggcccac tgacagccct    900

ggtgcctctg gccggctgca cacctcctgg cgggcagctg tgaatctggt gagccactgt    960
```

```
tcttgttctg gcaatacctg agaacagtcc cccaccagat tcacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
```

-continued

```
aagatccttg agagttttcg ccccgaagaa cgttttccaa tgatgagcac ttttaaagtt   3360

ctgctatgtg gcgcggtatt atcccgtatt gacgccgggc aagagcaact cggtcgccgc   3420

atacactatt ctcagaatga cttggttgag tactcaccag tcacagaaaa gcatcttacg   3480

gatggcatga cagtaagaga attatgcagt gctgccataa ccatgagtga taacactgcg   3540

gccaacttac ttctgacaac gatcggagga ccgaaggagc taaccgcttt tttgcacaac   3600

atgggggatc atgtaactcg ccttgatcgt tgggaaccgg agctgaatga agccatacca   3660

aacgacgagc gtgacaccac gatgcctgta gcaatggcaa caacgttgcg caaactatta   3720

actggcgaac tacttactct agcttcccgg caacaattaa tagactggat ggaggcggat   3780

aaagttgcag gaccacttct gcgctcggcc cttccggctg gctggtttat tgctgataaa   3840

tctggagccg gtgagcgtgg gtctcgcggt atcattgcag cactggggcc agatggtaag   3900

ccctcccgta tcgtagttat ctacacgacg gggagtcagg caactatgga tgaacgaaat   3960

agacagatcg ctgagatagg tgcctcactg attaagcatt ggtaactgtc agaccaagtt   4020

tactcatata tactttagat tgatttaaaa cttcattttt aatttaaaag gatctaggtg   4080

aagatccttt ttgataatct catgaccaaa atcccttaac gtgagttttc gttccactga   4140

gcgtcagacc ccgtagaaaa gatcaaagga tcttcttgag atcctttttt tctgcgcgta   4200

atctgctgct tgcaaacaaa aaaaccaccg ctaccagcgg tggtttgttt gccggatcaa   4260

gagctaccaa ctctttttcc gaaggtaact ggcttcagca gagcgcagat accaaatact   4320

gttcttctag tgtagccgta gttaggccac cacttcaaga actctgtagc accgcctaca   4380

tacctcgctc tgctaatcct gttaccagtg gctgctgcca gtggcgataa gtcgtgtctt   4440

accgggttgg actcaagacg atagttaccg gataaggcgc agcggtcggg ctgaacgggg   4500

ggttcgtgca cacagcccag cttggagcga acgacctaca ccgaactgag atacctacag   4560

cgtgagctat gagaaagcgc cacgcttccc gaagggagaa aggcggacag gtatccggta   4620

agcggcaggg tcggaacagg agagcgcacg agggagcttc cagggggaaa cgcctggtat   4680

ctttatagtc ctgtcgggtt tcgccacctc tgacttgagc gtcgattttt gtgatgctcg   4740

tcaggggggc ggagcctatg gaaaaacgcc agcaacgcgg cctttttacg gttcctggcc   4800

ttttgctggc cttttgctca catgttcttt cctgcgttat cccctgattc tgtggataac   4860

cgtattaccg cctttgagtg agctgatacc gctcgccgca gccgaacgac cgagcgcagc   4920

gagtcagtga gcgaggaagc ggaagagcgc ccaatacgca aaccgcctct ccccgcgcgt   4980

tggccgattc attaatgcag ctggcacgac aggtttcccg actggaaagc gggcagtgag   5040

cgcaacgcaa ttaatgtgag ttagctcact cattaggcac cccaggcttt acactttatg   5100

cttccggctc gtatgttgtg tggaattgtg agcggataac aatttcacac aggaaacagc   5160

tatgaccatg attacgccag atttaattaa ggccttaatt agg                     5203
```

<210> SEQ ID NO 21
<211> LENGTH: 5203
<212> TYPE: DNA
<213> ORGANISM: Artificial Sequence
<220> FEATURE:
<223> OTHER INFORMATION: Synthetic

<400> SEQUENCE: 21

```
ctgcgcgctc gctcgctcac tgaggccgcc cgggcaaagc ccgggcgtcg ggcgaccttt     60

ggtcgcccgg cctcagtgag cgagcgagcg cgcagagagg gagtgtagcc atgctctagg    120

aagatcaatt cggtacaatt cacgcgtcga cattgattat tgactagctc tggtcgttac    180
```

```
ataacttacg gtaaatggcc cgcctggctg accgcccaac gacccccgcc cattgacgtc    240
aataatgacg tatgttccca tagtaacgcc aatagggact ttccattgac gtcaatgggt    300
ggagtattta cggtaaactg cccacttggc agtacatcaa gtgtatcata tgccaagtac    360
gccccctatt gacgtcaatg acggtaaatg gcccgcctgg cattatgccc agtacatgac    420
cttatgggac tttcctactt ggcagtacat ctactcgagg ccacgttctg cttcactctc    480
cccatctccc ccccctcccc acccccaatt ttgtatttat ttatttttta attattttgt    540
gcagcgatgg gggcgggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggcctaga gtcgacgagg aactgaaaaa    780
ccagaaagtt aactggtaag tttagtcttt ttgtctttta tttcaggtcc cagatctagg    840
gctctgcgtt tgctccaggt agtccgctgc tcccttgggc ctgggcccac tgacagccct    900
ggtgcctctg gccggctgca cacctcctgg cgggcagctg tgaagctggt gagccactgt    960
tcttgttctg gcaatacctg agaacagtcc cccaccagct tcacggaggc ctgccctgac   1020
tgcccacggt gccgtggcca aagaggatct aagggcaccg ctgagggcct acctaaccat   1080
cgtggggaat aaggacagtg tcacccctgc aggggatccg gtggtggtgc aaatcaaaga   1140
actgctcctc agtggatgtt gcctttactt ctaggcctgt acggaagtgt tacttctgct   1200
ctaaaagctg cggaattgta cccgcggccg atccaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagttcat ctgcaccacc ggcaagctgc ccgtgccctg gcccaccctc gtgaccaccc   1440
tgacctacgg cgtgcagtgc ttcagccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcatgg ccgacaagca gaagaacggc atcaaggtga   1740
acttcaagat ccgccacaac atcgaggacg gcagcgtgca gctcgccgac cactaccagc   1800
agaacacccc catcggcgac ggccccgtgc tgctgcccga caaccactac ctgagcaccc   1860
agtccgccct gagcaaagac cccaacgaga agcgcgatca catggtcctg ctggagttcg   1920
tgaccgccgc cgggatcact ctcggcatgg acgagctgta caagtaaagc ggccatcaag   1980
cttatcgata ccgtcgacta gagctcgctg atcagcctcg actgtgcctt ctagttgcca   2040
gccatctgtt gtttgcccct cccccgtgcc ttccttgacc ctggaaggtg ccactcccac   2100
tgtcctttcc taataaaatg aggaaattgc atcgcattgt ctgagtaggt gtcattctat   2160
tctggggggt ggggtggggc aggacagcaa gggggaggat tgggaagaca attaggtaga   2220
taagtagcat ggcgggttaa tcattaacta caaggaaccc ctagtgatgg agttggccac   2280
tccctctctg cgcgctcgct cgctcactga ggccgggcga ccaaaggtcg cccgacgccc   2340
gggctttgcc cgggcggcct cagtgagcga gcgagcgcgc agccttaatt aacctaattc   2400
actggccgtc gttttacaac gtcgtgactg ggaaaaccct ggcgttaccc aacttaatcg   2460
ccttgcagca catccccctt tcgccagctg gcgtaatagc gaagaggccc gcaccgatcg   2520
```

-continued

```
cccttcccaa cagttgcgca gcctgaatgg cgaatgggac gcgccctgta gcggcgcatt   2580
aagcgcggcg ggtgtggtgg ttacgcgcag cgtgaccgct acacttgcca gcgccctagc   2640
gcccgctcct ttcgctttct tcccttcctt tctcgccacg ttcgccggct ttccccgtca   2700
agctctaaat cgggggctcc ctttagggtt ccgatttagt gctttacggc acctcgaccc   2760
caaaaaactt gattagggtg atggttcacg tagtgggcca tcgccctgat agacggtttt   2820
tcgccctttg acgttggagt ccacgttctt taatagtgga ctcttgttcc aaactggaac   2880
aacactcaac cctatctcgg tctattcttt tgatttataa gggattttgc cgatttcggc   2940
ctattggtta aaaaatgagc tgatttaaca aaaatttaac gcgaatttta acaaaatatt   3000
aacgcttaca atttaggtgg cacttttcgg ggaaatgtgc gcggaacccc tatttgttta   3060
tttttctaaa tacattcaaa tatgtatccg ctcatgagac aataaccctg ataaatgctt   3120
caataatatt gaaaaaggaa gagtatgagt attcaacatt tccgtgtcgc ccttattccc   3180
ttttttgcgg cattttgcct tcctgttttt gctcacccag aaacgctggt gaaagtaaaa   3240
gatgctgaag atcagttggg tgcacgagtg ggttacatcg aactggatct caacagcggt   3300
aagatccttg agagttttcg ccccgaagaa cgttttccaa tgatgagcac ttttaaagtt   3360
ctgctatgtg gcgcggtatt atcccgtatt gacgccgggc aagagcaact cggtcgccgc   3420
atacactatt ctcagaatga cttggttgag tactcaccag tcacagaaaa gcatcttacg   3480
gatggcatga cagtaagaga attatgcagt gctgccataa ccatgagtga taacactgcg   3540
gccaacttac ttctgacaac gatcggagga ccgaaggagc taaccgcttt tttgcacaac   3600
atgggggatc atgtaactcg ccttgatcgt tgggaaccgg agctgaatga agccatacca   3660
aacgacgagc gtgacaccac gatgcctgta gcaatggcaa caacgttgcg caaactatta   3720
actggcgaac tacttactct agcttcccgg caacaattaa tagactggat ggaggcggat   3780
aaagttgcag gaccacttct gcgctcggcc cttccggctg gctggtttat tgctgataaa   3840
tctggagccg gtgagcgtgg gtctcgcggt atcattgcag cactggggcc agatggtaag   3900
ccctcccgta tcgtagttat ctacacgacg gggagtcagg caactatgga tgaacgaaat   3960
agacagatcg ctgagatagg tgcctcactg attaagcatt ggtaactgtc agaccaagtt   4020
tactcatata tactttagat tgatttaaaa cttcattttt aatttaaaag gatctaggtg   4080
aagatccttt ttgataatct catgaccaaa atcccttaac gtgagttttc gttccactga   4140
gcgtcagacc ccgtagaaaa gatcaaagga tcttcttgag atcctttttt tctgcgcgta   4200
atctgctgct tgcaaacaaa aaaaccaccg ctaccagcgg tggtttgttt gccggatcaa   4260
gagctaccaa ctctttttcc gaaggtaact ggcttcagca gagcgcagat accaaatact   4320
gttcttctag tgtagccgta gttaggccac cacttcaaga actctgtagc accgcctaca   4380
tacctcgctc tgctaatcct gttaccagtg gctgctgcca gtggcgataa gtcgtgtctt   4440
accgggttgg actcaagacg atagttaccg gataaggcgc agcggtcggg ctgaacgggg   4500
ggttcgtgca cacagcccag cttggagcga acgacctaca ccgaactgag atacctacag   4560
cgtgagctat gagaaagcgc cacgcttccc gaagggagaa aggcggacag gtatccggta   4620
agcggcaggg tcggaacagg agagcgcacg agggagcttc cagggggaaa cgcctggtat   4680
ctttatagtc ctgtcgggtt tcgccacctc tgacttgagc gtcgattttt gtgatgctcg   4740
tcaggggggc ggagcctatg gaaaaacgcc agcaacgcgg cctttttacg gttcctggcc   4800
ttttgctggc cttttgctca catgttcttt cctgcgttat cccctgattc tgtggataac   4860
cgtattaccg cctttgagtg agctgatacc gctcgccgca gccgaacgac cgagcgcagc   4920
```

gagtcagtga gcgaggaagc ggaagagcgc ccaatacgca aaccgcctct ccccgcgcgt 4980
tggccgattc attaatgcag ctggcacgac aggtttcccg actggaaagc gggcagtgag 5040
cgcaacgcaa ttaatgtgag ttagctcact cattaggcac cccaggcttt acactttatg 5100
cttccggctc gtatgttgtg tggaattgtg agcggataac aatttcacac aggaaacagc 5160
tatgaccatg attacgccag atttaattaa ggccttaatt agg 5203

<210> SEQ ID NO 22
<211> LENGTH: 6290
<212> TYPE: DNA
<213> ORGANISM: Homo sapiens

<400> SEQUENCE: 22
agatctgcgc agcaccatgg cctgaaataa cctctgaaag aggaacttgg ttaggtacct 60
tctgaggcgg aaagaaccag ctgtggaatg tgtgtcagtt agggtgtgga aagtccccag 120
gctccccagc aggcagaagt atgcaaagca tgcatctcaa ttagtcagca accaggtgtg 180
gaaagtcccc aggctcccca gcaggcagaa gtatgcaaag catgcatctc aattagtcag 240
caaccatagt cccgccccta actccgccca tcccgcccct aactccgccc agttccgccc 300
attctccgcc ccatggctga ctaatttttt ttatttatgc agaggccgag gccgcctcgg 360
cctctgagct attccagaag tagtgaggag gcttttttgg aggcctaggc ttttgcaaaa 420
agcttgattc ttctgacaca acagtctcga acttaagctg cagaagttgg tcgtgaggca 480
ctgggcaggt aagtatcaag gttacaagac aggtttaagg agaccaatag aaactgggct 540
tgtcgagaca gagaagactc ttgcgtttct gataggcacc tattggtctt actgacatcc 600
actttgcctt tctctccaca ggtgtccact cccagttcaa ttacagctct taaggctaga 660
gtacttaata cgactcacta taggctagcc accatggctt ccaaggtgta cgaccccgag 720
caacgcaaac gcatgatcac tgggcctcag tggtgggctc gctgcaagca aatgaacgtg 780
ctggactcct tcatcaacta ctatgattcc gagaagcacg ccgagaacgc cgtgattttt 840
ctgcatggta acgctgcctc cagctacctg tggaggcacg tcgtgcctca catcgagccc 900
gtggctagat gcatcatccc tgatctgatc ggaatgggta agtccggcaa gagcgggaat 960
ggctcatatc gcctcctgga tcactacaag tacctcaccg cttggttcga gctgctgaac 1020
cttccaaaga aaatcatctt tgtgggccac gactgggggg cttgtctggc ctttcactac 1080
tcctacgagc accaagacaa gatcaaggcc atcgtccatg ctgagagtgt cgtggacgtg 1140
atcgagtcct gggacgagtg gcctgacatc gaggaggata tcgccctgat caagagcgaa 1200
gagggcgaga aaatggtgct tgagaataac ttcttcgtcg agaccatgct cccaagcaag 1260
atcatgcgga aactggagcc tgaggagttc gctgcctacc tggagccatt caaggagaag 1320
ggcgaggtta gacggcctac cctctcctgg cctcgcgaga tccctctcgt taagggaggc 1380
aagcccgacg tcgtccagat tgtccgcaac tacaacgcct accttcgggc cagcgacgat 1440
ctgcctaaga tgttcatcga gtccgaccct gggttctttt ccaacgctat tgtcgaggga 1500
gctaagaagt tccctaacac cgagttcgtg aaggtgaagg gcctccactt cagccaggag 1560
gacgctccag atgaaatggg taagtacatc aagagcttcg tggagcgcgt gctgaagaac 1620
gagcagtaat tctaggcgat cgctcgaggg tacaaagaac agtggctcgc cagattacac 1680
tgttggagtg cggccgctgg ccgcaataaa atatctttat tttcattaca tctgtgtgtt 1740
ggttttttgt gtgaggatct aaatgagtct tcggacctcg cgggggccgc ttaagcggtg 1800

-continued

```
gttagggttt gtctgacgcg gggggagggg gaaggaacga aacactctca ttcggaggcg   1860
gctcggggtt tggtcttggt ggccacgggc acgcagaaga gcgccgcgat cctcttaagc   1920
acccccccgc cctccgtgga ggcgggggtt tggtcggcgg gtggtaactg gcgggccgct   1980
gactcgggcg ggtcgcgcgc cccagagtgt gaccttttcg gtctgctcgc agacccccgg   2040
gcggcgccgc cgcggcggcg acgggctcgc tgggtcctag gctccatggg gaccgtatac   2100
gtggacaggc tctggagcat ccgcacgact gcggtgatat taccggagac cttctgcggg   2160
acgagccggg tcacgcggct gacgcggagc gtccgttggg cgacaaacac caggacgggg   2220
cacaggtaca ctatcttgtc acccggaggc gcgagggact gcaggagctt cagggagtgg   2280
cgcagctgct tcatccccgt ggcccgttgc tcgcgtttgc tggcggtgtc cccggaagaa   2340
atatatttgc atgtctttag ttctatgatg acacaaaccc cgcccagcgt cttgtcattg   2400
gcgaattcga acacgcagat gcagtcgggg cggcgcggtc ccaggtccac ttcgcatatt   2460
aaggtgacgc gtgtggcctc gaacaccgag cgaccctgca gcgacccgct taaaagcttg   2520
gcattccggt actgttggta aagccaccat ggccgatgct aagaacatta agaagggccc   2580
tgctcccttc taccctctgg aggatggcac cgctggcgag cagctgcaca aggccatgaa   2640
gaggtatgcc ctggtgcctg gcaccattgc cttcaccgat gcccacattg aggtggacat   2700
cacctatgcc gagtacttcg agatgtctgt gcgcctggcc gaggccatga agaggtacgg   2760
cctgaacacc aaccaccgca tcgtggtgtg ctctgagaac tctctgcagt tcttcatgcc   2820
agtgctgggc gccctgttca tcggagtggc cgtggcccct gctaacgaca tttacaacga   2880
gcgcgagctg ctgaacagca tgggcatttc tcagcctacc gtggtgttcg tgtctaagaa   2940
gggcctgcag aagatcctga acgtgcagaa gaagctgcct atcatccaga agatcatcat   3000
catggactct aagaccgact accagggctt ccagagcatg tacacattcg tgacatctca   3060
tctgcctcct ggcttcaacg agtacgactt cgtgccagag tctttcgaca gggacaaaac   3120
cattgccctg atcatgaaca gctctgggtc taccggcctg cctaagggcg tggccctgcc   3180
tcatcgcacc gcctgtgtgc gcttctctca cgcccgcgac cctattttcg gcaaccagat   3240
catccccgac accgctattc tgagcgtggt gccattccac cacggcttcg gcatgttcac   3300
caccctgggc tacctgattt gcggctttcg ggtggtgctg atgtaccgct tcgaggagga   3360
gctgttcctg cgcagcctgc aagactacaa aattcagtct gccctgctgg tgccaaccct   3420
gttcagcttc ttcgctaaga gcaccctgat cgacaagtac gacctgtcta acctgcacga   3480
gattgcctct ggcggcgccc cactgtctaa ggaggtgggc gaagccgtgg ccaagcgctt   3540
tcatctgcca ggcatccgcc agggctacgg cctgaccgag acaaccagcg ccattctgat   3600
taccccagag ggcgacgaca agcctggcgc cgtgggcaag gtggtgccat tcttcgaggc   3660
caaggtggtg gacctggaca ccggcaagac cctgggagtg aaccagcgcg gcgagctgtg   3720
tgtgcgcggc cctatgatta tgtccggcta cgtgaataac cctgaggcca caaacgccct   3780
gatcgacaag gacggctggc tgcactctgg cgacattgcc tactgggacg aggacgagca   3840
cttcttcatc gtggaccgcc tgaagtctct gatcaagtac aagggctacc aggtggcccc   3900
agccgagctg gagtctatcc tgctgcagca ccctaacatt ttcgacgccg gagtggccgg   3960
cctgcccgac gacgatgccg gcgagctgcc tgccgccgtc gtcgtgctgg aacacggcaa   4020
gaccatgacc gagaaggaga tcgtggacta tgtggccagc caggtgacaa ccgccaagaa   4080
gctgcgcggc ggagtggtgt tcgtggacga ggtgcccaag ggcctgaccg gcaagctgga   4140
cgcccgcaag atccgcgaga tcctgatcaa ggctaagaaa ggcggcaaga tcgccgtgta   4200
```

```
ataattctag agtcggggcg gccggccgct tcgagcagac atgataagat acattgatga   4260
gtttggacaa accacaacta gaatgcagtg aaaaaaatgc tttatttgtg aaatttgtga   4320
tgctattgct ttatttgtaa ccattataag ctgcaataaa caagttaaca acaacaattg   4380
cattcatttt atgtttcagg ttcaggggga ggtgtgggag gtttttttaaa gcaagtaaaa   4440
cctctacaaa tgtggtaaaa tcgataagga tccaggtggc acttttcggg gaaatgtgcg   4500
cggaacccct atttgtttat ttttctaaat acattcaaat atgtatccgc tcatgagaca   4560
ataaccctga taaatgcttc aataatattg aaaaaggaag agtatgagta ttcaacattt   4620
ccgtgtcgcc cttattccct tttttgcggc attttgcctt cctgtttttg ctcacccaga   4680
aacgctggtg aaagtaaaag atgctgaaga tcagttgggt gcacgagtgg gttacatcga   4740
actggatctc aacagcggta agatccttga gagttttcgc cccgaagaac gttttccaat   4800
gatgagcact tttaaagttc tgctatgtgg cgcggtatta tcccgtattg acgccgggca   4860
agagcaactc ggtcgccgca tacactattc tcagaatgac ttggttgagt actcaccagt   4920
cacagaaaag catcttacgg atggcatgac agtaagagaa ttatgcagtg ctgccataac   4980
catgagtgat aacactgcgg ccaacttact tctgacaacg atcggaggac cgaaggagct   5040
aaccgctttt ttgcacaaca tgggggatca tgtaactcgc cttgatcgtt gggaaccgga   5100
gctgaatgaa gccataccaa acgacgagcg tgacaccacg atgcctgtag caatggcaac   5160
aacgttgcgc aaactattaa ctggcgaact acttactcta gcttcccggc aacaattaat   5220
agactggatg gaggcggata aagttgcagg accacttctg cgctcggccc ttccggctgg   5280
ctggtttatt gctgataaat ctggagccgg tgagcgtggg tctcgcggta tcattgcagc   5340
actggggcca gatggtaagc cctcccgtat cgtagttatc tacacgacgg ggagtcaggc   5400
aactatggat gaacgaaata gacagatcgc tgagataggt gcctcactga ttaagcattg   5460
gtaactgtca gaccaagttt actcatatat actttagatt gatttaaaac ttcattttta   5520
atttaaaagg atctaggtga agatcctttt tgataatctc atgaccaaaa tcccttaacg   5580
tgagttttcg ttccactgag cgtcagaccc cgtagaaaag atcaaaggat cttcttgaga   5640
tccttttttt ctgcgcgtaa tctgctgctt gcaaacaaaa aaaccaccgc taccagcggt   5700
ggtttgtttg ccggatcaag agctaccaac tctttttccg aaggtaactg gcttcagcag   5760
agcgcagata ccaaatactg ttcttctagt gtagccgtag ttaggccacc acttcaagaa   5820
ctctgtagca ccgcctacat acctcgctct gctaatcctg ttaccagtgg ctgctgccag   5880
tggcgataag tcgtgtctta ccgggttgga ctcaagacga tagttaccgg ataaggcgca   5940
gcggtcgggc tgaacggggg gttcgtgcac acagcccagc ttggagcgaa cgacctacac   6000
cgaactgaga tacctacagc gtgagctatg agaaagcgcc acgcttcccg aagggagaaa   6060
ggcggacagg tatccggtaa gcggcagggt cggaacagga gagcgcacga gggagcttcc   6120
agggggaaac gcctggtatc tttatagtcc tgtcgggttt cgccacctct gacttgagcg   6180
tcgatttttg tgatgctcgt caggggggcg gagcctatgg aaaaacgcca gcaacgcggc   6240
ctttttacgg ttcctggcct tttgctggcc ttttgctcac atggctcgac               6290
```

<210> SEQ ID NO 23
<211> LENGTH: 6290
<212> TYPE: DNA
<213> ORGANISM: Artificial Sequence
<220> FEATURE:
<223> OTHER INFORMATION: Synthetic -continued

<400> SEQUENCE: 23

```
agatctgcgc agcaccatgg cctgaaataa cctctgaaag aggaacttgg ttaggtacct     60
tctgaggcgg aaagaaccag ctgtggaatg tgtgtcagtt agggtgtgga aagtccccag    120
gctccccagc aggcagaagt atgcaaagca tgcatctcaa ttagtcagca accaggtgtg    180
gaaagtcccc aggctcccca gcaggcagaa gtatgcaaag catgcatctc aattagtcag    240
caaccatagt cccgccccta actccgccca tcccgcccct aactccgccc agttccgccc    300
attctccgcc ccatggctga ctaatttttt ttatttatgc agaggccgag gccgcctcgg    360
cctctgagct attccagaag tagtgaggag gcttttttgg aggcctaggc ttttgcaaaa    420
agcttgattc ttctgacaca acagtctcga acttaagctg cagaagttgg tcgtgaggca    480
ctgggcaggt aagtatcaag gttacaagac aggtttaagg agaccaatag aaactgggct    540
tgtcgagaca gagaagactc ttgcgtttct gataggcacc tattggtctt actgacatcc    600
actttgcctt tctctccaca ggtgtccact cccagttcaa ttacagctct taaggctaga    660
gtacttaata cgactcacta taggctagcc accatggctt ccaaggtgta cgaccccgag    720
caacgcaaac gcatgatcac tgggcctcag tggtgggctc gctgcaagca aatgaacgtg    780
ctggactcct tcatcaacta ctatgattcc gagaagcacg ccgagaacgc cgtgattttt    840
ctgcatggta acgctgcctc cagctacctg tggaggcacg tcgtgcctca catcgagccc    900
gtggctagat gcatcatccc tgatctgatc ggaatgggta agtccggcaa gagcgggaat    960
ggctcatatc gcctcctgga tcactacaag tacctcaccg cttggttcga gctgctgaac   1020
cttccaaaga aaatcatctt tgtgggccac gactgggggg cttgtctggc ctttcactac   1080
tcctacgagc accaagacaa gatcaaggcc atcgtccatg ctgagagtgt cgtggacgtg   1140
atcgagtcct gggacgagtg gcctgacatc gaggaggata tcgccctgat caagagcgaa   1200
gagggcgaga aaatggtgct tgagaataac ttcttcgtcg agaccatgct cccaagcaag   1260
atcatgcgga aactggagcc tgaggagttc gctgcctacc tggagccatt caaggagaag   1320
ggcgaggtta gacggcctac cctctcctgg cctcgcgaga tccctctcgt taagggaggc   1380
aagcccgacg tcgtccagat tgtccgcaac tacaacgcct accttcgggc cagcgacgat   1440
ctgcctaaga tgttcatcga gtccgaccct gggttctttt ccaacgctat tgtcgaggga   1500
gctaagaagt tccctaacac cgagttcgtg aaggtgaagg gcctccactt cagccaggag   1560
gacgctccag atgaaatggg taagtacatc aagagcttcg tggagcgcgt gctgaagaac   1620
gagcagtaat tctaggcgat cgctcgaggg tacaaagaac agtggctcac cagattacac   1680
tgttggagtg cggccgctgg ccgcaataaa atatctttat tttcattaca tctgtgtgtt   1740
ggttttttgt gtgaggatct aaatgagtct tcggacctcg cgggggccgc ttaagcggtg   1800
gttagggttt gtctgacgcg gggggagggg gaaggaacga aacactctca ttcggaggcg   1860
gctcggggtt tggtcttggt ggccacgggc acgcagaaga gcgccgcgat cctcttaagc   1920
acccccccgc cctccgtgga ggcgggggtt tggtcggcgg gtggtaactg gcgggccgct   1980
gactcgggcg ggtcgcgcgc cccagagtgt gaccttttcg gtctgctcgc agacccccgg   2040
gcggcgccgc cgcggcggcg acgggctcgc tgggtcctag gctccatggg gaccgtatac   2100
gtggacaggc tctggagcat ccgcacgact gcggtgatat taccggagac cttctgcggg   2160
acgagccggg tcacgcggct gacgcggagc gtccgttggg cgacaaacac caggacgggg   2220
cacaggtaca ctatcttgtc acccggaggc gcgagggact gcaggagctt cagggagtgg   2280
cgcagctgct tcatccccgt ggcccgttgc tcgcgtttgc tggcggtgtc cccggaagaa   2340
```

-continued

```
atatatttgc atgtctttag ttctatgatg acacaaaccc cgcccagcgt cttgtcattg   2400
gcgaattcga acacgcagat gcagtcgggg cggcgcggtc ccaggtccac ttcgcatatt   2460
aaggtgacgc gtgtggcctc gaacaccgag cgaccctgca gcgacccgct taaaagcttg   2520
gcattccggt actgttggta aagccaccat ggccgatgct aagaacatta agaagggccc   2580
tgctcccttc taccctctgg aggatggcac cgctggcgag cagctgcaca aggccatgaa   2640
gaggtatgcc ctggtgcctg gcaccattgc cttcaccgat gcccacattg aggtggacat   2700
cacctatgcc gagtacttcg agatgtctgt gcgcctggcc gaggccatga agaggtacgg   2760
cctgaacacc aaccaccgca tcgtggtgtg ctctgagaac tctctgcagt tcttcatgcc   2820
agtgctgggc gccctgttca tcggagtggc cgtggcccct gctaacgaca tttacaacga   2880
gcgcgagctg ctgaacagca tgggcatttc tcagcctacc gtggtgttcg tgtctaagaa   2940
gggcctgcag aagatcctga acgtgcagaa gaagctgcct atcatccaga agatcatcat   3000
catggactct aagaccgact accagggctt ccagagcatg tacacattcg tgacatctca   3060
tctgcctcct ggcttcaacg agtacgactt cgtgccagag tctttcgaca gggacaaaac   3120
cattgccctg atcatgaaca gctctgggtc taccggcctg cctaagggcg tggccctgcc   3180
tcatcgcacc gcctgtgtgc gcttctctca cgcccgcgac cctattttcg gcaaccagat   3240
catccccgac accgctattc tgagcgtggt gccattccac cacggcttcg gcatgttcac   3300
caccctgggc tacctgattt gcggctttcg ggtggtgctg atgtaccgct tcgaggagga   3360
gctgttcctg cgcagcctgc aagactacaa aattcagtct gccctgctgg tgccaaccct   3420
gttcagcttc ttcgctaaga gcaccctgat cgacaagtac gacctgtcta acctgcacga   3480
gattgcctct ggcggcgccc cactgtctaa ggaggtgggc gaagccgtgg ccaagcgctt   3540
tcatctgcca ggcatccgcc agggctacgg cctgaccgag acaaccagcg ccattctgat   3600
taccccagag ggcgacgaca agcctggcgc cgtgggcaag gtggtgccat tcttcgaggc   3660
caaggtggtg gacctggaca ccggcaagac cctgggagtg aaccagcgcg gcgagctgtg   3720
tgtgcgcggc cctatgatta tgtccggcta cgtgaataac cctgaggcca caaacgccct   3780
gatcgacaag gacggctggc tgcactctgg cgacattgcc tactgggacg aggacgagca   3840
cttcttcatc gtggaccgcc tgaagtctct gatcaagtac aagggctacc aggtggcccc   3900
agccgagctg gagtctatcc tgctgcagca ccctaacatt ttcgacgccg gagtggccgg   3960
cctgcccgac gacgatgccg gcgagctgcc tgccgccgtc gtcgtgctgg aacacggcaa   4020
gaccatgacc gagaaggaga tcgtggacta tgtggccagc caggtgacaa ccgccaagaa   4080
gctgcgcggc ggagtggtgt tcgtggacga ggtgcccaag ggcctgaccg gcaagctgga   4140
cgcccgcaag atccgcgaga tcctgatcaa ggctaagaaa ggcggcaaga tcgccgtgta   4200
ataattctag agtcggggcg gccggccgct tcgagcagac atgataagat acattgatga   4260
gtttggacaa accacaacta gaatgcagtg aaaaaaatgc tttatttgtg aaatttgtga   4320
tgctattgct ttatttgtaa ccattataag ctgcaataaa caagttaaca acaacaattg   4380
cattcatttt atgtttcagg ttcaggggga ggtgtgggag gtttttttaaa gcaagtaaaa   4440
cctctacaaa tgtggtaaaa tcgataagga tccaggtggc acttttcggg gaaatgtgcg   4500
cggaacccct atttgtttat ttttctaaat acattcaaat atgtatccgc tcatgagaca   4560
ataaccctga taaatgcttc aataatattg aaaaaggaag agtatgagta ttcaacattt   4620
ccgtgtcgcc cttattccct tttttgcggc attttgcctt cctgtttttg ctcacccaga   4680
```

aacgctggtg aaagtaaaag atgctgaaga tcagttgggt gcacgagtgg gttacatcga 4740
actggatctc aacagcggta agatccttga gagttttcgc cccgaagaac gttttccaat 4800
gatgagcact tttaaagttc tgctatgtgg cgcggtatta tcccgtattg acgccgggca 4860
agagcaactc ggtcgccgca tacactattc tcagaatgac ttggttgagt actcaccagt 4920
cacagaaaag catcttacgg atggcatgac agtaagagaa ttatgcagtg ctgccataac 4980
catgagtgat aacactgcgg ccaacttact tctgacaacg atcggaggac cgaaggagct 5040
aaccgctttt ttgcacaaca tgggggatca tgtaactcgc cttgatcgtt gggaaccgga 5100
gctgaatgaa gccataccaa acgacgagcg tgacaccacg atgcctgtag caatggcaac 5160
aacgttgcgc aaactattaa ctggcgaact acttactcta gcttcccggc aacaattaat 5220
agactggatg gaggcggata aagttgcagg accacttctg cgctcggccc ttccggctgg 5280
ctggtttatt gctgataaat ctggagccgg tgagcgtggg tctcgcggta tcattgcagc 5340
actggggcca gatggtaagc cctcccgtat cgtagttatc tacacgacgg ggagtcaggc 5400
aactatggat gaacgaaata gacagatcgc tgagataggt gcctcactga ttaagcattg 5460
gtaactgtca gaccaagttt actcatatat actttagatt gatttaaaac ttcattttta 5520
atttaaaagg atctaggtga agatcctttt tgataatctc atgaccaaaa tcccttaacg 5580
tgagttttcg ttccactgag cgtcagaccc cgtagaaaag atcaaaggat cttcttgaga 5640 tcctttttt ctgcgcgtaa tctgctgctt gcaaacaaaa aaaccaccgc taccagcggt 5700
ggtttgtttg ccggatcaag agctaccaac tctttttccg aaggtaactg gcttcagcag 5760
agcgcagata ccaaatactg ttcttctagt gtagccgtag ttaggccacc acttcaagaa 5820
ctctgtagca ccgcctacat acctcgctct gctaatcctg ttaccagtgg ctgctgccag 5880
tggcgataag tcgtgtctta ccgggttgga ctcaagacga tagttaccgg ataaggcgca 5940
gcggtcgggc tgaacggggg gttcgtgcac acagcccagc ttggagcgaa cgacctacac 6000
cgaactgaga tacctacagc gtgagctatg agaaagcgcc acgcttcccg aagggagaaa 6060
ggcggacagg tatccggtaa gcggcagggt cggaacagga gagcgcacga gggagcttcc 6120
agggggaaac gcctggtatc tttatagtcc tgtcgggttt cgccacctct gacttgagcg 6180
tcgatttttg tgatgctcgt caggggggcg gagcctatgg aaaaacgcca gcaacgcggc 6240
ctttttacgg ttcctggcct tttgctggcc ttttgctcac atggctcgac 6290

<210> SEQ ID NO 24
<211> LENGTH: 6290
<212> TYPE: DNA
<213> ORGANISM: Artificial Sequence
<220> FEATURE:
<223> OTHER INFORMATION: Synthetic

<400> SEQUENCE: 24
agatctgcgc agcaccatgg cctgaaataa cctctgaaag aggaacttgg ttaggtacct 60
tctgaggcgg aaagaaccag ctgtggaatg tgtgtcagtt agggtgtgga aagtccccag 120
gctccccagc aggcagaagt atgcaaagca tgcatctcaa ttagtcagca accaggtgtg 180
gaaagtcccc aggctcccca gcaggcagaa gtatgcaaag catgcatctc aattagtcag 240
caaccatagt cccgcccta actccgccca tcccgcccct aactccgccc agttccgccc 300
attctccgcc ccatggctga ctaatttttt ttatttatgc agaggccgag gccgcctcgg 360
cctctgagct attccagaag tagtgaggag gcttttttgg aggcctaggc ttttgcaaaa 420
agcttgattc ttctgacaca acagtctcga acttaagctg cagaagttgg tcgtgaggca 480

```
ctgggcaggt aagtatcaag gttacaagac aggtttaagg agaccaatag aaactgggct    540
tgtcgagaca gagaagactc ttgcgtttct gataggcacc tattggtctt actgacatcc    600
actttgcctt tctctccaca ggtgtccact cccagttcaa ttacagctct taaggctaga    660
gtacttaata cgactcacta taggctagcc accatggctt ccaaggtgta cgaccccgag    720
caacgcaaac gcatgatcac tggcctcag tggtgggctc gctgcaagca aatgaacgtg    780
ctggactcct tcatcaacta ctatgattcc gagaagcacg ccgagaacgc cgtgattttt    840
ctgcatggta acgctgcctc cagctacctg tggaggcacg tcgtgcctca catcgagccc    900
gtggctagat gcatcatccc tgatctgatc ggaatgggta agtccggcaa gagcgggaat    960
ggctcatatc gcctcctgga tcactacaag tacctcaccg cttggttcga gctgctgaac   1020
cttccaaaga aaatcatctt tgtgggccac gactgggggg cttgtctggc ctttcactac   1080
tcctacgagc accaagacaa gatcaaggcc atcgtccatg ctgagagtgt cgtggacgtg   1140
atcgagtcct gggacgagtg gcctgacatc gaggaggata tcgccctgat caagagcgaa   1200
gagggcgaga aaatggtgct tgagaataac ttcttcgtcg agaccatgct cccaagcaag   1260
atcatgcgga aactggagcc tgaggagttc gctgcctacc tggagccatt caaggagaag   1320
ggcgaggtta gacggcctac cctctcctgg cctcgcgaga tccctctcgt taagggaggc   1380
aagcccgacg tcgtccagat tgtccgcaac tacaacgcct accttcgggc cagcgacgat   1440
ctgcctaaga tgttcatcga gtccgaccct gggttctttt ccaacgctat tgtcgaggga   1500
gctaagaagt tccctaacac cgagttcgtg aaggtgaagg gcctccactt cagccaggag   1560
gacgctccag atgaaatggg taagtacatc aagagcttcg tggagcgcgt gctgaagaac   1620
gagcagtaat tctaggcgat cgctcgaggg tgcagaggac cgtggcccgg cagatcaccc   1680
tgctggagtg cggccgctgg ccgcaataaa atatctttat tttcattaca tctgtgtgtt   1740
ggtttttgt gtgaggatct aaatgagtct tcggacctcg cgggggccgc ttaagcggtg   1800
gttagggttt gtctgacgcg gggggagggg gaaggaacga aacactctca ttcggaggcg   1860
gctcggggtt tggtcttggt ggccacgggc acgcagaaga gcgccgcgat cctcttaagc   1920
acccccccgc cctccgtgga ggcgggggtt tggtcggcgg gtggtaactg gcgggccgct   1980
gactcgggcg ggtcgcgcgc cccagagtgt gaccttttcg gtctgctcgc agacccccgg   2040
gcggcgccgc cgcggcggcg acgggctcgc tgggtcctag gctccatggg gaccgtatac   2100
gtggacaggc tctggagcat ccgcacgact gcggtgatat taccggagac cttctgcggg   2160
acgagccggg tcacgcggct gacgcggagc gtccgttggg cgacaaacac caggacgggg   2220
cacaggtaca ctatcttgtc acccggaggc gcgagggact gcaggagctt cagggagtgg   2280
cgcagctgct tcatccccgt ggcccgttgc tcgcgtttgc tggcggtgtc cccggaagaa   2340
atatatttgc atgtctttag ttctatgatg acacaaaccc cgcccagcgt cttgtcattg   2400
gcgaattcga acacgcagat gcagtcgggg cggcgcggtc ccaggtccac ttcgcatatt   2460
aaggtgacgc gtgtggcctc gaacaccgag cgaccctgca gcgacccgct taaaagcttg   2520
gcattccggt actgttggta aagccaccat ggccgatgct aagaacatta agaagggccc   2580
tgctcccttc taccctctgg aggatggcac cgctggcgag cagctgcaca aggccatgaa   2640
gaggtatgcc ctggtgcctg gcaccattgc cttcaccgat gcccacattg aggtggacat   2700
cacctatgcc gagtacttcg agatgtctgt gcgcctggcc gaggccatga agaggtacgg   2760
cctgaacacc aaccaccgca tcgtggtgtg ctctgagaac tctctgcagt tcttcatgcc   2820
```

-continued agtgctgggc gccctgttca tcggagtggc cgtggcccct gctaacgaca tttacaacga 2880
gcgcgagctg ctgaacagca tgggcatttc tcagcctacc gtggtgttcg tgtctaagaa 2940
gggcctgcag aagatcctga acgtgcagaa gaagctgcct atcatccaga agatcatcat 3000
catggactct aagaccgact accagggctt ccagagcatg tacacattcg tgacatctca 3060
tctgcctcct ggcttcaacg agtacgactt cgtgccagag tctttcgaca gggacaaaac 3120
cattgccctg atcatgaaca gctctgggtc taccggcctg cctaagggcg tggccctgcc 3180
tcatcgcacc gcctgtgtgc gcttctctca cgcccgcgac cctattttcg gcaaccagat 3240
catccccgac accgctattc tgagcgtggt gccattccac cacggcttcg gcatgttcac 3300
caccctgggc tacctgattt gcggctttcg ggtggtgctg atgtaccgct tcgaggagga 3360
gctgttcctg cgcagcctgc aagactacaa aattcagtct gccctgctgg tgccaaccct 3420
gttcagcttc ttcgctaaga gcaccctgat cgacaagtac gacctgtcta acctgcacga 3480
gattgcctct ggcggcgccc cactgtctaa ggaggtgggc gaagccgtgg ccaagcgctt 3540
tcatctgcca ggcatccgcc agggctacgg cctgaccgag acaaccagcg ccattctgat 3600
taccccagag ggcgacgaca agcctggcgc cgtgggcaag gtggtgccat tcttcgaggc 3660
caaggtggtg gacctggaca ccggcaagac cctgggagtg aaccagcgcg gcgagctgtg 3720
tgtgcgcggc cctatgatta tgtccggcta cgtgaataac cctgaggcca caaacgccct 3780
gatcgacaag gacggctggc tgcactctgg cgacattgcc tactgggacg aggacgagca 3840
cttcttcatc gtggaccgcc tgaagtctct gatcaagtac aagggctacc aggtggcccc 3900
agccgagctg gagtctatcc tgctgcagca ccctaacatt ttcgacgccg gagtggccgg 3960
cctgcccgac gacgatgccg gcgagctgcc tgccgccgtc gtcgtgctgg aacacggcaa 4020
gaccatgacc gagaaggaga tcgtggacta tgtggccagc caggtgacaa ccgccaagaa 4080
gctgcgcggc ggagtggtgt tcgtggacga ggtgcccaag ggcctgaccg gcaagctgga 4140
cgcccgcaag atccgcgaga tcctgatcaa ggctaagaaa ggcggcaaga tcgccgtgta 4200
ataattctag agtcggggcg gccggccgct tcgagcagac atgataagat acattgatga 4260
gtttggacaa accacaacta gaatgcagtg aaaaaaatgc tttatttgtg aaatttgtga 4320
tgctattgct ttatttgtaa ccattataag ctgcaataaa caagttaaca acaacaattg 4380
cattcatttt atgtttcagg ttcaggggga ggtgtgggag gtttttttaaa gcaagtaaaa 4440
cctctacaaa tgtggtaaaa tcgataagga tccaggtggc acttttcggg gaaatgtgcg 4500
cggaacccct atttgtttat ttttctaaat acattcaaat atgtatccgc tcatgagaca 4560
ataaccctga taaatgcttc aataatattg aaaaaggaag agtatgagta ttcaacattt 4620
ccgtgtcgcc cttattccct tttttgcggc attttgcctt cctgtttttg ctcacccaga 4680
aacgctggtg aaagtaaaag atgctgaaga tcagttgggt gcacgagtgg gttacatcga 4740
actggatctc aacagcggta agatccttga gagttttcgc cccgaagaac gttttccaat 4800
gatgagcact tttaaagttc tgctatgtgg cgcggtatta tcccgtattg acgccgggca 4860
agagcaactc ggtcgccgca tacactattc tcagaatgac ttggttgagt actcaccagt 4920
cacagaaaag catcttacgg atggcatgac agtaagagaa ttatgcagtg ctgccataac 4980
catgagtgat aacactgcgg ccaacttact tctgacaacg atcggaggac cgaaggagct 5040
aaccgctttt ttgcacaaca tgggggatca tgtaactcgc cttgatcgtt gggaaccgga 5100
gctgaatgaa gccataccaa acgacgagcg tgacaccacg atgcctgtag caatggcaac 5160
aacgttgcgc aaactattaa ctggcgaact acttactcta gcttcccggc aacaattaat 5220
agactggatg gaggcggata aagttgcagg accacttctg cgctcggccc ttccggctgg 5280
ctggtttatt gctgataaat ctggagccgg tgagcgtggg tctcgcggta tcattgcagc 5340
actggggcca gatggtaagc cctcccgtat cgtagttatc tacacgacgg ggagtcaggc 5400
aactatggat gaacgaaata gacagatcgc tgagataggt gcctcactga ttaagcattg 5460
gtaactgtca gaccaagttt actcatatat actttagatt gatttaaaac ttcattttta 5520
atttaaaagg atctaggtga agatcctttt tgataatctc atgaccaaaa tcccttaacg 5580
tgagttttcg ttccactgag cgtcagaccc cgtagaaaag atcaaaggat cttcttgaga 5640
tccttttttt ctgcgcgtaa tctgctgctt gcaaacaaaa aaaccaccgc taccagcggt 5700
ggtttgtttg ccggatcaag agctaccaac tctttttccg aaggtaactg gcttcagcag 5760
agcgcagata ccaaatactg ttcttctagt gtagccgtag ttaggccacc acttcaagaa 5820
ctctgtagca ccgcctacat acctcgctct gctaatcctg ttaccagtgg ctgctgccag 5880
tggcgataag tcgtgtctta ccgggttgga ctcaagacga tagttaccgg ataaggcgca 5940
gcggtcgggc tgaacggggg gttcgtgcac acagcccagc ttggagcgaa cgacctacac 6000
cgaactgaga tacctacagc gtgagctatg agaaagcgcc acgcttcccg aagggagaaa 6060
ggcggacagg tatccggtaa gcggcagggt cggaacagga gagcgcacga gggagcttcc 6120
agggggaaac gcctggtatc tttatagtcc tgtcgggttt cgccacctct gacttgagcg 6180
tcgatttttg tgatgctcgt caggggggcg gagcctatgg aaaaacgcca gcaacgcggc 6240
ctttttacgg ttcctggcct tttgctggcc ttttgctcac atggctcgac 6290

<210> SEQ ID NO 25
<211> LENGTH: 6091
<212> TYPE: DNA
<213> ORGANISM: Artificial Sequence
<220> FEATURE:
<223> OTHER INFORMATION: Synthetic

<400> SEQUENCE: 25
cttaattagg ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctaccag 180
ggtaatgggg atcctctaga actatagcta gtcgacattg attattgact agttattaat 240
agtaatcaat tacggggtca ttagttcata gcccatatat ggagttccgc gttacataac 300
ttacggtaaa tggcccgcct ggctgaccgc ccaacgaccc ccgcccattg acgtcaataa 360
tgacgtatgt tcccatagta acgccaatag ggactttcca ttgacgtcaa tgggtggagt 420
atttacggta aactgcccac ttggcagtac atcaagtgta tcatatgcca agtacgcccc 480
ctattgacgt caatgacggt aaatggcccg cctggcatta tgcccagtac atgaccttat 540
gggactttcc tacttggcag tacatctacg tattagtcat cgctattacc atgtcgaggc 600
cacgttctgc ttcactctcc ccatctcccc cccctcccca cccccaattt tgtatttatt 660 tatttttaa ttattttgtg cagcgatggg ggcggggggg gggggcgcgc gccaggcggg 720
gcggggcggg gcgaggggcg gggcggggcg aggcggagag gtgcggcggc agccaatcag 780
agcggcgcgc tccgaaagtt tccttttatg gcgaggcggc ggcggcggcg gccctataaa 840
aagcgaagcg cgcggcgggc gggagcacca ccgcggtggc ggccctagag tcgatcgagg 900
aactgaaaaa ccagaaagtt aactggtaag tttagtcttt ttgtctttta tttcaggtcc 960

-continued

```
cagatctagg gctctgcgtt tgctccaggt agtccgctgc tcccttgggc ctgggcccac   1020
tgacagccct ggtgcctctg gccggctgca cacctcctgg cgggcagctg tgtgtaatct   1080
ggtgagccac tgttgttctg gcaatacctg acagtggcag atcagattac acacggaggc   1140
ctgccctgac tgcccacggt gccgtggcca aagaggatct aagggcaccg ctgagggcct   1200
acctaaccat cgtggggaat aaggacagtg tcacccctgc aggggatccg gtggtggtgc   1260
aaatcaaaga actgctcctc agtggatgtt gcctttactt ctaggcctgt acggaagtgt   1320
tacttctgct ctaaaagctg cggaattgta cccgcggccg atccaccggt gaattccgcc   1380
accatggtcg atggagtgat gatcctgcct gtcctgatta tgattgccct gcccagcccc   1440
agcatggaag atgaaaaacc taaagtcaac cctaagctgt atatgtgcgt gtgcgagggc   1500
ctgagctgcg gaaacgagga tcactgcgag ggccagcagt gtttcagctc cctgtccatc   1560
aatgacggct tccacgtgta ccagaagggc tgctttcagg tgtatgagca gggcaagatg   1620
acctgtaaga caccaccttc cccaggacag gcagtggagt gctgtcaggg cgattggtgt   1680
aaccggaata tcaccgccca gctgccaaca aagggcaagt ctttccccgg cacacagaac   1740
tttcacctgg aagtgggcct gatcatcctg agcgtggtgt tcgccgtgtg cctgctggca   1800
tgtctgctgg gagtggccct gagaaagttt aagcggagaa accaggagcg gctgaatcca   1860
agagatgtgg agtacggcac catcgagggc ctgatcacca caaatgtggg cgactctaca   1920
ctggccgacc tgctggatca cagctgcacc agcggctccg gatctggcct gccctttctg   1980
gtgcagagga ccgtggcccg gcagatcacc ctgctggagt gcgtgggcaa gggccggtac   2040
ggagaagtgt ggagaggatc ctggcaggga gagaacgtgg cagtgaagat cttctctagc   2100
cgggatgaga agtcttggtt tagagagaca gagctgtata acacagtgat gctgaggcac   2160
gagaatatcc tgggcttcat cgcctccgac atgacctctc gccactcctc tacacagctg   2220
tggctgatca cccactacca cgagatgggc tccctgtacg attacctcca gctgaccaca   2280
ctggacacag tgtcttgcct gcggatcgtg ctgtctatcg ccagcggcct ggcacacctg   2340
cacatcgaga tctttggaac ccagggcaag ccagcaatcg cacacactga agtctaagaa   2400
catcctggtg aagaagaatg gccagtgctg tatcgccgat ctgggcctgg ccgtgatgca   2460
cagccagtcc accaaccagc tggacgtggg caacaatcct cgggtgggca caaagagata   2520
catggcccca gaggtgctgg atgagacaat ccaggtggac tgcttcgata gctataagag   2580
ggtggacatc tgggcctttg gcctggtgct gtgggaggtg gcaaggagga tggtgagcaa   2640
cggcatcgtg gaggactaca agccaccctt ctatgacgtg gtgcctaatg atccatcctt   2700
tgaggacatg cgcaaggtgg tgtgcgtgga tcagcagagg cccaacatcc ctaatcgctg   2760
gttcagcgac cccaccctga catccctggc caagctgatg aaggagtgtt ggtatcagaa   2820
tcctagcgcc aggctgaccg ccctgcgcat caagaaaact ctgactaaaa tcgacaatag   2880
cctggataaa ctgaaaaccg actgctgacc tgagggcggc cgcgtcgacg gatccgatct   2940
ttttccctct gccaaaaatt atggggacat catgaagccc cttgagcatc tgacttctgg   3000
ctaataaagg aaatttattt tcattgcaat agtgtgttgg aattttttgt gtctctcact   3060
cggaagcaat tcgttgatct gaatttcgac cacccataat acccattacc ctggtagata   3120
agtagcatgg cgggttaatc attaactaca aggaacccct agtgatggag ttggccactc   3180
cctctctgcg cgctcgctcg ctcactgagg ccgggcgacc aaaggtcgcc cgacgcccgg   3240
gctttgcccg ggcggcctca gtgagcgagc gagcgcgcag ccttaattaa cctaattcac   3300
tggccgtcgt tttacaacgt cgtgactggg aaaaccctgg cgttacccaa cttaatcgcc   3360
```

-continued

```
ttgcagcaca tccccctttc gccagctggc gtaatagcga agaggcccgc accgatcgcc   3420
cttcccaaca gttgcgcagc ctgaatggcg aatgggacgc gccctgtagc ggcgcattaa   3480
gcgcggcggg tgtggtggtt acgcgcagcg tgaccgctac acttgccagc gccctagcgc   3540
ccgctccttt cgctttcttc ccttcctttc tcgccacgtt cgccggcttt ccccgtcaag   3600
ctctaaatcg ggggctccct ttagggttcc gatttagtgc tttacggcac ctcgacccca   3660
aaaaacttga ttagggtgat ggttcacgta gtgggccatc gccctgatag acggtttttc   3720
gccctttgac gttggagtcc acgttcttta atagtggact cttgttccaa actggaacaa   3780
cactcaaccc tatctcggtc tattcttttg atttataagg gattttgccg atttcggcct   3840
attggttaaa aaatgagctg atttaacaaa aatttaacgc gaattttaac aaaatattaa   3900
cgcttacaat ttaggtggca cttttcgggg aaatgtgcgc ggaaccccta tttgtttatt   3960
tttctaaata cattcaaata tgtatccgct catgagacaa taaccctgat aaatgcttca   4020
ataatattga aaaaggaaga gtatgagtat tcaacatttc cgtgtcgccc ttattccctt   4080
ttttgcggca ttttgccttc ctgtttttgc tcacccagaa acgctggtga aagtaaaaga   4140
tgctgaagat cagttgggtg cacgagtggg ttacatcgaa ctggatctca acagcggtaa   4200
gatccttgag agttttcgcc ccgaagaacg ttttccaatg atgagcactt ttaaagttct   4260
gctatgtggc gcggtattat cccgtattga cgccgggcaa gagcaactcg gtcgccgcat   4320
acactattct cagaatgact tggttgagta ctcaccagtc acagaaaagc atcttacgga   4380
tggcatgaca gtaagagaat tatgcagtgc tgccataacc atgagtgata acactgcggc   4440
caacttactt ctgacaacga tcggaggacc gaaggagcta accgcttttt tgcacaacat   4500
gggggatcat gtaactcgcc ttgatcgttg ggaaccggag ctgaatgaag ccataccaaa   4560
cgacgagcgt gacaccacga tgcctgtagc aatggcaaca acgttgcgca aactattaac   4620
tggcgaacta cttactctag cttcccggca acaattaata gactggatgg aggcggataa   4680
agttgcagga ccacttctgc gctcggccct tccggctggc tggtttattg ctgataaatc   4740
tggagccggt gagcgtgggt ctcgcggtat cattgcagca ctggggccag atggtaagcc   4800
ctcccgtatc gtagttatct acacgacggg gagtcaggca actatggatg aacgaaatag   4860
acagatcgct gagataggtg cctcactgat taagcattgg taactgtcag accaagttta   4920
ctcatatata ctttagattg atttaaaact tcatttttaa tttaaaagga tctaggtgaa   4980
gatccttttt gataatctca tgaccaaaat cccttaacgt gagttttcgt tccactgagc   5040
gtcagacccc gtagaaaaga tcaaaggatc ttcttgagat cctttttttc tgcgcgtaat   5100
ctgctgcttg caaacaaaaa aaccaccgct accagcggtg gtttgtttgc cggatcaaga   5160
gctaccaact ctttttccga aggtaactgg cttcagcaga gcgcagatac caaatactgt   5220
tcttctagtg tagccgtagt taggccacca cttcaagaac tctgtagcac cgcctacata   5280
cctcgctctg ctaatcctgt taccagtggc tgctgccagt ggcgataagt cgtgtcttac   5340
cgggttggac tcaagacgat agttaccgga taaggcgcag cggtcgggct gaacgggggg   5400
ttcgtgcaca cagcccagct tggagcgaac gacctacacc gaactgagat acctacagcg   5460
tgagctatga gaaagcgcca cgcttcccga agggagaaag gcggacaggt atccggtaag   5520
cggcagggtc ggaacaggag agcgcacgag ggagcttcca gggggaaacg cctggtatct   5580
ttatagtcct gtcgggtttc gccacctctg acttgagcgt cgatttttgt gatgctcgtc   5640
aggggggcgg agcctatgga aaaacgccag caacgcggcc tttttacggt tcctggcctt   5700
```

-continued

```
ttgctggcct tttgctcaca tgttctttcc tgcgttatcc cctgattctg tggataaccg   5760

tattaccgcc tttgagtgag ctgataccgc tcgccgcagc cgaacgaccg agcgcagcga   5820

gtcagtgagc gaggaagcgg aagagcgccc aatacgcaaa ccgcctctcc ccgcgcgttg   5880

gccgattcat taatgcagct ggcacgacag gtttcccgac tggaaagcgg gcagtgagcg   5940

caacgcaatt aatgtgagtt agctcactca ttaggcaccc caggctttac actttatgct   6000

tccggctcgt atgttgtgtg gaattgtgag cggataacaa tttcacacag gaaacagcta   6060

tgaccatgat tacgccagat ttaattaagg c                                  6091
```

```
<210> SEQ ID NO 26
<211> LENGTH: 6095
<212> TYPE: DNA
<213> ORGANISM: Artificial Sequence
<220> FEATURE:
<223> OTHER INFORMATION: Synthetic

<400> SEQUENCE: 26
```

```
cttaattagg ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctaccag    180

ggtaatgggg atcctctaga actatagcta gtcgacattg attattgact agttattaat    240

agtaatcaat tacggggtca ttagttcata gcccatatat ggagttccgc gttacataac    300

ttacggtaaa tggcccgcct ggctgaccgc ccaacgaccc ccgcccattg acgtcaataa    360

tgacgtatgt tcccatagta acgccaatag ggactttcca ttgacgtcaa tgggtggagt    420

atttacggta aactgcccac ttggcagtac atcaagtgta tcatatgcca agtacgcccc    480

ctattgacgt caatgacggt aaatggcccg cctggcatta tgcccagtac atgaccttat    540

gggactttcc tacttggcag tacatctacg tattagtcat cgctattacc atgtcgaggc    600

cacgttctgc ttcactctcc ccatctcccc cccctcccca cccccaattt tgtatttatt    660

tatttttaa ttattttgtg cagcgatggg ggcggggggg gggggcgcgc gccaggcggg    720

gcggggcggg gcgaggggcg gggcggggcg aggcggagag gtgcggcggc agccaatcag    780

agcggcgcgc tccgaaagtt tccttttatg gcgaggcggc ggcggcggcg gccctataaa    840

aagcgaagcg cgcggcgggc gggagcacca ccgcggtggc ggccctagag tcgatcgagg    900

aactgaaaaa ccagaaagtt aactggtaag tttagtcttt ttgtctttta tttcaggtcc    960

cagatctagg gctctgcgtt tgctccaggt agtccgctgc tcccttgggc ctgggcccac   1020

tgacagccct ggtgcctctg gccggctgca cacctcctgg cgggcagctg tggtaatctg   1080

gtgagccact gtttgttctg gcaatacctg aacagtgggc gccagattac cacggaggcc   1140

tgccctgact gcccacggtg ccgtggccaa agaggatcta agggcaccgc tgagggccta   1200

cctaaccatc gtggggaata aggacagtgt caccccctgca ggggatccgg tggtggtgca   1260

aatcaaagaa ctgctcctca gtggatgttg cctttacttc taggcctgta cggaagtgtt   1320

acttctgctc taaaagctgc ggaattgtac ccgcggccga tccaccggtg aattccgcca   1380

ccatggtcga tggagtgatg atcctgcctg tcctgattat gattgccctg cccagcccca   1440

gcatggaaga tgaaaaacct aaagtcaacc ctaagctgta tatgtgcgtg tgcgagggcc   1500

tgagctgcgg aaacgaggat cactgcgagg gccagcagtg tttcagctcc ctgtccatca   1560

atgacggctt ccacgtgtac cagaagggct gctttcaggt gtatgagcag ggcaagatga   1620

cctgtaagac accaccttcc ccaggacagg cagtggagtg ctgtcagggc gattggtgta   1680
```

accggaatat caccgcccag ctgccaacaa agggcaagtc tttccccggc acacagaact 1740
ttcacctgga agtgggcctg atcatcctga gcgtggtgtt cgccgtgtgc ctgctggcat 1800
gtctgctggg agtggccctg agaaagttta agcggagaaa ccaggagcgg ctgaatccaa 1860
gagatgtgga gtacggcacc atcgagggcc tgatcaccac aaatgtgggc gactctacac 1920
tggccgacct gctggatcac agctgcacca gcggctccgg atctggcctg ccctttctgg 1980
tgcagaggac cgtggcccgg cagatcaccc tgctggagtg cgtgggcaag ggccggtacg 2040
gagaagtgtg gagaggatcc tggcagggag agaacgtggc agtgaagatc ttctctagcc 2100
gggatgagaa gtcttggttt agagagacag agctgtataa cacagtgatg ctgaggcacg 2160
agaatatcct gggcttcatc gcctccgaca tgacctctcg ccactcctct acacagctgt 2220
ggctgatcac ccactaccac gagatgggct ccctgtacga ttacctccag ctgaccacac 2280
tggacacagt gtcttgcctg cggatcgtgc tgtctatcgc cagcggcctg gcacacctgc 2340
acatcgagat ctttggaacc cagggcaagc cagcaatcgc acacagagat ctgaagtcta 2400
agaacatcct ggtgaagaag aatggccagt gctgtatcgc cgatctgggc ctggccgtga 2460
tgcacagcca gtccaccaac cagctggacg tgggcaacaa tcctcgggtg ggcacaaaga 2520
gatacatggc cccagaggtg ctggatgaga caatccaggt ggactgcttc gatagctata 2580
agagggtgga catctgggcc tttggcctgg tgctgtggga ggtggcaagg aggatggtga 2640
gcaacggcat cgtggaggac tacaagccac ccttctatga cgtggtgcct aatgatccat 2700
cctttgagga catgcgcaag gtggtgtgcg tggatcagca gaggcccaac atccctaatc 2760
gctggttcag cgaccccacc ctgacatccc tggccaagct gatgaaggag tgttggtatc 2820
agaatcctag cgccaggctg accgccctgc gcatcaagaa aactctgact aaaatcgaca 2880
atagcctgga taaactgaaa accgactgct gacctgaggg cggccgcgtc gacggatccg 2940
atctttttcc ctctgccaaa aattatgggg acatcatgaa gccccttgag catctgactt 3000
ctggctaata aaggaaattt attttcattg caatagtgtg ttggaatttt ttgtgtctct 3060
cactcggaag caattcgttg atctgaattt cgaccaccca taatacccat taccctggta 3120
gataagtagc atggcgggtt aatcattaac tacaaggaac ccctagtgat ggagttggcc 3180
actccctctc tgcgcgctcg ctcgctcact gaggccgggc gaccaaaggt cgcccgacgc 3240
ccgggctttg cccgggcggc ctcagtgagc gagcgagcgc gcagccttaa ttaacctaat 3300
tcactggccg tcgttttaca acgtcgtgac tgggaaaacc ctggcgttac ccaacttaat 3360
cgccttgcag cacatccccc tttcgccagc tggcgtaata gcgaagaggc ccgcaccgat 3420
cgcccttccc aacagttgcg cagcctgaat ggcgaatggg acgcgccctg tagcggcgca 3480
ttaagcgcgg cgggtgtggt ggttacgcgc agcgtgaccg ctacacttgc cagcgcccta 3540
gcgcccgctc ctttcgcttt cttcccttcc tttctcgcca cgttcgccgg ctttccccgt 3600
caagctctaa atcgggggct ccctttaggg ttccgattta gtgctttacg gcacctcgac 3660
cccaaaaaac ttgattaggg tgatggttca cgtagtgggc catcgccctg atagacggtt 3720
tttcgccctt tgacgttgga gtccacgttc tttaatagtg gactcttgtt ccaaactgga 3780
acaacactca accctatctc ggtctattct tttgatttat aagggatttt gccgatttcg 3840
gcctattggt taaaaaatga gctgatttaa caaaaattta acgcgaattt taacaaaata 3900
ttaacgctta caatttaggt ggcacttttc ggggaaatgt gcgcggaacc cctatttgtt 3960
tatttttcta aatacattca aatatgtatc cgctcatgag acaataaccc tgataaatgc 4020

-continued

```
ttcaataata ttgaaaaagg aagagtatga gtattcaaca tttccgtgtc gcccttattc   4080
ccttttttgc ggcattttgc cttcctgttt ttgctcaccc agaaacgctg gtgaaagtaa   4140
aagatgctga agatcagttg ggtgcacgag tgggttacat cgaactggat ctcaacagcg   4200
gtaagatcct tgagagtttt cgccccgaag aacgttttcc aatgatgagc acttttaaag   4260
ttctgctatg tggcgcggta ttatcccgta ttgacgccgg gcaagagcaa ctcggtcgcc   4320
gcatacacta ttctcagaat gacttggttg agtactcacc agtcacagaa aagcatctta   4380
cggatggcat gacagtaaga gaattatgca gtgctgccat aaccatgagt gataacactg   4440
cggccaactt acttctgaca acgatcggag gaccgaagga gctaaccgct tttttgcaca   4500
acatggggga tcatgtaact cgccttgatc gttgggaacc ggagctgaat gaagccatac   4560
caaacgacga gcgtgacacc acgatgcctg tagcaatggc aacaacgttg cgcaaactat   4620
taactggcga actacttact ctagcttccc ggcaacaatt aatagactgg atggaggcgg   4680
ataaagttgc aggaccactt ctgcgctcgg cccttccggc tggctggttt attgctgata   4740
aatctggagc cggtgagcgt gggtctcgcg gtatcattgc agcactgggg ccagatggta   4800
agccctcccg tatcgtagtt atctacacga cggggagtca ggcaactatg gatgaacgaa   4860
atagacagat cgctgagata ggtgcctcac tgattaagca ttggtaactg tcagaccaag   4920
tttactcata tatactttag attgatttaa aacttcattt ttaatttaaa aggatctagg   4980
tgaagatcct ttttgataat ctcatgacca aaatccctta acgtgagttt tcgttccact   5040
gagcgtcaga ccccgtagaa aagatcaaag gatcttcttg agatcctttt tttctgcgcg   5100
taatctgctg cttgcaaaca aaaaaaccac cgctaccagc ggtggtttgt ttgccggatc   5160
aagagctacc aactcttttt ccgaaggtaa ctggcttcag cagagcgcag ataccaaata   5220
ctgttcttct agtgtagccg tagttaggcc accacttcaa gaactctgta gcaccgccta   5280
catacctcgc tctgctaatc ctgttaccag tggctgctgc cagtggcgat aagtcgtgtc   5340
ttaccgggtt ggactcaaga cgatagttac cggataaggc gcagcggtcg ggctgaacgg   5400
ggggttcgtg cacacagccc agcttggagc gaacgaccta caccgaactg agatacctac   5460
agcgtgagct atgagaaagc gccacgcttc ccgaagggag aaaggcggac aggtatccgg   5520
taagcggcag ggtcggaaca ggagagcgca cgagggagct tccaggggga aacgcctggt   5580
atctttatag tcctgtcggg tttcgccacc tctgacttga gcgtcgattt ttgtgatgct   5640
cgtcaggggg gcggagccta tggaaaaacg ccagcaacgc ggccttttta cggttcctgg   5700
ccttttgctg gccttttgct cacatgttct ttcctgcgtt atcccctgat tctgtggata   5760
accgtattac cgcctttgag tgagctgata ccgctcgccg cagccgaacg accgagcgca   5820
gcgagtcagt gagcgaggaa gcggaagagc gcccaatacg caaaccgcct ctccccgcgc   5880
gttggccgat tcattaatgc agctggcacg acaggtttcc cgactggaaa gcgggcagtg   5940
agcgcaacgc aattaatgtg agttagctca ctcattaggc accccaggct ttacacttta   6000
tgcttccggc tcgtatgttg tgtggaattg tgagcggata acaatttcac acaggaaaca   6060
gctatgacca tgattacgcc agatttaatt aaggc                              6095
```

<210> SEQ ID NO 27
<211> LENGTH: 6246
<212> TYPE: DNA
<213> ORGANISM: Artificial Sequence
<220> FEATURE:
<223> OTHER INFORMATION: Synthetic

<400> SEQUENCE: 27

-continued

```
cttaattagg ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctaccag    180
ggtaatgggg atcctctaga actatagcta gtcgacattg attattgact agttattaat    240
agtaatcaat tacggggtca ttagttcata gcccatatat ggagttccgc gttacataac    300
ttacggtaaa tggcccgcct ggctgaccgc ccaacgaccc ccgcccattg acgtcaataa    360
tgacgtatgt tcccatagta acgccaatag ggactttcca ttgacgtcaa tgggtggagt    420
atttacggta aactgcccac ttggcagtac atcaagtgta tcatatgcca agtacgcccc    480
ctattgacgt caatgacggt aaatggcccg cctggcatta tgcccagtac atgaccttat    540
gggactttcc tacttggcag tacatctacg tattagtcat cgctattacc atgtcgaggc    600
cacgttctgc ttcactctcc ccatctcccc cccctcccca cccccaattt tgtatttatt    660
tatttttaa ttattttgtg cagcgatggg ggcggggggg gggggcgcgc gccaggcggg    720
gcggggcggg gcgaggggcg gggcggggcg aggcggagag gtgcggcggc agccaatcag    780
agcggcgcgc tccgaaagtt tccttttatg gcgaggcggc ggcggcggcg gccctataaa    840
aagcgaagcg cgcggcgggc gggagcaagc tttcagatcg cctggagacg ccatccacgc    900
tgttttgacc tccatagaag acaccgggac cgatccagcc tccgcggccg ggaacggtgc    960
attggaacgc ggattccccg tgccaagagt gacgtaagta ccgcctatag agtctatagg   1020
cccacccccct tggcttctta tgcatgctat actgtttttg gcttggggtc tatacacccc   1080
cgcttcctca tgtttgctgc ccgtgaccag cacgtcaacg attttgtggg cacgggcgac   1140
accgcagtgt agtctgagca gtactcgttg ctgccgcgcg cgccaccaga cataatagct   1200
gacagactaa cagactgttc ctttccatgg gtcttttctg caagggctct gcgtttgctc   1260
caggtagtcc gctgctccct tgggcctggg cccactgaca gccctggtgc ctctggccgg   1320
ctgcacacct cctggcgggc agctgtgtgt aatctggtga gccactgttg ttctggcaat   1380
acctgacagt ggcagatcag attacacacg gaggcctgcc ctgactgccc acggtgccgt   1440
ggccaaagag gatctaaggg caccgctgag ggcctaccta accatcgtgg ggaataagga   1500
cagtgtcacc ctgcagtcac cgtcgccgcc accggtgaat tccgccacca tggtcgatgg   1560
agtgatgatc ctgcctgtcc tgattatgat tgccctgccc agccccagca tggaagatga   1620
aaaacctaaa gtcaacccta agctgtatat gtgcgtgtgc gagggcctga gctgcggaaa   1680
cgaggatcac tgcgagggcc agcagtgttt cagctccctg tccatcaatg acggcttcca   1740
cgtgtaccag aagggctgct ttcaggtgta tgagcagggc aagatgacct gtaagacacc   1800
accttcccca ggacaggcag tggagtgctg tcagggcgat tggtgtaacc ggaatatcac   1860
cgcccagctg ccaacaaagg gcaagtcttt ccccggcaca cagaactttc acctggaagt   1920
gggcctgatc atcctgagcg tggtgttcgc cgtgtgcctg ctggcatgtc tgctgggagt   1980
ggccctgaga aagtttaagc ggagaaacca ggagcggctg aatccaagag atgtggagta   2040
cggcaccatc gagggcctga tcaccacaaa tgtgggcgac tctacactgg ccgacctgct   2100
ggatcacagc tgcaccagcg gctccggatc tggcctgccc tttctggtgc agaggaccgt   2160
ggcccggcag atcaccctgc tggagtgcgt gggcaagggc cggtacggag aagtgtggag   2220
aggatcctgg cagggagaga acgtggcagt gaagatcttc tctagccggg atgagaagtc   2280
ttggtttaga gagacagagc tgtataacac agtgatgctg aggcacgaga atatcctggg   2340
```

-continued

```
cttcatcgcc tccgacatga cctctcgcca ctcctctaca cagctgtggc tgatcaccca   2400
ctaccacgag atgggctccc tgtacgatta cctccagctg accacactgg acacagtgtc   2460
ttgcctgcgg atcgtgctgt ctatcgccag cggcctggca cacctgcaca tcgagatctt   2520
tggaacccag ggcaagccag caatcgcaca cagagatctg aagtctaaga acatcctggt   2580
gaagaagaat ggccagtgct gtatcgccga tctgggcctg gccgtgatgc acagccagtc   2640
caccaaccag ctggacgtgg gcaacaatcc tcgggtgggc acaaagagat acatggcccc   2700
agaggtgctg gatgagacaa tccaggtgga ctgcttcgat agctataaga gggtggacat   2760
ctgggccttt ggcctggtgc tgtgggaggt ggcaaggagg atggtgagca acggcatcgt   2820
ggaggactac aagccaccct tctatgacgt ggtgcctaat gatccatcct ttgaggacat   2880
gcgcaaggtg gtgtgcgtgg atcagcagag gcccaacatc cctaatcgct ggttcagcga   2940
ccccaccctg acatccctgg ccaagctgat gaaggagtgt tggtatcaga atcctagcgc   3000
caggctgacc gccctgcgca tcaagaaaac tctgactaaa atcgacaata gcctggataa   3060
actgaaaacc gactgctgac ctgaggatcc gatcttttc cctctgccaa aaattatggg   3120
gacatcatga agccccttga gcatctgact tctggctaat aaaggaaatt tattttcatt   3180
gcaatagtgt gttggaattt tttgtgtctc tcactcggaa gcaattcgtt gatctgaatt   3240
tcgaccaccc ataataccca ttaccctggt agataagtag catggcgggt taatcattaa   3300
ctacaaggaa cccctagtga tggagttggc cactccctct ctgcgcgctc gctcgctcac   3360
tgaggccggg cgaccaaagg tcgcccgacg cccgggcttt gcccgggcgg cctcagtgag   3420
cgagcgagcg cgcagcctta attaacctaa ttcactggcc gtcgttttac aacgtcgtga   3480
ctgggaaaac cctggcgtta cccaacttaa tcgccttgca gcacatcccc ctttcgccag   3540
ctggcgtaat agcgaagagg cccgcaccga tcgcccttcc caacagttgc gcagcctgaa   3600
tggcgaatgg gacgcgccct gtagcggcgc attaagcgcg gcgggtgtgg tggttacgcg   3660
cagcgtgacc gctacacttg ccagcgccct agcgcccgct cctttcgctt tcttcccttc   3720
ctttctcgcc acgttcgccg gctttccccg tcaagctcta aatcgggggc tccctttagg   3780
gttccgattt agtgctttac ggcacctcga ccccaaaaaa cttgattagg gtgatggttc   3840
acgtagtggg ccatcgccct gatagacggt ttttcgccct ttgacgttgg agtccacgtt   3900
ctttaatagt ggactcttgt tccaaactgg aacaacactc aaccctatct cggtctattc   3960
ttttgattta taagggattt tgccgatttc ggcctattgg ttaaaaaatg agctgattta   4020
acaaaaattt aacgcgaatt ttaacaaaat attaacgctt acaatttagg tggcactttt   4080
cggggaaatg tgcgcggaac ccctatttgt ttatttttct aaatacattc aaatatgtat   4140
ccgctcatga gacaataacc ctgataaatg cttcaataat attgaaaaag gaagagtatg   4200
agtattcaac atttccgtgt cgcccttatt cccttttttg cggcattttg ccttcctgtt   4260
tttgctcacc cagaaacgct ggtgaaagta aaagatgctg aagatcagtt gggtgcacga   4320
gtgggttaca tcgaactgga tctcaacagc ggtaagatcc ttgagagttt tcgccccgaa   4380
gaacgttttc caatgatgag cacttttaaa gttctgctat gtggcgcggt attatcccgt   4440
attgacgccg ggcaagagca actcggtcgc cgcatacact attctcagaa tgacttggtt   4500
gagtactcac cagtcacaga aaagcatctt acggatggca tgacagtaag agaattatgc   4560
agtgctgcca taaccatgag tgataacact gcggccaact tacttctgac aacgatcgga   4620
ggaccgaagg agctaaccgc ttttttgcac aacatggggg atcatgtaac tcgccttgat   4680
cgttgggaac cggagctgaa tgaagccata ccaaacgacg agcgtgacac cacgatgcct   4740
```

```
gtagcaatgg caacaacgtt gcgcaaacta ttaactggcg aactacttac tctagcttcc   4800
cggcaacaat taatagactg gatggaggcg gataaagttg caggaccact tctgcgctcg   4860
gcccttccgg ctggctggtt tattgctgat aaatctggag ccggtgagcg tgggtctcgc   4920
ggtatcattg cagcactggg gccagatggt aagccctccc gtatcgtagt tatctacacg   4980
acggggagtc aggcaactat ggatgaacga aatagacaga tcgctgagat aggtgcctca   5040
ctgattaagc attggtaact gtcagaccaa gtttactcat atatacttta gattgattta   5100
aaacttcatt tttaatttaa aaggatctag gtgaagatcc tttttgataa tctcatgacc   5160
aaaatccctt aacgtgagtt ttcgttccac tgagcgtcag accccgtaga aaagatcaaa   5220
ggatcttctt gagatccttt ttttctgcgc gtaatctgct gcttgcaaac aaaaaaacca   5280
ccgctaccag cggtggtttg tttgccggat caagagctac caactctttt tccgaaggta   5340
actggcttca gcagagcgca gataccaaat actgttcttc tagtgtagcc gtagttaggc   5400
caccacttca agaactctgt agcaccgcct acatacctcg ctctgctaat cctgttacca   5460
gtggctgctg ccagtggcga taagtcgtgt cttaccgggt tggactcaag acgatagtta   5520
ccggataagg cgcagcggtc gggctgaacg gggggttcgt gcacacagcc cagcttggag   5580
cgaacgacct acaccgaact gagataccta cagcgtgagc tatgagaaag cgccacgctt   5640
cccgaaggga gaaaggcgga caggtatccg gtaagcggca gggtcggaac aggagagcgc   5700
acgagggagc ttccaggggg aaacgcctgg tatctttata gtcctgtcgg gtttcgccac   5760
ctctgacttg agcgtcgatt tttgtgatgc tcgtcagggg ggcggagcct atggaaaaac   5820
gccagcaacg cggccttttt acggttcctg gccttttgct ggccttttgc tcacatgttc   5880
tttcctgcgt tatcccctga ttctgtggat aaccgtatta ccgcctttga gtgagctgat   5940
accgctcgcc gcagccgaac gaccgagcgc agcgagtcag tgagcgagga agcggaagag   6000
cgcccaatac gcaaaccgcc tctccccgcg cgttggccga ttcattaatg cagctggcac   6060
gacaggtttc ccgactggaa agcgggcagt gagcgcaacg caattaatgt gagttagctc   6120
actcattagg caccccaggc tttacacttt atgcttccgg ctcgtatgtt gtgtggaatt   6180
gtgagcggat aacaatttca cacaggaaac agctatgacc atgattacgc cagatttaat   6240
taaggc                                                              6246
```

```
<210> SEQ ID NO 28
<211> LENGTH: 6246
<212> TYPE: DNA
<213> ORGANISM: Artificial Sequence
<220> FEATURE:
<223> OTHER INFORMATION: Synthetic

<400> SEQUENCE: 28
```

```
cttaattagg ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctaccag    180
ggtaatgggg atcctctaga actatagcta gtcgacattg attattgact agttattaat    240
agtaatcaat tacggggtca ttagttcata gcccatatat ggagttccgc gttacataac    300
ttacggtaaa tggcccgcct ggctgaccgc ccaacgaccc ccgcccattg acgtcaataa    360
tgacgtatgt tcccatagta acgccaatag ggactttcca ttgacgtcaa tgggtggagt    420
atttacggta aactgcccac ttggcagtac atcaagtgta tcatatgcca agtacgcccc    480
```

```
ctattgacgt caatgacggt aaatggcccg cctggcatta tgcccagtac atgaccttat    540
gggactttcc tacttggcag tacatctacg tattagtcat cgctattacc atgtcgaggc    600
cacgttctgc ttcactctcc ccatctcccc cccctcccca cccccaattt tgtatttatt    660
tattttttaa ttattttgtg cagcgatggg ggcggggggg ggggggcgcgc gccaggcggg    720
gcggggcggg gcgaggggcg gggcggggcg aggcggagag gtgcggcggc agccaatcag    780
agcggcgcgc tccgaaagtt tccttttatg gcgaggcggc ggcggcggcg gccctataaa    840
aagcgaagcg cgcggcgggc gggagcaagc tttcagatcg cctggagacg ccatccacgc    900
tgttttgacc tccatagaag acaccgggac cgatccagcc tccgcggccg ggaacggtgc    960
attggaacgc ggattccccg tgccaagagt gacgtaagta ccgcctatag agtctatagg   1020
cccacccccct tggcttctta tgcatgctat actgtttttg gcttggggtc tatacacccc   1080
cgcttcctca tgtttgctgc ccgtgaccag cacgtcaacg attttgtggg cacgggcgac   1140
accgcagtgt agtctgagca gtactcgttg ctgccgcgcg cgccaccaga cataatagct   1200
gacagactaa cagactgttc ctttccatgg gtcttttctg caagggctct gcgtttgctc   1260
caggtagtcc gctgctccct tgggcctggg cccactgaca gccctggtgc ctctggccgg   1320
ctgcacacct cctggcgggc agctgtggta atctggtgag ccactgtttg ttctggcaat   1380
acctgaacag tgggacgcca gattaccacg gaggcctgcc ctgactgccc acggtgccgt   1440
ggccaaagag gatctaaggg caccgctgag ggcctaccta accatcgtgg ggaataagga   1500
cagtgtcacc ctgcagtcac cgtcgccgcc accggtgaat tccgccacca tggtcgatgg   1560
agtgatgatc ctgcctgtcc tgattatgat tgccctgccc agccccagca tggaagatga   1620
aaaacctaaa gtcaacccta agctgtatat gtgcgtgtgc gagggcctga gctgcggaaa   1680
cgaggatcac tgcgagggcc agcagtgttt cagctccctg tccatcaatg acggcttcca   1740
cgtgtaccag aagggctgct ttcaggtgta tgagcagggc aagatgacct gtaagacacc   1800
accttcccca ggacaggcag tggagtgctg tcagggcgat tggtgtaacc ggaatatcac   1860
cgcccagctg ccaacaaagg gcaagtcttt ccccggcaca cagaactttc acctggaagt   1920
gggcctgatc atcctgagcg tggtgttcgc cgtgtgcctg ctggcatgtc tgctgggagt   1980
ggccctgaga aagtttaagc ggagaaacca ggagcggctg aatccaagag atgtggagta   2040
cggcaccatc gagggcctga tcaccacaaa tgtgggcgac tctacactgg ccgacctgct   2100
ggatcacagc tgcaccagcg gctccggatc tggcctgccc tttctggtgc agaggaccgt   2160
ggcccggcag atcaccctgc tggagtgcgt gggcaagggc cggtacggag aagtgtggag   2220
aggatcctgg cagggagaga acgtggcagt gaagatcttc tctagccggg atgagaagtc   2280
ttggtttaga gagacagagc tgtataacac agtgatgctg aggcacgaga atatcctggg   2340
cttcatcgcc tccgacatga cctctcgcca ctcctctaca cagctgtggc tgatcaccca   2400
ctaccacgag atgggctccc tgtacgatta cctccagctg accacactgg acacagtgtc   2460
ttgcctgcgg atcgtgctgt ctatcgccag cggcctggca cacctgcaca tcgagatctt   2520
tggaacccag ggcaagccag caatcgcaca cagagatctg aagtctaaga acatcctggt   2580
gaagaagaat ggccagtgct gtatcgccga tctgggcctg gccgtgatgc acagccagtc   2640
caccaaccag ctggacgtgg gcaacaatcc tcgggtgggc acaaagagat acatggcccc   2700
agaggtgctg gatgagacaa tccaggtgga ctgcttcgat agctataaga gggtggacat   2760
ctgggccttt ggcctggtgc tgtgggaggt ggcaaggagg atggtgagca acggcatcgt   2820
ggaggactac aagccaccct tctatgacgt ggtgcctaat gatccatcct ttgaggacat   2880
```

-continued gcgcaaggtg gtgtgcgtgg atcagcagag gcccaacatc cctaatcgct ggttcagcga 2940
ccccaccctg acatccctgg ccaagctgat gaaggagtgt tggtatcaga atcctagcgc 3000
caggctgacc gccctgcgca tcaagaaaac tctgactaaa atcgacaata gcctggataa 3060
actgaaaacc gactgctgac ctgaggatcc gatcttttc cctctgccaa aaattatggg 3120
gacatcatga agccccttga gcatctgact tctggctaat aaaggaaatt tattttcatt 3180
gcaatagtgt gttggaattt tttgtgtctc tcactcggaa gcaattcgtt gatctgaatt 3240
tcgaccaccc ataataccca ttaccctggt agataagtag catggcgggt taatcattaa 3300
ctacaaggaa cccctagtga tggagttggc cactccctct ctgcgcgctc gctcgctcac 3360
tgaggccggg cgaccaaagg tcgcccgacg cccgggcttt gcccgggcgg cctcagtgag 3420
cgagcgagcg cgcagcctta attaacctaa ttcactggcc gtcgttttac aacgtcgtga 3480
ctgggaaaac cctggcgtta cccaacttaa tcgccttgca gcacatcccc ctttcgccag 3540
ctggcgtaat agcgaagagg cccgcaccga tcgcccttcc caacagttgc gcagcctgaa 3600
tggcgaatgg gacgcgccct gtagcggcgc attaagcgcg gcgggtgtgg tggttacgcg 3660
cagcgtgacc gctacacttg ccagcgccct agcgcccgct cctttcgctt tcttcccttc 3720
ctttctcgcc acgttcgccg gctttccccg tcaagctcta aatcgggggc tccctttagg 3780
gttccgattt agtgctttac ggcacctcga ccccaaaaaa cttgattagg gtgatggttc 3840
acgtagtggg ccatcgccct gatagacggt ttttcgccct ttgacgttgg agtccacgtt 3900
ctttaatagt ggactcttgt tccaaactgg aacaacactc aaccctatct cggtctattc 3960
ttttgattta taagggattt tgccgatttc ggcctattgg ttaaaaaatg agctgattta 4020
acaaaaattt aacgcgaatt ttaacaaaat attaacgctt acaatttagg tggcactttt 4080
cggggaaatg tgcgcggaac ccctatttgt ttatttttct aaatacattc aaatatgtat 4140
ccgctcatga gacaataacc ctgataaatg cttcaataat attgaaaaag gaagagtatg 4200
agtattcaac atttccgtgt cgcccttatt cccttttttg cggcattttg ccttcctgtt 4260
tttgctcacc cagaaacgct ggtgaaagta aaagatgctg aagatcagtt gggtgcacga 4320
gtgggttaca tcgaactgga tctcaacagc ggtaagatcc ttgagagttt tcgccccgaa 4380
gaacgttttc caatgatgag cacttttaaa gttctgctat gtggcgcggt attatcccgt 4440
attgacgccg ggcaagagca actcggtcgc cgcatacact attctcagaa tgacttggtt 4500
gagtactcac cagtcacaga aaagcatctt acggatggca tgacagtaag agaattatgc 4560
agtgctgcca taaccatgag tgataacact gcggccaact tacttctgac aacgatcgga 4620
ggaccgaagg agctaaccgc ttttttgcac aacatggggg atcatgtaac tcgccttgat 4680
cgttgggaac cggagctgaa tgaagccata ccaaacgacg agcgtgacac cacgatgcct 4740
gtagcaatgg caacaacgtt gcgcaaacta ttaactggcg aactacttac tctagcttcc 4800
cggcaacaat taatagactg gatggaggcg gataaagttg caggaccact tctgcgctcg 4860
gcccttccgg ctggctggtt tattgctgat aaatctggag ccggtgagcg tgggtctcgc 4920
ggtatcattg cagcactggg gccagatggt aagccctccc gtatcgtagt tatctacacg 4980
acggggagtc aggcaactat ggatgaacga aatagacaga tcgctgagat aggtgcctca 5040
ctgattaagc attggtaact gtcagaccaa gtttactcat atatacttta gattgattta 5100
aaacttcatt tttaatttaa aaggatctag gtgaagatcc tttttgataa tctcatgacc 5160
aaaatccctt aacgtgagtt ttcgttccac tgagcgtcag accccgtaga aaagatcaaa 5220

-continued

```
ggatcttctt gagatccttt ttttctgcgc gtaatctgct gcttgcaaac aaaaaaacca   5280
ccgctaccag cggtggtttg tttgccggat caagagctac caactctttt tccgaaggta   5340
actggcttca gcagagcgca gataccaaat actgttcttc tagtgtagcc gtagttaggc   5400
caccacttca agaactctgt agcaccgcct acatacctcg ctctgctaat cctgttacca   5460
gtggctgctg ccagtggcga taagtcgtgt cttaccgggt tggactcaag acgatagtta   5520
ccggataagg cgcagcggtc gggctgaacg gggggttcgt gcacacagcc cagcttggag   5580
cgaacgacct acaccgaact gagataccta cagcgtgagc tatgagaaag cgccacgctt   5640
cccgaaggga gaaaggcgga caggtatccg gtaagcggca gggtcggaac aggagagcgc   5700
acgagggagc ttccaggggg aaacgcctgg tatctttata gtcctgtcgg gtttcgccac   5760
ctctgacttg agcgtcgatt tttgtgatgc tcgtcagggg ggcggagcct atggaaaaac   5820
gccagcaacg cggccttttt acggttcctg gccttttgct ggccttttgc tcacatgttc   5880
tttcctgcgt tatcccctga ttctgtggat aaccgtatta ccgcctttga gtgagctgat   5940
accgctcgcc gcagccgaac gaccgagcgc agcgagtcag tgagcgagga agcggaagag   6000
cgcccaatac gcaaaccgcc tctccccgcg cgttggccga ttcattaatg cagctggcac   6060
gacaggtttc ccgactggaa agcgggcagt gagcgcaacg caattaatgt gagttagctc   6120
actcattagg caccccaggc tttacacttt atgcttccgg ctcgtatgtt gtgtggaatt   6180
gtgagcggat aacaatttca cacaggaaac agctatgacc atgattacgc cagatttaat   6240
taaggc                                                              6246
```

<210> SEQ ID NO 29
<211> LENGTH: 7380
<212> TYPE: DNA
<213> ORGANISM: Artificial Sequence
<220> FEATURE:
<223> OTHER INFORMATION: Synthetic

<400> SEQUENCE: 29

```
ccaactccat cactaggggt tcctgcggcc gcaaggtcgg gcaggaagag ggcctatttc     60
ccatgattcc ttcatatttg catatacgat acaaggctgt tagagagata attagaatta    120
atttgactgt aaacacaaag atattagtac aaaatacgtg acgtagaaag taataatttc    180
ttgggtagtt tgcagtttta aaattatgtt ttaaaatgga ctatcatatg cttaccgtaa    240
cttgaaagta tttcgatttc ttggctttat atatcttgtg gaaaggacga aacaccggct    300
caccagatta cactgtgttt tagagctaga aatagcaagt taaaataagg ctagtccgtt    360
atcaacttga aaaagtggca ccgagtcggt gctttttttc tcgagccata gagcccaccg    420
catccccagc atgcctgcta ttgtcttccc aatcctcccc cttgctgtcc tgccccaccc    480
cacccccag aatagaatga cacctactca gacaatgcga tgcaatttcc tcattttatt     540
aggaaaggac agtgggagtg gcaccttcca gggtcaagga aggcacgggg gaggggcaaa    600
caacagatgg ctggcaacta gaaggcacag tcgcaccacg gaattgtcag tgcccaacag    660
ccgagcccct gtccagcagc gggcaaggca ggcggcgatg agttccgccg tggcaagaac    720
taaccaggat ttatacaagg aggagaaaat gaaagccata cgggaagcaa tagcatgata    780
caaaggcatt aaagcagcgt atccacatag cgtaaaagga gcaacatagt taagaatacc    840
agtcaatctt tcacaaattt tgtaatccag aggttgatta tcagatctta gactttcctc    900
ttcttcttgg gctcgaattc gctgccgtcg gcggttcttt ttgagccgcc agagtcacct    960
cccagctgag acaggtcgat ccgtgtctcg tacaggccgg tgatgctctg gtggatcagg   1020
```

-continued

```
gtggcgtcca gcacctcttt ggtgctggtg tacctcttcc ggtcgatggt ggtgtcaaag   1080
tacttgaagg cggcaggggc tcccagattg gtcagggtaa acaggtggat gatattctcg   1140
gcctgctctc tgatgggctt atcccggtgc ttgttgtagg cggacagcac tttgtccaga   1200
ttagcgtcgg ccaggatcac tctcttggag aactcgctga tctgctcgat gatctcgtcc   1260
aggtagtgct tgtgctgttc cacaaacagc tgtttctgct cattatcctc gggggagccc   1320
ttcagcttct catagtggct ggccaggtac aggaagttca catatttgga gggcagggcc   1380
agttcgtttc ccttctgcag ttcgccggca gaggccagca ttctcttccg gccgttttcc   1440
agctcgaaca gggagtactt aggcagcttg atgatcaggt ccttttcac ttctttgtag   1500
cccttggctt ccagaaagtc gatgggattc ttctcgaagc tgcttctttc catgatggtg   1560
atccccagca gctctttcac actcttcagt ttcttggact tgcccttttc cactttggcc   1620
accaccagca cagaataggc cacggtgggg ctgtcgaagc cgccgtactt cttagggtcc   1680
cagtccttct ttctggcgat cagcttatcg ctgttcctct tgggcaggat agactctttg   1740
ctgaagccgc ctgtctgcac ctcggtcttt ttcacgatat tcacttgggg catgctcagc   1800
actttccgca cggtggcaaa atcccggccc ttatcccaca cgatctcccc ggtttcgccg   1860
tttgtctcga tcagaggccg cttccggatc tcgccgttgg ccagggtaat ctcggtcttg   1920
aaaaagttca tgatgttgct gtagaagaag tacttggcgg tagccttgcc gatttcctgc   1980
tcgctcttgg cgatcatctt ccgcacgtcg tacaccttgt agtcgccgta cacgaactcg   2040
ctttccagct tagggtactt tttgatcagg gcggttccca cgacggcgtt caggtaggcg   2100
tcgtgggcgt ggtggtagtt gttgatctcg cgcactttgt aaaactggaa atccttccgg   2160
aaatcggaca ccagcttgga cttcagggtg atcactttca cttcccggat cagcttgtca   2220
ttctcgtcgt acttagtgtt catccgggag tccaggatct gtgccacgtg ctttgtgatc   2280
tgccgggttt ccaccagctg tctcttgatg aagccggcct tatccagttc gctcaggccg   2340
cctctctcgg ccttggtcag attgtcgaac tttctctggg taatcagctt ggcgttcagc   2400
agctgccgcc agtagttctt catcttcttc acgacctctt cggagggcac gttgtcgctc   2460
ttgccccggt tcttgtcgct tctggtcagc accttgttgt cgatggagtc gtccttcaga   2520
aagctctgag gcacgatatg gtccacatcg tagtcggaca gccggttgat gtccagttcc   2580
tggtccacgt acatatcccg cccattctgc aggtagtaca ggtacagctt ctcgttctgc   2640
agctgggtgt tttccacggg gtgttctttc aggatctggc tgcccagctc tttgatgccc   2700
tcttcgatcc gcttcattct ctcgcggctg ttcttctgtc ccttctgggt ggtctggttc   2760
tctctggcca tttcgatcac gatgttctcg ggcttgtgcc ggcccatcac tttcacgagc   2820
tcgtccacca ccttcactgt ctgcaggatg cccttcttaa tggcggggct gccggccaga   2880
ttggcaatgt gctcgtgcag gctatcgccc tggccggaca cctgggcttt ctggatgtcc   2940
tctttaaagg tcaggctgtc gtcgtggatc agctgcatga agtttctgtt ggcgaagccg   3000
tcggacttca ggaaatccag gattgtcttg ccggactgct tgtcccggat gccgttgatc   3060
agcttccggc tcagcctgcc ccagccggtg tatctccgcc gcttcagctg cttcatcact   3120
ttgtcgtcga acaggtgggc ataggttttc agccgttcct cgatcatctc tctgtcctca   3180
aacagtgtca gggtcagcac gatatcttcc agaatgtcct cgttttcctc attgtccagg   3240
aagtccttgt ccttgataat tttcagcaga tcgtggtatg tgcccaggga ggcgttgaac   3300
cgatcttcca cgccggagat ttccacggag tcgaagcaat tgctggcgat aaagccattc   3360
```

```
ttcagggcga agttgtgatc ccgctccacg ccgatgtcgt acacgttctg ctttcccagg   3420
tatttccgtg tagcaatctt gatgactttc cgcttcttct ttggtgactc gaactcgctt   3480
ccgtcggctg tccgtttcat ggtggcaccg gtccaacctg aaaaaaagtg atttcaggca   3540
ggtgctccag gtaattaaac attaataccc caccaaccaa ccatccctta aacccttacc   3600
tcttgctcag ctaattacag cccggaggag aagggccgtc ccgcccgctc acctgtggga   3660
gtaacgcggt cagtcagagc cggggcgggc ggcgcgaggc ggcggcggag cggggcacgg   3720
ggcgaaggca gcgtcgcagc gactcccgcc cgccgcgcgc ttcgcttttt atagggccgc   3780
cgccgccgcc gcctcgccat aaaaggaaac tttcggagcg cgccgctctg attggctgcc   3840
gccgcacctc tccgcctcgc cccgccccgc ccctcgcccc gccccgcccc gcctggcgcg   3900
cgcccccccc cccccccgc ccccatcgct gcacaaaata attaaaaaat aaataaatac   3960
aaaattgggg gtggggaggg gggggagatg gggagagtga agcagaacgt ggggctcacc   4020
tcgaccatgg taatagcgat gactaatacg tagatgtact gccaagtagg aaagtcccat   4080
aaggtcatgt actgggcaca atgccaggcg ggccatttac cgtcattgac gtcaataggg   4140
ggcgtacttg gcatatgata cacttgatgt actgccaagt gggcagttta ccgtaaatac   4200
tccacccatt gacgtcaatg gaaagtccct attggcgtta ctattgacgt caatgggcgg   4260
gggtcgttgg gcggtcagcc aggcgggcca tttaccgtaa gttatgtaac gggtaccctg   4320
atctagaggc cgcaggaacc cctagtgatg gagttggcca ctccctctct gcgcgctcgc   4380
tcgctcactg aggccgggcg accaaaggtc gcccgacgcc cgggctttgc ccgggcggcc   4440
tcagtgagcg agcgagcgcg cagccttaat taaatctggc gtaatcatgg tcatagctgt   4500
ttcctgtgtg aaattgttat ccgctcacaa ttccacacaa catacgagcc ggaagcataa   4560
agtgtaaagc ctggggtgcc taatgagtga gctaactcac attaattgcg ttgcgctcac   4620
tgcccgcttt ccagtcggga aacctgtcgt gccagctgca ttaatgaatc ggccaacgcg   4680
cggggagagg cggtttgcgt attgggcgct cttccgcttc ctcgctcact gactcgctgc   4740
gctcggtcgt tcggctgcgg cgagcggtat cagctcactc aaaggcggta atacggttat   4800
ccacagaatc aggggataac gcaggaaaga acatgtgagc aaaaccgcag caaaaggcca   4860
ggaaccgtaa aaaggccgcg ttgctggcgt ttttccatag gctccgcccc cctgacgagc   4920
atcacaaaaa tcgacgctca agtcagaggt ggcgaaaccc gacaggacta taaagatacc   4980
aggcgtttcc ccctggaagc tccctcgtgc gctctcctgt tccgaccctg ccgcttaccg   5040
gatacctgtc cgcctttctc ccttcgggaa gcgtggcgct ttctcatagc tcacgctgta   5100
ggtatctcag ttcggtgtag gtcgttcgct ccaagctggg ctgtgtgcac gaaccccccg   5160
ttcagcccga ccgctgcgcc ttatccggta actatcgtct tgagtccaac ccggtaagac   5220
acgacttatc gccactggca gcagccactg gtaacaggat tagcagagcg aggtatgtag   5280
gcggtgctac agagttcttg aagtggtggc ctaactacgg ctacactaga aggacagtat   5340
ttggtatctg cgctctgctg aagccagtta ccttcggaaa aagagttggt agctcttgat   5400
ccggcaaaca aaccaccgct ggtagcggtg gtttttttgt ttgcaagcag cagattacgc   5460
gcagaaaaaa aggatctcaa gaagatcctt tgatcttttc tacggggtct gacgctcagt   5520
ggaacgaaaa ctcacgttaa gggattttgg tcatgagatt atcaaaaagg atcttcacct   5580
agatcctttt aaattaaaaa tgaagtttta aatcaatcta aagtatatat gagtaaactt   5640
ggtctgacag ttaccaatgc ttaatcagtg aggcacctat ctcagcgatc tgtctatttc   5700
gttcatccat agttgcctga ctccccgtcg tgtagataac tacgatacgg gagggcttac   5760
```

catctggccc cagtgctgca atgataccgc gagacccacg ctcaccggct ccagatttat 5820
cagcaataaa ccagccagcc ggaagggccg agcgcagaag tggtcctgca actttatccg 5880
cctccatcca gtctattaat tgttgccggg aagctagagt aagtagttcg ccagttaata 5940
gtttgcgcaa cgttgttacc attactacag gcatcgtggt gtcacgctcg tcgtttggta 6000
tggcttcatt cagctccggt tcccaacgat caaggcgagt tacatgatcc cccatgttgt 6060
gcaaaaaagc ggttagctcc ttcggtcctc cgatcgttgt cagaagtaag ttggccgcag 6120
tgttatcact catggttatg gcagcactgc ataattctct tactgtcatg ccatccgtaa 6180
gatgcttttc tgtgactggt gagtactcaa ccaagtcatt ctgagaatag tgtatgcggc 6240
gaccgagttg ctcttgcccg gcgtcaatac gggataatac cgcgccacat agcagaactt 6300
taaaagtgct catcattgga aaacgttctt cggggcgaaa actctcaagg atcttaccgc 6360
tgttgagatc cagttcgatg taacccactc gtgcacccaa ctgatcttca gcatctttta 6420
ctttcaccag cgtttctggg tgagcaaaaa caggaaggca aaatgccgca aaaaagggaa 6480
taagggcgac acggaaatgt tgaatactca tactcttcct ttttcaatat tattgaagca 6540
tttatcaggg ttattgtctc atgagcggat acatatttga atgtatttag aaaaataaac 6600
aaataggggt tccgcgcaca tttccccgaa agatgccacc tgaaattata aacgttaata 6660
ttttgttaaa attcgcgtta aatttttgtt aaatcagctc atttttaac caataggccg 6720 aaatcggcaa aatcccttat aaatcaaaag aatagaccga gatagggttg agtgttgttc 6780
cagtttggaa caagagtcca ctattaaaga acgtggactc caacgtcaaa gggcgaaaaa 6840
ccgtctatca gggcgatggc ccactacgtg aaccatcacc ctaatcaagt tttttggggt 6900
cgaggtgccg taaagcacta aatcggaacc ctaaagggag cccccgattt agagcttgac 6960
ggggaaagcc ggcgaacgtg gcgagaaagg aagggaagaa agcgaaagga gcgggcgcta 7020
gggcgctggc aagtgtagcg gtcacgctgc gcgtaaccac cacacccgcc gcgcttaatg 7080
cgccgctaca gggcgcgtcc cattcgccat tcaggctgcg caactgttgg gaagggcgat 7140
cggtgcgggc ctcttcgcta ttacgccagc tggcgaaagg gggatgtgct gcaaggcgat 7200
taagttgggt aacgccaggg ttttcccagt cacgacgttg taaaacgacg gccagtgaat 7260
taggttaatt aaggctgcgc gctcgctcgc tcactgaggc cgcccgggca aagcccgggc 7320
gtcgggcgac ctttggtcgc ccggcctcag tgagcgagcg agcgcgcaga gagggagtgg 7380

<210> SEQ ID NO 30
<211> LENGTH: 247
<212> TYPE: DNA
<213> ORGANISM: Artificial Sequence
<220> FEATURE:
<223> OTHER INFORMATION: Synthetic

<400> SEQUENCE: 30
tgagctcaca gaggggactt tccgagagat ctacagaggg gactttccga gagcgagctt 60
gggctgcagg tcgaccgtcc atccattcac agcgcttcta taaaggcgcc agctgaggcg 120
cctactactc caaccgcgac tgcagcgagc aactgagaag actggataga gccggcggtt 180
ccgcgaacga gcagtgaccg cgctcccacc cagctctgct ctgcagctcc accagtgtct 240
ctctaga 247

<210> SEQ ID NO 31
<211> LENGTH: 220
<212> TYPE: DNA

<213> ORGANISM: Artificial Sequence
<220> FEATURE:
<223> OTHER INFORMATION: Synthetic

<400> SEQUENCE: 31
gcttcgcgcc ctaagtctgc aggtgacggg ctcaggggcg gggctgggt gggggggagc 60 ggagaatgct ccagcccagt ttgccgtctc catggcgacc gcccgcgcgg cgccagcctg 120
acagcccgtc cgggttttat gaatgggtga cgtcacgggc ctggcgtcta acggtctgag 180
ccgcttgttc agacgctgac acagaccagc ccgggaaagg 220

<210> SEQ ID NO 32
<211> LENGTH: 4688
<212> TYPE: DNA
<213> ORGANISM: Artificial Sequence
<220> FEATURE:
<223> OTHER INFORMATION: Synthetic

<400> SEQUENCE: 32
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgccgcgtcg acattgatta ttgactctgg tcgttacata 180
acttacggta aatggcccgc ctggctgacc gcccaacgac ccccgcccatt gacgtcaata 240 atgacgtatg ttcccatagt aacgccaata gggactttcc attgacgtca atgggtggag 300
tatttacggt aaactgccca cttggcagta catcaagtgt atcatatgcc aagtacgccc 360
cctattgacg tcaatgacgg taaatggccc gcctggcatt atgcccagta catgacctta 420
tgggactttc ctacttggca gtacatctac tcgaggccac gttctgcttc acgcttcgcg 480
ccctaagtct gcaggtgacg ggctcagggg cgggggctgg gtgggggga gcggagaatg 540 ctccagccca gtttgccgtc tccatggcga ccgcccgcgc ggcgccagcc tgacagcccg 600
tccgggtttt atgaatgggt gacgtcacgg gcctggcgtc taacggtctg agccgcttgt 660
tcagacgctg acacagacca gcccgggaaa ggtgagctca cagaggggac tttccgagag 720
atctacagag ggactttcc gagagcgagc ttgggctgca ggtcgaccgt ccatccattc 780
acagcgcttc tataaaggcg ccagctgagg cgcctactac tccaaccgcg actgcagcga 840
gcaactgaga agactggata gagccggcgg ttccgcgaac gagcagtgac cgcgctccca 900
cccagctctg ctctgcagct ccaccagtgt ctctctagag ccaccgcggt ggcggcccta 960
gagtcgatcg aggaactgaa aaaccagaaa gttaactggt aagtttagtc tttttgtctt 1020
ttatttcagg tcccggatcc ggtggtggtg caaatcaaag aactgctcct cagtggatgt 1080
tgcctttact tctaggcctg tacggaagtg ttacttctgc tctaaaagct gcggaattgt 1140
acccgcggcc gatccaccgg tcgccaccat ctagcatggg agtcaaagtt ctgtttgccc 1200
tgatctgcat cgctgtggcc gaggccaagc ccaccgagaa caacgaagac ttcaacatcg 1260
tggccgtggc cagcaacttc gcgaccacgg atctcgatgc tgaccgcggg aagttgcccg 1320
gcaagaagct gccgctggag gtgctcaaag agatggaagc caatgcccgg aaagctggct 1380
gcaccagggg ctgtctgatc tgcctgtccc acatcaagtg cacgcccaag atgaagaagt 1440
tcatcccagg acgctgccac acctacgaag gcgacaaaga gtccgcacag ggcggcatag 1500
gcgaggcgat cgtcgacatt cctgagattc ctgggttcaa ggacttggag cccatggagc 1560
agttcatcgc acaggtcgat ctgtgtgtgg actgcacaac tggctgcctc aaagggcttg 1620
ccaacgtgca gtgttctgac ctgctcaaga agtggctgcc gcaacgctgt gcgacctttg 1680

-continued

```
ccagcaagat ccagggccag gtggacaaga tcaaggggc cggtggtgac tagctcgacg   1740
ctgatcagcc tcgactgtgc cttctagttg ccagccatct gttgtttgcc cctcccccgt   1800
gccttccttg accctggaag gtgccactcc cactgtcctt tcctaataaa atgaggaaat   1860
tgcatcgcat tgtctgagta ggtgtcattc tattctgggg ggtggggtgg ggcaggacag   1920
caagggggag gattgggaag acaaggccgc aggaacccct agtgatggag ttggccactc   1980
cctctctgcg cgctcgctcg ctcactgagg ccgggcgacc aaaggtcgcc cgacgcccgg   2040
gctttgcccg ggcggcctca gtgagcgagc gagcgcgcag ctgcctgcag gggcgcctga   2100
tgcggtattt tctccttacg catctgtgcg gtatttcaca ccgcatacgt caaagcaacc   2160
atagtacgcg ccctgtagcg gcgcattaag cgcggcgggt gtggtggtta cgcgcagcgt   2220
gaccgctaca cttgccagcg ccctagcgcc cgctcctttc gctttcttcc cttcctttct   2280
cgccacgttc gccggctttc cccgtcaagc tctaaatcgg gggctccctt tagggttccg   2340
atttagtgct ttacggcacc tcgaccccaa aaaacttgat ttgggtgatg gttcacgtag   2400
tgggccatcg ccctgataga cggtttttcg ccctttgacg ttggagtcca cgttctttaa   2460
tagtggactc ttgttccaaa ctggaacaac actcaaccct atctcgggct attcttttga   2520
tttataaggg attttgccga tttcggccta ttggttaaaa aatgagctga tttaacaaaa   2580
atttaacgcg aattttaaca aaatattaac gtttacaatt ttatggtgca ctctcagtac   2640
aatctgctct gatgccgcat agttaagcca gccccgacac ccgccaacac ccgctgacgc   2700
gccctgacgg gcttgtctgc tcccggcatc cgcttacaga caagctgtga ccgtctccgg   2760
gagctgcatg tgtcagaggt tttcaccgtc atcaccgaaa cgcgcgagac gaaagggcct   2820
cgtgatacgc ctatttttat aggttaatgt catgataata atggtttctt agacgtcagg   2880
tggcactttt cggggaaatg tgcgcggaac ccctatttgt ttatttttct aaatacattc   2940
aaatatgtat ccgctcatga gacaataacc ctgataaatg cttcaataat attgaaaaag   3000
gaagagtatg agtattcaac atttccgtgt cgcccttatt cccttttttg cggcattttg   3060
ccttcctgtt tttgctcacc cagaaacgct ggtgaaagta aaagatgctg aagatcagtt   3120
gggtgcacga gtgggttaca tcgaactgga tctcaacagc ggtaagatcc ttgagagttt   3180
tcgccccgaa gaacgttttc caatgatgag cacttttaaa gttctgctat gtggcgcggt   3240
attatcccgt attgacgccg ggcaagagca actcggtcgc cgcatacact attctcagaa   3300
tgacttggtt gagtactcac cagtcacaga aaagcatctt acggatggca tgacagtaag   3360
agaattatgc agtgctgcca taaccatgag tgataacact gcggccaact tacttctgac   3420
aacgatcgga ggaccgaagg agctaaccgc ttttttgcac aacatggggg atcatgtaac   3480
tcgccttgat cgttgggaac cggagctgaa tgaagccata ccaaacgacg agcgtgacac   3540
cacgatgcct gtagcaatgg caacaacgtt gcgcaaacta ttaactggcg aactacttac   3600
tctagcttcc cggcaacaat taatagactg gatggaggcg gataaagttg caggaccact   3660
tctgcgctcg gcccttccgg ctggctggtt tattgctgat aaatctggag ccggtgagcg   3720
tgggtctcgc ggtatcattg cagcactggg gccagatggt aagccctccc gtatcgtagt   3780
tatctacacg acggggagtc aggcaactat ggatgaacga aatagacaga tcgctgagat   3840
aggtgcctca ctgattaagc attggtaact gtcagaccaa gtttactcat atatacttta   3900
gattgattta aaacttcatt tttaatttaa aaggatctag gtgaagatcc tttttgataa   3960
tctcatgacc aaaatccctt aacgtgagtt ttcgttccac tgagcgtcag accccgtaga   4020
```

-continued

```
aaagatcaaa ggatcttctt gagatccttt ttttctgcgc gtaatctgct gcttgcaaac   4080
aaaaaaacca ccgctaccag cggtggtttg tttgccggat caagagctac caactctttt   4140
tccgaaggta actggcttca gcagagcgca gataccaaat actgtccttc tagtgtagcc   4200
gtagttaggc caccacttca agaactctgt agcaccgcct acatacctcg ctctgctaat   4260
cctgttacca gtggctgctg ccagtggcga taagtcgtgt cttaccgggt tggactcaag   4320
acgatagtta ccggataagg cgcagcggtc gggctgaacg gggggttcgt gcacacagcc   4380
cagcttggag cgaacgacct acaccgaact gagataccta cagcgtgagc tatgagaaag   4440
cgccacgctt cccgaaggga gaaaggcgga caggtatccg gtaagcggca gggtcggaac   4500
aggagagcgc acgagggagc ttccaggggg aaacgcctgg tatctttata gtcctgtcgg   4560
gtttcgccac ctctgacttg agcgtcgatt tttgtgatgc tcgtcagggg ggcggagcct   4620
atggaaaaac gccagcaacg cggccttttt acggttcctg gccttttgct ggccttttgc   4680
tcacatgt                                                             4688
```

<210> SEQ ID NO 33
<211> LENGTH: 5806
<212> TYPE: DNA
<213> ORGANISM: Artificial Sequence
<220> FEATURE:
<223> OTHER INFORMATION: Synthetic

<400> SEQUENCE: 33

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgccgcgtcg acattgatta ttgactctgg tcgttacata    180
acttacggta aatggcccgc ctggctgacc gcccaacgac ccccgcccatt gacgtcaata    240
atgacgtatg ttcccatagt aacgccaata gggactttcc attgacgtca atgggtggag    300
tatttacggt aaactgccca cttggcagta catcaagtgt atcatatgcc aagtacgccc    360
cctattgacg tcaatgacgg taaatggccc gcctggcatt atgcccagta catgacctta    420
tgggactttc ctacttggca gtacatctac tcgaggccac gttctgcttc actctcccca    480
tctccccccc ctccccaccc ccaattttgt atttatttat tttttaatta ttttgtgcag    540
cgatgggggc gggggggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggccctag agtcgatcga ggaactgaaa    780
aaccagaaag ttaactggta agtttagtct ttttgtcttt tatttcaggt cccggatccg    840
gtggtggtgc aaatcaaaga actgctcctc agtggatgtt gcctttactt ctaggcctgt    900
acggaagtgt tacttctgct ctaaaagctg cggaattgta cccgcggccg atccaccggt    960
gccaccatgg tccgcgcgag gcaccagccg ggtgggcttt gcctcctgct gctgctgctc   1020
tgccagttca tggaggaccg cagtgcccag gctgggaact gctggctccg tcaagcgaag   1080
aacggccgct gccaggtcct gtacaagacc gaactgagca aggaggagtg ctgcagcacc   1140
ggccggctga gcacctcgtg gaccgaggag gacgtgaatg acaacacact cttcaagtgg   1200
atgattttca acgggggcgc ccccaactgc atcccctgta aagaaacgtg tgagaacgtg   1260
gactgtggac ctgggaaaaa atgccgaatg aacaagaaga acaaaccccg ctgcgtctgc   1320
gccccggatt gttccaacat cacctggaag ggtccagtct gcgggctgga tgggaaaacc   1380
```

-continued

```
taccgcaatg aatgtgcact cctaaaggca agatgtaaag agcagccaga actggaagtc   1440
cagtaccaag gcagatgtaa aaagacttgt cgggatgttt tctgtccagg cagctccaca   1500
tgtgtggtgg accagaccaa taatgcctac tgtgtgacct gtaatcggat ttgcccagag   1560
cctgcttcct ctgagcaata tctctgtggg aatgatggag tcacctactc cagtgcctgc   1620
cacctgagaa aggctacctg cctgctgggc agatctattg gattagccta tgagggaaag   1680
tgtatcaaag caaagtcctg tgaagatatc cagtgcactg gtgggaaaaa atgtttatgg   1740
gatttcaagg ttgggagagg ccggtgttcc ctctgtgatg agctgtgccc tgacagtaag   1800
tcggatgagc ctgtctgtgc cagtgacaat gccacttatg ccagcgagtg tgccatgaag   1860
gaagctgcct gctcctcagg tgtgctactg gaagtaaagc actccggatc ttgcaacgga   1920
tccggagagg gcagaggaag tctgctaaca tgcggtgacg tcgaggagaa tcctggacct   1980
atggcgcccg tcgccgtctg ggccgcgctg gccgtcggac tggagctctg ggctgcggcg   2040
cacgccttgc ccgcccaggt ggcatttaca ccctacgccc cggagcccgg gagcacatgc   2100
cggctcagag aatactatga ccagacagct cagatgtgct gcagcaaatg ctcgccgggc   2160
caacatgcaa aagtcttctg taccaagacc tcggacaccg tgtgtgactc ctgtgaggac   2220
agcacataca cccagctctg gaactgggtt cccgagtgct tgagctgtgg ctcccgctgt   2280
agctctgacc aggtggaaac tcaagcctgc actcgggaac agaaccgcat ctgcacctgc   2340
aggcccggct ggtactgcgc gctgagcaag caggaggggt gccggctgtg cgcgccgctg   2400
cgcaagtgcc gcccgggctt cggcgtggcc agaccaggaa ctgaaacatc agacgtggtg   2460
tgcaagccct gtgccccggg gacgttctcc aacacgactt catccacgga tatttgcagg   2520
ccccaccaga tctgtaacgt ggtggccatc cctgggaatg caagcatgga tgcagtctgc   2580
acgtccacgt cccccacccg gagtatggcc ccaggggcag tacacttacc ccagccagtg   2640
tccacacgat cccaacacac gcagccaact ccagaaccca gcactgctcc aagcacctcc   2700
ttcctgctcc caatgggccc cagcccccca gctgaaggga gcactggcga cttcgctctt   2760
ccagtttgag cggccgccaa acaccattgt cacactccaa caaacaccat tgtcacactc   2820
caacaaacac cattgtcaca ctccagcggc cgcacgcgtt gatcagcctc gactgtgcct   2880
tctagttgcc agccatctgt tgtttgcccc tcccccgtgc cttccttgac cctggaaggt   2940
gccactccca ctgtcctttc ctaataaaat gaggaaattg catcgcattg tctgagtagg   3000
tgtcattcta ttctgggggg tggggtgggg caggacagca agggggagga ttgggaagac   3060
aaggccgcag gaacccctag tgatggagtt ggccactccc tctctgcgcg ctcgctcgct   3120
cactgaggcc gggcgaccaa aggtcgcccg acgcccgggc tttgcccggg cggcctcagt   3180
gagcgagcga gcgcgcagct gcctgcaggg gcgcctgatg cggtattttc tccttacgca   3240
tctgtgcggt atttcacacc gcatacgtca aagcaaccat agtacgcgcc ctgtagcggc   3300
gcattaagcg cggcgggtgt ggtggttacg cgcagcgtga ccgctacact tgccagcgcc   3360
ctagcgcccg ctcctttcgc tttcttccct tcctttctcg ccacgttcgc cggctttccc   3420
cgtcaagctc taaatcgggg gctcccttta gggttccgat ttagtgcttt acggcacctc   3480
gaccccaaaa aacttgattt gggtgatggt tcacgtagtg ggccatcgcc ctgatagacg   3540
gtttttcgcc ctttgacgtt ggagtccacg ttctttaata gtggactctt gttccaaact   3600
ggaacaacac tcaaccctat ctcgggctat tcttttgatt tataagggat tttgccgatt   3660
tcggcctatt ggttaaaaaa tgagctgatt taacaaaaat ttaacgcgaa ttttaacaaa   3720
```

-continued atattaacgt ttacaatttt atggtgcact ctcagtacaa tctgctctga tgccgcatag 3780
ttaagccagc cccgacaccc gccaacaccc gctgacgcgc cctgacgggc ttgtctgctc 3840
ccggcatccg cttacagaca agctgtgacc gtctccggga gctgcatgtg tcagaggttt 3900
tcaccgtcat caccgaaacg cgcgagacga aagggcctcg tgatacgcct atttttatag 3960
gttaatgtca tgataataat ggtttcttag acgtcaggtg gcacttttcg gggaaatgtg 4020
cgcggaaccc ctatttgttt atttttctaa atacattcaa atatgtatcc gctcatgaga 4080
caataaccct gataaatgct tcaataatat tgaaaaagga agagtatgag tattcaacat 4140
ttccgtgtcg cccttattcc cttttttgcg gcattttgcc ttcctgtttt tgctcaccca 4200
gaaacgctgg tgaaagtaaa agatgctgaa gatcagttgg gtgcacgagt gggttacatc 4260
gaactggatc tcaacagcgg taagatcctt gagagttttc gccccgaaga acgttttcca 4320
atgatgagca cttttaaagt tctgctatgt ggcgcggtat tatcccgtat tgacgccggg 4380
caagagcaac tcggtcgccg catacactat tctcagaatg acttggttga gtactcacca 4440
gtcacagaaa agcatcttac ggatggcatg acagtaagag aattatgcag tgctgccata 4500
accatgagtg ataacactgc ggccaactta cttctgacaa cgatcggagg accgaaggag 4560
ctaaccgctt ttttgcacaa catgggggat catgtaactc gccttgatcg ttgggaaccg 4620
gagctgaatg aagccatacc aaacgacgag cgtgacacca cgatgcctgt agcaatggca 4680
acaacgttgc gcaaactatt aactggcgaa ctacttactc tagcttcccg gcaacaatta 4740
atagactgga tggaggcgga taaagttgca ggaccacttc tgcgctcggc ccttccggct 4800
ggctggttta ttgctgataa atctggagcc ggtgagcgtg ggtctcgcgg tatcattgca 4860
gcactggggc cagatggtaa gccctcccgt atcgtagtta tctacacgac ggggagtcag 4920
gcaactatgg atgaacgaaa tagacagatc gctgagatag gtgcctcact gattaagcat 4980
tggtaactgt cagaccaagt ttactcatat atactttaga ttgatttaaa acttcatttt 5040
taatttaaaa ggatctaggt gaagatcctt tttgataatc tcatgaccaa aatcccttaa 5100
cgtgagtttt cgttccactg agcgtcagac cccgtagaaa agatcaaagg atcttcttga 5160
gatccttttt ttctgcgcgt aatctgctgc ttgcaaacaa aaaaaccacc gctaccagcg 5220
gtggtttgtt tgccggatca agagctacca actctttttc cgaaggtaac tggcttcagc 5280
agagcgcaga taccaaatac tgtccttcta gtgtagccgt agttaggcca ccacttcaag 5340
aactctgtag caccgcctac atacctcgct ctgctaatcc tgttaccagt ggctgctgcc 5400
agtggcgata agtcgtgtct taccgggttg gactcaagac gatagttacc ggataaggcg 5460
cagcggtcgg gctgaacggg gggttcgtgc acacagccca gcttggagcg aacgacctac 5520
accgaactga gatacctaca gcgtgagcta tgagaaagcg ccacgcttcc cgaagggaga 5580
aaggcggaca ggtatccggt aagcggcagg gtcggaacag gagagcgcac gagggagctt 5640
ccagggggaa acgcctggta tctttatagt cctgtcgggt ttcgccacct ctgacttgag 5700
cgtcgatttt tgtgatgctc gtcagggggg cggagcctat ggaaaaacgc cagcaacgcg 5760
gcctttttac ggttcctggc cttttgctgg ccttttgctc acatgt 5806

<210> SEQ ID NO 34
<211> LENGTH: 4555
<212> TYPE: DNA
<213> ORGANISM: Artificial Sequence
<220> FEATURE:
<223> OTHER INFORMATION: Synthetic

<400> SEQUENCE: 34

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgccgcgtcg acattgatta ttgactctgg tcgttacata    180
acttacggta aatggcccgc ctggctgacc gcccaacgac ccgcccatt gacgtcaata    240
atgacgtatg ttcccatagt aacgccaata gggactttcc attgacgtca atgggtggag    300
tatttacggt aaactgccca cttggcagta catcaagtgt atcatatgcc aagtacgccc    360
cctattgacg tcaatgacgg taaatggccc gcctggcatt atgcccagta catgacctta    420
tgggactttc ctacttggca gtacatctac tcgaggccac gttctgcttc actctcccca    480
tctccccccc ctccccaccc ccaattttgt atttatttat tttttaatta ttttgtgcag    540
cgatgggggc gggggggggg gggggggggg cgcgcgccag gcggggcggg gcggggcgag    600
gggcggggcg gggcgaggcg gagaggtgcg gcggcagcca atcagagcgg cgcgctccga    660
aagtttcctt ttatggcgag gcggcggcgg cggcggccct ataaaaagcg aagcgcgcgg    720
cgggcgggag cgggatcagc caccgcggtg gcggccctag agtcgatcga ggaactgaaa    780
aaccagaaag ttaactggta agtttagtct ttttgtcttt tatttcaggt cccggatccg    840
gtggtggtgc aaatcaaaga actgctcctc agtggatgtt gcctttactt ctaggcctgt    900
acggaagtgt tacttctgct ctaaaagctg cggaattgta cccgcggccg atccaccggt    960
cgccaccatc tagcatggga gtcaaagttc tgtttgccct gatctgcatc gctgtggccg   1020
aggccaagcc caccgagaac aacgaagact tcaacatcgt ggccgtggcc agcaacttcg   1080
cgaccacgga tctcgatgct gaccgcggga agttgcccgg caagaagctg ccgctggagg   1140
tgctcaaaga gatggaagcc aatgcccgga aagctggctg caccaggggc tgtctgatct   1200
gcctgtccca catcaagtgc acgcccaaga tgaagaagtt catcccagga cgctgccaca   1260
cctacgaagg cgacaaagag tccgcacagg gcggcatagg cgaggcgatc gtcgacattc   1320
ctgagattcc tgggttcaag gacttggagc ccatggagca gttcatcgca caggtcgatc   1380
tgtgtgtgga ctgcacaact ggctgcctca aagggcttgc caacgtgcag tgttctgacc   1440
tgctcaagaa gtggctgccg caacgctgtg cgacctttgc cagcaagatc cagggccagg   1500
tggacaagat caagggggcc ggtggtgact agctcgacgc tcaaacacca ttgtcacact   1560
ccaacaaaca ccattgtcac actccaacaa acaccattgt cacactccag atcagcctcg   1620
actgtgcctt ctagttgcca gccatctgtt gtttgcccct cccccgtgcc ttccttgacc   1680
ctggaaggtg ccactcccac tgtcctttcc taataaaatg aggaaattgc atcgcattgt   1740
ctgagtaggt gtcattctat tctggggggt ggggtggggc aggacagcaa gggggaggat   1800
tgggaagaca aggccgcagg aacccctagt gatggagttg gccactccct ctctgcgcgc   1860
tcgctcgctc actgaggccg ggcgaccaaa ggtcgcccga cgcccgggct ttgcccgggc   1920
ggcctcagtg agcgagcgag cgcgcagctg cctgcagggg cgcctgatgc ggtattttct   1980
ccttacgcat ctgtgcggta tttcacaccg catacgtcaa agcaaccata gtacgcgccc   2040
tgtagcggcg cattaagcgc ggcgggtgtg gtggttacgc gcagcgtgac cgctacactt   2100
gccagcgccc tagcgcccgc tcctttcgct ttcttccctt cctttctcgc cacgttcgcc   2160
ggctttcccc gtcaagctct aaatcggggg ctccctttag ggttccgatt tagtgcttta   2220
cggcacctcg accccaaaaa acttgatttg ggtgatggtt cacgtagtgg gccatcgccc   2280
tgatagacgg tttttcgccc tttgacgttg gagtccacgt tctttaatag tggactcttg   2340
```

-continued

```
ttccaaactg gaacaacact caaccctatc tcgggctatt cttttgattt ataagggatt   2400
ttgccgattt cggcctattg gttaaaaaat gagctgattt aacaaaaatt taacgcgaat   2460
tttaacaaaa tattaacgtt tacaatttta tggtgcactc tcagtacaat ctgctctgat   2520
gccgcatagt taagccagcc ccgacacccg ccaacacccg ctgacgcgcc ctgacgggct   2580
tgtctgctcc cggcatccgc ttacagacaa gctgtgaccg tctccgggag ctgcatgtgt   2640
cagaggtttt caccgtcatc accgaaacgc gcgagacgaa agggcctcgt gatacgccta   2700
tttttatagg ttaatgtcat gataataatg gtttcttaga cgtcaggtgg cacttttcgg   2760
ggaaatgtgc gcggaacccc tatttgttta tttttctaaa tacattcaaa tatgtatccg   2820
ctcatgagac aataaccctg ataaatgctt caataatatt gaaaaaggaa gagtatgagt   2880
attcaacatt tccgtgtcgc ccttattccc ttttttgcgg cattttgcct tcctgttttt   2940
gctcacccag aaacgctggt gaaagtaaaa gatgctgaag atcagttggg tgcacgagtg   3000
ggttacatcg aactggatct caacagcggt aagatccttg agagttttcg ccccgaagaa   3060
cgttttccaa tgatgagcac ttttaaagtt ctgctatgtg gcgcggtatt atcccgtatt   3120
gacgccgggc aagagcaact cggtcgccgc atacactatt ctcagaatga cttggttgag   3180
tactcaccag tcacagaaaa gcatcttacg gatggcatga cagtaagaga attatgcagt   3240
gctgccataa ccatgagtga taacactgcg gccaacttac ttctgacaac gatcggagga   3300
ccgaaggagc taaccgcttt tttgcacaac atgggggatc atgtaactcg ccttgatcgt   3360
tgggaaccgg agctgaatga agccatacca aacgacgagc gtgacaccac gatgcctgta   3420
gcaatggcaa caacgttgcg caaactatta actggcgaac tacttactct agcttcccgg   3480
caacaattaa tagactggat ggaggcggat aaagttgcag gaccacttct gcgctcggcc   3540
cttccggctg gctggtttat tgctgataaa tctggagccg gtgagcgtgg gtctcgcggt   3600
atcattgcag cactggggcc agatggtaag ccctcccgta tcgtagttat ctacacgacg   3660
gggagtcagg caactatgga tgaacgaaat agacagatcg ctgagatagg tgcctcactg   3720
attaagcatt ggtaactgtc agaccaagtt tactcatata tactttagat tgatttaaaa   3780
cttcattttt aatttaaaag gatctaggtg aagatccttt ttgataatct catgaccaaa   3840
atcccttaac gtgagttttc gttccactga gcgtcagacc ccgtagaaaa gatcaaagga   3900
tcttcttgag atcctttttt tctgcgcgta atctgctgct tgcaaacaaa aaaaccaccg   3960
ctaccagcgg tggtttgttt gccggatcaa gagctaccaa ctctttttcc gaaggtaact   4020
ggcttcagca gagcgcagat accaaatact gtccttctag tgtagccgta gttaggccac   4080
cacttcaaga actctgtagc accgcctaca tacctcgctc tgctaatcct gttaccagtg   4140
gctgctgcca gtggcgataa gtcgtgtctt accgggttgg actcaagacg atagttaccg   4200
gataaggcgc agcggtcggg ctgaacgggg ggttcgtgca cacagcccag cttggagcga   4260
acgacctaca ccgaactgag atacctacag cgtgagctat gagaaagcgc cacgcttccc   4320
gaagggagaa aggcggacag gtatccggta agcggcaggg tcggaacagg agagcgcacg   4380
agggagcttc cagggggaaa cgcctggtat ctttatagtc ctgtcgggtt tcgccacctc   4440
tgacttgagc gtcgattttt gtgatgctcg tcaggggggc ggagcctatg gaaaaacgcc   4500
agcaacgcgg cctttttacg gttcctggcc ttttgctggc cttttgctca catgt        4555
```

<210> SEQ ID NO 35
<211> LENGTH: 537
<212> TYPE: DNA
<213> ORGANISM: Artificial Sequence
<220> FEATURE:
<223> OTHER INFORMATION: Synthetic

<400> SEQUENCE: 35
atggaaatct gcagaggcct ccgcagtcac ctaatcactc tcctcctctt cctgttccat 60
tcagagacga tctgccgacc ctctgggaga aaatccagca agatgcaagc cttcagaatc 120
tgggatgtta accagaagac cttctatctg aggaacaacc aactagttgc tggatacttg 180
caaggaccaa atgtcaattt agaagaaaag atagatgtgg tacccattga gcctcatgct 240
ctgttcttgg gaatccatgg agggaagatg tgcctgtcct gtgtcaagtc tggtgatgag 300
accagactcc agctggaggc agttaacatc actgacctga gcgagaacag aaagcaggac 360
aagcgcttcg ccttcatccg ctcagacagt ggccccacca ccagttttga gtctgccgcc 420
tgccccggtt ggttcctctg cacagcgatg gaagctgacc agcccgtcag cctcaccaat 480
atgcctgacg aaggcgtcat ggtcaccaaa ttctacttcc aggaggacga gtagtaa 537

<210> SEQ ID NO 36
<211> LENGTH: 171
<212> TYPE: DNA
<213> ORGANISM: Artificial Sequence
<220> FEATURE:
<223> OTHER INFORMATION: Synthetic

<400> SEQUENCE: 36
gaactgaaaa accagaaagt taactggtaa gtttagtctt tttgtctttt atttcaggtc 60
ccggatccgg tggtggtgca aatcaaagaa ctgctcctca gtggatgttg cctttacttc 120
aggcctgtac ggaagtgtta cttctgctct aaaagctgcg gaattgtacc c 171

<210> SEQ ID NO 37
<211> LENGTH: 384
<212> TYPE: DNA
<213> ORGANISM: Artificial Sequence
<220> FEATURE:
<223> OTHER INFORMATION: Synthetic

<400> SEQUENCE: 37
tcagatcgcc tggagacgcc atccacgctg ttttgacctc catagaagac accgggaccg 60
atccagcctc cgcggccggg aacggtgcat tggaacgcgg attccccgtg ccaagagtga 120
cgtaagtacc gcctatagag tctataggcc cacccccttg gcttcttatg catgctatac 180
tgtttttggc ttggggtcta tacacccccg cttcctcatg tttgctgccc gtgaccagca 240
cgtcaacgat tttgtgggca cgggcgacac cgcagtgtag tctgagcagt actcgttgct 300
gccgcgcgcg ccaccagaca taatagctga cagactaaca gactgttcct ttccatgggt 360
cttttctgca gtcaccgtcg ccgc 384

<210> SEQ ID NO 38
<211> LENGTH: 509
<212> TYPE: PRT
<213> ORGANISM: Artificial Sequence
<220> FEATURE:
<223> OTHER INFORMATION: Synthetic

<400> SEQUENCE: 38

Met Val Asp Gly Val Met Ile Leu Pro Val Leu Ile Met Ile Ala Leu
1 5 10 15

Pro Ser Pro Ser Met Glu Asp Glu Lys Pro Lys Val Asn Pro Lys Leu
20 25 30

-continued

```
Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
```

```
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505


<210> SEQ ID NO 39
<211> LENGTH: 100
<212> TYPE: PRT
<213> ORGANISM: Artificial Sequence
<220> FEATURE:
<223> OTHER INFORMATION: Synthetic

<400> SEQUENCE: 39

Val Phe Tyr Phe Arg Ser Gln Ile Gly Ser Ala Phe Ala Pro Gly Ser
1               5                   10                  15

Pro Leu Leu Pro Trp Ala Trp Ala His Gln Pro Trp Cys Leu Trp Pro
            20                  25                  30

Ala Ala His Leu Leu Ala Gly Ser Cys Glu Cys Asn Leu Val Ser His
        35                  40                  45

Leu Phe Trp Gln Tyr Leu Ser Gly Ser Ala Asp Tyr Thr His Gly Gly
    50                  55                  60

Leu Pro Leu Pro Thr Val Pro Trp Pro Lys Arg Ile Gly His Arg Gly
65                  70                  75                  80

Pro Thr Pro Ser Trp Gly Ile Arg Thr Val Ser Pro Leu Gln Gly Ile
                85                  90                  95

Arg Trp Trp Cys
            100


<210> SEQ ID NO 40
<211> LENGTH: 87
<212> TYPE: PRT
<213> ORGANISM: Artificial Sequence
<220> FEATURE:
<223> OTHER INFORMATION: Synthetic

<400> SEQUENCE: 40

Arg Ala Leu Arg Leu Leu Gln Val Val Arg Cys Ser Leu Gly Pro Gly
1               5                   10                  15

Pro Thr Asp Ser Pro Gly Ala Ser Gly Arg Leu His Thr Ser Trp Arg
            20                  25                  30

Ala Ala Val Ser Val Ser Trp Ala Thr Cys Ser Gly Asn Thr Val Ala
        35                  40                  45

Leu Arg Leu Thr Leu Thr Glu Ala Cys Pro Asp Cys Pro Arg Cys Arg
    50                  55                  60

Gly Gln Arg Gly Ser Lys Gly Thr Ala Glu Gly Leu Pro Asn His Arg
65                  70                  75                  80

Gly Glu Gly Gln Cys His Pro
                85


<210> SEQ ID NO 41
<211> LENGTH: 16
<212> TYPE: PRT
<213> ORGANISM: Homo sapiens

<400> SEQUENCE: 41

Ser Arg Val Gln Arg Thr Val Ala Arg Gln Ile Thr Leu Leu Glu Cys
```

1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Ser Arg Val Gln Arg Thr Val Ala Arg Gln Ile Thr Leu Leu Glu Cys
1 5 10 15

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Gly Ser Pro Asp Tyr Thr Val
1 5

<210> SEQ ID NO 44
<211> LENGTH: 795
<212> TYPE: PRT
<213> ORGANISM: Artificial Sequence
<220> FEATURE:
<223> OTHER INFORMATION: Synthetic

<400> SEQUENCE: 44

Val Thr Ser Gln Leu Arg Gln Val Asp Pro Cys Leu Val Gln Ala Gly
1 5 10 15

Asp Ala Leu Val Asp Gln Gly Gly Val Gln His Leu Phe Gly Ala Gly
20 25 30

Val Pro Leu Pro Val Asp Gly Gly Val Lys Val Leu Glu Gly Gly Arg
35 40 45

Gly Ser Gln Ile Gly Gln Gly Lys Gln Val Asp Asp Ile Leu Gly Leu
50 55 60

Leu Ser Asp Gly Leu Ile Pro Val Leu Val Val Gly Gly Gln His Phe
65 70 75 80

Val Gln Ile Ser Val Gly Gln Asp His Ser Leu Gly Glu Leu Ala Asp
85 90 95

Leu Leu Asp Asp Leu Val Gln Val Val Leu Val Leu Phe His Lys Gln
100 105 110

Leu Phe Leu Leu Ile Ile Leu Gly Gly Ala Leu Gln Leu Leu Ile Val
115 120 125

Ala Gly Gln Val Gln Glu Val His Ile Phe Gly Gly Gln Gly Gln Phe
130 135 140

Val Ser Leu Leu Gln Phe Ala Gly Arg Gly Gln His Ser Leu Pro Ala
145 150 155 160

Val Phe Gln Leu Glu Gln Gly Val Leu Arg Gln Leu Asp Asp Gln Val
165 170 175

Leu Phe His Phe Phe Val Ala Leu Gly Phe Gln Lys Val Asp Gly Ile
180 185 190

Leu Leu Glu Ala Ala Ser Phe His Asp Gly Asp Pro Gln Gln Leu Phe
195 200 205

His Thr Leu Gln Phe Leu Gly Leu Ala Leu Phe His Phe Gly His His
210 215 220

-continued

```
Gln His Arg Ile Gly His Gly Gly Ala Val Glu Ala Ala Val Leu Leu
225                 230                 235                 240

Arg Val Pro Val Leu Leu Ser Gly Asp Gln Leu Ile Ala Val Pro Leu
                245                 250                 255

Gly Gln Asp Arg Leu Phe Ala Glu Ala Ala Cys Leu His Leu Gly Leu
            260                 265                 270

Phe His Asp Ile His Leu Gly His Ala Gln His Phe Pro His Gly Gly
        275                 280                 285

Lys Ile Pro Ala Leu Ile Pro His Asp Leu Pro Gly Phe Ala Val Cys
    290                 295                 300

Leu Asp Gln Arg Pro Leu Pro Asp Leu Ala Val Gly Gln Gly Asn Leu
305                 310                 315                 320

Gly Leu Glu Lys Val His Asp Val Ala Val Glu Glu Val Leu Gly Gly
                325                 330                 335

Ser Leu Ala Asp Phe Leu Leu Ala Leu Gly Asp His Leu Pro His Val
            340                 345                 350

Val His Leu Val Val Ala Val His Glu Leu Ala Phe Gln Leu Arg Val
        355                 360                 365

Leu Phe Asp Gln Gly Gly Ser His Asp Gly Val Gln Val Gly Val Val
    370                 375                 380

Gly Val Val Val Val Val Asp Leu Ala His Phe Val Lys Leu Glu Ile
385                 390                 395                 400

Leu Pro Glu Ile Gly His Gln Leu Gly Leu Gln Gly Asp His Phe His
                405                 410                 415

Phe Pro Asp Gln Leu Val Ile Leu Val Val Leu Ser Val His Pro Gly
            420                 425                 430

Val Gln Asp Leu Cys His Val Leu Cys Asp Leu Pro Gly Phe His Gln
        435                 440                 445

Leu Ser Leu Asp Glu Ala Gly Leu Ile Gln Phe Ala Gln Ala Ala Ser
    450                 455                 460

Leu Gly Leu Gly Gln Ile Val Glu Leu Ser Leu Gly Asn Gln Leu Gly
465                 470                 475                 480

Val Gln Gln Leu Pro Pro Val Val Leu His Leu Leu His Asp Leu Phe
                485                 490                 495

Gly Gly His Val Val Ala Leu Ala Pro Val Leu Val Ala Ser Gly Gln
            500                 505                 510

His Leu Val Val Asp Gly Val Val Leu Gln Lys Ala Leu Arg His Asp
        515                 520                 525

Met Val His Ile Val Val Gly Gln Pro Val Asp Val Gln Phe Leu Val
    530                 535                 540

His Val His Ile Pro Pro Ile Leu Gln Val Val Gln Val Gln Leu Leu
545                 550                 555                 560

Val Leu Gln Leu Gly Val Phe His Gly Val Phe Phe Gln Asp Leu Ala
                565                 570                 575

Ala Gln Leu Phe Asp Ala Leu Phe Asp Pro Leu His Ser Leu Ala Ala
            580                 585                 590

Val Leu Leu Ser Leu Leu Gly Gly Leu Val Leu Ser Gly His Phe Asp
        595                 600                 605

His Asp Val Leu Gly Leu Val Pro Ala His His Phe His Glu Leu Val
    610                 615                 620

His His Leu His Cys Leu Gln Asp Ala Leu Leu Asn Gly Gly Ala Ala
625                 630                 635                 640
```

-continued

```
Gly Gln Ile Gly Asn Val Leu Val Gln Ala Ile Ala Leu Ala Gly His
                645                 650                 655

Leu Gly Phe Leu Asp Val Leu Phe Lys Gly Gln Ala Val Val Val Asp
            660                 665                 670

Gln Leu His Glu Val Ser Val Gly Glu Ala Val Gly Leu Gln Glu Ile
        675                 680                 685

Gln Asp Cys Leu Ala Gly Leu Leu Val Pro Asp Ala Val Asp Gln Leu
    690                 695                 700

Pro Ala Gln Pro Ala Pro Ala Gly Val Ser Pro Pro Leu Gln Leu Leu
705                 710                 715                 720

His His Phe Val Val Glu Gln Val Gly Ile Gly Phe Gln Pro Phe Leu
                725                 730                 735

Asp His Leu Ser Val Leu Lys Gln Cys Gln Gly Gln His Asp Ile Phe
            740                 745                 750

Gln Asn Val Leu Val Phe Leu Ile Val Gln Glu Val Leu Val Leu Asp
        755                 760                 765

Asn Phe Gln Gln Ile Val Val Cys Ala Gln Gly Gly Val Glu Pro Ile
    770                 775                 780

Phe His Ala Gly Asp Phe His Gly Val Glu Ala
785                 790                 795


<210> SEQ ID NO 45
<211> LENGTH: 317
<212> TYPE: PRT
<213> ORGANISM: Artificial Sequence
<220> FEATURE:
<223> OTHER INFORMATION: Synthetic

<400> SEQUENCE: 45

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205
```

```
Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315


<210> SEQ ID NO 46
<211> LENGTH: 262
<212> TYPE: PRT
<213> ORGANISM: Artificial Sequence
<220> FEATURE:
<223> OTHER INFORMATION: Synthetic

<400> SEQUENCE: 46

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255
```

```
Asp Phe Ala Leu Pro Val
            260


<210> SEQ ID NO 47
<211> LENGTH: 22
<212> TYPE: PRT
<213> ORGANISM: Artificial Sequence
<220> FEATURE:
<223> OTHER INFORMATION: Synthetic

<400> SEQUENCE: 47

Gln Thr Pro Leu Ser His Ser Asn Lys His His Cys His Thr Pro Thr
1               5                   10                  15

Asn Thr Ile Val Thr Leu
            20


<210> SEQ ID NO 48
<211> LENGTH: 66
<212> TYPE: DNA
<213> ORGANISM: Artificial Sequence
<220> FEATURE:
<223> OTHER INFORMATION: Synthetic

<400> SEQUENCE: 48

acaagctttt tgctcgtctt atacaagctt tttgctcgtc ttatacaagc tttttgctcg      60

tcttat                                                                  66


<210> SEQ ID NO 49
<211> LENGTH: 3563
<212> TYPE: DNA
<213> ORGANISM: Artificial Sequence
<220> FEATURE:
<223> OTHER INFORMATION: Synthetic

<400> SEQUENCE: 49

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctaccag ggtaatgggg     180

atcctctaga actatagcta gtcgacattg attattgact agttattaat agtaatcaat     240

tacggggtca ttagttcata gcccatatat ggagttccgc gttacataac ttacggtaaa     300

tggcccgcct ggctgaccgc ccaacgaccc ccgcccattg acgtcaataa tgacgtatgt     360

tcccatagta acgccaatag ggactttcca ttgacgtcaa tgggtggagt atttacggta     420

aactgcccac ttggcagtac atcaagtgta tcatatgcca agtacgcccc ctattgacgt     480

caatgacggt aaatggcccg cctggcatta tgcccagtac atgaccttat gggactttcc     540

tacttggcag tacatctacg tattagtcat cgctattacc atgtcgaggc cacgttctgc     600

ttcactctcc ccatctcccc cccctcccca cccccaattt tgtatttatt tattttttaa     660

ttattttgtg cagcgatggg ggcggggggg gggggcgcgc gccaggcggg gcggggcggg     720

gcgaggggcg gggcggggcg aggcggagag gtgcggcggc agccaatcag agcggcgcgc     780

tccgaaagtt tccttttatg gcgaggcggc ggcggcggcg gccctataaa aagcgaagcg     840

cgcggcgggc gggagcaagc tttcagatcg cctggagacg ccatccacgc tgttttgacc     900

tccatagaag acaccgggac cgatccagcc tccgcggccg ggaacggtgc attggaacgc     960

ggattccccg tgccaagagt gacgtaagta ccgcctatag agtctatagg cccaccccct    1020

tggcttctta tgcatgctat actgtttttg gcttggggtc tatacacccc cgcttcctca    1080
```

-continued

```
tgtttgctgc ccgtgaccag cacgtcaacg attttgtggg cacgggcgac accgcagtgt   1140
agtctgagca gtactcgttg ctgccgcgcg cgccaccaga cataatagct gacagactaa   1200
cagactgttc ctttccatgg gtcttttctg caagggctct gcgtttgctc caggtagtcc   1260
gctgctccct tgggcctggg cccactgaca gccctggtgc ctctggccgg ctgcacacct   1320
cctggcgggc agctgtgtgt aatctggtga gccactgttg ttctggcaat acctgacagt   1380
ggcagatcag attacacacg gaggcctgcc ctgactgccc acggtgccgt ggccaaagag   1440
gatctaaggg caccgctgag ggcctaccta accatcgtgg ggaataagga cagtgtcacc   1500
ctgcagtcac cgtcgccgcc accggtgaat tccgccacca tggtcgatgg agtgatgatc   1560
ctgcctgtcc tgattatgat tgccctgccc agccccagca tggaagatga aaaacctaaa   1620
gtcaacccta agctgtatat gtgcgtgtgc gagggcctga gctgcggaaa cgaggatcac   1680
tgcgagggcc agcagtgttt cagctccctg tccatcaatg acggcttcca cgtgtaccag   1740
aagggctgct ttcaggtgta tgagcagggc aagatgacct gtaagacacc accttcccca   1800
ggacaggcag tggagtgctg tcagggcgat tggtgtaacc ggaatatcac cgcccagctg   1860
ccaacaaagg gcaagtcttt ccccggcaca cagaactttc acctggaagt gggcctgatc   1920
atcctgagcg tggtgttcgc cgtgtgcctg ctggcatgtc tgctgggagt ggccctgaga   1980
aagtttaagc ggagaaacca ggagcggctg aatccaagag atgtggagta cggcaccatc   2040
gagggcctga tcaccacaaa tgtgggcgac tctacactgg ccgacctgct ggatcacagc   2100
tgcaccagcg gctccggatc tggcctgccc tttctggtgc agaggaccgt ggcccggcag   2160
atcaccctgc tggagtgcgt gggcaagggc cggtacggag aagtgtggag aggatcctgg   2220
cagggagaga acgtggcagt gaagatcttc tctagccggg atgagaagtc ttggtttaga   2280
gagacagagc tgtataacac agtgatgctg aggcacgaga atatcctggg cttcatcgcc   2340
tccgacatga cctctcgcca ctcctctaca cagctgtggc tgatcaccca ctaccacgag   2400
atgggctccc tgtacgatta cctccagctg accacactgg acacagtgtc ttgcctgcgg   2460
atcgtgctgt ctatcgccag cggcctggca cacctgcaca tcgagatctt tggaacccag   2520
ggcaagccag caatcgcaca cagagatctg aagtctaaga acatcctggt gaagaagaat   2580
ggccagtgct gtatcgccga tctgggcctg gccgtgatgc acagccagtc caccaaccag   2640
ctggacgtgg gcaacaatcc tcgggtgggc acaaagagat acatggcccc agaggtgctg   2700
gatgagacaa tccaggtgga ctgcttcgat agctataaga gggtggacat ctgggccttt   2760
ggcctggtgc tgtgggaggt ggcaaggagg atggtgagca acggcatcgt ggaggactac   2820
aagccaccct tctatgacgt ggtgcctaat gatccatcct ttgaggacat gcgcaaggtg   2880
gtgtgcgtgg atcagcagag gcccaacatc cctaatcgct ggttcagcga ccccaccctg   2940
acatccctgg ccaagctgat gaaggagtgt tggtatcaga atcctagcgc caggctgacc   3000
gccctgcgca tcaagaaaac tctgactaaa atcgacaata gcctggataa actgaaaacc   3060
gactgctgac ctgaacaagc tttttgctcg tcttatacaa gctttttgct cgtcttatac   3120
aagctttttg ctcgtcttat acaaacacca ttgtcacact ccaacaaaca ccattgtcac   3180
actccaacaa acaccattgt cacactccat gaggatccga tctttttccc tctgccaaaa   3240
attatgggga catcatgaag ccccttgagc atctgacttc tggctaataa aggaaattta   3300
ttttcattgc aatagtgtgt tggaattttt tgtgtctctc actcggaagc aattcgttga   3360
tctgaatttc gaccacccat aatacccatt accctggtag ataagtagca tggcgggtta   3420
atcattaact acaaggaacc cctagtgatg gagttggcca ctccctctct gcgcgctcgc   3480
```

```
tcgctcactg aggccgggcg accaaaggtc gcccgacgcc cgggctttgc ccgggcggcc   3540

tcagtgagcg agcgagcgcg cag                                            3563


<210> SEQ ID NO 50
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(3)
<223> OTHER INFORMATION: n is a, g, c, or t
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (24)..(24)
<223> OTHER INFORMATION: r is g or a
<220> FEATURE:
<221> NAME/KEY: modified_base
<222> LOCATION: (45)..(47)
<223> OTHER INFORMATION: n is a, g, c, or t
<220> FEATURE:
<221> NAME/KEY: misc_feature
<222> LOCATION: (45)..(47)
<223> OTHER INFORMATION: n is a, c, g, or t

<400> SEQUENCE: 50

nnnggtacaa agaacagtgg ctcrccagat tacactgttg gagtnnn                   47


<210> SEQ ID NO 51
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(3)
<223> OTHER INFORMATION: n is a, g, c, or t
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (45)..(47)
<223> OTHER INFORMATION: n is a, g, c, or t
<220> FEATURE:
<221> NAME/KEY: misc_feature
<222> LOCATION: (45)..(47)
<223> OTHER INFORMATION: n is a, c, g, or t

<400> SEQUENCE: 51

nnnggtacaa agaacagtgg ctcaccagat tacactgttg gagtnnn                   47


<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Arg Thr Val Ala His Gln Ile Thr Leu
1               5
```

<210> SEQ ID NO 53
<211> LENGTH: 47
<212> TYPE: DNA
<213> ORGANISM: Homo sapiens
<220> FEATURE:
<221> NAME/KEY: modified_base
<222> LOCATION: (1)..(3)
<223> OTHER INFORMATION: n is a, g, c, or t
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (45)..(47)
<223> OTHER INFORMATION: n is a, g, c, or t
<220> FEATURE:
<221> NAME/KEY: misc_feature
<222> LOCATION: (45)..(47)
<223> OTHER INFORMATION: n is a, c, g, or t

<400> SEQUENCE: 53
nnnggtacaa agaacagtgg ctcgccagat tacactgttg gagtnnn 47

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Arg Thr Val Ala Arg Gln Ile Thr Leu
1 5

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
ggctcaccag attacactgt tgg 23

<210> SEQ ID NO 56
<211> LENGTH: 269
<212> TYPE: DNA
<213> ORGANISM: Artificial Sequence
<220> FEATURE:
<223> OTHER INFORMATION: Synthetic

<400> SEQUENCE: 56
agggctctgc gtttgctcca ggtagtccgc tgctcccttg ggcctgggcc cactgacagc 60
cctggtgcct ctggccggct gcacacctcc tggcgggcag ctgtggtgta atctggtgag 120
ccactgtgtt ctggcaatac ctgcagtggc tgtctagatt acaccacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 57
<211> LENGTH: 269
<212> TYPE: DNA
<213> ORGANISM: Artificial Sequence
<220> FEATURE:
<223> OTHER INFORMATION: Synthetic

<400> SEQUENCE: 57
agggctctgc gtttgctcca ggtagtccgc tgctcccttg ggcctgggcc cactgacagc 60
cctggtgcct ctggccggct gcacacctcc tggcgggcag ctgtggtgta agctggtgag 120
ccactgtgtt ctggcaatac ctgcagtggc tgtctagctt acaccacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 58
<211> LENGTH: 269
<212> TYPE: DNA
<213> ORGANISM: Artificial Sequence
<220> FEATURE:
<223> OTHER INFORMATION: Synthetic

<400> SEQUENCE: 58
agggctctgc gtttgctcca ggtagtccgc tgctcccttg ggcctgggcc cactgacagc 60
cctggtgcct ctggccggct gcacacctcc tggcgggcag ctgtgtgtaa gctggtgagc 120
cactgttgtt ctggcaatac ctgacagtgg cagatcagct tacacacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 59
<211> LENGTH: 269
<212> TYPE: DNA
<213> ORGANISM: Artificial Sequence
<220> FEATURE:
<223> OTHER INFORMATION: Synthetic

<400> SEQUENCE: 59
agggctctgc gtttgctcca ggtagtccgc tgctcccttg ggcctgggcc cactgacagc 60
cctggtgcct ctggccggct gcacacctcc tggcgggcag ctgtgtgtaa tctggtgagc 120
cactgttgtt ctggcaatac ctgacagtgg cagatcagat tacacacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 60
<211> LENGTH: 269
<212> TYPE: DNA
<213> ORGANISM: Artificial Sequence
<220> FEATURE:
<223> OTHER INFORMATION: Synthetic

<400> SEQUENCE: 60
agggctctgc gtttgctcca ggtagtccgc tgctcccttg ggcctgggcc cactgacagc 60
cctggtgcct ctggccggct gcacacctcc tggcgggcag ctgtggtaat ctggtgagcc 120
actgtttgtt ctggcaatac ctgaacagtg ggacgccaga ttaccacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 61
<211> LENGTH: 269
<212> TYPE: DNA
<213> ORGANISM: Artificial Sequence
<220> FEATURE:
<223> OTHER INFORMATION: Synthetic

<400> SEQUENCE: 61
agggctctgc gtttgctcca ggtagtccgc tgctcccttg ggcctgggcc cactgacagc 60
cctggtgcct ctggccggct gcacacctcc tggcgggcag ctgtggtaag ctggtgagcc 120
actgtttgtt ctggcaatac ctgaacagtg ggacgccagc ttaccacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 62
<211> LENGTH: 269
<212> TYPE: DNA
<213> ORGANISM: Artificial Sequence
<220> FEATURE:
<223> OTHER INFORMATION: Synthetic

<400> SEQUENCE: 62
agggctctgc gtttgctcca ggtagtccgc tgctcccttg ggcctgggcc cactgacagc 60
cctggtgcct ctggccggct gcacacctcc tggcgggcag ctgtgtaatc tggtgagcca 120
ctgttctgtt ctggcaatac ctggaacagt gcgttaccag attacacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 63
<211> LENGTH: 269
<212> TYPE: DNA
<213> ORGANISM: Artificial Sequence
<220> FEATURE:
<223> OTHER INFORMATION: Synthetic

<400> SEQUENCE: 63
agggctctgc gtttgctcca ggtagtccgc tgctcccttg ggcctgggcc cactgacagc 60
cctggtgcct ctggccggct gcacacctcc tggcgggcag ctgtgtaagc tggtgagcca 120
ctgttctgtt ctggcaatac ctggaacagt gcgttaccag cttacacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 64
<211> LENGTH: 269
<212> TYPE: DNA
<213> ORGANISM: Artificial Sequence
<220> FEATURE:
<223> OTHER INFORMATION: Synthetic

<400> SEQUENCE: 64
agggctctgc gtttgctcca ggtagtccgc tgctcccttg ggcctgggcc cactgacagc 60
cctggtgcct ctggccggct gcacacctcc tggcgggcag ctgtgaatct ggtgagccac 120
tgttcttgtt ctggcaatac ctgagaacag tcccccacca gattcacgga ggcctgccct 180
gactgcccac ggtgccgtgg ccaaagagga tctaagggca ccgctgaggg cctacctaac 240
catcgtgggg aataaggaca gtgtcaccc 269

<210> SEQ ID NO 65
<211> LENGTH: 269
<212> TYPE: DNA
<213> ORGANISM: Artificial Sequence
<220> FEATURE:
<223> OTHER INFORMATION: Synthetic -continued

```
<400> SEQUENCE: 65

agggctctgc gtttgctcca ggtagtccgc tgctcccttg ggcctgggcc cactgacagc     60

cctggtgcct ctggccggct gcacacctcc tggcgggcag ctgtgaagct ggtgagccac    120

tgttcttgtt ctggcaatac ctgagaacag tcccccacca gcttcacgga ggcctgccct    180

gactgcccac ggtgccgtgg ccaaagagga tctaagggca ccgctgaggg cctacctaac    240

catcgtgggg aataaggaca gtgtcaccc                                      269
```

GENE THERAPEUTICS FOR FIBRODYSPLASIA OSSIFICANS PROGRESSIVA

CROSS REFERENCE TO RELATED APPLICATIONS

This application claims the benefit under 35 U.S.C. 119(e) of U.S. Provisional Application No. 63/121,221, filed Dec. 3, 2020, entitled "DEVELOPMENT OF NOVEL GENE THERAPEUTICS FOR FIBRODYSPLASIA OSSIFICANS PROGRESSIVA" and U.S. Provisional Application No. 63/251,822, filed Oct. 4, 2021, entitled "DEVELOPMENT OF NOVEL GENE THERAPEUTICS FOR FIBRODYSPLASIA OSSIFICANS PROGRESSIVA," the entire disclosures of each of which are hereby incorporated by reference in their entireties.

REFERENCE TO A SEQUENCE LISTING SUBMITTED AS A TEXT FILE VIA EFS-WEB

The instant application contains a sequence listing which has been submitted in ASCII format via EFS-web and is hereby incorporated by reference in its entirety. The ASCII file, created on Dec. 2, 2021 is named U012070152US02-SEQ-SXT.txt and is 232,210 bytes in size.

BACKGROUND

Fibrodysplasia ossificans progressiva (FOP) occurs at an incidence of one per 1.36 million to 2 million people. Patients exhibit abnormal bone formation in the skeletal muscle and in connective tissues. This heterotopic ossification (HO) leads to immobility and severe pain through progressive extra-skeletal bone formation in skeletal muscles, tendons, and cartilage. However, no effective treatments are currently available, except for high dose of corticosteroids for flare-up conditions, which can reduce the intense pain and edema as a symptomatic relief.

SUMMARY

Aspects of the disclosure relate to compositions and methods for treating fibrodysplasia ossificans progressiva (FOP) or reducing the flare-up conditions associated with FOP. The disclosure is based, in part, on isolated nucleic acids and expression constructs encoding one or more transgenes such as inhibitory nucleic acids or codon optimized proteins, that inhibit the expression of the mutated ACVR1 gene, reduce heterotopic ossification and promote the expression of the wild type ACVR1 gene in a subject in need thereof.

Accordingly, in some aspects, the disclosure provides a recombinant adeno-associated virus (rAAV) comprising (i) an isolated nucleic acid comprising a transgene comprising a promoter operably linked to a codon optimized nucleic acid sequence encoding an ACVR1; and (ii) at least one AAV capsid protein.

In some aspects, the disclosure provides a recombinant adeno-associated virus (rAAV) comprising (i) at least one AAV capsid protein; and (ii) a nucleic acid that encodes an artificial miRNA (ami-RNA) comprising a nucleic acid having sufficient sequence complementary with an endogenous mRNA of a subject to hybridize with and inhibit expression of the endogenous mRNA, wherein the endogenous mRNA encodes an ACVR1 protein; and/or (iii) a nucleic acid that encodes a transgene comprising a codon optimized nucleic acid sequence encoding an ACVR1.

In some aspects, the disclosure provides a recombinant gene editing complex comprising: (i) a single guide RNA (sgRNA) that specifically hybridizes to a target nucleic acid sequence of an ACVR1 gene; (ii) a first rAAV particle encoding a first recombinant gene editing protein or fragment thereof; and (iii) a second rAAV particle encoding a second recombinant gene editing protein or fragment thereof.

In some embodiments, the isolated nucleic acid is positioned within a vector. In some embodiments, the promoter is a chicken beta-actin (CBA) promoter. In some embodiments, the CBA promoter comprises a CBA intron in the vector. In some embodiments, the CBA promoter comprises a MASSBIOLOGICS® novel (MBL) intron comprising a sequence as set forth in SEQ ID NO: 37. In some embodiments, the CBA promoter comprises a synthetic intron comprising a sequence as set forth in SEQ ID NO: 36 in the vector.

In some embodiments, the MBL intron reduces the size of the vector genome (e.g., relative to the size of a vector genome having a CBA promoter or the like). In some embodiments, the synthetic intron reduces the size of the vector genome. In some embodiments, the size of the vector genome is reduced by at least 15-25%.

In some embodiments, the intron is present between the promoter and the sequence of the transgene encoding the codon optimized ACVR1. In some embodiments, the codon optimized ACVR1 comprises a sequence as set for in SEQ ID NO: 1.

In some embodiments, the vector is a plasmid. In some embodiments, the vector is a bacmid. In some embodiments, the vector is a cosmid. In some embodiments, the vector is a viral, closed-ended linear DNA (ceDNA). In some embodiments, the vector is a Baculovirus vector. In some embodiments, the vector is an adeno-associated virus (AAV) vector.

In some embodiments, the transgene is flanked by AAV inverted terminal repeat (ITRs).

In some embodiments, the ACVR1 protein comprises a single base mutation of guanine to adenine at position 206 of the sequence of the wild type ACVR1. In some embodiments, the ACVR1 protein is human ACVR1-R206H. In some embodiments, the ami-RNA is encoded by the sequence set forth in any one of SEQ ID NOs: 5, 6 and 56-65.

In some embodiments, the vector is a plasmid. In some embodiments, the vector is a bacmid. In some embodiments, the vector is a cosmid. In some embodiments, the vector is a viral, closed-ended linear DNA (ceDNA). In some embodiments, the vector is a Baculovirus vector. In some embodiments, the vector is an adeno-associated virus (AAV) vector.

In some embodiments, the AAV vector comprises at least one inverted terminal repeat (ITR). In some embodiments, the ami-RNA comprises a human miRNA backbone. In some embodiments, the ami-RNA is a human miR-33 backbone.

In some embodiments, the isolated nucleic acid is positioned within a viral vector. In some embodiments, the viral vector is an adeno-associated virus (AAV) vector. In some embodiments, the AAV vector is encapsidated by a capsid protein selected from AAV1, AAV2, AAV3, AAV4, AAV5, AAV6, AAV6.2, AAV7, AAV8, AAVrh.8, AAV9, AAVrh.10, AAVrh39, and AAVrh.43. In some embodiments, the rAAV is a self-complementary AAV (scAAV).

In some embodiments, the ami-RNA and the transgene are operably linked to a promoter. In some embodiments, the promoter is a chicken beta-actin (CBA) promoter. In some embodiments, the CBA promoter comprises a CBA intron in the vector.

In some embodiments, the CBA promoter comprises a MASSBIOLOGICS® novel (MBL) intron comprising a sequence as set forth in SEQ ID NO: 37 in the vector. In some embodiments, the ACVR1 protein is a mutated protein having a single base mutation of guanine to adenine. In some embodiments, the ACVR1 protein is human ACVR1-R206H. In some embodiments, the isolated nucleic acid comprises the sequence set for in any one of SEQ ID NOs: 25-28.

In some embodiments, the ami-RNA comprises a human miRNA backbone. In some embodiments, the human miRNA backbone is a human miR-33 backbone.

In some embodiments, the ami-RNA and the transgene replace ACVR1-R206H with wild type ACVR1. In some embodiments, the present disclosure provides a vector comprising the sequence set for in any one of SEQ ID NOs: 25-28.

In some embodiments, the first recombinant gene editing protein comprises a Cas9-based adenine base editor (ABE) N-terminus portion and its fragments thereof.

In some embodiments, the second recombinant gene editing protein comprises a Cas9-based adenine base editor (ABE) C-terminus portion and its fragments thereof.

In some embodiments, the recombinant gene editing complex further comprises a protospacer adjacent motif. In some embodiments, the recombinant gene editing protein is a protein of the Crisper/Cas9 system. In some embodiments, the first and the second rAAV particles comprises an AAV9 capsid protein or variant thereof. In some embodiments, the first and the second rAAV particles comprises an AAV6.2 capsid protein or variant thereof.

In some embodiments, each of the N-terminal ABE construct and the C-terminal ABE construct is divided by using a trans-splicing intein sequence. In some embodiments, the N-terminal ABE construct comprises protospacer having the ACVR1-R206H mutation. In some embodiments, the C-terminal ABE construct is integrated into the AAV6.2 or AAV9 capsid protein. In some embodiments, the ABE converts adenine into guanine in the ACVR1-R206H allele.

The present disclosure provides a method of treating a subject having or suspected of having fibrodysplasia ossificans progressiva (FOP). In some embodiments, the method comprises administering to the subject the rAAV of (i) at least one AAV capsid protein; and (ii) a nucleic acid that encodes an artificial miRNA (ami-RNA) comprising a nucleic acid having sufficient sequence complementary with an endogenous mRNA of a subject to hybridize with and inhibit expression of the endogenous mRNA, wherein the endogenous mRNA encodes an ACVR1 protein; and/or (iii) a nucleic acid that encodes a transgene comprising a codon optimized nucleic acid sequence encoding an ACVR1.

In some embodiments, the subject comprises a nucleic acid sequence encoding a mutant ACVR1 protein. In some embodiments, the mutant ACVR1 protein is an ACVR1-R206H protein.

In some embodiments, the subject is a mammalian subject. In some embodiments, the mammalian subject is a human subject.

In some embodiments, the administration or delivery occurs by injection. In some embodiments, the injection is intravenous injection.

In some embodiments, the administration or delivery occurs by implantation of a tissue or graft comprising the rAAV as disclosed herein into the subject.

In some embodiments, the administration or delivery occurs by interdermal delivery of the rAAV as disclosed herein into the subject.

In some embodiments, the administration or delivery results in reduction of flare-up conditions in the subject.

BRIEF DESCRIPTION OF DRAWINGS

FIG. 1A illustrates the schematic diagram showing FOP mutations. FIG. 1B shows the BMP/Activin A signaling pathway in normal subjects and FOP patients. Abbreviations: SP, signal peptide; LBD, ligand binding domain; TM, transmembrane; GS, gly-ser-rich domain.

FIG. 2A shows a schematic diagram of plasmid construction. The CBA promoter is operably linked to chicken beta-actin intron, MBL intron, or synthetic intron. FIG. 2B shows validation of the expression of opt-ACVR1. Vector genomes were transiently transfected into HEK293 cells and cell lysates were subjected to immunoblotting with anti-ACVR1 antibody. Anti-Hsp90 antibody was used for loading control.

FIG. 3A is a schematic diagram showing 12 artificial miRNAs (amiRs) that target different sequence sites of human ACVR1-R206H miRNA (amiR-ACVR1.R206H) and amiR-sensor plasmids for human ACVR1-R206H, -WT (wild type), or—opt (optimized) (FIG. 3B). FIG. 3C shows that amiR-ctrl (control) or amiR-ACVR1.R206H were transiently transfected into HEK293 cells along with amiR-sensor plasmids and luciferase assay was performed to measure *renilla* and firefly activities. Lower ratio of *renilla* to firefly indicates higher silencing efficacy of amiRs. FIG. 3D depicts images showing that amiR-ctrl or amiR-ACVR1.R206H were transiently transfected into HEK293 and cell lysates were subjected to immunoblotting with anti-ACVR1 antibody. Anti-Hsp90 antibody was used for loading control. Abbreviations: Fluc, firefly luciferase; Rluc, *renilla* luciferase.

FIG. 4A is a schematic diagram of plasmid construction containing a synthetic intron (SEQ ID NO: 36) or an MBL intron (SEQ ID NO: 37), artificial miRNAs (amiRs; RH6 or RH7) ACVR1. FIG. 4B shows a graph measuring luciferase activity after a vector or four AAV vector genome (RH6 or RH7 with the synthetic intron and RH6 or RH7 with the MBL intron) was transiently transfected into HEK293 cells along with amiR-sensor plasmids and luciferase assay was performed to measure *renilla* and firefly activities. FIG. 4C shows opt-ACVR1 expression assessed by immunoblotting with anti-ACVR1 antibody. Anti-Hsp90 antibody was used for loading control. FIG. 4D shows a graph measuring BRE-luciferase activity after a vector control or AAV vector genome was transiently transfected into HEK293 cells along with BRE-luc reporter gene and treated with activin A (100 ng/ml). 24 hours later, activin A signaling activity was measured by luciferase assay. Values represent mean±SD: , $P<0.01$ and *, $P<0.001$ by an unpaired two-tailed Student's t-test or by one-way ANOVA test.

FIG. 7A is a schematic diagram of the generation of rAAV vector, which contains MBL intron (SEQ ID NO: 37), rAAV6.2 or rAAV9, amiR-RH6 or amiR-RH7, and codon optimized ACVR1. FIG. 7B shows a gel image after electrophoresis to assess the genome integrity of rAAV6.2 containing amiR-RH6 or -RH7 after digestion. Abbreviation: ss, single-stranded.

FIG. 8E shows that mRNA levels of osteoblast marker genes, including type 1 collagen (Col1a1) and bone sialoprotein (ibsp), were markedly reduced by rAAV6.2 carrying amiR-RH7 and opt-ACVR1, not by rAAV6.2 carrying amiR-RH6 and opt-ACVR1 or rAAV6.2.amiR-ctrl. Values represent mean±SD: , P<0.01, *, P<0.001 and **, P<0.0001 by an unpaired two-tailed Student's t-test in all panels. FIG. 8F shows that $5\times10^{10}$ GCs of tAAV6.2 vectors carrying ctrl, amiR-RH6.ACVR1$^{opt}$, or amiR-RH7.ACVR1$^{opt}$ were transduced to human FOP-iPSCs and cultured under osteogenic conditions for 4 days. Total RNA was subjected for cDNAs synthesis, followed by next generation sequencing (NGS) (top figure) or RT-PCR for ACVR1$^{opt}$ mRNA expression (bottom figure). FIG. 8G shows that human FOP patient-derived iPSCs were treated with PBS or $5\times10^{10}$ genome copies (GCs) of 14 different AAV capsids packaged with the same CBA-Egfp transgene. Two days later, EGFP expression was assessed by immunoblotting with an anti-GFP antibody. Anti-HSP90 antibody was used for loading control. FIG. 8H-8K show that $5\times10^{10}$ GCs of AAV6.2 vectors carrying ctrl, amiR-RH6.ACVR1$^{opt}$, or amiR-RH7.ACVR1$^{opt}$ were transduced to human iPSCs derived from healthy donor (WT-iPSC) or FOP patient (R206H-iPSC). Osteogenic gene expression was assessed by RT-PCR (FIG. 8H). AAV-treated cells were incubated with PBS or activin A (100 ng/ml) for six hours and ID1 mRNA levels were measured by RT-PCR (FIG. 8I). FIG. 8J shows PDGFRa$^+$Sca1$^+$CD31$^-$CD45$^-$ fibroadipogenic progenitors (FAPs) were FACS sorted from the digested tibial muscle of 4 week old Acvr1$^{(R206H)F1}$; PDGFRα mice and treated with $5\times10^{10}$ GCs of the AAV6.2 vectors carrying ctrl, amiR-RH6.ACVR1$^{opt}$, or amiR-RH7.ACVR1$^{opt}$. Two days later, AAV-treated cells were cultured under osteogenic conditions with PBS or activin A (50 ng/ml) for six days and ALP activity was assessed for osteoblast differentiation (FIG. 8**K). Values represent mean±SD: ns, non-significant; *, P<0.05; , P<0.01; *, P<0.001; ****, P<0.0001 by one-way ANOVA test.

FIG. 13A is a schematic diagram of plasmid construction having pBRE and pNF-kB promoters, ITRs, and *Gaussia* reporter gene. FIGS. 13B-13D show results after HEK293 cells were transiently transfected with either PB2-luc or AAV vector genome (eBRE/NF-κB-luc) and 24 hours later, cells were stimulated with different concentrations of TNF or IL-1β (FIG. 13B), BMP4 (FIG. 13C), or the combination (FIG. 13D). The responsiveness of the vectors was measured using luciferase assay. Values represent mean±SD: *, P<0.05, , P<0.01, *, and P<0.001 by an unpaired two-tailed Student's t-test in all panels.

FIG. 14A is a schematic diagram of plasmid constructions. FIG. 14B shows results after HEK293 cells were transfected with control vector or AAV vector genome encoding FST-288 and sTNFR2 and 48 hours later, the supernatant was harvested. Either PB2-luc or 3TP-lux was transfected into HEK293 cells and 24 hours later, the culture medium was changed with the fresh medium: harvested supernatant (1:1) that contains different concentrations of TNF or activin A. 24 hours later, luciferase assay was performed to assess TNF-induced NF-kB and activin A-induced SMAD activation. Values represent mean±SD: ns, not significant, *, P<0.05, , P<0.01, **, and P<0.0001 by an unpaired two-tailed Student's t-test in all panels.

FIG. 15A shows $5\times10^{10}$ GC of AAV6.2 vectors carrying ctrl, amiR-RH6.optACVR1, or amiR-RH7.optACVR1 were transduced to human FOP-iPSCs for 2 days and cultured under osteogenic conditions for 4 days. Total RNA was subjected for cDNAs synthesis, followed by RT-PCR for Egfp expression. FIG. 15B shows total RNA was subjected for RNA sequencing and a volcano plot comparing the gene expression for up/downregulated genes in the cells expressing amiR-RH6.optACVR1 relative to amiR-RH7.optACVR1 was produced. FIG. 15C shows $Sca1^+$ $PDGFRa^+CD31^-CD45^-$fibroadipogenic progenitors (FAPs) were FACS sorted from tibial muscle of 4 week old $Acvr1R^{206H}$; PDGFRa mice and treated with $5\times10^{10}$ GC of the AAV6.2 vectors carrying ctrl, amiR-RH6.optACVR1, or amiR-RH7.optACVR1. Two days later, AAV-treated cells were cultured under osteogenic conditions with PBS or Activin A (50 ng/ml) for six days and osteogenic gene expression was assessed by RT-PCR. FIG. 15D shows that a volcano plot showing the gene expression for upregulated and downregulated genes in the cells expressing amiR-RH6.$ACVK1^{opt}$ or amiR-RH7.$ACVK1^{opt}$ relative to ctrl-expressing cells was displayed.

FIG. 16A shows primary bone marrow-derived stromal cells (BMSCs) were isolated from 4 week old $Acvr1R^{206H}$; Prx1 femurs and treated with $5\times10^{10}$ GC of the AAV6.2 vectors carrying ctrl, amiR-RH6, optACVR1, or amiR-RH6.optACVR1. Two days later, AAV-treated cells were cultured under osteogenic conditions for four days, stimulated with Activin A (100 ng/ml) for 6 or 24 hours and expression of Activin A-responsive genes Id1 and Msx2 was assessed using RT-PCR, respectively. FIGS. 16B-16C show AAV-treated cells were cultured under osteogenic conditions with PBS or Activin A (50 ng/ml), and ALP (FIG. 16B) and alizarin red staining (FIG. 16C) were performed to assess osteoblast differentiation at 6 and 12 days of osteogenic culture, respectively.

FIGS. 17A-17D show primary bone marrow-derived stromal cells (BMSCs) were isolated from 4 week old $Acvr1R^{206H}$; Prx1 femurs and treated with $5\times10^{10}$ GC of the AAV6.2 vectors carrying ctrl, amiR-RH6, optACVR1, or amiR-RH6.optACVR1. Two days later, AAV-treated cells were cultured under osteogenic conditions for four days and $Acvr1^{R206H}$ and optAcvr1 mRNA levels were measured by RT-PCR (FIG. 17A). AAV-treated cells were stimulated with Activin A (100 ng/ml) for 30 min and immunoblotted for phospho-Smad1/5. Anti-Gapdh antibody was used for loading control (FIG. 17B). AAV-treated cells were cultured under osteogenic conditions with PBS or Activin A (50 ng/ml), and ALP (FIG. 17C, left) and alizarin red staining (FIG. 17C, right) were performed to assess osteoblast differentiation at 6 and 12 days of osteogenic culture, respectively. AAV-treated cells were cultured under osteogenic conditions with PBS or BMP4 (50 ng/ml) for 12 days, and alizarin red staining (FIG. 17C, right) was performed for mineralization (FIG. 17D). FIG. 17E shows $5\times10^{12}$ vg/kg of rAAV9 expressing EGFP was intradermally (i.d.) injected into the femoral muscle of 2 month old male Tie2-cre; Ai9 mice (n=3) one week after rBMP2/7-matrigel injection and muscle injury, and X-radiography of hindlimbs (left top) and frozen-section of HO tissues (left bottom, right) were performed in treated mice. Box indicates HO in the skeletal muscle. M, muscle; HO-BM, heterotopic ossification bone marrow. Blue, DAPI; Red, $Tie2^+$ cells; Green, AAV-transduced cells. FIGS. 17F-17G show $5\times10^{12}$ vg/kg of rAAV9 expressing vector or CRE recombinase was i.d. injected into the tibial muscle of 6 week old female $Acvr1R^{206H}$; Cre-$ER^{T2}$ mice (n=8) and two days later, pinch injury and 1 mM cardiotoxin were employed into the injection sites. Four weeks later, $Acvr1^{R206H}$ and CRE recombinase mRNA levels in the tibial muscle were measured by RT-PCR (FIG. 17F) and HO in the tibial muscle was assessed using X-radiography and microCT. 3D reconstruction images (FIG. 17G, left) and quantification of HO volume are displayed (FIG. 17G, right). FIG. 17H shows $5\times10^{12}$ vg/kg of rAAV9 carrying ctrl, amiR-RH6, optACVR1, or amiR-RH6.optACVR1 was i.d. injected into the tibial muscle of 6 week old male $Acvr1R^{206H}$; Cre-$ER^{T2}$ mice (n=8) two days after five times intraperitoneal (i.p.) injection of tamoxifen (10 mg/kg). Two days later, pinch injury and 1 mM cardiotoxin were employed into the injection sites and four weeks later, and HO in the tibial muscle was assessed using microCT. 3D reconstruction images (left) and quantification of HO volume is displayed (right). FIG. 17I shows $5\times10^{12}$ vg/kg of rAAV9 expressing ctrl or amiR-RH6.optACVR1 was i.d. injected into the femoral muscle of 2 month old male wildtype mice (n=5) and two days later, rBMP2/7-matrigel injection and muscle injury were employed into the injection sites. Four weeks later, HO in the femoral muscle was assessed using X-radiography and microCT. 3D reconstruction images (left) and quantification of HO volume is displayed (right).

FIGS. 18A-18B show a diagram of the study and treatment design. $5\times10^{12}$ vg/kg of rAAV6.2 expressing EGFP was i.d. injected into the femoral muscle of 2 month old male wildtype mice (n=3) one week after rBMP2/7-matrigel injection and muscle injury, and X-radiography of hindlimbs (FIG. 18B, left) and frozen-section of HO tissues (FIG. 18B, right) were performed in treated mice. Box indicates HO in the skeletal muscle. FIGS. 18C-18D show a diagram of additional study and treatment designs. FIG. 18E shows $5\times10^{12}$ vg/kg of rAAV9 carrying ctrl, amiR-RH6, optACVR1, or amiR-RH6.optACVR1 was i.d. injected into the tibial muscle of 6 week old male Acvr1R206H; Cre-ERT2 mice (n=8) Three days after five times intraperitoneal (i.p.) injection of tamoxifen (10 mg/kg). Three days later, pinch injury and 1 μM cardiotoxin were employed into the injection sites and four weeks later, and Acvr1R206H and optAcvr1 mRNA levels were measured by RT-PCR (right). FIG. 18F shows a diagram of an additional study and treatment design.

FIGS. 19A-19B show P1 PDGFRa-GFP neonates (n=3) were treated with $10^{11}$ GC of rAAV9 expressing mCherry via facial vein injection and two weeks later, tissue distribution of vectors was assessed by mCherry expression using IVIS-100 optical imaging system (FIG. 19A) or frozen section of AAV-treated hindlimbs (FIG. 19B). BM: bone marrow. FIGS. 19C-19E show P1

$Acvr1R^{206H}$; $Cre\text{-}ER^{T2}$ neonates (n=10) were treated with $10^{11}$ GC of rAAV9 carrying ctrl, amiR-RH6, optACVR1, or amiR-RH6.optACVR1 via facial vein injection, and six weeks later, mice were treated five times with i.p. injection of tamoxifen (10 mg/kg). Two days later, pinch injury and 1 mM cardiotoxin were employed into the injection sites and four weeks later, and $Acvr1^{R206H}$ and optAcvr1 mRNA levels were measured by RT-PCR (FIG. 19C). HO in the tibial muscle was assessed using microCT or histology. 3D reconstruction images (FIG. 19D, left) and quantification of HO volume is displayed (FIG. 19D, right). FIG. 19E shows representative histology data. FIG. 19F shows P1 $Acvr1R^{206H}$; $Cre\text{-}ER^{T2}$ neonates (n=3) were treated with $10^{11}$ GC of rAAV9 carrying ctrl or amiR-RH6.optACVR1 via facial vein injection, and six weeks later, mice were treated five times with i.p. injection of tamoxifen (10 mg/kg). Three days later, pinch injury and 1 mM cardiotoxin were employed into the injection sites and 3, 7, 14, 28 days later, HO in the tibial muscle was assessed by X-radiography. Boxes indicate HO in the tibial muscle.

FIG. 20A shows a diagram of study and treatment design. FIGS. 20B-20C show P1 PDGFRa-GFP neonates (n=3) were treated with $10^{11}$ GC of rAAV9 expressing mCherry via facial vein injection and two weeks later, PDGFRα expression was assessed by IVIS-100 optical imaging system using GFP expression (FIG. 20B). AAV-transduced cells in the hindlimbs were also assessed by mCherry expression in the hindlimbs using fluorescence microscopy. IVIS-100 optical imaging system (FIG. 20B) or frozen section of AAV-treated hindlimbs (FIG. 20C). BM: bone marrow. FIG. 20D shows P1 wildtype neonates (n=3) were treated with $10^{11}$ GC of rAAV9 expressing LacZ via facial vein injection and two weeks later, frozen-sections of AAV-transduced tissues were stained for X-galactosidase. BM: bone marrow, CB: cortical bone, M: muscle. FIG. 20E shows that P1 PDGFRα-GFP neonates (n=3) were treated with $10^{11}$ GCs of rAAV9 expressing mCherry via facial vein injection and two weeks later, PDGFRα expression was assessed by IVIS-100 optical imaging system using GFP expression. FIG. 20F shows a diagram of a study and treatment methods design. FIG. 20G shows a diagram of a study and treatment methods design.

FIG. 21A shows $5\times10^{13}$ vg/kg of rAAV9 carrying ctrl or amiR-RH6.optACVR1 was i.v. injected into 6 week old $Acvr1R^{206H}$; $Cre\text{-}ER^{T2}$ mice (n=10) three days after five times consecutive i.p. injection of tamoxifen (10 mg/kg). Ten weeks later, $Acvr1^{R206H}$ and optACVR1 mRNA levels in the liver were assessed by RT-PCR. MicroCT analysis of whole body (FIG. 21B), torso (FIG. 21C), and lower body (FIG. 21D) demonstrates that AAV-mediated expression of amiR-RH6.optACVR1 prevents chronic HO in $Acvr1R^{206H}$; PDGFRa-Cre mice. Arrows indicate HO areas. Total HO volume (FIG. 21E) and number of HO areas (FIG. 21F) in whole body were quantitated. Percentage of clinical HO incidence was assessed (FIG. 21G). MicroCT and histology of knee joints were performed to assess heterotopic bone (FIG. 21H, left and middle), degeneration of articular cartilage (FIG. 21H, middle), and growth plate (FIG. 21H, right). Boxes indicate HO areas and articular cartilage and growth plate. Frequency of immune cells within the population of total splenocytes indicate little to no effects of AAV vectors on systemic immune responses (n=6-8, FIG. 21I). FIG. 21J show MicroCT and histology images of degeneration of articular cartilage (left image), and growth plate (right image).

FIG. 22A shows a diagram of a study and treatment design. FIG. 22B shows $5\times10^{13}$ vg/kg of rAAV9 expressing mCherry was i.v. injected into 6 week old Acvr1R206H; Cre-ERT2 mice (n=3) three days after five times consecutive i.p. injection of tamoxifen (10 mg/kg). mCherry expression in individual tissues was monitored by IVIS-100 optical imaging two weeks post-injection. FIGS. 22C-2F show $5\times10^{13}$ vg/kg of rAAV9 carrying ctrl or amiR-RH6.optACVR1 was i.v. injected into 6 week old Acvr1R206H; Cre-ERT2 mice (n=10) three days after five times consecutive i.p. injection of tamoxifen (10 mg/kg). Ten weeks later, the movements of 16 week old AAV-treated mice, including Acvr1R206H (ctrl) mouse with normal locomotion, Acvr1R206H; Cre-ERT2 (ctrl) mouse with slow locomotion, and Acvr1R206H; Cre-ERT2 (amiR-RH6.optACVR1) mouse with normal locomotion. Arrow indicates amiR-RH6.optACVR1-treated mouse (FIG. 22C). FIG. 22D shows the heterotopic bone near knee joints. FIG. 22E shows H&E staining of the longitudinal sections of the AAV-treated spleens. FIG. 22F shows frequency of monocytes, macrophages, and neutrophils within the population of total splenocytes (n=6-8).

FIG. 24A shows $5\times10^{13}$ vg/kg of rAAV9 expressing LacZ was i.v. injected into 3 week old $Acvr1R^{206H}$; PDGFRa-Cre mice (n=3) and two weeks later, X-radiography of whole body was performed to locate HO sites (top). Frozen-sections of HO tissues were stained for X-galactosidase (bottom). Boxes indicate HO tissues. FIGS. 24B-24H show P1 $Acvr1R^{206H}$; PDGFRa-Cre neonates (n=12) were treated with $10^{11}$ GC of rAAV9 carrying ctrl, amiR-RH6, optACVR1, or amiR-RH6.optACVR1 via facial vein injection. Survival (FIG. 24B) and body weight (FIG. 24C) of AAV-treated mice were weekly analyzed from the age of three weeks old to eight weeks old. MicroCT analysis of 5 week old AAV-treated skulls shows the ability of AAV vectors to reverse jaw ankylosis of $Acvr1R^{206H}$; PDGFRa-Cre mice (FIGS. 24D-24E). Images of 3D reconstruction (FIG. 24D, top) and 2D transverse section (FIG. 24D, bottom) and distance of open mouth (FIG. 24E) are displayed. Arrows indicate the areas of temporomandibular joint ankylosis. MicroCT analysis of maxillary and mandibular bones demonstrates that AAV-mediated expression of amiR-RH6.optACVR1 reverses low bone mass of $Acvr1R^{206H}$; PDGFRa-Cre mice (FIGS. 24F-24G). MicroCT analysis showed maxillary and mandibular bones of AAV-treated mice. 2D cross (FIG. 24F) and transverse (FIG. 24G) section images are displayed. Arrows indicate dental root bones. MicroCT analysis of whole body shows the ability of AAV vectors to prevent chronic HO in $Acvr1R^{206H}$; PDGFRa-Cre mice (FIG. 24H). MicroCT analysis showed a whole body of AAV-treated mice. Images of 3D reconstruction (FIG. 24H, left) and 2D transverse section (FIG. 24H, right) are displayed.

FIG. 25A shows Alcian blue staining of HO tissues in 5 week old Acvr1R206H; PDGFRα-Cre mice (n=3). FIG. 25B shows $5\times10^{13}$ vg/kg of rAAV9 expressing LacZ was i.v. injected into 3 week old Acvr1R206H; PDGFRα-Cre mice (n=3) and two weeks later, X-radiography of whole body was performed to locate HO sites. Frozen-sections of HO tissues were stained for X-galactosidase.

FIG. 26A shows P1 Acvr1R$^{206H}$; PDGFRα-Cre neonates (n=12) were treated with $10^{11}$ GC of rAAV9 carrying ctrl, amiR-RH6, optACVR1, or amiR-RH6.optACVR1 via facial vein injection. Movements of 5 week old AAV-treated mice, including normal sized Acvr1R$^{206H}$ mouse (ctrl), small sized Acvr1R$^{206H}$; PDGFRα-Cre mouse (ctrl), and normal sized Acvr1R$^{206H}$; PDGFRα-Cre mouse (amiR-RH6.optACVR1), are shown. FIG. 26B shows X-radiography showing whole body of 5 week old AAV-treated mice.

FIG. 27A shows photography demonstrating the ability of 5 week old AAV-treated mice to open mouth. FIG. 27B shows photography showing individual tissues of 5 week old AAV-treated mice demonstrates that AAV-mediated expression of optACVR1 or amiR-RH6.optACVR1 prevents a decay of Acvr1R$^{206H}$; PDGFRa-Cre intestines by starvation. FIG. 27C shows that frozen section of mandibular bones of 2-month-old PDGFRa-GFP mice (n=3) was assessed for PDGFRa expression in the root of alveolar bone by fluorescence microscopy. DAPI: nucleus staining. FIG. 27D shows MicroCT analysis showing 2D sagittal-section images maxillary and mandibular bones of AAV-treated mice. Arrows indicate roots of alveolar bones in the teeth.

FIG. 28A shows a schematic diagram of plasmid construction. CMV enhancer/chicken β-actin promoter (CBA), MBL intron (MBLi), β-globin polyA sequence (PA), and inverted terminal repeat (TR). miR-122: liver-specific miRNA, miR-208a: cardiac muscle-specific miRNA, TS: target sequence. miR-122/miR208a-TS is used to repress AAV's expression in the liver and heart. EndoID1-BRE: BMP-responsive elements. pNF-kB: inflammation-responsive elements. The promoter containing EndoID1-BRE/pNF-kB is used to induce AAV's expression in response to BMPs, activin A, and/or pro-inflammatory cytokines. FIG. 28B shows a schematic diagram of plasmid construction. FIG. 28C shows 6 week old wildtype mice were treated with i.v. injection of PBS or $5\times10^{13}$ vg/kg of rAAV9.egfp or rAAV9.egfp.MIR-TS and two weeks later, tissue distribution of AAV vectors were monitored by IVIS-100 optical imaging system using EGFP expression.

FIG. 30A shows schematic diagram of mammalian expression vectors (pcDNA6, pAAV) that encode human ACVR1$^{R206H}$, ACVR1$^{WT}$, or ACVKP1$^{opt}$ cDNA. FIG. 30B shows control or four combination vectors were transiently transfected into HEK293 cells along with plasmids expressing human ACVR1$^{R206H}$, ACVR1$^{WT}$, or ACVR1$^{opt}$ and human ACVR1 mRNA levels were assessed by RT-PCR.

FIG. 32C shows that $5\times10^{13}$ vg/kg of rAAV9.egfp was i.v. injected into 2-month-old male mice (n=3) and two weeks later, tissue distribution of vectors was assessed by EGFP expression using IVIS-100 optical imaging system. FIGS. 32D and 32E show $5\times10^{12}$ vg/kg of rAAV9 expressing mCherry was interdermally (i.d.) injected into the tibial muscle of 2-month-old male wildtype mice (n=3). Two weeks later, tissue distribution of vectors was assessed by mCherry expression using IVIS-100 optical imaging system (FIG. 32D) or frozen section of AAV-treated hindlimbs (FIG. 32E).

DETAILED DESCRIPTION

Figure 1A:
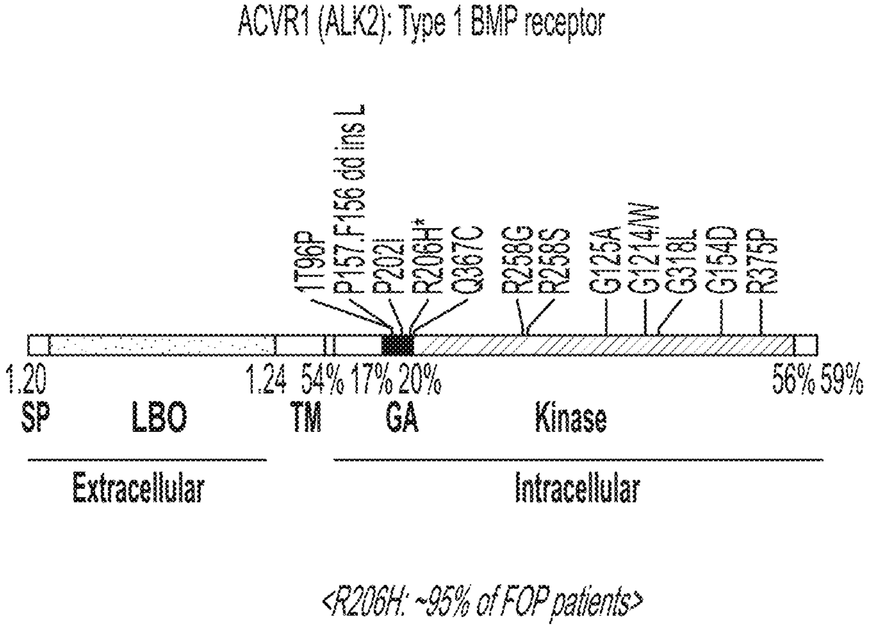
FIGS. 1A-1B show the mechanisms and signaling pathways that are involved in fibrodysplasia ossificans progressiva (FOP).
Figure 1B:
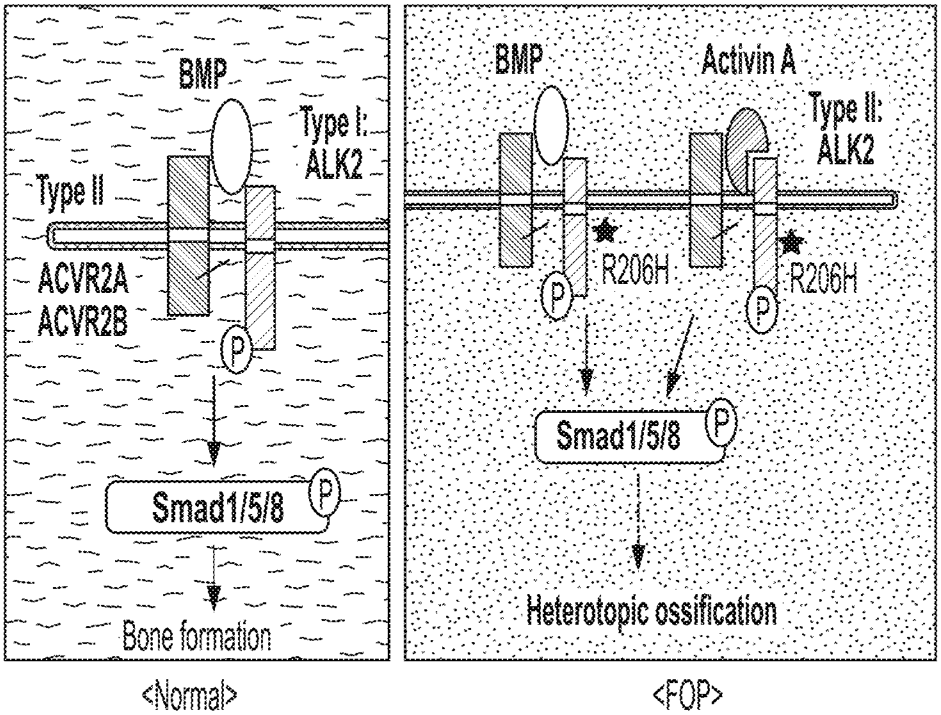

Aspects of the disclosure relate to methods and compositions for treating fibrodysplasia ossificans progressiva (FOP) and the flare-up conditions. The disclosure is based, in part, on compositions (e.g., isolated nucleic acids, vectors, rAAVs, etc.) that reduce the expression of the mutated activin A type 1 receptor (ACVR1). In some embodiments, the compositions as disclosed herein (AAV-mediated gene transfer platforms) at least inhibit heterotopic ossification and/or the flare-up conditions when delivered to the affected tissues with abnormal bone formation, such as skeletal muscles, tendons, and cartilage in a subject, for example, by inducing activin A antagonist and/or TNF antagonist. Accordingly, methods and compositions described by the disclosure are useful, in some embodiments, for the treatment of diseases and disorders associated with FOP.

Isolated Nucleic Acids

Compositions and methods for delivering a transgene (e.g. an inhibitory RNA, such as an shRNA, miRNA, etc.) to a subject are provided in the disclosure. The compositions typically comprise an isolated nucleic acid encoding a transgene (e.g., a protein, an inhibitory nucleic acid, etc.)

capable of modulating bone metabolism and/or treating FOP. For example, in some embodiments, a transgene reduces expression of a target protein, such as a target protein associated with promoting bone formation.

In some embodiments, an isolated nucleic acid, a vector, a recombinant gene editing complex or an rAAV as described by the disclosure comprises a transgene encoding at least one codon optimized ACVR1 (e.g., 1, 2, 3, 4, 5, 6, 7, 8, 9, 10, or more codon optimized ACVR1). In some embodiments, codon optimized ACVR1 is a wild type ACVR1. In some embodiments, the codon composition of the recombinant ACVR1 gene can be improved or optimized without altering the amino acid sequence of ACVR1. In some embodiments, the codon optimized ACVR1 is a competitive inhibitor of ACVR1-R206H. without wishing to be bound by any theory, the codon optimized ACVR1 competes with the mutated ACVR1, such as ACVR1-R206H, for the binding.

In some embodiments, the codon optimized ACVR1 comprises a sequence as set for in SEQ ID NO: 1. In some embodiments, vector constructs comprising the codon optimized ACVR1 comprises a sequence as set for in SEQ ID NOs: 2-4. In some embodiments, rAAV-mediated gene transfer carrying a codon optimized ACVR1 is a gene addition platform. In some embodiments, the codon-optimized, wild type human ACVR1 cDNA is about 1.5 kb in size (FIG. 2).

In some embodiments, the transgene is operably linked to a promoter. In some embodiments, the promoter is a chicken beta-actin (CBA) promoter. In some embodiments, the promoter can be any promoter that is suitable for inducing the expression of the codon optimized ACVR1. In some embodiments, the CBA promoter comprises a CBA intron in the vector. In some embodiments, the CBA promoter comprises a MASSBIOLOGICS® novel (MBL) intron (e.g., SEQ ID NO: 37) in the vector. In some embodiments, the CBA promoter comprises a synthetic intron in the vector. In some embodiments, the CBA intron can be substituted by a MBL intron or a synthetic intron. Without wishing to be bound by any theory, a synthetic intron, in part, can be substituted with an endogenous intron and lead to enhanced mRNA production. In some embodiments, the CBA promoter can comprise any promoter that is suitable for vector constructs designed for the codon optimized ACVR1. In some aspects, the use of MBL intron and/or the synthetic intron reduces the size of the vector genome, preferably reduced by at least 15%, 16%, 17%, 18%, 19%, 20%, 21%, 22%, 23%, 24%, or 25%. In some embodiments, the transgene is flanked by AAV inverted terminal repeat (ITRs).

In some embodiments, an isolated nucleic acid, a vector, or an rAAV encodes one or more (e.g., 1, 2, 3, 4, 5, 6, 7, 8, 9, 10, or more) inhibitory nucleic acids, for example dsRNA, siRNA, shRNA, miRNA, artificial microRNA (ami-RNA), etc.). Generally, an inhibitory nucleic acid specifically binds to (e.g., hybridizes with) at least two (e.g., 2, 3, 4, 5, 6, 7, 8, 9, 10, 11, 12, 13, 14, 15, 16, 17, 18, 19, 20, 21, 22, 23, 24, 25, or more) continuous bases of a gene encoding a gene product (e.g., a protein) associated with FOP (e.g., ACVR1). As used herein "continuous bases" refers to two or more nucleotide bases that are covalently bound (e.g., by one or more phosphodiester bond, etc.) to each other (e.g. as part of a nucleic acid molecule). In some embodiments, the at least one inhibitory nucleic acid is about 50%, about 60% about 70% about 80% about 90%, about 95%, about 99% or about 100% identical to the two or more (e.g., 2, 3, 4, 5, 6, 7, 8, 9, 10, 11, 12, 13, 14, 15, 16, 17, 18, 19, 20, 21, 22, 23, 24, 25, or more) continuous nucleotide bases of a gene encoding a gene product (e.g., a protein) associated with FOP (e.g., ACVR1).

A "microRNA" or "miRNA" is a small non-coding RNA molecule capable of mediating transcriptional or post-translational gene silencing. Typically, miRNA is transcribed as a hairpin or stem-loop (e.g., having a self-complementarity, single-stranded backbone) duplex structure, referred to as a primary miRNA (pri-miRNA), which is enzymatically processed (e.g., by Drosha, DGCR8, Pasha, etc.) into a pre-miRNA. The length of a pri-miRNA can vary. In some embodiments, a pri-miRNA ranges from about 100 to about 5000 base pairs (e.g., about 100, about 200, about 500, about 1000, about 1200, about 1500, about 1800, or about 2000 base pairs) in length. In some embodiments, a pri-miRNA is greater than 200 base pairs in length (e.g., 2500, 5000, 7000, 9000, or more base pairs in length.

Pre-miRNA, which is also characterized by a hairpin or stem-loop duplex structure, can also vary in length. In some embodiments, pre-miRNA ranges in size from about 40 base pairs in length to about 500 base pairs in length. In some embodiments, pre-miRNA ranges in size from about 50 to 100 base pairs in length. In some embodiments, pre-miRNA ranges in size from about 50 to about 90 base pairs in length (e.g., about 50, about 52, about 54, about 56, about 58, about 60, about 62, about 64, about 66, about 68, about 70, about 72, about 74, about 76, about 78, about 80, about 82, about 84, about 86, about 88, or about 90 base pairs in length).

Generally, pre-miRNA is exported into the cytoplasm, and enzymatically processed by Dicer to first produce an imperfect miRNA/miRNA* duplex and then a single-stranded mature miRNA molecule, which is subsequently loaded into the RNA-induced silencing complex (RISC). Typically, a mature miRNA molecule ranges in size from about 19 to about 30 base pairs in length. In some embodiments, a mature miRNA molecule is about 19, about 20, about 21, about 22, about 23, about 24, about 25, about 26, about 27, about 28, about 29, or 30 base pairs in length.

In some aspects, the disclosure provides isolated nucleic acids, vectors (e.g., rAAV vectors) that encode one or more artificial miRNAs. As used herein "artificial miRNA" or "amiRNA" refers to an endogenous pri-miRNA or pre-miRNA (e.g., a miRNA backbone, which is a precursor miRNA capable of producing a functional mature miRNA), in which the miRNA and miRNA* (e.g., passenger strand of the miRNA duplex) sequences have been replaced with corresponding amiRNA/amiRNA* sequences that direct highly efficient RNA silencing of the targeted gene, for example as described by Eamens et al. (2014), Methods Mol. Biol. 1062:211-224. For example, in some embodiments an artificial miRNA comprises a miR-33 pri-miRNA backbone into which a sequence encoding a bone metabolism modulating (e.g., bone formation inhibiting agent) miRNA has been inserted in place of the endogenous miR-33 mature miRNA-encoding sequence. In some embodiments, miRNA (e.g., an artificial miRNA) as described by the disclosure comprises a miR-33 backbone sequence.

In some embodiments, the vector is a plasmid, bacmid, cosmid, viral, closed-ended linear DNA (ceDNA), or Baculovirus vector.

In some embodiments, the present disclosure provides an isolated nucleic acid comprising a transgene encoding an artificial miRNA targeting the AVCR1 gene, which encodes the ACVR1 protein. ACVR1 (ALK2) is a type 1 BMP receptor that contains extracellular ligand binding domain (LBD), transmembrane domain (TM), a glycine-serine-rich domain (GS) and serine/threonine kinase domain. An autosomal dominant mutation in ACVR1 leads to the development of FOP, a monogenic skeletal rare disease. The majority of the FOP patients carry the classical single point mutation (ACVR1-R206H, G>A), which results in spontaneous activation of bone morphogenic protein (BMP) signaling pathways. Without wishing to be bound by any theory, activin A is also identified as a ligand for ACVR1 in FOP. Under normal conditions, activin A binding to the wild type ACVR1 receptor leads to TGF-β signaling through the SMAD2/3 pathway, which functions as a competitive inhibitor of BMP signaling at the wild type ACVR1. When the ACVR1 is mutated, Activin A binding to the ACVR1-R206H receptor activates BMP signaling through the SMAD1/5/9 pathway, resulting in bone formation.

In some aspects, the disclosure relates to an isolated nucleic acid comprising a transgene encoding an artificial microRNA is used to reduce ACVR1 expression. In some embodiments, the artificial microRNA is used to inhibit ACVR1 expression. In some embodiments, the ACVR1 is mutated. In some embodiments, at least one, at least two, at least three, at least four, at least five, at least six, at least seven, at least eight, at least nine, at least ten, at least eleven, at least twelve, at least thirteen mutations ACVR1 mutations are identified that are associated with FOP (FIG. 1A). In some embodiments, the ACVR1 carries a single point mutation (ACVR1-R206H, G>A). In some embodiments, the ACVR1 mutation is human ACVR1-R206H. Without wishing to be bound by any theory, approximately 97% of FOP patients bear an autosomal dominant mutation (G>A) in the ACVR1 gene with an arginine to histidine substitution at position 206 (R206H, G>A) (FIG. 1A). In some embodiments, the promoter as used in the vector construct for the microRNA is a chicken beta-actin (CBA) promoter. In some embodiments, the promoter as used in the vector construct for the microRNA can be any promoter suitable for the expression of the microRNA.

In some embodiments, an artificial microRNA targets (e.g., binds to, or comprises a region of complementarity with) at least 6 continuous nucleotides of an ACVR1 gene. In some embodiments, an artificial microRNA targets (e.g., binds to, or comprises a region of complementarity with) between 6 and 30 continuous nucleotides of an ACVR1 gene. In some embodiments, an artificial microRNA targets between 12-24 continuous nucleotides of an ACVR1 gene. In some embodiments, an artificial microRNA targets between 9-27 continuous nucleotides of the ACVR1 gene. In some embodiments, an artificial microRNA targets at least 6, 7, 8, 9, 10, 11, 12, 13, 14, 15, 16, 17, 18, 19, 20, 21, 22, 23, 24, 25, 26, 27, 28, 29, or 30 continuous nucleotides of an ACVR1 gene.

In some embodiments, an artificial microRNA is between 6-50 nucleotides in length. In some embodiments, an artificial microRNA is between 8-24 nucleotides in length. In some embodiments, an artificial microRNA is between 12-36 nucleotides in length. In some embodiments, an artificial microRNA is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, an isolated inhibitory nucleic acid such as an artificial microRNA decreases expression of a target gene by between 50% and 99% (e.g., any integer between 50% and 99%, inclusive). In some aspects, an isolated inhibitory nucleic acid such as an artificial microRNA decreases expression of a target gene by between 75% and 90%. In some aspects, an isolated inhibitory nucleic acid such as an artificial microRNA decreases expression of a target gene by between 80% and 99%. In some embodiments, an isolated inhibitory nucleic acid such as an artificial microRNA decreases expression of an ACVR1 gene by between 50% and 99% (e.g., any integer between 50% and 99%, inclusive). In some embodiments, an isolated inhibitory nucleic acid such as an artificial microRNA decreases expression of an ACVR1 gene by between 75% and 90%. In some aspects, an isolated inhibitory nucleic acid such as an artificial microRNA decreases expression of an ACVR1 gene by between 80% and 99%.

A region comprising a transgene (e.g., a second region, third region, fourth region, etc.) may be positioned at any suitable location of the isolated nucleic acid. The region may be positioned in any untranslated portion of the nucleic acid, including, for example, an intron, a 5' or 3' untranslated region, etc.

In some cases, it may be desirable to position the region (e.g., the second region, third region, fourth region, etc.) upstream of the first codon of a nucleic acid sequence encoding a protein (e.g., a protein coding sequence). For example, the region may be positioned between the first codon of a protein coding sequence) and 2000 nucleotides upstream of the first codon. The region may be positioned between the first codon of a protein coding sequence and 1000 nucleotides upstream of the first codon. The region may be positioned between the first codon of a protein coding sequence and 500 nucleotides upstream of the first codon. The region may be positioned between the first codon of a protein coding sequence and 250 nucleotides upstream of the first codon. The region may be positioned between the first codon of a protein coding sequence and 150 nucleotides upstream of the first codon.

In some cases (e.g., when a transgene lacks a protein coding sequence), it may be desirable to position the region (e.g., the second region, third region, fourth region, etc.) upstream of the poly-A tail of a transgene. For example, the region may be positioned between the first base of the poly-A tail and 2000 nucleotides upstream of the first base. The region may be positioned between the first base of the poly-A tail and 1000 nucleotides upstream of the first base. The region may be positioned between the first base of the poly-A tail and 500 nucleotides upstream of the first base. The region may be positioned between the first base of the poly-A tail and 250 nucleotides upstream of the first base. The region may be positioned between the first base of the poly-A tail and 150 nucleotides upstream of the first base. The region may be positioned between the first base of the poly-A tail and 100 nucleotides upstream of the first base. The region may be positioned between the first base of the poly-A tail and 50 nucleotides upstream of the first base. The region may be positioned between the first base of the poly-A tail and 20 nucleotides upstream of the first base. In some embodiments, the region is positioned between the last nucleotide base of a promoter sequence and the first nucleotide base of a poly-A tail sequence.

In some cases, the region may be positioned downstream of the last base of the poly-A tail of a transgene. The region may be between the last base of the poly-A tail and a position 2000 nucleotides downstream of the last base. The region may be between the last base of the poly-A tail and a position 1000 nucleotides downstream of the last base. The region may be between the last base of the poly-A tail and a position 500 nucleotides downstream of the last base. The region may be between the last base of the poly-A tail and a position 250 nucleotides downstream of the last base. The region may be between the last base of the poly-A tail and a position 150 nucleotides downstream of the last base.

It should be appreciated that in cases where a transgene encodes more than one miRNA, each miRNA may be positioned in any suitable location within the transgene. For example, a nucleic acid encoding a first miRNA may be positioned in an intron of the transgene and a nucleic acid sequence encoding a second miRNA may be positioned in another untranslated region (e.g., between the last codon of a protein coding sequence and the first base of the poly-A tail of the transgene).

In some embodiments, the transgene further comprises a nucleic acid sequence encoding one or more expression control sequences (e.g., a promoter, etc.). Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. As disclosed herein, one possible intron sequence is derived from SV-40 and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Aspects of the disclosure relate to an isolated nucleic acid comprising more than one promoter (e.g., 2, 3, 4, 5, or more promoters). For example, in the context of a construct having a transgene comprising a first region encoding a protein and an second region encoding an inhibitory RNA (e.g., miRNA), it may be desirable to drive expression of the protein coding region using a first promoter sequence (e.g., a first promoter sequence operably linked to the protein coding region), and to drive expression of the inhibitory RNA encoding region with a second promoter sequence (e.g., a second promoter sequence operably linked to the inhibitory RNA encoding region). Generally, the first promoter sequence and the second promoter sequence can be the same promoter sequence or different promoter sequences. In some embodiments, the first promoter sequence (e.g., the promoter driving expression of the protein coding region) is an RNA polymerase III (polIII) promoter sequence. Non-limiting examples of polIII promoter sequences include U6 and H1 promoter sequences. In some embodiments, the second promoter sequence (e.g., the promoter sequence driving expression of the inhibitory RNA) is an RNA polymerase II (polII) promoter sequence. Non-limiting examples of polII promoter sequences include 7, T3, SP6, RSV, and cytomegalovirus promoter sequences. In some embodiments, a polIII promoter sequence drives expression of an inhibitory RNA (e.g., miRNA) encoding region. In some embodiments, a polII promoter sequence drives expression of a protein coding region. In some embodiments, the first promoter sequence (e.g., the promoter driving expression of the protein coding region) is a BMP response element (pBRE) promoter sequence and the second promoter sequence (e.g., a second promoter sequence operably linked to the inhibitory RNA encoding region) is a NF-kB promoter sequence.

As disclosed herein, the artificial microRNA (ami-RNA) that decreases the expression of the target gene ACVR1 is selected from an RH1 ami-RNA that is encoded by the sequence set forth in SEQ ID NO: 5, an RH2 ami-RNA that is encoded by the sequence set forth in SEQ ID NO: 6, an RH3 ami-RNA that is encoded by the sequence set forth in SEQ ID NO: 56, an RH4 ami-RNA that is encoded by the sequence set forth in SEQ ID NO: 57, an RH5 ami-RNA that is encoded by the sequence set forth in SEQ ID NO: 58, an RH6 ami-RNA that is encoded by the sequence set forth in SEQ ID NO: 59, an RH7 ami-RNA that is encoded by the sequence set forth in SEQ ID NO: 60, an RH8 ami-RNA that is encoded by the sequence set forth in SEQ ID NO: 61, an RH9 ami-RNA that is encoded by the sequence set forth in SEQ ID NO: 62, an RH10 ami-RNA that is encoded by the sequence set forth in SEQ ID NO: 63, RH11 ami-RNA that is encoded by the sequence set forth in SEQ ID NO: 64, and RH12 ami-RNA that is encoded by the sequence set forth in SEQ ID NO: 65 (FIG. 3). In some embodiments, the ami-RNA that decreases the expression of the target gene ACVR1 is an RH1 ami-RNA that is encoded by the sequence set forth in SEQ ID NO: 5, an RH2 ami-RNA that is encoded by the sequence set forth in SEQ ID NO: 6, an RH4 ami-RNA that is encoded by the sequence set forth in SEQ ID NO: 57, an RH5 ami-RNA that is encoded by the sequence set forth in SEQ ID NO: 58, an RH6 ami-RNA that is encoded by the sequence set forth in SEQ ID NO: 59, and an RH7 ami-RNA that is encoded by the sequence set forth in SEQ ID NO: 60. In some embodiments, the ami-RNA that decreases the expression of the target gene ACVR1 does not affect the expression of wild type ACVR1. In some embodiments, the ami-RNA that decreases the expression of the target gene ACVR1 does not affect the expression of the codon optimized ACVR1. In some embodiments, rAAV-mediated gene transfer carrying an ami-RNA targeting a mutated ACVR1 is a gene replacement platform as disclosed herein.

Aspects of the disclosure relate to an isolated nucleic acid comprising an isolated nucleic acid comprising a transgene encoding an artificial microRNA for reducing ACVR1 expression and a transgene encoding at least one codon optimized ACVR1 (e.g., 1, 2, 3, 4, 5, 6, 7, 8, 9, 10, or more codon optimized ACVR1). In some embodiments, coexpression of amiR-ACVR1-RH (e.g., amiR-33) and codon optimized ACVR1 replaces ACVR1-R206H mRNA with wild type ACVR1 mRNA. As used herein, "replace" ACVR1-R206H mRNA with wild type ACVR1 mRNA means that the expression of the mutated ACVR1 gene (e.g., ACVR1-R206H) is reduced or inhibited due to the competitive binding of the codon optimized ACVR1. In some embodiments, at least 50%, 60%, 70%, 80%, 90%, 91%, 92%, 93%, 94%, 95%, 96%, 97%, 98%, 99%, inclusive all ranges and subranges therein, of the mutated ACVR1 gene (e.g., ACVR1-R206H) is reduced or inhibited. In some embodiments, at least 50%, 60%, 70%, 80%, 90%, 91%, 92%, 93%, 94%, 95%, 96%, 97%, 98%, 99%, inclusive all ranges and subranges therein, of the wild type ACVR1 gene (e.g., codon optimized ACVR1) replaces the mutated ACVR1 gene (e.g., ACVR1-R206H).

In some aspects, the isolated nucleic acid comprising an isolated nucleic acid comprising a transgene encoding an artificial microRNA for reducing ACVR1 expression and a transgene encoding at least one codon optimized ACVR1 comprises a promoter. In some embodiments, the promoter as used in the vector construct is a chicken beta-actin (CBA) promoter. In some embodiments, the promoter as used in the vector construct can be any promoter suitable gene replacement platform. In some embodiments, the CBA promoter comprises a MASSBIOLOGICS® novel (MBL) intron in the vector. In some embodiments, the CBA promoter comprises a synthetic intron in the vector. In some embodiments, the CBA intron can be substituted by a MBL intron or a synthetic intron in the isolated nucleic acid as disclosed herein.

Gene Editing Molecules

In some aspects, the disclosure provides a recombinant gene editing complex comprising a single guide RNA (sgRNA) that specifically hybridizes to a target nucleic acid sequence of an ACVR1 gene, a first rAAV particle encoding a first recombinant gene editing protein or fragment thereof, and a second rAAV particle encoding a second recombinant gene editing protein or fragment thereof.

In some embodiments, the first recombinant gene editing protein comprises a Cas9-based adenine base editor (ABE) N-terminus portion and its fragments thereof. In some embodiments, the second recombinant gene editing protein comprises a Cas9-based adenine base editor (ABE) C-terminus portion and its fragments thereof.

In some embodiments, the recombinant gene editing complex further comprises a protospacer adjacent motif. Without wishing to be bound by any theory, protospacer adjacent motif (PAM) is a 2-6-base pair DNA sequence immediately following the DNA sequence targeted by the Cas9 nuclease in the CRISPR bacterial adaptive immune system. The PAM is a component of the invading virus or plasmid but is not found in the bacterial host genome and hence is not a component of the bacterial CRISPR locus.

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence), for example by causing one or more double stranded breaks (DSBs) in a target DNA. Examples of gene editing complexes include but are not limited to Transcription Activator-like Effector Nucleases (TALENs), Zinc Finger Nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., recombinant gene editing proteins) related to the CRISPR/Cas system, including but not limited to Cas9, Cas6, Cpf1, CRISPR RNA (crRNA), trans-activating crRNA (tracrRNA), and variants thereof.

In some embodiments, a recombinant gene editing protein is a nuclease. As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and CRISPR-associated proteins (Cas nucleases). In some embodiments, the nuclease is a ZFN. In some embodiments, the ZFN comprises a FokI cleavage domain. In some embodiments, the ZFN comprises $Cys_2His_2$ fold group. In some embodiments, the nuclease is a TALEN. In some embodiments, the TALEN comprises a FokI cleavage domain. In some embodiments, the nuclease is a meganuclease. Examples of meganucleases include but are not limited to I-SceI, I-CreI, I-DmoI, and combinations thereof (e.g., E-DreI, DmoCre).

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, dCas9, Cas6, Cpf1, and variants thereof. In some embodiments, the nuclease is Cas9. In some embodiments, the Cas9 is derived from the bacteria *Streptococcus pyogenes* (e.g., SpCas9) or *Staphylococcus aureus* (e.g., SaCas9). In some embodiments, a Cas protein or variant thereof does not exceed the packaging capacity of a viral vector, such as a lentiviral vector or an adeno-associated virus (AAV) vector, for example as described by Ran et al. (2015) *Nature.* 520(7546); 186-91. For example, in some embodiments, a nucleic acid encoding a Cas protein is less than about 4.6 kb in length.

For the purpose of genome editing, the CRISPR system can be modified to combine the tracrRNA and crRNA into a single guide RNA (sgRNA) or just (gRNA). As used herein, the terms "guide RNA", "gRNA", and "sgRNA" refer to a polynucleotide sequence that is complementary to a target sequence in a cell and associates with a Cas nuclease, thereby directing the Cas nuclease to the target sequence. In some embodiments, a gRNA (e.g., sgRNA) ranges between 1 and 30 nucleotides in length. In some embodiments, a gRNA (e.g., sgRNA) ranges between 5 and 25 nucleotides in length. In some embodiments, a gRNA (e.g., sgRNA) ranges between 10 and 22 nucleotides in length. In some embodiments, a gRNA (e.g., sgRNA) ranges between 14 and 24 nucleotides in length. In some embodiments, a Cas protein and a guide RNA (e.g., sgRNA) are expressed from the same vector. In some embodiments, a Cas protein and a guide RNA (e.g., sgRNA) are expressed from separate vectors (e.g., two or more vectors). Typically, a guide RNA (e.g., a gRNA or sgRNA) hybridizes (e.g., binds specifically to, for example by Watson-Crick base pairing) to a target sequence and thus directs the CRISPR/Cas protein or simple protein to the target sequence. In some embodiments, a guide RNA hybridizes to (e.g., targets) a nucleic acid sequence.

As disclosed herein, the recombinant gene editing complex comprises a Cas9-based adenine base editor (ABE). Cas9-based adenine base editor (ABE) compatible to rAAV has been developed to directly convert a target base pair to a different base pair without creating double-stranded DNA breaks. Thus, an rAAV9-compatible ABE construct was used to convert "A" into "G" in the ACVR1-R206H allele. The ABE is divided into halves that are smaller than the AAV packaging size limit (~4.7 kb) using a trans-splicing intein sequence, which enables dual-AAV packaging of base editors. Without wishing to be bound by theory, delivery via AAVs is limited by AAV packaging capacity, which precludes the use of full-length base editors. The application of dual AAVs for the delivery of split cytosine and adenine base editors that are then reconstituted by trans-splicing inteins. In some embodiments, the ABE as disclosed herein is divided into a N-terminal ABE construct and a C-terminal ABE construct. In some embodiments, the ABE is divided by using a trans-splicing intein sequence. In some embodiments, the N-terminal ABE construct comprises protospacer having the ACVR1-R206H mutation. In some embodiments, the C-terminal ABE construct is integrated into the AAV6.2 or AAV9 capsid protein. In some embodiments, the ABE converts adenine into guanine in the ACVR1-R206H allele.

The present disclosure provides an isolated nucleic acid comprising a first transgene comprising a NF-kB promoter (pNF-kB) and a second transgene comprising a bone morphogenic protein promoter (pBRE). In some embodiments, the pNF-kB induces the expression of soluble follistatin (sFST). In some embodiments, the pBRE induces the expression of TNFR2. In some embodiments, activin A triggers the expression of sFST and TNFR2. In some embodiments, a BMP ligand triggers the expression of sFST and TNFR2. In some embodiments, inflammation triggers the expression of sFST and TNFR2. In some embodiments, the isolated nucleic acid induces the expression of a human soluble IL1Rα (sIL1Rα) (SEQ ID NO: 35). Anakinra (Kineret), an interleukin 1 receptor antagonist protein that treats rheumatoid arthritis, has been shown to effectively slow the progression of FOP. The isolated nucleic acid as disclosed herein provides expression of activin A antagonist, TNF antagonist, and IL-1 antagonist, for example. In some embodiments, the isolated nucleic acid is integrated into an AAV vector.

In some embodiments, the pNF-kB is a PB2 promoter (SEQ ID NO: 30). In some embodiments, the pBRE comprises the sequence of SEQ ID NO: 31. In some embodiments, the isolated nucleic acid has the sequence of SEQ ID NO: 32.

Inflammation and activin A have been shown to involve in heterotopic ossification (HO). As levels of activin A, BMP ligands, and inflammatory cytokines are elevated in the area of flare-up, the Applicant found that rAAV9 vectors can secret a natural activin A antagonist, soluble follistatin (sFST), and a natural TNF antagonist, soluble TNFR2 (sTNFR2), in response to flare-up. In some embodiments, the expression of sFST and TNFR2 suppress activin A signaling pathways in flare-up conditions. In some embodiments, the expression of sFST and TNFR2 suppress TNF signaling pathways in flare-up conditions.

Local or systemic injection of rAAV9 is highly effective for the transduction of skeletal muscle, which produces sFST and sTNFR2 in the area of flare-up, suppressing the development of neighboring HO. In some embodiments, the isolated nucleic acid further comprises a *Gaussia* luciferase reporter gene (eBRE/NF-kB-Luc). Without wishing to be bound any theory, *Gaussia* luciferase is a 20 kDa protein from the marine copepod, *Gaussia princeps*. The bioluminescent enzyme is highly secreted into the cell culture media, allowing for live cell monitoring of reporter activity. Light output generated by the luciferase reaction can be correlated to the amount of *Gaussia* luciferase protein produced and used to determine the activity of the promoter driving *Gaussia* expression.

The present disclosure provides an isolated nucleic acid comprising a first transgene comprising a nucleic acid sequence encoding a soluble follistatin (sFST) and a second transgene comprising a nucleic acid sequence encoding TNFR2. In some embodiments, the first and the second transgene is operably linked to a promoter, such as chicken β-actin promoter. In some embodiments, the promoter is a pBRE/pNF-kB promoter. In some embodiments, the isolated nucleic acid comprises a transgene encoding an artificial miRNA (ami-RNA). In some embodiments, the ami-RNA comprises a miR-122. In some embodiments, the isolated nucleic acid as disclosed herein provides a natural activin A antagonist, soluble human follistatin (e.g., FST-288) and a natural TNF antagonist, soluble human TNFR2, that is cloned into the AAV vector genome. In some embodiments, the AAV vector is an rAAV9 vector.

Without wishing to be bound by any theory, follistatin and sTNFR2 competitively bind activin A and TNFα against their cognate receptors and therefore, suppress activin A and TNFα-induced signal transduction, respectively. However, following systemic delivery, rAAV9 vectors can target additional tissues such as liver, heart, and skeletal muscle, which may cause adverse effects. Therefore, the present disclosure provides tissue-specific, endogenous miRNAs (e.g., miR-122) to repress rAAV expression in liver, by engineering perfectly complementary miR-122-binding sites into the AAV vector genome. In some embodiments, the isolated nucleic acid comprises the sequence of SEQ ID NO: 33. In some embodiments, the isolated nucleic acid comprises the sequence of SEQ ID NO: 34. In some embodiments, an rAAV vector comprises one or more miRNA binding sites that de-target expression of a transgene from heart tissue (e.g., cardiac muscle). In some embodiments, the miRNA binding site is a miR-208 binding site. In some embodiments, an rAAV comprises one or more (e.g., 1, 2, 3, 4, or more) miR-208 binding sites. In some embodiments, the one or more miR-208 binding sites comprises the sequence set forth in SEQ ID NO: 48.

Recombinant AAVs (rAAVs)

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins and/or inhibitory nucleic acids (e.g., shRNA, miRNAs, etc.) comprising a nucleic acid that targets an endogenous mRNA of a subject. The transgene may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV3, AAV4, AAV5, AAV6, AAV6.2, AAV7, AAV8, AAV9, AAVrh.8, AAVrh.10, AAVrh.39, and AAVrh.43, and variants thereof. In some embodiments, the isolated nucleic acid comprises a region (e.g., a first region) encoding an AAV9 ITR. In some embodiments, the isolated nucleic acid comprises a region (e.g., a first region) encoding an AAV6.2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV3, AAV4, AAV5, AAV6, AAV6.2, AAV7, AAV8, AAV9, AAVrh.8, AAVrh.10, AAVrh.39, and AAVrh.43, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or mis sense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

As used herein, the term "self-complementary AAV vector" (scAAV) refers to a vector containing a double-stranded vector genome generated by the absence of a terminal resolution site (TR) from one of the ITRs of the AAV. The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle. The instant invention is based, in part, on the recognition that DNA fragments encoding RNA hairpin structures (e.g. shRNA, miRNA, and ami-RNA) can serve a function similar to a mutant inverted terminal repeat (mTR) during viral genome replication, generating self-complementary AAV vector genomes. For example, in some embodiments, the disclosure provides rAAV (e.g. self-complementary AAV; scAAV) vectors comprising a single-stranded self-complementary nucleic acid with inverted terminal repeats (ITRs) at each of two ends and a central portion comprising a promoter operably linked with a sequence encoding a hairpin-forming RNA (e.g., shRNA, miRNA, ami-RNA, etc.). In some embodiments, the sequence encoding a hairpin-forming RNA (e.g., shRNA, miRNA, ami-RNA, etc.) is substituted at a position of the self-complementary nucleic acid normally occupied by a mutant ITR.

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR. Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, and/or AAVrh10 ITR sequence.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g. AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125. In some embodiments, an AAV capsid protein is of a serotype derived from a non-human primate, for example scAAV.rh8, AAV.rh39, or AAV.rh43 serotype. In some embodiments, an AAV capsid protein is of an AAV9 serotype. In some embodiments, an AAV capsid protein is of an AAV6.2 serotype.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from HEK293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, N.Y., Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. In some embodiments, a host cell is a bacterial cell, yeast cell, insect cell (Sf9), or a mammalian (e.g., human, rodent, non-human primate, etc.) cell. In some embodiments, the mammalian cell is a HEK293 cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

In some aspects, the present disclosure provides a recombinant AAV comprising a capsid protein and an isolated nucleic acid comprising a first region encoding an AAV ITR and a second region comprising a transgene, wherein the transgene encodes an artificial microRNA. The artificial microRNA may decrease the expression of a target gene in a cell or tissue (e.g. skeletal muscles, tendons, and cartilage) or a subject. In some embodiments, the rAAV comprises an artificial microRNA that decreases the expression of ACVR1 in a cell, tissue, or a subject.

Expression of the mutated ACVR1 gene in a cell, tissue, or subject may be decreased by between 50% and 99% (e.g., any integer between 50% and 99%, inclusive) using rAAVs of the present disclosure. Expression of ACVR1 gene in a cell, tissue, or subject may be decreased by between 75% and 90% using rAAVs of the present disclosure. Expression of ACVR1 gene in a cell, tissue, or subject may be decreased by between 80% and 99% using rAAVs of the present disclosure.

The foregoing methods for packaging recombinant vectors in desired AAV capsids to produce the rAAVs of the disclosure are not meant to be limiting and other suitable methods will be apparent to the skilled artisan.

Modes of Administration and Compositions

The rAAVs of the disclosure may be delivered to a subject in compositions according to any appropriate methods known in the art. For example, an rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human. In some embodiments, a subject is an adult. In some embodiments, a subject is a juvenile or infant.

In some embodiments, the rAAV comprises an isolated nucleic acid comprising the codon optimized ACVR1 having the sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, or are 100% identical, including all values in between to any one of SEQ ID NOs: 1-4. In some embodiments, the rAAV comprises an isolated nucleic acid comprising the codon optimized ACVR1 having the sequence set forth in any one of SEQ ID NOs: 1-4 (or the complementary sequence thereof), or a portion thereof.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the skeletal muscle and/or to the connective tissues of a subject. Recombinant AAVs may be delivered directly to the skeletal muscle and/or to the connective tissues by injection into, e.g., directly into the muscle or the tissue, via intrasynovial injection, knee injection, etc., with a needle, catheter or related device, using surgical techniques known in the art.

In some embodiments, rAAV as described in the disclosure are administered by interdermal delivery or intradermal delivery. The delivery procedures and methods can be any techniques that are known in the art and/or suitable for the present disclosure.

In some embodiments, rAAV as described in the disclosure are administered by microneedle drug delivery such as transdermal application. In some embodiments, rAAV as described in the disclosure are administered by the use of dermal patches for providing controlled delivery. A dermal patch, skin patch, or the like as used herein refers to a medicated adhesive patch that is placed on the skin to deliver a specific dose of a composition into the skin. Dermal or skin patches can include but are not limited to single-layer drug-in-adhesive, multi-layer drug-in-adhesive, reservoir, matrix, and vapour patches. Alternatively, or additionally, the rate can be controlled by either providing a rate controlling membrane and/or by dispersing the active ingredient in a polymer matrix and/or gel. In some embodiments, permeation enhancers can be used for enhancing the permeation of rAAV in the patch. In some embodiments, rAAV as described in the disclosure are administered by intravenous injection. In some embodiments, the rAAV are administered by intramuscular injection.

Aspects of the instant disclosure relate to compositions comprising a recombinant AAV comprising a capsid protein and a nucleic acid encoding a transgene, wherein the transgene comprises a codon optimized nucleic acid sequence encoding one or more ACVR1 or an artificial miRNA, for example. In some embodiments, the nucleic acid further comprises one or more AAV ITRs. In some embodiments, a composition further comprises a pharmaceutically acceptable carrier. In some embodiments, compositions comprise a recombinant AAV comprising a capsid protein and a nucleic acid comprising a first region encoding an AAV ITR and a second region comprising a transgene, wherein the transgene encodes an artificial microRNA that targets ACVR1.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An "effective amount" of an rAAV is an amount sufficient to target infect an animal, target a desired tissue (e.g., connective tissue). The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target bone tissue.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., $-10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

In some embodiments, administering the isolated nucleic acid, the rAAV, and/or the vector as disclosed herein results in a decrease of ACVR1 protein comprises a single base mutation of guanine to adenine at position 206 of the sequence of the wild type ACVR1 by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control. In some embodiments, administering the isolated nucleic acid, the rAAV, the vector as disclosed herein results in a decrease of the human ACVR1-R206H protein by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control.

In some embodiments, administering the isolated nucleic acid, the rAAV, and/or the vector as disclosed herein ameliorates heterotopic bone formation or heterotopic ossification by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control.

In some embodiments, administering the isolated nucleic acid, the rAAV, and/or the vector as disclosed herein ameliorates severe osteoarthritis by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control.

In some embodiments, administering the isolated nucleic acid, the rAAV, and/or the vector as disclosed herein decreases heterotopic bone mass by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control.

In some embodiments, administering the isolated nucleic acid, the rAAV, and/or the vector as disclosed herein decreases chondrogenic anlagen by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control.

In some embodiments, administering the isolated nucleic acid, the rAAV, and/or the vector as disclosed herein decreases BMP-responsive genes by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control. In some embodiments, the BMP-responsive genes is ID1. In some embodiments, the BMP-responsive gene is MSX2. In some embodiments, the BMP-responsive gene is any gene that can be affected by the BMP signaling pathway.

As used herein, the improvement or stimulation is relative to a control. The control can be in a state that is prior to the administration of the isolated nucleic acid, the rAAV, and the vector. The improvement or stimulation is relative to a subject that has not been administered the isolated nucleic acid, the rAAV, and the vector.

In some embodiments, a “control” can refer to a subject or a tissue that contains human ACVR1-R206H proteins or the ACVR1 protein that comprises a single base mutation of guanine to adenine at position 206 of the sequence of the wild type ACVR1 while not being treated by the methods and compositions described in the present disclosure or any other methods.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intradermally, intrathecally, femoral intramedullary, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection. In some embodiments, a preferred mode of administration is by systemic injection, for example intravenous injection. In some embodiments, a preferred mode of administration is by intramuscular injection. In some embodiments, a preferred mode of administration is by intradermal injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, “Remington's Pharmaceutical Sciences” 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes are generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Therapeutic Methods

As disclosed herein, isolated nucleic acids, rAAVs, and compositions described herein are useful for treating a subject having or suspected of having FOP. In some embodiments, aspects of the present disclosure provide methods of inhibiting heterotopic ossification in a subject. In some embodiments, aspects of the present disclosure provide methods of improving flare-up conditions in a subject having or suspected of having FOP. In some embodiments, aspects of the present disclosure provide methods of inhibiting ACVR1 expression in a cell.

As used herein, the term "treating" refers to the application or administration of a composition as described herein to a subject, who has a disease associated with heterotopic ossification (HO), such as FOP, a symptom of a disease associated with heterotopic ossification (HO), such as FOP, or a predisposition toward a disease associated with heterotopic ossification (HO), such as FOP (e.g., one or more mutations in a gene associated with FOP, such as AVCR1), with the purpose to cure, heal, alleviate, relieve, alter, remedy, ameliorate, improve, or affect the disorder, the symptom of the disease, or the predisposition toward the disease.

Alleviating a disease includes delaying the development or progression of the disease, or reducing disease severity. Alleviating the disease does not necessarily require curative results. As used therein, "delaying" the development of a disease (such as a disease associated with HO) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease associated with heterotopic ossification (HO), such as FOP, includes initial onset and/or recurrence.

In some embodiments, the therapeutic methods as disclosed in this section comprise administering to a subject in need thereof an isolate nucleic acid, a recombinant AAV (rAAV), a recombinant gene editing complex, or a vector, comprising a transgene as disclosed herein. A rAAV may comprise a modification that promotes its targeting to skeletal muscle or connective tissues. In some embodiments, the therapeutic methods as disclosed herein comprise administering to a subject a rAAV comprising a capsid protein and an isolated nucleic acid encoding an inhibitory nucleic acid. The rAAV may comprise an inhibitory nucleic acid (e.g., siRNA, shRNA, miRNA, or amiRNA). The inhibitory nucleic acid may decrease or increase expression of a target gene associated with FOP. In some embodiments, the rAAV or isolated nucleic acid comprises a transgene encoding an artificial microRNA that targets a gene associated with heterotopic ossification or the development of FOP. In some embodiments, the target gene is AVCR1. In some embodiments, the target gene is a mutated AVCR1.

Expression of ACRV1 in a cell or subject may be decreased by between 50% and 99% (e.g., any integer between 50% and 99%, inclusive) using methods of the present disclosure. Expression of ACVR1 in a cell or subject may be decreased by between 75% and 90% using methods of the present disclosure. Expression of ACVR1 in a cell or subject may be decreased by between 80% and 99% using methods of the present disclosure.

Heterotopic ossification may be inhibited by between 50% and 99% (e.g., any integer between 50% and 99%, inclusive) using methods of the present disclosure. Flare-up conditions in a subject having or suspected of having FOP may be inhibited by between 50% and 99% (e.g., any integer between 50% and 99%, inclusive) using methods of the present disclosure. Without wishing to be bound by any theory, flare-up conditions refer to an exacerbation of a chronic disease such as FOP.

As disclosed herein, "identity" of sequences refers to the measurement or calculation of the percent of identical matches between two or more sequences with gap alignments addressed by a mathematical model, algorithm, or computer program that is known to one of ordinary skill in the art. The percent identity of two sequences (e.g., nucleic acid or amino acid sequences) may, for example, be determined using Basic Local Alignment Search Tool (BLAST®) such as NB LAST® and XBLAST® programs (version 2.0). Alignment technique such as Clustal Omega may be used for multiple sequence alignments. Other algorithms or alignment methods may include but are not limited to the Smith-Waterman algorithm, the Needleman-Wunsch algorithm, or Fast Optimal Global Sequence Alignment Algorithm (FOGSAA).

In some embodiments, an "effective amount" of a substance is an amount sufficient to produce a desired effect (e.g., to transduce bone cells or bone tissue). In some embodiments, an effective amount of an isolated nucleic acid is an amount sufficient to transfect (or infect in the context of rAAV-mediated delivery) a sufficient number of target cells of a target tissue of a subject. In some embodiments, a target tissue is skeletal muscle or connective tissues. In some embodiments, an effective amount of an isolated nucleic acid (e.g., which may be delivered via an rAAV) may be an amount sufficient to have a therapeutic benefit in a subject, e.g., to inhibit heterotopic ossification, to improve flare-up conditions, etc. The effective amount will depend on a variety of factors such as, for example, the species, age, weight, health of the subject, and the tissue to be targeted, and may thus vary among subject and tissue as described elsewhere in the disclosure.

Exemplary embodiments of the invention will be described in more detail by the following examples. These embodiments are exemplary of the invention, which one skilled in the art will recognize is not limited to the exemplary embodiments.

EXAMPLES

Figure 2A:
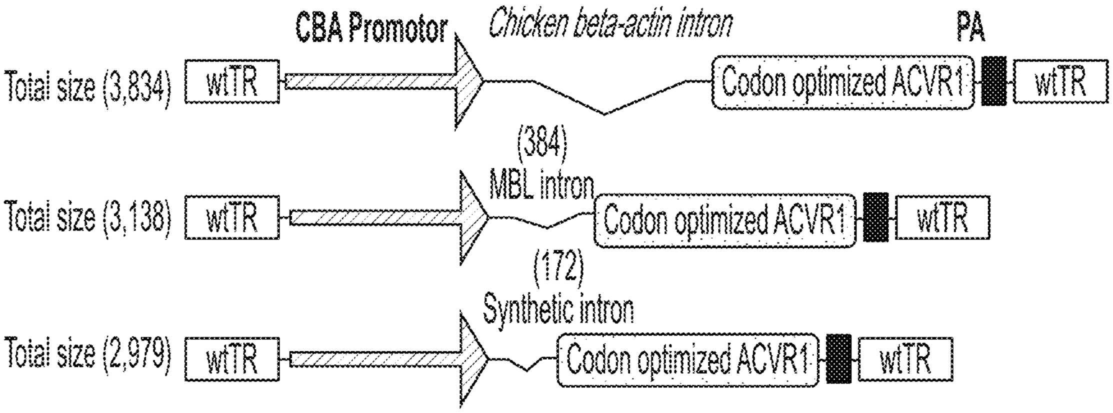
FIGS. 2A-2B show the generation of AAV vector genome for gene addition.
Figure 2B:
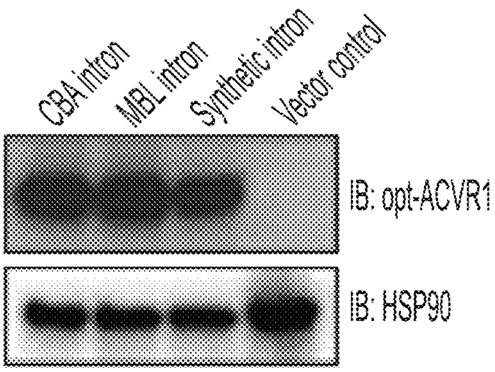
Figure 3A:
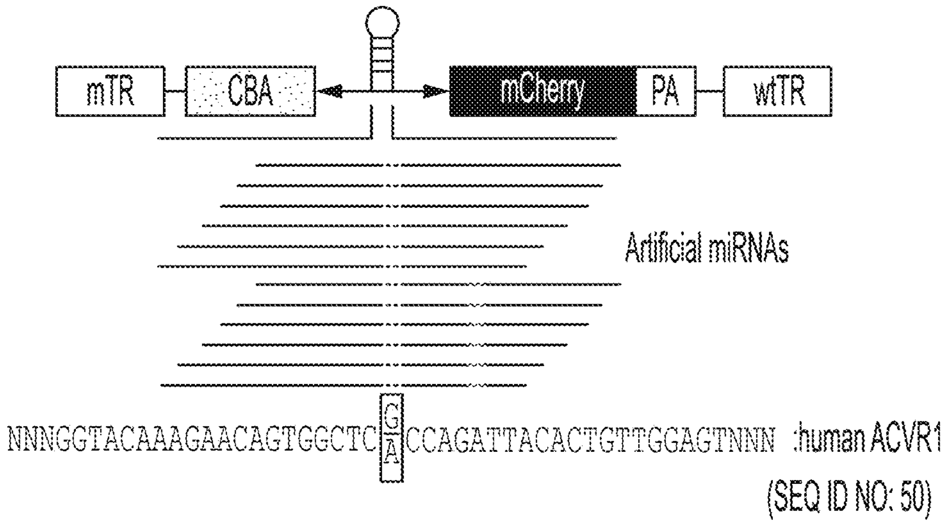
FIGS. 3A-3D show the generation of AAV vector genome for gene silencing.
Figure 3B:
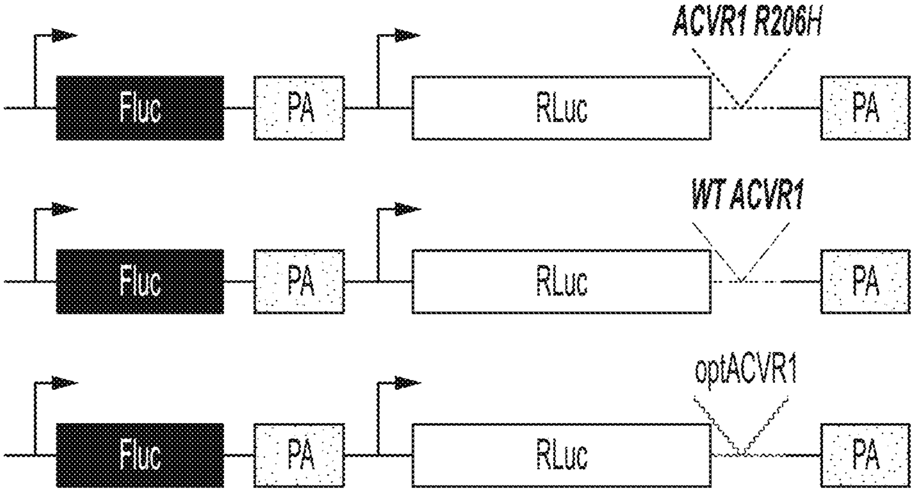
Figure 3C:
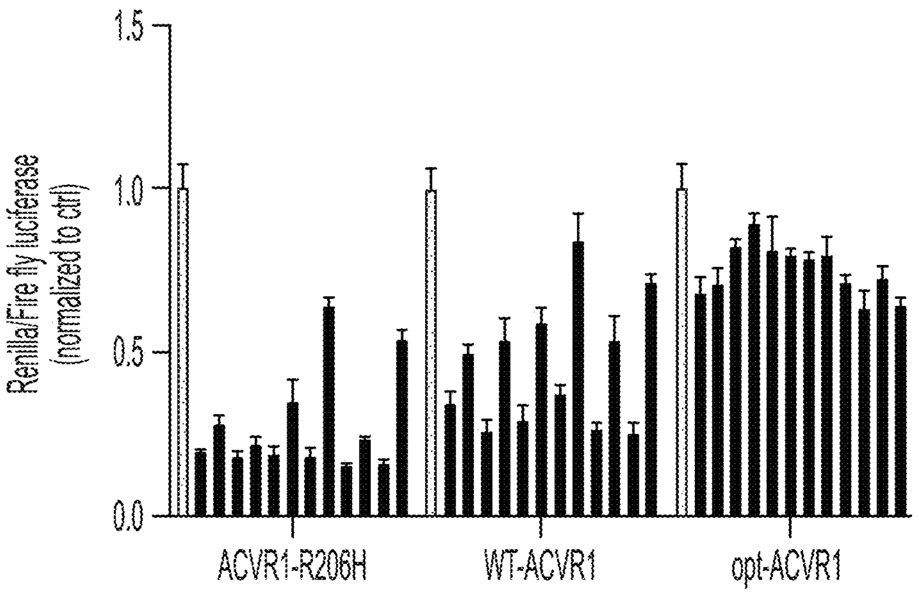
Figure 3D:
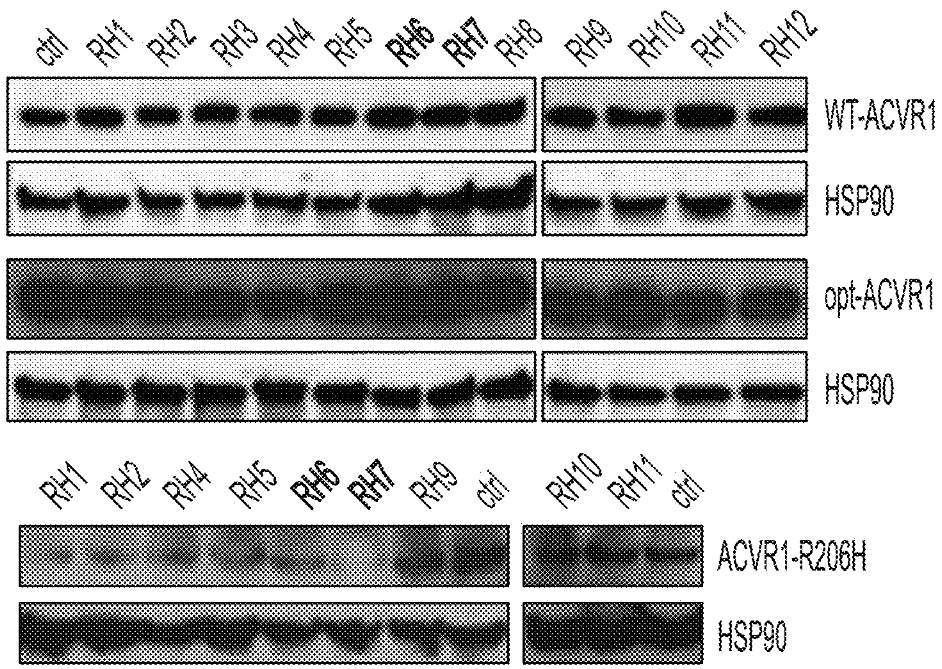
Figure 30A:
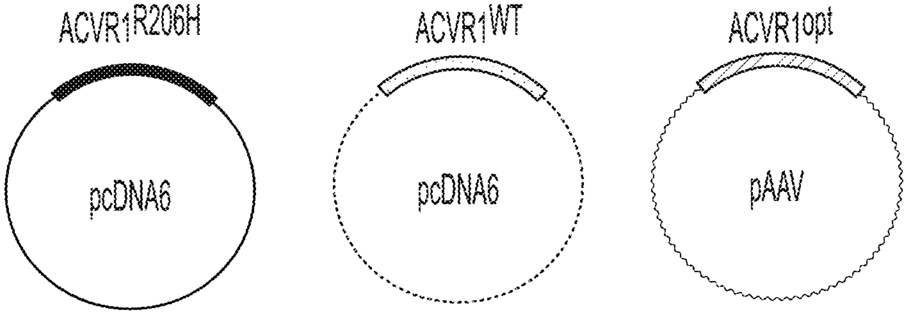
FIGS. 30A and 30B show generate AAV vector genome for gene replacement, silencing, and the combination.
Figure 30B:
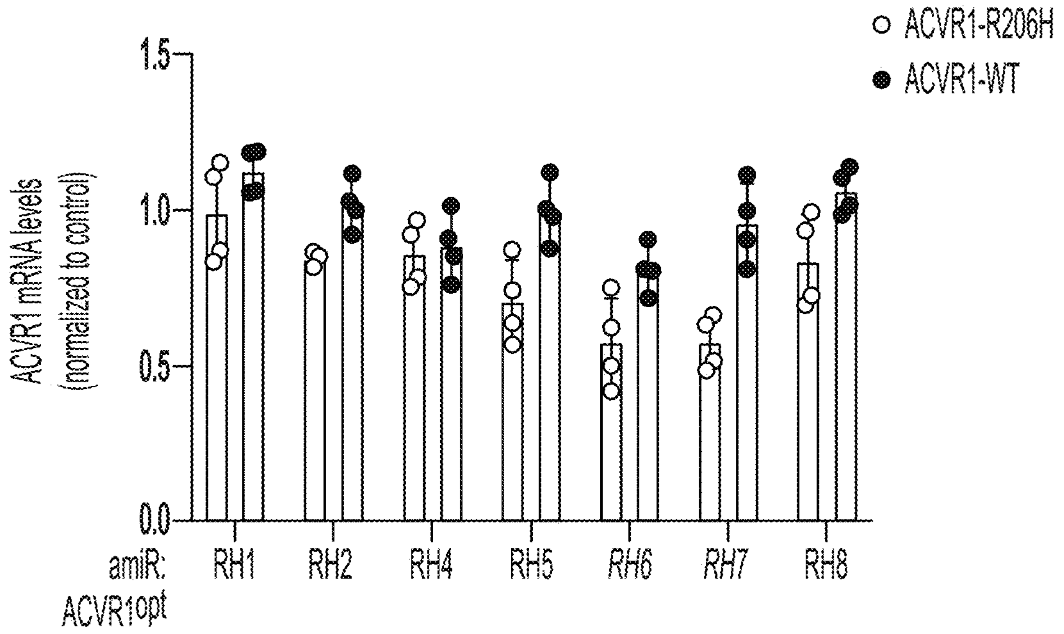

Example 1: Generation of AAV Vector Genome for Gene Addition or Gene Silencing It has been reported that about 97% FOP is caused by a heterozygous, gain of function mutation of ACVR1 (G>A, R206H). To replace human ACVR1$^{R206H}$ with human wild-type ACVR1 (ACVR1$^{WT}$), a codon-optimized version of the human ACVR1 complementary DNA (ACVR1$^{opt}$, 74% nucleotide identity compared to wild-type coding sequence) was designed and cloned into the AAV vector genome containing the chicken b-actin promoter (CBA, FIG. 2A). Specifically, gene addition strategy was initiated by generating AAV vector genome that expresses codon-optimized, wild type human ACVR1 cDNA (opt-ACVR1, -1.5 kb) under the chicken beta-actin (CBA) promoter (FIG. 2). The CBA intron (1080 bp) was substituted by either the MBL intron (384 bp) or the synthetic intron (172 bp) to reduce the vector genome size (FIG. 2A). Immunoblotting analysis demonstrated that all of three introns were able to express opt-ACVR1 protein in HEK293 cells under the CBA promoter (FIG. 2B). Since it has been reported that high levels of AAV-delivered shRNAs can perturb the RNAi machinery and cause off-target silencing effects, the guide strand of a small silencing RNA was inserted into mouse miR-33-derived miRNA scaffold (artificial miRNA, amiR) to improve conventional shRNA-related toxicity and off-target silencing. Therefore, AAV vector genome expressing 12 artificial miRNAs (amiRs) that target different sequence sites of human ACVR1-R206H mRNA under the CBA promoter was generated for gene silencing (FIG. 3A). Additionally, amiR-sensor plasmids containing *renilla* luciferase reporter gene followed by miRNA binding sites specific to human ACVR1-R206H, ACVR1-WT, or ACVR1-opt (codon optimized) were generated to screen which amiRs are effective to knockdown human ACVR1-R206H mRNA without any decrease in human ACVR1-WT and/or ACVR1-opt mRNA levels (FIG. 3B). ACVR1-R206H activity was markedly reduced by the expression of most of the amiRs, except for RH8 and 12 while these amiRs showed little to no effect on opt-ACVR1 luciferase activity. In this design, the amiR was inserted intronically between the CBA promoter and the mCherry reporter gene, which allows for visual tracking of positively transduced cells. amiR-R206Hs targeting ACVR1$^{R206H}$, not ACVR1$^{WT}$ or ACVR1$^{opt}$ were screened by measuring *Renilla* activity of the sensor plasmids that represent the silencing efficiency (FIG. 3C). Among these amiRs, four amiRs, including RH3, 5, 9, and 11, induced significant decrease in ACVR1-WT activity (FIG. 3C). Immunoblotting analysis further confirmed that protein levels of ACVR1-R206H were substantially reduced by amiR-RH1, 2, 4, 5, 6, and 7 compared to amiR-ctrl and amiR-RH9, 10, and 11. Of note, both WT- and opt-ACVR1 expression was not affected by these amiRs (FIG. 3D, FIGS. 30A and 30B). These results identified amiR-RH6 and amiR-RH7 as the most effective gene silencers targeting of ACVR1$^{R206H}$, but not ACVR1$^{WT}$ and ACVRP1$^{opt}$. Since levels of ACVR1-R206H mRNA were most reduced by amiR-RH6 and -RH7, these amiRs were used on for further experiments.

Example 2: Generation of AAV Vector Genome for Gene Replacement

Figure 4A:
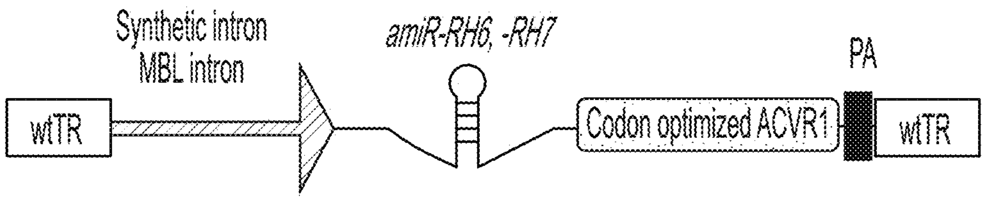
FIGS. 4A-4D show the generation of AAV vector genome for gene replacement.
Figure 4B:
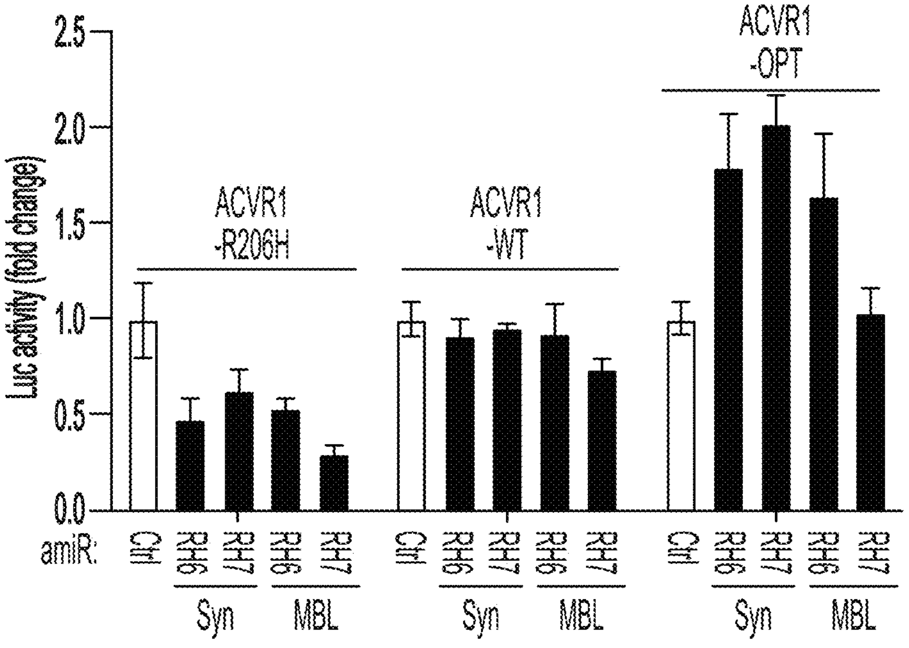
Figure 4C:
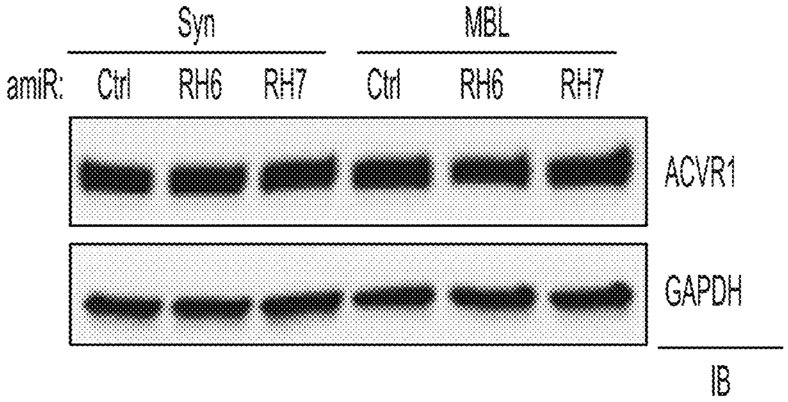
Figure 4D:
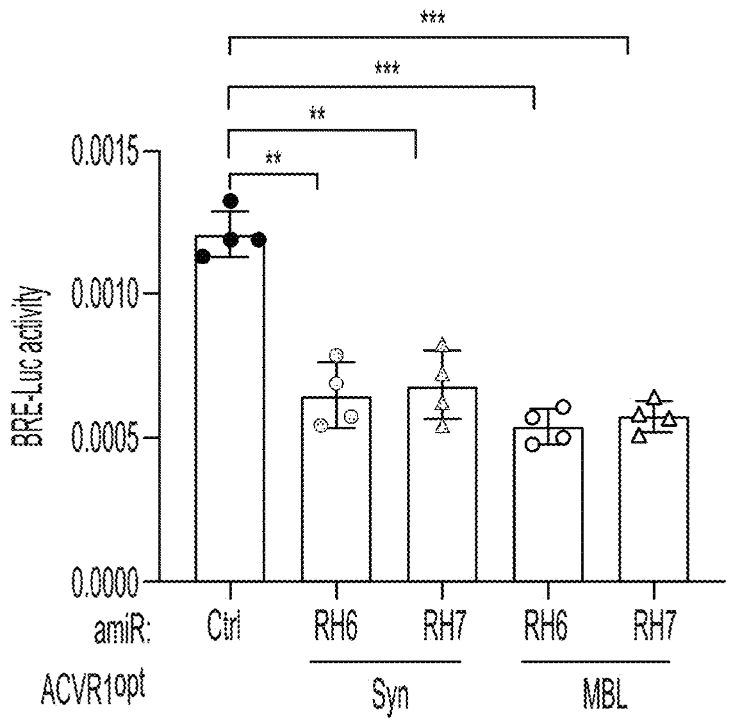

For the gene replacement strategy, four AAV vector genomes containing the combination of the CBA promoter, synthetic or MBL intron, amiR-ACVR1.RH6 or RH7, and codon optimized (opt-) ACVR1 was generated (FIG. 4A). Similar to the gene silencing plasmids, these plasmids were also effective to decrease ACVR1-R206H luciferase activity without affecting ACVR1-WT activity (FIG. 4B). Unlike an increased luciferase activity of ACVR1-OPT, immunoblotting analysis showed no difference in protein levels of opt-ACVR1 (FIG. 4C), indicating that amiR-RH6 or amiR-RH7 in these plasmids does not affect opt-ACVR1 expression. BRE-luciferase activity was markedly decreased in the presence of these plasmids, compared to vector control, demonstrating their ability to suppress Activin A-induced luciferase activity (FIG. 4D).

Figure 5:
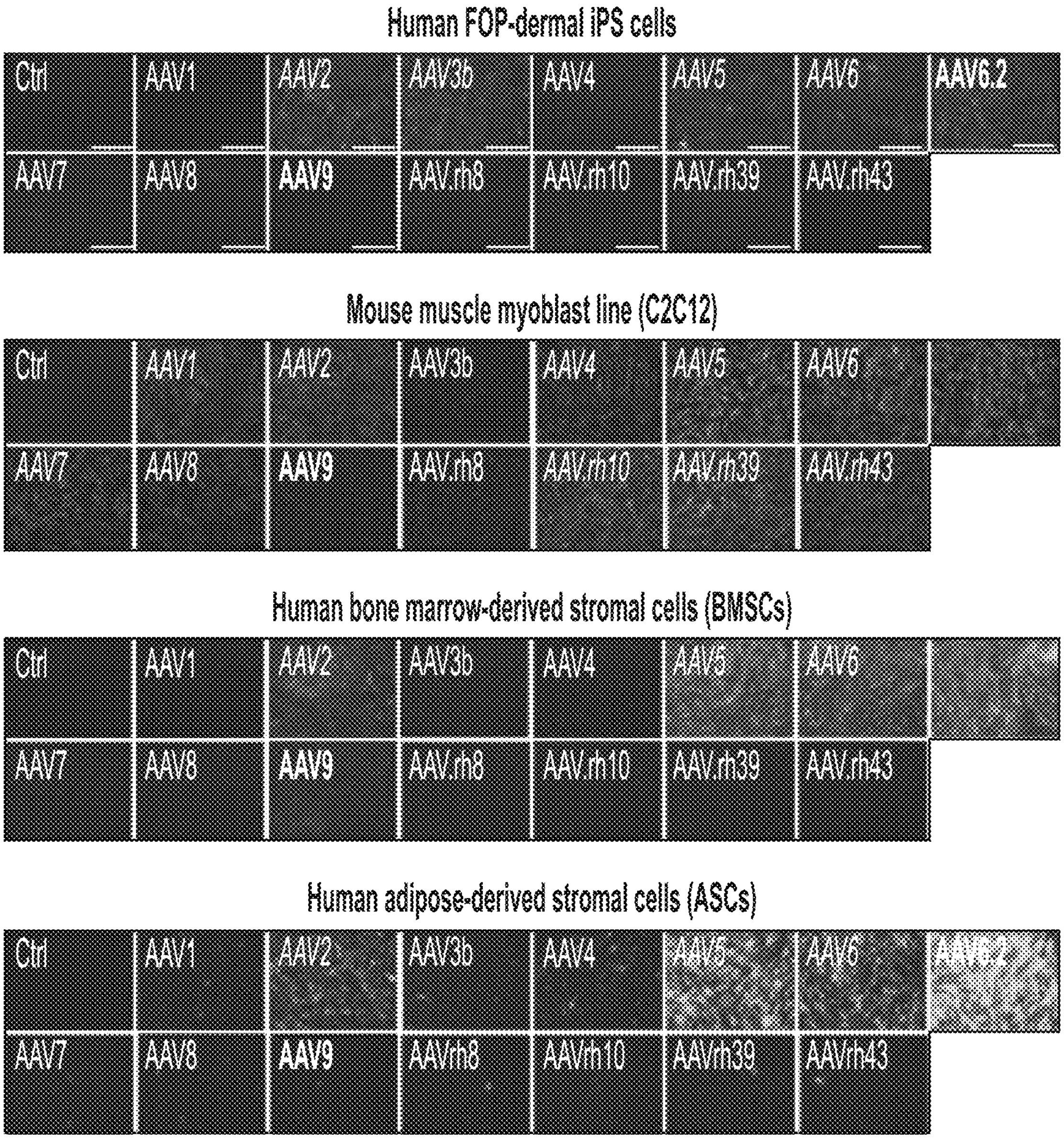
FIG. 5 shows the screening of rAAV serotypes effective for in vitro transduction of multiple cells. PBS (control) or $5\times10^{10}$ GC of 14 different rAAV serotyptes (AAV1, AAV2, AAV3b, AAV4, AAV5, AAV6, AAV6.2, AAV7, AAV8, AAV9, AAV.rh8, AAV.rh10, AAV.rh39, and AAV.rh43 expressing EGFP were incubated with the indicated cells for 2 days and cultured under osteogenic conditions for 4 days. The transduction of AAV was assessed by GFP expression using epifluorescence microscopy. Scale bar: 400 μm.
Figure 8A:
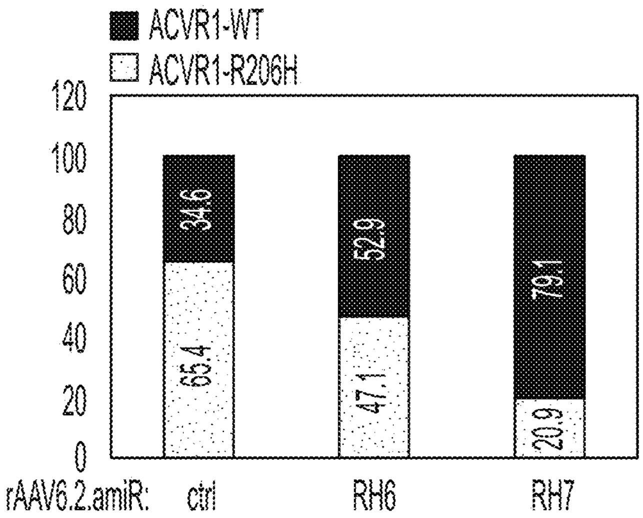
FIGS. 8A-8K show in vitro functional validation of rAAV6.2 vectors for gene replacement. Human FOP-iPSCs were treated with $5\times10^{10}$ GC of the vectors (rAAV6.2-amiR-ctrl, -amiRH6, or -amiRH7 in combination with either ACVR1-WT or ACVR1-R206H) for 2 days and cultured under osteogenic conditions for 4 days. Total RNA was subjected for cDNAs synthesis, followed by next generation sequencing (NGS) (FIG. 8A) or RT-PCR analysis (FIG. 8B). Alkaline phosphatase activity (ALP) (FIG. 8C) and alizarin red staining (FIG. 8D) were performed to assess osteoblast differentiation at 6 and 21 days of osteogenic culture, respectively.
Figure 8B:
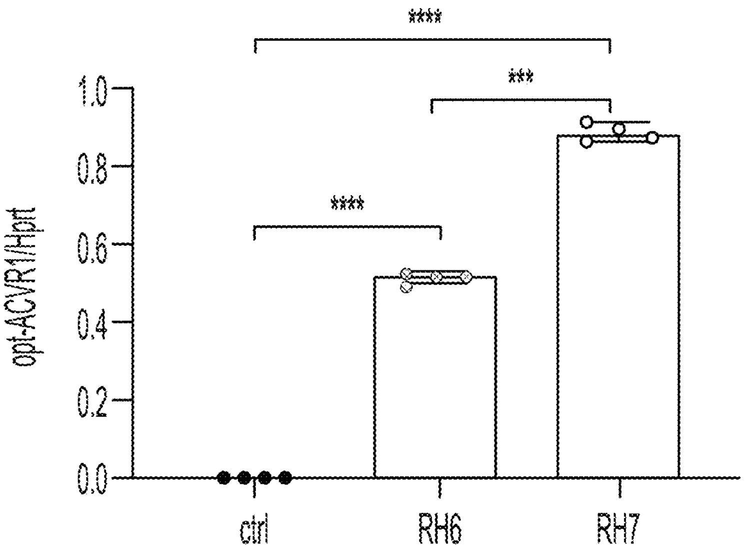
Figure 8C:
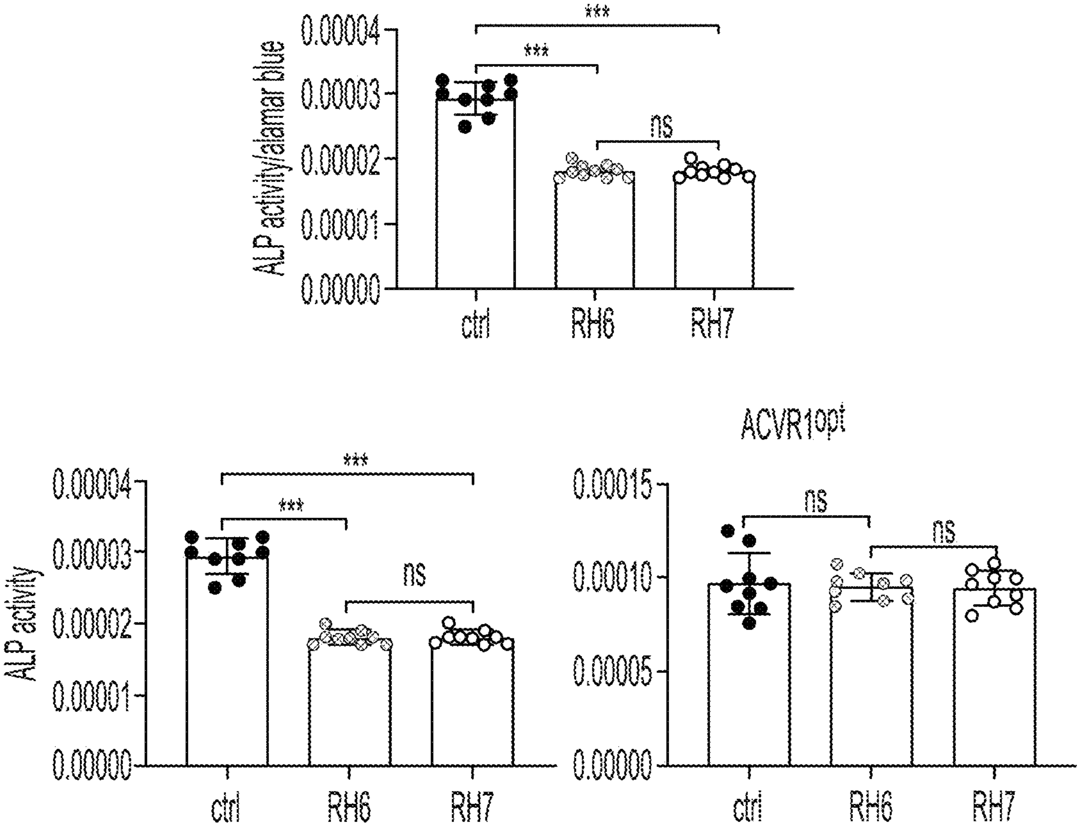
Figure 8D:
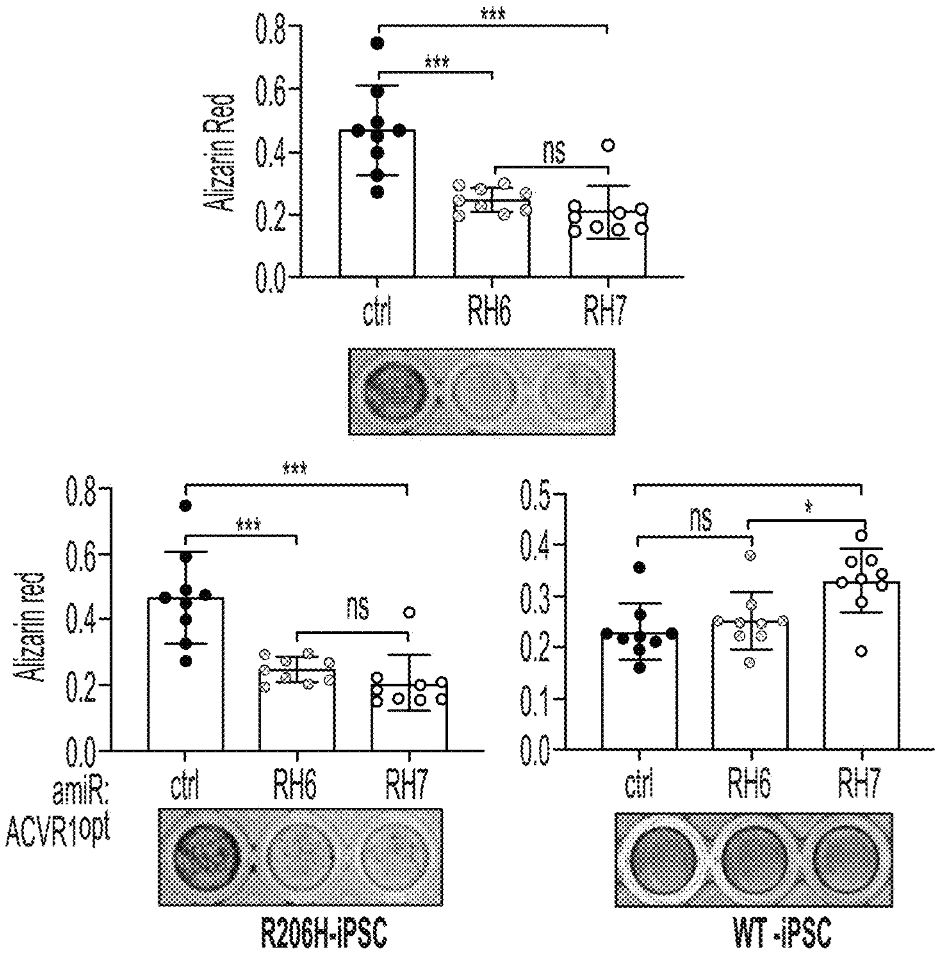
Figure 8E:
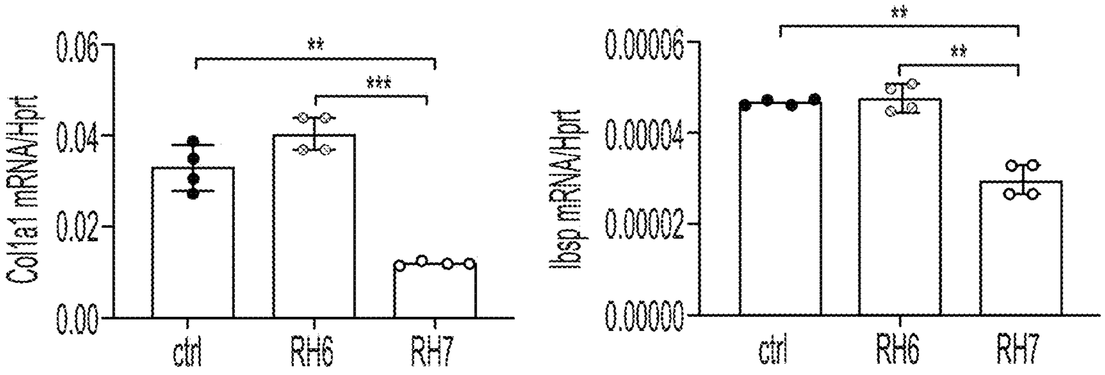
Figure 8F:
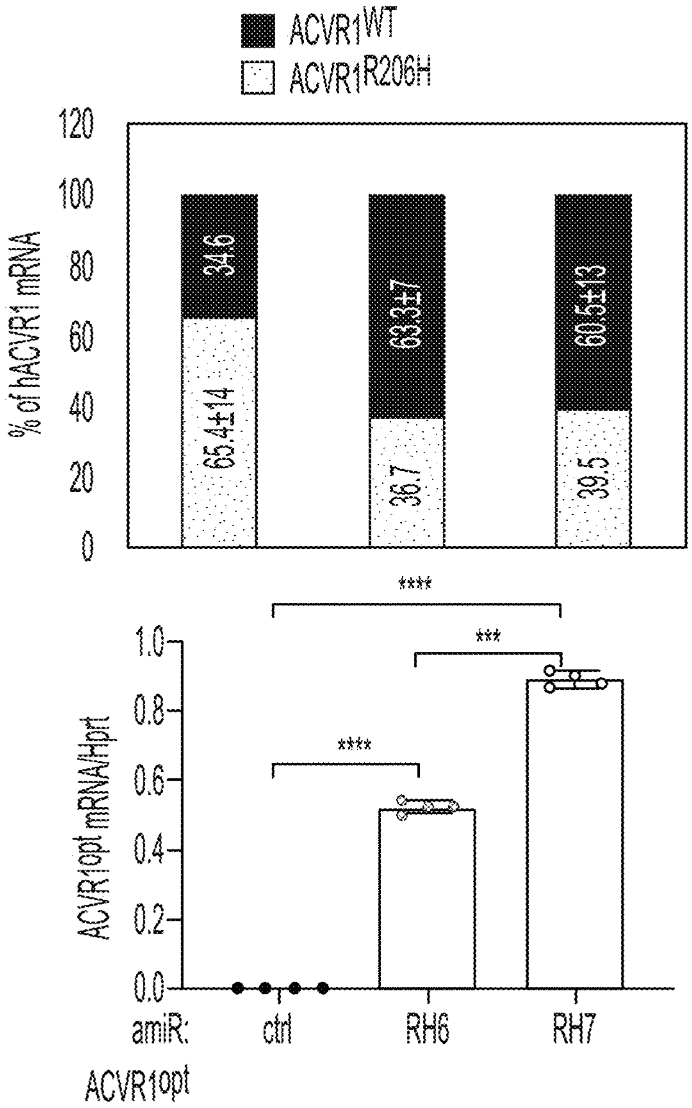
Figure 8G:
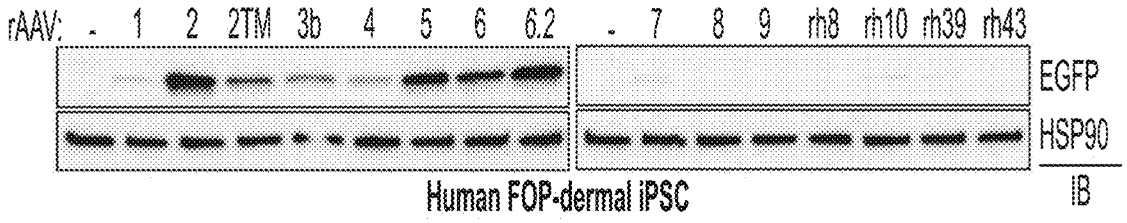

Example 3: Screening of rAAV Serotypes Effective for In Vitro Transduction of Multiple Cells To identify the best AAV serotype for transducing cells responsible for FOP in vitro, an scAAV vector construct expressing the enhanced green fluorescent protein (Egfp) reporter gene was packaged into 14 conventional AAV capsids (AAV1, AAV2, AAV3, AAV4, AAV5, AAV6, AAV6.2, AAV7, AAV8, AAV9, AAVrh.8, AAVrh.10, AAVrh.39, and AAVrh.43) and incubated with human FOP patient dermal fibroblast-derived inducible pluripotent stem cells (FOP-iPSC), mouse muscle myoblast line (C2C12), human bone marrow-derived stromal cells (BMSC), or human adipose tissue-derived stromal cells (ASC). Expression of EGFP in transduced cells was assessed by fluorescence microscopy (FIG. 5) and immunoblotting with an anti-EGFP antibody (FIG. 8G). While almost all of AAV serotype vectors transduced C2C12 cells, only five AAV serotype vectors, including rAAV2, rAAV3b, rAAV5, rAAV6, and rAAV6.2 were able to transduce human FOP-iPSCs. Among these, rAAV2, rAAV5, rAAV6, and rAAV6.2 also transduced human BMSCs and ASCs. Of note, rAAV9 shows a low transduction efficacy to human FOP-iPSC, ASC, and C2C12 cells.

Given that rAAV6.2, an rAAV6-F129L mutant, is the most effective serotype transducing all of four cell types in vitro and that rAAV9 can transduce human BMSCs as well as mouse skeleton, the ability of rAAV6.2 and rAAV9 to transduce heterotopic bone-residing cells in the skeletal muscle was examined in a mouse model of heterotopic ossification (HO).

Figure 6A:
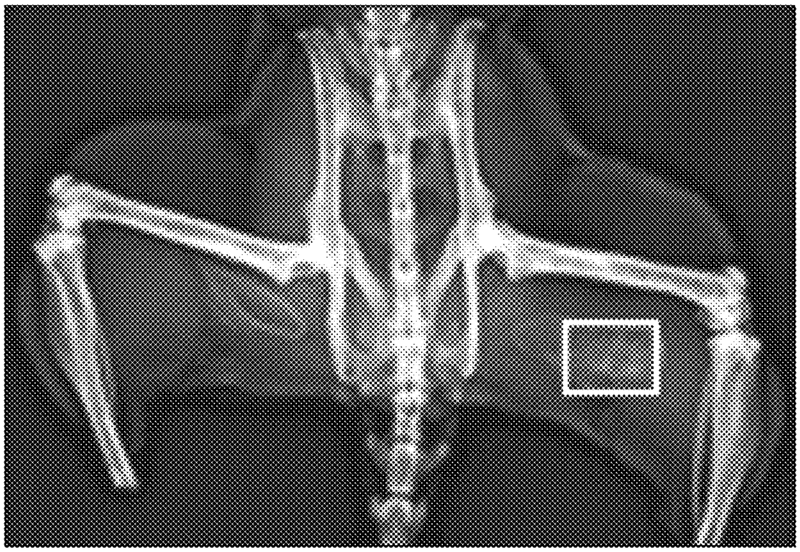
FIGS. 6A-6D show that rAAV6.2 and rAAV9 transduce heterotopic bone-residing cells in the skeletal muscle. Four (FIGS. 6A and 6B) or eight (FIGS. 6C and 6D) days after rBMP2/7 injection and muscle injury, $5\times10^{12}$ vg/kg of rAAV6.2.egfp or rAAV9.egfp was intramuscularly injected into 2 month old male Tie2-cre; Ai9 mice (n=3), respectively. X-radiography of whole body (FIGS. 6A and 6C) and frozen-section of the affected tissues (FIGS. 6B and 6D) were performed in treated mice. The blue image corresponds to DAPI; The red image corresponds to Tie2+ cells; green image correspond to AAV-transduced cells. Abbreviations: M, muscle; HO-BM, heterotopic ossification bone marrow.
Figure 6B:
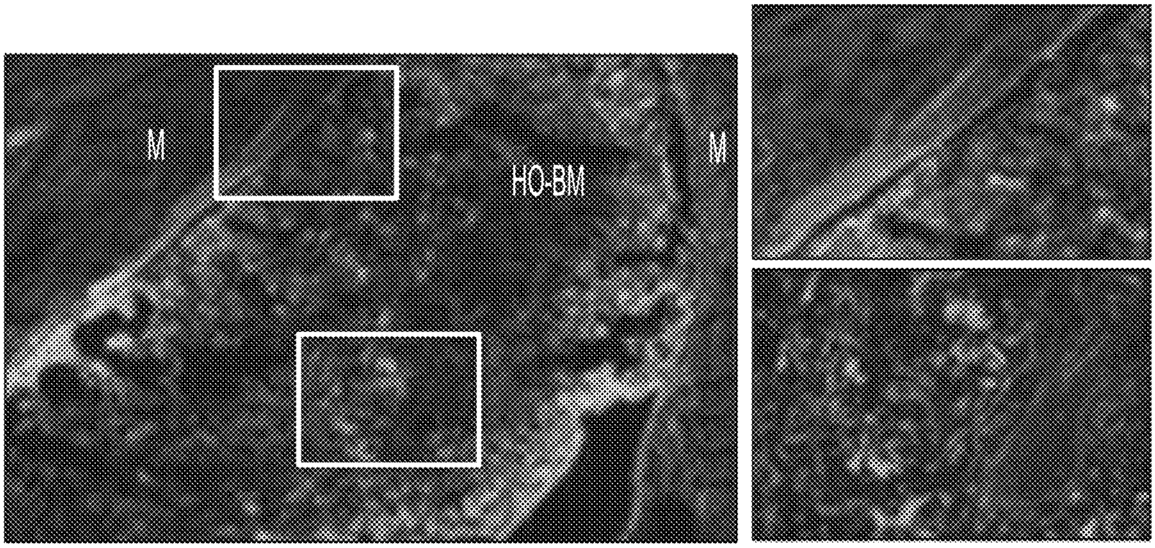
Figure 6C:
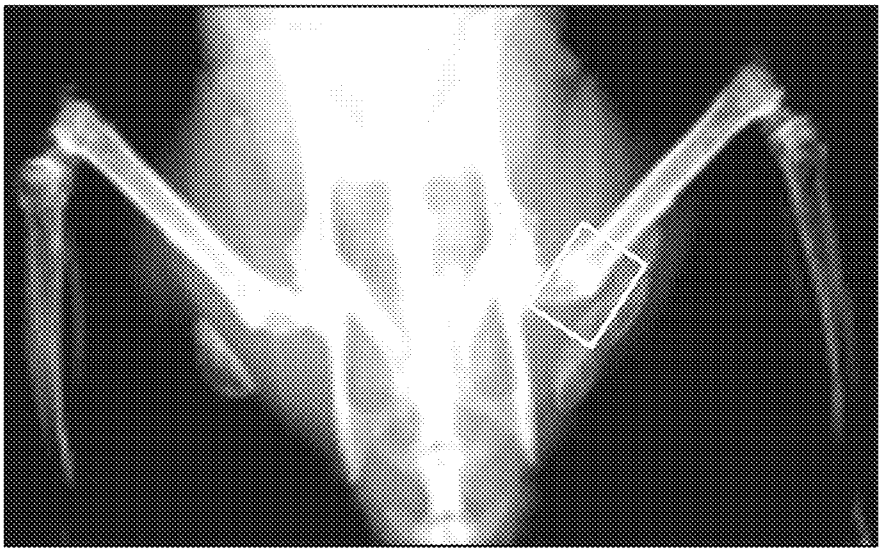
Figure 6D:
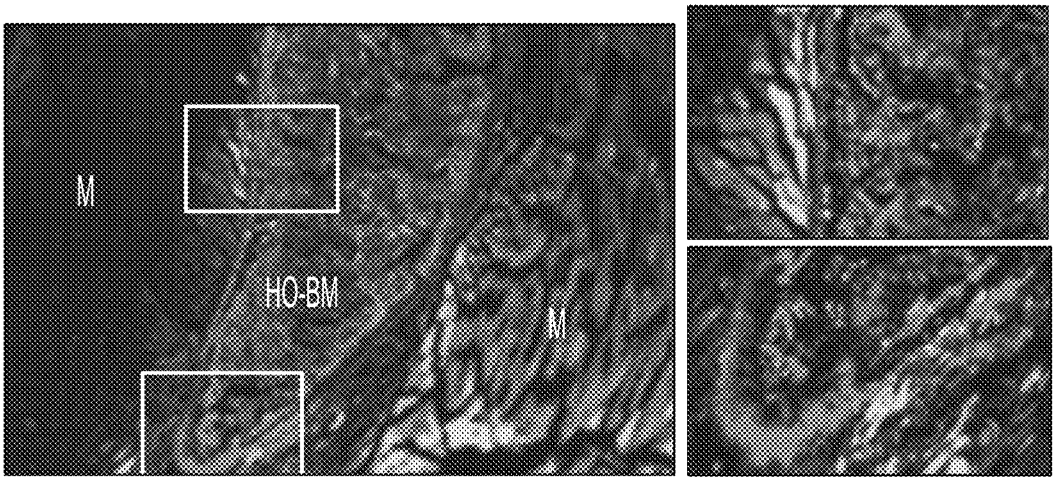
Figure 7A:
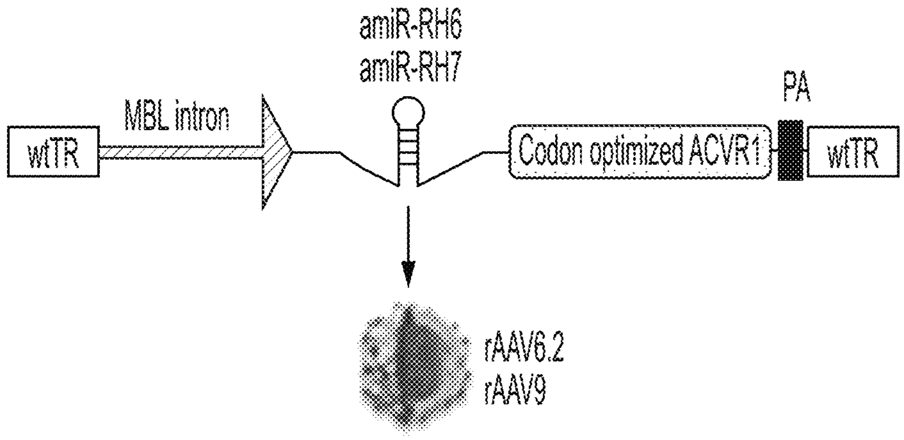
FIGS. 7A-7B show the generation of rAAV6.2 and rAAV9 vectors for gene replacement.
Figure 7B:
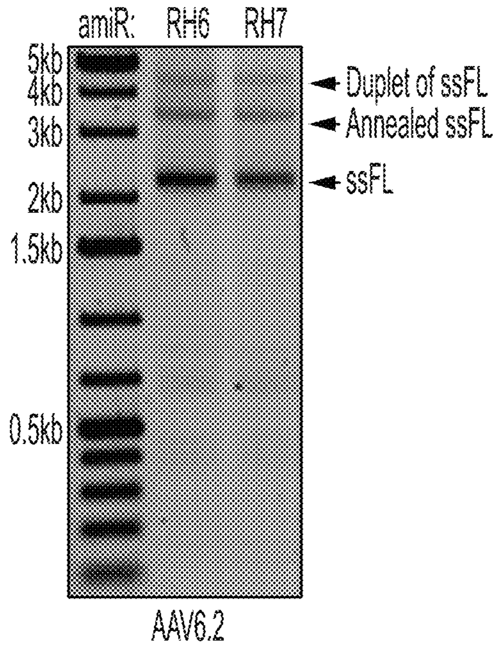
Figure 15A:
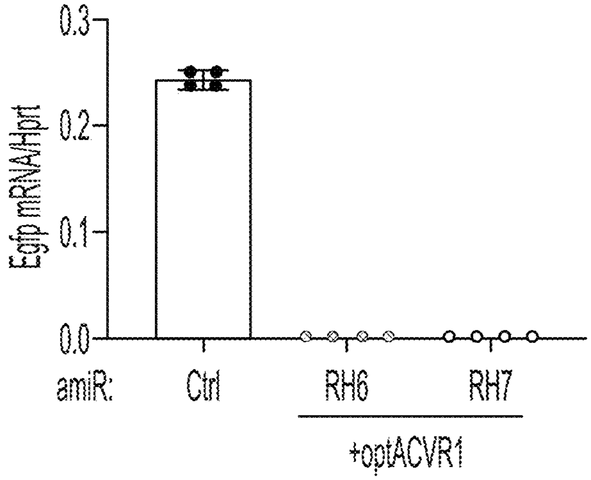
FIGS. 15A-15D show AAV-gene therapeutics reverses enhanced osteogenesis by ACVR1-R206H mutation.

Tie2-Cre lineage-labeling experiments demonstrated that Tie2-expressing cells were present at all stages of HO, including fibroproliferative, chondrogenic, and osteogenic stages, and they contribute to heterotopic cartilage and bone formation after BMP ligand implantation and following muscle injury in the skeletal muscle. These cells are a sub-population of fibro/adipogenic cells (FAPs), discovered for their adipogenic and fibrogenic capacities. To visualize Tie2+ lineage cells in the heterotopic bone using tdTomato expression, Tie2-cre mice were crossed with the Cre reporter Ai9 mice and treated with intramuscular (i.m.) injection of recombinant BMP2/7, following muscle injury in the skeletal muscle (FIG. 6). Four days (fibroproliferative stage) or eight days (pre-osseous analgen stage) later, rAAV6.2 or rAAV9 expressing EGFP was intramuscularly injected, respectively. Twenty four days after the HO induction, HO was assessed by X-radiography (FIGS. 6A and C) and AAV-transduced cells residing in the heterotopic bone were visualized using fluorescence microscopy (FIGS. 6B and D). While both of rAAV6.2 and rAAV9 are effective for transduction of HO-residing cells and skeletal muscle, only a sub-population of Tie2-expressing cells was transduced by these AAV vectors (FIGS. 6B and D). the AAV vector genome that contains the CBA promoter, MBL intron, amiR-RH6 or -RH7, and opt-ACVR1, developed for gene replacement (FIG. 4A), was packaged into AAV6.2 or AAV9 capsid (FIG. 7A) and their AAV genome integrity was validated (FIG. 7B). Since rAAV6.2 shows a higher in vitro transduction efficiency to human FOP-iPSCs than rAAV9 (FIG. 5), AAV's functional validation was performed using rAAV6.2 vectors (FIG. 8). To examine the ACVR1-R206H mutant allele-specific silencing efficiency of amiR-RH6 or amiR-RH7 in human FOP-iPSCs, mRNAs extracted from AAV-transduced cells were subjected to next generation sequencing (FIG. 8A). Compared to amiR-ctrl-treated cells showing the transcript ratio of R206H to WT allele as 65.4% vs. 34.6%, the transcript ratio was altered by 47.1% vs. 52.9% and 20.9% vs. 79.1%, when treated with rAAV6.2 carrying amiR-RH6 or amiR-RH7, respectively. This result demonstrates that amiR-RH7 is more effective for the ACVR1-R206H mutant allele-specific silencing in human FOP-iPSCs than amiR-RH6. Of note, rAAV6.2 carrying amiR-RH7 and opt-ACVR1 also showed higher expression of codon-optimized, wild type ACVR1 mRNA in human FOP-iPSCs, compared to rAAV6.2 carrying amiR-RH6 and opt-ACVR1, while no ACVR1 expression was detected in rAAV6.2.amiR-ctrl-treated cells (FIG. 8B). Accordingly, treatment with the vectors resulted in a significant decrease in alkaline phosphatase (early osteogenic marker) and mineralization activities (late osteogenic marker) in comparison with rAAV6.amiR-ctrl (FIG. 8C and FIG. 8D), while mRNA levels of osteoblast marker genes, including type 1 collagen and bone sialoprotein, were markedly reduced by rAAV6.2 carrying amiR-RH7 and opt-ACVR1, not by rAAV6.2 carrying amiR-RH6 and opt-ACVR1 or rAAV6.2.amiR-ctrl (FIG. 8E). Thus, this result indicates that rAAV6.2 carrying amiR-RH7 and opt-ACVR1 is potent to replace the ACVR1-R206H with wild type ACVR1, thereby suppressing osteogenesis of FOP-iPSCs. rAAV6.2 vectors carrying control vector, amiR-RH6.ACVR1$^{opt}$, or amiR-RH7.ACVR1$^{opt}$ were then transduced into human FOP iPSCs and their expression and silencing efficiency and accuracy were examined using RT-PCR, next-generation sequencing (NGS), and whole transcriptome analysis. While 65.4% ACVR1$^{R206H}$ vs. 34.6% ACVR1$^{WT}$ transcripts are expressed in control-expressing cells, the transcript pattern was substantially changed to 36.7% vs. 63.3% and 39.5% vs. 60.5% in cells expressing amiR-RH6.ACVR1$^{opt}$ and amiR-RH7.ACVR1$^{opt}$, respectively (FIG. 8F, top). ACVR1$^{opt}$ expression was also confirmed in these cells (FIG. 8F, bottom) relative to control cells expressing EGFP (as shown in FIG. 15A).

Figure 8H:
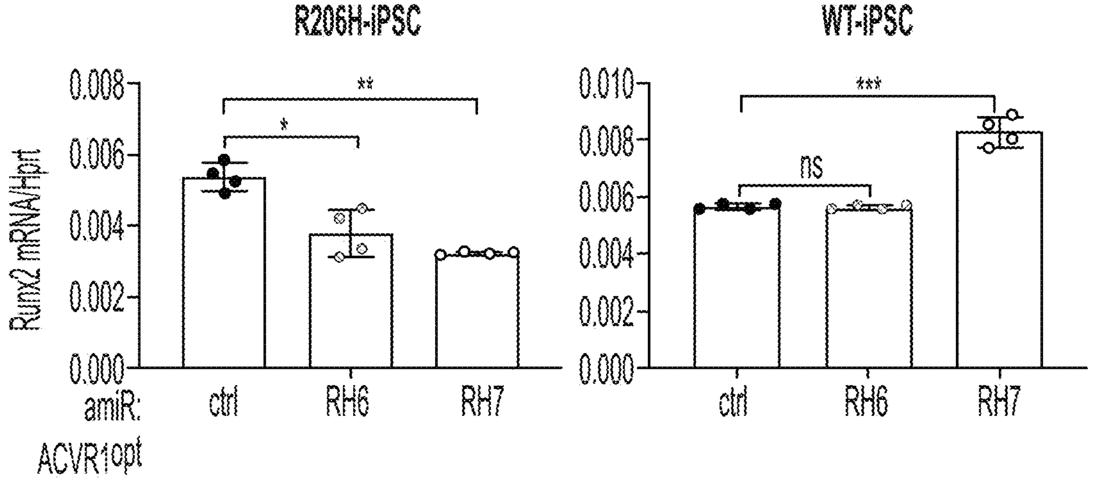

To examine the ability of amiR-RH6.ACVR1$^{opt}$ or amiR-RH7.ACVR1$^{opt}$ to suppress osteogenic potentials of human FOP iPSCs, alkaline phosphatase (ALP) activity, alizarin red staining, and osteogenic gene expression of treated cells were examined (FIGS. 8E and 8H). WT iPSCs were also generated from healthy donors and used as negative controls. These results demonstrate that amiR-RH6.ACVR1$^{opt}$ and amiR-RH7.ACVR1$^{opt}$ are both effective in inhibiting osteogenesis of FOP iPSCs while no effect or slight increase in osteogenesis of WT iPSCs. Thus, these AAV vectors are likely to act specific to human FOP cells.

Figure 8I:
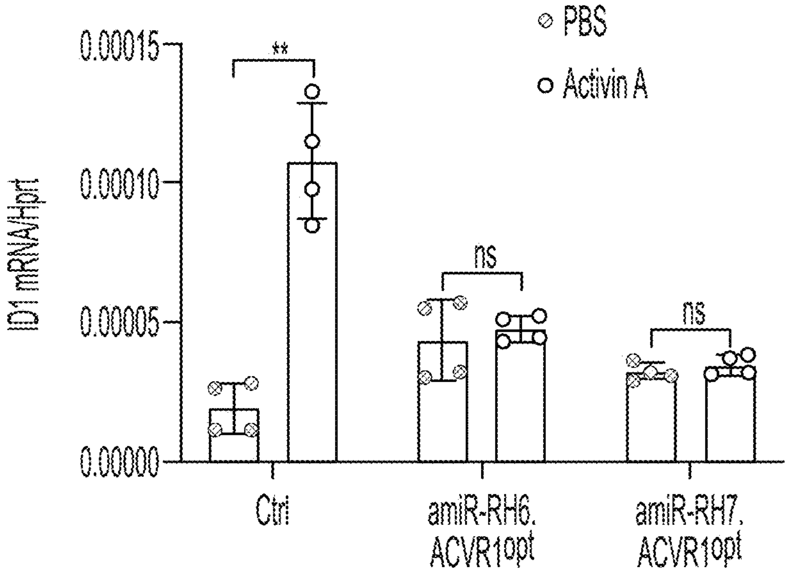
Figure 8J:
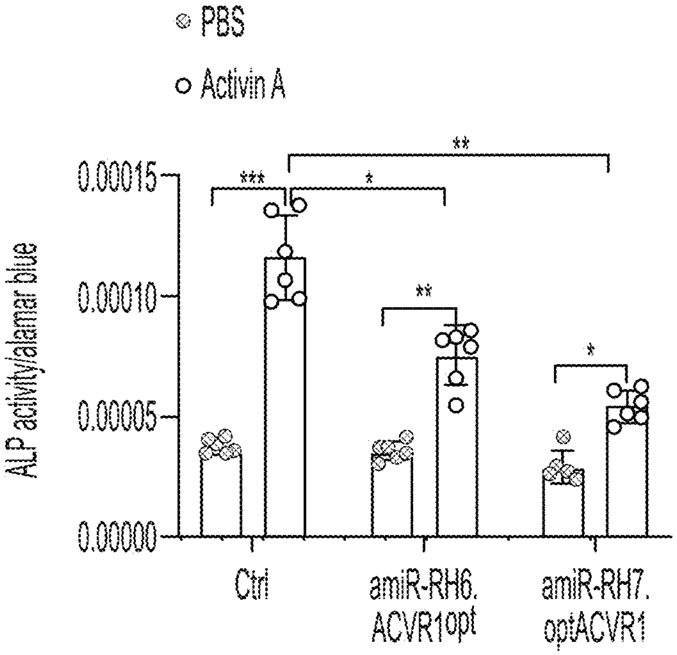
Figure 8K:
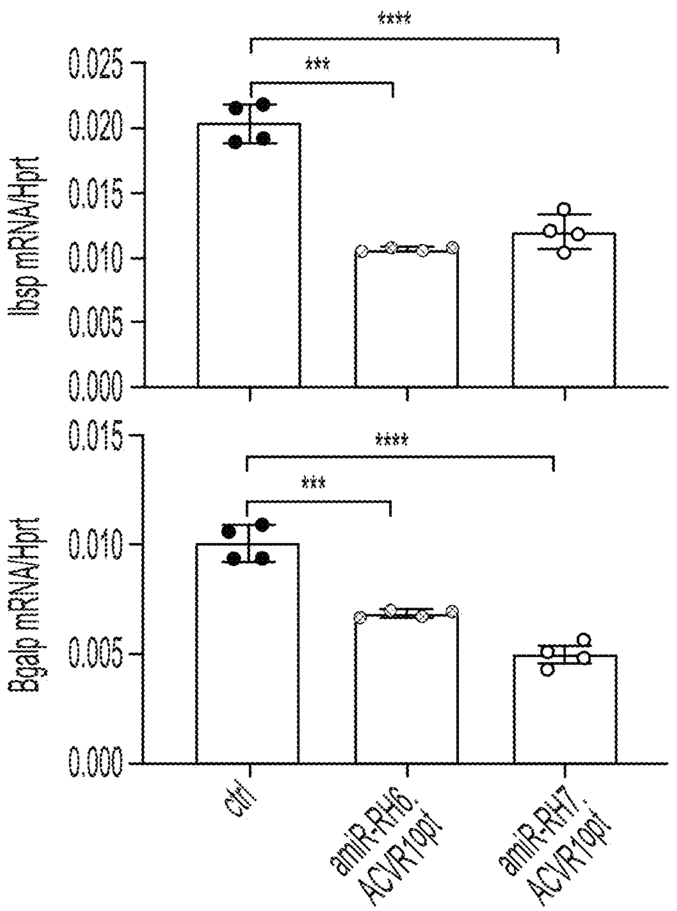
Figure 31:
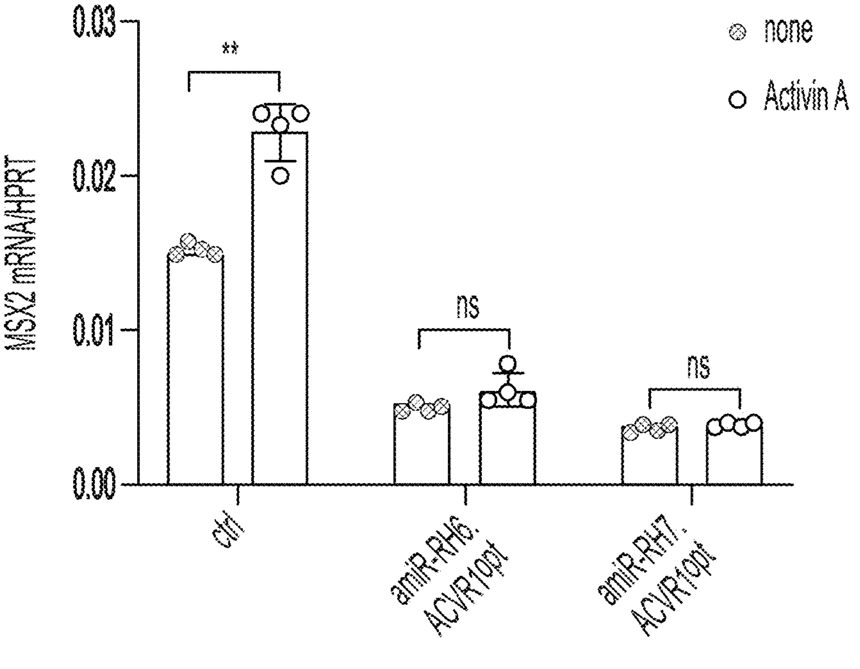
FIG. 31 shows effects of AAV gene therapeutics on activin A-induced osteogenesis in vitro. $5\times10^{10}$ GCs of the AAV6.2 vectors carrying ctrl, amiR-RH6.ACVR1$^{opt}$, or amiR-RH7.ACVR1$^{opt}$ were transduced to human iPSCs and two days later, cells were incubated with PBS or activin A (100 ng/ml) for six hours and MSX2 mRNA levels were measured by RT-PCR and normalized to HPRT.

It has been previously reported that ACVR1$^{R206H}$ mutation confers activation of Smad1/5/8-mediated BMP signaling in response to activin A, whereas no BMP signaling normally occurs via ACVR1$^{WT}$ receptor. In control-expressing FOP iPSCs, activin A treatment significantly upregulated expression of BMP-responsive genes, ID1 and MSX2, and this induction was abolished in cells expressing amiR-RH6.ACVR1$^{opt}$ or amiR-RH7.ACVK1$^{opt}$ (FIG. 8I and FIG. 31). These results were further evaluated and confirmed by using fibro/adipogenic progenitors (FAPs), a major cell-of-origin of HO in a humanized knock-in mouse model of FOP. Activin A-induced osteogenesis was examined in a subset of FAPs isolated from the skeletal muscle of Acvr1$^{(R206H)F1}$; pDGFRα mice using cell surface markers (PDGFRα$^+$ScaI$^+$ CD31$^-$CD45$^-$), demonstrating a significant decrease in activin A-induced ALP activity and osteogenic gene expression when treated with amiR-RH6.ACVR1$^{opt}$ or amiR-RH7.ACVR1$^{opt}$ (FIGS. 8J and 8K).

Figure 9:
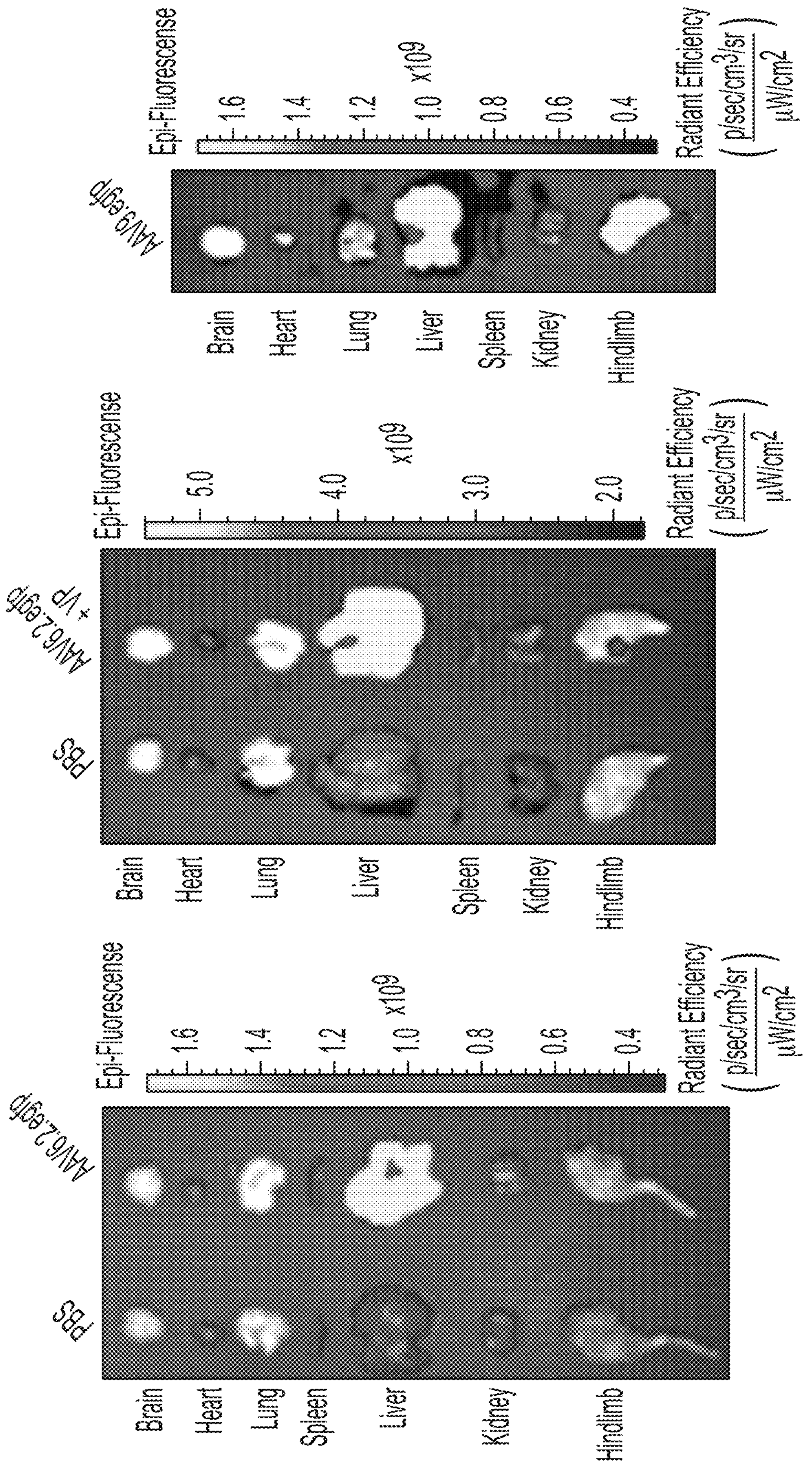
FIG. 9 shows tissue distribution of systemically injected rAAV6.2 or rAAV9 in mice. $5\times10^{13}$ vg/kg of rAAV6.2.egfp with or without vascular permeability (VP) agents or rAAV6 was intravenously injected into 2 month old male mice (n=3) and 2 weeks later, tissue distribution of vectors in brain, heart, lung, spleen, liver, kidney, and hindlimb was assessed by EGFP expression using IVIS-100 optical imaging system.
Figure 10A:
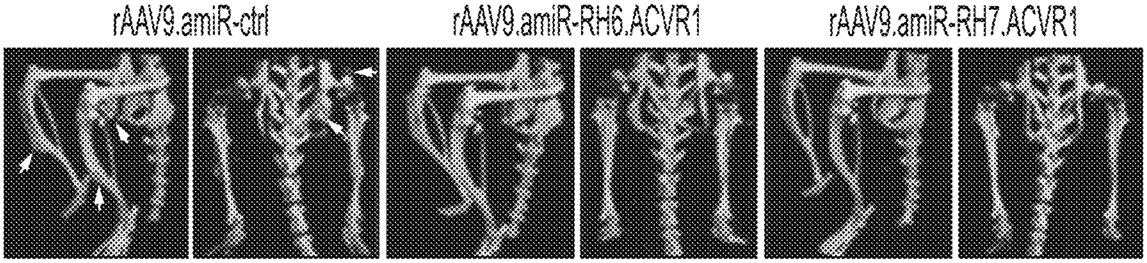
FIGS. 10A-10B show therapeutic effects of rAAV9 vectors in a mouse model of FOP. Three days after five consecutive injection of tamoxifen, six week old male ACVR1$^{(R206H)FIEx}$; ERT-Cre mice were intravenously injected with $5\times10^{13}$ vg/kg of rAAV9 vectors (rAAV9 vector carrying amiR-RH6 and opt-ACVR1, rAAV9 vector carrying amiR-RH7 and opt-ACVR1, and rAAV9 vector carrying amiR and control). Ten weeks later, spontaneous heterotopic ossification (HO) was assessed by microCT. Representative 3D-reconstruction microCT images of treated mice (FIG. 10A, n=5) and HO sites were quantitated (FIG. 10B).
Figure 10B:
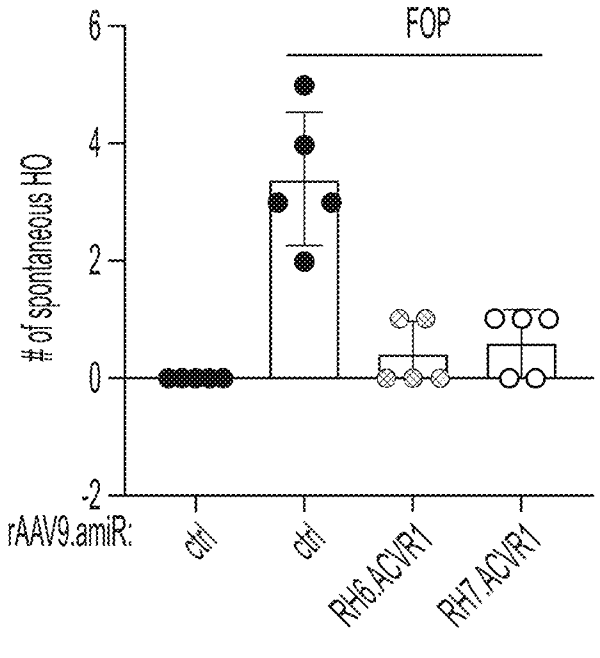

To examine the ability of systemically injected rAAV6.2 to transduce skeletal muscle, rAAV6.2 expressing EGFP (rAAV6.2.egfp) was intravenously (i.v.) injected into 2 month old wild type mice and two weeks later, individual organ imaging was performed, demonstrating strong EGFP expression in the liver, while no expression was detected in the skeletal muscle (FIG. 9, left). vascular permeability agents, including human VEGF-166 and sodium heparin, improved rAAV6.2's ability to transduce heart and skeletal muscle (FIG. 9, middle). However, compared to rAAV6.2, intravenous injection of rAAV9 even in the absence of vascular permeability agents was highly effective for the transduction of heart and skeletal muscle (FIG. 9, right). Thus, rAAV9 capsid was used to deliver the gene replacement machinery to a mouse model of FOP. ACVR1(R206H) FlEx mice carrying a Cre recombinase-dependent conditional-on knock-in allele of human ACVR1-R206H were crossed with ERT2-Cre mice expressing a tamoxifen-induced Cre recombinase (ACVR1(R206H)FlEx; ERT-Cre) in order to generate an inducible mouse model of FOP. As previously reported, spontaneous HO develops at multiple areas ten weeks after tamoxifen treatment. Compared to amiR-ctrl-treated mice with multiple HO sites, almost no HO sites were detected in FOP mice when treated with rAAV9 carrying amiR-RH6 or -RH7 and opt-ACVR1 (FIG. 10). These results demonstrate that systemically delivered AAV9 vectors are effective for the replacement of ACVR1-R206H mutant mRNA with codon-optimized, wild type ACVR1 mRNA in the skeletal muscle, and suppressed the development of spontaneous HO in vivo. Thus, gene replacement using the rAAV9.amiR-RH6.opt-ACVR1 or amiR-RH7.opt-ACVR1 vector may be a promising approach for the treatment of HO.

Example 4: Generation of AAV Vector Genome for Gene Editing

Figure 11:
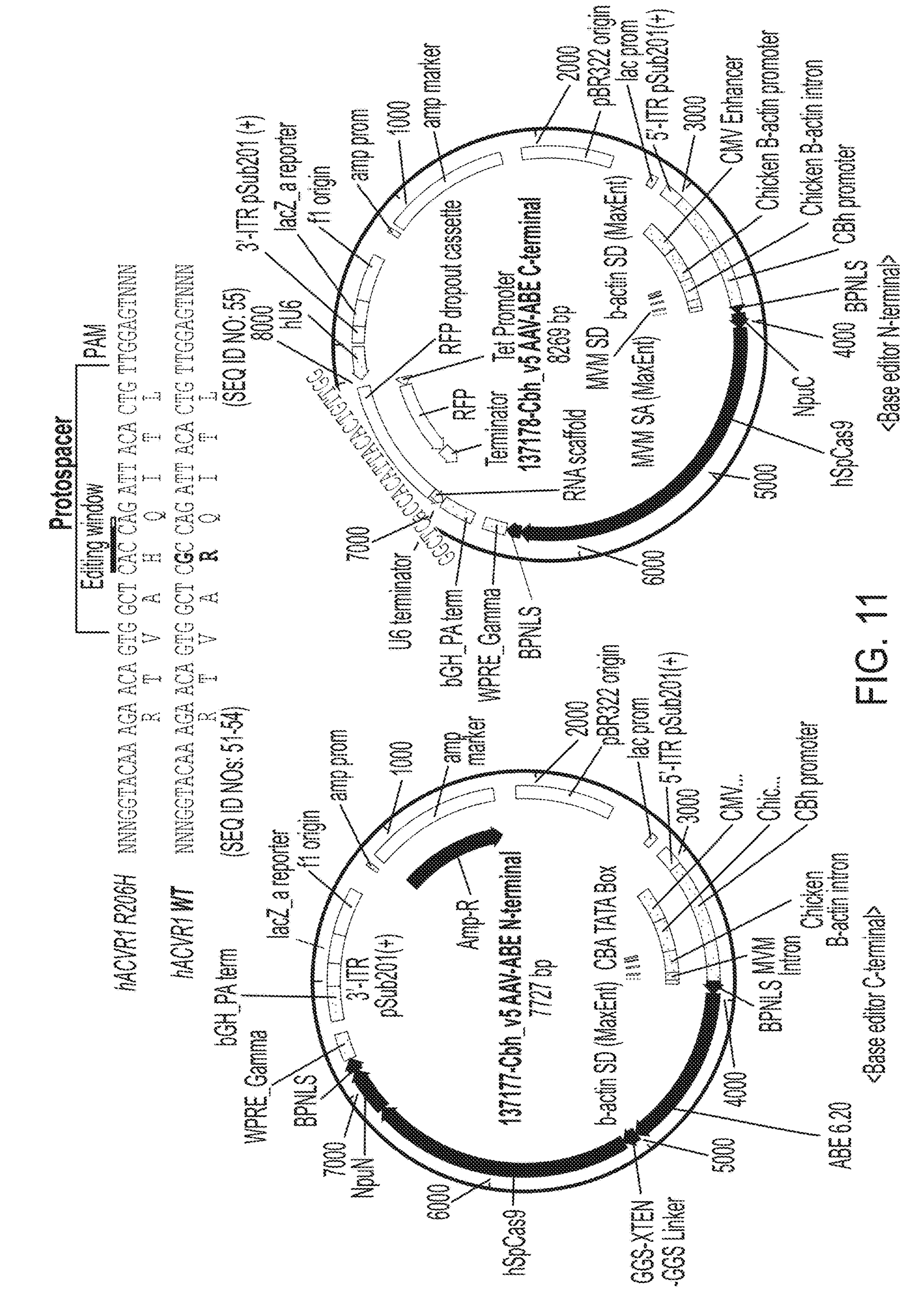
FIG. 11 illustrates schematic diagram showing plasmid constructions of a Cas9-based adenine base editor (ABE) for ACVR1-R206H editing. The C-terminal ABE construct (left image) is packaged into AAV6.2 or AAV9 capsid. The N-terminal ABE construct (right image) contains protospacer having the R206H mutation site.

Cas9-based adenine base editor (ABE) compatible to rAAV has been developed to directly convert a target base pair to a different base pair without creating double-stranded DNA breaks. Thus, rAAV9-compatible ABE construct was developed to convert "A" into "G" in the ACVR1-R206H allele. The ABE was divided into halves that are smaller than the AAV packaging size limit (~4.7 kb) using a trans-splicing intein sequence, which enabled dual-AAV packaging of base editors. The N-terminal ABE construct contained protospacer bearing the R206H mutation site. The C-terminal ABE construct was packaged into AAV6.2 or AAV9 capsid (FIG. 11).

Figure 12:
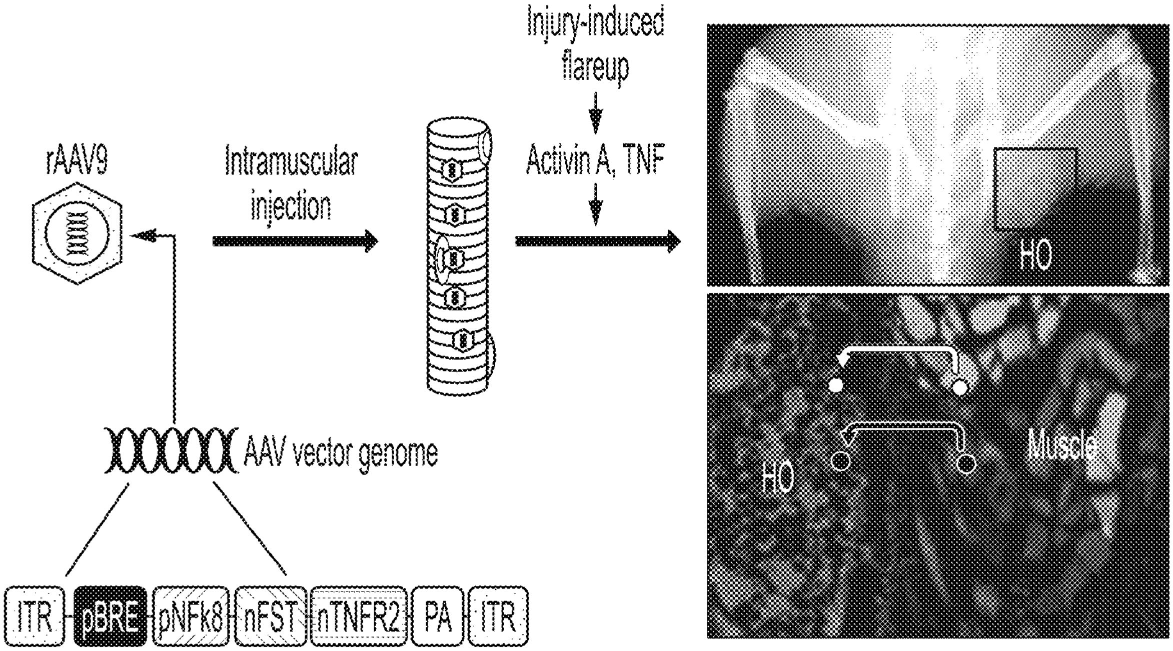
FIG. 12 is a schematic diagram showing AAV-mediated treatment approach for FOP. The promoters, pBRE and pNF-κB, induce the expression of soluble follistatin (sFST) and TNFR2 in responsive to Activin A/BMP ligand and inflammation, respectively. Three days after intramuscular or intravenous injection of rAAV9 vectors, cardiotoxin-induced muscle injury will be executed in ACVR1$^{(R206H)FIEx}$; ERT-Cre mice to develop HO. Upregulation of activin A and TNF in the area of injury-induced flare-up in the skeletal muscle results in the production of soluble FST and TNFR2 that suppress activin A and TNF signaling in heterotopic bone. Abbreviations: pBRE, BMP-responsive element; pNF-κB, NF-κB-binding sites.
Figure 13A:
FIGS. 13A-13D show the generation of the AAV vector genome responding to inflammatory cytokines and/or bone morphogenetic protein (BMPs).
Figure 13B:
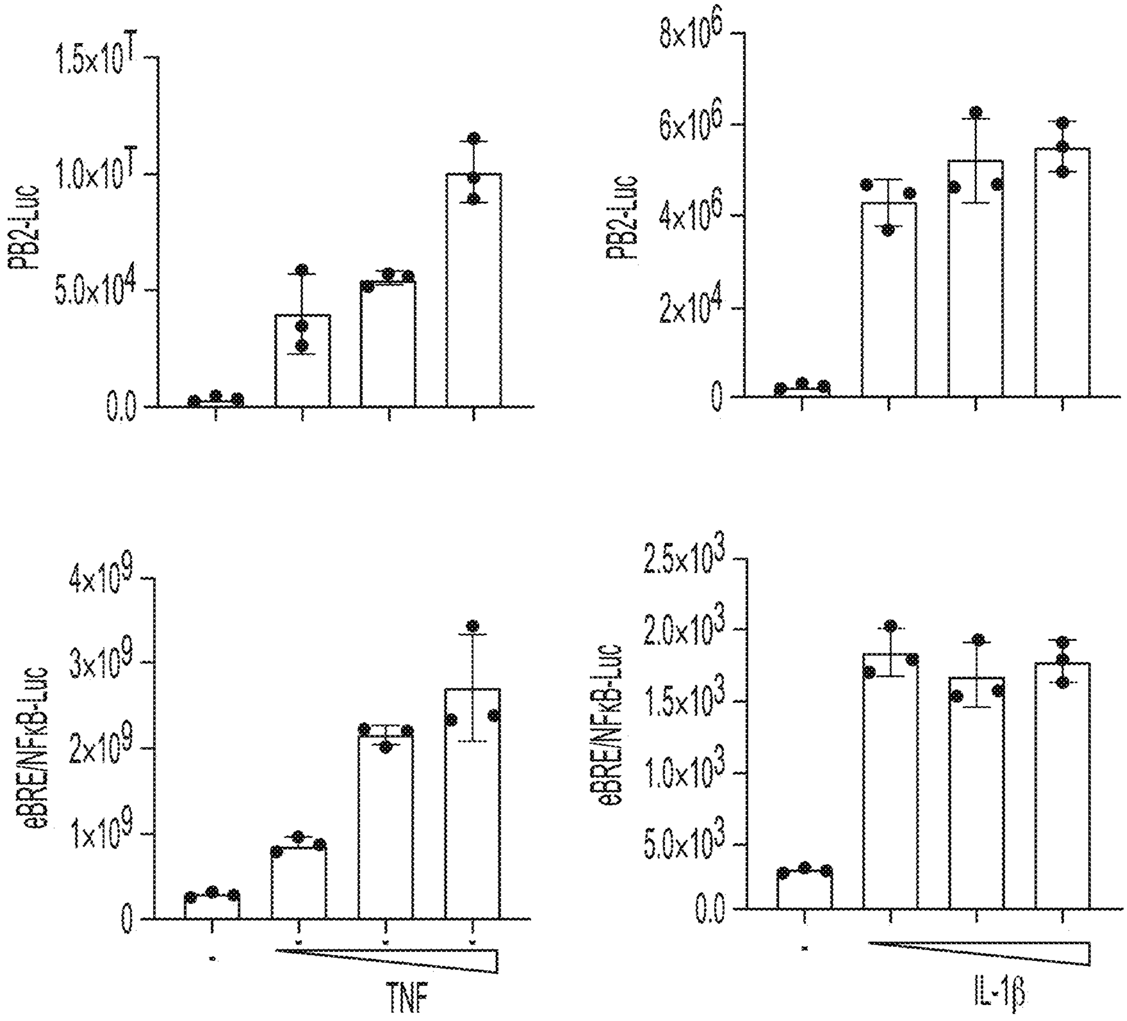
Figure 13C:
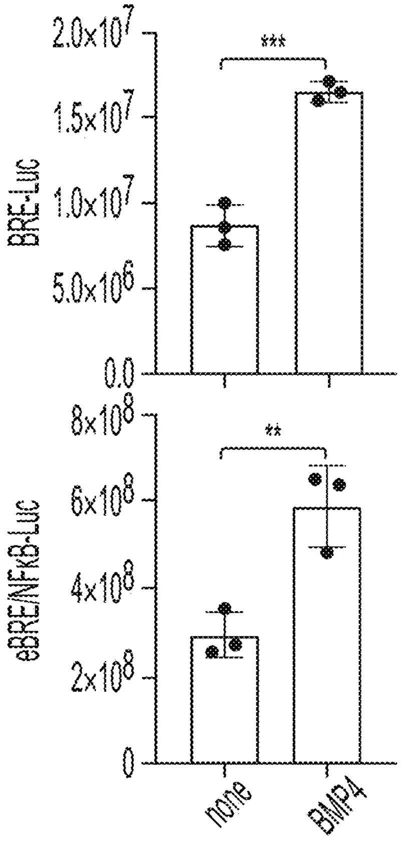
Figure 13D:
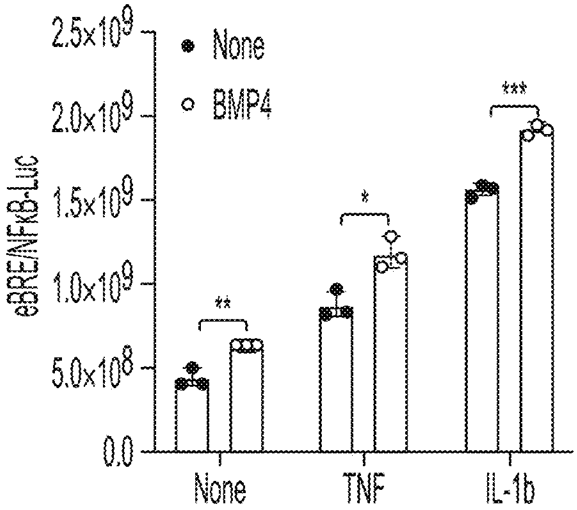

Example 5: Generation of the AAV Vector Genome Responding to Inflammatory Cytokines and/or BMPs It has been shown that inflammation and activin A play a role in HO. Macrophages and mast cells are highly abundant in the areas of developing HO in a mouse model of FOP and when depleted, HO was markedly reduced. In a mouse model of trauma-induced HO, Achilles' tenotomy and dorsal burn resulted in upregulation of inflammatory cytokines, including TNF and IL-1β within 48 hours after injury, while elevation of MCP1 and VEGF was persistent in saliva one week after injury. As levels of activin A, BMP ligands, and inflammatory cytokines are elevated in the area of flare-up, rAAV9 vectors that can secret a natural activin A antagonist, soluble follistatin (sFST), and a natural TNF antagonist, soluble TNFR2 (sTNFR2), in response to flare-up were generated. Local or systemic injection of rAAV9 is highly effective for the transduction of skeletal muscle, which produces sFST and sTNFR2 in the area of flare-up, suppressing the development of neighboring HO (FIG. 12). To this end, the promoters containing endogenous BMP-responsive elements (BRE, EndolD1-BRE) and NF-kB-binding sites (pNF-kB) were cloned into the AAV vector genome encoding *Gaussia* reporter gene (eBRE/NF-kB-Luc, FIG. 13A). Luciferase activity was substantially increased in a dose-dependent manner when stimulated with inflammatory cytokines, including TNF and IL-1β recapitulating induction kinetics seen in a conventional NF-kB-responsive reporter gene PB2-luc (FIG. 13B). Like a conventional BMP-responsive reporter gene BRE-luc, this reporter gene was also responsive to recombinant BMP4 (FIG. 13C). Additive increase of luciferase activity was observed in the eBRE/NF-kB-Luc when treated with both inflammatory cytokines and BMP4 (FIG. 13D). These results indicates the eBRE/NF-kB-Luc as a promising sensor plasmid that can respond to elevated levels of inflammatory cytokines and activin A/BMPs in the areas of flare-up.

Example 6: Generation of the AAV Vector Genome that Produces Soluble Follistatin (FST-288) and TNFR2

Figure 14A:
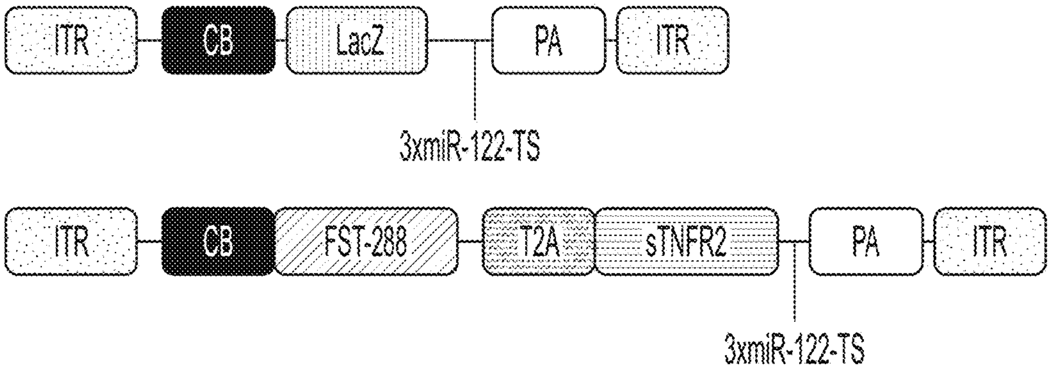
FIGS. 14A-14B shows the generation of the AAV vector genome that produces soluble follistatin (FST-288) and TNFR2.
Figure 14B:
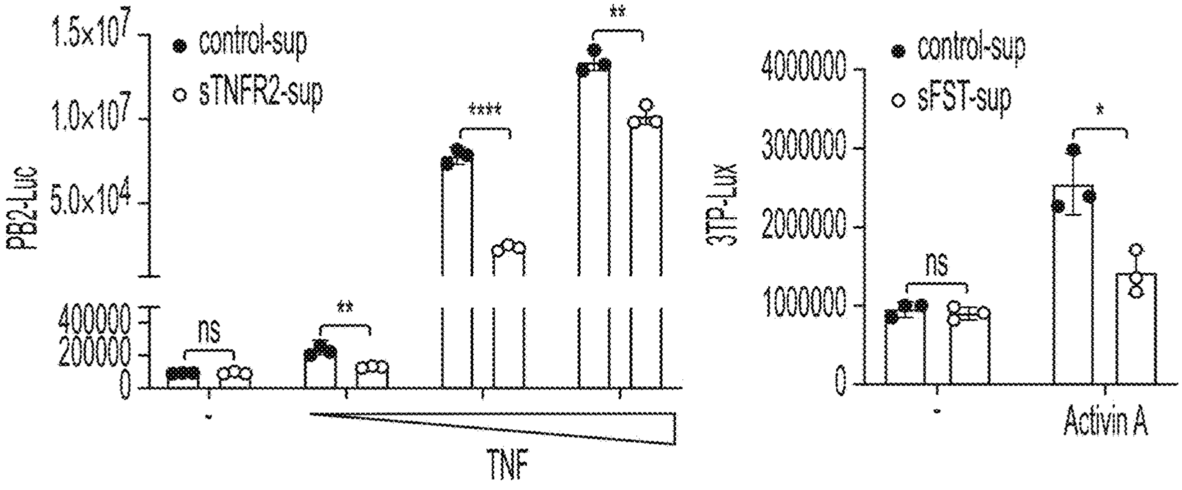

It has been previously reported that follistatin and sTNFR2 competitively bind activin A and TNFα against their cognate receptors and therefore, suppress activin A- and TNFα-induced signal transduction, respectively. Thus, a natural activin A antagonist, soluble human follistatin (FST-288) and a natural TNF antagonist, soluble human TNFR2 were cloned into the AAV vector genome under the chicken β-actin promoter (CB) (FIG. 14A). However, following systemic delivery, rAAV9 vectors also target liver, heart, and skeletal muscle, in addition to bone, which may cause untoward effects. To circumvent this, tissue-specific, endogenous miRNAs to repress rAAV expression in liver was developed, by engineering perfectly complementary miR-122-binding sites into the AAV vector genome. Silencing of transgene expression in liver exploited the natural expression of the abundant (≥60,000 copies/cell) miRNAs, miR-122, which is expressed in hepatocytes, and miR-1, a miRNA found in the heart and skeletal muscle of virtually all animals. Complementary site for miR-122 was inserted into the 3' untranslated region (UTR) of the transgenes (FIG. 14A). To test whether sTNFR2 and FST-288 produced from the AAV vector genome can inhibit TNF- and activin A-induced signal transduction, control vector or the AAV vector genome was transfected into HEK293 cells and the supernatant was harvested from these cells. Compared to control supernatant, TNF- and activin A-induced activation was both markedly reduced in the presence of sTNFR2 and sFST-producing supernatant (FIG. 14B). Next, the CB promoter in this plasmid will be replaced with the eBRE/NF-kB promoter, which enables to produce secreted TNFR2 and FST-288 in response to inflammatory cytokines and activin A.

Example 7: In Vitro and In Vivo Studies

This example describes novel gene therapeutics that can prevent disabling FOP pathology. Direct muscle administration of rAAVs (e.g., as described in the Examples above) carrying gene replacement by exogenous expression of healthy ACVR1, Acvr1R206H allele-specific silencing, or the combination of gene replacement and silencing, markedly decreased trauma-induced heterotopic ossification (HO) in mice harboring a human Acvr1R206H knock-in allele. Additionally, the AAV vectors also suppressed traumatic HO in the skeletal muscle when systemically administered at infant stages. Fibrosis, chondrogenesis, and ossification in the injury sites were all substantially decreased in AAV-treated muscle, while inflammation normally occurred. It was also observed that systemic delivery of a rAAV9 vector carrying the combination of gene replacement and silencing was effective for preventing chronic HO in both juvenile and adult FOP mice, as shown by reversal of progressive HO, jaw ankylosis, osteoporosis, short stature, and weight loss. It was also observed that delivery of rAAV9 vectors to skeletal muscle via intradermal (id) injection using a micro needle (e.g., microject 600) was effective to transduce FOP-causing cells in the skeletal muscle, alleviating concerns about intramuscular injections inducing HO in FOP patients.

Figure 15B:
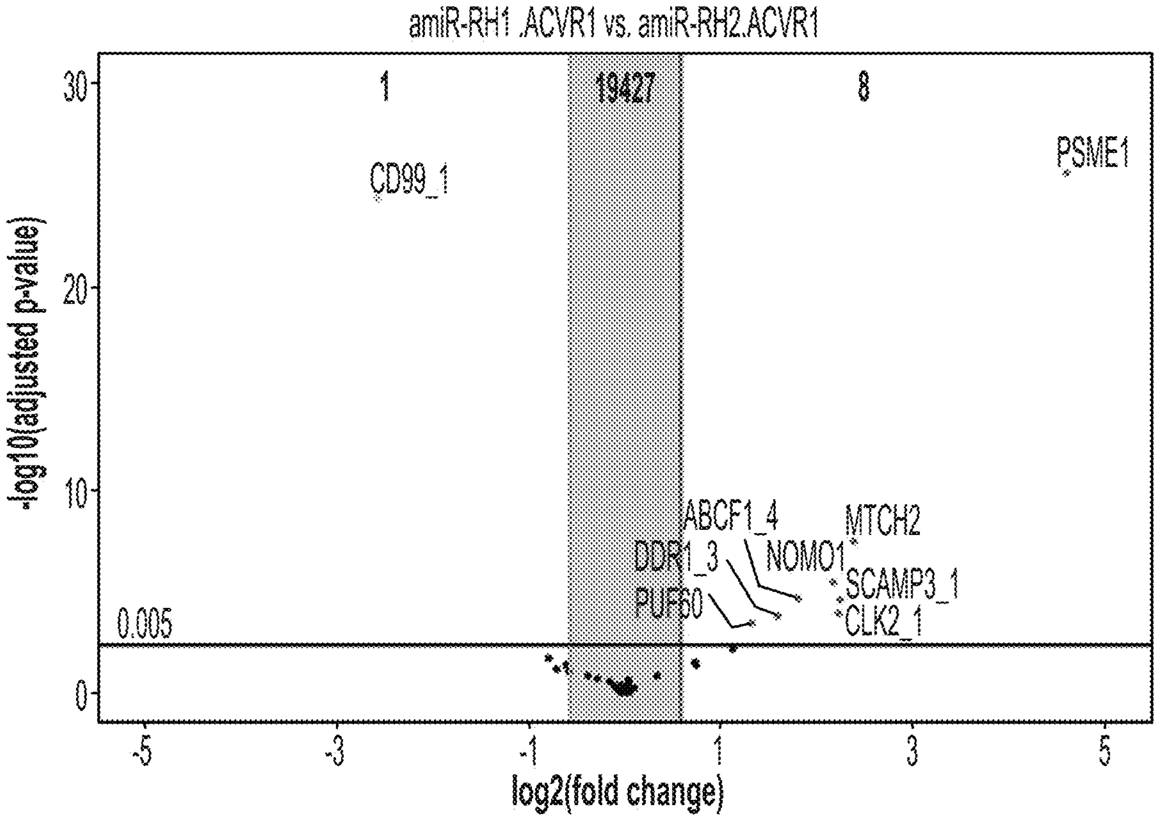
Figure 15C:
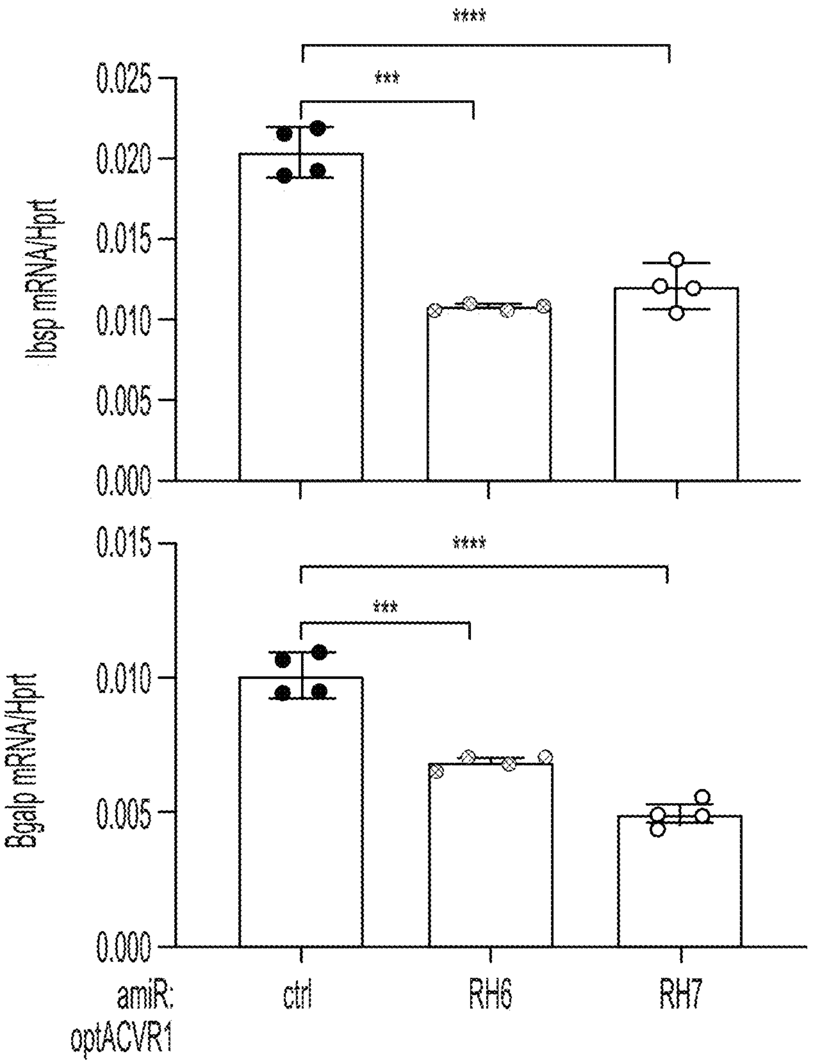
Figure 15D:
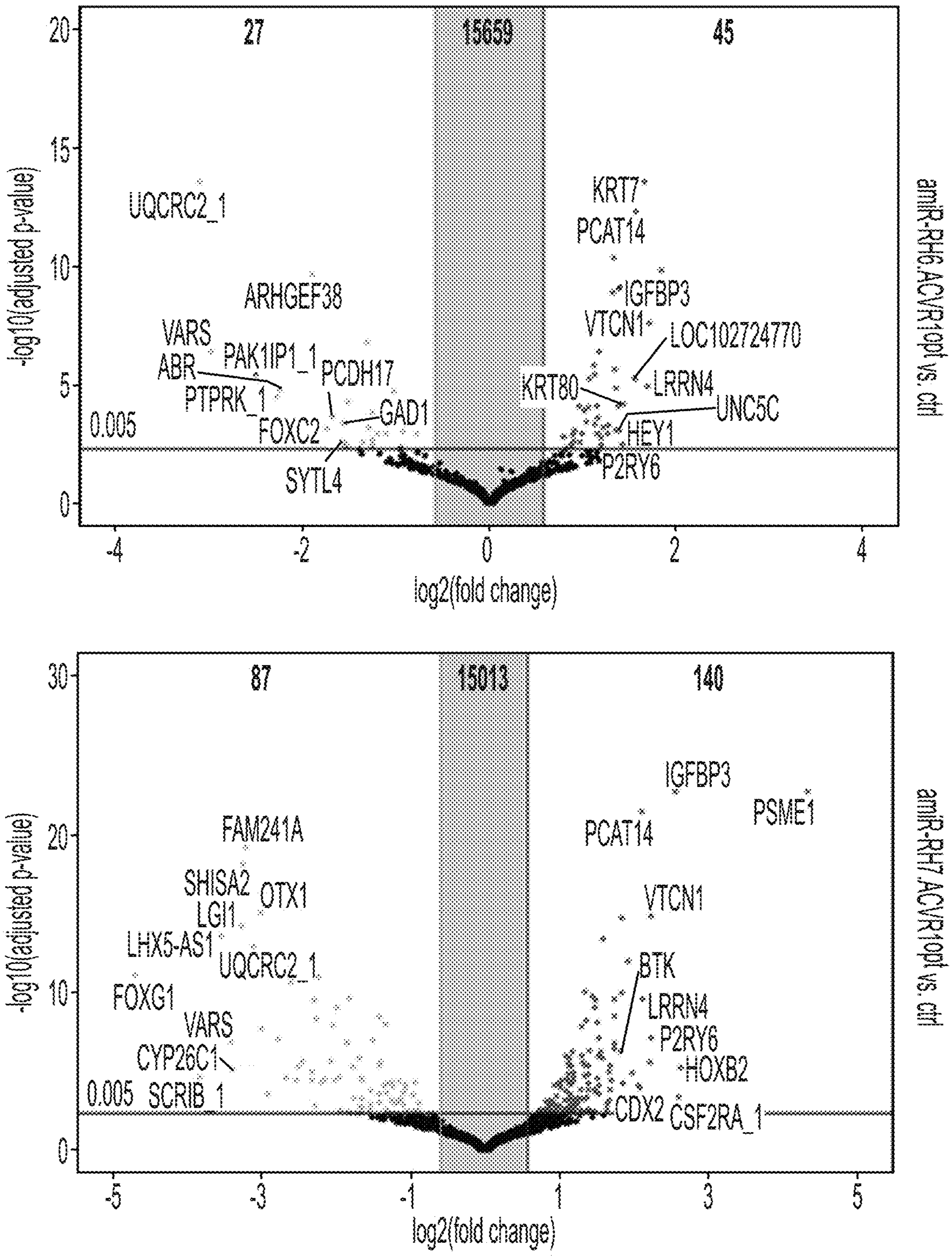

FIGS. 15A-15D show AAV-gene therapeutics reverses enhanced osteogenesis by ACVR1-R206H mutation. FIG. 15A shows $5\times10^{10}$ GC of AAV6.2 vectors carrying ctrl, amiR-RH6.optACVR1, or amiR-RH7.optACVR1 were transduced to human FOP-iPSCs for 2 days and cultured under osteogenic conditions for 4 days. Total RNA was subjected for cDNAs synthesis, followed by RT-PCR for Egfp expression. FIG. 15B and FIG. 15D show total RNA was subjected for RNA sequencing and a volcano plot comparing the gene expression for up/downregulated genes in the cells expressing amiR-RH6.optACVR1 relative to amiR-RH7.optACVR1 was produced. In comparison with control vector, treatment with amiR-RH6.ACVK$1^{opt}$ or amiR-RH7.ACVK$1^{opt}$ upregulated 45 or 140 genes and downregulated 27 or 87 genes, respectively (FIG. 15D). FIG. 15C shows $Sca1^+PDGFR\alpha^+CD31^-CD45^-$fibroadipogenic progenitors (FAPs) were FACS sorted from tibial muscle of 4 week old Acvr1$R^{206H}$; PDGFRα mice and treated with $5\times10^{10}$ GC of the AAV6.2 vectors carrying ctrl, amiR-RH6.optACVR1, or amiR-RH7.optACVR1. Two days later, AAV-treated cells were cultured under osteogenic conditions with PBS or Activin A (50 ng/ml) for six days and osteogenic gene expression was assessed by RT-PCR.

Figure 16A:
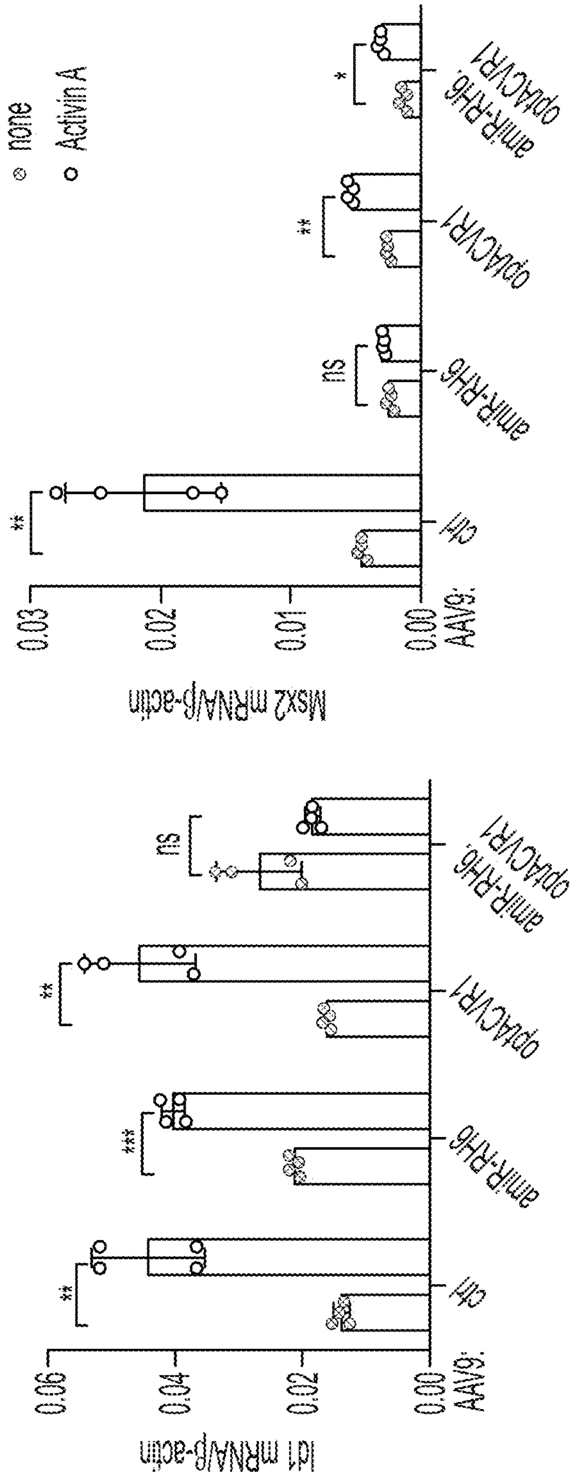
FIGS. 16A-16C show effects of AAV-gene therapeutics on Activin A-induced osteogenesis in vitro.
Figure 16B:
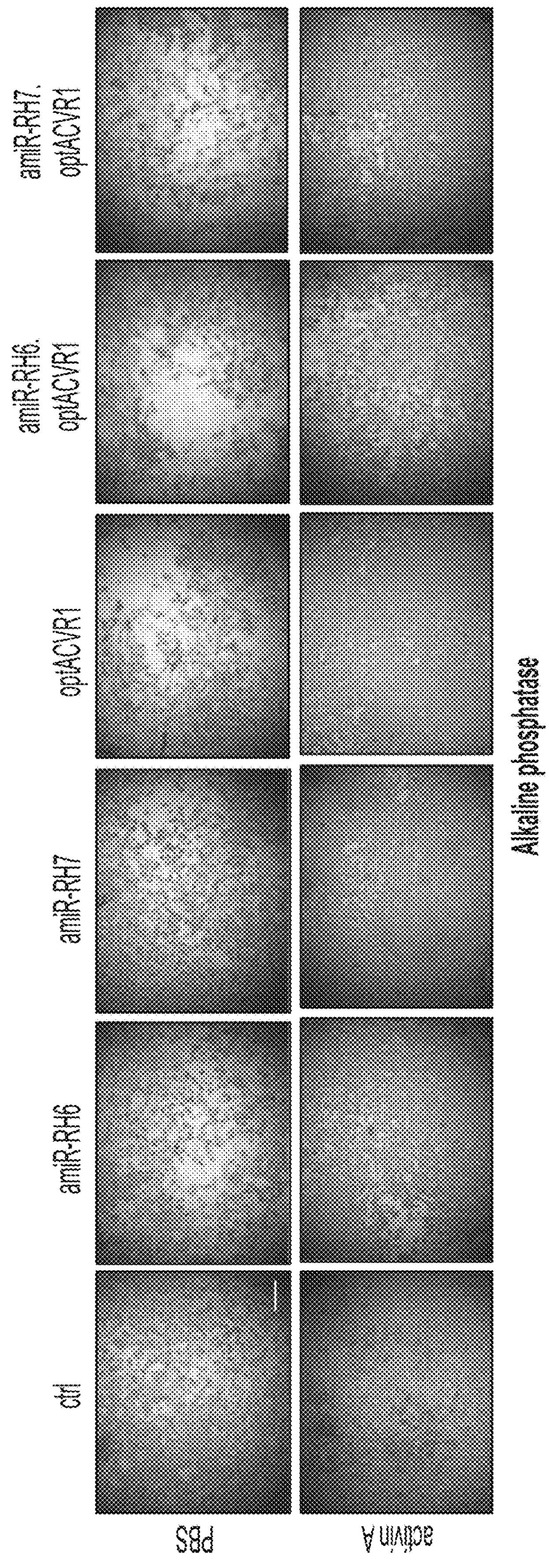
Figure 16C:
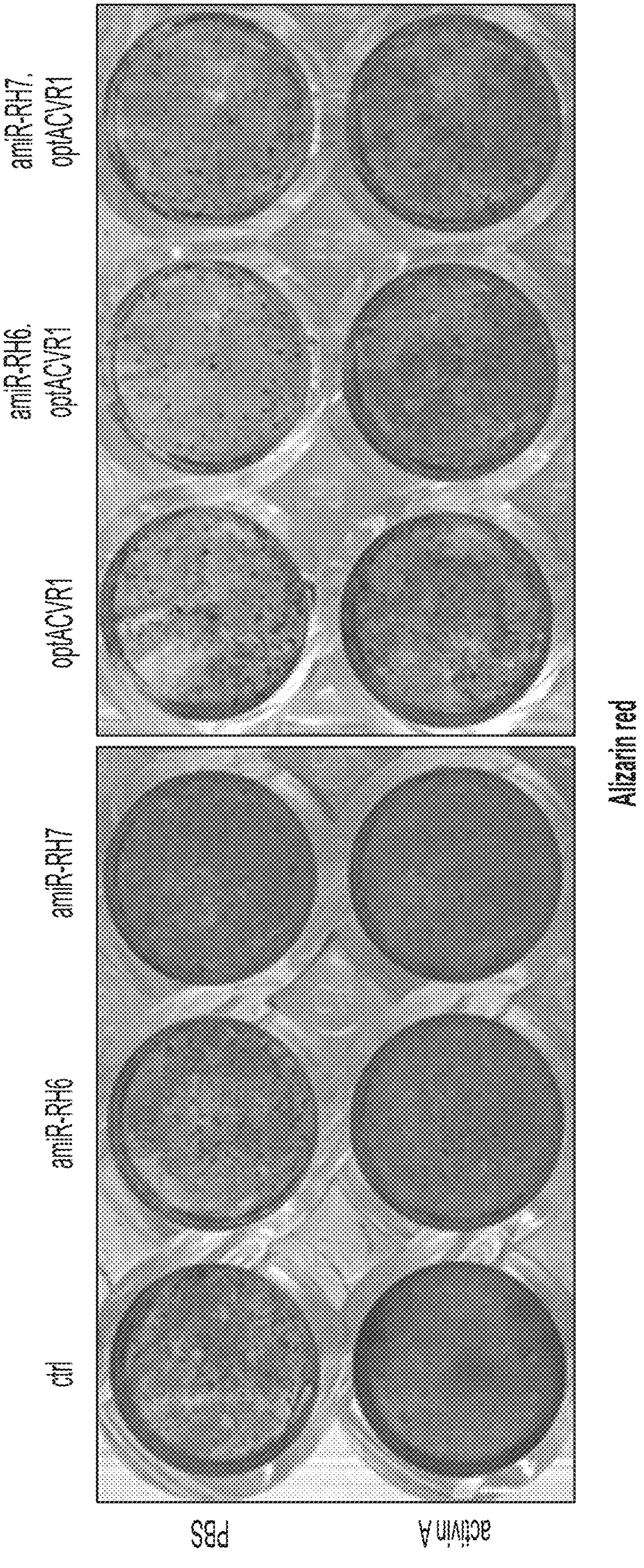

FIGS. 16A-16C show effects of AAV-gene therapeutics on Activin A-induced osteogenesis in vitro. FIG. 16A shows primary bone marrow-derived stromal cells (BMSCs) were isolated from 4 week old Acvr1$R^{206H}$; Prx1 femurs and treated with $5\times10^{10}$ GC of the AAV6.2 vectors carrying ctrl, amiR-RH6, optACVR1, or amiR-RH6.optACVR1. Two days later, AAV-treated cells were cultured under osteogenic conditions for four days, stimulated with Activin A (100 ng/ml) for 6 or 24 hours and expression of Activin A-responsive genes Id1 and Msx2 was assessed using RT-PCR, respectively. FIGS. 16B-16C show AAV-treated cells were cultured under osteogenic conditions with PBS or Activin A (50 ng/ml), and ALP (FIG. 16B) and alizarin red staining (FIG. 16C) were performed to assess osteoblast differentiation at 6 and 12 days of osteogenic culture, respectively.

Figure 17A:
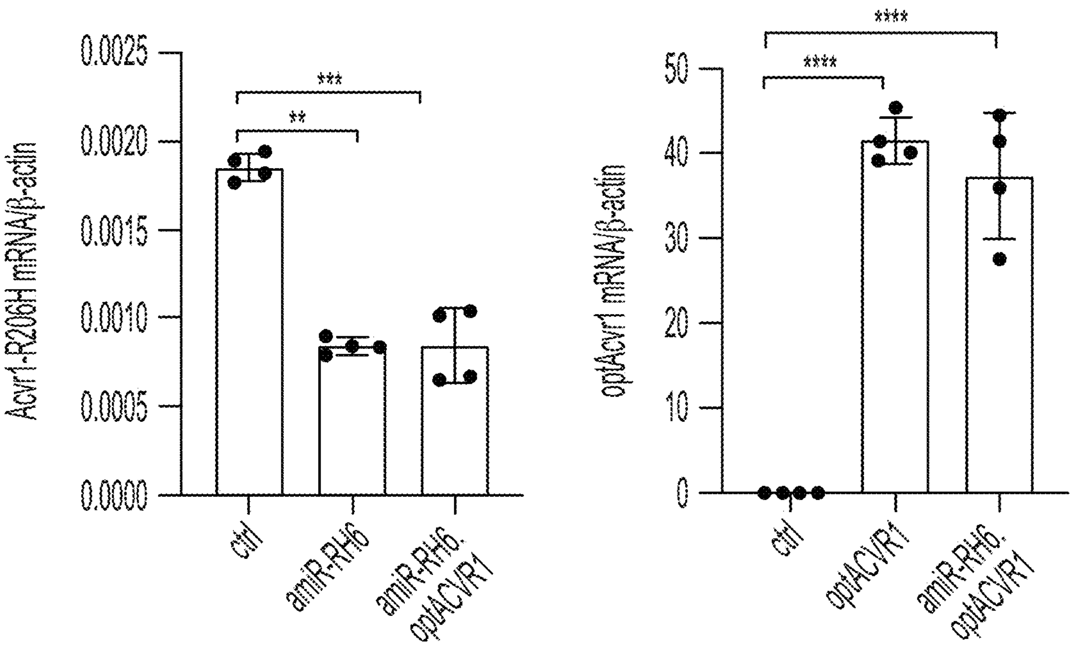
FIGS. 17A-17I show effects of AAV-gene therapeutics on Activin A signaling and traumatic heterotopic ossification.
Figure 17B:
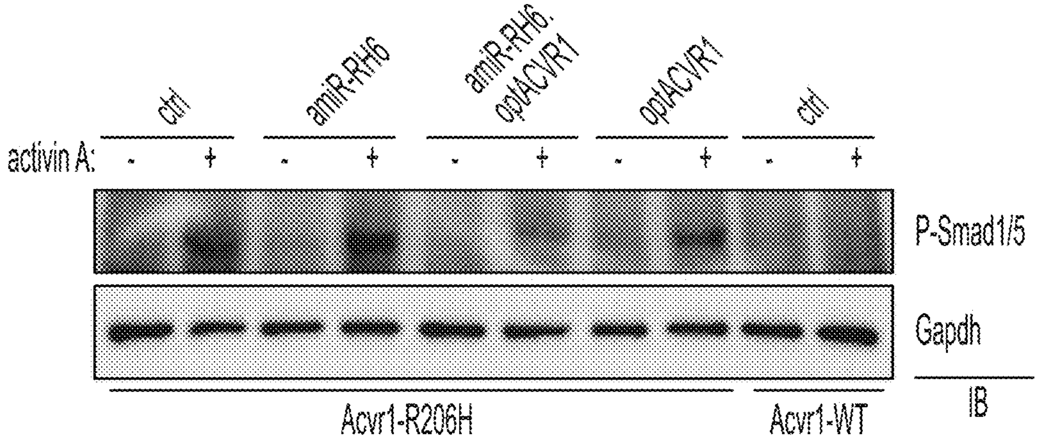
Figure 17C:
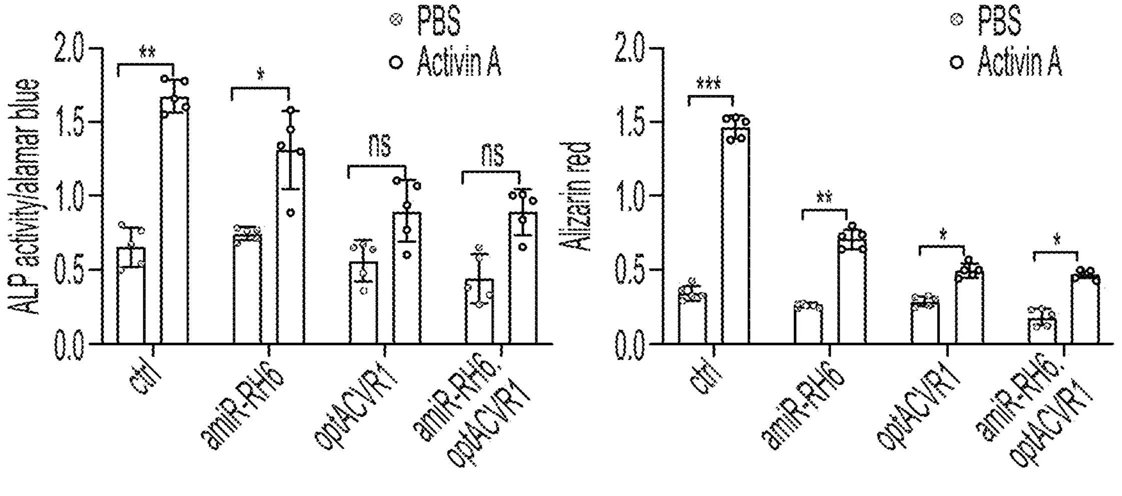
Figure 17D:
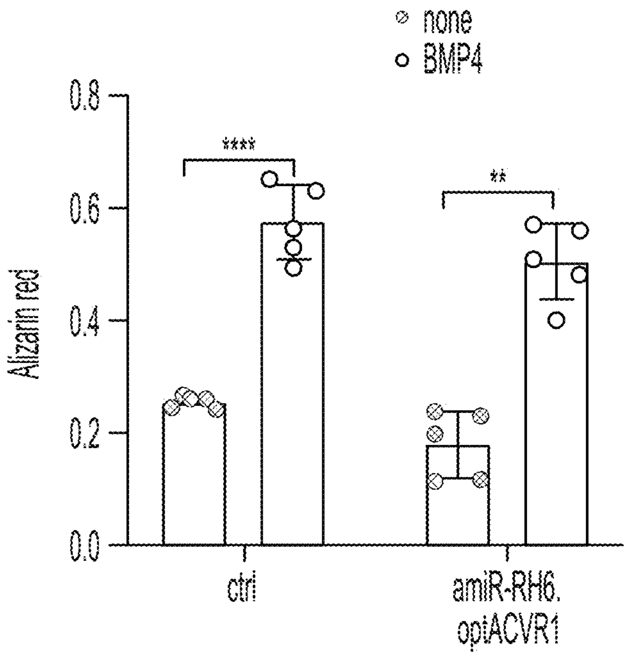
Figure 17E:
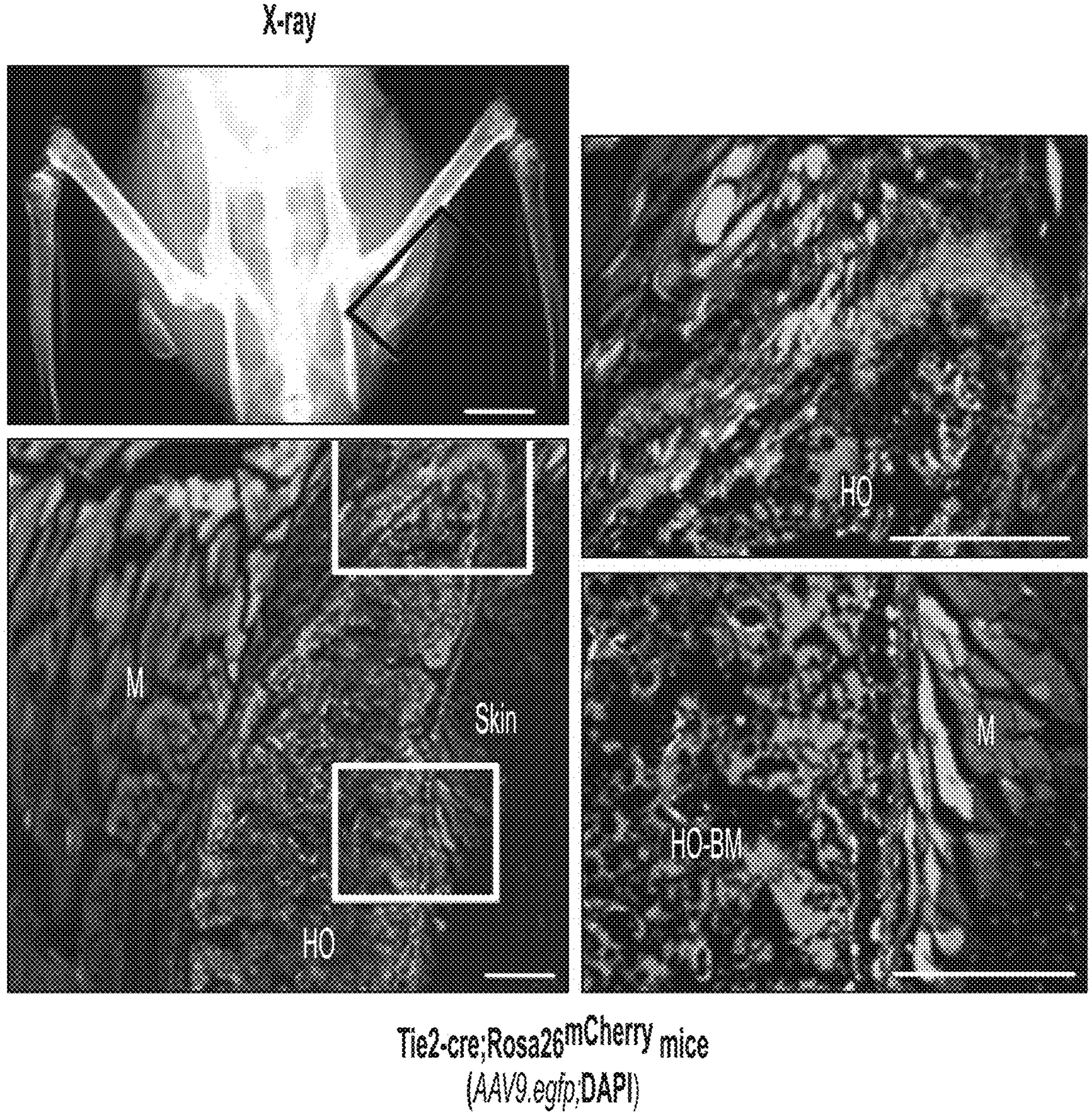
Figure 17F:
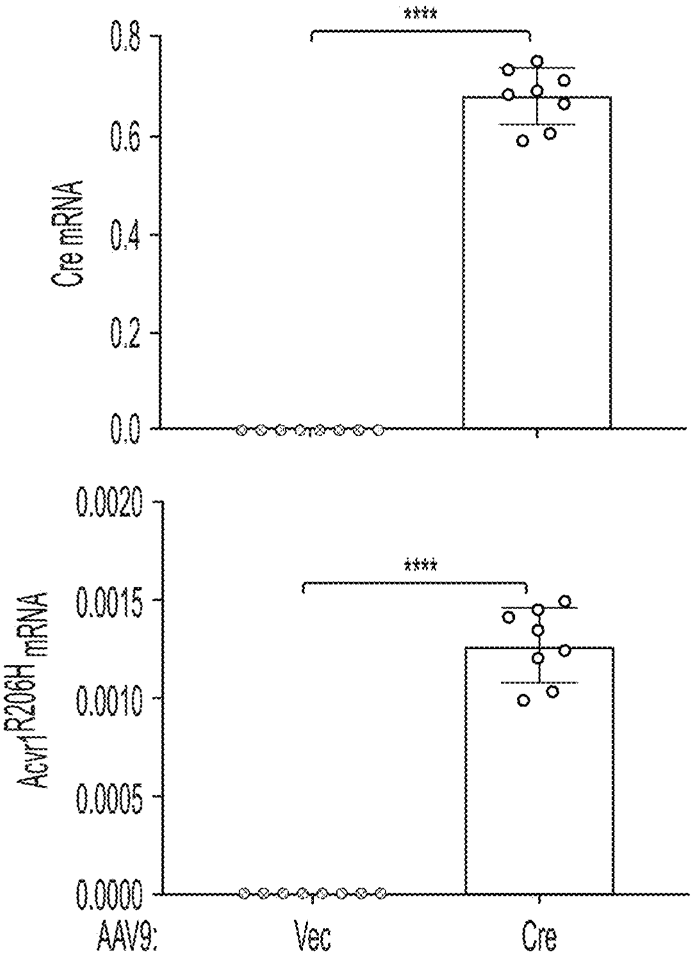
Figure 17G:
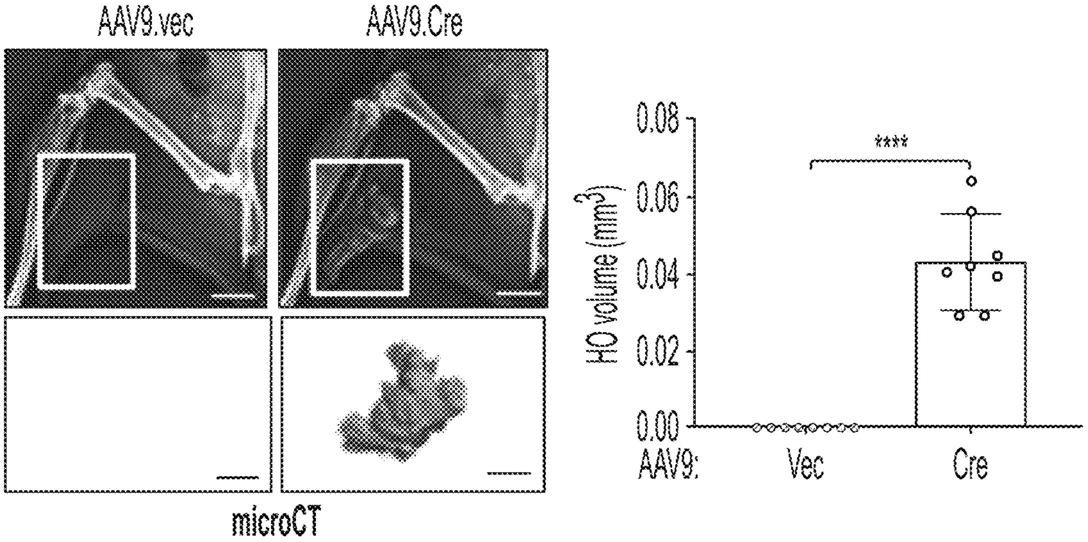
Figure 17H:
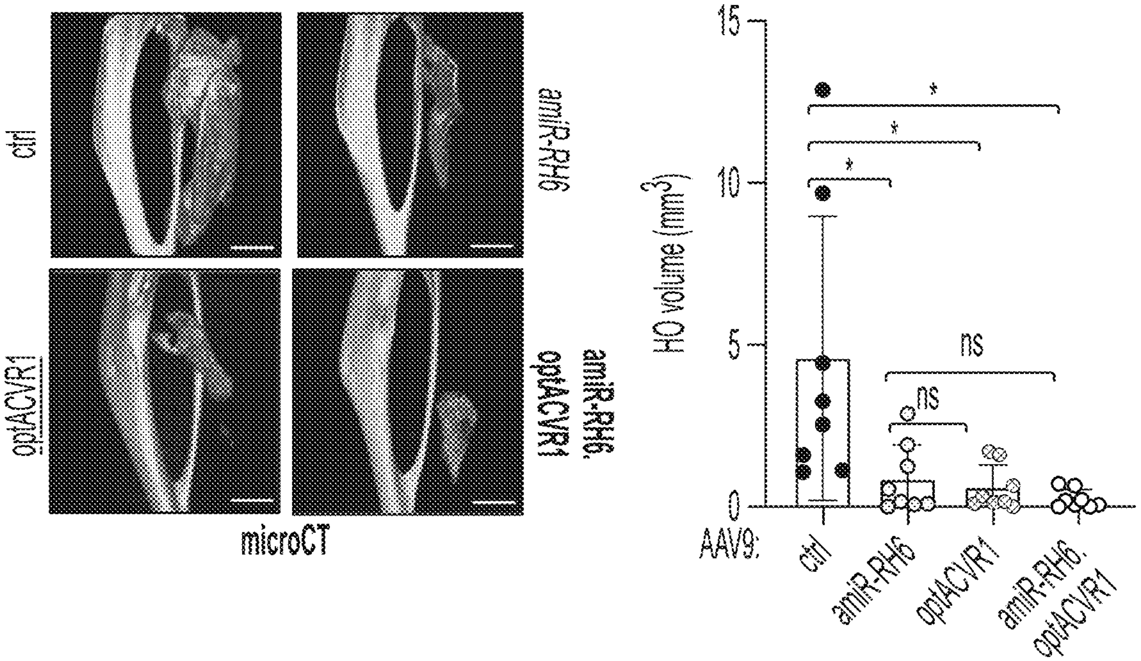
Figure 17I:
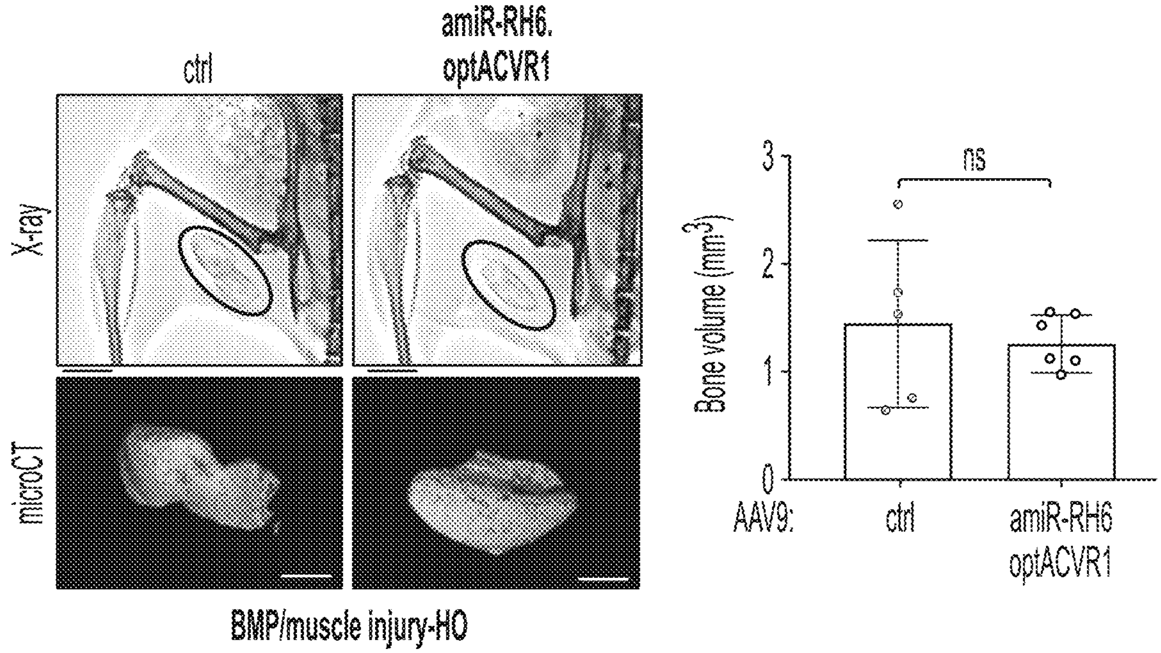

FIGS. 17A-17I show effects of AAV-gene therapeutics on Activin A signaling and traumatic heterotopic ossification. FIGS. 17A-17D show primary bone marrow-derived stromal cells (BMSCs) were isolated from 4 week old Acvr1$R^{206H}$; Prx1 femurs and treated with $5\times10^{10}$ GC of the AAV6.2 vectors carrying ctrl, amiR-RH6, optACVR1, or amiR-RH6.optACVR1. Two days later, AAV-treated cells were cultured under osteogenic conditions for four days and Acvr$1^{R206H}$ and optAcvr1 mRNA levels were measured by RT-PCR (FIG. 17A). AAV-treated cells were stimulated with Activin A (100 ng/ml) for 30 min and immunoblotted for phospho-Smad1/5. Anti-Gapdh antibody was used for loading control (FIG. 17B). AAV-treated cells were cultured under osteogenic conditions with PBS or Activin A (50 ng/ml), and ALP (FIG. 17C, left) and alizarin red staining (FIG. 17C, right) were performed to assess osteoblast differentiation at 6 and 12 days of osteogenic culture, respectively. AAV-treated cells were cultured under osteogenic conditions with PBS or BMP4 (50 ng/ml) for 12 days, and alizarin red staining (FIG. 17C, right) was performed for mineralization (FIG. 17D). FIG. 17E shows $5\times10^{12}$ vg/kg of rAAV9 expressing EGFP was intradermally (i.d.) injected into the femoral muscle of 2 month old male Tie2-cre; Ai9 mice (n=3) one week after rBMP2/7-matrigel injection and muscle injury, and X-radiography of hindlimbs (left top) and frozen-section of HO tissues (left bottom, right) were performed in treated mice. Red box indicates HO in the skeletal muscle. M, muscle; HO-BM, heterotopic ossification bone marrow. Blue, DAPI; Red, $Tie2^+$ cells; Green, AAV-transduced cells. FIGS. 17F-17G show $5\times10^{12}$ vg/kg of rAAV9 expressing vector or CRE recombinase was i.d. injected into the tibial muscle of 6 week old female Acvr1$R^{206H}$; Cre-$ER^{T2}$ mice (n=8) and two days later, pinch injury and 1 mM cardiotoxin were employed into the injection sites. Four weeks later, Acvr$1^{R206H}$ and CRE recombinase mRNA levels in the tibial muscle were measured by RT-PCR (FIG. 17F) and HO in the tibial muscle was assessed using X-radiography and microCT. 3D reconstruction images (FIG. 17G, left) and quantification of HO volume are displayed (FIG. 17G, right). FIG. 17H shows $5\times10^{12}$ vg/kg of rAAV9 carrying ctrl, amiR-RH6, optACVR1, or amiR-RH6.optACVR1 was i.d. injected into the tibial muscle of 6 week old male Acvr1$R^{206H}$; Cre-$ER^{T2}$ mice (n=8) two days after five times intraperitoneal (i.p.) injection of tamoxifen (10 mg/kg). Two days later, pinch injury and 1 mM cardiotoxin were employed into the injection sites and four weeks later, and HO in the tibial muscle was assessed using microCT. 3D reconstruction images (left) and quantification of HO volume is displayed (right). FIG. 17I shows $5\times10^{12}$ vg/kg of rAAV9 expressing ctrl or amiR-RH6.optACVR1 was i.d. injected into the femoral muscle of 2 month old male wildtype mice (n=5) and two days later, rBMP2/7-matrigel injection and muscle injury were employed into the injection sites. Four weeks later, HO in the femoral muscle was assessed using X-radiography and microCT. 3D reconstruction images (left) and quantification of HO volume is displayed (right).

Figure 18A:
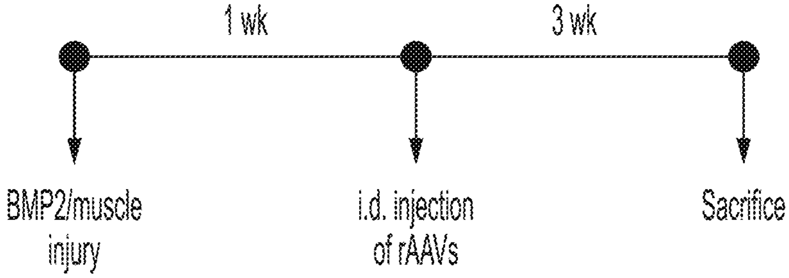
FIGS. 18A-18F show assessment of traumatic heterotopic ossification in AAV-treated skeletal muscle.
Figure 18B:
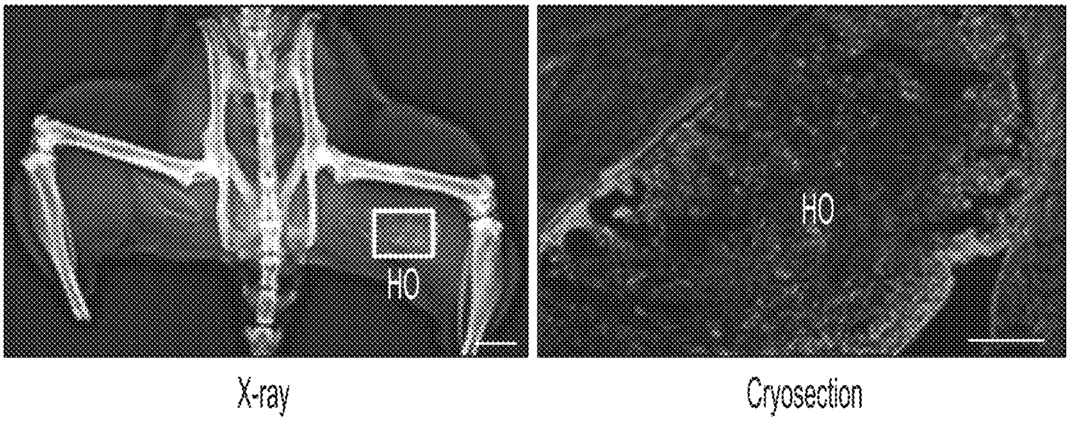
Figure 18C:
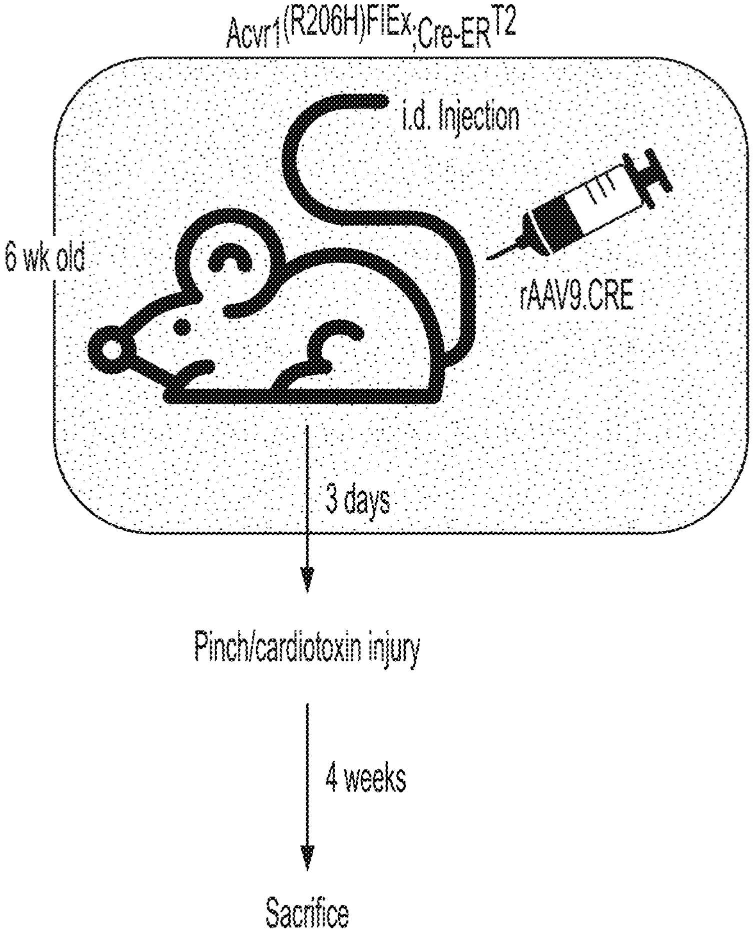
Figure 18D:
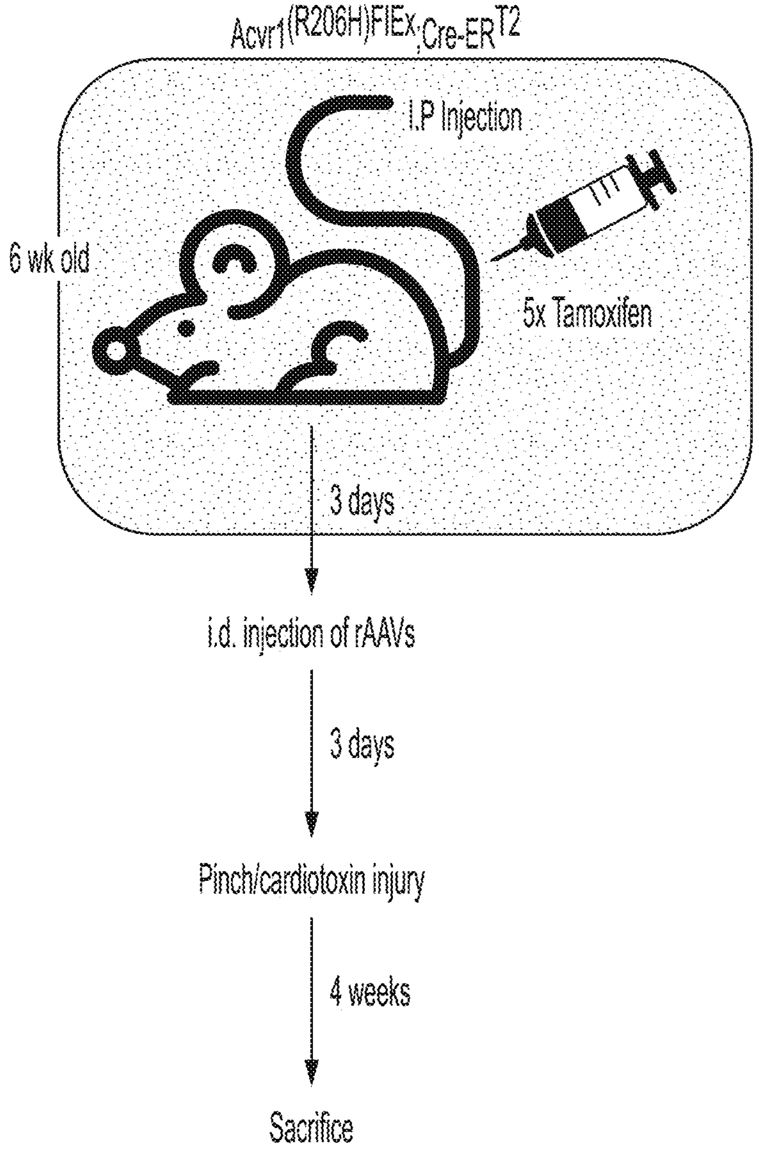
Figure 18E:
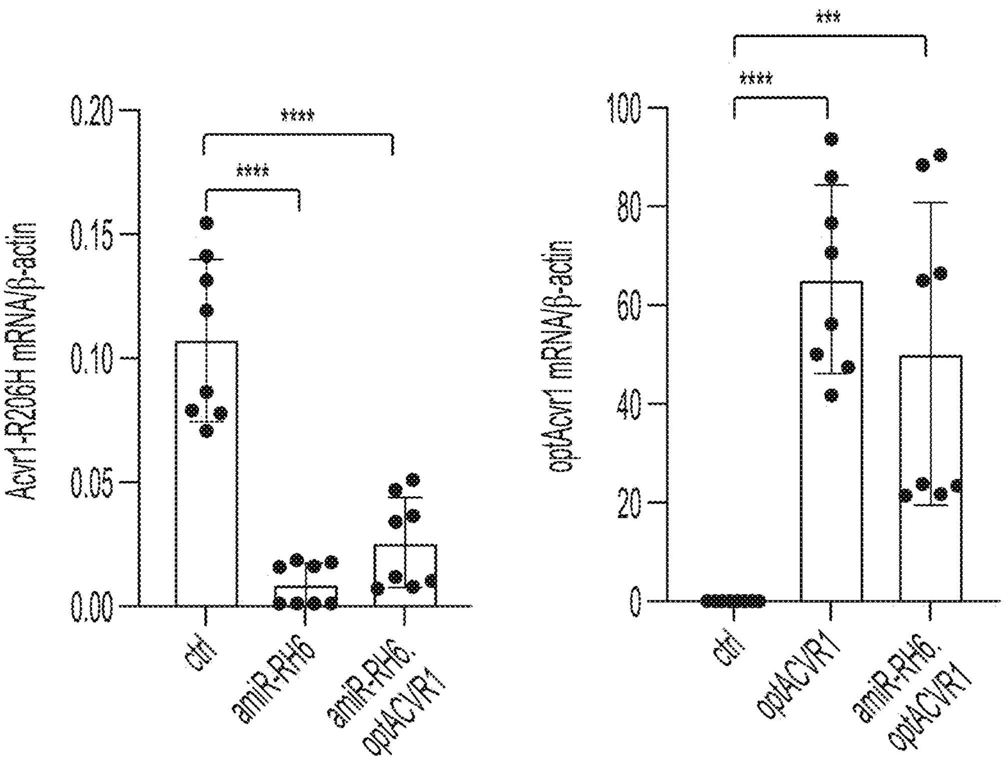
Figure 18F:
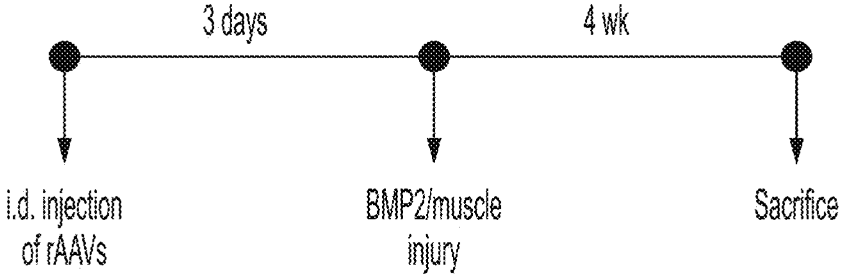

FIGS. 18A-18F show assessment of traumatic heterotopic ossification in AAV-treated skeletal muscle. FIGS. 18A-18B show a diagram of the study and treatment design. $5\times10^{12}$ vg/kg of rAAV6.2 expressing EGFP was i.d. injected into the femoral muscle of 2 month old male wildtype mice (n=3) one week after rBMP2/7-matrigel injection and muscle injury, and X-radiography of hindlimbs (FIG. 18B, left) and frozen-section of HO tissues (FIG. 18B, right) were performed in treated mice. Box indicates HO in the skeletal muscle. FIGS. 18C-18D show a diagram of additional study and treatment designs. FIG. 18E shows $5\times10^{12}$ vg/kg of rAAV9 carrying ctrl, amiR-RH6, optACVR1, or amiR-RH6.optACVR1 was i.d. injected into the tibial muscle of 6 week old male Acvr1R206H; Cre-ERT2 mice (n=8) Three days after five times intraperitoneal (i.p.) injection of tamoxifen (10 mg/kg). Three days later, pinch injury and 1 μM cardiotoxin were employed into the injection sites and four weeks later, and Acvr1R206H and optAcvr1 mRNA levels were measured by RT-PCR (right). FIG. 18F shows a diagram of an additional study and treatment design.

Figure 19A:
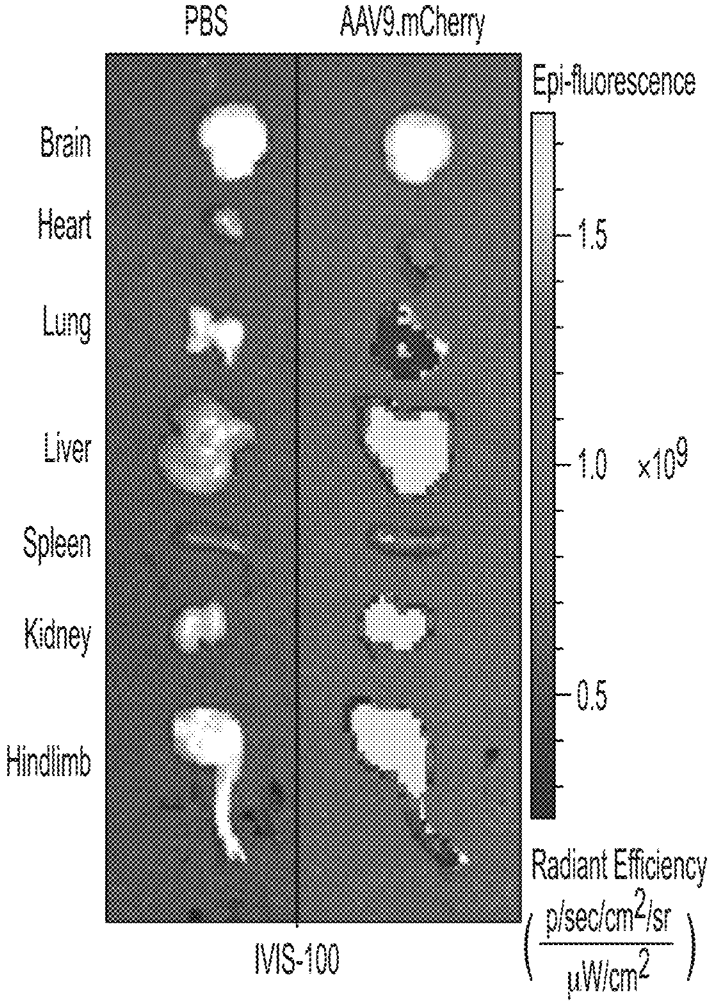
FIGS. 19A-19F show systemic delivery of AAV-gene therapeutics prevents traumatic heterotopic ossification in adult FOP mice.
Figure 19B:
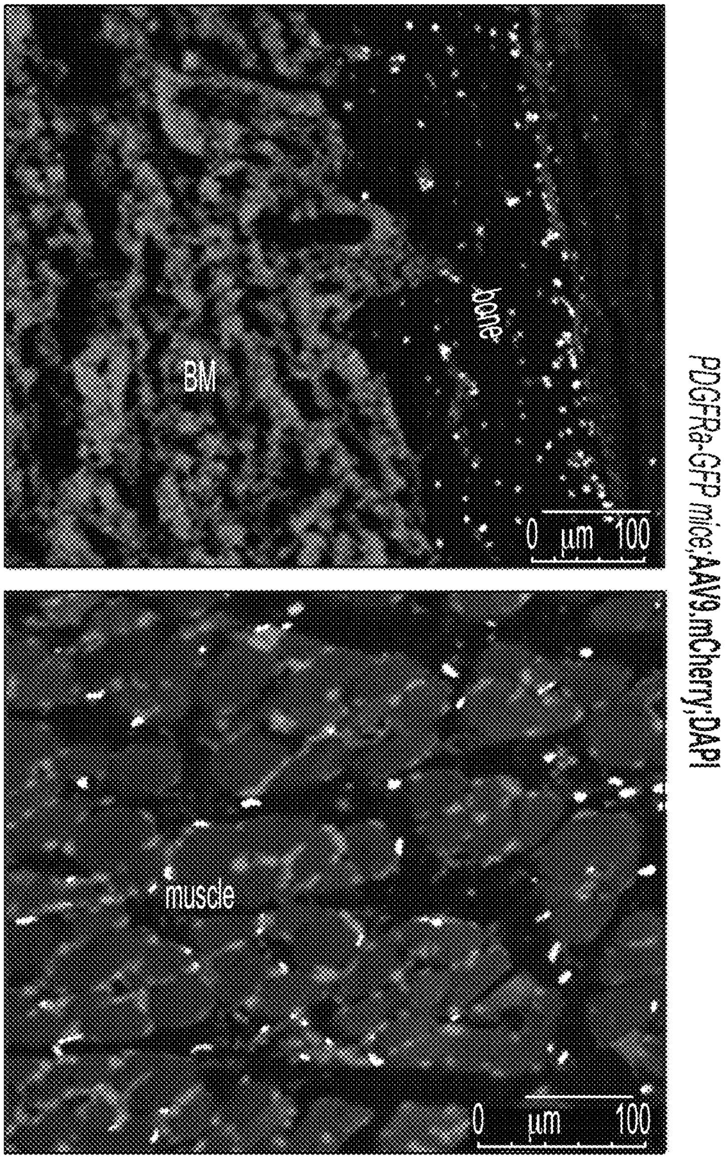
Figure 19C:
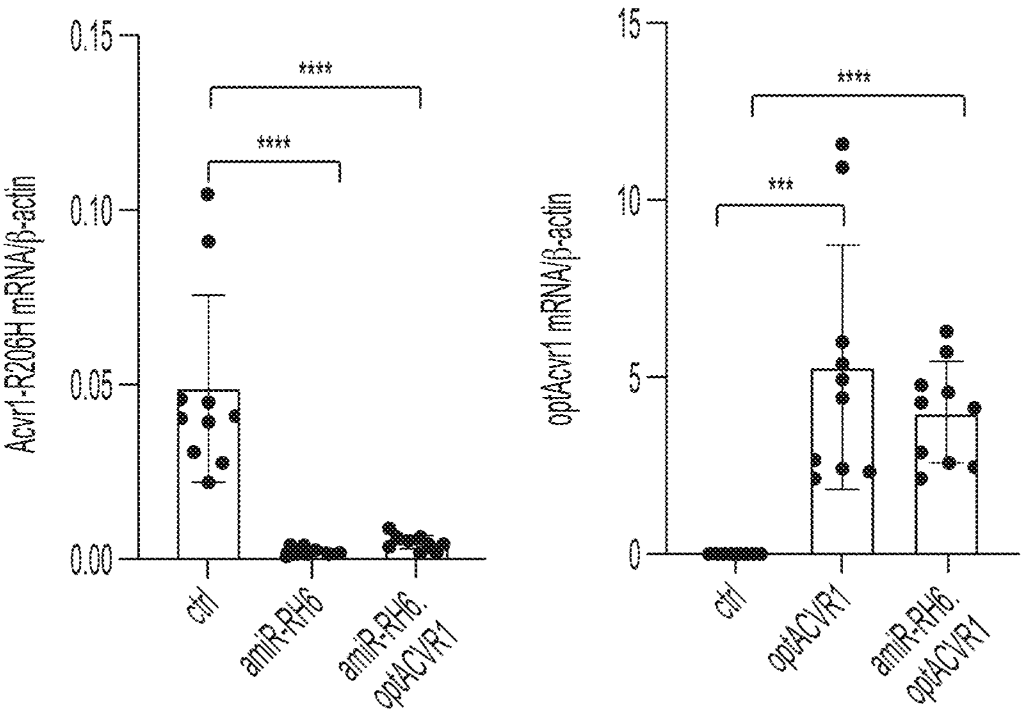
Figure 19D:
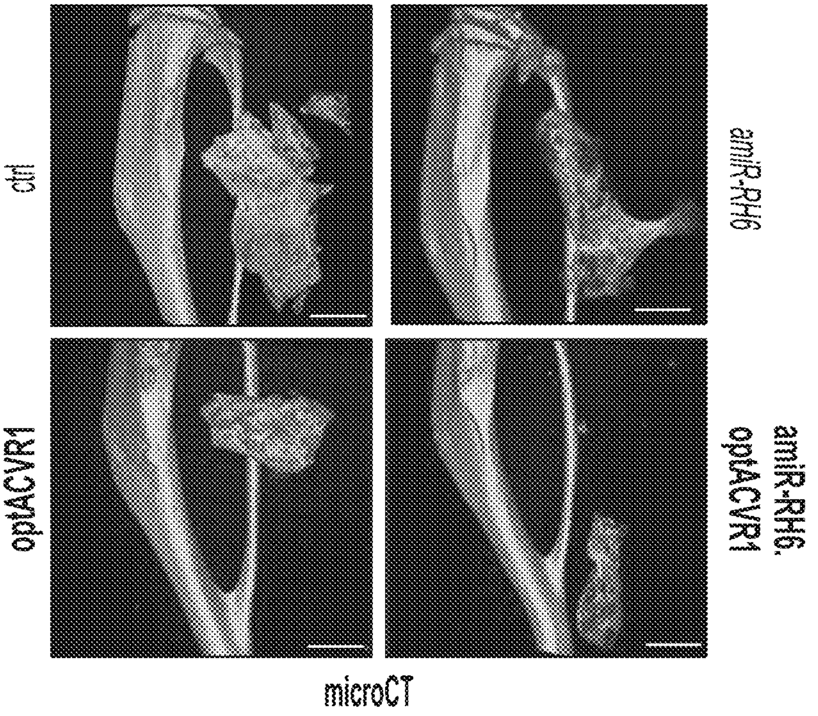
Figure 19E:
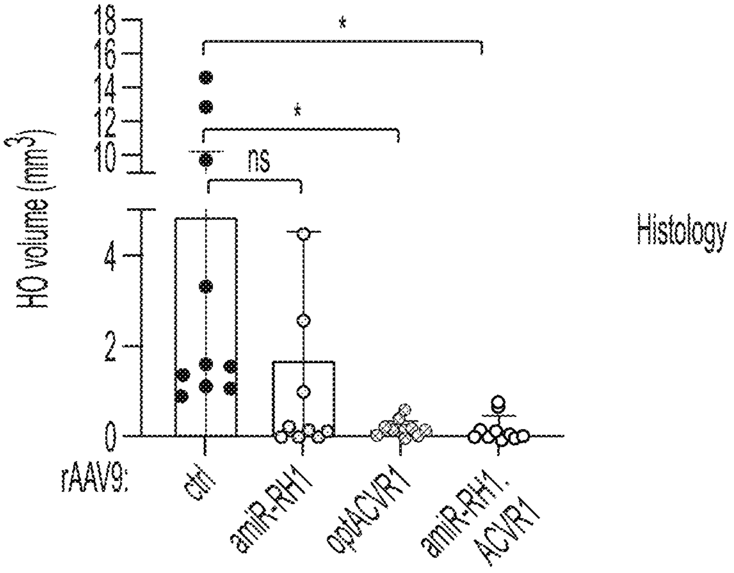
Figure 29A:
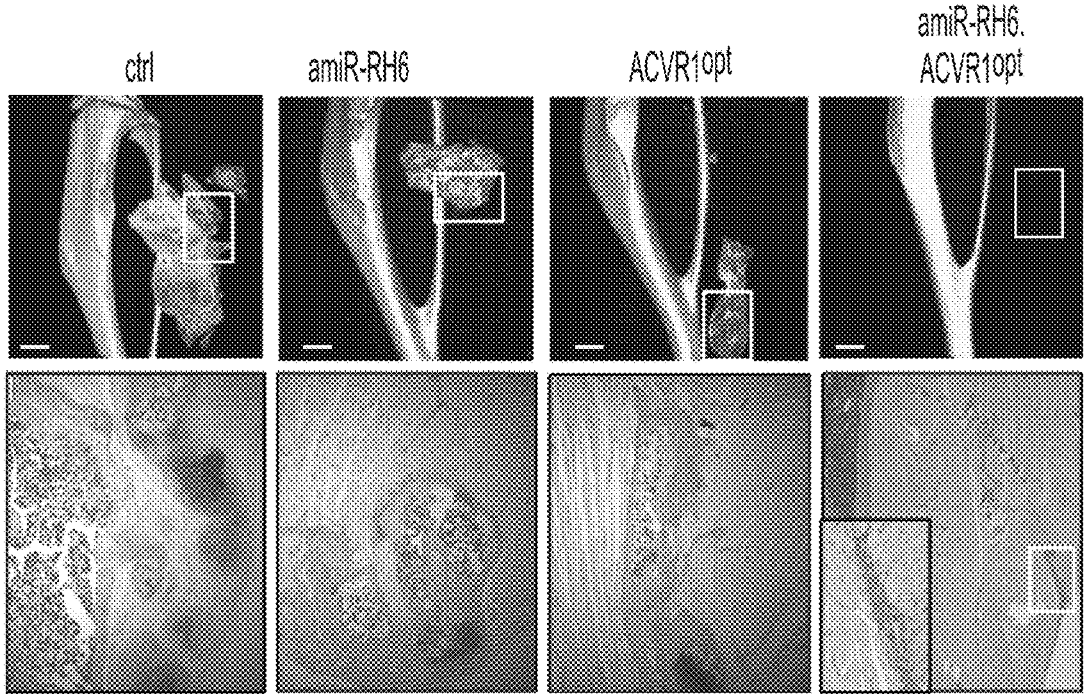
FIGS. 29A-29C show systemic delivery of AAV-gene therapeutics prevents traumatic HO in adult FOP mice. P1 Acvr1R$^{206H}$Cre-ER$^{T2}$ neonates (n=10) were treated with $10^{11}$ GCs of rAAV9 carrying ctrl, amiR-RH6, ACVR$^{opt}$, or amiR-RH6.ACVR1$^{opt}$ via facial vein injection, and six weeks later, mice were i.p. injected with tamoxifen (10 mg/kg). Two days later, pinch injury and 1 mM cardiotoxin were employed into the injection sites. Heterotopic bone in the tibial muscle was assessed using microCT or histology. 3D reconstruction images (FIG. 29A, top figure) of HO volume is displayed. P1 Acvr1R$^{206H}$; Cre-ER$^{T2}$ neonates (n=3) treated with $10^{11}$ GCs of rAAV9 carrying ctrl or amiR-RH6.ACVR1$^{opt}$ were aged to 6 week old and i.p. injected with tamoxifen. Three days later, pinch injury and 1 mM cardiotoxin were employed into the injection sites. 7, 14, and 28 days later, HO in the tibial muscle was assessed by histology (FIG. 29B). Longitudinal section of the injured areas at day 3 was immunostained for F4/80 (FIG. 29C).

FIGS. 19A-19F show systemic delivery of AAV-gene therapeutics prevents traumatic heterotopic ossification in adult FOP mice. FIGS. 19A-19B show P1 PDGFRα-GFP neonates (n=3) were treated with $10^{11}$ GC of rAAV9 expressing mCherry via facial vein injection and two weeks later, tissue distribution of vectors was assessed by mCherry expression using IVIS-100 optical imaging system (FIG. 19A) or frozen section of AAV-treated hindlimbs (FIG. 19B). BM: bone marrow. FIGS. 19C-19E show P1 Acvr1R$^{206H}$; Cre-ER$^{T2}$ neonates (n=10) were treated with $10^{11}$ GC of rAAV9 carrying ctrl, amiR-RH6, optACVR1, or amiR-RH6.optACVR1 via facial vein injection, and six weeks later, mice were treated five times with i.p. injection of tamoxifen (10 mg/kg). Two days later, pinch injury and 1 mM cardiotoxin were employed into the injection sites and four weeks later, and Acvr1$^{R206H}$ and optAcvr1 mRNA levels were measured by RT-PCR (FIG. 19C). HO in the tibial muscle was assessed using microCT or histology. 3D reconstruction images (FIG. 19D, left) and quantification of HO volume is displayed (FIG. 19D, right). Heterotopic bone mass and chondrogenic anlagen were both markedly decreased by the treatment with ACVR1$^{opt}$ or amiR-RH6.ACVR1$^{opt}$ relative to control vector, whereas therapeutic effects of amiR-RH6 were highly variable (FIG. 19D and FIG. 29A). amiR-RH6.ACVK1$^{opt}$ was most effective in suppression of traumatic HO and nearly complete regeneration and reestablishment of normal muscle architecture.

Figure 19F:
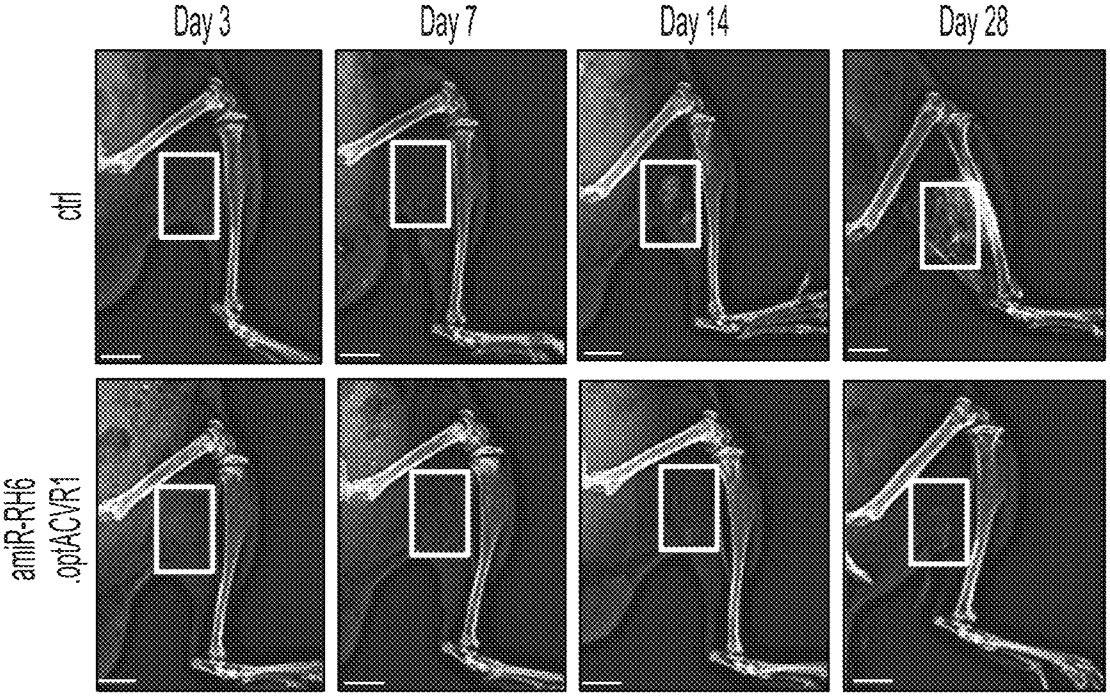

It has been previously shown that muscle injury in a mouse model of FOP induces the major sequential pathological changes in HO, including perivascular immune cell infiltration (Day 1-3), muscle degeneration and fibroproliferative response (Day 3-7), chondrogenesis (Day 7-14), and osteogenesis with heterotopic bone marrow (Day 14-28). FIG. 19E shows representative histology data. P1 Acvr1$^{(R206H)F1}$; Cre-ER$^{T2}$ neonates treated with control vector or amiR-RH6.ACVR1$^{opt}$ were aged to 6 weeks old and then, X-radiography and histopathological evaluation at different time points were performed four weeks after muscle injury (FIG. 19F and FIG. 29B). FIG. 19F shows P1 Acvr1R$^{206H}$; Cre-ER$^{T2}$ neonates (n=3) were treated with $10^{11}$ GC of rAAV9 carrying ctrl or amiR-RH6.optACVR1 via facial vein injection, and six weeks later, mice were treated five times with i.p. injection of tamoxifen (10 mg/kg). Three days later, pinch injury and 1 mM cardiotoxin were employed into the injection sites and 3, 7, 14, 28 days later, HO in the tibial muscle was assessed by X-radiography. Boxes indicate HO in the tibial muscle. As expected, chondrogenic anlagen and heterotopic bone develops in control-treated muscle seven and fourteen days after the injury, respectively. However, amiR-RH6.ACVR1$^{opt}$-treated muscle showed little to no evidence of cartilage and heterotopic bone formation, but fibroproliferative responses at day 7 that began to disappear fourteen days after the injury. Early injury responses at day 3, including infiltration of inflammatory macrophages and mast cells, muscle degeneration, and fibroproliferation, were relatively comparable between the tibial muscles treated with control and amiR-RH6.ACVK1$^{opt}$ (FIGS. 28B and 29C).

Figure 20A:
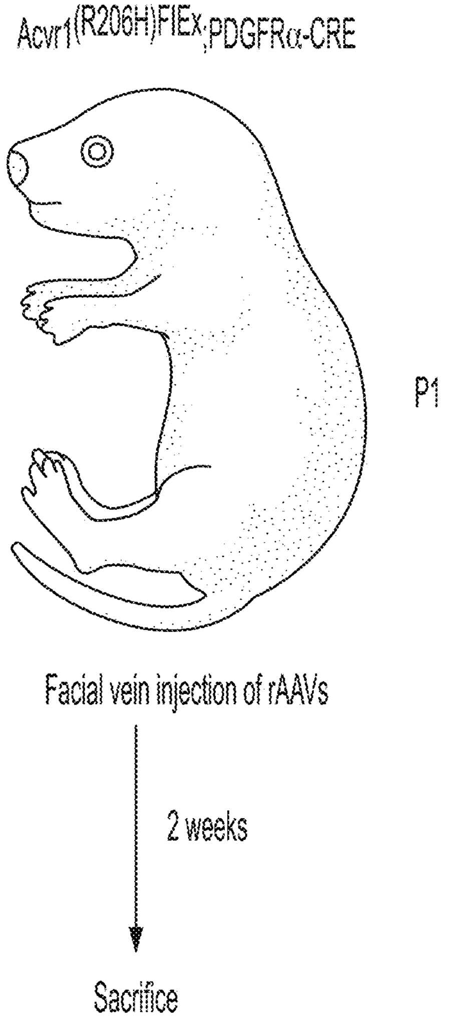
FIGS. 20A-20G show systemic delivery of AAV-gene therapeutics prevents traumatic heterotopic ossification.
Figure 20B:
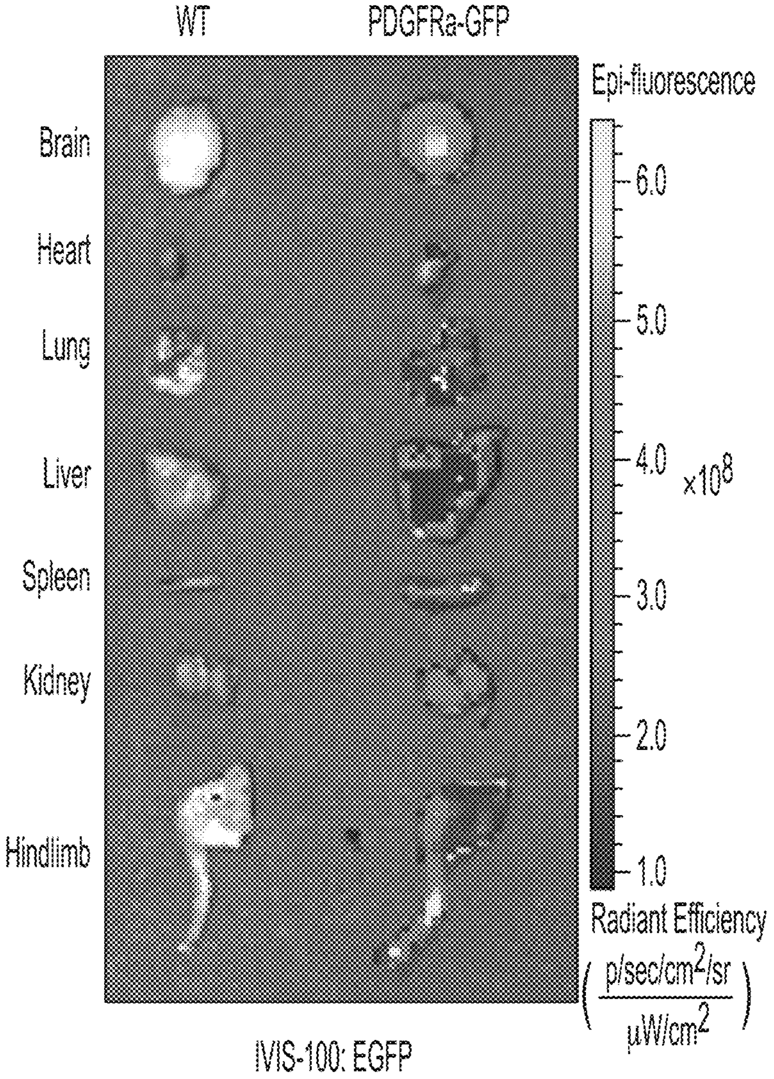
Figure 20C:
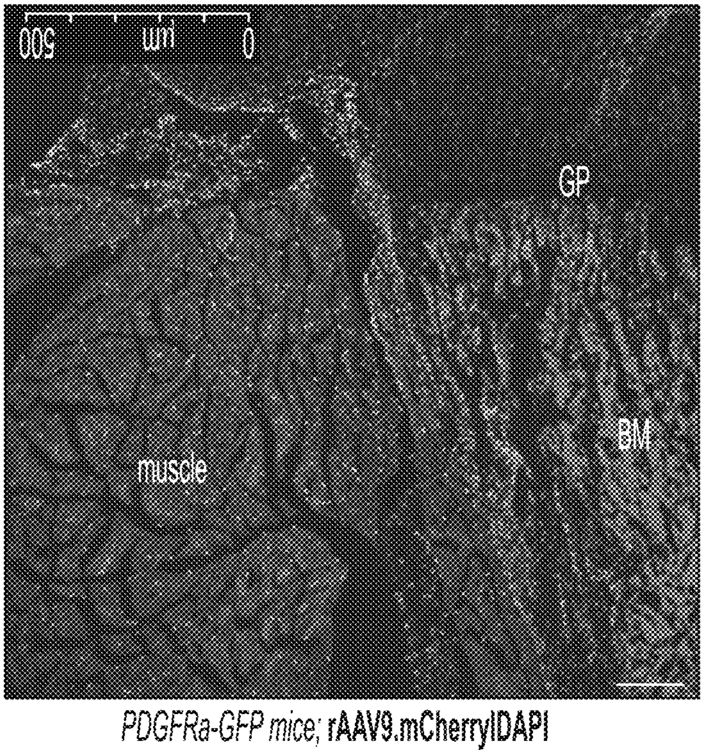
Figure 20D:
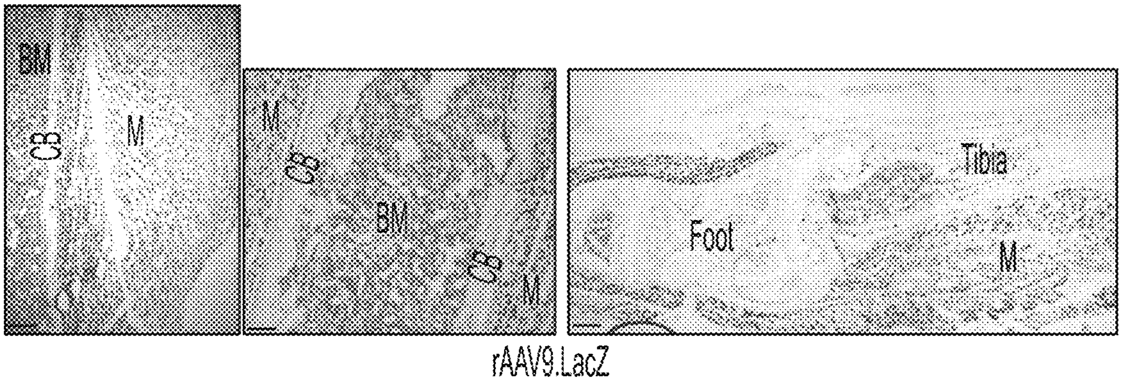
Figure 20E:
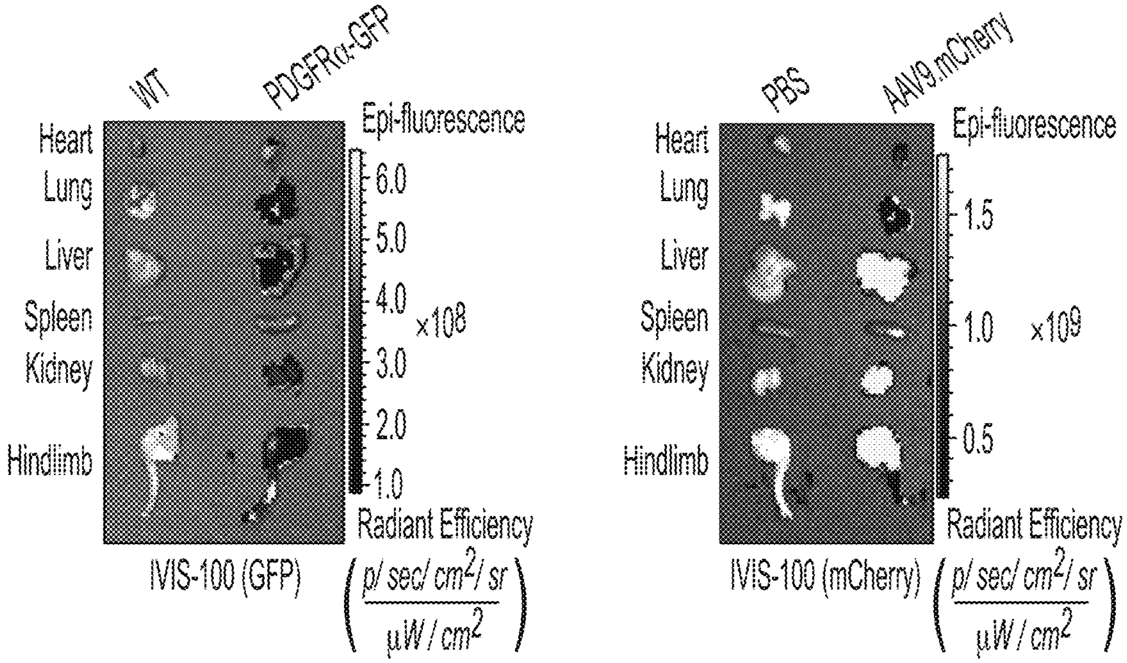
Figure 20F:
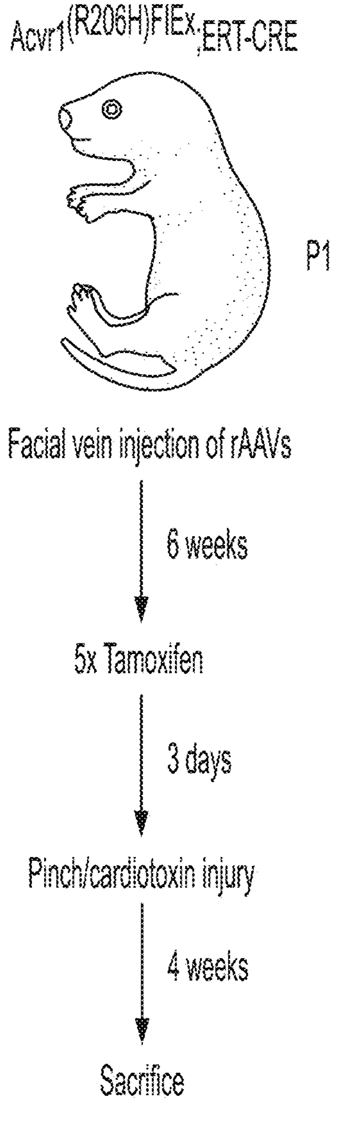
Figure 20G:
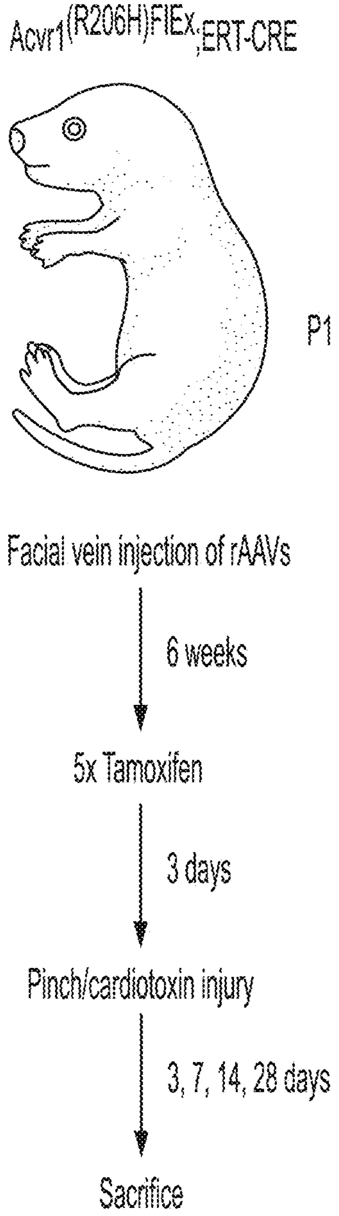

FIGS. 20A-20G show systemic delivery of AAV-gene therapeutics prevents traumatic heterotopic ossification. FIG. 20A shows a diagram of study and treatment design. FIGS. 20B-20C show P1 PDGFRα-GFP neonates (n=3) were treated with 1011 GC of rAAV9 expressing mCherry via facial vein injection and two weeks later, PDGFRα expression was assessed by IVIS-100 optical imaging system using GFP expression (FIG. 20B). AAV-transduced cells in the hindlimbs were also assessed by mCherry expression in the hindlimbs using fluorescence microscopy. IVIS-100 optical imaging system (FIG. 20B) or frozen section of AAV-treated hindlimbs (FIG. 20C). BM: bone marrow. FIG. 20D shows P1 wildtype neonates (n=3) were treated with $10^{11}$ GC of rAAV9 expressing LacZ via facial vein injection and two weeks later, frozen-sections of AAV-transduced tissues were stained for X-galactosidase. BM: bone marrow, CB: cortical bone, M: muscle. FIG. 20F shows a diagram of a study and treatment methods design. FIG. 20G shows a diagram of a study and treatment methods design. mCherry expression was detected in a subset of PDGFRα$^{+}$ FAPs in the skeletal muscle and PDGFRα$^{+}$ osteoblasts and osteocytes in the cortical bone (FIG. 31) along with the expression in the heart, lung, liver, and kidney (FIG. 20E).

Figure 21A:
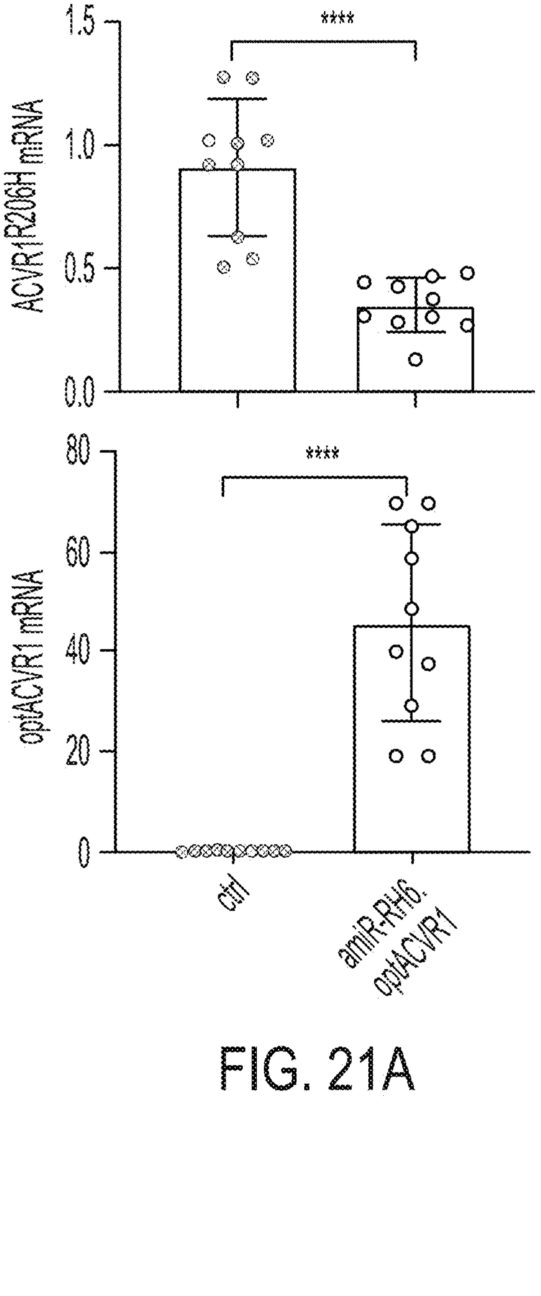
FIGS. 21A-21J show systemic delivery of AAV-gene therapeutics prevents chronic heterotopic ossification in adult FOP mice.
Figure 21B:
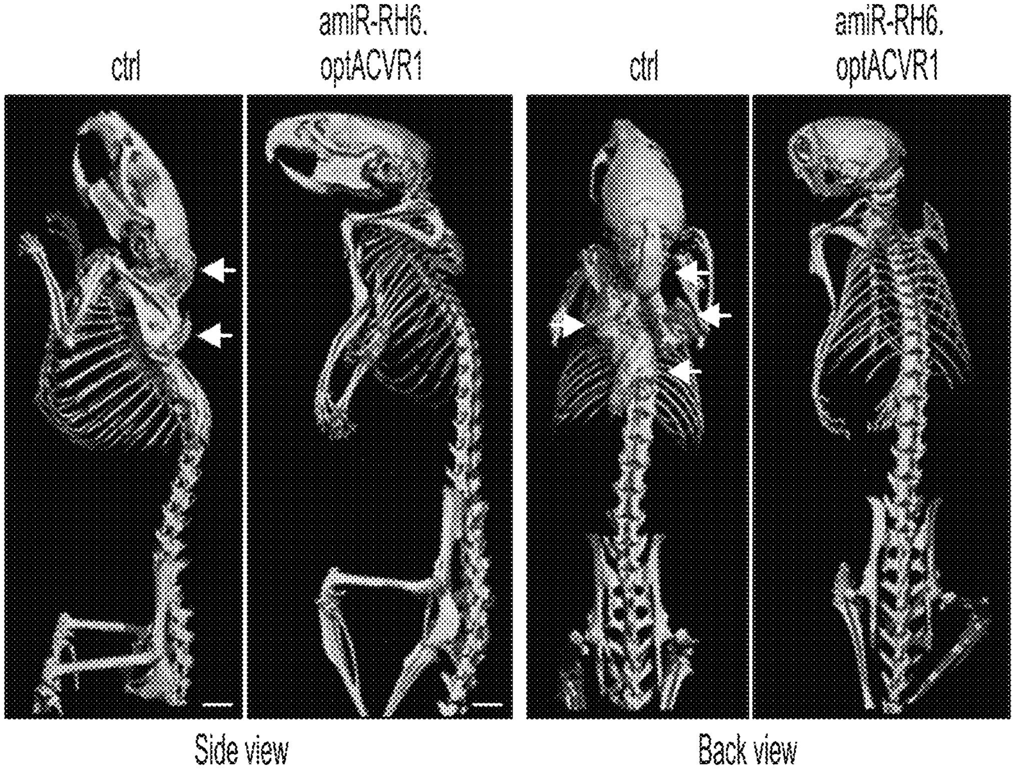
Figure 21C:
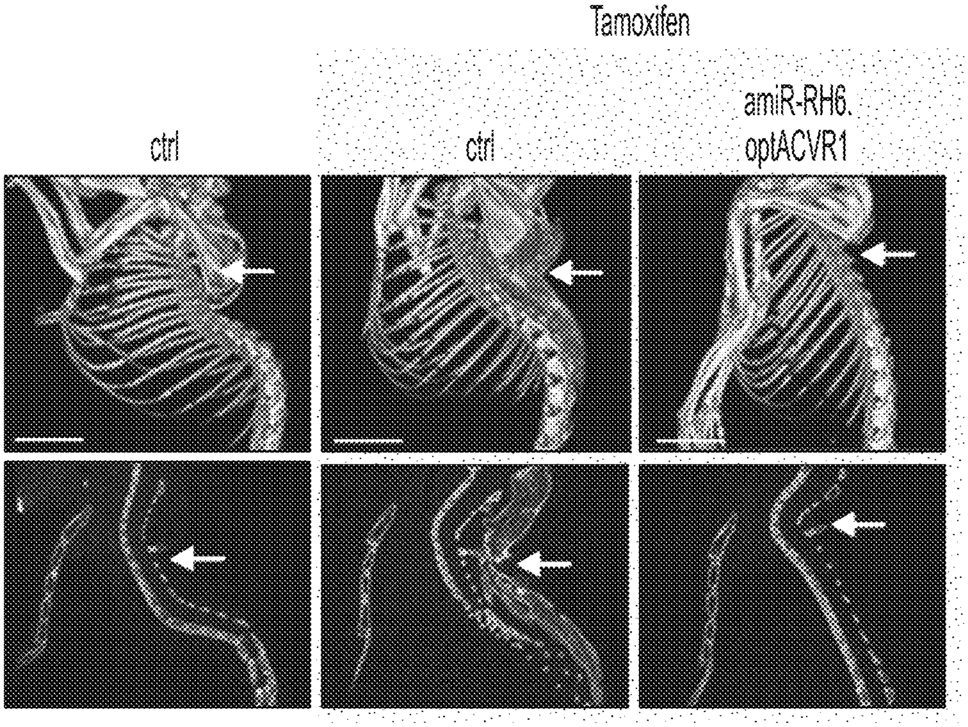
Figure 21D:
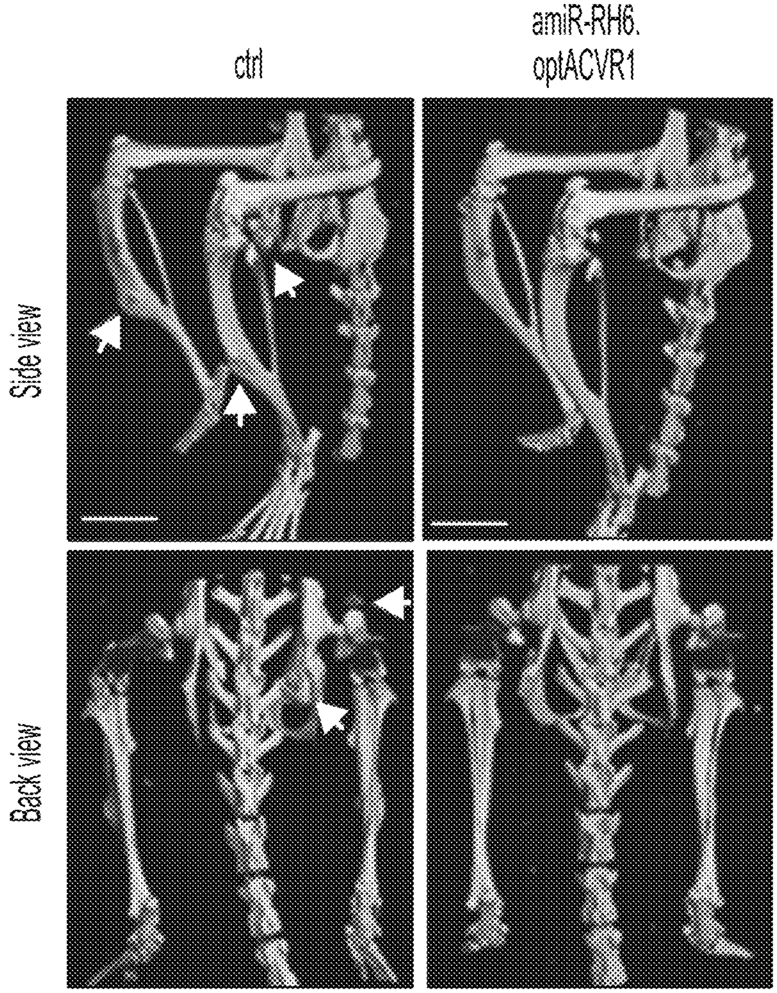
Figure 21E:
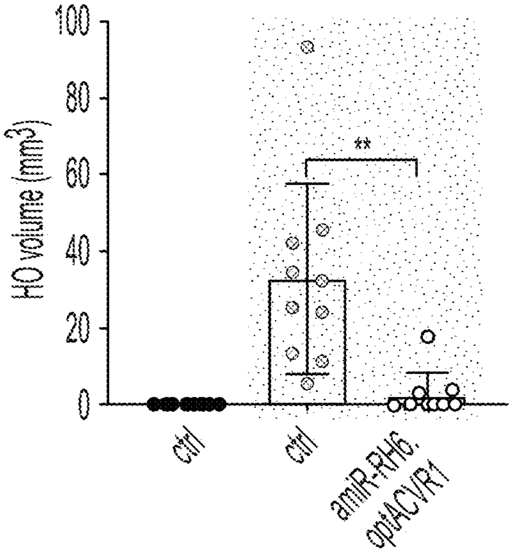
Figure 21F:
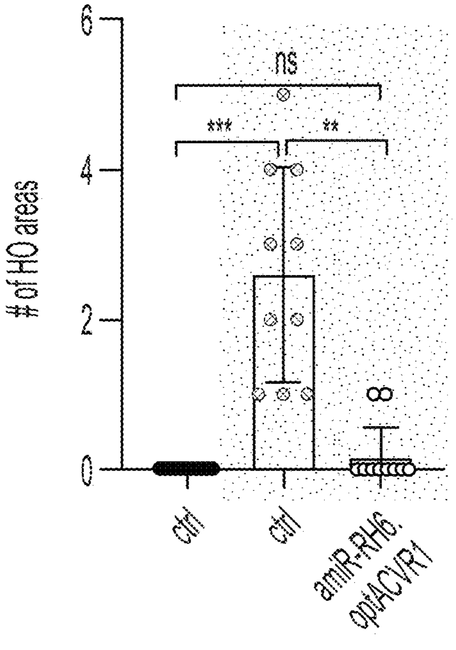
Figure 21G:
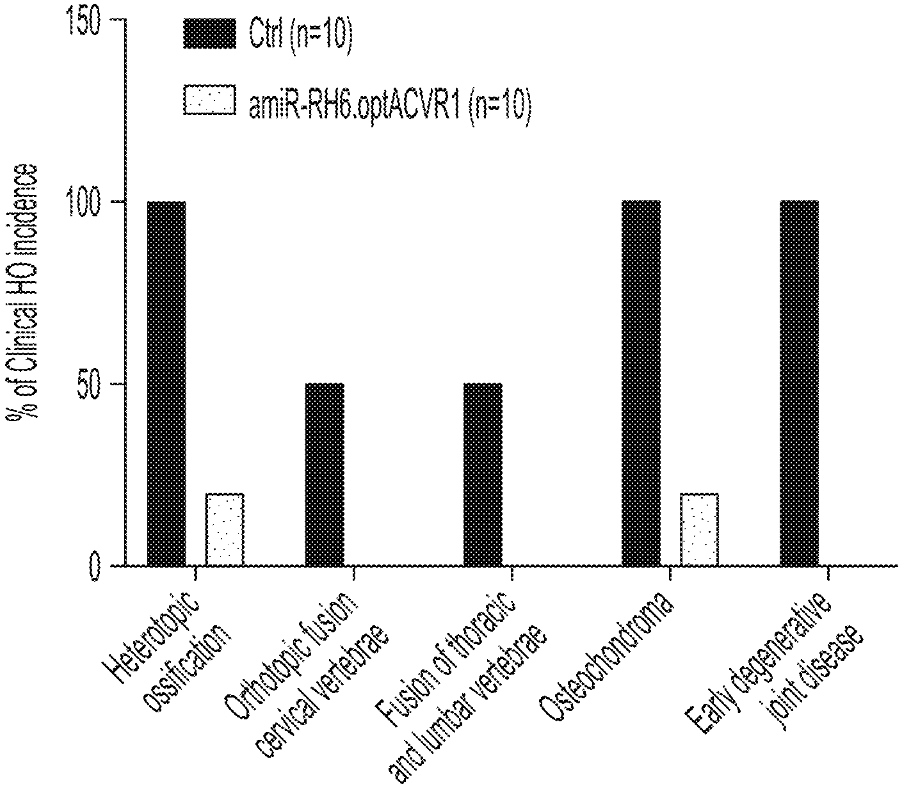
Figure 21H:
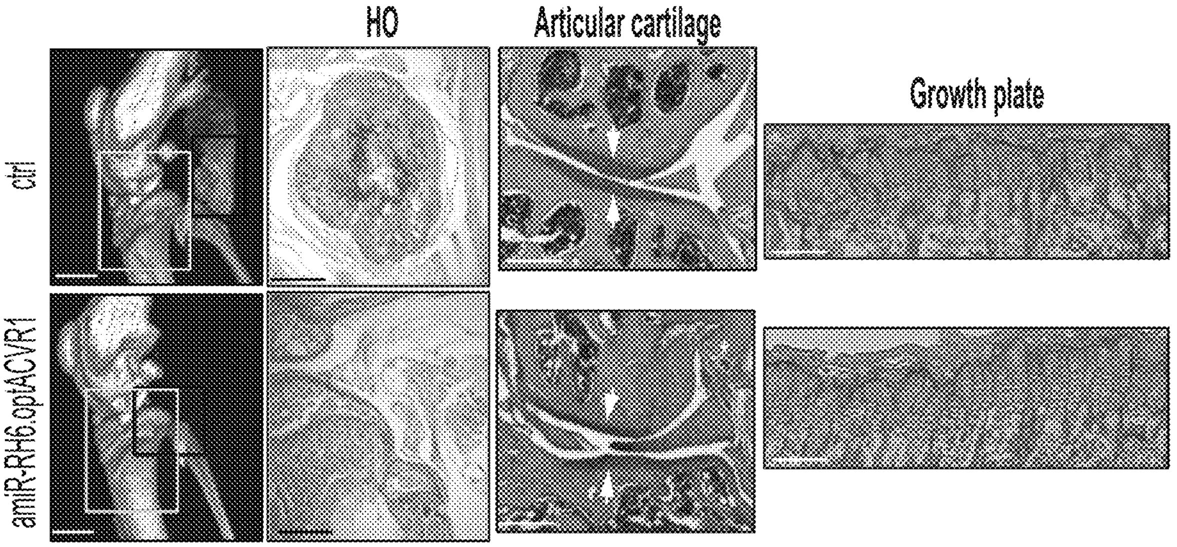
Figure 21I:
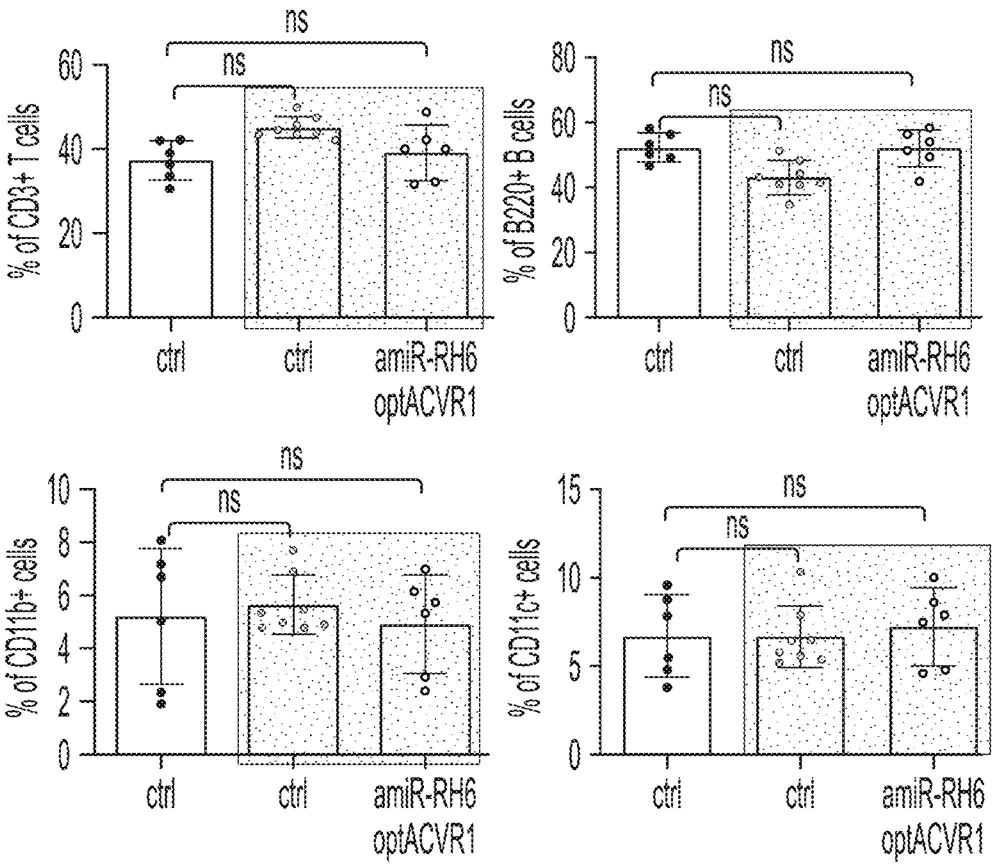
Figure 21J:
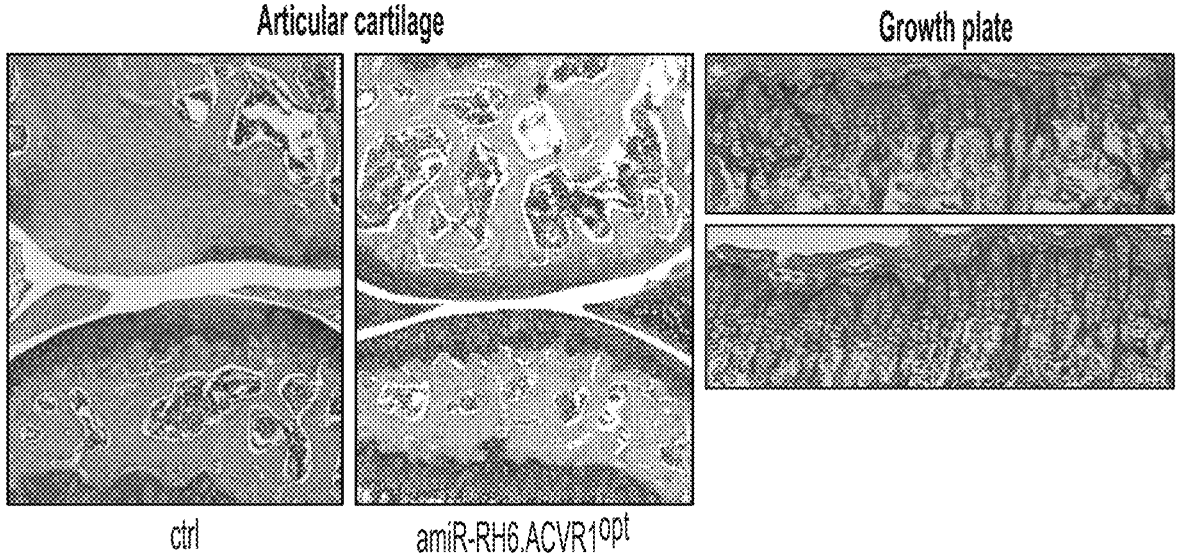

FIGS. 21A-21J show systemic delivery of AAV-gene therapeutics prevents chronic heterotopic ossification in adult FOP mice. FIG. 21A shows $5\times10^{13}$ vg/kg of rAAV9 carrying ctrl or amiR-RH6.optACVR1 was i.v. injected into 6 week old Acvr1R$^{206H}$; Cre-ER$^{T2}$ mice (n=10) three days after five times consecutive i.p. injection of tamoxifen (10 mg/kg). Ten weeks later, Acvr1$^{R206H}$ and optACVR1 mRNA levels in the liver were assessed by RT-PCR. MicroCT analysis of whole body (FIG. 21B), torso (FIG. 21C), and lower body (FIG. 21D) demonstrates that AAV-mediated expression of amiR-RH6.optACVR1 prevents chronic HO in Acvr1R$^{206H}$; PDGFRα-Cre mice. Arrows indicate HO areas. Total HO volume (FIG. 21E) and number of HO areas (FIG. 21F) in whole body were quantitated. Percentage of clinical HO incidence was assessed (FIG. 21G). MicroCT and histology of knee joints were performed to assess heterotopic bone (FIG. 21H, left and middle), degeneration of articular cartilage (FIG. 21H, middle), and growth plate (FIG. 21H, right). Boxes indicate HO areas and articular cartilage and growth plate. Frequency of immune cells within the population of total splenocytes indicate little to no effects of AAV vectors on systemic immune responses (n=6-8, FIG. 21I). Heterotopic bone bridging the femur to the fibular head (FIG. 21H) and severe osteoarthritis in the knee joints (FIG. 21J, left) are likely to cause immobility of hindlimbs in these mice, which was also substantially ameliorated by amiR-RH6.ACVK1$^{opt}$ treatment. Notably, unlike palovarotene treated mice, the chondrocytes residing in the growth plate were normal in amiR-RH6.ACVK1$^{opt}$-treated mice (FIG. 21J, right). Histopathology evaluation of the lung, liver, kidney, heart, and skeletal muscle was performed in these mice (FIG. 23), demonstrating little to no adverse effects of amiR-RH6.ACVK1$^{opt}$ treatment. These results demonstrate that systemic delivery of amiR-RH6.ACVK1$^{opt}$ by rAAV9 capsid can prevent spontaneous HO in adult FOP mice. Taken together, systemic delivery of AAV gene therapeutics that execute ACVR1$^{R206H}$-specific silencing and gene replacement with ACVR1$^{opt}$ simultaneously is effective in suppressing disabling FOP pathology at juvenile and adult stages, providing the potential for clinical translation to FOP patients.

Figure 22A:
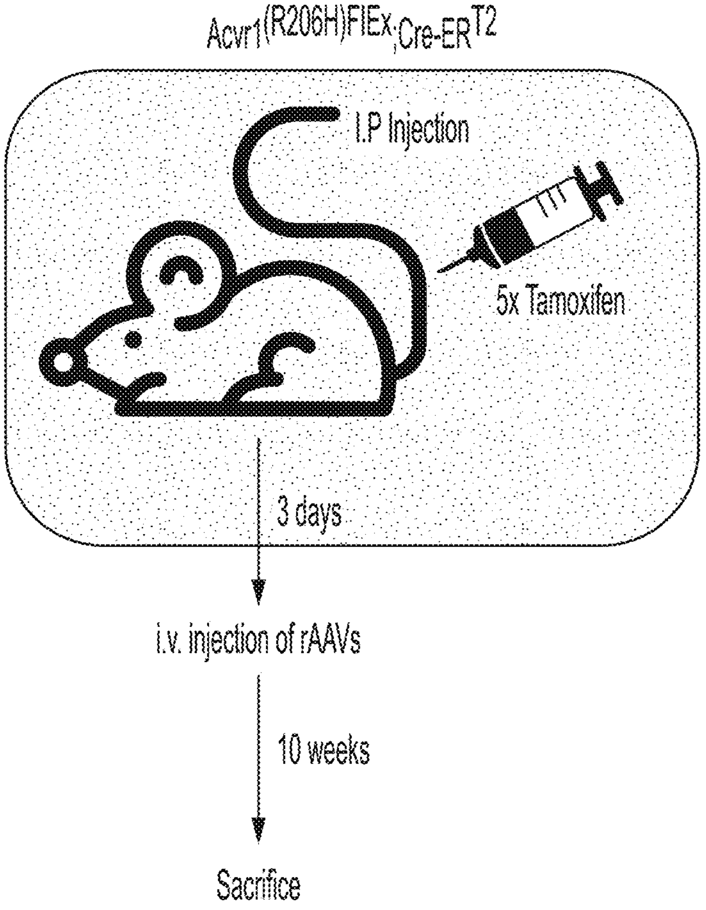
FIGS. 22A-22F show systemic delivery of AAV-gene therapeutics prevents chronic heterotopic ossification in adult FOP mice.
Figure 22B:
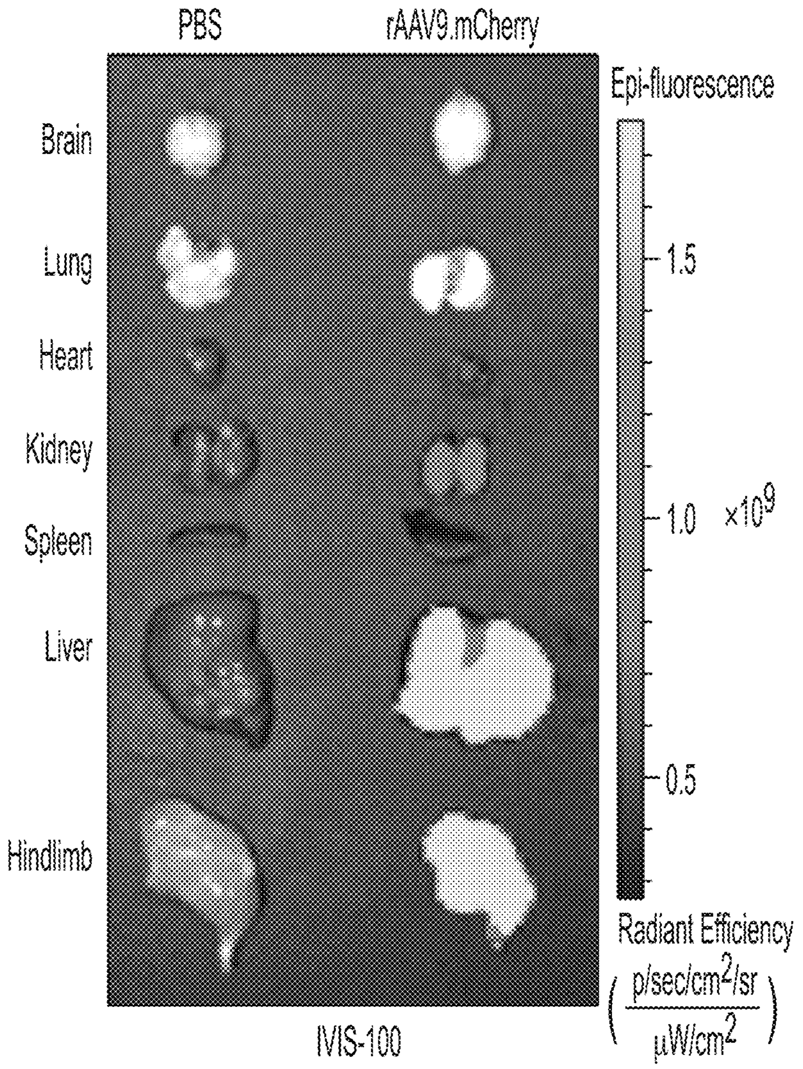
Figure 22C:
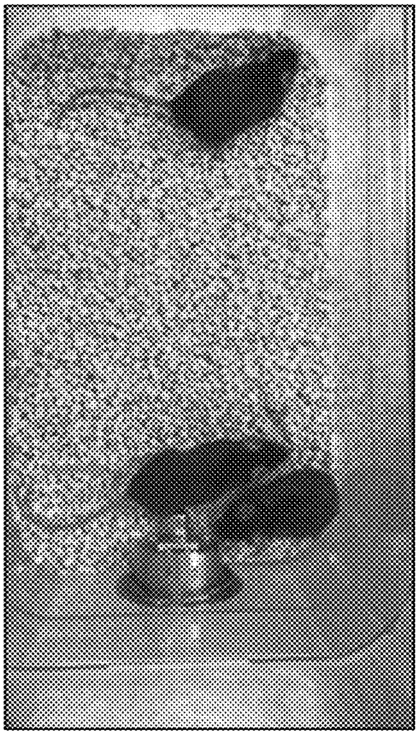
Figure 22D:
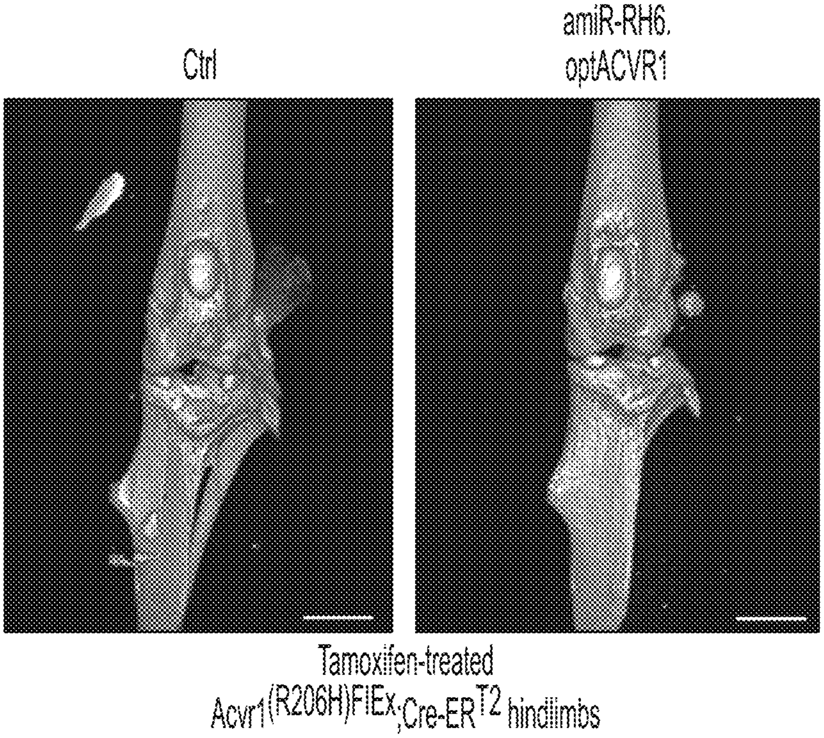
Figure 22E:
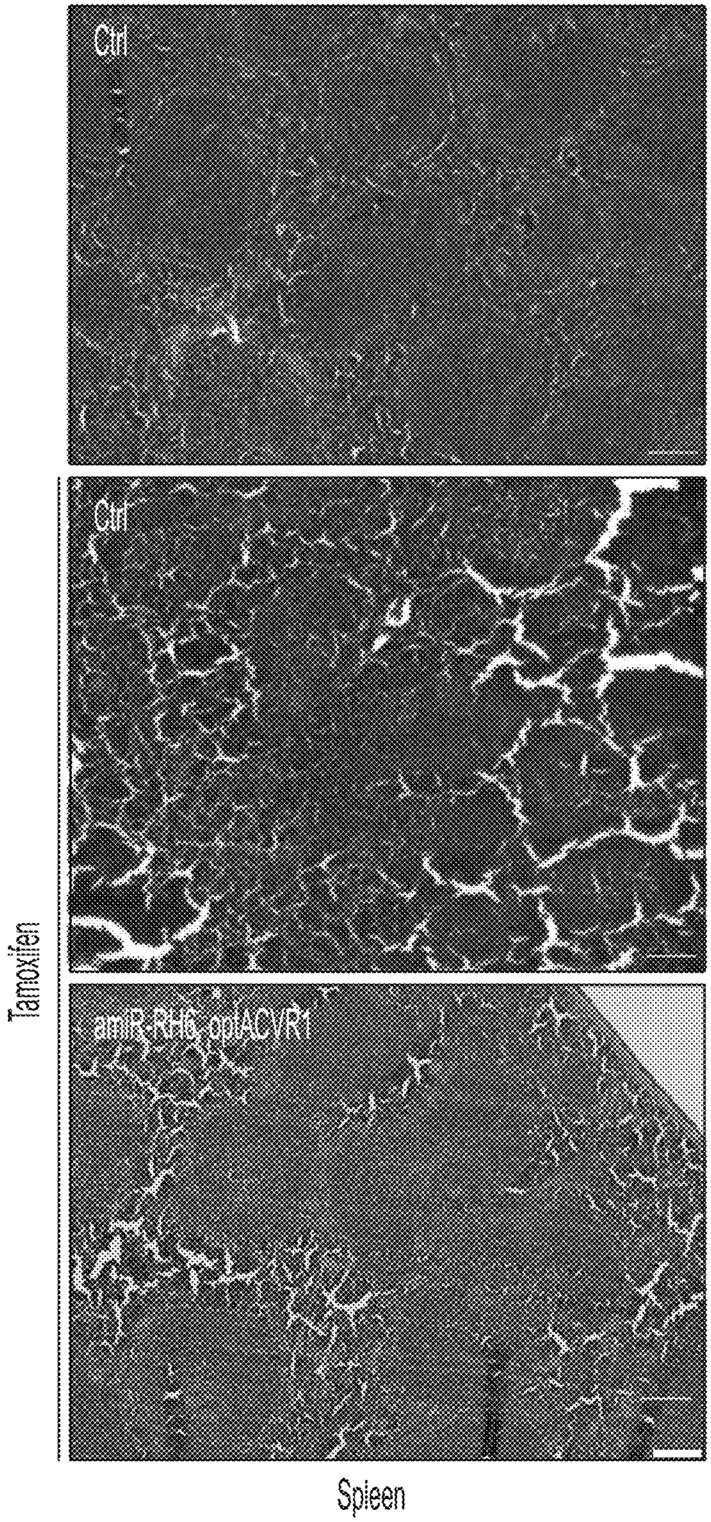
Figure 22F:
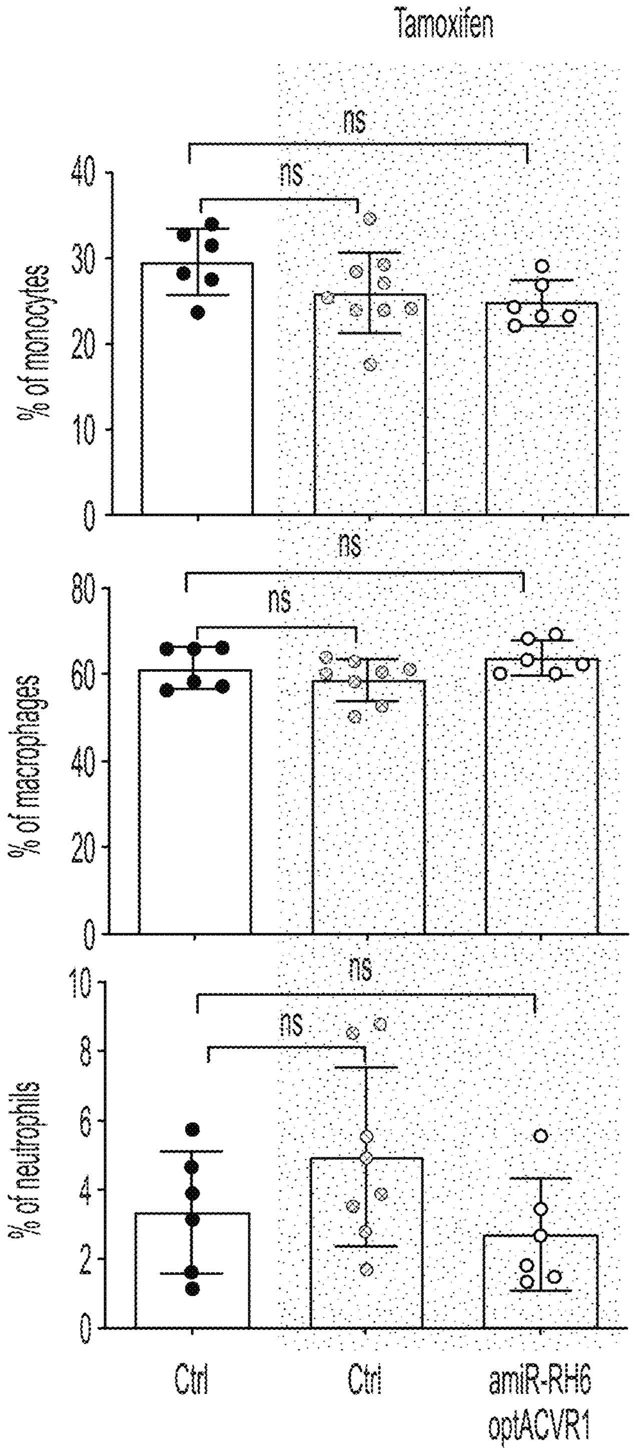

FIGS. 22A-22F show systemic delivery of AAV-gene therapeutics prevents chronic heterotopic ossification in adult FOP mice. FIG. 22A shows a diagram of a study and treatment design. FIG. 22B shows 5x10$^{13}$ vg/kg of rAAV9 expressing mCherry was i.v. injected into 6 week old Acvr1R206H; Cre-ERT2 mice (n=3) three days after five times consecutive i.p. injection of tamoxifen (10 mg/kg). mCherry expression in individual tissues was monitored by IVIS-100 optical imaging two weeks post-injection. FIGS. 22C-2F show 5x10$^{13}$ vg/kg of rAAV9 carrying ctrl or amiR-RH6.optACVR1 was i.v. injected into 6 week old Acvr1R206H; Cre-ERT2 mice (n=10) three days after five times consecutive i.p. injection of tamoxifen (10 mg/kg). Ten weeks later, the movements of 16 week old AAV-treated mice, including Acvr1R206H (ctrl) mouse with normal locomotion, Acvr1R206H; Cre-ERT2 (ctrl) mouse with slow locomotion, and Acvr1R206H; Cre-ERT2 (amiR-RH6.optACVR1) mouse with normal locomotion. Arrow indicates amiR-RH6.optACVR1-treated mouse (FIG. 22C). FIG. 22D shows the heterotopic bone near knee joints. FIG. 22E shows H&E staining of the longitudinal sections of the AAV-treated spleens. FIG. 22F shows frequency of monocytes, macrophages, and neutrophils within the population of total splenocytes (n=6-8).

Figure 23:
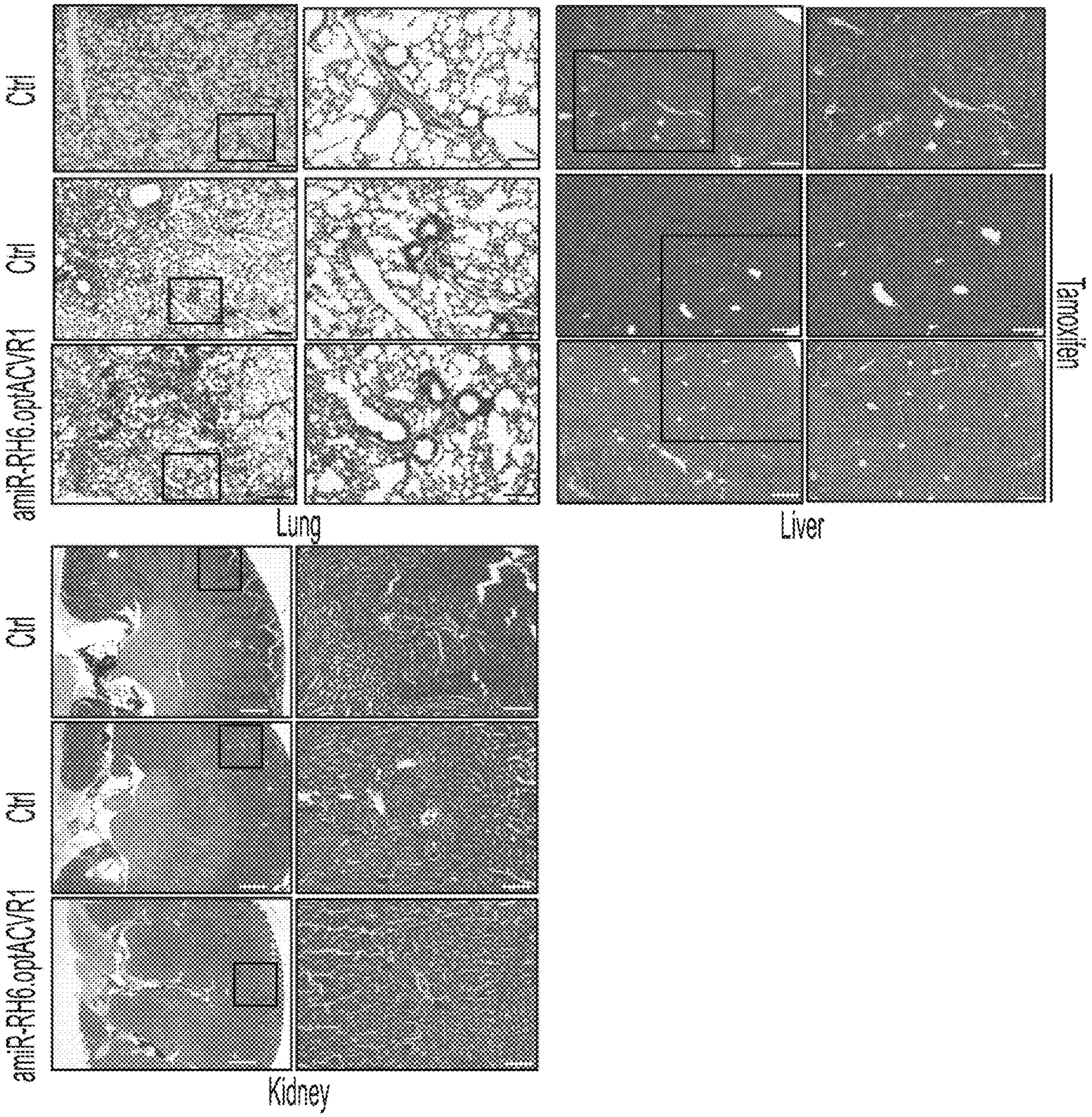
FIG. 23 shows effects of AAV-gene therapeutics on tissue histopathology in adult FOP mice. $5\times10^{13}$ vg/kg of rAAV9 carrying ctrl or amiR-RH6.optACVR1 was i.v. injected into 6 week old Acvr1R206H; Cre-ERT2 mice (n=3) three days after five times consecutive i.p. injection of tamoxifen (10 mg/kg). Ten weeks later, H&E staining in lung, liver, kidney, heart, and skeletal muscle was performed to assess tissue histopathology (n=3).

FIG. 23 shows effects of AAV-gene therapeutics on tissue histopathology in adult FOP mice. 5x10$^{13}$ vg/kg of rAAV9 carrying ctrl or amiR-RH6.optACVR1 was i.v. injected into 6 week old Acvr1R206H; Cre-ERT2 mice (n=3) three days after five times consecutive i.p. injection of tamoxifen (10 mg/kg). Ten weeks later, H&E staining in lung, liver, kidney, heart, and skeletal muscle was performed to assess tissue histopathology (n=3).

Figure 24A:
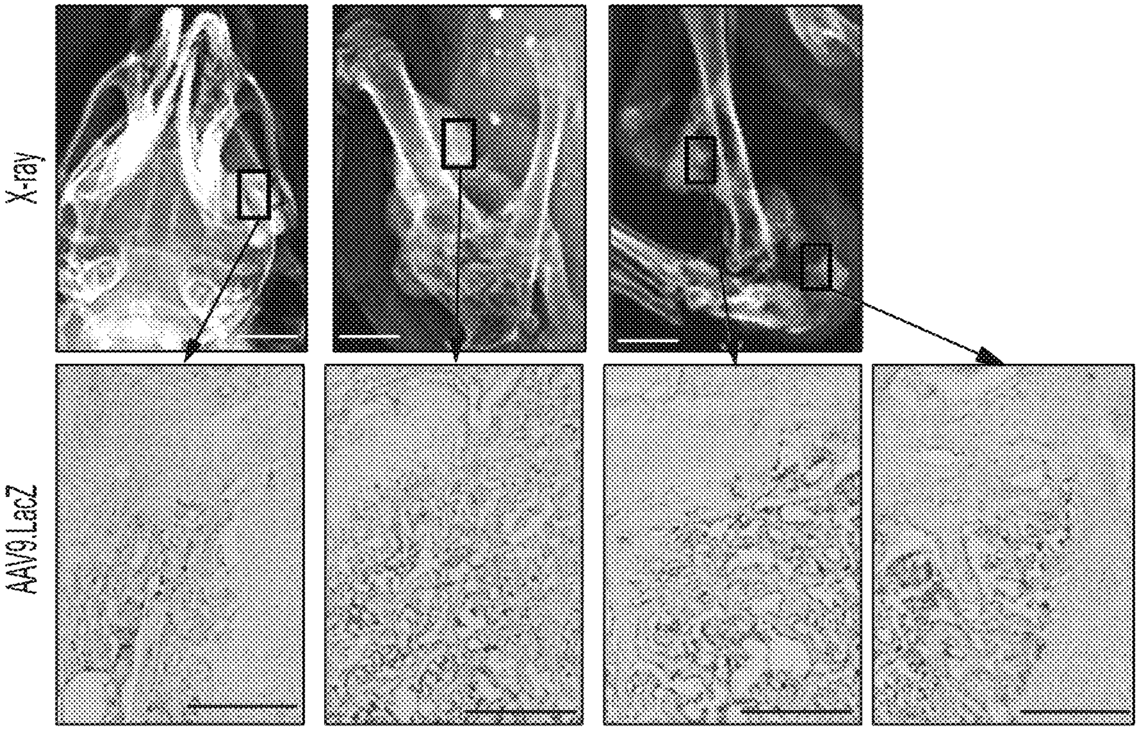
FIGS. 24A-24H show systemic delivery of AAV-gene therapeutics prevents chronic heterotopic ossification in juvenile FOP mice.
Figure 24B:
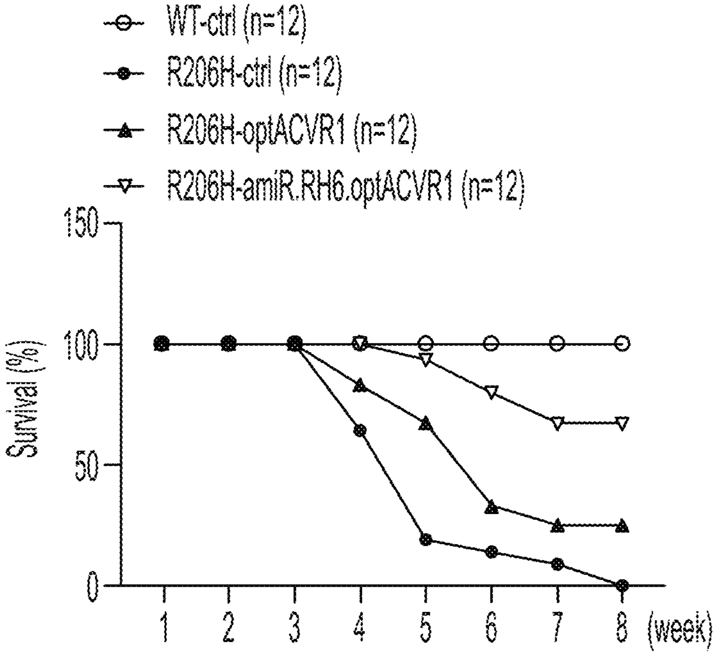
Figure 24C:
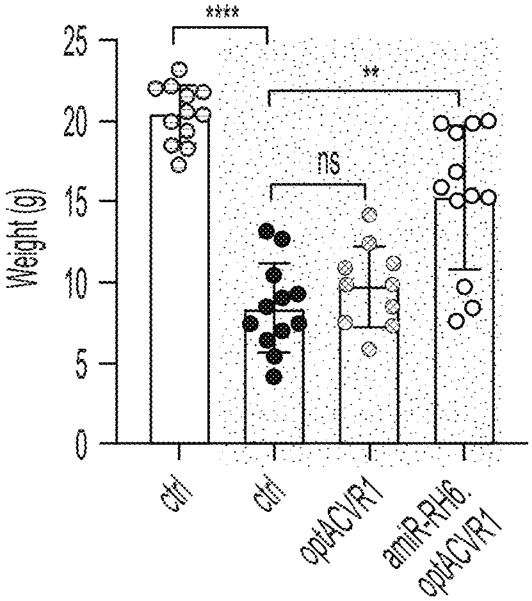
Figure 24D:
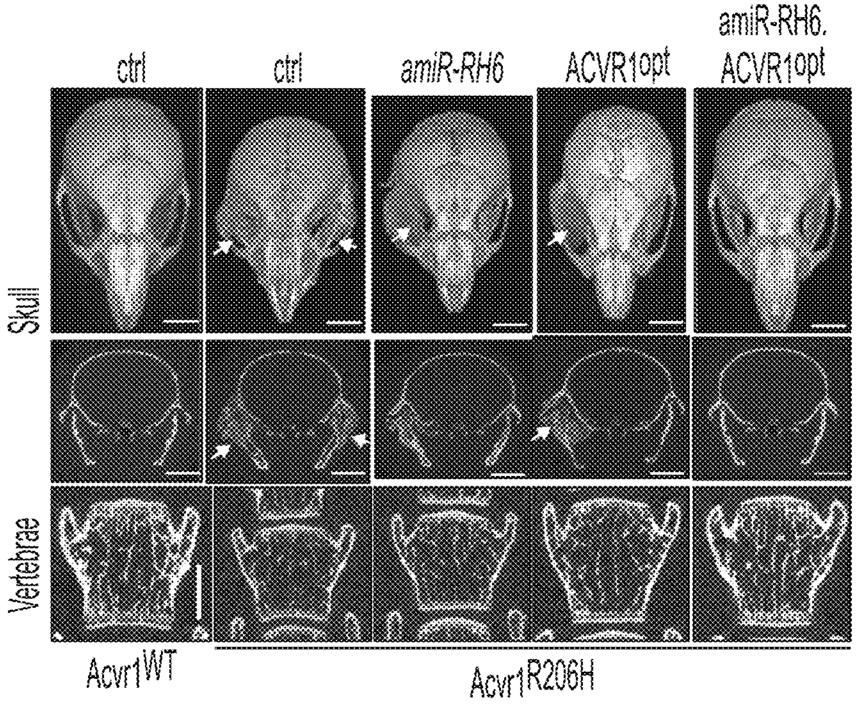
Figure 24E:
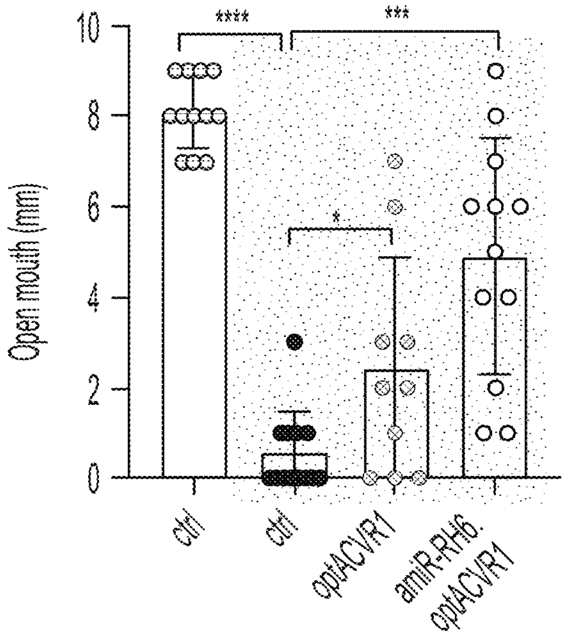
Figure 24F:
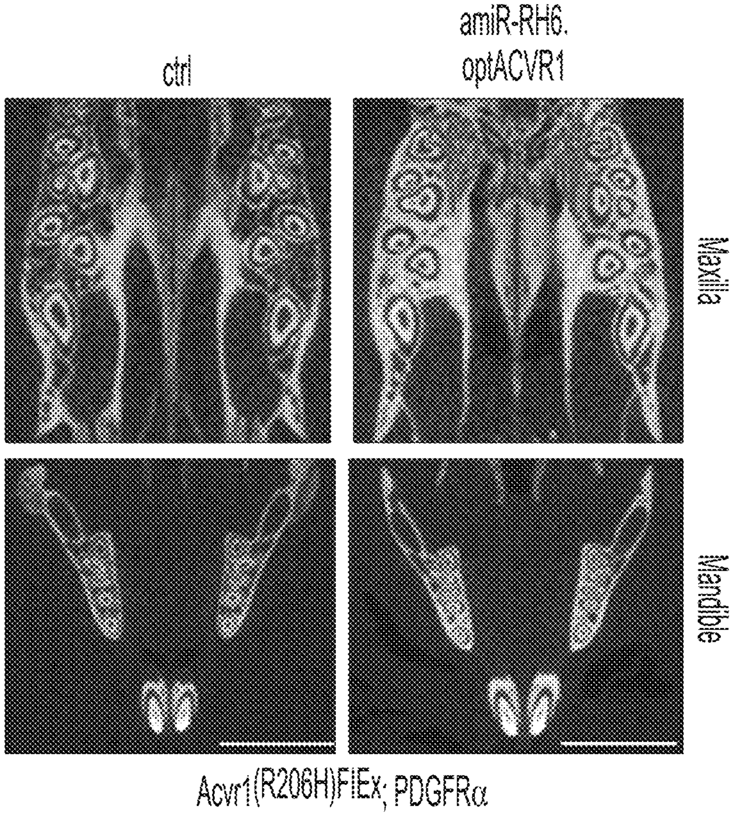

FIGS. 24A-24H show systemic delivery of AAV-gene therapeutics prevents chronic heterotopic ossification in juvenile FOP mice. FIG. 24A shows 5x10$^{13}$ vg/kg of rAAV9 expressing LacZ was i.v. injected into 3 week old Acvr1R$^{206H}$; PDGFRα-Cre mice (n=3) and two weeks later, X-radiography of whole body was performed to locate HO sites (top). Frozen-sections of HO tissues were stained for X-galactosidase (bottom). Boxes indicate HO tissues. FIGS. 24B-24H show P1 Acvr1R$^{206H}$; PDGFRα-Cre neonates (n=12) were treated with 10$^{11}$ GC of rAAV9 carrying ctrl, amiR-RH6, optACVR1, or amiR-RH6.optACVR1 via facial vein injection. Survival (FIG. 24B) and body weight (FIG. 24C) of AAV-treated mice were weekly analyzed from the age of three weeks old to eight weeks old. MicroCT analysis of 5 week old AAV-treated skulls shows the ability of AAV vectors to reverse jaw ankylosis of Acvr1R$^{206H}$; PDGFRα-Cre mice (FIGS. 24D-24E). Images of 3D reconstruction (FIG. 24D, top) and 2D transverse section (FIG. 24D, bottom) and distance of open mouth (FIG. 24E) are displayed. Arrows indicate the areas of temporomandibular joint ankylosis. It was likely that reduced survival and substantial weight loss of control-treated Acvr1R$^{206H}$ mice were primarily associated with jaw ankylosis, which was observed in all mice that failed to open mouth and died early due to starvation (FIG. 24D). While these mice developed HO at both sides of temporomandibular joints (TMJ), most of HO developed at only one side of TMJs by treatment with amiR-RH6 or ACVR1$^{opt}$. amiR-RH6.ACVR1$^{opt}$ treatment almost completely suppressed HO at both sides of TMJs, resulting in a significant increase in survival rate and body weight. These results suggest that compared to Acvr1$^{R206H}$-specific silencing and gene replacement with ACVR1$^{opt}$, the combinatory approach using amiR-RH6.ACVR1$^{opt}$ is most effective in preventing early-onset HO at TMJs in juvenile FOP mice.

Since osteoporosis has been considered as a major clinical feature of advanced FOP patients, vertebral bone mass and architecture of 5-week-old Acvr1$^{R206H}$ mice were assessed by microCT (FIG. 24D), demonstrating ~70% decrease of trabecular bone mass compared to littermate controls. This phenotype was substantially ameliorated by treatment with amiR-RH6.ACVR1$^{opt}$, not amiR-RH6 and ACVR1$^{opt}$. Additionally, as previously reported, Acvr1$^{R206H}$ mice developed spontaneous HO at multiple anatomical locations, including cervical spine and joints in the hip, forelimb, hindlimb, and ankle, which was substantially ameliorated by treatment with amiR-RH6, ACVR1$^{opt}$, or amiR-RH6.ACVR1$^{opt}$ (FIG. 24D).

Figure 24G:
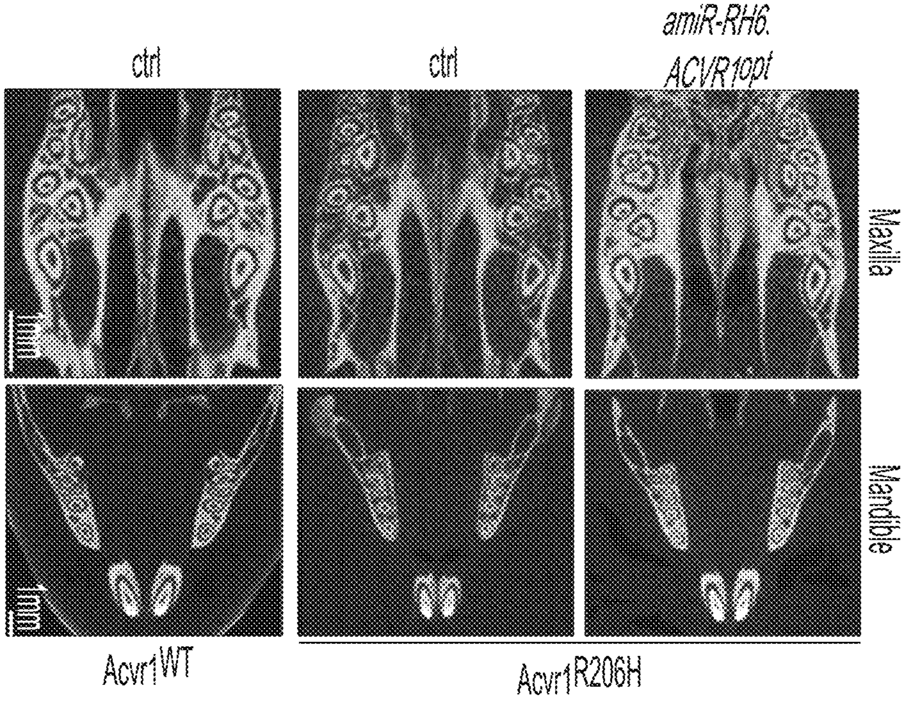
Figure 24H:
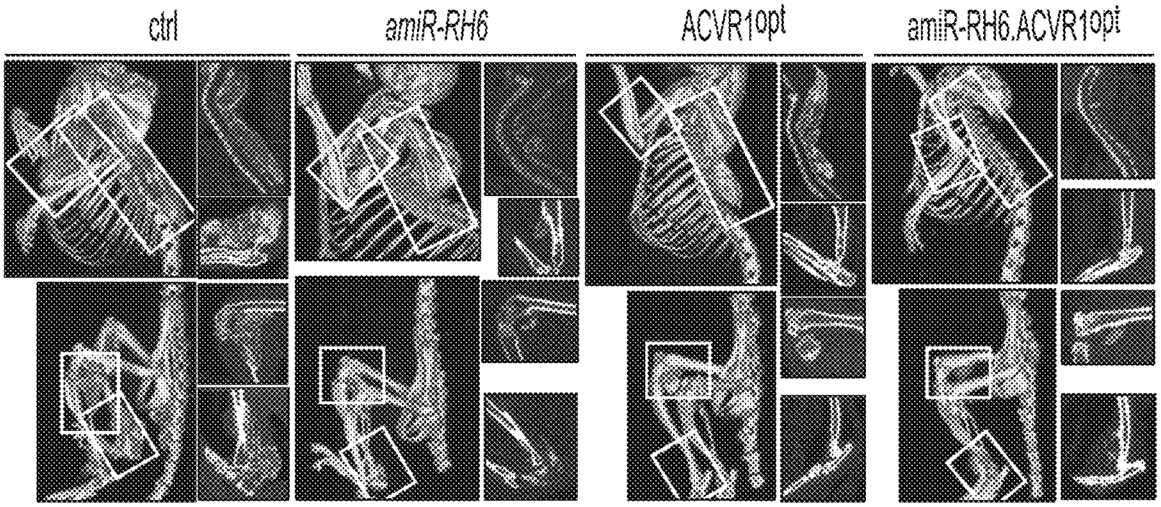
Figure 27A:
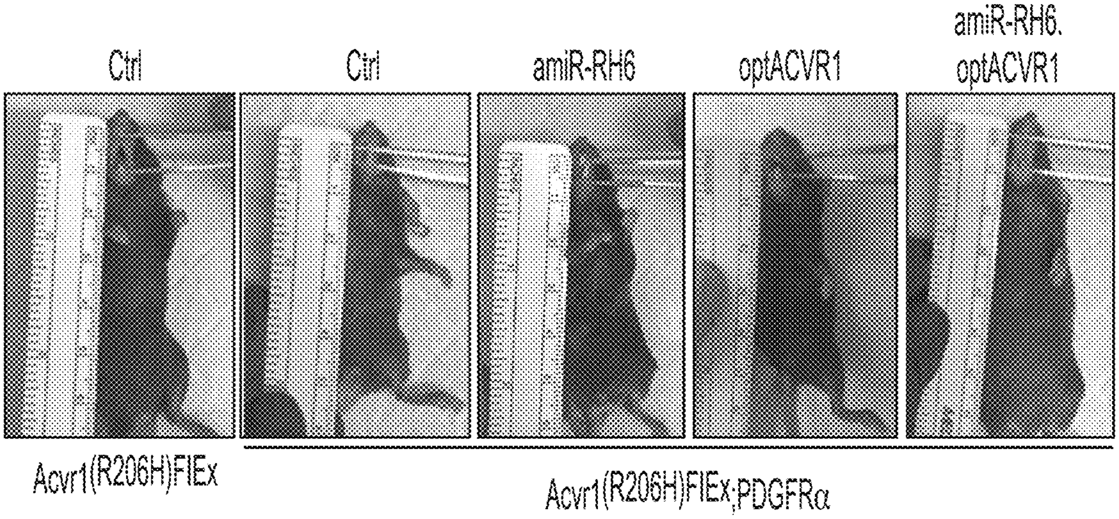
FIGS. 27A-27D show systemic delivery of AAV-gene therapeutics prevents jaw ankylosis in juvenile FOP mice. P1 Acvr1R$^{206H}$; PDGFRa-Cre neonates (n=12) were treated with $10^{11}$ GC of rAAV9 carrying ctrl, amiR-RH6, optACVR1, or amiR-RH6.optACVR1 via facial vein injection.
Figure 27B:
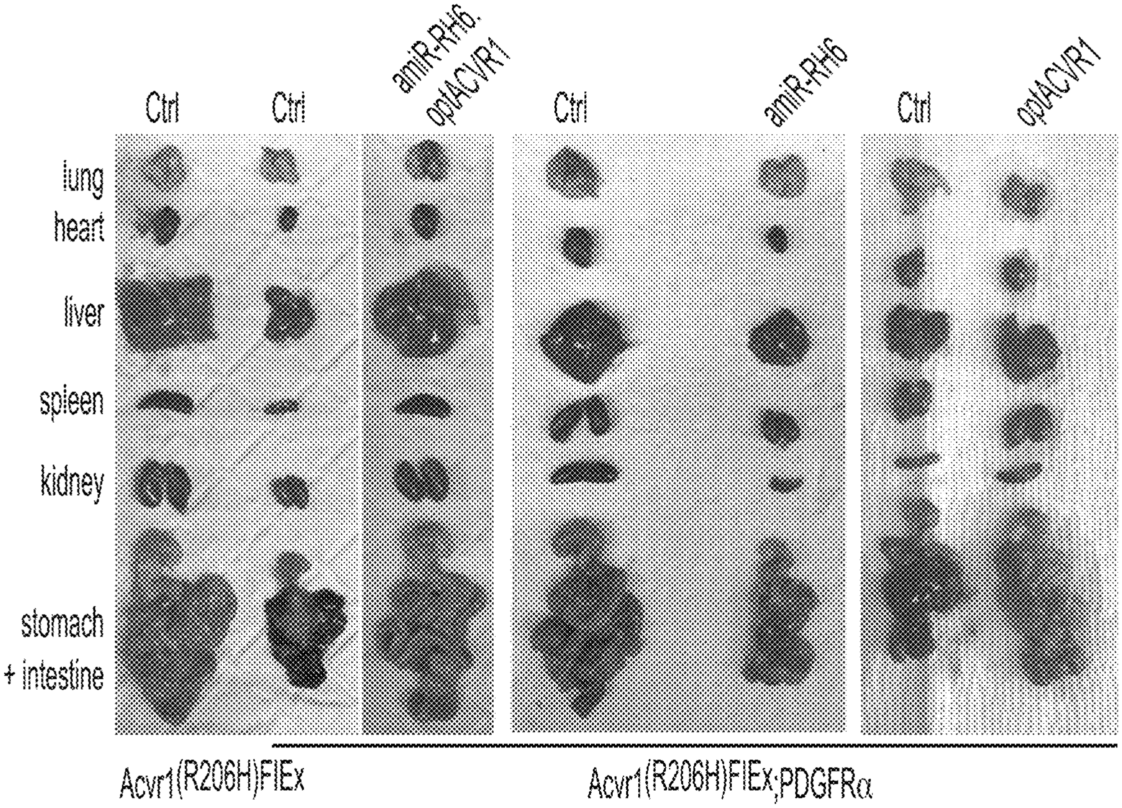
Figure 27C:
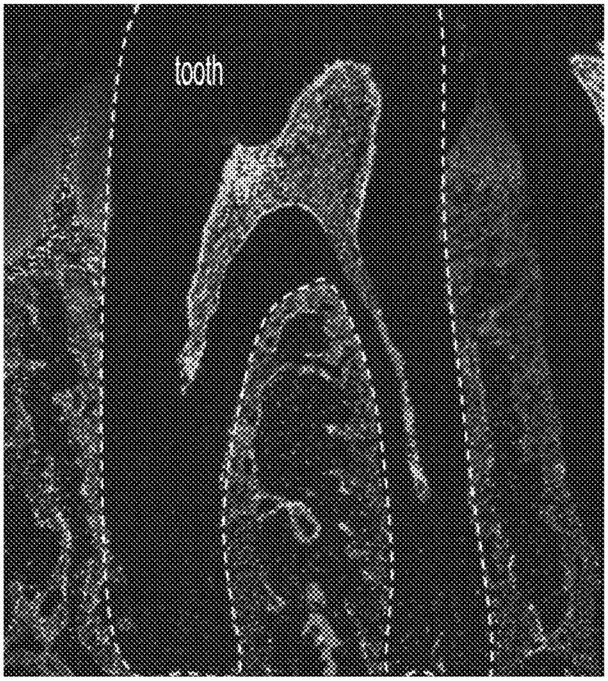
Figure 27D:
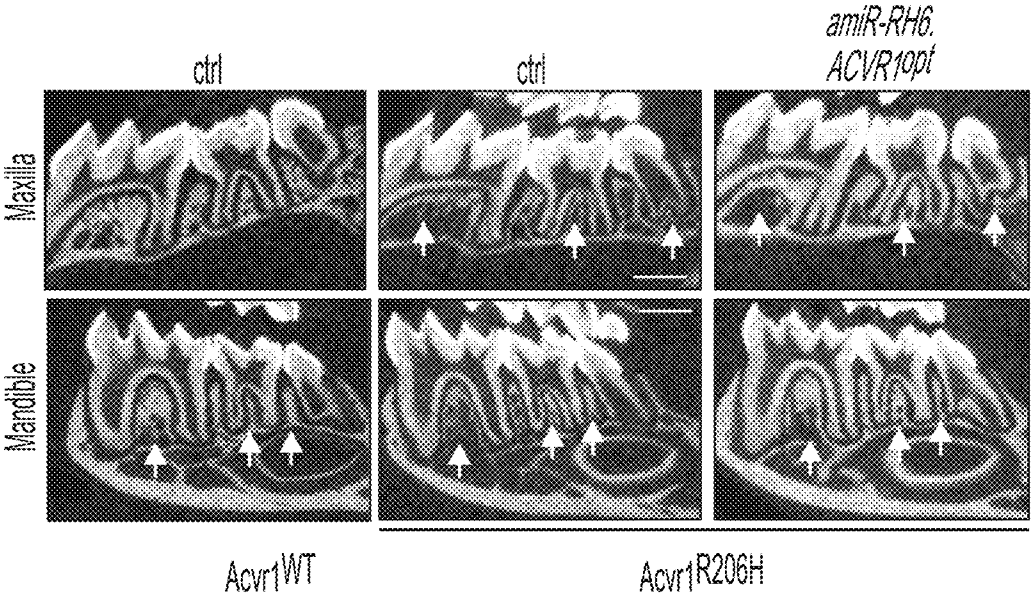

As shown in the present disclosure, since PDGFRα is highly expressed in dental mesenchymal stem cells and odontoblasts (FIG. 27C), targeting Acvr1$^{R206H}$ using PDGFRα driver also resulted in low alveolar bone mass in both maxillary and mandibular bones, which was markedly improved by treatment with amiR-RH6.ACVR1$^{opt}$ (FIG. 24G and FIG. 27D). Notably, tooth morphology and dentin mass were both normal in Acvr1$^{R206H}$ mice, suggesting that ACVR1$^{206H}$ mutation is dispensable of dental development and homeostasis. (FIG. 24D). MicroCT analysis of maxillary and mandibular bones demonstrates that AAV-mediated expression of amiR-RH6.optACVR1 reverses low bone mass of Acvr1R$^{206H}$; PDGFRa-Cre mice (FIGS. 24F-24G). 2D cross (FIG. 24F) and transverse (FIG. 24G) section images are displayed. Arrows indicate dental root bones. MicroCT analysis of whole body shows the ability of AAV vectors to prevent chronic HO in Acvr1R$^{206H}$; PDGFRa-Cre mice (FIG. 24H). Images of 3D reconstruction (FIG. 24H, left) and 2D transverse section (FIG. 24H, right) are displayed. While multiple residual HO lesions were detected in Acvr1$^{R206H}$ mice treated with amiR-RH6 or ACVR1$^{opt}$, amiR-RH6.ACVR1$^{opt}$ treatment almost completely prevented spontaneous HO throughout the body. Thus, accompanied with a low incidence of jaw ankylosis, a single treatment of amiR-RH6.ACVR1$^{opt}$ at infant stages can prevent early-onset osteoporosis and progressive HO in FOP mice during skeletal development.

Figure 25A:
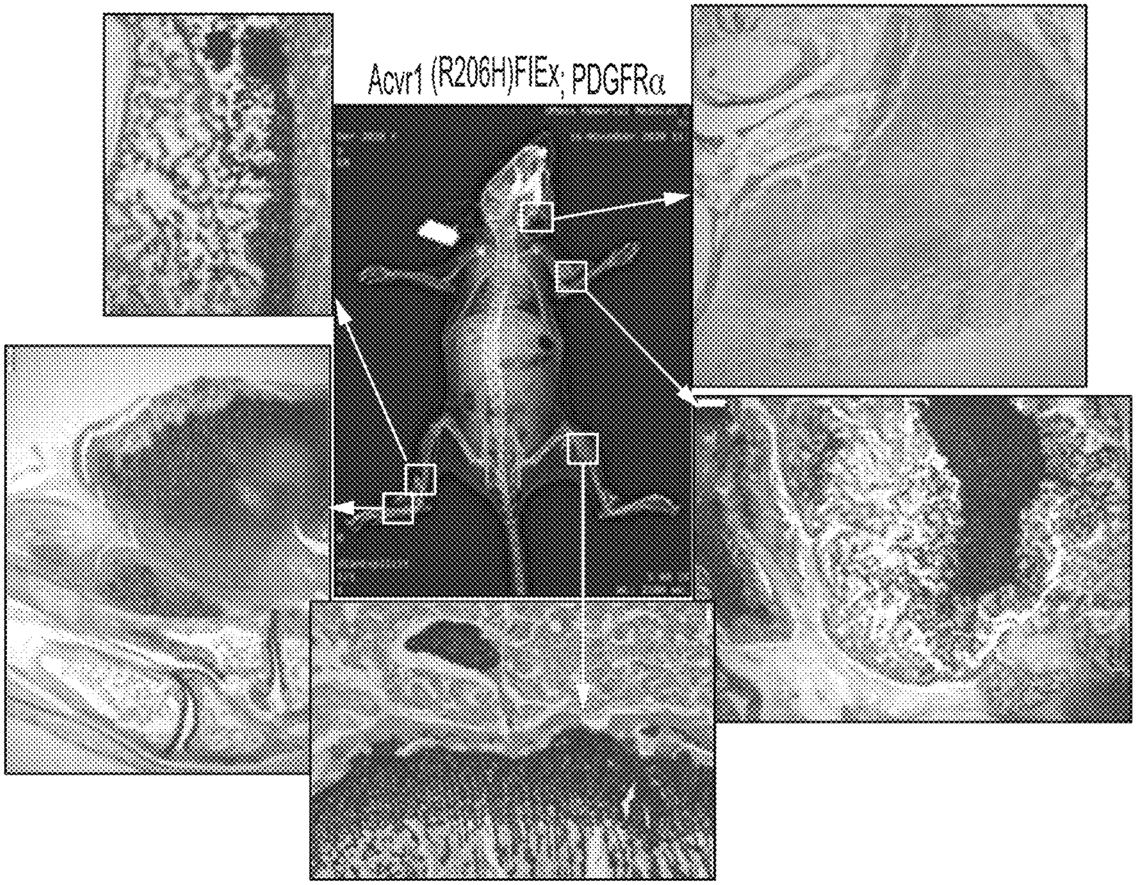
FIGS. 25A-25B show systemic delivery of AAV9 is effective for the transduction of HO tissues in juvenile FOP mice.
Figure 25B:
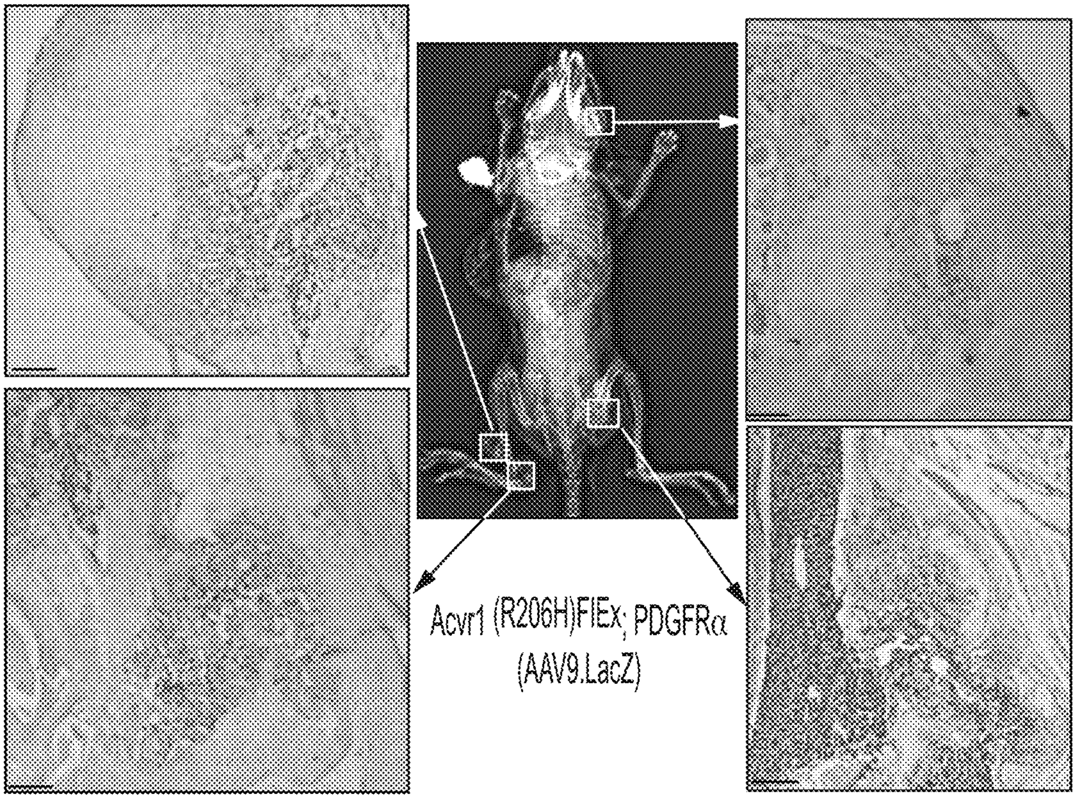

FIGS. 25A-25B show systemic delivery of AAV9 is effective for the transduction of HO tissues in juvenile FOP mice. Since PDGFRα$^{+}$ progenitors in the skeletal muscle interstitium have been known as major cell populations of origin responsible for HO, mice harboring a conditional knock-in allele of Acvr1$^{(R206H)F1}$ were crossed with PDGFRα-cre mice (Acvr1$^{(R206H)F1}$; PDGFRα), resulting in early-onset and widely distributed HO phenotypes of the musculature, tendons, and ligaments at multiple anatomical locations (FIG. 25A). Specifically, FIG. 25A shows Alcian blue staining of HO tissues in 5 week old Acvr1R206H; PDGFRα-Cre mice (n=3). FIG. 25B shows 5×10$^{13}$ vg/kg of rAAV9 expressing LacZ was i.v. injected into 3 week old Acvr1R206H; PDGFRα-Cre mice (n=3) and two weeks later, X-radiography of whole body was performed to locate HO sites. Frozen-sections of HO tissues were stained for X-galactosidase.

Figure 26A:
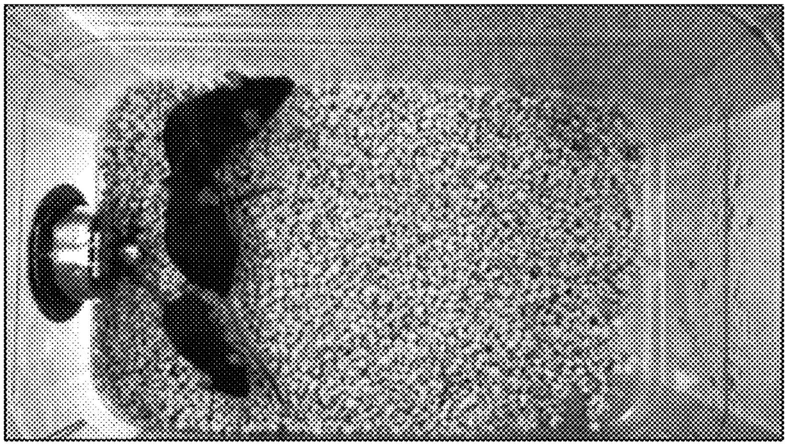
FIGS. 26A-26B show systemic delivery of AAV-gene therapeutics prevents chronic heterotopic ossification in juvenile FOP mice.
Figure 26B:
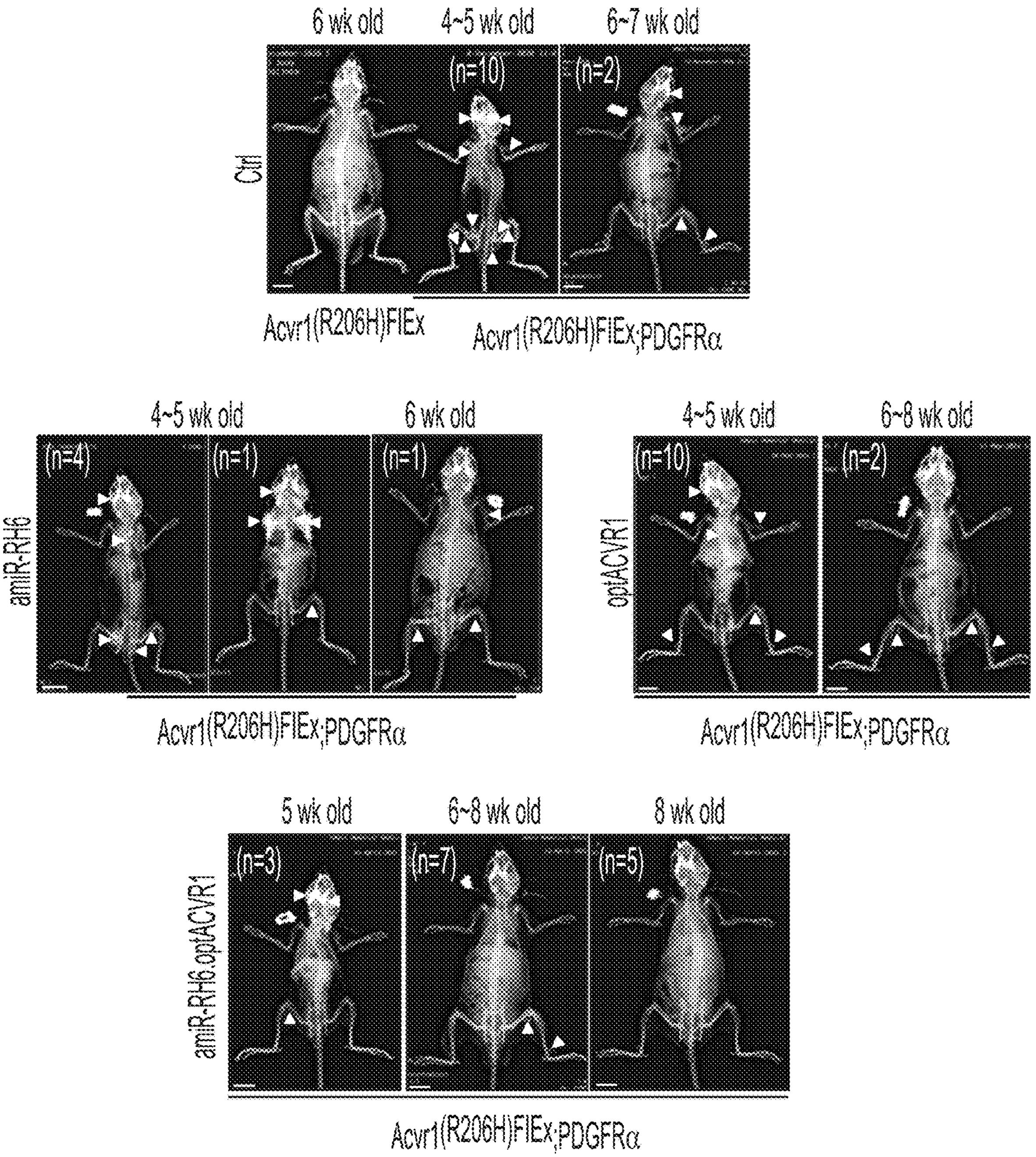

FIGS. 26A-26B show systemic delivery of AAV-gene therapeutics prevents chronic heterotopic ossification in juvenile FOP mice. FIG. 26A shows P1 Acvr1R$^{206H}$; PDGFRα-Cre neonates (n=12) were treated with 10$^{11}$ GC of rAAV9 carrying ctrl, amiR-RH6, optACVR1, or amiR-RH6.optACVR1 via facial vein injection. Movements of 5 week old AAV-treated mice, including normal sized Acvr1R$^{206H}$ mouse (ctrl), small sized Acvr1R$^{206H}$; PDGFRα-Cre mouse (ctrl), and normal sized Acvr1R$^{206H}$; PDGFRα-Cre mouse (amiR-RH6.optACVR1), are shown. FIG. 26B shows X-radiography showing whole body of 5 week old AAV-treated mice.

FIGS. 27A-27D show systemic delivery of AAV-gene therapeutics prevents jaw ankylosis in juvenile FOP mice. P1 Acvr1R$^{206H}$; PDGFRα-Cre neonates (n=12) were treated with 10$^{11}$ GC of rAAV9 carrying ctrl, amiR-RH6, optACVR1, or amiR-RH6.optACVR1 via facial vein injection. FIG. 27A shows photography demonstrating the ability of 5 week old AAV-treated mice to open mouth. FIG. 27B shows photography showing individual tissues of 5 week old AAV-treated mice demonstrates that AAV-mediated expression of optACVR1 or amiR-RH6.optACVR1 prevents a decay of Acvr1R$^{206H}$; PDGFRα-Cre intestines by starvation.

Figure 28A:
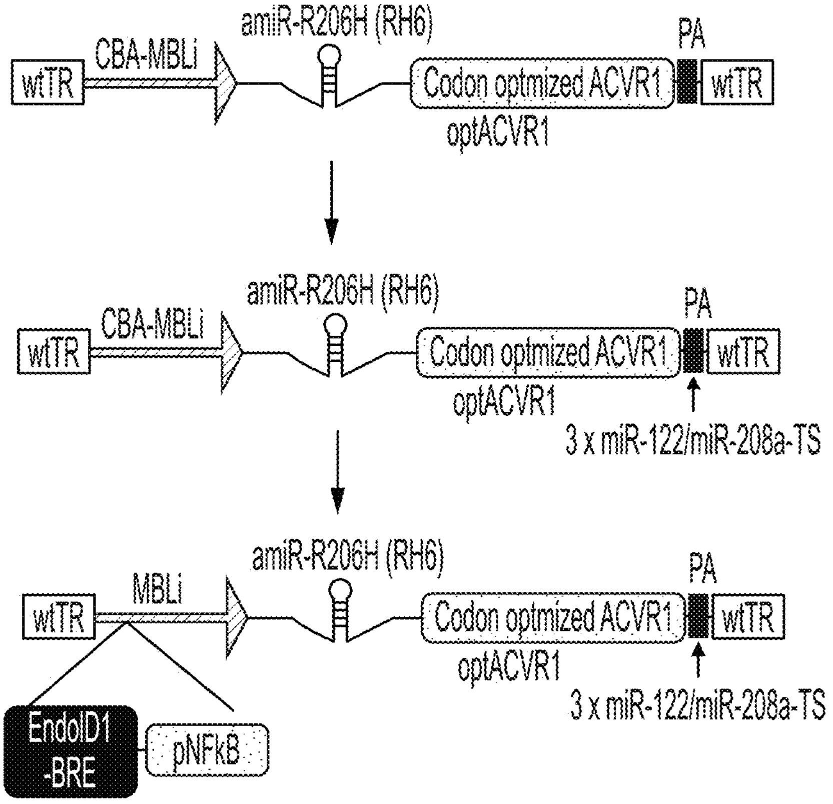
FIGS. 28A-28C show modification of the AAV vector genome to control the expression of therapeutic genes.
Figure 28B:
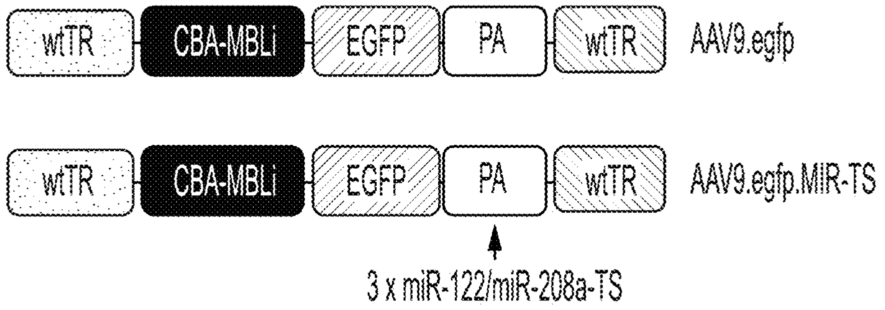
Figure 28C:
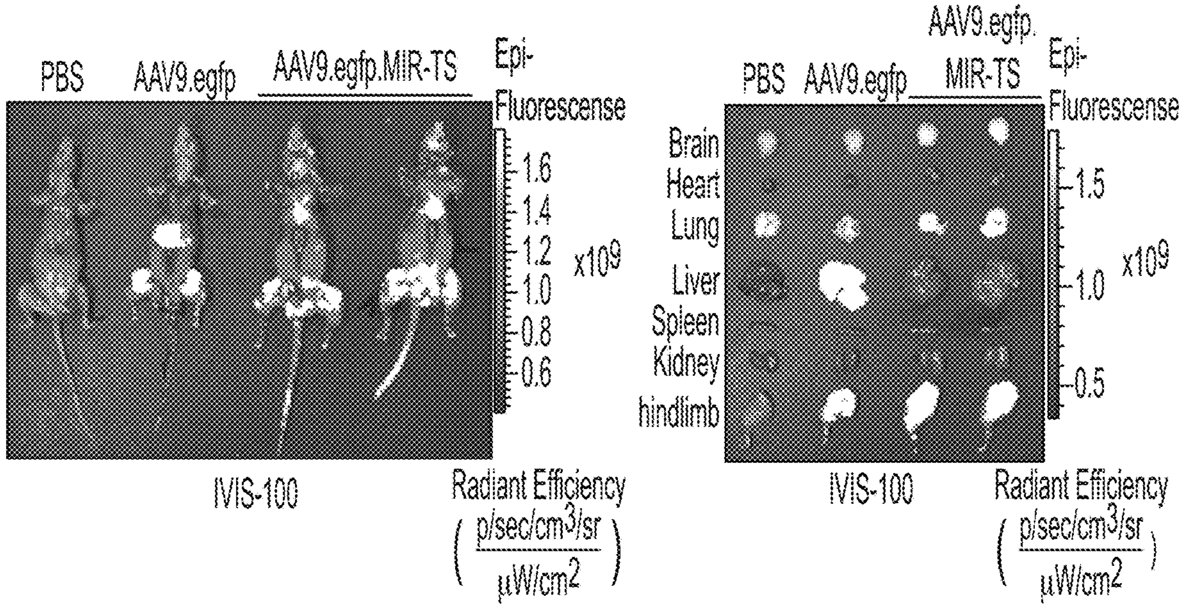
Figure 29B:
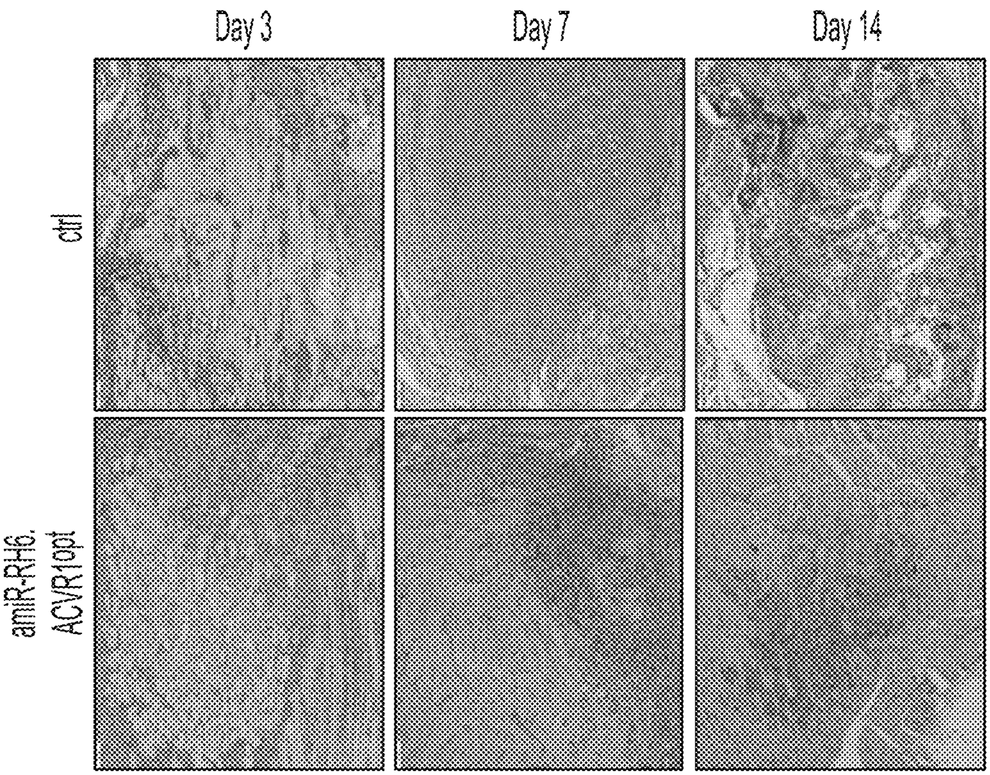
Figure 29C:
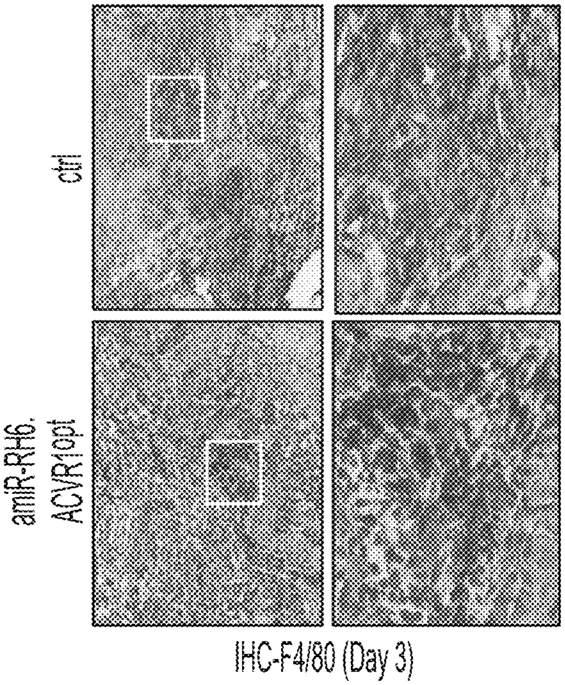

FIGS. 28A-28C show modification of the AAV vector genome to control the expression of therapeutic genes. FIG. 28A shows a schematic diagram of plasmid construction. CMV enhancer/chicken β-actin promoter (CBA), MBL intron (MBLi), β-globin polyA sequence (PA), and inverted terminal repeat (TR). miR-122: liver-specific miRNA, miR-208a: cardiac muscle-specific miRNA, TS: target sequence. miR-122/miR208a-TS is used to repress AAV's expression in the liver and heart. EndoID1-BRE: BMP-responsive elements. pNF-kB: inflammation-responsive elements. The promoter containing EndoID1-BRE/pNF-kB is used to induce AAV's expression in response to BMPs, activin A, and/or pro-inflammatory cytokines. FIG. 28B shows a schematic diagram of plasmid construction. FIG. 28C shows 6 week old wildtype mice were treated with i.v. injection of PBS or 5×10$^{13}$ vg/kg of rAAV9.egfp or rAAV9.egfp.MIR-TS and two weeks later, tissue distribution of AAV vectors were monitored by IVIS-100 optical imaging system using EGFP expression.

Figure 32A:
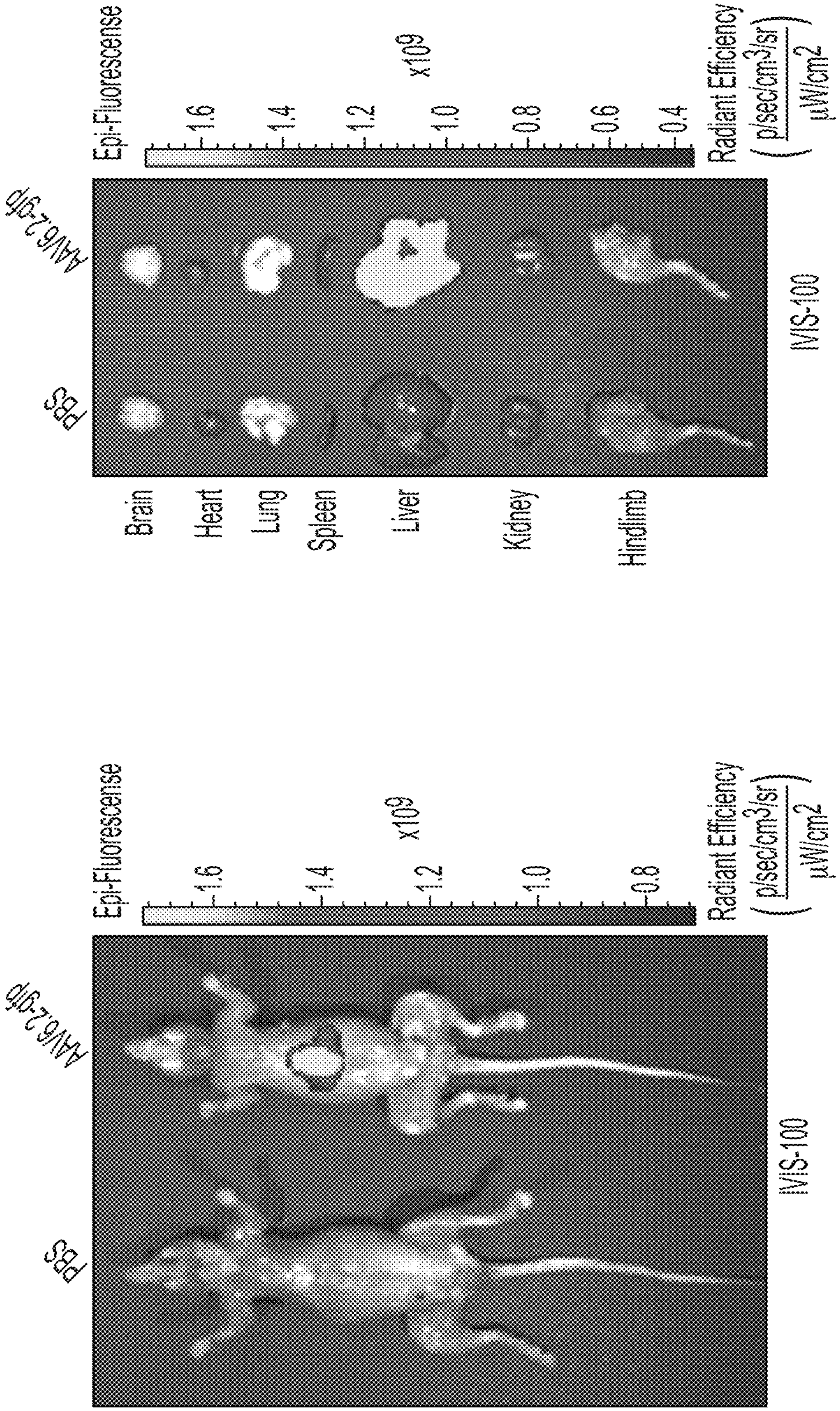
FIGS. 32A-32E show biodistribution of rAAV6.2 or rAAV9 in mice. $5\times10^{13}$ vg/kg of rAAV6.2.egfp alone (FIG. 32A) or together with vascular permeability agents (VP, human VEGF-166+sodium heparin+serum albumin, FIG. 32B) was i.v. injected into 2-month-old male mice (n=3) and two weeks later, tissue distribution of vectors was assessed by EGFP expression using IVIS-100 optical imaging system.
Figure 32B:
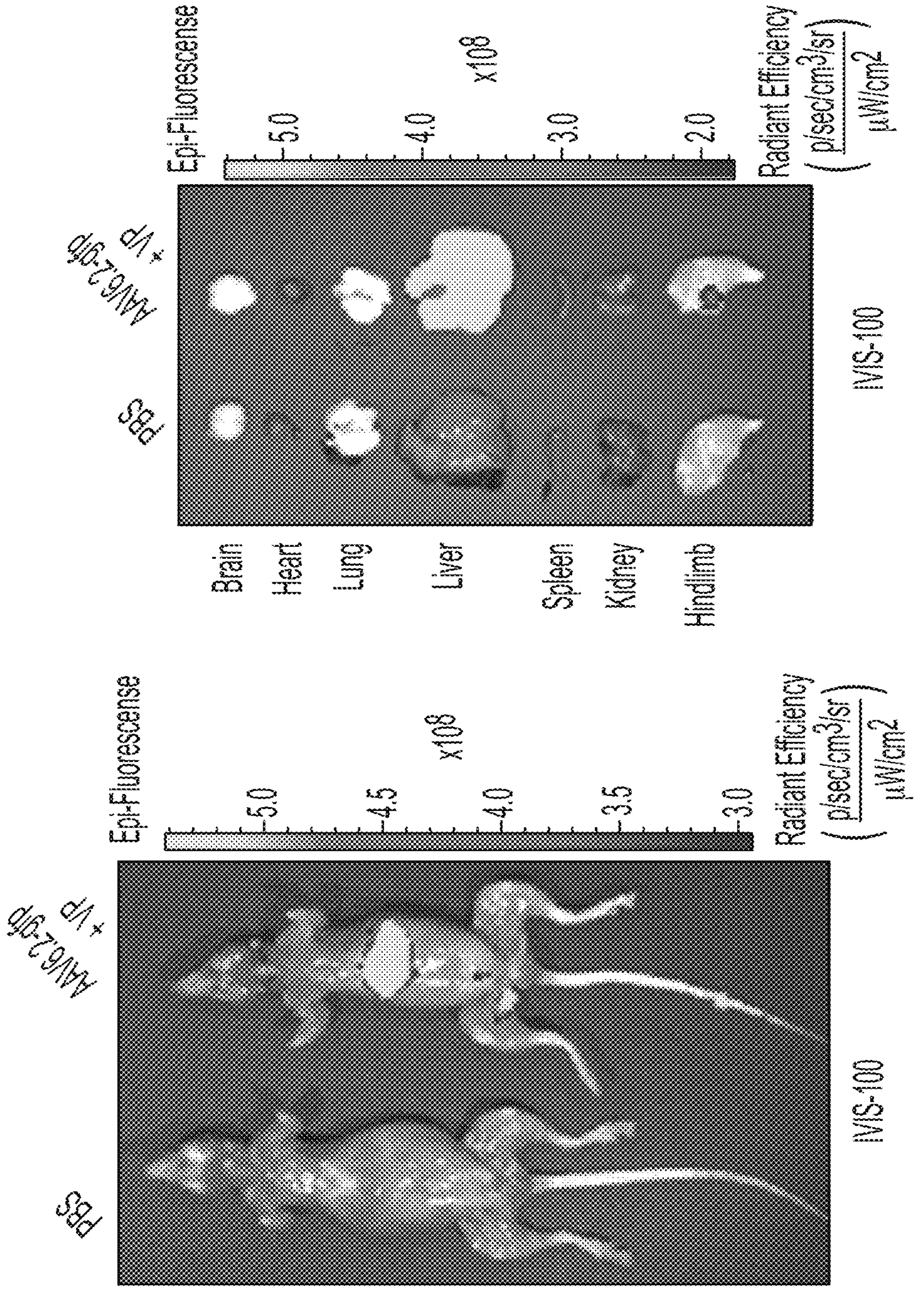
Figure 32C:
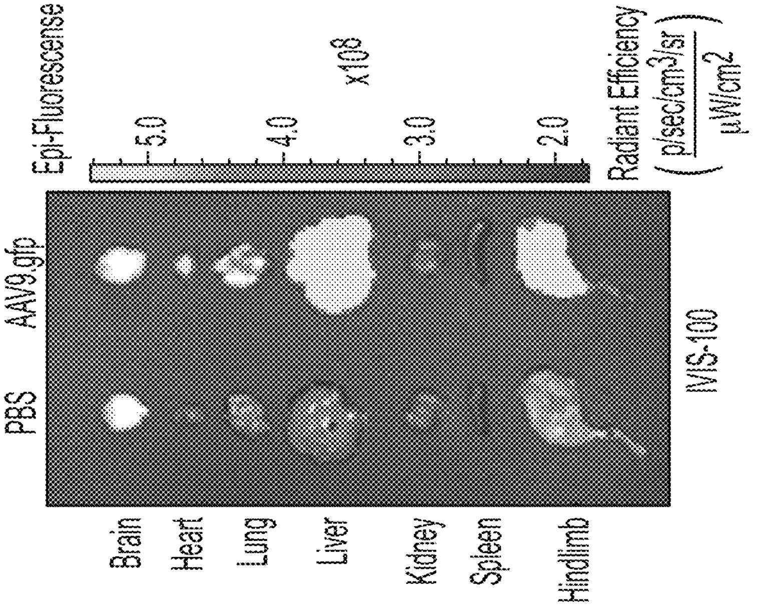
Figure 32D:
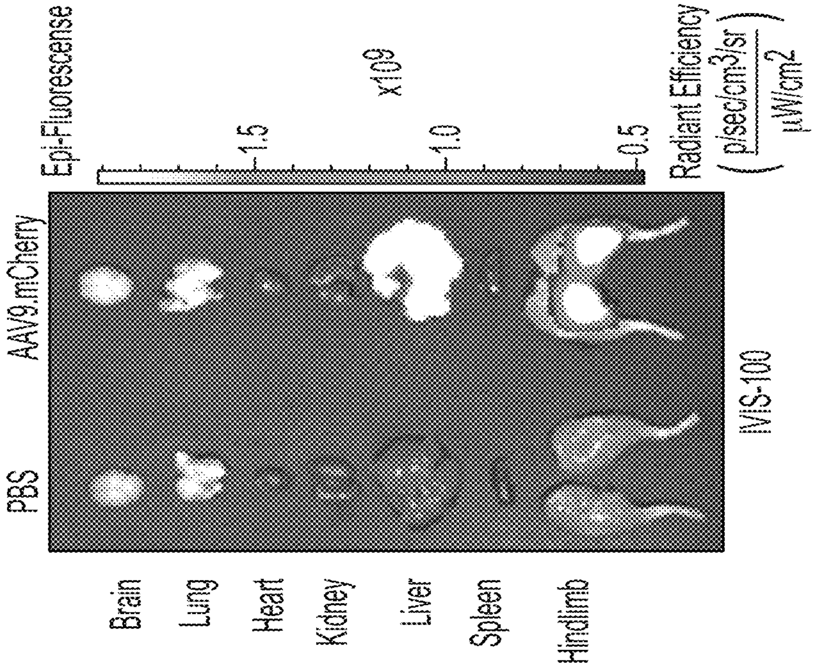
Figure 32E:
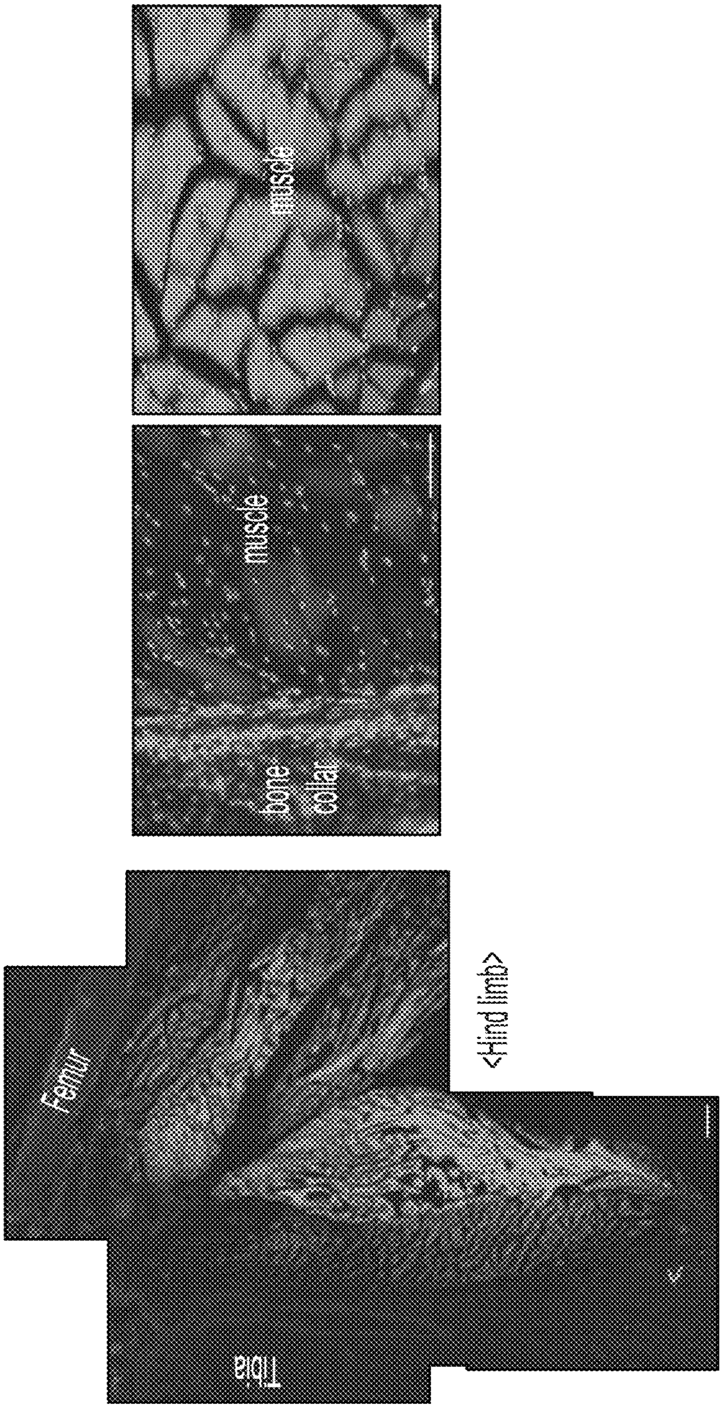

Example 8: In Vivo Therapeutic Effects of AAV Gene Therapeutics on Traumatic HO in FOP Mice The transduction efficiencies of rAAVs in vitro have been known to be challenging to predict the in vivo performance due to the presence of multiple physiological barriers, including the route of administration, serum factors, circulating neutralizing antibodies, and extracellular barriers. Therefore, to examine the ability of rAAV6.2 to transduce the skeletal muscle where HO primarily develops in FOP mice, rAAV6.2-egfp vector was intravenously (i.v.) injected into mice and EGFP expression in individual tissues was monitored by IVIS-100 optical imaging (FIG. 32A). It was observed that EGFP expression was only detected in the liver while the expression in the skeletal muscle was slightly increased when supplemented with vascular agents, including recombinant vascular endothelial growth factor (VEGF)-166, sodium heparin, and serum albumin (FIG. 32B). It has been previously shown that i.v. injection of rAAV9 vector transduces the skeletal muscle and intramuscular (i.m.) injection of rAAV9 is effective in transducing muscle-resident mesenchymal stem cells (MSCs, FIG. 32C). Since i.m. injection often causes HO lesions in FOP patients, interdermal (i.d.) delivery of rAAV9.mCherry to the tibial muscle using a hollow microneedle was examined, demonstrating the expression of mCherry throughout the muscle fiber (FIGS. 32D and 32E).

To examine the ability of i.d. injected rAAV9 to transduce HO-forming FAPs, a mouse model representing acquired forms of HO, muscle injury/BMP-induced HO, was employed in Tie2-cre; Rosa26$^{mcherrY}$ reporter mice that express mCherry in a subset of FAPs. One week after blunt muscle trauma and administration of recombinant BMP2/7, rAAV9.egfp was i.d. injected into the femoral muscle and three weeks later, HO and EGFP expression were assessed by X-radiography and fluorescence microscopy, respectively (FIG. 18A). EGFP was highly expressed in the femoral muscle as well as in Tie2$^{+}$ FAPs in the heterotopic bone (FIG. 6D), demonstrating that i.d. injected rAAV9 were effective in transducing myocytes and FAPs in the skeletal muscle during HO development. There was little to no EGFP expression in rAAV6.2-treated heterotopic bone (FIGS. 6A and 6B). To directly test whether i.d. delivery of rAAV9 can transduce HO-forming FAPs in FOP mice, a conditional knock-in model of ACVR1$^{(R206H)F1}$ was treated with i.d. injection of rAAC9 expressing the Cre recombinase and trauma-induced HO was assessed by microCT (FIG. 18C). Cre-mediated induction of ACVR1$^{R206H}$ mRNA in the femoral muscle was validated by RT-PCR analysis (FIG. 17F). This corresponds to heterotopic bone formation in the femoral muscle treated with rAAV9.Cre, not rAAV9.Vec (FIG. 17G), demonstrating the effectiveness of i.d. delivery of rAAV9 to HO-forming FAPs in the skeletal muscle. Finally, rAAV9 vectors carrying control vector, amiR-RH6, ACVR1$^{opt}$, or amiR-RH6.ACVR1$^{opt}$ were i.d. injected into the tibial muscle of Acvr1$^{(R206H)F1}$; Cre-ERT2 mice expressing a tamoxifen-induced Cre recombinase and knockdown efficiency of ACVR1$^{R206H}$ and ACVR1$^{opt}$ expression in the tibial muscle were validated (FIGS. 18D and 18E). Trauma-induced HO was substantially decreased by the treatment with therapeutic AAV vectors relative to control AAV vector (FIG. 19D), demonstrating that ACVR1$^{R206H}$-specific silencing, gene replacement, and the combinatory approaches were all effective in suppressing traumatic HO in young adult FOP mice. As BMP4-induced osteogenesis of Acvr1$^{R206H}$ BMSCs was not affected by amiR-RH6.ACVR1$^{opt}$ (FIG. 19D), there were little to no effects on muscle injury/BMP-induced HO (FIG. 17I), suggesting that therapeutic effects of the AAV vectors on traumatic HO are specific to ACVR1$^{R206H}$ receptor without affecting acquired forms of HO.

SEQUENCES

>Opt ACVR1 nucleic acid sequence

SEQ ID NO: 1 atggtcgatggagtgatgatcctgcctgtcctgattatgattgccctgcccagccccagcatggaagatgaaaaacctaaagtcaaccctaa
gctgtatatgtgcgtgtgcgagggcctgagctgcggaaacgaggatcactgcgagggccagcagtgtttcagctccctgtccatcaatgac
ggcttccacgtgtaccagaagggctgctttcaggtgtatgagcagggcaagatgacctgtaagacaccaccttccccaggacaggcagtg
gagtgctgtcagggcgattggtgtaaccggaatatcaccgcccagctgccaacaaagggcaagtctttccccggcacacagaactttcac
ctggaagtgggcctgatcatcctgagcgtggtgttcgccgtgtgcctgctggcatgtctgctgggagtggccctgagaaagtttaagcgga
gaaaccaggagcggctgaatccaagagatgtggagtacggcaccatcgagggcctgatcaccacaaatgtgggcgactctacactggc
cgacctgctggatcacagctgcaccagcggctccggatctggcctgccctttctggtgcagaggaccgtggcccggcagatcaccctgct
ggagtgcgtgggcaagggccggtacggagaagtgtggagaggatcctggcagggagagaacgtggcagtgaagatcttctctagccg
ggatgagaagtcttggtttagagagacagagctgtataacacagtgatgctgaggcacgagaatatcctgggcttcatcgcctccgacatg
acctctcgccactcctctacacagctgtggctgatcacccactaccacgagatgggctccctgtacgattacctccagctgaccacactgga
cacagtgtcttgcctgcggatcgtgctgtctatcgccagcggcctggcacacctgcacatcgagatctttggaacccagggcaagccagca
atcgcacacagagatctgaagtctaagaacatcctggtgaagaagaatggccagtgctgtatcgccgatctgggcctggccgtgatgcac
agccagtccaccaaccagctggacgtgggcaacaatcctcgggtgggcacaaagagatacatggccccagaggtgctggatgagacaa
tccaggtggactgcttcgatagctataagagggtggacatctgggcctttggcctggtgctgtgggaggtggcaaggaggatggtgagca
acggcatcgtggaggactacaagccacccttctatgacgtggtgcctaatgatccatcctttgaggacatgcgcaaggtggtgtgcgtggat
cagcagaggcccaacatccctaatcgctggttcagcgaccccaccctgacatccctggccaagctgatgaaggagtgttggtatcagaatc
ctagcgccaggctgaccgccctgcgcatcaagaaaactctgactaaaatcgacaatagcctggataaactgaaaaccgactgctga;

>AAV-CBA-opt-ACVR1 nucleic acid sequence

SEQ ID NO: 2 gctgcgcgctcgctcgctcactgaggccgcccgggcaaagcccgggcgtcgggcgacctttggtcgcccggcctcagtgagcgagcg
agcgcgcagagagggagtggccaactccatcactaggggttccttgtagttaatgattaacccgccatgctacttatctaccagggtaatgg
ggatcctctagaactatagctagtcgacattgattattgactagttattaatagtaatcaattacggggtcattagttcatagcccatatatggagt
tccgcgttacataacttacggtaaatggcccgcctggctgaccgcccaacgacccccgcccattgacgtcaataatgacgtatgttcccata
gtaacgccaatagggactttccattgacgtcaatgggtggagtatttacggtaaactgcccacttggcagtacatcaagtgtatcatatgccaa
gtacgccccctattgacgtcaatgacggtaaatggcccgcctggcattatgcccagtacatgaccttatgggactttcctacttggcagtacat
ctacgtattagtcatcgctattaccatggtcgaggtgagccccacgttctgcttcactctccccatctcccccccctccccacccccaattttgt
atttatttatttttttaattattttgtgcagcgatgggggcgggggggggggggggcgcgcgccaggcggggcggggcggggcgaggg
gcggggcggggcgaggcggagaggtgcggcggcagccaatcagagcggcgcgctccgaaagtttccttttatggcgaggcggcggc
ggcggcggccctataaaaagcgaagcgcgcggcgggcggggagtcgctgcgacgctgccttcgccccgtgccccgctccgccgccg
cctcgcgccgcccgccccggctctgactgaccgcgttactcccacaggtgagcgggcgggacggcccttctcctccgggctgtaattagc
gcttggtttaatgacggcttgtttcttttctgtggctgcgtgaaagccttgaggggctccgggagggccctttgtgcggggggagcggctcg
gggggtgcgtgcgtgtgtgtgtgcgtggggagcgccgcgtgcggctccgcgctgcccggcggctgtgagcgctgcgggcgcggcgc
ggggctttgtgcgctccgcagtgtgcgcgaggggagcgcggccgggggcggtgccccgcggtgcggggggggctgcgaggggaac
aaaggctgcgtgcggggtgtgtgcgtgggggggtgagcagggggtgtgggcgcgtcggtcgggctgcaacccccccctgcacccccct
ccccgagttgctgagcacggcccggcttcgggtgcggggctccgtacggggcgtggcgcggggctcgccgtgccgggcgggggtg
gcggcaggtgggggtgccgggcggggcggggccgcctcgggccggggagggctcgggggagggcgcggcggcccccggagc
gccggcggctgtcgaggcgcggcgagccgcagccattgccttttatggtaatcgtgcgagagggcgcagggacttcctttgtcccaaatct
gtgcggagccgaaatctgggaggcgccgccgcacccccctctagcgggcgcggggcgaagcggtgcggcgccggcaggaaggaaat
gggcggggagggccttcgtgcgtcgccgcgccgccgtccccttctccctctccagcctcggggctgtccgcgggggggacggctgccttc
gggggggacggggcagggcggggttcggcttctggcgtgtgaccggcggctctagagcctctgctaaccatgttcatgccttcttctttttc -continued ctacagctcctgggcaacgtgctggttattgtgctgtctcatcattttggcaaagaattccgccaccatggtcgatggagtgatgatcctgcct gtcctgattatgattgccctgcccagccccagcatggaagatgaaaaacctaaagtcaaccctaagctgtatatgtgcgtgtgcgagggcct gagctgcggaaacgaggatcactgcgagggccagcagtgtttcagctccctgtccatcaatgacggcttccacgtgtaccagaagggctg ctttcaggtgtatgagcagggcaagatgacctgtaagacaccaccttccccaggacaggcagtggagtgctgtcagggcgattggtgtaa ccggaatatcaccgcccagctgccaacaaagggcaagtctttccccggcacacagaactttcacctggaagtgggcctgatcatcctgag cgtggtgttcgccgtgtgcctgctggcatgtctgctgggagtggccctgagaaagtttaagcggagaaaccaggagcggctgaatccaag agatgtggagtacggcaccatcgagggcctgatcaccacaaatgtgggcgactctacactggccgacctgctggatcacagctgcacca gcggctccggatctggcctgccctttctggtgcagaggaccgtggcccggcagatcaccctgctggagtgcgtgggcaagggccggtac ggagaagtgtggagaggatcctggcagggagagaacgtggcagtgaagatcttctctagccgggatgagaagtcttggtttagagagac agagctgtataacacagtgatgctgaggcacgagaatatcctgggcttcatcgcctccgacatgacctctcgccactcctctacacagctgt ggctgatcacccactaccacgagatgggctccctgtacgattacctccagctgaccacactggacacagtgtcttgcctgcggatcgtgctg tctatcgccagcggcctggcacacctgcacatcgagatctttggaacccagggcaagccagcaatcgcacacagagatctgaagtctaag aacatcctggtgaagaagaatggccagtgctgtatcgccgatctgggcctggccgtgatgcacagccagtccaccaaccagctggacgtg ggcaacaatcctcgggtgggcacaaagagatacatggccccagaggtgctggatgagacaatccaggtggactgcttcgatagctataa gagggtggacatctgggcctttggcctggtgctgtgggaggtggcaaggaggatggtgagcaacggcatcgtggaggactacaagcca cccttctatgacgtggtgcctaatgatccatcctttgaggacatgcgcaaggtggtgtgcgtggatcagcagaggcccaacatccctaatcg ctggttcagcgaccccaccctgacatccctggccaagctgatgaaggagtgttggtatcagaatcctagcgccaggctgaccgccctgcg catcaagaaaactctgactaaaatcgacaatagcctggataaactgaaaaccgactgctgacctgaggatccgatctattccctctgccaaa aattatggggacatcatgaagccccttgagcatctgacttctggctaataaaggaaatttattttcattgcaatagtgtgttggaattattgtgtct ctcactcggaagcaattcgttgatctgaatttcgaccacccataatacccattaccctggtagataagtagcatggcgggttaatcattaactac aaggaacccctagtgatggagttggccactccctctctgcgcgctcgctcgctcactgaggccgggcgaccaaaggtcgcccgacgccc gggctttgcccgggcggcctcagtgagcgagcgagcgcgcagccttaattaacctaattcactggccgtcgttttacaacgtcgtgactgg gaaaaccctggcgttacccaacttaatcgccttgcagcacatccccctttcgccagctggcgtaatagcgaagaggcccgcaccgatcgc ccttcccaacagttgcgcagcctgaatggcgaatgggacgcgccctgtagcggcgcattaagcgcggcgggtgtggtggttacgcgcag cgtgaccgctacacttgccagcgccctagcgcccgctcctttcgctttcttcccttcctttctcgccacgttcgccggctttccccgtcaagctc taaatcgggggctccctttagggttccgatttagtgctttacggcacctcgaccccaaaaaacttgattagggtgatggttcacgtagtgggc catcgccctgatagacggtttttcgccctttgacgttggagtccacgttctttaatagtggactcttgttccaaactggaacaacactcaaccct a tctcggtctattcttttgatttataagggattttgccgatttcggcctattggttaaaaaatgagctgatttaacaaaaatttaacgcgaattttaaca aaatattaacgcttacaatttaggtggcacttttcggggaaatgtgcgcggaacccctatttgtttatttttctaaatacattcaaatatgtatccgc tcatgagacaataaccctgataaatgcttcaataatattgaaaaaggaagagtatgattgaacaagatggattgcacgcaggttctccggccg cttgggtggagaggctattcggctatgactgggcacaacagacaatcggctgctctgatgccgccgtgttccggctgtcagcgcaggggc gcccggttctttttgtcaagaccgacctgtccggtgccctgaatgaactgcaagacgaggcagcgcggctatcgtggctggccacgacgg gcgttccttgcgcagctgtgctcgacgttgtcactgaagcgggaagggactggctgctattgggcgaagtgccggggcaggatctcctgtc atctcaccttgctcctgccgagaaagtatccatcatggctgatgcaatgcggcggctgcatacgcttgatccggctacctgcccattcgacca ccaagcgaaacatcgcatcgagcgagcacgtactcggatggaagccggtcttgtcgatcaggatgatctggacgaagagcatcaggggc tcgcgccagccgaactgttcgccaggctcaaggcgagcatgcccgacggcgaggatctcgtcgtgacccatggcgatgcctgcttgccg aatatcatggtggaaaatggccgcttttctggattcatcgactgtggccggctgggtgtggcggaccgctatcaggacatagcgttggctac ccgtgatattgctgaagagcttggcggcgaatgggctgaccgcttcctcgtgctttacggtatcgccgctcccgattcgcagcgcatcgcctt ctatcgccttcttgacgagttcttctgataactgtcagaccaagtttactcatatatactttagattgatttaaaacttcatttttaatttaaaaggatct aggtgaagatcctttttgataatctcatgaccaaaatcccttaacgtgagttttcgttccactgagcgtcagaccccgtagaaaagatcaaagg atcttcttgagatcctttttttctgcgcgtaatctgctgcttgcaaacaaaaaaaccaccgctaccagcggtggtttgtttgccggatcaagagct -continued accaactctttttccgaaggtaactggcttcagcagagcgcagataccaaatactgttcttctagtgtagccgtagttaggccaccacttcaag aactctgtagcaccgcctacatacctcgctctgctaatcctgttaccagtggctgctgccagtggcgataagtcgtgtcttaccgggttggact caagacgatagttaccggataaggcgcagcggtcgggctgaacggggggttcgtgcacacagcccagcttggagcgaacgacctacac cgaactgagatacctacagcgtgagctatgagaaagcgccacgcttcccgaagggagaaaggcggacaggtatccggtaagcggcag ggtcggaacaggagagcgcacgagggagcttccagggggaaacgcctggtatctttatagtcctgtcgggtttcgccacctctgacttgag cgtcgatttttgtgatgctcgtcaggggggcggagcctatggaaaaacgccagcaacgcggcctttttacggttcctggccttttgctggcct tttgctcacatgttctttcctgcgttatcccctgattctgtggataaccgtattaccgcctttgagtgagctgataccgctcgccgcagccgaacg accgagcgcagcgagtcagtgagcgaggaagcggaagagcgcccaatacgcaaaccgcctctccccgcgcgttggccgattcattaat gcagctggcacgacaggtttcccgactggaaagcgggcagtgagcgcaacgcaattaatgtgagttagctcactcattaggcaccccagg ctttacactttatgcttccggctcgtatgttgtgtggaattgtgagcggataacaatttcacacaggaaacagctatgaccatgattacgccaga tttaattaaggccttaattag >AAV-CBA-MBL-opt-ACVR1 nucleic acid sequence

SEQ ID NO: 3 cttaattaggctgcgcgctcgctcgctcactgaggccgcccgggcaaagcccgggcgtcgggcgacctaggtcgcccggcctcagtga gcgagcgagcgcgcagagagggagtggccaactccatcactaggggaccagtagttaatgattaacccgccatgctacttatctaccag ggtaatggggatcctctagaactatagctagtcgacattgattattgactagttattaatagtaatcaattacggggtcattagttcatagcccat atatggagaccgcgttacataacttacggtaaatggcccgcctggctgaccgcccaacgacccccgcccattgacgtcaataatgacgtat gttcccatagtaacgccaatagggactaccattgacgtcaatgggtggagtatttacggtaaactgcccacttggcagtacatcaagtgtatc atatgccaagtacgccccctattgacgtcaatgacggtaaatggcccgcctggcattatgcccagtacatgaccttatgggactacctacttg gcagtacatctacgtattagtcatcgctattaccatgtcgaggccacgttctgcttcactctccccatctcccccccctccccacccccaattttg tatttatttattttttaattattttgtgcagcgatgggggcgggggggggggggcgcgcgccaggcggggcggggcggggcgaggggcgg ggcggggcgaggcggagaggtgcggcggcagccaatcagagcggcgcgctccgaaagtttccttttatggcgaggcggcggcggcg gcggccctataaaaagcgaagcgcgcggcgggcgggagcaagctttcagatcgcctggagacgccatccacgctgttttgacctccata gaagacaccgggaccgatccagcctccgcggccgggaacggtgcattggaacgcggattccccgtgccaagagtgacgtaagtaccg cctatagagtctataggcccacccccttggcttcttatgcatgctatactgtttttggcttggggtctatacacccccgcttcctcatgtttgctgc ccgtgaccagcacgtcaacgattttgtgggcacgggcgacaccgcagtgtagtctgagcagtactcgttgctgccgcgcgcgccaccag acataatagctgacagactaacagactgttcctttccatgggtcttttctgcagtcaccgtcgccgccaccggtgaattccgccaccatggtc gatggagtgatgatcctgcctgtcctgattatgattgccctgcccagccccagcatggaagatgaaaaacctaaagtcaaccctaagctgtat atgtgcgtgtgcgagggcctgagctgcggaaacgaggatcactgcgagggccagcagtgtttcagctccctgtccatcaatgacggcttc cacgtgtaccagaagggctgctttcaggtgtatgagcagggcaagatgacctgtaagacaccaccttccccaggacaggcagtggagtg ctgtcagggcgattggtgtaaccggaatatcaccgcccagctgccaacaaagggcaagtctttccccggcacacagaactttcacctggaa gtgggcctgatcatcctgagcgtggtgttcgccgtgtgcctgctggcatgtctgctgggagtggccctgagaaagtttaagcggagaaacc aggagcggctgaatccaagagatgtggagtacggcaccatcgagggcctgatcaccacaaatgtgggcgactctacactggccgacctg ctggatcacagctgcaccagcggctccggatctggcctgccctttctggtgcagaggaccgtggcccggcagatcaccctgctggagtgc gtgggcaagggccggtacggagaagtgtggagaggatcctggcagggagagaacgtggcagtgaagatcttctctagccgggatgag aagtcttggtttagagagacagagctgtataacacagtgatgctgaggcacgagaatatcctgggcttcatcgcctccgacatgacctctcg ccactcctctacacagctgtggctgatcacccactaccacgagatgggctccctgtacgattacctccagctgaccacactggacacagtgt cttgcctgcggatcgtgctgtctatcgccagcggcctggcacacctgcacatcgagatctttggaacccagggcaagccagcaatcgcac acagagatctgaagtctaagaacatcctggtgaagaagaatggccagtgctgtatcgccgatctgggcctggccgtgatgcacagccagt ccaccaaccagctggacgtgggcaacaatcctcgggtgggcacaaagagatacatggccccagaggtgctggatgagacaatccaggt ggactgcttcgatagctataagagggtggacatctgggcctttggcctggtgctgtgggaggtggcaaggaggatggtgagcaacggcat cgtggaggactacaagccacccttctatgacgtggtgcctaatgatccatcctttgaggacatgcgcaaggtggtgtgcgtggatcagcag -continued aggcccaacatccctaatcgctggttcagcgaccccaccctgacatccctggccaagctgatgaaggagtgttggtatcagaatcctagcg ccaggctgaccgccctgcgcatcaagaaaactctgactaaaatcgacaatagcctggataaactgaaaaccgactgctgacctgaggatc cgatctttttccctctgccaaaaattatggggacatcatgaagccccttgagcatctgacttctggctaataaaggaaatttattttcattgcaata gtgtgttggaattttttgtgtctctcactcggaagcaattcgttgatctgaatttcgaccacccataatacccattaccctggtagataagtagcat ggcgggttaatcattaactacaaggaacccctagtgatggagttggccactccctctctgcgcgctcgctcgctcactgaggccgggcgac caaaggtcgcccgacgcccgggctttgcccgggcggcctcagtgagcgagcgagcgcgcagccttaattaacctaattcactggccgtc gttttacaacgtcgtgactgggaaaaccctggcgttacccaacttaatcgccttgcagcacatccccctttcgccagctggcgtaatagcgaa gaggcccgcaccgatcgcccttcccaacagttgcgcagcctgaatggcgaatgggacgcgccctgtagcggcgcattaagcgcggcgg gtgtggtggttacgcgcagcgtgaccgctacacttgccagcgccctagcgcccgctcctttcgctttcttcccttcctttctcgccacgttcgc cggctttccccgtcaagctctaaatcgggggctccctttagggttccgatttagtgctttacggcacctcgaccccaaaaaacttgattagggt gatggttcacgtagtgggccatcgccctgatagacggtttttcgccctttgacgttggagtccacgttctttaatagtggactcttgttccaaact ggaacaacactcaaccctatctcggtctattcttttgatttataagggattttgccgatttcggcctattggttaaaaaatgagctgatttaacaaa aatttaacgcgaattttaacaaaatattaacgcttacaatttaggtggcacttttcggggaaatgtgcgcggaacccctatttgtttatttttctaaa tacattcaaatatgtatccgctcatgagacaataaccctgataaatgcttcaataatattgaaaaaggaagagtatgagtattcaacatttccgtg tcgcccttattcccttttttgcggcattttgccttcctgtttttgctcacccagaaacgctggtgaaagtaaaagatgctgaagatcagttgggtgc acgagtgggttacatcgaactggatctcaacagcggtaagatccttgagagttttcgccccgaagaacgttttccaatgatgagcacttttaaa gttctgctatgtggcgcggtattatcccgtattgacgccgggcaagagcaactcggtcgccgcatacactattctcagaatgacttggttgag tactcaccagtcacagaaaagcatcttacggatggcatgacagtaagagaattatgcagtgctgccataaccatgagtgataacactgcgg ccaacttacttctgacaacgatcggaggaccgaaggagctaaccgcttttttgcacaacatgggggatcatgtaactcgccttgatcgttggg aaccggagctgaatgaagccataccaaacgacgagcgtgacaccacgatgcctgtagcaatggcaacaacgttgcgcaaactattaactg gcgaactacttactctagcttcccggcaacaattaatagactggatggaggcggataaagttgcaggaccacttctgcgctcggcccttccg gctggctggtttattgctgataaatctggagccggtgagcgtgggtctcgcggtatcattgcagcactggggccagatggtaagccctcccg tatcgtagttatctacacgacggggagtcaggcaactatggatgaacgaaatagacagatcgctgagataggtgcctcactgattaagcatt ggtaactgtcagaccaagtttactcatatatactttagattgatttaaaacttcatttttaatttaaaaggatctaggtgaagatcctttttgataatct catgaccaaaatcccttaacgtgagttttcgttccactgagcgtcagaccccgtagaaaagatcaaaggatcttcttgagatcctttttttctgcg cgtaatctgctgcttgcaaacaaaaaaaccaccgctaccagcggtggtttgtttgccggatcaagagctaccaactctttttccgaaggtaact ggcttcagcagagcgcagataccaaatactgttcttctagtgtagccgtagttaggccaccacttcaagaactctgtagcaccgcctacatac ctcgctctgctaatcctgttaccagtggctgctgccagtggcgataagtcgtgtcttaccgggttggactcaagacgatagttaccggataag gcgcagcggtcgggctgaacggggggttcgtgcacacagcccagcttggagcgaacgacctacaccgaactgagatacctacagcgtg agctatgagaaagcgccacgcttcccgaagggagaaaggcggacaggtatccggtaagcggcagggtcggaacaggagagcgcacg agggagcttccagggggaaacgcctggtatctttatagtcctgtcgggtttcgccacctctgacttgagcgtcgatttttgtgatgctcgtcag gggggcggagcctatggaaaaacgccagcaacgcggcctttttacggttcctggccttttgctggccttttgctcacatgttctttcctgcgtta tcccctgattctgtggataaccgtattaccgcctttgagtgagctgataccgctcgccgcagccgaacgaccgagcgcagcgagtcagtga gcgaggaagcggaagagcgcccaatacgcaaaccgcctctccccgcgcgttggccgattcattaatgcagctggcacgacaggtttccc gactggaaagcgggcagtgagcgcaacgcaattaatgtgagttagctcactcattaggcaccccaggctttacactttatgcttccggctcgt atgttgtgtggaattgtgagcggataacaatttcacacaggaaacagctatgaccatgattacgccagatttaattaaggc;

>AAV-PBP (synthetic intron)-opt-ACVR1 nucleic acid sequence

SEQ ID NO: 4 cttaattaggctgcgcgctcgctcgctcactgaggccgcccgggcaaagcccgggcgtcgggcgacctttggtcgcccggcctcagtga gcgagcgagcgcgcagagagggagtggccaactccatcactaggggttccttgtagttaatgattaacccgccatgctacttatctaccag ggtaatggggatcctctagaactatagctagtcgacattgattattgactagttattaatagtaatcaattacggggtcattagttcatagcccat atatggagttccgcgttacataacttacggtaaatggcccgcctggctgaccgcccaacgacccccgcccattgacgtcaataatgacgtat -continued gttcccatagtaacgccaatagggactttccattgacgtcaatgggtggagtatttacggtaaactgcccacttggcagtacatcaagtgtatc atatgccaagtacgccccctattgacgtcaatgacggtaaatggcccgcctggcattatgcccagtacatgaccttatgggactttcctacttg gcagtacatctacgtattagtcatcgctattaccatgtcgaggccacgttctgcttcactctccccatctcccccccctccccacccccaattttg tatttatttattttttaattattttgtgcagcgatgggggcgggggggggggggcgcgcgccaggcggggcggggcggggcgaggggcgg ggcggggcgaggcggagaggtgcggcggcagccaatcagagcggcgcgctccgaaagtttccttttatggcgaggcggcggcggcg gcggccctataaaaagcgaagcgcgcggcgggcgggagcaccaccgcggtggcggccctagagtcgatcgaggaactgaaaaacca gaaagttaactggtaagtttagtctttttgtcttttatttcaggtcccggatccggtggtggtgcaaatcaaagaactgctcctcagtggatgttgc ctttacttctaggcctgtacggaagtgttacttctgctctaaaagctgcggaattgtacccgcggccgatccaccggtgaattccgccaccatg gtcgatggagtgatgatcctgcctgtcctgattatgattgccctgcccagccccagcatggaagatgaaaaacctaaagtcaaccctaagct gtatatgtgcgtgtgcgagggcctgagctgcggaaacgaggatcactgcgagggccagcagtgtttcagctccctgtccatcaatgacgg cttccacgtgtaccagaagggctgctttcaggtgtatgagcagggcaagatgacctgtaagacaccaccttccccaggacaggcagtgga gtgctgtcagggcgattggtgtaaccggaatatcaccgcccagctgccaacaaagggcaagtctttccccggcacacagaactttcacctg gaagtgggcctgatcatcctgagcgtggtgttcgccgtgtgcctgctggcatgtctgctgggagtggccctgagaaagtttaagcggagaa accaggagcggctgaatccaagagatgtggagtacggcaccatcgagggcctgatcaccacaaatgtgggcgactctacactggccga cctgctggatcacagctgcaccagcggctccggatctggcctgccctttctggtgcagaggaccgtggcccggcagatcaccctgctgga gtgcgtgggcaagggccggtacggagaagtgtggagaggatcctggcagggagagaacgtggcagtgaagatcttctctagccgggat gagaagtcttggtttagagagacagagctgtataacacagtgatgctgaggcacgagaatatcctgggcttcatcgcctccgacatgacctc tcgccactcctctacacagctgtggctgatcacccactaccacgagatgggctccctgtacgattacctccagctgaccacactggacaca gtgtcttgcctgcggatcgtgctgtctatcgccagcggcctggcacacctgcacatcgagatctttggaacccagggcaagccagcaatcg cacacagagatctgaagtctaagaacatcctggtgaagaagaatggccagtgctgtatcgccgatctgggcctggccgtgatgcacagcc agtccaccaaccagctggacgtgggcaacaatcctcgggtgggcacaaagagatacatggccccagaggtgctggatgagacaatcca ggtggactgcttcgatagctataagagggtggacatctgggcctttggcctggtgctgtgggaggtggcaaggaggatggtgagcaacgg catcgtggaggactacaagccacccttctatgacgtggtgcctaatgatccatcctttgaggacatgcgcaaggtggtgtgcgtggatcagc agaggcccaacatccctaatcgctggttcagcgaccccaccctgacatccctggccaagctgatgaaggagtgttggtatcagaatcctag cgccaggctgaccgccctgcgcatcaagaaaactctgactaaaatcgacaatagcctggataaactgaaaaccgactgctgacctgaggg cggccgcgtcgacggatccgatcttttttccctctgccaaaaattatggggacatcatgaagccccttgagcatctgacttctggctaataaag gaaatttattttcattgcaatagtgtgttggaattttttgtgtctctcactcggaagcaattcgttgatctgaatttcgaccacccataatacccatta ccctggtagataagtagcatggcgggttaatcattaactacaaggaacccctagtgatggagttggccactccctctctgcgcgctcgctcg ctcactgaggccgggcgaccaaaggtcgcccgacgcccgggctttgcccgggcggcctcagtgagcgagcgagcgcgcagccttaatt aacctaattcactggccgtcgttttacaacgtcgtgactgggaaaaccctggcgttacccaacttaatcgccttgcagcacatccccctttcgc cagctggcgtaatagcgaagaggcccgcaccgatcgcccttcccaacagttgcgcagcctgaatggcgaatgggacgcgccctgtagc ggcgcattaagcgcggcgggtgtggtggttacgcgcagcgtgaccgctacacttgccagcgccctagcgcccgctcctttcgctttcttcc cttcctttctcgccacgttcgccggctttccccgtcaagctctaaatcgggggctccctttagggttccgatttagtgctttacggcacctcgac cccaaaaaacttgattagggtgatggttcacgtagtgggccatcgccctgatagacggtttttcgccctttgacgttggagtccacgttctttaa tagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgcttacaatttaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaaga tgctgaagatcagttgggtgcacgagtgggttacatcgaactggatctcaacagcggtaagatccttgagagttttcgccccgaagaacgttt tccaatgatgagcacttttaaagttctgctatgtggcgcggtattatcccgtattgacgccgggcaagagcaactcggtcgccgcatacacta ttctcagaatgacttggttgagtactcaccagtcacagaaaagcatcttacggatggcatgacagtaagagaattatgcagtgctgccataac -continued catgagtgataacactgcggccaacttacttctgacaacgatcggaggaccgaaggagctaaccgcttttttgcacaacatgggggatcat gtaactcgccttgatcgttgggaaccggagctgaatgaagccataccaaacgacgagcgtgacaccacgatgcctgtagcaatggcaaca acgttgcgcaaactattaactggcgaactacttactctagcttcccggcaacaattaatagactggatggaggcggataaagttgcaggacc acttctgcgctcggcccttccggctggctggtttattgctgataaatctggagccggtgagcgtgggtctcgcggtatcattgcagcactggg gccagatggtaagccctcccgtatcgtagttatctacacgacggggagtcaggcaactatggatgaacgaaatagacagatcgctgagata ggtgcctcactgattaagcattggtaactgtcagaccaagtttactcatatatactttagattgatttaaaacttcatttttaatttaaaaggatctag gtgaagatcctttttgataatctcatgaccaaaatcccttaacgtgagttttcgttccactgagcgtcagaccccgtagaaaagatcaaaggat cttcttgagatcctttttttctgcgcgtaatctgctgcttgcaaacaaaaaaaccaccgctaccagcggtggtttgtttgccggatcaagagcta ccaactctttttccgaaggtaactggcttcagcagagcgcagataccaaatactgttcttctagtgtagccgtagttaggccaccacttcaaga actctgtagcaccgcctacatacctcgctctgctaatcctgttaccagtggctgctgccagtggcgataagtcgtgtcttaccgggttggactc aagacgatagttaccggataaggcgcagcggtcgggctgaacggggggttcgtgcacacagcccagcttggagcgaacgacctacacc gaactgagatacctacagcgtgagctatgagaaagcgccacgcttcccgaagggagaaaggcggacaggtatccggtaagcggcagg gtcggaacaggagagcgcacgagggagcttccagggggaaacgcctggtatctttatagtcctgtcgggtttcgccacctctgacttgagc gtcgatttttgtgatgctcgtcaggggggcggagcctatggaaaaacgccagcaacgcggcctttttacggttcctggccttttgctggccttt tgctcacatgttctttcctgcgttatcccctgattctgtggataaccgtattaccgcctttgagtgagctgataccgctcgccgcagccgaacga ccgagcgcagcgagtcagtgagcgaggaagcggaagagcgcccaatacgcaaaccgcctctccccgcgcgttggccgattcattaatg cagctggcacgacaggtttcccgactggaaagcgggcagtgagcgcaacgcaattaatgtgagttagctcactcattaggcaccccaggc tttacactttatgcttccggctcgtatgttgtgtggaattgtgagcggataacaatttcacacaggaaacagctatgaccatgattacgccagatt taattaaggc;

>Nucleic acid sequence encoding RH1 ami-RNA

SEQ ID NO: 5 gtcttttatttcaggtcccagatctagggctctgcgtttgctccaggtagtccgctgctcccttgggcctgggcccactgacagccctggtgcc tctggccggctgcacacctcctggcgggcagctgtgagtgtaatctggtgagccacttgttctggcaatacctgagtggctctgcggattac actcacggaggcctgccctgactgcccacggtgccgtggccaaagaggatctaagggcaccgctgagggcctacctaaccatcgtggg gaataaggacagtgtcacccctgcaggggatccggtggtggtgc;

>Nucleic acid sequence encoding RH2 ami-RNA

SEQ ID NO: 6 agggctctgcgtttgctccaggtagtccgctgctcccttgggcctgggcccactgacagccctggtgcctctggccggctgcacacctcct ggcgggcagctgtgagtgtaagctggtgagccacttgttctggcaatacctgagtggctctgcggcttacactcacggaggcctgccctga ctgcccacggtgccgtggccaaagaggatctaagggcaccgctgagggcctacctaaccatcgtggggaataaggacagtgtcaccc;

>wtACVR1 nucleic acid sequence

SEQ ID NO: 7 tcgagggtacaaagaacagtggctcgccagattacactgttggagtgc;

>ACVR1-R206H nucleic acid sequence

SEQ ID NO: 8 tcgagggtacaaagaacagtggctcaccagattacactgttggagtgc;

>ACVR1-optAVCR1 nucleic acid sequence

SEQ ID NO: 9 tcgagggtgcagaggaccgtggcccggcagatcaccctgctggagtgc;

>AAVscCB6 (amiR33-ACVR1-A7) EGFP nucleic acid sequence

SEQ ID NO: 10 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag -continued gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgagtgtaatctggtgagccacttgttctggcaatacctgagtggctctgcggattacac tcacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa -continued aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A7-14) EGFP nucleic acid sequence

SEQ ID NO: 11 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg gggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctattgt cttttatttcaggtcccagatctagggctctgcgtttgctccaggtagtccgctgctcccttgggcctgggcccactgacagccctggtgcctc tggccggctgcacacctcctggcgggcagctgtgagtgtaagctggtgagccacttgttctggcaatacctgagtggctctgcggcttaca ctcacggaggcctgccctgactgcccacggtgccgtggccaaagaggatctaagggcaccgctgagggcctacctaaccatcgtgggg aataaggacagtgtcacccctgcaggggatccggtggtggtgcaaatcaaagaactgctcctcagtggatgttgcctttacttctaggcctgt acggaagtgttacttctgctctaaaagctgcggaattgtacccgcggccgatccaccggtcgccaccatggtgagcaagggcgaggagct gttcaccggggtggtgcccatcctggtcgagctggacggcgacgtaaacggccacaagttcagcgtgtccggcgagggcgagggcgat gccacctacggcaagctgaccctgaagttcatctgcaccaccggcaagctgcccgtgccctggcccaccctcgtgaccaccctgacctac ggcgtgcagtgcttcagccgctaccccgaccacatgaagcagcacgacttcttcaagtccgccatgcccgaaggctacgtccaggagcg caccatcttcttcaaggacgacggcaactacaagacccgcgccgaggtgaagttcgagggcgacaccctggtgaaccgcatcgagctga agggcatcgacttcaaggaggacggcaacatcctggggcacaagctggagtacaactacaacagccacaacgtctatatcatggccgac aagcagaagaacggcatcaaggtgaacttcaagatccgccacaacatcgaggacggcagcgtgcagctcgccgaccactaccagcag aacacccccatcggcgacggccccgtgctgctgcccgacaaccactacctgagcacccagtccgccctgagcaaagaccccaacgaga agcgcgatcacatggtcctgctggagttcgtgaccgccgccgggatcactctcggcatggacgagctgtacaagtaaagcggccatcaa gcttatcgataccgtcgactagagctcgctgatcagcctcgactgtgccttctagttgccagccatctgttgtttgcccctcccccgtgccttcc ttgaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatcccccttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg -continued ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A8) EGFP nucleic acid sequence

SEQ ID NO: 12 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctattgt cttttatttcaggtcccagatctagggctctgcgtttgctccaggtagtccgctgctcccttgggcctgggcccactgacagccctggtgcctc tggccggctgcacacctcctggcgggcagctgtggtgtaatctggtgagccactgtgttctggcaatacctgcagtggctgtctagattaca ccacggaggcctgccctgactgcccacggtgccgtggccaaagaggatctaagggcaccgctgagggcctacctaaccatcgtgggga -continued ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttattgcggcattttg ccttcctgatttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt -continued attaccgcctttgagtgagctgataccgctcgccgcagccgaacgaccgagcgcagcgagtcagtgagcgaggaagcggaagagcgc
ccaatacgcaaaccgcctctccccgcgcgttggccgattcattaatgcagctggcacgacaggtttcccgactggaaagcgggcagtgag
cgcaacgcaattaatgtgagttagctcactcattaggcaccccaggctttacactttatgcttccggctcgtatgttgtgtggaattgtgagcgg
ataacaatttcacacaggaaacagctatgaccatgattacgccagatttaattaaggccttaattagg;

>AAVscCB6 (amiR33-ACVR1-A8-14) EGFP nucleic acid sequence

SEQ ID NO: 13 ctgcgcgctcgctcgctcactgaggccgcccgggcaaagcccgggcgtcgggcgacctttggtcgcccggcctcagtgagcgagcga
gcgcgcagagagggagtgtagccatgctctaggaagatcaattcggtacaattcacgcgtcgacattgattattgactagctctggtcgttac
ataacttacggtaaatggcccgcctggctgaccgcccaacgacccccgcccattgacgtcaataatgacgtatgttcccatagtaacgcca
atagggactttccattgacgtcaatgggtggagtatttacggtaaactgcccacttggcagtacatcaagtgtatcatatgccaagtacgcccc
ctattgacgtcaatgacggtaaatggcccgcctggcattatgcccagtacatgaccttatgggactttcctacttggcagtacatctactcgag
gccacgttctgcttcactctccccatctcccccccctccccacccccaattttgtatttatttattttttaattattttgtgcagcgatgggggcggg
gggggggggggggcgcgcgccaggcggggcggggcggggcgaggggcggggcggggcgaggcggagaggtgcggcggcag
ccaatcagagcggcgcgctccgaaagtttccttttatggcgaggcggcggcggcggcggccctataaaaagcgaagcgcgcggcggg
cgggagcgggatcagccaccgcggtggcggcctagagtcgacgaggaactgaaaaaccagaaagttaactggtaagtttagtctttttgt
cttttatttcaggtcccagatctagggctctgcgtttgctccaggtagtccgctgctcccttgggcctgggcccactgacagccctggtgcctc
tggccggctgcacacctcctggcgggcagctgtggtgtaagctggtgagccactgtgttctggcaatacctgcagtggctgtctagcttaca
ccacggaggcctgccctgactgcccacggtgccgtggccaaagaggatctaagggcaccgctgagggcctacctaaccatcgtgggga
ataaggacagtgtcacccctgcaggggatccggtggtggtgcaaatcaaagaactgctcctcagtggatgttgcctttacttctaggcctgta
cggaagtgttacttctgctctaaaagctgcggaattgtacccgcggccgatccaccggtcgccaccatggtgagcaagggcgaggagctg
ttcaccggggtggtgcccatcctggtcgagctggacggcgacgtaaacggccacaagttcagcgtgtccggcgagggcgagggcgatg
ccacctacggcaagctgaccctgaagttcatctgcaccaccggcaagctgcccgtgccctggcccaccctcgtgaccaccctgacctacg
gcgtgcagtgcttcagccgctaccccgaccacatgaagcagcacgacttcttcaagtccgccatgcccgaaggctacgtccaggagcgc
accatcttcttcaaggacgacggcaactacaagacccgcgccgaggtgaagttcgagggcgacaccctggtgaaccgcatcgagctgaa
gggcatcgacttcaaggaggacggcaacatcctggggcacaagctggagtacaactacaacagccacaacgtctatatcatggccgaca
agcagaagaacggcatcaaggtgaacttcaagatccgccacaacatcgaggacggcagcgtgcagctcgccgaccactaccagcaga
acacccccatcggcgacggccccgtgctgctgcccgacaaccactacctgagcacccagtccgccctgagcaaagaccccaacgagaa
gcgcgatcacatggtcctgctggagttcgtgaccgccgccgggatcactctcggcatggacgagctgtacaagtaaagcggccatcaag
cttatcgataccgtcgactagagctcgctgatcagcctcgactgtgccttctagttgccagccatctgttgtttgcccctcccccgtgccttcctt
gaccctggaaggtgccactcccactgtcctttcctaataaaatgaggaaattgcatcgcattgtctgagtaggtgtcattctattctggggggt
ggggtggggcaggacagcaagggggaggattgggaagacaattaggtagataagtagcatggcgggttaatcattaactacaaggaac
ccctagtgatggagttggccactccctctctgcgcgctcgctcgctcactgaggccgggcgaccaaaggtcgcccgacgcccgggctttg
cccgggcggcctcagtgagcgagcgagcgcgcagccttaattaacctaattcactggccgtcgttttacaacgtcgtgactgggaaaaccc
tggcgttacccaacttaatcgccttgcagcacatccccctttcgccagctggcgtaatagcgaagaggcccgcaccgatcgcccttcccaa
cagttgcgcagcctgaatggcgaatgggacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggctttccccgtcaagctctaaatcgg
gggctccctttagggttccgatttagtgctttacggcacctcgaccccaaaaaacttgattagggtgatggttcacgtagtgggccatcgccct
gatagacggtttttcgccctttgacgttggagtccacgttctttaatagtggactcttgttccaaactggaacaacactcaaccctatctcggtct
attcttttgatttataagggattttgccgatttcggcctattggttaaaaaatgagctgatttaacaaaaatttaacgcgaattttaacaaaatattaa
cgcttacaatttaggtggcacttttcggggaaatgtgcgcggaacccctatttgtttatttttctaaatacattcaaatatgtatccgctcatgaga
caataaccctgataaatgcttcaataatattgaaaaaggaagagtatgagtattcaacatttccgtgtcgcccttattccctttttttgcggcattttg
ccttcctgtttttgctcacccagaaacgctggtgaaagtaaaagatgctgaagatcagttgggtgcacgagtgggttacatcgaactggatct -continued caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A9) EGFP nucleic acid sequence

SEQ ID NO: 14 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg gggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgtgtaatctggtgagccactgttgttctggcaatacctgacagtggcagatcagattac acacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca -continued agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A9-14) EGFP nucleic acid sequence

SEQ ID NO: 15 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac -continued ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgtgtaagctggtgagccactgttgttctggcaatacctgacagtggcagatcagcttac acacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg -continued agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A10) EGFP nucleic acid sequence

SEQ ID NO: 16 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg gggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtggtaatctggtgagccactgtttgttctggcaatacctgaacagtgggacgccagatta ccacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg -continued cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A10-14) EGFP nucleic acid sequence

SEQ ID NO: 17 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg gggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt -continued cttttatttcaggtcccagatctagggctctgcgtttgctccaggtagtccgctgctcccttgggcctgggcccactgacagccctggtgcctc tggccggctgcacacctcctggcgggcagctgtggtaagctggtgagccactgtttgttctggcaatacctgaacagtgggacgccagctt accacggaggcctgccctgactgcccacggtgccgtggccaaagaggatctaagggcaccgctgagggcctacctaaccatcgtgggg aataaggacagtgtcacccctgcaggggatccggtggtggtgcaaatcaaagaactgctcctcagtggatgttgcctttacttctaggcctgt acggaagtgttacttctgctctaaaagctgcggaattgtacccgcggccgatccaccggtcgccaccatggtgagcaagggcgaggagct gttcaccggggtggtgcccatcctggtcgagctggacggcgacgtaaacggccacaagttcagcgtgtccggcgagggcgagggcgat gccacctacggcaagctgaccctgaagttcatctgcaccaccggcaagctgcccgtgccctggcccaccctcgtgaccaccctgacctac ggcgtgcagtgcttcagccgctaccccgaccacatgaagcagcacgacttcttcaagtccgccatgcccgaaggctacgtccaggagcg caccatcttcttcaaggacgacggcaactacaagacccgcgccgaggtgaagttcgagggcgacaccctggtgaaccgcatcgagctga agggcatcgacttcaaggaggacggcaacatcctggggcacaagctggagtacaactacaacagccacaacgtctatatcatggccgac aagcagaagaacggcatcaaggtgaacttcaagatccgccacaacatcgaggacggcagcgtgcagctcgccgaccactaccagcag aacacccccatcggcgacggccccgtgctgctgcccgacaaccactacctgagcacccagtccgccctgagcaaagaccccaacgaga agcgcgatcacatggtcctgctggagttcgtgaccgccgccgggatcactctcggcatggacgagctgtacaagtaaagcggccatcaa gcttatcgataccgtcgactagagctcgctgatcagcctcgactgtgccttctagttgccagccatctgttgtttgcccctcccccgtgccttcc ttgaccctggaaggtgccactcccactgtcctttcctaataaaatgaggaaattgcatcgcattgtctgagtaggtgtcattctattctggggggg tggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattccctttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt -continued cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A11) EGFP nucleic acid sequence

SEQ ID NO: 18 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgtaatctggtgagccactgttctgttctggcaatacctggaacagtgcgttaccagatta cacggaggcctgccctgactgcccacggtgccgtggccaaagaggatctaagggcaccgctgagggcctacctaaccatcgtggggaa taaggacagtgtcacccctgcaggggatccggtggtggtgcaaatcaaagaactgctcctcagtggatgttgcctttacttctaggcctgtac ggaagtgttacttctgctctaaaagctgcggaattgtacccgcggccgatccaccggtcgccaccatggtgagcaagggcgaggagctgt tcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa -continued cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A11-14) EGFP nucleic acid sequence

SEQ ID NO: 19 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggccccactgacagccctggtgcctc tggccggctgcacacctcctggcgggcagctgtgtaagctggtgagccactgttctgttctggcaatacctggaacagtgcgttaccagctt acacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg -continued gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

-continued

>AAVscCB6 (amiR33-ACVR1-A12) EGFP nucleic acid sequence

SEQ ID NO: 20 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg ggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgaatctggtgagccactgttcttgttctggcaatacctgagaacagtcccccaccagat tcacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attctttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc -continued aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>AAVscCB6 (amiR33-ACVR1-A12-14) EGFP nucleic acid sequence

SEQ ID NO: 21 ctgcgcgctcgctcgctcactgaggccgcccgggcaaagcccgggcgtcgggcgacctttggtcgcccggcctcagtgagcgagcga gcgcgcagagagggagtgtagccatgctctaggaagatcaattcggtacaattcacgcgtcgacattgattattgactagctctggtcgttac ataacttacggtaaatggcccgcctggctgaccgcccaacgacccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctactcgag gccacgttctgcttcactctccccatctcccccccctccccacccccaattttgtatttatttattttttaattattttgtgcagcgatgggggcggg gggggggggggggcgcgcgccaggcggggcggggcggggcgaggggcggggcggggcgaggcggagaggtgcggcggcag ccaatcagagcggcgcgctccgaaagtttccttttatggcgaggcggcggcggcggcggccctataaaaagcgaagcgcgcggcggg cgggagcgggatcagccaccgcggtggcggcctagagtcgacgaggaactgaaaaaccagaaagttaactggtaagtttagtctttttgt cttttatttcaggtcccagatctagggctctgcgtttgctccaggtagtccgctgctcccttgggcctgggcccactgacagccctggtgcctc tggccggctgcacacctcctggcgggcagctgtgaagctggtgagccactgttcttgttctggcaatacctgagaacagtcccccaccagc ttcacggaggcctgccctgactgcccacggtgccgtggccaaagaggatctaagggcaccgctgagggcctacctaaccatcgtgggga ataaggacagtgtcacccctgcaggggatccggtggtggtgcaaatcaaagaactgctcctcagtggatgttgcctttacttctaggcctgta cggaagtgttacttctgctctaaaagctgcggaattgtacccgcggccgatccaccggtcgccaccatggtgagcaagggcgaggagctg ttcaccggggtggtgcccatcctggtcgagctggacggcgacgtaaacggccacaagttcagcgtgtccggcgagggcgagggcgatg ccacctacggcaagctgaccctgaagttcatctgcaccaccggcaagctgcccgtgccctggcccaccctcgtgaccaccctgacctacg gcgtgcagtgcttcagccgctaccccgaccacatgaagcagcacgacttcttcaagtccgccatgcccgaaggctacgtccaggagcgc accatcttcttcaaggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctatatcatggccgaca agcagaagaacggcatcaaggtgaacttcaagatccgccacaacatcgaggacggcagcgtgcagctcgccgaccactaccagcaga acacccccatcggcgacggccccgtgctgctgcccgacaaccactacctgagcacccagtccgccctgagcaaagaccccaacgagaa gcgcgatcacatggtcctgctggagttcgtgaccgccgccgggatcactctcggcatggacgagctgtacaagtaaagcggccatcaag -continued cttatcgataccgtcgactagagctcgctgatcagcctcgactgtgccttctagttgccagccatctgttgtttgcccctcccccgtgccttcctt gaccctggaaggtgccactcccactgtcctttcctaataaaatgaggaaattgcatcgcattgtctgagtaggtgtcattctattctggggggt ggggtggggcaggacagcaagggggaggattgggaagacaattaggtagataagtagcatggcgggttaatcattaactacaaggaac ccctagtgatggagttggccactccctctctgcgcgctcgctcgctcactgaggccgggcgaccaaaggtcgcccgacgcccgggctttg cccgggcggcctcagtgagcgagcgagcgcgcagccttaattaacctaattcactggccgtcgttttacaacgtcgtgactgggaaaaccc tggcgttacccaacttaatcgccttgcagcacatccccctttcgccagctggcgtaatagcgaagaggcccgcaccgatcgcccttcccaa cagttgcgcagcctgaatggcgaatgggacgcgccctgtagcggcgcattaagcgcggcgggtgtggtggttacgcgcagcgtgaccg ctacacttgccagcgccctagcgcccgctcctttcgctttcttcccttcctttctcgccacgttcgccggctttccccgtcaagctctaaatcgg gggctccctttagggttccgatttagtgctttacggcacctcgaccccaaaaaacttgattagggtgatggttcacgtagtgggccatcgccct gatagacggtttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaatattaa cgcttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattcccttttttgcggcattttg ccttcctgtttttgctcacccagaaacgctggtgaaagtaaaagatgctgaagatcagttgggtgcacgagtgggttacatcgaactggatct caacagcggtaagatccttgagagttttcgccccgaagaacgttttccaatgatgagcacttttaaagttctgctatgtggcgcggtattatccc gtattgacgccgggcaagagcaactcggtcgccgcatacactattctcagaatgacttggttgagtactcaccagtcacagaaaagcatctt acggatggcatgacagtaagagaattatgcagtgctgccataaccatgagtgataacactgcggccaacttacttctgacaacgatcggag gaccgaaggagctaaccgcttttttgcacaacatgggggatcatgtaactcgccttgatcgttgggaaccggagctgaatgaagccatacc aaacgacgagcgtgacaccacgatgcctgtagcaatggcaacaacgttgcgcaaactattaactggcgaactacttactctagcttcccgg caacaattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacgggg agtcaggcaactatggatgaacgaaatagacagatcgctgagataggtgcctcactgattaagcattggtaactgtcagaccaagtttactc atatatactttagattgatttaaaacttcatttttaatttaaaaggatctaggtgaagatcctttttgataatctcatgaccaaaatcccttaacgtgag ttttcgttccactgagcgtcagaccccgtagaaaagatcaaaggatcttcttgagatcctttttttctgcgcgtaatctgctgcttgcaaacaaaa aaaccaccgctaccagcggtggtttgtttgccggatcaagagctaccaactctttttccgaaggtaactggcttcagcagagcgcagatacc aaatactgttcttctagtgtagccgtagttaggccaccacttcaagaactctgtagcaccgcctacatacctcgctctgctaatcctgttaccag tggctgctgccagtggcgataagtcgtgtcttaccgggttggactcaagacgatagttaccggataaggcgcagcggtcgggctgaacgg ggggttcgtgcacacagcccagcttggagcgaacgacctacaccgaactgagatacctacagcgtgagctatgagaaagcgccacgctt cccgaagggagaaaggcggacaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggggcggagcctatggaaaaa cgccagcaacgcggcctttttacggttcctggccttttgctggccttttgctcacatgttctttcctgcgttatcccctgattctgtggataaccgt attaccgcctttgagtgagctgataccgctcgccgcagccgaacgaccgagcgcagcgagtcagtgagcgaggaagcggaagagcgc ccaatacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgagcgg ataacaatttcacacaggaaacagctatgaccatgattacgccagatttaattaaggccttaattagg;

>wtACVR1 amiR-sensor plasmids nucleic acid sequence

SEQ ID NO: 22 agatctgcgcagcaccatggcctgaaataacctctgaaagaggaacttggttaggtaccttctgaggcggaaagaaccagctgtggaatgt gtgtcagttagggtgtggaaagtccccaggctccccagcaggcagaagtatgcaaagcatgcatctcaattagtcagcaaccaggtgtgg aaagtccccaggctccccagcaggcagaagtatgcaaagcatgcatctcaattagtcagcaaccatagtcccgcccctaactccgcccatc ccgcccctaactccgcccagttccgcccattctccgccccatggctgactaattttttttatttatgcagaggccgaggccgcctcggcctctg agctattccagaagtagtgaggaggcttttttggaggcctaggcttttgcaaaaagcttgattcttctgacacaacagtctcgaacttaagctgc -continued agaagttggtcgtgaggcactgggcaggtaagtatcaaggttacaagacaggtttaaggagaccaatagaaactgggcttgtcgagacag agaagactatgcgtttctgataggcacctattggtatactgacatccactttgcctttctctccacaggtgtccactcccagttcaattacagct cttaaggctagagtacttaatacgactcactataggctagccaccatggcttccaaggtgtacgaccccgagcaacgcaaacgcatgatca ctgggcctcagtggtgggctcgctgcaagcaaatgaacgtgctggactccttcatcaactactatgattccgagaagcacgccgagaacgc cgtgatttttctgcatggtaacgctgcctccagctacctgtggaggcacgtcgtgcctcacatcgagcccgtggctagatgcatcatccctga tctgatcggaatgggtaagtccggcaagagcgggaatggctcatatcgcctcctggatcactacaagtacctcaccgcttggttcgagctgc tgaaccttccaaagaaaatcatctttgtgggccacgactgggggggcttgtctggcctttcactactcctacgagcaccaagacaagatcaag gccatcgtccatgctgagagtgtcgtggacgtgatcgagtcctgggacgagtggcctgacatcgaggaggatatcgccctgatcaagagc gaagagggcgagaaaatggtgcttgagaataacttcttcgtcgagaccatgctcccaagcaagatcatgcggaaactggagcctgagga gttcgctgcctacctggagccattcaaggagaagggcgaggttagacggcctaccctctcctggcctcgcgagatccctctcgttaaggga ggcaagcccgacgtcgtccagattgtccgcaactacaacgcctaccttcgggccagcgacgatctgcctaagatgttcatcgagtccgacc ctgggttcttttccaacgctattgtcgagggagctaagaagttccctaacaccgagttcgtgaaggtgaagggcctccacttcagccaggag gacgctccagatgaaatgggtaagtacatcaagagcttcgtggagcgcgtgctgaagaacgagcagtaattctaggcgatcgctcgaggg tacaaagaacagtggctcgccagattacactgttggagtgcggccgctggccgcaataaaatatctttattttcattacatctgtgtgttggttttt tgtgtgaggatctaaatgagtcttcggacctcgcgggggccgcttaagcggtggttagggtttgtctgacgcgggggggagggggaagga acgaaacactctcattcggaggcggctcggggtttggtcttggtggccacgggcacgcagaagagcgccgcgatcctcttaagcacccc cccgccctccgtggaggcgggggtttggtcggcgggtggtaactggcgggccgctgactcgggcgggtcgcgcgccccagagtgtga ccttttcggtctgctcgcagacccccgggcggcgccgccgcggcggcgacgggctcgctgggtcctaggctccatggggaccgtatac gtggacaggctctggagcatccgcacgactgcggtgatattaccggagaccttctgcgggacgagccgggtcacgcggctgacgcgga gcgtccgttgggcgacaaacaccaggacggggcacaggtacactatcttgtcacccggaggcgcgagggactgcaggagcttcaggg agtggcgcagctgcttcatccccgtggcccgttgctcgcgtttgctggcggtgtccccggaagaaatatatttgcatgtctttagttctatgatg acacaaaccccgcccagcgtcttgtcattggcgaattcgaacacgcagatgcagtcggggcggcgcggtcccaggtccacttcgcatatt aaggtgacgcgtgtggcctcgaacaccgagcgaccctgcagcgacccgcttaaaagcttggcattccggtactgttggtaaagccaccat ggccgatgctaagaacattaagaagggccctgctcccttctaccctctggaggatggcaccgctggcgagcagctgcacaaggccatga agaggtatgccctggtgcctggcaccattgccttcaccgatgcccacattgaggtggacatcacctatgccgagtacttcgagatgtctgtg cgcctggccgaggccatgaagaggtacggcctgaacaccaaccaccgcatcgtggtgtgctctgagaactctctgcagttcttcatgccag tgctgggcgccctgttcatcggagtggccgtggcccctgctaacgacatttacaacgagcgcgagctgctgaacagcatgggcatttctca gcctaccgtggtgttcgtgtctaagaagggcctgcagaagatcctgaacgtgcagaagaagctgcctatcatccagaagatcatcatcatg gactctaagaccgactaccagggcttccagagcatgtacacattcgtgacatctcatctgcctcctggcttcaacgagtacgacttcgtgcca gagtctttcgacagggacaaaaccattgccctgatcatgaacagctctgggtctaccggcctgcctaagggcgtggccctgcctcatcgca ccgcctgtgtgcgcttctctcacgcccgcgaccctattttcggcaaccagatcatccccgacaccgctattctgagcgtggtgccattccacc acggcttcggcatgttcaccaccctgggctacctgatttgcggctttcgggtggtgctgatgtaccgcttcgaggaggagctgttcctgcgca gcctgcaagactacaaaattcagtctgccctgctggtgccaaccctgttcagcttcttcgctaagagcaccctgatcgacaagtacgacctgt ctaacctgcacgagattgcctctggcggcgccccactgtctaaggaggtgggcgaagccgtggccaagcgctttcatctgccaggcatcc gccagggctacggcctgaccgagacaaccagcgccattctgattaccccagagggcgacgacaagcctggcgccgtgggcaaggtgg tgccattcttcgaggccaaggtggtggacctggacaccggcaagaccctgggagtgaaccagcgcggcgagctgtgtgtgcgcggccc tatgattatgtccggctacgtgaataaccctgaggccacaaacgccctgatcgacaaggacggctggctgcactctggcgacattgcctact gggacgaggacgagcacttcttcatcgtggaccgcctgaagtctctgatcaagtacaagggctaccaggtggccccagccgagctggag tctatcctgctgcagcaccctaacattttcgacgccggagtggccggcctgcccgacgacgatgccggcgagctgcctgccgccgtcgtc gtgctggaacacggcaagaccatgaccgagaaggagatcgtggactatgtggccagccaggtgacaaccgccaagaagctgcgcggc ggagtggtgttcgtggacgaggtgcccaagggcctgaccggcaagctggacgcccgcaagatccgcgagatcctgatcaaggctaaga -continued aaggcggcaagatcgccgtgtaataattctagagtcggggcggccggccgcttcgagcagacatgataagatacattgatgagtttggac
aaaccacaactagaatgcagtgaaaaaaatgctttatttgtgaaatttgtgatgctattgctttatttgtaaccattataagctgcaataaacaagt
taacaacaacaattgcattcattttatgtttcaggttcagggggaggtgtgggaggttttttaaagcaagtaaaacctctacaaatgtggtaaaa
tcgataaggatccaggtggcacttttcggggaaatgtgcgcggaacccctatttgtttatttttctaaatacattcaaatatgtatccgctcatga
gacaataaccctgataaatgcttcaataatattgaaaaaggaagagtatgagtattcaacatttccgtgtcgcccttattcccttttttgcggcatt
ttgccttcctgtttttgctcacccagaaacgctggtgaaagtaaaagatgctgaagatcagttgggtgcacgagtgggttacatcgaactgga
tctcaacagcggtaagatccttgagagttttcgccccgaagaacgttttccaatgatgagcacttttaaagttctgctatgtggcgcggtattat
cccgtattgacgccgggcaagagcaactcggtcgccgcatacactattctcagaatgacttggttgagtactcaccagtcacagaaaagca
tcttacggatggcatgacagtaagagaattatgcagtgctgccataaccatgagtgataacactgcggccaacttacttctgacaacgatcg
gaggaccgaaggagctaaccgcttttttgcacaacatgggggatcatgtaactcgccttgatcgttgggaaccggagctgaatgaagccat
accaaacgacgagcgtgacaccacgatgcctgtagcaatggcaacaacgttgcgcaaactattaactggcgaactacttactctagcttcc
cggcaacaattaatagactggatggaggcggataaagttgcaggaccacttctgcgctcggcccttccggctggctggtttattgctgataa
atctggagccggtgagcgtgggtctcgcggtatcattgcagcactggggccagatggtaagccctcccgtatcgtagttatctacacgacg
gggagtcaggcaactatggatgaacgaaatagacagatcgctgagataggtgcctcactgattaagcattggtaactgtcagaccaagttta
ctcatatatactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaactggcttcagcagagcgcagat
accaaatactgttcttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccaggggga
aacgcctggtatctttatagtcctgtcgggtttcgccacctctgacttgagcgtcgatttttgtgatgctcgtcaggggggcggagcctatgga
aaaacgccagcaacgcggcctttttacggttcctggccttttgctggccttttgctcacatggctcgac;

>ACVR1-R206H amiR-sensor plasmids nucleic acid sequence

SEQ ID NO: 23 agatctgcgcagcaccatggcctgaaataacctctgaaagaggaacttggttaggtaccttctgaggcggaaagaaccagctgtggaatgt
gtgtcagttagggtgtggaaagtccccaggctccccagcaggcagaagtatgcaaagcatgcatctcaattagtcagcaaccaggtgtgg
aaagtccccaggctccccagcaggcagaagtatgcaaagcatgcatctcaattagtcagcaaccatagtcccgcccctaactccgcccatc
ccgcccctaactccgcccagttccgcccattctccgccccatggctgactaattttttttatttatgcagaggccgaggccgcctcggcctctg
agctattccagaagtagtgaggaggcttttttggaggcctaggcttttgcaaaaagcttgattcttctgacacaacagtctcgaacttaagctgc
agaagttggtcgtgaggcactgggcaggtaagtatcaaggttacaagacaggtttaaggagaccaatagaaactgggcttgtcgagacag
agaagactcttgcgtttctgataggcacctattggtcttactgacatccactttgcctttctctccacaggtgtccactcccagttcaattacagct
cttaaggctagagtacttaatacgactcactataggctagccaccatggcttccaaggtgtacgaccccgagcaacgcaaacgcatgatca
ctgggcctcagtggtgggctcgctgcaagcaaatgaacgtgctggactccttcatcaactactatgattccgagaagcacgccgagaacgc
cgtgatttttctgcatggtaacgctgcctccagctacctgtggaggcacgtcgtgcctcacatcgagcccgtggctagatgcatcatccctga
tctgatcggaatgggtaagtccggcaagagcgggaatggctcatatcgcctcctggatcactacaagtacctcaccgcttggttcgagctgc
tgaaccttccaaagaaaatcatctttgtgggccacgactgggggggcttgtctggcctttcactactcctacgagcaccaagacaagatcaag
gccatcgtccatgctgagagtgtcgtggacgtgatcgagtcctgggacgagtggcctgacatcgaggaggatatcgccctgatcaagagc
gaagagggcgagaaaatggtgcttgagaataacttcttcgtcgagaccatgctcccaagcaagatcatgcggaaactggagcctgagga
gttcgctgcctacctggagccattcaaggagaagggcgaggttagacggcctaccctctcctggcctcgcgagatccctctcgttaaggga
ggcaagcccgacgtcgtccagattgtccgcaactacaacgcctaccttcgggccagcgacgatctgcctaagatgttcatcgagtccgacc
ctgggttcttttccaacgctattgtcgagggagctaagaagttccctaacaccgagttcgtgaaggtgaagggcctccacttcagccaggag -continued gacgctccagatgaaatgggtaagtacatcaagagcttcgtggagcgcgtgctgaagaacgagcagtaattctaggcgatcgctcgaggg tacaaagaacagtggctcaccagattacactgaggagtgcggccgctggccgcaataaaatatctttattttcattacatctgtgtgttggtttttt tgtgtgaggatctaaatgagtcttcggacctcgcgggggccgcttaagcggtggttagggtttgtctgacgcgggggggagggggaagga acgaaacactctcattcggaggcggctcggggtttggtcttggtggccacgggcacgcagaagagcgccgcgatcctcttaagcacccc cccgccctccgtggaggcgggggtttggtcggcgggtggtaactggcgggccgctgactcgggcgggtcgcgcgccccagagtgtga ccttttcggtctgctcgcagacccccgggcggcgccgccgcggcggcgacgggctcgctgggtcctaggctccatggggaccgtatac gtggacaggctctggagcatccgcacgactgcggtgatattaccggagaccttctgcgggacgagccgggtcacgcggctgacgcgga gcgtccgttgggcgacaaacaccaggacggggcacaggtacactatcttgtcacccggaggcgcgagggactgcaggagcttcaggg agtggcgcagctgcttcatccccgtggcccgttgctcgcgtttgctggcggtgtccccggaagaaatatatttgcatgtctttagttctatgatg acacaaaccccgcccagcgtcttgtcattggcgaattcgaacacgcagatgcagtcggggcggcgcggtcccaggtccacttcgcatatt aaggtgacgcgtgtggcctcgaacaccgagcgaccctgcagcgacccgcttaaaagcttggcattccggtactgttggtaaagccaccat ggccgatgctaagaacattaagaagggccctgctcccttctaccctctggaggatggcaccgctggcgagcagctgcacaaggccatga agaggtatgccctggtgcctggcaccattgccttcaccgatgcccacattgaggtggacatcacctatgccgagtacttcgagatgtctgtg cgcctggccgaggccatgaagaggtacggcctgaacaccaaccaccgcatcgtggtgtgctctgagaactctctgcagttcttcatgccag tgctgggcgccctgttcatcggagtggccgtggcccctgctaacgacatttacaacgagcgcgagctgctgaacagcatgggcatttctca gcctaccgtggtgttcgtgtctaagaagggcctgcagaagatcctgaacgtgcagaagaagctgcctatcatccagaagatcatcatcatg gactctaagaccgactaccagggcttccagagcatgtacacattcgtgacatctcatctgcctcctggcttcaacgagtacgacttcgtgcca gagtctttcgacagggacaaaaccattgccctgatcatgaacagctctgggtctaccggcctgcctaagggcgtggccctgcctcatcgca ccgcctgtgtgcgcttctctcacgcccgcgaccctattttcggcaaccagatcatccccgacaccgctattctgagcgtggtgccattccacc acggcttcggcatgttcaccaccctgggctacctgatttgcggctttcgggtggtgctgatgtaccgcttcgaggaggagctgttcctgcgca gcctgcaagactacaaaattcagtctgccctgctggtgccaaccctgttcagcttcttcgctaagagcaccctgatcgacaagtacgacctgt ctaacctgcacgagattgcctctggcggcgccccactgtctaaggaggtgggcgaagccgtggccaagcgctttcatctgccaggcatcc gccagggctacggcctgaccgagacaaccagcgccattctgattaccccagagggcgacgacaagcctggcgccgtgggcaaggtgg tgccattcttcgaggccaaggtggtggacctggacaccggcaagaccctgggagtgaaccagcgcggcgagctgtgtgtgcgcggccc tatgattatgtccggctacgtgaataaccctgaggccacaaacgccctgatcgacaaggacggctggctgcactctggcgacattgcctact gggacgaggacgagcacttcttcatcgtggaccgcctgaagtctctgatcaagtacaagggctaccaggtggccccagccgagctggag tctatcctgctgcagcaccctaacattttcgacgccggagtggccggcctgcccgacgacgatgccggcgagctgcctgccgccgtcgtc gtgctggaacacggcaagaccatgaccgagaaggagatcgtggactatgtggccagccaggtgacaaccgccaagaagctgcgcggc ggagtggtgttcgtggacgaggtgcccaagggcctgaccggcaagctggacgcccgcaagatccgcgagatcctgatcaaggctaaga aaggcggcaagatcgccgtgtaataattctagagtcggggcggccggccgcttcgagcagacatgataagatacattgatgagtttggac aaaccacaactagaatgcagtgaaaaaaatgctttatttgtgaaatttgtgatgctattgctttatttgtaaccattataagctgcaataaacaagt taacaacaacaattgcattcattttatgtttcaggttcagggggaggtgtgggaggttttttaaagcaagtaaaacctctacaaatgtggtaaaa tcgataaggatccaggtggcacttttcggggaaatgtgcgcggaacccctatttgtttatttttctaaatacattcaaatatgtatccgctcatga gacaataaccctgataaatgcttcaataatattgaaaaaggaagagtatgagtattcaacatttccgtgtcgcccttattcccttttttgcggcatt ttgccttcctgtttttgctcacccagaaacgctggtgaaagtaaaagatgctgaagatcagttgggtgcacgagtgggttacatcgaactgga tctcaacagcggtaagatccttgagagttttcgccccgaagaacgttttccaatgatgagcacttttaaagttctgctatgtggcgcggtattat cccgtattgacgccgggcaagagcaactcggtcgccgcatacactattctcagaatgacttggttgagtactcaccagtcacagaaaagca tcttacggatggcatgacagtaagagaattatgcagtgctgccataaccatgagtgataacactgcggccaacttacttctgacaacgatcg gaggaccgaaggagctaaccgcttttttgcacaacatgggggatcatgtaactcgccttgatcgttgggaaccggagctgaatgaagccat accaaacgacgagcgtgacaccacgatgcctgtagcaatggcaacaacgttgcgcaaactattaactggcgaactacttactctagcttcc cggcaacaattaatagactggatggaggcggataaagttgcaggaccacttctgcgctcggcccttccggctggctggtttattgctgataa -continued atctggagccggtgagcgtgggtctcgcggtatcattgcagcactggggccagatggtaagccctcccgtatcgtagttatctacacgacg gggagtcaggcaactatggatgaacgaaatagacagatcgctgagataggtgcctcactgattaagcattggtaactgtcagaccaagttta ctcatatatactttagattgatttaaaacttcatttttaatttaaaaggatctaggtgaagatcctttttgataatctcatgaccaaaatcccttaacgt gagttttcgttccactgagcgtcagaccccgtagaaaagatcaaaggatcttcttgagatcctttttttctgcgcgtaatctgctgcttgcaaaca aaaaaaccaccgctaccagcggtggtttgtttgccggatcaagagctaccaactctttttccgaaggtaactggcttcagcagagcgcagat accaaatactgttcttctagtgtagccgtagttaggccaccacttcaagaactctgtagcaccgcctacatacctcgctctgctaatcctgttac cagtggctgctgccagtggcgataagtcgtgtcttaccgggttggactcaagacgatagttaccggataaggcgcagcggtcgggctgaa cggggggttcgtgcacacagcccagcttggagcgaacgacctacaccgaactgagatacctacagcgtgagctatgagaaagcgccac gcttcccgaagggagaaaggcggacaggtatccggtaagcggcagggtcggaacaggagagcgcacgagggagcttccaggggga aacgcctggtatctttatagtcctgtcgggtttcgccacctctgacttgagcgtcgatttttgtgatgctcgtcaggggggcggagcctatgga aaaacgccagcaacgcggcctttttacggttcctggccttttgctggccttttgctcacatggctcgac;

>ACVR1-optACVR1 amiR-sensor plasmids nucleic acid sequence

SEQ ID NO: 24 agatctgcgcagcaccatggcctgaaataacctctgaaagaggaacttggttaggtaccttctgaggcggaaagaaccagctgtggaatgt gtgtcagttagggtgtggaaagtccccaggctccccagcaggcagaagtatgcaaagcatgcatctcaattagtcagcaaccaggtgtgg aaagtccccaggctccccagcaggcagaagtatgcaaagcatgcatctcaattagtcagcaaccatagtcccgcccctaactccgcccatc ccgcccctaactccgcccagttccgcccattctccgccccatggctgactaattttttttatttatgcagaggccgaggccgcctcggcctctg agctattccagaagtagtgaggaggcttttttggaggcctaggcttttgcaaaaagatgattcttctgacacaacagtctcgaacttaagctgc agaagttggtcgtgaggcactgggcaggtaagtatcaaggttacaagacaggtttaaggagaccaatagaaactgggcttgtcgagacag agaagactatgcgtttctgataggcacctattggtatactgacatccactttgcctttctctccacaggtgtccactcccagttcaattacagct cttaaggctagagtacttaatacgactcactataggctagccaccatggcttccaaggtgtacgaccccgagcaacgcaaacgcatgatca ctgggcctcagtggtgggctcgctgcaagcaaatgaacgtgctggactccttcatcaactactatgattccgagaagcacgccgagaacgc cgtgatttttctgcatggtaacgctgcctccagctacctgtggaggcacgtcgtgcctcacatcgagcccgtggctagatgcatcatccctga tctgatcggaatgggtaagtccggcaagagcgggaatggctcatatcgcctcctggatcactacaagtacctcaccgcttggttcgagctgc tgaaccttccaaagaaaatcatctttgtgggccacgactgggggggcttgtctggcctttcactactcctacgagcaccaagacaagatcaag gccatcgtccatgctgagagtgtcgtggacgtgatcgagtcctgggacgagtggcctgacatcgaggaggatatcgccctgatcaagagc gaagagggcgagaaaatggtgcttgagaataacttcttcgtcgagaccatgctcccaagcaagatcatgcggaaactggagcctgagga gttcgctgcctacctggagccattcaaggagaagggcgaggttagacggcctaccctctcctggcctcgcgagatccctctcgttaaggga ggcaagcccgacgtcgtccagattgtccgcaactacaacgcctaccttcgggccagcgacgatctgcctaagatgttcatcgagtccgacc ctgggttcttttccaacgctattgtcgagggagctaagaagttccctaacaccgagttcgtgaaggtgaagggcctccacttcagccaggag gacgctccagatgaaatgggtaagtacatcaagagcttcgtggagcgcgtgctgaagaacgagcagtaattctaggcgatcgctcgaggg tgcagaggaccgtggcccggcagatcaccctgctggagtgcggccgctggccgcaataaaatatctttattttcattacatctgtgtgttggtt ttttgtgtgaggatctaaatgagtcttcggacctcgcgggggccgcttaagcggtggttagggtttgtctgacgcgggggggagggggaagg aacgaaacactctcattcggaggcggctcggggtttggtcttggtggccacgggcacgcagaagagcgccgcgatcctcttaagcaccc ccccgccctccgtggaggcgggggtttggtcggcgggtggtaactggcgggccgctgactcgggcgggtcgcgcgccccagagtgtg accttttcggtctgctcgcagacccccgggcggcgccgccgcggcggcgacgggctcgctgggtcctaggctccatggggaccgtatac gtggacaggctctggagcatccgcacgactgcggtgatattaccggagaccttctgcgggacgagccgggtcacgcggctgacgcgga gcgtccgttgggcgacaaacaccaggacggggcacaggtacactatcttgtcacccggaggcgcgagggactgcaggagcttcaggg agtggcgcagctgcttcatccccgtggcccgttgctcgcgtttgctggcggtgtccccggaagaaatatatttgcatgtctttagttctatgatg acacaaaccccgcccagcgtcttgtcattggcgaattcgaacacgcagatgcagtcggggcggcgcggtcccaggtccacttcgcatatt aaggtgacgcgtgtggcctcgaacaccgagcgaccctgcagcgacccgcttaaaagcttggcattccggtactgttggtaaagccaccat ggccgatgctaagaacattaagaagggccctgctcccttctaccctctggaggatggcaccgctggcgagcagctgcacaaggccatga -continued agaggtatgccctggtgcctggcaccattgccttcaccgatgcccacattgaggtggacatcacctatgccgagtacttcgagatgtctgtg cgcctggccgaggccatgaagaggtacggcctgaacaccaaccaccgcatcgtggtgtgctctgagaactctctgcagttcttcatgccag tgctgggcgccctgttcatcggagtggccgtggcccctgctaacgacatttacaacgagcgcgagctgctgaacagcatgggcatttctca gcctaccgtggtgttcgtgtctaagaagggcctgcagaagatcctgaacgtgcagaagaagctgcctatcatccagaagatcatcatcatg gactctaagaccgactaccagggcttccagagcatgtacacattcgtgacatctcatctgcctcctggcttcaacgagtacgacttcgtgcca gagtctttcgacagggacaaaaccattgccctgatcatgaacagctctgggtctaccggcctgcctaagggcgtggccctgcctcatcgca ccgcctgtgtgcgcttctctcacgcccgcgaccctattttcggcaaccagatcatccccgacaccgctattctgagcgtggtgccattccacc acggcttcggcatgttcaccaccctgggctacctgatttgcggctttcgggtggtgctgatgtaccgcttcgaggaggagctgttcctgcgca gcctgcaagactacaaaattcagtctgccctgctggtgccaaccctgttcagcttcttcgctaagagcaccctgatcgacaagtacgacctgt ctaacctgcacgagattgcctctggcggcgccccactgtctaaggaggtgggcgaagccgtggccaagcgctttcatctgccaggcatcc gccagggctacggcctgaccgagacaaccagcgccattctgattaccccagagggcgacgacaagcctggcgccgtgggcaaggtgg tgccattcttcgaggccaaggtggtggacctggacaccggcaagaccctgggagtgaaccagcgcggcgagctgtgtgtgcgcggccc tatgattatgtccggctacgtgaataaccctgaggccacaaacgccctgatcgacaaggacggctggctgcactctggcgacattgcctact gggacgaggacgagcacttcttcatcgtggaccgcctgaagtctctgatcaagtacaagggctaccaggtggccccagccgagctggag tctatcctgctgcagcaccctaacattttcgacgccggagtggccggcctgcccgacgacgatgccggcgagctgcctgccgccgtcgtc gtgctggaacacggcaagaccatgaccgagaaggagatcgtggactatgtggccagccaggtgacaaccgccaagaagctgcgcggc ggagtggtgttcgtggacgaggtgcccaagggcctgaccggcaagctggacgcccgcaagatccgcgagatcctgatcaaggctaaga aaggcggcaagatcgccgtgtaataattctagagtcggggcggccggccgcttcgagcagacatgataagatacattgatgagtttggac aaaccacaactagaatgcagtgaaaaaaatgctttatttgtgaaatttgtgatgctattgctttatttgtaaccattataagctgcaataaacaagt taacaacaacaattgcattcattttatgtttcaggttcagggggaggtgtgggaggttttttaaagcaagtaaaacctctacaaatgtggtaaaa tcgataaggatccaggtggcacttttcggggaaatgtgcgcggaacccctatttgtttatttttctaaatacattcaaatatgtatccgctcatga gacaataaccctgataaatgcttcaataatattgaaaaaggaagagtatgagtattcaacatttccgtgtcgcccttattcccttttttgcggcatt ttgccttcctgtttttgctcacccagaaacgctggtgaaagtaaaagatgctgaagatcagttgggtgcacgagtgggttacatcgaactgga tctcaacagcggtaagatccttgagagttttcgccccgaagaacgttttccaatgatgagcacttttaaagttctgctatgtggcgcggtattat cccgtattgacgccgggcaagagcaactcggtcgccgcatacactattctcagaatgacttggttgagtactcaccagtcacagaaaagca tcttacggatggcatgacagtaagagaattatgcagtgctgccataaccatgagtgataacactgcggccaacttacttctgacaacgatcg gaggaccgaaggagctaaccgcttttttgcacaacatgggggatcatgtaactcgccttgatcgttgggaaccggagctgaatgaagccat accaaacgacgagcgtgacaccacgatgcctgtagcaatggcaacaacgttgcgcaaactattaactggcgaactacttactctagcttcc cggcaacaattaatagactggatggaggcggataaagttgcaggaccacttctgcgctcggcccttccggctggctggtttattgctgataa atctggagccggtgagcgtgggtctcgcggtatcattgcagcactggggccagatggtaagccctcccgtatcgtagttatctacacgacg gggagtcaggcaactatggatgaacgaaatagacagatcgctgagataggtgcctcactgattaagcattggtaactgtcagaccaagttta ctcatatatactttagattgatttaaaacttcatttttaatttaaaaggatctaggtgaagatcctttttgataatctcatgaccaaaatcccttaacgt gagttttcgttccactgagcgtcagaccccgtagaaaagatcaaaggatcttcttgagatcctttttttctgcgcgtaatctgctgcttgcaaaca aaaaaaccaccgctaccagcggtggtttgtttgccggatcaagagctaccaactctttttccgaaggtaactggcttcagcagagcgcagat accaaatactgttcttctagtgtagccgtagttaggccaccacttcaagaactctgtagcaccgcctacatacctcgctctgctaatcctgttac cagtggctgctgccagtggcgataagtcgtgtcttaccgggttggactcaagacgatagttaccggataaggcgcagcggtcgggctgaa cggggggttcgtgcacacagcccagcttggagcgaacgacctacaccgaactgagatacctacagcgtgagctatgagaaagcgccac gcttcccgaagggagaaaggcggacaggtatccggtaagcggcagggtcggaacaggagagcgcacgagggagcttccaggggga aacgcctggtatctttatagtcctgtcgggtttcgccacctctgacttgagcgtcgatttttgtgatgctcgtcaggggggcggagcctatgga aaaacgccagcaacgcggcctttttacggttcctggccttttgctggccttttgctcacatggctcgac;

-continued

>AAV-CBA (synthetic intron) (amiR-33-ACVR1-A9)-opt-ACVR1

SEQ ID NO: 25 cttaattaggctgcgcgctcgctcgctcactgaggccgcccgggcaaagcccgggcgtcgggcgacctttggtcgcccggcctcagtga gcgagcgagcgcgcagagagggagtggccaactccatcactaggggttccttgtagttaatgattaacccgccatgctacttatctaccag ggtaatggggatcctctagaactatagctagtcgacattgattattgactagttattaatagtaatcaattacggggtcattagttcatagcccat atatggagttccgcgttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggcagtacatcaagtgtatc atatgccaagtacgccccctattgacgtcaatgacggtaaatggcccgcctggcattatgcccagtacatgaccttatgggactttcctacttg gcagtacatctacgtattagtcatcgctattaccatgtcgaggccacgttctgcttcactctccccatctcccccccctccccacccccaattttg tatttatttattttttaattattttgtgcagcgatgggggcgggggggggggggcgcgcgccaggcggggcggggcggggcgaggggcgg ggcggggcgaggcggagaggtgcggcggcagccaatcagagcggcgcgctccgaaagtttccttttatggcgaggcggcggcggcg gcggccctataaaaagcgaagcgcgcggcgggcgggagcaccaccgcggtggcggccctagagtcgatcgaggaactgaaaaacca gaaagttaactggtaagtttagtctttttgtcttttatttcaggtcccagatctAGGGCTCTGCGTTTGCTCCAGGTAGTC

CGCTGCTCCCTTGGGCCTGGGCCCACTGACAGCCCTGGTGCCTCTGGCCGGCTGCAC

ACCTCCTGGCGGGCAGCTGTGtgtaatctggtgagccactgtTGTTCTGGCAATACCTGACAGTG

GCAGATCAGATTACACACGGAGGCCTGCCCTGACTGCCCACGGTGCCGTGGCCAAA

GAGGATCTAAGGGCACCGCTGAGGGCCTACCTAACCATCGTGGGGAATAAGGACA

GTGTCACCCctgcaggggatccggtggtggtgcaaatcaaagaactgctcctcagtggatgttgcctttacttctaggcctgtacgg aagtgttacttctgctctaaaagctgcggaattgtacccgcggccgatccaccggtgaattccgccaccatggtcgatggagtgatgatcct gcctgtcctgattatgattgccctgcccagccccagcatggaagatgaaaaacctaaagtcaaccctaagctgtatatgtgcgtgtgcgagg gcctgagctgcggaaacgaggatcactgcgagggccagcagtgtttcagctccctgtccatcaatgacggcttccacgtgtaccagaagg gctgctttcaggtgtatgagcagggcaagatgacctgtaagacaccaccttccccaggacaggcagtggagtgctgtcagggcgattggt gtaaccggaatatcaccgcccagctgccaacaaagggcaagtctttccccggcacacagaactttcacctggaagtgggcctgatcatcct gagcgtggtgttcgccgtgtgcctgctggcatgtctgctgggagtggccctgagaaagtttaagcggagaaaccaggagcggctgaatcc aagagatgtggagtacggcaccatcgagggcctgatcaccacaaatgtgggcgactctacactggccgacctgctggatcacagctgca ccagcggctccggatctggcctgccctttctggtgcagaggaccgtggcccggcagatcaccctgctggagtgcgtgggcaagggccg gtacggagaagtgtggagaggatcctggcagggagagaacgtggcagtgaagatcttctctagccgggatgagaagtcttggtttagaga gacagagctgtataacacagtgatgctgaggcacgagaatatcctgggcttcatcgcctccgacatgacctctcgccactcctctacacagc tgtggctgatcacccactaccacgagatgggctccctgtacgattacctccagctgaccacactggacacagtgtcttgcctgcggatcgtg ctgtctatcgccagcggcctggcacacctgcacatcgagatctttggaacccagggcaagccagcaatcgcacacactgaagtctaagaa catcctggtgaagaagaatggccagtgctgtatcgccgatctgggcctggccgtgatgcacagccagtccaccaaccagctggacgtgg gcaacaatcctcgggtgggcacaaagagatacatggccccagaggtgctggatgagacaatccaggtggactgcttcgatagctataaga gggtggacatctgggcctttggcctggtgctgtgggaggtggcaaggaggatggtgagcaacggcatcgtggaggactacaagccacc cttctatgacgtggtgcctaatgatccatcctttgaggacatgcgcaaggtggtgtgcgtggatcagcagaggcccaacatccctaatcgct ggttcagcgaccccaccctgacatccctggccaagctgatgaaggagtgttggtatcagaatcctagcgccaggctgaccgccctgcgca tcaagaaaactctgactaaaatcgacaatagcctggataaactgaaaaccgactgctgacctgagggcggccgcgtcgacggatccgatc tttttccctctgccaaaaattatggggacatcatgaagccccttgagcatctgacttctggctaataaaggaaatttattttcattgcaatagtgtg ttggaattttttgtgtctctcactcggaagcaattcgttgatctgaatttcgaccacccataatacccattaccctggtagataagtagcatggcg ggttaatcattaactacaaggaacccctagtgatggagttggccactccctctctgcgcgctcgctcgctcactgaggccgggcgaccaaa ggtcgcccgacgcccgggctttgcccgggcggcctcagtgagcgagcgagcgcgcagccttaattaacctaattcactggccgtcgtttta caacgtcgtgactgggaaaaccctggcgttacccaacttaatcgccttgcagcacatccccctttcgccagctggcgtaatagcgaagagg cccgcaccgatcgcccttcccaacagttgcgcagcctgaatggcgaatgggacgcgccctgtagcggcgcattaagcgcggcgggtgt -continued ggtggttacgcgcagcgtgaccgctacacttgccagcgccctagcgcccgctcctttcgctttcttcccttcctttctcgccacgttcgccggc tttccccgtcaagctctaaatcgggggctccctttagggttccgatttagtgctttacggcacctcgaccccaaaaaacttgattagggtgatg gttcacgtagtgggccatcgccctgatagacggtttttcgccctttgacgttggagtccacgttctttaatagtggactcttgttccaaactggaa caacactcaaccctatctcggtctattcttttgatttataagggattttgccgatttcggcctattggttaaaaaatgagctgatttaacaaaaattta acgcgaattttaacaaaatattaacgcttacaatttaggtggcacttttcggggaaatgtgcgcggaacccctatttgtttatttttctaaatacatt caaatatgtatccgctcatgagacaataaccctgataaatgcttcaataatattgaaaaaggaagagtatgagtattcaacatttccgtgtcgcc cttattcccttttttgcggcattttgccttcctgtttttgctcacccagaaacgctggtgaaagtaaaagatgctgaagatcagttgggtgcacga gtgggttacatcgaactggatctcaacagcggtaagatccttgagagttttcgccccgaagaacgttttccaatgatgagcacttttaaagttct gctatgtggcgcggtattatcccgtattgacgccgggcaagagcaactcggtcgccgcatacactattctcagaatgacttggttgagtactc accagtcacagaaaagcatcttacggatggcatgacagtaagagaattatgcagtgctgccataaccatgagtgataacactgcggccaac ttacttctgacaacgatcggaggaccgaaggagctaaccgcttttttgcacaacatgggggatcatgtaactcgccttgatcgttgggaacc ggagctgaatgaagccataccaaacgacgagcgtgacaccacgatgcctgtagcaatggcaacaacgttgcgcaaactattaactggcg aactacttactctagcttcccggcaacaattaatagactggatggaggcggataaagttgcaggaccacttctgcgctcggcccttccggct ggctggtttattgctgataaatctggagccggtgagcgtgggtctcgcggtatcattgcagcactggggccagatggtaagccctcccgtat cgtagttatctacacgacggggagtcaggcaactatggatgaacgaaatagacagatcgctgagataggtgcctcactgattaagcattggt aactgtcagaccaagtttactcatatatactttagattgatttaaaacttcatttttaatttaaaaggatctaggtgaagatcctttttgataatctcat gaccaaaatcccttaacgtgagttttcgttccactgagcgtcagaccccgtagaaaagatcaaaggatcttcttgagatcctttttttctgcgcg taatctgctgcttgcaaacaaaaaaaccaccgctaccagcggtggtttgtttgccggatcaagagctaccaactctttttccgaaggtaactg gcttcagcagagcgcagataccaaatactgttcttctagtgtagccgtagttaggccaccacttcaagaactctgtagcaccgcctacatacc tcgctctgctaatcctgttaccagtggctgctgccagtggcgataagtcgtgtcttaccgggttggactcaagacgatagttaccggataagg cgcagcggtcgggctgaacggggggttcgtgcacacagcccagcttggagcgaacgacctacaccgaactgagatacctacagcgtga gctatgagaaagcgccacgcttcccgaagggagaaaggcggacaggtatccggtaagcggcagggtcggaacaggagagcgcacga gggagcttccagggggaaacgcctggtatctttatagtcctgtcgggtttcgccacctctgacttgagcgtcgatttttgtgatgctcgtcagg ggggcggagcctatggaaaaacgccagcaacgcggcctttttacggttcctggccttttgctggccttttgctcacatgttctttcctgcgttat cccctgattctgtggataaccgtattaccgcctttgagtgagctgataccgctcgccgcagccgaacgaccgagcgcagcgagtcagtga gcgaggaagcggaagagcgcccaatacgcaaaccgcctctccccgcgcgttggccgattcattaatgcagctggcacgacaggtttccc gactggaaagcgggcagtgagcgcaacgcaattaatgtgagttagctcactcattaggcaccccaggctttacactttatgcttccggctcgt atgttgtgtggaattgtgagcggataacaatttcacacaggaaacagctatgaccatgattacgccagatttaattaaggc;

>AAV-CBA (synthetic intron) (amiR-33-ACVR1-A10)-opt-ACVR1 nucleic acid sequence

SEQ ID NO: 26 cttaattaggctgcgcgctcgctcgctcactgaggccgcccgggcaaagcccgggcgtcgggcgacctttggtcgcccggcctcagtga gcgagcgagcgcgcagagagggagtggccaactccatcactaggggttccttgtagttaatgattaacccgccatgctacttatctaccag ggtaatggggatcctctagaactatagctagtcgacattgattattgactagttattaatagtaatcaattacggggtcattagttcatagcccat atatggagttccgcgttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggcagtacatcaagtgtatc atatgccaagtacgccccctattgacgtcaatgacggtaaatggcccgcctggcattatgcccagtacatgaccttatgggactttcctacttg gcagtacatctacgtattagtcatcgctattaccatgtcgaggccacgttctgcttcactctccccatctcccccccctccccacccccaattttg tatttatttattttttaattattttgtgcagcgatgggggcgggggggggggggcgcgcgccaggcggggcggggcggggcgaggggcgg ggcggggcgaggcggagaggtgcggcggcagccaatcagagcggcgcgctccgaaagtttccttttatggcgaggcggcggcggcg gcggccctataaaaagcgaagcgcgcggcgggcgggagcaccaccgcggtggcggccctagagtcgatcgaggaactgaaaaacca gaaagttaactggtaagtttagtctttttgtcttttatttcaggtcccagatctAGGGCTCTGCGTTTGCTCCAGGTAGTC

CGCTGCTCCCTTGGGCCTGGGCCCACTGACAGCCCTGGTGCCTCTGGCCGGCTGCAC

-continued

ACCTCCTGGCGGGCAGCTGTGgtaatctggtgagccactgttTGTTCTGGCAATACCTGAACAGT

GGGCGCCAGATTACCACGGAGGCCTGCCCTGACTGCCCACGGTGCCGTGGCCAAAG

AGGATCTAAGGGCACCGCTGAGGGCCTACCTAACCATCGTGGGGAATAAGGACAGT

GTCACCCctgcaggggatccggtggtggtgcaaatcaaagaactgctcctcagtggatgttgcctttacttctaggcctgtacggaag tgttacttctgctctaaaagctgcggaattgtacccgcggccgatccaccggtgaattccgccaccatggtcgatggagtgatgatcctgcct gtcctgattatgattgccctgcccagccccagcatggaagatgaaaaacctaaagtcaaccctaagctgtatatgtgcgtgtgcgagggcct gagctgcggaaacgaggatcactgcgagggccagcagtgtttcagctccctgtccatcaatgacggcttccacgtgtaccagaagggctg ctttcaggtgtatgagcagggcaagatgacctgtaagacaccaccttccccaggacaggcagtggagtgctgtcagggcgattggtgtaa ccggaatatcaccgcccagctgccaacaaagggcaagtctttccccggcacacagaactttcacctggaagtgggcctgatcatcctgag cgtggtgttcgccgtgtgcctgctggcatgtctgctgggagtggccctgagaaagtttaagcggagaaaccaggagcggctgaatccaag agatgtggagtacggcaccatcgagggcctgatcaccacaaatgtgggcgactctacactggccgacctgctggatcacagctgcacca gcggctccggatctggcctgccctttctggtgcagaggaccgtggcccggcagatcaccctgctggagtgcgtgggcaagggccggtac ggagaagtgtggagaggatcctggcagggagagaacgtggcagtgaagatcttctctagccgggatgagaagtcttggtttagagagac agagctgtataacacagtgatgctgaggcacgagaatatcctgggcttcatcgcctccgacatgacctctcgccactcctctacacagctgt ggctgatcacccactaccacgagatgggctccctgtacgattacctccagctgaccacactggacacagtgtcttgcctgcggatcgtgctg tctatcgccagcggcctggcacacctgcacatcgagatctttggaacccagggcaagccagcaatcgcacacagagatctgaagtctaag aacatcctggtgaagaagaatggccagtgctgtatcgccgatctgggcctggccgtgatgcacagccagtccaccaaccagctggacgtg ggcaacaatcctcgggtgggcacaaagagatacatggccccagaggtgctggatgagacaatccaggtggactgcttcgatagctataa gagggtggacatctgggcctttggcctggtgctgtgggaggtggcaaggaggatggtgagcaacggcatcgtggaggactacaagcca cccttctatgacgtggtgcctaatgatccatcctttgaggacatgcgcaaggtggtgtgcgtggatcagcagaggcccaacatccctaatcg ctggttcagcgaccccaccctgacatccctggccaagctgatgaaggagtgttggtatcagaatcctagcgccaggctgaccgccctgcg catcaagaaaactctgactaaaatcgacaatagcctggataaactgaaaaccgactgctgacctgagggcggccgcgtcgacggatccg atctttttccctctgccaaaaattatggggacatcatgaagccccttgagcatctgacttctggctaataaaggaaatttattttcattgcaatagt gtgttggaattttttgtgtctctcactcggaagcaattcgttgatctgaatttcgaccacccataatacccattaccctggtagataagtagcatg gcgggttaatcattaactacaaggaacccctagtgatggagttggccactccctctctgcgcgctcgctcgctcactgaggccgggcgacc aaaggtcgcccgacgcccgggctttgcccgggcggcctcagtgagcgagcgagcgcgcagccttaattaacctaattcactggccgtcg ttttacaacgtcgtgactgggaaaaccctggcgttacccaacttaatcgccttgcagcacatccccctttcgccagctggcgtaatagcgaag aggcccgcaccgatcgcccttcccaacagttgcgcagcctgaatggcgaatgggacgcgccctgtagcggcgcattaagcgcggcggg tgtggtggttacgcgcagcgtgaccgctacacttgccagcgccctagcgcccgctcctttcgctttcttcccttcctttctcgccacgttcgcc ggctttccccgtcaagctctaaatcgggggctccctttagggttccgatttagtgctttacggcacctcgaccccaaaaaacttgattagggtg atggttcacgtagtgggccatcgccctgatagacggtttttcgccctttgacgttggagtccacgttctttaatagtggactcttgttccaaactg gaacaacactcaaccctatctcggtctattcttttgatttataagggattttgccgatttcggcctattggttaaaaaatgagctgatttaacaaaa atttaacgcgaattttaacaaaatattaacgcttacaatttaggtggcacttttcggggaaatgtgcgcggaacccctatttgtttatttttctaaat acattcaaatatgtatccgctcatgagacaataaccctgataaatgcttcaataatattgaaaaaggaagagtatgagtattcaacatttccgtgt cgcccttattcccttttttgcggcattttgccttcctgtttttgctcacccagaaacgctggtgaaagtaaaagatgctgaagatcagttgggtgc acgagtgggttacatcgaactggatctcaacagcggtaagatccttgagagttttcgccccgaagaacgttttccaatgatgagcacttttaaa gttctgctatgtggcgcggtattatcccgtattgacgccgggcaagagcaactcggtcgccgcatacactattctcagaatgacttggttgag tactcaccagtcacagaaaagcatcttacggatggcatgacagtaagagaattatgcagtgctgccataaccatgagtgataacactgcgg ccaacttacttctgacaacgatcggaggaccgaaggagctaaccgcttttttgcacaacatgggggatcatgtaactcgccttgatcgttggg aaccggagctgaatgaagccataccaaacgacgagcgtgacaccacgatgcctgtagcaatggcaacaacgttgcgcaaactattaactg gcgaactacttactctagcttcccggcaacaattaatagactggatggaggcggataaagttgcaggaccacttctgcgctcggcccttccg -continued gctggctggtttattgctgataaatctggagccggtgagcgtgggtctcgcggtatcattgcagcactggggccagatggtaagccctcccg
tatcgtagttatctacacgacggggagtcaggcaactatggatgaacgaaatagacagatcgctgagataggtgcctcactgattaagcatt
ggtaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgttcttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcag
gggggcggagcctatggaaaaacgccagcaacgcggcctttttacggttcctggccttttgctggccttttgctcacatgttctttcctgcgtta
tcccctgattctgtggataaccgtattaccgcctttgagtgagctgataccgctcgccgcagccgaacgaccgagcgcagcgagtcagtga
gcgaggaagcggaagagcgcccaatacgcaaaccgcctctccccgcgcgttggccgattcattaatgcagctggcacgacaggtttccc
gactggaaagcgggcagtgagcgcaacgcaattaatgtgagttagctcactcattaggcaccccaggctttacactttatgcttccggctcgt
atgttgtgtggaattgtgagcggataacaatttcacacaggaaacagctatgaccatgattacgccagatttaattaaggc;

>AAV-CBA (MBL-amiR-ACVR1-A9)-opt-ACVR1 nucleic acid sequence

SEQ ID NO: 27 cttaattaggctgcgcgctcgctcgctcactgaggccgcccgggcaaagcccgggcgtcgggcgacctttggtcgcccggcctcagtga
gcgagcgagcgcgcagagagggagtggccaactccatcactaggggttccttgtagttaatgattaacccgccatgctacttatctaccag
ggtaatggggatcctctagaactatagctagtcgacattgattattgactagttattaatagtaatcaattacggggtcattagttcatagcccat
atatggagttccgcgttacataacttacggtaaatggcccgcctggctgaccgcccaacgacccccgcccattgacgtcaataatgacgtat
gttcccatagtaacgccaatagggactttccattgacgtcaatgggtggagtatttacggtaaactgcccacttggcagtacatcaagtgtatc
atatgccaagtacgccccctattgacgtcaatgacggtaaatggcccgcctggcattatgcccagtacatgaccttatgggactttcctacttg
gcagtacatctacgtattagtcatcgctattaccatgtcgaggccacgttctgcttcactctccccatctcccccccctccccacccccaatttg
tatttatttattttttaattattttgtgcagcgatgggggcgggggggggggggcgcgcgccaggcggggcggggcggggcgaggggcgg
ggcggggcgaggcggagaggtgcggcggcagccaatcagagcggcgcgctccgaaagtttccttttatggcgaggcggcggcggcg
gcggccctataaaaagcgaagcgcgcggcgggcgggagcaagctttcagatcgcctggagacgccatccacgctgttttgacctccata
gaagacaccgggaccgatccagcctccgcggccgggaacggtgcattggaacgcggattccccgtgccaagagtgacgtaagtaccg
cctatagagtctataggcccacccccttggcttcttatgcatgctatactgtttttggcttggggtctatacacccccgcttcctcatgttTGCT
GCCCGTGACCAGCACGTCAACGATTTTGTGGGCACGGGCGACACcgcagtgtagtctgagcagt
actcgttgctgccgcgcgcgccaccagacataatagctgacagactaacagactgttcctttccatgggtcttttctgcaAGGGCTCT
GCGTTTGCTCCAGGTAGTCCGCTGCTCCCTTGGGCCTGGGCCCACTGACAGCCCTGG
TGCCTCTGGCCGGCTGCACACCTCCTGGCGGGCAGCTGTGtgtaatctggtgagccactgtTGTT
CTGGCAATACCTGACAGTGGCAGATCAGATTACACACGGAGGCCTGCCCTGACTGC
CCACGGTGCCGTGGCCAAAGAGGATCTAAGGGCACCGCTGAGGGCCTACCTAACCA
TCGTGGGGAATAAGGACAGTGTCACCCtgcagtcaccgtcgccgccaccggtgaattccgccaccatggtcgat
ggagtgatgatcctgcctgtcctgattatgattgccctgcccagccccagcatggaagatgaaaaacctaaagtcaaccctaagctgtatatg
tgcgtgtgcgagggcctgagctgcggaaacgaggatcactgcgagggccagcagtgtttcagctccctgtccatcaatgacggcttccac
gtgtaccagaagggctgctttcaggtgtatgagcagggcaagatgacctgtaagacaccaccttccccaggacaggcagtggagtgctgt
cagggcgattggtgtaaccggaatatcaccgcccagctgccaacaaagggcaagtctttccccggcacacagaactttcacctggaagtg
ggcctgatcatcctgagcgtggtgttcgccgtgtgcctgctggcatgtctgctgggagtggccctgagaaagtttaagcggagaaaccagg
agcggctgaatccaagagatgtggagtacggcaccatcgagggcctgatcaccacaaatgtgggcgactctacactggccgacctgctg -continued gatcacagctgcaccagcggctccggatctggcctgccctttctggtgcagaggaccgtggcccggcagatcaccctgctggagtgcgtg ggcaagggccggtacggagaagtgtggagaggatcctggcagggagagaacgtggcagtgaagatcttctctagccgggatgagaagt cttggtttagagagacagagctgtataacacagtgatgctgaggcacgagaatatcctgggcttcatcgcctccgacatgacctctcgccac tcctctacacagctgtggctgatcacccactaccacgagatgggctccctgtacgattacctccagctgaccacactggacacagtgtcttg cctgcggatcgtgctgtctatcgccagcggcctggcacacctgcacatcgagatctttggaacccagggcaagccagcaatcgcacacag agatctgaagtctaagaacatcctggtgaagaagaatggccagtgctgtatcgccgatctgggcctggccgtgatgcacagccagtccac caaccagctggacgtgggcaacaatcctcgggtgggcacaaagagatacatggccccagaggtgctggatgagacaatccaggtggac tgcttcgatagctataagagggtggacatctgggcctttggcctggtgctgtgggaggtggcaaggaggatggtgagcaacggcatcgtg gaggactacaagccacccttctatgacgtggtgcctaatgatccatcctttgaggacatgcgcaaggtggtgtgcgtggatcagcagaggc ccaacatccctaatcgctggttcagcgaccccaccctgacatccctggccaagctgatgaaggagtgttggtatcagaatcctagcgccag gctgaccgccctgcgcatcaagaaaactctgactaaaatcgacaatagcctggataaactgaaaaccgactgctgacctgaggatccgatc tttttccctctgccaaaaattatggggacatcatgaagccccttgagcatctgacttctggctaataaaggaaatttattttcattgcaatagtgtg ttggaattttttgtgtctctcactcggaagcaattcgttgatctgaatttcgaccacccataatacccattaccctggtagataagtagcatggcg ggttaatcattaactacaaggaacccctagtgatggagttggccactccctctctgcgcgctcgctcgctcactgaggccgggcgaccaaa ggtcgcccgacgcccgggctttgcccgggcggcctcagtgagcgagcgagcgcgcagccttaattaacctaattcactggccgtcgtttta caacgtcgtgactgggaaaaccctggcgttacccaacttaatcgccttgcagcacatccccctttcgccagctggcgtaatagcgaagagg cccgcaccgatcgcccttcccaacagttgcgcagcctgaatggcgaatgggacgcgccctgtagcggcgcattaagcgcggcgggtgt ggtggttacgcgcagcgtgaccgctacacttgccagcgccctagcgcccgctcctttcgctttcttcccttcctttctcgccacgttcgccggc tttccccgtcaagctctaaatcgggggctccctttagggttccgatttagtgctttacggcacctcgaccccaaaaaacttgattagggtgatg gttcacgtagtgggccatcgccctgatagacggtttttcgccctttgacgttggagtccacgttctttaatagtggactcttgttccaaactggaa caacactcaaccctatctcggtctattcttttgatttataagggattttgccgatttcggcctattggttaaaaaatgagctgatttaacaaaaattta acgcgaattttaacaaaatattaacgcttacaatttaggtggcacttttcggggaaatgtgcgcggaacccctatttgtttatttttctaaatacatt caaatatgtatccgctcatgagacaataaccctgataaatgcttcaataatattgaaaaaggaagagtatgagtattcaacatttccgtgtcgcc cttattcccttttttgcggcattttgccttcctgtttttgctcacccagaaacgctggtgaaagtaaaagatgctgaagatcagttgggtgcacga gtgggttacatcgaactggatctcaacagcggtaagatccttgagagttttcgccccgaagaacgttttccaatgatgagcacttttaaagttct gctatgtggcgcggtattatcccgtattgacgccgggcaagagcaactcggtcgccgcatacactattctcagaatgacttggttgagtactc accagtcacagaaaagcatcttacggatggcatgacagtaagagaattatgcagtgctgccataaccatgagtgataacactgcggccaac ttacttctgacaacgatcggaggaccgaaggagctaaccgcttttttgcacaacatgggggatcatgtaactcgccttgatcgttgggaacc ggagctgaatgaagccataccaaacgacgagcgtgacaccacgatgcctgtagcaatggcaacaacgttgcgcaaactattaactggcg aactacttactctagcttcccggcaacaattaatagactggatggaggcggataaagttgcaggaccacttctgcgctcggcccttccggct ggctggtttattgctgataaatctggagccggtgagcgtgggtctcgcggtatcattgcagcactggggccagatggtaagccctcccgtat cgtagttatctacacgacggggagtcaggcaactatggatgaacgaaatagacagatcgctgagataggtgcctcactgattaagcattggt aactgtcagaccaagtttactcatatatactttagattgatttaaaacttcatttttaatttaaaaggatctaggtgaagatcctttttgataatctcat gaccaaaatcccttaacgtgagttttcgttccactgagcgtcagaccccgtagaaaagatcaaaggatcttcttgagatcctttttttctgcgcg taatctgctgcttgcaaacaaaaaaaccaccgctaccagcggtggtttgtttgccggatcaagagctaccaactctttttccgaaggtaactg gcttcagcagagcgcagataccaaatactgttcttctagtgtagccgtagttaggccaccacttcaagaactctgtagcaccgcctacatacc tcgctctgctaatcctgttaccagtggctgctgccagtggcgataagtcgtgtcttaccgggttggactcaagacgatagttaccggataagg cgcagcggtcgggctgaacggggggttcgtgcacacagcccagcttggagcgaacgacctacaccgaactgagatacctacagcgtga gctatgagaaagcgccacgcttcccgaagggagaaaggcggacaggtatccggtaagcggcagggtcggaacaggagagcgcacga gggagcttccagggggaaacgcctggtatctttatagtcctgtcgggtttcgccacctctgacttgagcgtcgatttttgtgatgctcgtcagg ggggcggagcctatggaaaaacgccagcaacgcggcctttttacggttcctggccttttgctggccttttgctcacatgttctttcctgcgttat -continued cccctgattctgtggataaccgtattaccgcctttgagtgagctgataccgctcgccgcagccgaacgaccgagcgcagcgagtcagtga gcgaggaagcggaagagcgcccaatacgcaaaccgcctctccccgcgcgttggccgattcattaatgcagctggcacgacaggtttccc gactggaaagcgggcagtgagcgcaacgcaattaatgtgagttagctcactcattaggcaccccaggctttacactttatgcttccggctcgt atgttgtgtggaattgtgagcggataacaatttcacacaggaaacagctatgaccatgattacgccagatttaattaaggc;

>AAV-CBA (MBL-amiR-ACVR1-A10)-opt-ACVR1 nucleic acid sequence

SEQ ID NO: 28 cttaattaggctgcgcgctcgctcgctcactgaggccgcccgggcaaagcccgggcgtcgggcgacctttggtcgcccggcctcagtga gcgagcgagcgcgcagagagggagtggccaactccatcactaggggttccttgtagttaatgattaacccgccatgctacttatctaccag ggtaatggggatcctctagaactatagctagtcgacattgattattgactagttattaatagtaatcaattacggggtcattagttcatagcccat atatggagttccgcgttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggcagtacatcaagtgtatc atatgccaagtacgccccctattgacgtcaatgacggtaaatggcccgcctggcattatgcccagtacatgaccttatgggactttcctacttg gcagtacatctacgtattagtcatcgctattaccatgtcgaggccacgttctgcttcactctccccatctcccccccctccccacccccaattttg tatttatttattttttaattattttgtgcagcgatgggggcgggggggggggggcgcgcgccaggcggggcggggcggggcgaggggcgg ggcggggcgaggcggagaggtgcggcggcagccaatcagagcggcgcgctccgaaagtttccttttatggcgaggcggcggcggcg gcggccctataaaaagcgaagcgcgcggcgggcgggagcaagctttcagatcgcctggagacgccatccacgctgttttgacctccata gaagacaccgggaccgatccagcctccgcggccgggaacggtgcattggaacgcggattccccgtgccaagagtgacgtaagtaccg cctatagagtctataggcccacccccttggcttcttatgcatgctatactgtttttggcttggggtctatacacccccgcttcctcatgttTGCT GCCCGTGACCAGCACGTCAACGATTTTGTGGGCACGGGCGACACcgcagtgtagtctgagcagt actcgttgctgccgcgcgcgccaccagacataatagctgacagactaacagactgttcctttccatgggtcttttctgcaAGGGCTCT

GCGTTTGCTCCAGGTAGTCCGCTGCTCCCTTGGGCCTGGGCCCACTGACAGCCCTGG

TGCCTCTGGCCGGCTGCACACCTCCTGGCGGGCAGCTGTGgtaatctggtgagccactgttTGTT

CTGGCAATACCTGAACAGTGGGACGCCAGATTACCACGGAGGCCTGCCCTGACTGC

CCACGGTGCCGTGGCCAAAGAGGATCTAAGGGCACCGCTGAGGGCCTACCTAACCA

TCGTGGGGAATAAGGACAGTGTCACCCtgcagtcaccgtcgccgccaccggtgaattccgccaccatggtcgat ggagtgatgatcctgcctgtcctgattatgattgccctgcccagccccagcatggaagatgaaaaacctaaagtcaaccctaagctgtatatg tgcgtgtgcgagggcctgagctgcggaaacgaggatcactgcgagggccagcagtgtttcagctccctgtccatcaatgacggcttccac gtgtaccagaagggctgctttcaggtgtatgagcagggcaagatgacctgtaagacaccaccttccccaggacaggcagtggagtgctgt cagggcgattggtgtaaccggaatatcaccgcccagctgccaacaaagggcaagtctttccccggcacacagaactttcacctggaagtg ggcctgatcatcctgagcgtggtgttcgccgtgtgcctgctggcatgtctgctgggagtggccctgagaaagtttaagcggagaaaccagg agcggctgaatccaagagatgtggagtacggcaccatcgagggcctgatcaccacaaatgtgggcgactctacactggccgacctgctg gatcacagctgcaccagcggctccggatctggcctgccctttctggtgcagaggaccgtggcccggcagatcaccctgctggagtgcgtg ggcaagggccggtacggagaagtgtggagaggatcctggcagggagagaacgtggcagtgaagatcttctctagccgggatgagaagt cttggtttagagagacagagctgtataacacagtgatgctgaggcacgagaatatcctgggcttcatcgcctccgacatgacctctcgccac tcctctacacagctgtggctgatcacccactaccacgagatgggctccctgtacgattacctccagctgaccacactggacacagtgtcttg cctgcggatcgtgctgtctatcgccagcggcctggcacacctgcacatcgagatctttggaacccagggcaagccagcaatcgcacacag agatctgaagtctaagaacatcctggtgaagaagaatggccagtgctgtatcgccgatctgggcctggccgtgatgcacagccagtccac caaccagctggacgtgggcaacaatcctcgggtgggcacaaagagatacatggccccagaggtgctggatgagacaatccaggtggac tgcttcgatagctataagagggtggacatctgggcctttggcctggtgctgtgggaggtggcaaggaggatggtgagcaacggcatcgtg gaggactacaagccacccttctatgacgtggtgcctaatgatccatcctttgaggacatgcgcaaggtggtgtgcgtggatcagcagaggc ccaacatccctaatcgctggttcagcgaccccaccctgacatccctggccaagctgatgaaggagtgttggtatcagaatcctagcgccag gctgaccgccctgcgcatcaagaaaactctgactaaaatcgacaatagcctggataaactgaaaaccgactgctgacctgaggatccgatc -continued tttttccctctgccaaaaattatggggacatcatgaagccccttgagcatctgacttctggctaataaaggaaatttattttcattgcaatagtgtg ttggaattttttgtgtctctcactcggaagcaattcgttgatctgaatttcgaccacccataatacccattaccctggtagataagtagcatggcg ggttaatcattaactacaaggaacccctagtgatggagttggccactccctctctgcgcgctcgctcgctcactgaggccgggcgaccaaa ggtcgcccgacgcccgggctttgcccgggcggcctcagtgagcgagcgagcgcgcagccttaattaacctaattcactggccgtcgtttta caacgtcgtgactgggaaaaccctggcgttacccaacttaatcgccttgcagcacatccccctttcgccagctggcgtaatagcgaagagg cccgcaccgatcgcccttcccaacagttgcgcagcctgaatggcgaatgggacgcgccctgtagcggcgcattaagcgcggcgggtgt ggtggttacgcgcagcgtgaccgctacacttgccagcgccctagcgcccgctcctttcgctttcttcccttcctttctcgccacgttcgccggc tttccccgtcaagctctaaatcgggggctccctttagggttccgatttagtgctttacggcacctcgaccccaaaaaacttgattagggtgatg gttcacgtagtgggccatcgccctgatagacggtttttcgccctttgacgttggagtccacgttctttaatagtggactcttgttccaaactggaa caacactcaaccctatctcggtctattcttttgatttataagggattttgccgatttcggcctattggttaaaaaatgagctgatttaacaaaaattta acgcgaattttaacaaaatattaacgcttacaatttaggtggcacttttcggggaaatgtgcgcggaacccctatttgtttatttttctaaatacatt caaatatgtatccgctcatgagacaataaccctgataaatgcttcaataatattgaaaaaggaagagtatgagtattcaacatttccgtgtcgcc cttattcccttttttgcggcattttgccttcctgtttttgctcacccagaaacgctggtgaaagtaaaagatgctgaagatcagttgggtgcacga gtgggttacatcgaactggatctcaacagcggtaagatccttgagagttttcgccccgaagaacgttttccaatgatgagcacttttaaagttct gctatgtggcgcggtattatcccgtattgacgccgggcaagagcaactcggtcgccgcatacactattctcagaatgacttggttgagtactc accagtcacagaaaagcatcttacggatggcatgacagtaagagaattatgcagtgctgccataaccatgagtgataacactgcggccaac ttacttctgacaacgatcggaggaccgaaggagctaaccgcttttttgcacaacatgggggatcatgtaactcgccttgatcgttgggaacc ggagctgaatgaagccataccaaacgacgagcgtgacaccacgatgcctgtagcaatggcaacaacgttgcgcaaactattaactggcg aactacttactctagcttcccggcaacaattaatagactggatggaggcggataaagttgcaggaccacttctgcgctcggcccttccggct ggctggtttattgctgataaatctggagccggtgagcgtgggtctcgcggtatcattgcagcactggggccagatggtaagccctcccgtat cgtagttatctacacgacggggagtcaggcaactatggatgaacgaaatagacagatcgctgagataggtgcctcactgattaagcattggt aactgtcagaccaagtttactcatatatactttagattgatttaaaacttcatttttaatttaaaaggatctaggtgaagatcctttttgataatctcat gaccaaaatcccttaacgtgagttttcgttccactgagcgtcagaccccgtagaaaagatcaaaggatcttcttgagatcctttttttctgcgcg taatctgctgcttgcaaacaaaaaaaccaccgctaccagcggtggtttgtttgccggatcaagagctaccaactctttttccgaaggtaactg gcttcagcagagcgcagataccaaatactgttcttctagtgtagccgtagttaggccaccacttcaagaactctgtagcaccgcctacatacc tcgctctgctaatcctgttaccagtggctgctgccagtggcgataagtcgtgtcttaccgggttggactcaagacgatagttaccggataagg cgcagcggtcgggctgaacggggggttcgtgcacacagcccagcttggagcgaacgacctacaccgaactgagatacctacagcgtga gctatgagaaagcgccacgcttcccgaagggagaaaggcggacaggtatccggtaagcggcagggtcggaacaggagagcgcacga gggagcttccagggggaaacgcctggtatctttatagtcctgtcgggtttcgccacctctgacttgagcgtcgatttttgtgatgctcgtcagg ggggcggagcctatggaaaaacgccagcaacgcggcctttttacggttcctggccttttgctggccttttgctcacatgttctttcctgcgttat cccctgattctgtggataaccgtattaccgcctttgagtgagctgataccgctcgccgcagccgaacgaccgagcgcagcgagtcagtga gcgaggaagcggaagagcgcccaatacgcaaaccgcctctccccgcgcgttggccgattcattaatgcagctggcacgacaggtttccc gactggaaagcgggcagtgagcgcaacgcaattaatgtgagttagctcactcattaggcaccccaggctttacactttatgcttccggctcgt atgttgtgtggaattgtgagcggataacaatttcacacaggaaacagctatgaccatgattacgccagatttaattaaggc;

>AAV-ABE C-terminal sghACVR1 nucleic acid sequence

SEQ ID NO: 29 ccaactccatcactaggggttcctgcggccgcaaggtcgggcaggaagagggcctatttcccatgattccttcatatttgcatatacgataca aggctgttagagagataattagaattaatttgactgtaaacacaaagatattagtacaaaatacgtgacgtagaaagtaataatttcttgggtag tttgcagttttaaaattatgattaaaatggactatcatatgcttaccgtaacttgaaagtatttcgatttcttggctttatatatcttgtggaaaggac gaaacaccGGCTCaCCAGATTACACTGTgttttagagctagaaatagcaagttaaaataaggctagtccgttatcaacttga aaaagtggcaccgagtcggtgctttttttctcgagccatagagcccaccgcatccccagcatgcctgctattgtcttcccaatcctcccccttg ctgtcctgccccaccccaccccccagaatagaatgacacctactcagacaatgcgatgcaatttcctcattttattaggaaaggacagtggg -continued agtggcaccttccagggtcaaggaaggcacgggggaggggcaaacaacagatggctggcaactagaaggcacagtcgcaccacgga attgtcagtgcccaacagccgagcccctgtccagcagcgggcaaggcaggcggcgatgagttccgccgtggcaagaactaaccaggat ttatacaaggaggagaaaatgaaagccatacgggaagcaatagcatgatacaaaggcattaaagcagcgtatccacatagcgtaaaagg agcaacatagttaagaataccagtcaatctttcacaaattttgtaatccagaggttgattatcagatcttagactttcctcttcttcttgggctcgaa ttcgctgccgtcggcggttcttttgagccgccagagtcacctcccagctgagacaggtcgatccgtgtctcgtacaggccggtgatgctct ggtggatcagggtggcgtccagcacctctttggtgctggtgtacctcttccggtcgatggtggtgtcaaagtacttgaaggcggcaggggct cccagattggtcagggtaaacaggtggatgatattctcggcctgctctctgatgggcttatcccggtgcttgttgtaggcggacagcactttgt ccagattagcgtcggccaggatcactctcttggagaactcgctgatctgctcgatgatctcgtccaggtagtgcttgtgctgttccacaaaca gctgtttctgctcattatcctcgggggagcccttcagcttctcatagtggctggccaggtacaggaagttcacatatttggagggcagggcca gttcgtttcccttctgcagttcgccggcagaggccagcattctcttccggccgttttccagctcgaacagggagtacttaggcagcttgatgat caggtcctttttcacttctttgtagcccttggcttccagaaagtcgatgggattcttctcgaagctgcttctttccatgatggtgatccccagcagc tctttcacactcttcagtttcttggacttgcccttttccactttggccaccaccagcacagaataggccacggtggggctgtcgaagccgccgt acttcttagggtcccagtccttctttctggcgatcagcttatcgctgttcctcttgggcaggatagactctttgctgaagccgcctgtctgcacct cggtctttttcacgatattcacttggggcatgctcagcactttccgcacggtggcaaaatcccggcccttatcccacacgatctccccggtttc gccgtttgtctcgatcagaggccgcttccggatctcgccgttggccagggtaatctcggtcttgaaaaagttcatgatgttgctgtagaagaa gtacttggcggtagccttgccgatttcctgctcgctcttggcgatcatcttccgcacgtcgtacaccttgtagtcgccgtacacgaactcgcttt ccagcttagggtactttttgatcagggcggttcccacgacggcgttcaggtaggcgtcgtgggcgtggtggtagttgttgatctcgcgcactt tgtaaaactggaaatccttccggaaatcggacaccagcttggacttcagggtgatcactttcacttcccggatcagcttgtcattctcgtcgtac ttagtgttcatccgggagtccaggatctgtgccacgtgctttgtgatctgccgggtttccaccagctgtctcttgatgaagccggccttatccag ttcgctcaggccgcctctctcggccttggtcagattgtcgaactttctctgggtaatcagcttggcgttcagcagctgccgccagtagttcttca tcttcttcacgacctcttcggagggcacgttgtcgctcttgccccggttcttgtcgcttctggtcagcaccttgttgtcgatggagtcgtccttca gaaagctctgaggcacgatatggtccacatcgtagtcggacagccggttgatgtccagttcctggtccacgtacatatcccgcccattctgc aggtagtacaggtacagcttctcgttctgcagctgggtgttttccacggggtgttctttcaggatctggctgcccagctctttgatgccctcttcg atccgcttcattctctcgcggctgttcttctgtcccttctgggtggtctggttctctctggccatttcgatcacgatgttctcgggcttgtgccggc ccatcactttcacgagctcgtccaccaccttcactgtctgcaggatgcccttcttaatggcggggctgccggccagattggcaatgtgctcgt gcaggctatcgccctggccggacacctgggctttctggatgtcctctttaaaggtcaggctgtcgtcgtggatcagctgcatgaagtttctgtt ggcgaagccgtcggacttcaggaaatccaggattgtcttgccggactgcttgtcccggatgccgttgatcagcttccggctcagcctgccc cagccggtgtatctccgccgcttcagctgcttcatcactttgtcgtcgaacaggtgggcataggttttcagccgttcctcgatcatctctctgtc ctcaaacagtgtcagggtcagcacgatatcttccagaatgtcctcgttttcctcattgtccaggaagtccttgtccttgataattttcagcagatc gtggtatgtgcccagggaggcgttgaaccgatcttccacgccggagatttccacggagtcgaagcaattgctggcgataaagccattcttc agggcgaagttgtgatcccgctccacgccgatgtcgtacacgttctgctttcccaggtatttccgtgtagcaatcttgatgactttccgcttcttc tttggtgactcgaactcgcttccgtcggctgtccgtttcatggtggcaccggtccaacctgaaaaaaagtgatttcaggcaggtgctccaggt aattaaacattaataccccaccaaccaaccatcccttaaacccttacctcttgctcagctaattacagcccggaggagaagggccgtcccgc ccgctcacctgtgggagtaacgcggtcagtcagagccggggcgggcggcgcgaggcggcggcggagcggggcacggggcgaagg cagcgtcgcagcgactcccgcccgccgcgcgcttcgctttttatagggccgccgccgccgccgcctcgccataaaaggaaactttcgga gcgcgccgctctgattggctgccgccgcacctctccgcctcgccccgccccgcccctcgccccgccccgccccgcctggcgcgcgccc ccccccccccccgcccccatcgctgcacaaaataattaaaaaataaataaatacaaaattgggggtggggaggggggggagatgggg agagtgaagcagaacgtggggctcacctcgaccatggtaatagcgatgactaatacgtagatgtactgccaagtaggaaagtcccataag gtcatgtactgggcacaatgccaggcgggccatttaccgtcattgacgtcaatagggggcgtacttggcatatgatacacttgatgtactgcc aagtgggcagtttaccgtaaatactccacccattgacgtcaatggaaagtccctattggcgttactattgacgtcaatgggcgggggtcgttg ggcggtcagccaggcgggccatttaccgtaagttatgtaacgggtaccctgatctagaggccgcaggaacccctagtgatggagttggcc -continued actccctctctgcgcgctcgctcgctcactgaggccgggcgaccaaaggtcgcccgacgcccgggctttgcccgggcggcctcagtgag cgagcgagcgcgcagccttaattaaatctggcgtaatcatggtcatagctgtttcctgtgtgaaattgttatccgctcacaattccacacaacat acgagccggaagcataaagtgtaaagcctggggtgcctaatgagtgagctaactcacattaattgcgttgcgctcactgcccgctttccagt cgggaaacctgtcgtgccagctgcattaatgaatcggccaacgcgcggggagaggcggtttgcgtattgggcgctcttccgcttcctcgct cactgactcgctgcgctcggtcgttcggctgcggcgagcggtatcagctcactcaaaggcggtaatacggttatccacagaatcaggggat aacgcaggaaagaacatgtgagcaaaaggccagcaaaaggccaggaaccgtaaaaaggccgcgttgctggcgtttttccataggctccg cccccctgacgagcatcacaaaaatcgacgctcaagtcagaggtggcgaaacccgacaggactataaagataccaggcgtttccccctg gaagctccctcgtgcgctctcctgttccgaccctgccgcttaccggatacctgtccgcctttctcccttcgggaagcgtggcgctttctcatag ctcacgctgtaggtatctcagttcggtgtaggtcgttcgctccaagctgggctgtgtgcacgaaccccccgttcagcccgaccgctgcgcct tatccggtaactatcgtcttgagtccaacccggtaagacacgacttatcgccactggcagcagccactggtaacaggattagcagagcgag gtatgtaggcggtgctacagagttcttgaagtggtggcctaactacggctacactagaaggacagtatttggtatctgcgctctgctgaagcc agttaccttcggaaaaagagttggtagctcttgatccggcaaacaaaccaccgctggtagcggtggtttttttgtttgcaagcagcagattacg cgcagaaaaaaaggatctcaagaagatcctttgatcttttctacggggtctgacgctcagtggaacgaaaactcacgttaagggattttggtc atgagattatcaaaaaggatcttcacctagatccttttaaattaaaaatgaagttttaaatcaatctaaagtatatatgagtaaacttggtctgaca gttaccaatgcttaatcagtgaggcacctatctcagcgatctgtctatttcgttcatccatagttgcctgactccccgtcgtgtagataactacga tacgggagggcttaccatctggccccagtgctgcaatgataccgcgagacccacgctcaccggctccagatttatcagcaataaaccagc cagccggaagggccgagcgcagaagtggtcctgcaactttatccgcctccatccagtctattaattgttgccgggaagctagagtaagtagt tcgccagttaatagtttgcgcaacgttgttaccattactacaggcatcgtggtgtcacgctcgtcgtttggtatggcttcattcagctccggttcc caacgatcaaggcgagttacatgatcccccatgttgtgcaaaaaagcggttagctccttcggtcctccgatcgttgtcagaagtaagttggcc gcagtgttatcactcatggttatggcagcactgcataattctcttactgtcatgccatccgtaagatgcttttctgtgactggtgagtactcaacc aagtcattctgagaatagtgtatgcggcgaccgagttgctcttgcccggcgtcaatacgggataataccgcgccacatagcagaactttaaa agtgctcatcattggaaaacgttcttcggggcgaaaactctcaaggatcttaccgctgttgagatccagttcgatgtaacccactcgtgcacc caactgatcttcagcatcttttactttcaccagcgtttctgggtgagcaaaaacaggaaggcaaaatgccgcaaaaaagggaataagggcg acacggaaatgttgaatactcatactcttcctttttcaatattattgaagcatttatcagggttattgtctcatgagcggatacatatttgaatgtattt agaaaaataaacaaataggggttccgcgcacatttccccgaaaagtgccacctgaaattataaacgttaatattttgttaaaattcgcgttaaat ttttgttaaatcagctcattttttaaccaataggccgaaatcggcaaaatcccttataaatcaaaagaatagaccgagatagggttgagtgttgtt ccagtttggaacaagagtccactattaaagaacgtggactccaacgtcaaagggcgaaaaaccgtctatcagggcgatggcccactacgt gaaccatcaccctaatcaagttttttggggtcgaggtgccgtaaagcactaaatcggaaccctaaagggagcccccgatttagagcttgacg gggaaagccggcgaacgtggcgagaaaggaagggaagaaagcgaaaggagcgggcgctagggcgctggcaagtgtagcggtcac gctgcgcgtaaccaccacacccgccgcgcttaatgcgccgctacagggcgcgtcccattcgccattcaggctgcgcaactgttgggaag ggcgatcggtgcgggcctcttcgctattacgccagctggcgaaagggggatgtgctgcaaggcgattaagttgggtaacgccagggttttc ccagtcacgacgttgtaaaacgacggccagtgaattaggttaattaaggctgcgcgctcgctcgctcactgaggccgcccgggcaaagcc cgggcgtcgggcgacctttggtcgcccggcctcagtgagcgagcgagcgcgcagagagggagtgg;

>PB2 (NF-kB promoter) nucleic acid sequence

SEQ ID NO: 30

TGAGCTCACAGAGGGGACTTTCCGAGAGATCTACAGAGGGGACTTTCCGAGAGCGA

GCTTGGGCTGCAGGTCGACCGTCCATCCATTCACAGCGCTTCTATAAAGGCGCCAGC

TGAGGCGCCTACTACTCCAACCGCGACTGCAGCGAGCAACTGAGAAGACTGGATAG

AGCCGGCGGTTCCGCGAACGAGCAGTGACCGCGCTCCCACCCAGCTCTGCTCTGCA

GCTCCACCAGTGTCTCTCTAGA;

-continued

>BRE nucleic acid sequence

SEQ ID NO: 31

GCTTCGCGCCCTAAGTCTGCAGGTGACGGGCTCAGGGGCGGGGGCTGGGTGGGGGG

GAGCGGAGAATGCTCCAGCCCAGTTTGCCGTCTCCATGGCGACCGCCCGCGCGGCG

CCAGCCTGACAGCCCGTCCGGGTTTTATGAATGGGTGACGTCACGGGCCTGGCGTCT

AACGGTCTGAGCCGCTTGTTCAGACGCTGACACAGACCAGCCCGGGAAAGG;

>AAV BRE-NFkB-Gaussia nucleic acid sequence

SEQ ID NO: 32 cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgccgcgtcgacattgattattgactctggtcgttacat aacttacggtaaatggcccgcctggctgaccgcccaacgacccccgcccattgacgtcaataatgacgtatgttcccatagtaacgccaata gggactttccattgacgtcaatgggtggagtatttacggtaaactgcccacttggcagtacatcaagtgtatcatatgccaagtacgccccta ttgacgtcaatgacggtaaatggcccgcctggcattatgcccagtacatgaccttatgggactttcctacttggcagtacatctactcgaggcc acgttctgcttcacGCTTCGCGCCCTAAGTCTGCAGGTGACGGGCTCAGGGGCGGGGGCTGG

GTGGGGGGGAGCGGAGAATGCTCCAGCCCAGTTTGCCGTCTCCATGGCGACCGCCC

GCGCGGCGCCAGCCTGACAGCCCGTCCGGGTTTTATGAATGGGTGACGTCACGGGC

CTGGCGTCTAACGGTCTGAGCCGCTTGTTCAGACGCTGACACAGACCAGCCCGGGA

AAGGTGAGCTCACAGAGGGGACTTTCCGAGAGATCTACAGAGGGGACTTTCCGAGA

GCGAGCTTGGGCTGCAGGTCGACCGTCCATCCATTCACAGCGCTTCTATAAAGGCG

CCAGCTGAGGCGCCTACTACTCCAACCGCGACTGCAGCGAGCAACTGAGAAGACTG

GATAGAGCCGGCGGTTCCGCGAACGAGCAGTGACCGCGCTCCCACCCAGCTCTGCT

CTGCAGCTCCACCAGTGTCTCTCTAGAgccaccgcggtggcggccctagagtcgatcgaggaactgaaaaacc agaaagttaactggtaagtttagtctttttgtcttttatttcaggtcccggatccggtggtggtgcaaatcaaagaactgctcctcagtggatgttg cctttacttctaggcctgtacggaagtgttacttctgctctaaaagctgcggaattgtacccgcggccgatccaccggtcgccaccatctagc atgggagtcaaagttctgtttgccctgatctgcatcgctgtggccgaggccaagcccaccgagaacaacgaagacttcaacatcgtggccg tggccagcaacttcgcgaccacggatctcgatgctgaccgcgggaagttgcccggcaagaagctgccgctggaggtgctcaaagagat ggaagccaatgcccggaaagctggctgcaccaggggctgtctgatctgcctgtcccacatcaagtgcacgcccaagatgaagaagttcat cccaggacgctgccacacctacgaaggcgacaaagagtccgcacagggcggcataggcgaggcgatcgtcgacattcctgagattcct gggttcaaggacttggagcccatggagcagttcatcgcacaggtcgatctgtgtgtggactgcacaactggctgcctcaaagggcttgcca acgtgcagtgttctgacctgctcaagaagtggctgccgcaacgctgtgcgacctttgccagcaagatccagggccaggtggacaagatca agggggccggtggtgactagctcgacgctgatcagcctcgactgtgccttctagttgccagccatctgttgtttgcccctcccccgtgccttc cttgaccctggaaggtgccactcccactgtcctttcctaataaaatgaggaaattgcatcgcattgtctgagtaggtgtcattctattctggggg gtggggtggggcaggacagcaagggggaggattgggaagacaaggccgcaggaacccctagtgatggagttggccactccctctctg cgcgctcgctcgctcactgaggccgggcgaccaaaggtcgcccgacgcccgggctttgcccgggcggcctcagtgagcgagcgagcg cgcagctgcctgcaggggcgcctgatgcggtattttctccttacgcatctgtgcggtatttcacaccgcatacgtcaaagcaaccatagtacg cgccctgtagcggcgcattaagcgcggcgggtgtggtggttacgcgcagcgtgaccgctacacttgccagcgccctagcgcccgctcctt tcgctttcttcccttcctttctcgccacgttcgccggctttccccgtcaagctctaaatcgggggctccctttagggttccgatttagtgctttacg gcacctcgaccccaaaaaacttgatttgggtgatggttcacgtagtgggccatcgccctgatagacggtttttcgccctttgacgttggagtcc acgttctttaatagtggactcttgttccaaactggaacaacactcaaccctatctcgggctattcttttgatttataagggattttgccgatttcggc ctattggttaaaaaatgagctgatttaacaaaaatttaacgcgaattttaacaaaatattaacgtttacaattttatggtgcactctcagtacaatct gctctgatgccgcatagttaagccagccccgacacccgccaacacccgctgacgcgccctgacgggcttgtctgctcccggcatccgctt acagacaagctgtgaccgtctccgggagctgcatgtgtcagaggttttcaccgtcatcaccgaaacgcgcgagacgaaagggcctcgtga tacgcctatttttataggttaatgtcatgataataatggtttcttagacgtcaggtggcacttttcggggaaatgtgcgcggaacccctatttgttta -continued tttttctaaatacattcaaatatgtatccgctcatgagacaataaccctgataaatgcttcaataatattgaaaaaggaagagtatgagtattcaac atttccgtgtcgcccttattcccttttttgcggcattttgccttcctgtttttgctcacccagaaacgctggtgaaagtaaaagatgctgaagatca gttgggtgcacgagtgggttacatcgaactggatctcaacagcggtaagatccttgagagttttcgccccgaagaacgttttccaatgatgag cacttttaaagttctgctatgtggcgcggtattatcccgtattgacgccgggcaagagcaactcggtcgccgcatacactattctcagaatgac ttggttgagtactcaccagtcacagaaaagcatcttacggatggcatgacagtaagagaattatgcagtgctgccataaccatgagtgataa cactgcggccaacttacttctgacaacgatcggaggaccgaaggagctaaccgcttttttgcacaacatgggggatcatgtaactcgccag atcgagggaaccggagctgaatgaagccataccaaacgacgagcgtgacaccacgatgcctgtagcaatggcaacaacgagcgcaaa ctattaactggcgaactacttactctagcacccggcaacaattaatagactggatggaggcggataaagagcaggaccacactgcgctcg gcccaccggctggctggatattgctgataaatctggagccggtgagcgtgggtctcgcggtatcattgcagcactggggccagatggtaa gccctcccgtatcgtagttatctacacgacggggagtcaggcaactatggatgaacgaaatagacagatcgctgagataggtgcctcactg attaagcattggtaactgtcagaccaagtttactcatatatactttagattgatttaaaacttcatttttaatttaaaaggatctaggtgaagatccttt ttgataatctcatgaccaaaatcccttaacgtgagttttcgttccactgagcgtcagaccccgtagaaaagatcaaaggatcttcttgagatcct ttttttctgcgcgtaatctgctgcttgcaaacaaaaaaaccaccgctaccagcggtggtttgtttgccggatcaagagctaccaactctttttcc gaaggtaactggcttcagcagagcgcagataccaaatactgtccactagtgtagccgtagttaggccaccacttcaagaactctgtagcac cgcctacatacctcgctctgctaatcctgaaccagtggctgctgccagtggcgataagtcgtgtcttaccgggttggactcaagacgatagtt accggataaggcgcagcggtcgggctgaacggggggttcgtgcacacagcccagcttggagcgaacgacctacaccgaactgagata cctacagcgtgagctatgagaaagcgccacgcttcccgaagggagaaaggcggacaggtatccggtaagcggcagggtcggaacagg agagcgcacgagggagcttccagggggaaacgcctggtatctttatagtcctgtcgggtttcgccacctctgacttgagcgtcgatttttgtg atgctcgtcaggggggcggagcctatggaaaaacgccagcaacgcggcctttttacggacctggccttttgctggccttttgctcacatgt;

>AAV CBA-FST-TNFR2-miR122 nucleic acid sequence

SEQ ID NO: 33 cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgccgcgtcgacattgattattgactctggtcgttacat aacttacggtaaatggcccgcctggctgaccgcccaacgacccccgcccattgacgtcaataatgacgtatgttcccatagtaacgccaata gggactttccattgacgtcaatgggtggagtatttacggtaaactgcccacttggcagtacatcaagtgtatcatatgccaagtacgccccta ttgacgtcaatgacggtaaatggcccgcctggcattatgcccagtacatgaccttatgggactttcctacttggcagtacatctactcgaggcc acgttctgcttcactctccccatctcccccccctccccacccccaattttgtatttatttattttttaattattttgtgcagcgatgggggcgggggg ggggggggggggggcgcgcgccaggcggggcggggcggggcgaggggcggggcggggcgaggcggagaggtgcggcggca gccaatcagagcggcgcgctccgaaagtttccttttatggcgaggcggcggcggcggcggccctataaaaagcgaagcgcgcggcgg gcgggagcgggatcagccaccgcggtggcggccctagagtcgatcgaggaactgaaaaaccagaaagttaactggtaagtttagtctttt tgtcttttatttcaggtcccggatccggtggtggtgcaaatcaaagaactgctcctcagtggatgttgcctttacttctaggcctgtacggaagt gttacttctgctctaaaagctgcggaattgtacccgcggccgatccaCCGGTgccaccATGGTCCGCGCGAGGCACC

AGCCGGGTGGGCTTTGCCTCCTGCTGCTGCTGCTCTGCCAGTTCATGGAGGACCGCA

GTGCCCAGGCTGGGAACTGCTGGCTCCGTCAAGCGAAGAACGGCCGCTGCCAGGTC

CTGTACAAGACCGAACTGAGCAAGGAGGAGTGCTGCAGCACCGGCCGGCTGAGCA

CCTCGTGGACCGAGGAGGACGTGAATGACAACACACTCTTCAAGTGGATGATTTTC

AACGGGGGCGCCCCCAACTGCATCCCCTGTAAAGAAACGTGTGAGAACGTGGACTG

TGGACCTGGGAAAAAATGCCGAATGAACAAGAAGAACAAACCCCGCTGCGTCTGC

GCCCCGGATTGTTCCAACATCACCTGGAAGGGTCCAGTCTGCGGGCTGGATGGGAA

AACCTACCGCAATGAATGTGCACTCCTAAAGGCAAGATGTAAAGAGCAGCCAGAAC

TGGAAGTCCAGTACCAAGGCAGATGTAAAAAGACTTGTCGGGATGTTTTCTGTCCA

GGCAGCTCCACATGTGTGGTGGACCAGACCAATAATGCCTACTGTGTGACCTGTAA

-continued

TCGGATTTGCCCAGAGCCTGCTTCCTCTGAGCAATATCTCTGTGGGAATGATGGAGT

CACCTACTCCAGTGCCTGCCACCTGAGAAAGGCTACCTGCCTGCTGGGCAGATCTAT

TGGATTAGCCTATGAGGGAAAGTGTATCAAAGCAAAGTCCTGTGAAGATATCCAGT

GCACTGGTGGGAAAAAATGTTTATGGGATTTCAAGGTTGGGAGAGGCCGGTGTTCC

CTCTGTGATGAGCTGTGCCCTGACAGTAAGTCGGATGAGCCTGTCTGTGCCAGTGAC

AATGCCACTTATGCCAGCGAGTGTGCCATGAAGGAAGCTGCCTGCTCCTCAGGTGT

GCTACTGGAAGTAAAGCACTCCGGATCTTGCAACggatccggagagggcagaggaagtctgctaacatg cggtgacgtcgaggagaatcctggacctatggcgcccgtcgccgtctgggccgcgctggccgtcggactggagctctgggctgcggcg cacgccttgcccgcccaggtggcatttacaccctacgccccggagcccgggagcacatgccggctcagagaatactatgaccagacagc tcagatgtgctgcagcaaatgctcgccgggccaacatgcaaaagtcttctgtaccaagacctcggacaccgtgtgtgactcctgtgaggac agcacatacacccagctctggaactgggttcccgagtgcttgagctgtggctcccgctgtagctctgaccaggtggaaactcaagcctgca ctcgggaacagaaccgcatctgcacctgcaggcccggctggtactgcgcgctgagcaagcaggaggggtgccggctgtgcgcgccgc tgcgcaagtgccgcccgggcttcggcgtggccagaccaggaactgaaacatcagacgtggtgtgcaagccctgtgccccggggacgtt ctccaacacgacttcatccacggatatttgcaggccccaccagatctgtaacgtggtggccatccctgggaatgcaagcatggatgcagtct gcacgtccacgtcccccacccggagtatggccccaggggcagtacacttaccccagccagtgtccacacgatcccaacacacgcagcc aactccagaacccagcactgctccaagcacctccttcctgctcccaatgggcccccagcccccccagctgaagggagcactggcgacttcg ctcttccagtttgaGCGGCCGCcaaacaccattgtcacactccaacaaacaccattgtcacactccaacaaacaccattgtcacactcc aGCGGCCGCACGCGTTgatcagcctcgactgtgccttctagttgccagccatctgttgtttgcccctcccccgtgccttccttga ccctggaaggtgccactcccactgtcctttcctaataaaatgaggaaattgcatcgcattgtctgagtaggtgtcattctattctggggggtgg ggtggggcaggacagcaagggggaggattgggaagacaaggccgcaggaacccctagtgatggagttggccactccctctctgcgcg ctcgctcgctcactgaggccgggcgaccaaaggtcgcccgacgcccgggctttgcccgggcggcctcagtgagcgagcgagcgcgca gctgcctgcaggggcgcctgatgcggtattttctccttacgcatctgtgcggtatttcacaccgcatacgtcaaagcaaccatagtacgcgcc ctgtagcggcgcattaagcgcggcgggtgtggtggttacgcgcagcgtgaccgctacacttgccagcgccctagcgcccgctcctttcgc tttcttcccttcctttctcgccacgttcgccggctttccccgtcaagctctaaatcgggggctccctttagggttccgatttagtgctttacggcac ctcgaccccaaaaaacttgatttgggtgatggttcacgtagtgggccatcgccctgatagacggtttttcgccctttgacgttggagtccacgt tctttaatagtggactcttgttccaaactggaacaacactcaaccctatctcgggctattcttttgatttataagggattttgccgatttcggcctatt ggttaaaaaatgagctgatttaacaaaaatttaacgcgaattttaacaaaatattaacgtttacaattttatggtgcactctcagtacaatctgctct gatgccgcatagttaagccagccccgacacccgccaacacccgctgacgcgccctgacgggcttgtctgctcccggcatccgcttacag acaagctgtgaccgtctccgggagctgcatgtgtcagaggttttcaccgtcatcaccgaaacgcgcgagacgaaagggcctcgtgatacg cctatttttataggttaatgtcatgataataatggtttcttagacgtcaggtggcacttttcggggaaatgtgcgcggaacccctatttgtttattttt ctaaatacattcaaatatgtatccgctcatgagacaataaccctgataaatgcttcaataatattgaaaaaggaagagtatgagtattcaacattt ccgtgtcgcccttattcccttttttgcggcattttgccttcctgtttttgctcacccagaaacgctggtgaaagtaaaagatgctgaagatcagttg ggtgcacgagtgggttacatcgaactggatctcaacagcggtaagatccttgagagttttcgccccgaagaacgttttccaatgatgagcac ttttaaagttctgctatgtggcgcggtattatcccgtattgacgccgggcaagagcaactcggtcgccgcatacactattctcagaatgacttg gttgagtactcaccagtcacagaaaagcatcttacggatggcatgacagtaagagaattatgcagtgctgccataaccatgagtgataacac tgcggccaacttacttctgacaacgatcggaggaccgaaggagctaaccgcttttttgcacaacatgggggatcatgtaactcgccttgatc gttgggaaccggagctgaatgaagccataccaaacgacgagcgtgacaccacgatgcctgtagcaatggcaacaacgttgcgcaaacta ttaactggcgaactacttactctagcttcccggcaacaattaatagactggatggaggcggataaagttgcaggaccacttctgcgctcggc ccttccggctggctggtttattgctgataaatctggagccggtgagcgtgggtctcgcggtatcattgcagcactggggccagatggtaagc cctcccgtatcgtagttatctacacgacggggagtcaggcaactatggatgaacgaaatagacagatcgctgagataggtgcctcactgatt aagcattggtaactgtcagaccaagtttactcatatatactttagattgatttaaaacttcatttttaatttaaaaggatctaggtgaagatcctttttg -continued ataatctcatgaccaaaatcccttaacgtgagttttcgttccactgagcgtcagaccccgtagaaaagatcaaaggatcttcttgagatcctttttt ttctgcgcgtaatctgctgcttgcaaacaaaaaaaccaccgctaccagcggtggtttgtttgccggatcaagagctaccaactctttttccgaa ggtaactggcttcagcagagcgcagataccaaatactgtccttctagtgtagccgtagttaggccaccacttcaagaactctgtagcaccgc ctacatacctcgctctgctaatcctgttaccagtggctgctgccagtggcgataagtcgtgtcttaccgggttggactcaagacgatagttacc ggataaggcgcagcggtcgggctgaacggggggttcgtgcacacagcccagcttggagcgaacgacctacaccgaactgagatacctacagcgtgagctatgagaaagcgccacgcttcccgaagggagaaaggcggacaggtatccggtaagcggcagggtcggaacaggaga gcgcacgagggagcttccagggggaaacgcctggtatctttatagtcctgtcgggtttcgccacctctgacttgagcgtcgatttttgtgatg ctcgtcaggggggcggagcctatggaaaaacgccagcaacgcggcctttttacggttcctggccttttgctggccttttgctcacatgt;

>AAV CBA-miR122 nucleic acid sequence

SEQ ID NO: 34 cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgccgcgtcgacattgattattgactctggtcgttacat aacttacggtaaatggcccgcctggctgaccgcccaacgacccccgcccattgacgtcaataatgacgtatgttcccatagtaacgccaata gggactttccattgacgtcaatgggtggagtatttacggtaaactgcccacttggcagtacatcaagtgtatcatatgccaagtacgccccccta ttgacgtcaatgacggtaaatggcccgcctggcattatgcccagtacatgaccttatgggactttcctacttggcagtacatctactcgaggcc acgttctgcttcactctccccatctcccccccctccccacccccaattttgtatttatttattttttaattattttgtgcagcgatgggggcgggggg ggggggggggggggcgcgcgccaggcggggcggggcggggcgaggggcggggcggggcgaggcggagaggtgcggcggca gccaatcagagcggcgcgctccgaaagtttccttttatggcgaggcggcggcggcggcggccctataaaaagcgaagcgcgcggcgg gcgggagcgggatcagccaccgcggtggcggccctagagtcgatcgaggaactgaaaaaccagaaagttaactggtaagtttagtctttt tgtcttttatttcaggtcccggatccggtggtggtgcaaatcaaagaactgctcctcagtggatgttgcctttacttctaggcctgtacggaagt gttacttctgctctaaaagctgcggaattgtacccgcggccgatccaccggtcgccaccatctagcatgggagtcaaagttctgtttgccctg atctgcatcgctgtggccgaggccaagcccaccgagaacaacgaagacttcaacatcgtggccgtggccagcaacttcgcgaccacgg atctcgatgctgaccgcgggaagttgcccggcaagaagctgccgctggaggtgctcaaagagatggaagccaatgcccggaaagctgg ctgcaccaggggctgtctgatctgcctgtcccacatcaagtgcacgcccaagatgaagaagttcatcccaggacgctgccacacctacga aggcgacaaagagtccgcacagggcggcataggcgaggcgatcgtcgacattcctgagattcctgggttcaaggacttggagcccatgg agcagttcatcgcacaggtcgatctgtgtgtggactgcacaactggctgcctcaaagggcttgccaacgtgcagtgttctgacctgctcaag aagtggctgccgcaacgctgtgcgacctttgccagcaagatccagggccaggtggacaagatcaagggggccggtggtgactagctcg acgctcaaacaccattgtcacactccaacaaacaccattgtcacactccaacaaacaccattgtcacactccagatcagcctcgactgtgcct tctagttgccagccatctgttgtttgcccctcccccgtgccttccttgaccctggaaggtgccactcccactgtcctttcctaataaaatgagga aattgcatcgcattgtctgagtaggtgtcattctattctggggggtggggtggggcaggacagcaagggggaggattgggaagacaaggc cgcaggaacccctagtgatggagttggccactccctctctgcgcgctcgctcgctcactgaggccgggcgaccaaaggtcgcccgacgc ccgggctttgcccgggcggcctcagtgagcgagcgagcgcgcagctgcctgcaggggcgcctgatgcggtattttctccttacgcatctg tgcggtatttcacaccgcatacgtcaaagcaaccatagtacgcgccctgtagcggcgcattaagcgcggcgggtgtggtggttacgcgca gcgtgaccgctacacttgccagcgccctagcgcccgctcctttcgctttcttcccttcctttctcgccacgttcgccggctttccccgtcaagct ctaaatcgggggctccctttagggttccgatttagtgctttacggcacctcgaccccaaaaaacttgatttgggtgatggttcacgtagtgggc catcgccctgatagacggtttttcgccctttgacgttggagtccacgttctttaatagtggactcttgttccaaactggaacaacactcaacccta tctcgggctattcttttgatttataagggattttgccgatttcggcctattggttaaaaaatgagctgatttaacaaaaatttaacgcgaattttaaca aaatattaacgtttacaattttatggtgcactctcagtacaatctgctctgatgccgcatagttaagccagccccgacacccgccaacacccgc tgacgcgccctgacgggcttgtctgctcccggcatccgcttacagacaagctgtgaccgtctccgggagctgcatgtgtcagaggttttcac cgtcatcaccgaaacgcgcgagacgaaagggcctcgtgatacgcctatttttataggttaatgtcatgataataatggtttcttagacgtcagg tggcacttttcggggaaatgtgcgcggaacccctatttgtttatttttctaaatacattcaaatatgtatccgctcatgagacaataaccctgataa atgcttcaataatattgaaaaaggaagagtatgagtattcaacatttccgtgtcgcccttattcccttttttgcggcattttgccttcctgtttttgctc -continued acccagaaacgctggtgaaagtaaaagatgctgaagatcagttgggtgcacgagtgggttacatcgaactggatctcaacagcggtaaga tccttgagagttttcgccccgaagaacgttttccaatgatgagcacttttaaagttctgctatgtggcgcggtattatcccgtattgacgccggg caagagcaactcggtcgccgcatacactattctcagaatgacttggttgagtactcaccagtcacagaaaagcatcttacggatggcatgac agtaagagaattatgcagtgctgccataaccatgagtgataacactgcggccaacttacttctgacaacgatcggaggaccgaaggagcta accgcttttttgcacaacatgggggatcatgtaactcgccttgatcgttgggaaccggagctgaatgaagccataccaaacgacgagcgtg acaccacgatgcctgtagcaatggcaacaacgttgcgcaaactattaactggcgaactacttactctagcttcccggcaacaattaatagact ggatggaggcggataaagttgcaggaccacttctgcgctcggcccttccggctggctggtttattgctgataaatctggagccggtgagcgt gggtctcgcggtatcattgcagcactggggccagatggtaagccctcccgtatcgtagttatctacacgacggggagtcaggcaactatgg atgaacgaaatagacagatcgctgagataggtgcctcactgattaagcattggtaactgtcagaccaagtttactcatatatactttagattgat ttaaaacttcatttttaatttaaaaggatctaggtgaagatcctttttgataatctcatgaccaaaatcccttaacgtgagttttcgttccactgagcg tcagaccccgtagaaaagatcaaaggatcttcttgagatcctttttttctgcgcgtaatctgctgcttgcaaacaaaaaaaccaccgctaccag cggtggtttgtttgccggatcaagagctaccaactctttttccgaaggtaactggcttcagcagagcgcagataccaaatactgtccttctagt gtagccgtagttaggccaccacttcaagaactctgtagcaccgcctacatacctcgctctgctaatcctgttaccagtggctgctgccagtgg cgataagtcgtgtcttaccgggttggactcaagacgatagttaccggataaggcgcagcggtcgggctgaacggggggttcgtgcacaca gcccagcttggagcgaacgacctacaccgaactgagatacctacagcgtgagctatgagaaagcgccacgcttcccgaagggagaaag gcggacaggtatccggtaagcggcagggtcggaacaggagagcgcacgagggagcttccagggggaaacgcctggtatctttatagtc ctgtcgggtttcgccacctctgacttgagcgtcgatttttgtgatgctcgtcaggggggcggagcctatggaaaaacgccagcaacgcggc ctttttacggttcctggccttttgctggccttttgctcacatgt;

>human soluble IL1Rα nucleic acid sequence

SEQ ID NO: 35 atggaaatctgcagaggcctccgcagtcacctaatcactctcctcctcttcctgttccattcagagacgatctgccgaccctctgggagaaaa tccagcaagatgcaagccttcagaatctgggatgttaaccagaagaccttctatctgaggaacaaccaactagttgctggatacttgcaagg accaaatgtcaatttagaagaaaagatagatgtggtacccattgagcctcatgctctgttcttgggaatccatggagggaagatgtgcctgtc ctgtgtcaagtctggtgatgagaccagactccagctggaggcagttaacatcactgacctgagcgagaacagaaagcaggacaagcgctt cgccttcatccgctcagacagtggccccaccaccagttttgagtctgccgcctgccccggttggttcctctgcacagcgatggaagctgacc agcccgtcagcctcaccaatatgcctgacgaaggcgtcatggtcaccaaattctacttccaggaggacgagtagtaa;

>synthetic intron nucleic acid sequence

SEQ ID NO: 36 gaactgaaaaaccagaaagttaactggtaagtttagtctttttgtcttttatttcaggtcccggatccggtggtggtgcaaatcaaagaactgct cctcagtggatgttgcctttacttcaggcctgtacggaagtgttacttctgctctaaaagctgcggaattgtaccc;

>MBL intron nucleic acid sequence

SEQ ID NO: 37 tcagatcgcctggagacgccatccacgctgttttgacctccatagaagacaccgggaccgatccagcctccgcggccgggaacggtgca ttggaacgcggattccccgtgccaagagtgacgtaagtaccgcctatagagtctataggcccacccccttggcttcttatgcatgctatactgt ttttggcttggggtctatacacccccgcttcctcatgtttgctgcccgtgaccagcacgtcaacgattttgtgggcacgggcgacaccgcagt gtagtctgagcagtactcgttgctgccgcgcgcgccaccagacataatagctgacagactaacagactgttcctttccatgggtcttttctgca gtcaccgtcgccgc;

>OPT ACVR1 protein sequence

SEQ ID NO: 38

MVDGVMILPVLIMIALPSPSMEDEKPKVNPKLYMCVCEGLSCGNEDHCEGQQCFSSLSI

NDGFHVYQKGCFQVYEQGKMTCKTPPSPGQAVECCQGDWCNRNITAQLPTKGKSFPGT

QNFHLEVGLIILSVVFAVCLLACLLGVALRKFKRRNQERLNPRDVEYGTIEGLITTNVGD

STLADLLDHSCTSGSGSGLPFLVQRTVARQITLLECVGKGRYGEVWRGSWQGENVAVKI

FSSRDEKSWFRETELYNTVMLRHENILGFIASDMTSRHSSTQLWLITHYHEMGSLYDYL

QLTTLDTVSCLRIVLSIASGLAHLHIEIFGTQGKPAIAHRDLKSKNILVKKNGQCCIADLG

-continued

LAVMHSQSTNQLDVGNNPRVGTKRYMAPEVLDETIQVDCFDSYKRVDIWAFGLVLWEV

ARRMVSNGIVEDYKPPFYDVVPNDPSFEDMRKVVCVDQQRPNIPNRWFSDPTLTSLAKL

MKECWYQNPSARLTALRIKKTLTKIDNSLDKLKTDC*;

>Protein sequence corresponding to SEQ ID NO: 5

SEQ ID NO: 39

VFYFRSQI*GSAFAPGSPLLPWAWAH*QPWCLWPAAHLLAGSCECNLVSHLFWQYLSGS

ADYTHGGLP*LPTVPWPKRI*GHR*GPT*PSWGIRTVSPLQGIRWWC;

>Protein sequence corresponding to SEQ ID NO: 6

SEQ ID NO: 40

RALRLLQVVRCSLGPGPTDSPGASGRLHTSWRAAVSVSW*ATCSGNT*VALRLTLTEACP

DCPRCRGQRGSKGTAEGLPNHRGE*GQCHP;

>wtACVR1 protein sequence corresponding to SEQ ID NO: 7

SEQ ID NO: 41

SRVQRTVARQITLLEC;

>ACVR1-R206H protein sequence corresponding to SEQ ID NO: 8

SEQ ID NO: 42

SRVQRTVARQITLLEC;

>sgACVR1 protein sequence

SEQ ID NO: 43

GSPDYTV;

>hspCas9 protein sequence

SEQ ID NO: 44

VTSQLRQVDPCLVQAGDALVDQGGVQHLFGAGVPLPVDGGVKVLEGGRGSQIGQGKQ

VDDILGLLSDGLIPVLVVGGQHFVQISVGQDHSLGELADLLDDLVQVVLVLFHKQLFLLI

ILGGALQLLIVAGQVQEVHIFGGQGQFVSLLQFAGRGQHSLPAVFQLEQGVLRQLDDQV

LFHFFVALGFQKVDGILLEAASFHDGDPQQLFHTLQFLGLALFHFGHHQHRIGHGGAVE

AAVLLRVPVLLSGDQLIAVPLGQDRLFAEAACLHLGLFHDIHLGHAQHFPHGGKIPALIP

HDLPGFAVCLDQRPLPDLAVGQGNLGLEKVHDVAVEEVLGGSLADFLLALGDHLPHVV

HLVVAVHELAFQLRVLFDQGGSHDGVQVGVVGVVVVVDLAHFVKLEILPEIGHQLGLQ

GDHFHFPDQLVILVVLSVHPGVQDLCHVLCDLPGFHQLSLDEAGLIQFAQAASLGLGQIV

ELSLGNQLGVQQLPPVVLHLLHDLFGGHVVALAPVLVASGQHLVVDGVVLQKALRHD

MVHIVVGQPVDVQFLVHVHIPPILQVVQVQLLVLQLGVFHGVFFQDLAAQLFDALFDPL

HSLAAVLLSLLGGLVLSGHFDHDVLGLVPAHHFHELVHHLHCLQDALLNGGAAGQIGN

VLVQAIALAGHLGFLDVLFKGQAVVVDQLHEVSVGEAVGLQEIQDCLAGLLVPDAVDQ

LPAQPAPAGVSPPLQLLHHFVVEQVGIGFQPFLDHLSVLKQCQGQHDIFQNVLVFLIVQE

VLVLDNFQQIVVCAQGGVEPIFHAGDFHGVEA;

>sFST-288 protein sequence

SEQ ID NO: 45

MVRARHQPGGLCLLLLLLCQFMEDRSAQAGNCWLRQAKNGRCQVLYKTELSKEECCS

TGRLSTSWTEEDVNDNTLFKWMIFNGGAPNCIPCKETCENVDCGPGKKCRMNKKNKP

RCVCAPDCSNITWKGPVCGLDGKTYRNECALLKARCKEQPELEVQYQGRCKKTCRDV

FCPGSSTCVVDQTNNAYCVTCNRICPEPASSEQYLCGNDGVTYSSACHLRKATCLLGRSI

GLAYEGKCIKAKSCEDIQCTGGKKCLWDFKVGRGRCSLCDELCPDSKSDEPVCASDNAT

YASECAMKEAACSSGVLLEVKHSGSCN;

>sTNFR2 protein sequence

SEQ ID NO: 46

MAPVAVWAALAVGLELWAAAHALPAQVAFTPYAPEPGSTCRLREYYDQTAQMCCSKCS

PGQHAKVFCTKTSDTVCDSCEDSTYTQLWNWVPECLSCGSRCSSDQVETQACTREQNR

ICTCRPGWYCALSKQEGCRLCAPLRKCRPGFGVARPGTETSDVVCKPCAPGTFSNTTSS

-continued

TDICRPHQICNVVAIPGNASMDAVCTSTSPTRSMAPGAVHLPQPVSTRSQHTQPTPEPSTA

PSTSFLLPMGPSPPAEGSTGDFALPV;

>miR-122 protein sequence

SEQ ID NO: 47

QTPLSHSNKHHCHTPTNTIVTL;

miR-208 binding sites

SEQ ID NO: 48

ACAAGCTTTTTGCTCGTCTTATACAAGCTTTTTGCTCGTCTTATACAAGCTTTTTGCT

CGTCTTAT;

pAAVss-CB-PI(MBL-amiRACVR1-A9)-opt-ACVR1-miR-122T.miR-208aT

SEQ ID NO: 49 ctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctaccagggtaatggg gatcctctagaactatagctagtcgacattgattattgactagttattaatagtaatcaattacggggtcattagacatagcccatatatggaga ccgcgttacataacttacggtaaatggcccgcctggctgaccgcccaacgacccccgcccattgacgtcaataatgacgtatgacccatag taacgccaatagggactttccattgacgtcaatgggtggagtatttacggtaaactgcccacttggcagtacatcaagtgtatcatatgccaag tacgcccccctattgacgtcaatgacggtaaatggcccgcctggcattatgcccagtacatgaccttatgggactttcctacttggcagtacatc tacgtattagtcatcgctattaccatgtcgaggccacgactgcttcactctccccatctcccccccctccccacccccaattttgtatttatttattt tttaattattttgtgcagcgatgggggcgggggggggggggcgcgcgccaggcggggcggggcggggcgaggggcggggcggggcg aggcggagaggtgcggcggcagccaatcagagcggcgcgctccgaaagtttccttttatggcgaggcggcggcggcggcggccctat aaaaagcgaagcgcgcggcgggcgggagcaagctttcagatcgcctggagacgccatccacgctgttttgacctccatagaagacacc gggaccgatccagcctccgcggccgggaacggtgcattggaacgcggattccccgtgccaagagtgacgtaagtaccgcctatagagtc tataggcccacccccttggcttcttatgcatgctatactgtttttggcttggggtctatacacccccgcttcctcatgttTGCTGCCCGT GACCAGCACGTCAACGATTTTGTGGGCACGGGCGACACcgcagtgtagtctgagcagtactcgttgct gccgcgcgcgccaccagacataatagctgacagactaacagactgttcctttccatgggtcttttctgcaAGGGCTCTGCGTTT

GCTCCAGGTAGTCCGCTGCTCCCTTGGGCCTGGGCCCACTGACAGCCCTGGTGCCTC

TGGCCGGCTGCACACCTCCTGGCGGGCAGCTGTGtgtaatctggtgagccactgtTGTTCTGGCA

ATACCTGACAGTGGCAGATCAGATTACACACGGAGGCCTGCCCTGACTGCCCACGG

TGCCGTGGCCAAAGAGGATCTAAGGGCACCGCTGAGGGCCTACCTAACCATCGTGG

GGAATAAGGACAGTGTCACCCtgcagtcaccgtcgccgccaccggtgaattccgccaccatggtcgatggagtgatg atcctgcctgtcctgattatgattgccctgcccagccccagcatggaagatgaaaaacctaaagtcaaccctaagctgtatatgtgcgtgtgc gagggcctgagctgcggaaacgaggatcactgcgagggccagcagtgtttcagctccctgtccatcaatgacggcttccacgtgtaccag aagggctgctttcaggtgtatgagcagggcaagatgacctgtaagacaccaccttccccaggacaggcagtggagtgctgtcagggcgat tggtgtaaccggaatatcaccgcccagctgccaacaaagggcaagtctttccccggcacacagaactttcacctggaagtgggcctgatca tcctgagcgtggtgttcgccgtgtgcctgctggcatgtctgctgggagtggccctgagaaagtttaagcggagaaaccaggagcggctga atccaagagatgtggagtacggcaccatcgagggcctgatcaccacaaatgtgggcgactctacactggccgacctgctggatcacagct gcaccagcggctccggatctggcctgccctttctggtgcagaggaccgtggcccggcagatcaccctgctggagtgcgtgggcaaggg ccggtacggagaagtgtggagaggatcctggcagggagagaacgtggcagtgaagatcttctctagccgggatgagaagtcttggtttag agagacagagctgtataacacagtgatgctgaggcacgagaatatcctgggcttcatcgcctccgacatgacctctcgccactcctctacac agctgtggctgatcacccactaccacgagatgggctccctgtacgattacctccagctgaccacactggacacagtgtatgcctgcggatc gtgctgtctatcgccagcggcctggcacacctgcacatcgagatctttggaacccagggcaagccagcaatcgcacacagagatctgaag tctaagaacatcctggtgaagaagaatggccagtgctgtatcgccgatctgggcctggccgtgatgcacagccagtccaccaaccagctg gacgtgggcaacaatcctcgggtgggcacaaagagatacatggccccagaggtgctggatgagacaatccaggtggactgcttcgatag ctataagagggtggacatctgggcctttggcctggtgctgtgggaggtggcaaggaggatggtgagcaacggcatcgtggaggactaca -continued agccacccttctatgacgtggtgcctaatgatccatcctttgaggacatgcgcaaggtggtgtgcgtggatcagcagaggcccaacatccct aatcgctggttcagcgaccccaccctgacatccctggccaagctgatgaaggagtgaggtatcagaatcctagcgccaggctgaccgcc ctgcgcatcaagaaaactctgactaaaatcgacaatagcctggataaactgaaaaccgactgctgaccTgAACAAGCTTTTTG CTCGTCTTATACAAGCTTTTTGCTCGTCTTATACAAGCTTTTTGCTCGTCTTATacaaaca ccattgtcacactccaacaaacaccattgtcacactccaacaaacaccattgtcacactccatgaggatccgatctttttccctctgccaaaaat tatggggacatcatgaagccccttgagcatctgacttctggctaataaaggaaatttattttcattgcaatagtgtgttggaattttttgtgtctctc actcggaagcaattcgttgatctgaatttcgaccacccataatacccattaccctggtagataagtagcatggcgggttaatcattaactacaa ggaacccctagtgatggagttggccactccctctctgcgcgctcgctcgctcactgaggccgggcgaccaaaggtcgcccgacgcccgg gctttgcccgggcggcctcagtgagcgagcgagcgcgcag;

Nucleic acid sequence encoding RH3 ami-RNA

SEQ ID NO: 56 gtcttttatttcaggtcccagatctagggctctgcgtttgctccaggtagtccgctgctcccttgggcctgggcccactgacagccctggtgcc tctggccggctgcacacctcctggcgggcagctgtgagtgtaatctggtgagccacttgttctggcaatacctgagtggctctgcggattac actcacggaggcctgccctgactgcccacggtgccgtggccaaagaggatctaagggcaccgctgagggcctacctaaccatcgtggg gaataaggacagtgtcacccctgcaggggatccggtggtggtgc;

Nucleic acid sequence encoding RH4 ami-RNA

SEQ ID NO: 57 agggctctgcgtttgctccaggtagtccgctgctcccttgggcctgggcccactgacagccctggtgcctctggccggctgcacacctcct ggcgggcagctgtggtgtaagctggtgagccactgtgttctggcaatacctgcagtggctgtctagcttacaccacggaggcctgccctga ctgcccacggtgccgtggccaaagaggatctaagggcaccgctgagggcctacctaaccatcgtggggaataaggacagtgtcaccc;

Nucleic acid sequence encoding RH5 ami-RNA

SEQ ID NO: 58 agggctctgcgtttgctccaggtagtccgctgctcccttgggcctgggcccactgacagccctggtgcctctggccggctgcacacctcct ggcgggcagctgtgtgtaagctggtgagccactgttgttctggcaatacctgacagtggcagatcagcttacacacggaggcctgccctga ctgcccacggtgccgtggccaaagaggatctaagggcaccgctgagggcctacctaaccatcgtggggaataaggacagtgtcaccc;

Nucleic acid sequence encoding RH6 ami-RNA

SEQ ID NO: 59 agggctctgcgtttgctccaggtagtccgctgctcccttgggcctgggcccactgacagccctggtgcctctggccggctgcacacctcct ggcgggcagctgtgtgtaatctggtgagccactgttgttctggcaatacctgacagtggcagatcagattacacacggaggcctgccctga ctgcccacggtgccgtggccaaagaggatctaagggcaccgctgagggcctacctaaccatcgtggggaataaggacagtgtcaccc;

Nucleic acid sequence encoding RH7 ami-RNA

SEQ ID NO: 60 agggctctgcgtttgctccaggtagtccgctgctcccttgggcctgggcccactgacagccctggtgcctctggccggctgcacacctcct ggcgggcagctgtggtaatctggtgagccactgtttgttctggcaatacctgaacagtgggacgccagattaccacggaggcctgccctga ctgcccacggtgccgtggccaaagaggatctaagggcaccgctgagggcctacctaaccatcgtggggaataaggacagtgtcaccc;

Nucleic acid sequence encoding RH8 ami-RNA

SEQ ID NO: 61 agggctctgcgtttgctccaggtagtccgctgctcccttgggcctgggcccactgacagccctggtgcctctggccggctgcacacctcct ggcgggcagctgtggtaagctggtgagccactgtttgttctggcaatacctgaacagtgggacgccagcttaccacggaggcctgccctg actgcccacggtgccgtggccaaagaggatctaagggcaccgctgagggcctacctaaccatcgtggggaataaggacagtgtcaccc;

Nucleic acid sequence encoding RH9 ami-RNA

SEQ ID NO: 62 agggctctgcgtttgctccaggtagtccgctgctcccttgggcctgggcccactgacagccctggtgcctctggccggctgcacacctcct ggcgggcagctgtgtaatctggtgagccactgttctgttctggcaatacctggaacagtgcgttaccagattacacggaggcctgccctgac tgcccacggtgccgtggccaaagaggatctaagggcaccgctgagggcctacctaaccatcgtggggaataaggacagtgtcaccc;

Nucleic acid sequence encoding RH10 ami-RNA

SEQ ID NO: 63 agggctctgcgtttgctccaggtagtccgctgctcccttgggcctgggcccactgacagccctggtgcctctggccggctgcacacctcct ggcgggcagctgtgtaagctggtgagccactgttctgttctggcaatacctggaacagtgcgttaccagcttacacggaggcctgccctga -continued ctgcccacggtgccgtggccaaagaggatctaagggcaccgctgagggcctacctaaccatcgtggggaataaggacagtgtcaccc;

Nucleic acid sequence encoding RH11 ami-RNA

SEQ ID NO: 64 agggctctgcgtttgctccaggtagtccgctgctcccttgggcctgggcccactgacagccctggtgcctctggccggctgcacacctcct ggcgggcagctgtgaatctggtgagccactgttcttgttctggcaatacctgagaacagtcccccaccagattcacggaggcctgccctga ctgcccacggtgccgtggccaaagaggatctaagggcaccgctgagggcctacctaaccatcgtggggaataaggacagtgtcaccc;

Nucleic acid sequence encoding RH12 ami-RNA

SEQ ID NO: 65 agggctctgcgtttgctccaggtagtccgctgctcccttgggcctgggcccactgacagccctggtgcctctggccggctgcacacctcct ggcgggcagctgtgaagctggtgagccactgttcttgttctggcaatacctgagaacagtcccccaccagcttcacggaggcctgccctga ctgcccacggtgccgtggccaaagaggatctaagggcaccgctgagggcctacctaaccatcgtggggaataaggacagtgtcaccc;

---

The invention claimed is:

1. A recombinant adeno-associated virus (rAAV) comprising:

(i) an isolated nucleic acid comprising a transgene comprising a promoter operably linked to a codon optimized nucleic acid sequence encoding an activin receptor type-1 (ACVR1) protein, wherein the codon optimized nucleic acid sequence comprises the sequence of SEQ ID NO: 1; and (ii) at least one AAV capsid protein.

2. The rAAV of claim 1, wherein the at least one AAV capsid protein is of a serotype selected from AAV1, AAV2, AAV3, AAV4, AAV5, AAV6, AAV6.2, AAV7, AAV8, AAVrh.8, AAV9, AAVrh.10, AAVrh39, and AAVrh.43.

3. The rAAV of claim 1, wherein the rAAV is a self-complementary AAV (scAAV).

4. The rAAV of claim 1, wherein the promoter is a chicken beta-actin (CBA) promoter or comprises an intron comprising the sequence of SEQ ID NO: 37 or comprises an intron comprising the sequence of SEQ ID NO: 36.

5. A recombinant adeno-associated virus (rAAV) comprising:

(i) at least one AAV capsid protein; and (ii) an isolated nucleic acid comprising:

a nucleic acid that encodes an artificial miRNA (ami-RNA) comprising a nucleic acid having sufficient sequence complementary with an endogenous mRNA of a subject to hybridize with and inhibit expression of the endogenous mRNA, wherein the endogenous mRNA encodes an activin receptor type-1 (ACVR1) protein; and a nucleic acid that encodes a transgene comprising a codon optimized nucleic acid sequence encoding an ACVR1 protein, wherein the codon optimized nucleic acid sequence comprises the sequence of SEQ ID NO: 1.

6. The rAAV of claim 5, wherein the at least one capsid protein is selected from AAV1, AAV2, AAV3, AAV4, AAV5, AAV6, AAV6.2, AAV7, AAV8, AAVrh.8, AAV9, AAVrh.10, AAVrh39, and AAVrh.43 capsid protein.

7. The rAAV of claim 5, wherein the ami-RNA and the transgene are operably linked to a promoter and wherein the ami-RNA comprises a human miRNA backbone.

8. The rAAV of claim 5, wherein the promoter is a chicken beta-actin (CBA) promoter or comprises an intron comprising the sequence of SEQ ID NO: 37.

9. The rAAV of claim 5, wherein the ACVR1 protein encoded by the endogenous mRNA is human ACVR1-R206H.

10. The rAAV of claim 5, wherein the isolated nucleic acid comprises the sequence set forth in any one of SEQ ID NOs: 26-28.

11. The rAAV of claim 5, wherein the ami-RNA is encoded by the sequence set forth in any one of SEQ ID NOs: 5, 6 and 56-65.

12. The rAAV of claim 7, wherein the human miRNA backbone is a miR-33 backbone.

* * * * *